US009150898B2

(12) United States Patent
Aricò et al.

(10) Patent No.: US 9,150,898 B2
(45) Date of Patent: Oct. 6, 2015

(54) HETEROLOGOUS EXPRESSION OF NEISSERIAL PROTEINS

(71) Applicant: Novartis AG, Basel (CH)

(72) Inventors: Maria Aricò, Siena (IT); Maurizio Comanducci, Siena (IT); Cesira Galeotti, Montegriggioni (IT); Vega Masignani, Siena (IT); Marzia Monica Giuliani, Siena (IT); Mariagrazia Pizza, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 14/448,792

(22) Filed: Jul. 31, 2014

(65) Prior Publication Data

US 2014/0363462 A1     Dec. 11, 2014

Related U.S. Application Data

(60) Continuation of application No. 14/244,806, filed on Apr. 3, 2014, which is a continuation of application No. 13/340,549, filed on Dec. 29, 2011, now Pat. No. 8,703,914, which is a division of application No. 12/825,210, filed on Jun. 28, 2010, now Pat. No. 8,114,960, which is a division of application No. 10/220,481, filed as application No. PCT/IB01/00452 on Feb. 28, 2001, now Pat. No. 7,803,387.

(30) Foreign Application Priority Data

Feb. 28, 2000   (GB) .................................. 0004695.3
Nov. 13, 2000   (GB) .................................. 0027675.8

(51) Int. Cl.
    *C12P 21/00*        (2006.01)
    *C12P 21/02*        (2006.01)
    *C07K 14/22*        (2006.01)
    *C12Q 1/68*         (2006.01)
    *A61K 38/00*        (2006.01)
    *A61K 39/095*      (2006.01)
    *A61K 39/00*        (2006.01)

(52) U.S. Cl.
    CPC ............... *C12P 21/02* (2013.01); *A61K 39/095* (2013.01); *C07K 14/22* (2013.01); *C12P 21/00* (2013.01); *C12Q 1/689* (2013.01); *A61K 38/00* (2013.01); *A61K 2039/55505* (2013.01); *C07K 2319/00* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,239,749 A | 12/1980 | Buchanan |
| 5,914,254 A | 6/1999 | Mascarenhas et al. |
| 6,248,329 B1 | 6/2001 | Chandrashekar et al. |
| 7,348,006 B2 | 3/2008 | Contorni et al. |
| 7,504,111 B2 | 3/2009 | Fontana et al. |
| 7,576,176 B1 * | 8/2009 | Fraser et al. ................... 530/350 |
| 7,612,192 B2 * | 11/2009 | Fraser et al. ................... 536/23.7 |
| 7,785,608 B2 | 8/2010 | Zlotnick et al. |
| 7,803,387 B2 * | 9/2010 | Arico et al. .................. 424/250.1 |
| 7,862,827 B2 * | 1/2011 | Giuliani et al. .............. 424/250.1 |
| 7,960,535 B2 * | 6/2011 | Ades et al. ..................... 536/23.7 |
| 8,101,194 B2 | 1/2012 | Zlotnick et al. |
| 8,114,960 B2 * | 2/2012 | Arico et al. .................... 530/324 |
| 8,226,960 B2 | 7/2012 | Masignani et al. |
| 8,273,360 B2 * | 9/2012 | Pizza et al. .................. 424/250.1 |
| 8,293,251 B2 | 10/2012 | Scarlato et al. |
| 8,394,390 B2 * | 3/2013 | Galeotti et al. ............. 424/250.1 |
| 8,398,988 B2 | 3/2013 | Contorni et al. |
| 8,398,999 B2 | 3/2013 | Masignani et al. |
| 8,524,251 B2 * | 9/2013 | Fraser et al. ................. 424/250.1 |
| 8,563,007 B1 | 10/2013 | Zlotnick et al. |
| 8,574,597 B2 | 11/2013 | Zlotnick |
| 8,663,656 B2 | 3/2014 | Pizza |
| 8,703,914 B2 * | 4/2014 | Arico et al. .................... 530/350 |
| 8,734,812 B1 * | 5/2014 | Galeotti et al. ............. 424/250.1 |
| 8,840,907 B2 | 9/2014 | Pizza |
| 8,980,286 B2 | 3/2015 | Comanducci |
| 9,011,869 B2 | 4/2015 | Pizza |
| 9,056,075 B2 | 6/2015 | Pizza |
| 2001/0031268 A1 | 10/2001 | Baldwin et al. |
| 2004/0092711 A1 | 5/2004 | Arico |
| 2004/0110670 A1 | 6/2004 | Arico et al. |
| 2004/0167068 A1 | 8/2004 | Zlotnick et al. |
| 2005/0222385 A1 | 10/2005 | Pizza |

(Continued)

FOREIGN PATENT DOCUMENTS

| | | |
|---|---|---|
| EP | 0467714 | 1/1992 |
| EP | 1645631 A2 | 4/2006 |
| EP | 1790660 A2 | 5/2007 |
| EP | 2351767 A2 | 8/2011 |
| JP | 2003-525050 A2 | 8/2003 |
| WO | WO-96/29412 A1 | 9/1996 |
| WO | WO-97/10844 A1 | 3/1997 |
| WO | WO-97/28273 A2 | 8/1997 |
| WO | WO-98/17805 | 4/1998 |
| WO | WO-99/41230 A1 | 8/1999 |

(Continued)

OTHER PUBLICATIONS

Nadolski et al FEBS J. 2007. 274:5202-5210.*

(Continued)

*Primary Examiner* — Nita M Minnifield
(74) *Attorney, Agent, or Firm* — Morrison & Foerster LLP

(57) ABSTRACT

Alternative and improved approaches to the heterologous expression of the proteins of *Neisseria meningitidis* and *Neisseria gonorrhoeae* are disclosed. These approaches typically affect the level of expression, the ease of purification, the cellular localization, and/or the immunological properties of the expressed protein.

12 Claims, 22 Drawing Sheets

(56) References Cited

U.S. PATENT DOCUMENTS

| | | | |
|---|---|---|---|
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0082014 A1 | 4/2007 | Costantino | |
| 2007/0253984 A1 | 11/2007 | Khandke et al. | |
| 2008/0241180 A1 | 10/2008 | Contorni | |
| 2009/0285845 A1 | 11/2009 | Masignani et al. | |
| 2010/0267931 A1 | 10/2010 | Arico et al. | |
| 2011/0020390 A1 | 1/2011 | Pizza et al. | |
| 2012/0107339 A1 | 5/2012 | Granoff et al. | |
| 2012/0276129 A1* | 11/2012 | Galeotti et al. | 424/190.1 |
| 2014/0037668 A1 | 2/2014 | Giuliani et al. | |
| 2014/0154286 A1* | 6/2014 | Malley et al. | 424/190.1 |
| 2014/0363462 A1* | 12/2014 | Aricò et al. | 424/190.1 |
| 2015/0079124 A1* | 3/2015 | Fraser et al. | 424/190.1 |
| 2015/0086582 A1* | 3/2015 | Fraser et al. | 424/190.1 |

FOREIGN PATENT DOCUMENTS

| | | |
|---|---|---|
| WO | WO-99/57280 A | 11/1999 |
| WO | WO-00/22430 A2 | 4/2000 |
| WO | WO-00/50075 | 8/2000 |
| WO | WO-00/66791 | 11/2000 |
| WO | WO-01/31019 | 5/2001 |
| WO | WO-01/40473 | 6/2001 |
| WO | WO-01/52885 | 7/2001 |
| WO | WO-01/64920 A | 9/2001 |
| WO | WO-01/64922 A2 | 9/2001 |
| WO | WO-01/81581 | 11/2001 |
| WO | WO-02/02606 A2 | 1/2002 |
| WO | WO-02/07763 A2 | 1/2002 |
| WO | WO-02/09746 A2 | 2/2002 |
| WO | WO-03/009869 A1 | 2/2003 |
| WO | WO-03/020756 A | 3/2003 |
| WO | WO-03/063766 | 8/2003 |
| WO | WO-2004/032958 A1 | 4/2004 |
| WO | WO-2004/048404 | 6/2004 |
| WO | WO-2004/065603 A2 | 8/2004 |
| WO | WO-2004/067030 A2 | 8/2004 |
| WO | WO-2004/094596 A2 | 11/2004 |
| WO | WO-2004/112832 | 12/2004 |
| WO | WO-2005/032583 A2 | 4/2005 |
| WO | WO-2005/033148 A1 | 4/2005 |
| WO | WO-2005/102384 A2 | 11/2005 |
| WO | WO-2006/024954 A2 | 3/2006 |
| WO | WO-2006/081259 | 8/2006 |
| WO | WO-2007/060548 A2 | 5/2007 |
| WO | WO-2007/127665 A2 | 11/2007 |
| WO | WO-2008/001224 A2 | 1/2008 |
| WO | WO-2008/125985 A2 | 10/2008 |
| WO | WO-2008/149238 A2 | 12/2008 |
| WO | WO-2009/104097 A2 | 8/2009 |
| WO | WO-2010/028859 A1 | 3/2010 |
| WO | WO-2010/046715 A1 | 4/2010 |

OTHER PUBLICATIONS

Tseng, et al. 2012. Appl Microbiol Biotech. 93:1539-1552.*
Chen et al. 2007. Vaccine 27:1400-1409).*
Adams (1996). "Should Non-Peer-Reviewed Raw DNA Sequence Data Release Be Forced on the Scientific Community?," Science, 274: 534-536.
BenMohamed et al. (2002). "Lipopeptide vaccines-yesterday, today, and tomorrow," Lancet 2(7):425-431.
Biswas et al. (1995). "Characterization of IbpA, the structural gene for a lactoferrin receptor in *Neisseria gonorrhoeae*," Infection and Immunity, 63(8): 2958-2967.
Blattner et al. (1997). "The complete genome sequence of *Escherichia coli* K-12," Science 277 (5331): 1453-1474.
Decision to refuse a patent application, filed in the Opposition against EP1645631, dated Apr. 28, 2009, 7 pages.
Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Elzanowski et al. (2013). "The Genetic Codes, a compilation," Retrived from http://www.bioinformatics.org/JaMBW/2/3/TranslationTables.html.
Gene Browser, Nature Technology Corporation, filed in the Opposition against EP1645631, dated Jun. 26, 2013, 6 pages.
Holst et al. (2014). "Variability of genes encoding surface proteins used as vaccine antigens in meningococcal endemic and epidemic strain panels from Norway," Vaccine 32:2722-2731.
Interlocutory decision in opposition proceedings, filed in the Opposition against EP1645631, dated May 21, 2012, 82 pages.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Mahadevan (1998). "Reconciling the spectrum of Sagittarius A* with a two-temperature plasma model," Nature 394:651-653.
Meyer et al. (1984). "Pilus genes of *Neisseria gonorrheae*: Chromosomal organization and DNA sequence," Proc. Nail. Acad. Sci. USA 81: 6110-6114.
Minutes of the oral proceedings, filed in the Opposition against EP1645631, dated Februray 11, 2014, 4 pages.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Opponent's Further Submission in Preparation of the Oral Proceedings, filed in the Opposition against EP1645631, dated Nov. 3, 2011, 6 pages.
Opponent's Response to the Patentee's Submission dated Feb. 18, 2013, filed in the Opposition against EP1645631, dated Jul. 24 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
Patentee's Submissions under Rule 116 EPC, filed in the Opposition against EP1645631, dated Sep. 13, 2011, 13 pages.
Sprengart et al. (1997). "Functional importance of RNA interactions in selection of translation initiation codons," Molecular Microbilogy, 24(1): 19-28.
Submission of the Patentee of Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplementary Submission to the Grounds of Appeal, filed in the Opposition against EP1645631, dated Sep. 28, 2012, 2 pages.
Swaminathan (1996). "Molecular cloning of the three base restriction endonuclease R.CviJI from eukaryotic Chlorella virus IL-3A," Nucleic Acids Research, 24(13): 2463-2469.
TIGR Microbal Database, filed in the Opposition against EP1645631, dated Jun. 20, 2012, 14 pages.
Zollinger et al. (2010). "Design and evaluation in mice of a broadly protective meningococcal group B native outer membrane vesicle vaccine," Vaccine, 28(31):5057-5067.
Abad et al. (2008). "PorB2/3 Protein Hybrid in *Neisseria meningitidis*," Emerging Infectious Diseases, 14(4):688-689.
Bartsevich et al. (Mar. 7, 1997). "Molecular Identification of a Novel Protein That Regulates Biogenesis of Photosystem I, a Membrane Protein Complex," *The Journal of Biological Chemistry* 272(10):6382-6387.
Bethell et al. (2002). "Meningococcal vaccines," Expert Review of Vaccines 1(1):75-84.
Blythe et al. (2005). "Benchmarking B cell epitope prediction: underperformance of existing methods," Protein Sci. 14:246-248.
Boslego et al. (1991). "Gonorrhea Vaccines," Chapter 17 In *Vaccines and Immunotherapy*, Cryz S.J. (Ed.), Pergamon Press: New York, NY, pp. 211-223.

(56) References Cited

OTHER PUBLICATIONS

Bowie, J. (1990). "Deciphering the Message in Protein Sequences: Tolerance to Amino Acid Substitutions," *Science* 247: 1306-1310.

Brandhorst et al. (1995). "Effects of leader Sequences upon the Heterologous Expression of Restriction in *Aspergillus nidulans* and *Aspergillus niger*," CJM 41(7):601-611.

Bygraves et al. (1992). "Analysis of the Clonal Relationships Between Strains of *Neisseria meningitidis* by Pulsed Field Gel Electrophoresis," Journal of General Microbiology 138:523531.

Cann et al. (1989). "Detection of Antibodies to Common Antigens of Pathogenic and Commensal *Neisseria* Species," Journal of Medical Microbiology 30:23-30.

Caugant et al. (1987). "Genetic Structure of *Neisseria meningitidis* Populations in Relation to Serogroup, Serotype, and Outer Membrane Protein Pattern," Journal of Bacteriology 169(6):2781-2792.

Christodoulides et al. (1994). "Immunization with a Multiple Antigen Peptide Containing Defined B- and T-Cell Epitopes: Production of Bacterial Antibodies Group B *Neisseria meningitidis*," *Microbiology* 140:2951-2960.

Cooney et al. (1993). "Three Contiguous Lipoprotein Genes in Pasteurella haemolytica A1 which are Homologous to a Lipoprotein Gene in Haemophilus Influenza Type B," *Infection and Immunity* 61 (11):4682-4688.

Cruse et al. (2003). Illustrated Dictionary of Immunology, $2^{nd}$ Ed. CRC Press, pp. 46, 166, and 382.

Dempsey et al. (1991). "Physical Map of the Chromosome of *Neisseria gonorrhoeae* FA1090 with Locations of Genetic Markers, including Opa and Pil Genes," Journal of Bacteriology 173(17):5476-5486.

Devries et al. (Aug. 1996). "Invasion of Primary Nasopharyngeal Epithelial Cells by *Neisseria meningitidis* is Controlled by Phase Variation of Multiple Surface Antigens," Infection and Immunity 64(8):2998-3006.

Ellis (1988). Chapter 29 in Vaccines, Plotkin, S.A. et al. eds., W. B. Saunders Company: Philadelphia, PA. pp. 568-574.

Feng et al. (1996). "P55, an Immunogenic but Nonprotective 55-Kilodalton *Borrelia burgdorferi* Protein in Murine Lyme Disease," Infection and Immunity. 64(1):363-365.

Greenspan et al. (1999). "Defining Epitopes: It's Not as Easy as it Seems," Nature Biotechnology 17:936-937.

Grifantini, R. et al. (2002). "Previously Unrecognized Vaccine Candidates against Group B Meningococcus Identified by DNA Microarrays," *Nature Biotechnology* 20(9): 914-921.

Guillen et al. (1996). "Expression in *Escherichia coli* and Immunological Characterization of a Hybrid Class I-P64K Protein from *Neisseria Meningitidis*," Biotecnologia aplicada 13(4):271-275.

Herbert et al. (Eds.) The Dictionary of Immunology, 1995, one page.

Herbert, W. et al. (1985). The Dictionary of Immunology. Academic Press: London $3^{rd}$ edition, pp. 58-59.

Holmes, E. (2001). "PSMA Specific Antibodies and their Diagnostic and Therapeutic Use," Expert Opinion on Investigational Drugs 10(3): 511-519.

Jacobsson et al. (2009). "Prevalence and sequence variations of the genes encoding the five antigens included in the novel 5CVMB vaccine covering group B meningococcal disease" Vaccine. 27:1579-1584.

Jolley et al. (2007). "Molecular typing of meningococci: recommendations for target choice and nomenclature," FEMS Microbiol. Rev. 31:89-96.

Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.

Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.

Maiden et al. (1998). "Multilocus Sequence Typing: a Portable Approach to the Identification of Clones within Populations of Pathogenic Microorganisms," Proceedings of the National Academy of Sciences USA 95:3140-3145.

Morley, S. et al. (Dec. 12, 2001). "Vaccine prevention of meningococcal disease, coming soon?" *Vaccine* 20(5-6):666-687.

Moudallal et al. (1982). "Monoclonal anti bodies as probes of the antigenic structure of tobacco mosaic virus," EMBO Journal 1:1005-1010.

Ni et al. (1992). "Phylogenetic and Epidemiological Analysis of *Neisseria meningitidis* Using DNA Probes," Epidemiology and Infection 109:227-239.

Nosoh et al. (1991). Protein Stability and Stabilization through Protein Engineering. Chapter 7, p. 197, second paragraph.

Parkhill, J. et al. (Mar. 2000). "Complete DNA Sequence of a Serogroup A Strain of *Neisseria meningitides* Z2491," *Nature* 404(6777):502-506.

Perrett et al. (2005). "Towards an improved serogroup B *Neisseria meningitidis* vaccine," Expert Opinion on Biological Therapy 5(12):1611-1625.

Pettersson et al. (1999). "Sequence Variability of the Meningococcal Lactoferrin-binding Protein LbpB," *Gene* 231:105-110.

Pizza et al. (2000). "Identification of Vaccine Candidates Against Serogroup B Meningococcus by Whole-Genome Sequencing," Science 287(5459):1816-1820.

Poolman et al. (1985). "Colony Variants of *Neisseria meningitidis* Strain 2996 (B:2b:P1.2): Influence of Class-5 Out Membrane Proteins and Lipolysaccharides," J. Med. Microbiol 19:203-209.

Poolman et al. (1988). "Outer membrane protein sero-subtyping of *Neisseria meningitidis*," European Journal of Clinical Microbiology and Infectious Diseases 7:291-292.

Roitt, I. et al. (1993). *Immunology*. Mosby: St. Louis, pp. 7,7-7,8.

Seiler et al. (1996). "Allelic Polymorphism and Site-specific Recombination in the Opc Locus of *Neisseria meningitidis*," Molecular Microbiology 19(4):841-856.

Telford (Jun. 2008). "Bacterial Genome Variability and Its Impact on Vaccine Design," Cell Host & Microbe 3(6):408-416.

Tettelin et al. (2006). "Towards a universal group B Streptococcus vaccine using multistrain genome analysis," Expert Rev Vaccines 25:687-694.

Tettelin et al. (Mar. 10, 2000). "Complete Genome Sequence of *Neisseria meningitidis* Serogroup B Strain MC58," Science 287(5459):1809-1815.

Thomas E. Creighton (1984). Proteins: Structures and Molecular Properties. pp. 314-315.

Thomas E. Creighton (1989). Protein Structure: A Pratical Approach. pp. 184-186.

Thompson et al. (1994). "Clustal W: Improving the Sensitivity of Progressive Multiple Sequence Alignment through Sequence Weighting, Position-specific Gap Penalties and Weight Matrix Choice," *Nucleic Acids Research* 22(22):4673-4680.

Thompson et al. (1998). "Multiple Sequence Alignment with Clustal X," *Trends in Biochemical Sciences* 23:403-405.

Virji et al. (1992). "Variations in the Expression of Pili: the Effect on Adherence of *Neisseria meningitidis* to Human Epithelial and Endothelial Cells," Molecular Microbiology 6:1271-1279.

Wolff et al. (1992). "Phylogeny and Nucleotide Sequence of a 23S rRNA Gene from *Neisseria gonorrhea* and *Neisseria meningitidis*," Nucleic Acids Research 20(17):4657.

1997-11-17-NM_shotgun.dbs and 1997-12-15-NM.dbs, located at <ftp://ftp.sanger.ac.uk/pub/pathogens/nm/old data/>.

Aderson et al. (2010). "Effectiveness of a bivalent factor H binding protein vaccine across *Neisseria meningitidis* serogroups," 17th International Pathogenic Neisseria Conference 2010, p. 196.

Ala'Aldeen et al. (2010) "Human antibody response to the meningococcal factor H binding protein (LP2086) during invasive disease, colonization and carriage," Vaccine 28:7667-75.

Ambrose et al. (2006). "Characterization of LP2086 expression in *Neisseria meningitidis*," 15th International Pathogenic Neisseria Conference 2006, p. 103.

(56) References Cited

OTHER PUBLICATIONS

Anderson et al. (2008). "Functional cross-reactive antibodies are elicited by a group B *Neisseria meningitidis* bivalent recombinant lipidated LP2086 vaccine in cynomolgusmacaques," 16th International Pathogenic Neisseria Conference (IPNC) P100, pp. 170-171.
Anderson et al. (2009). "Epidemiology of the serogroup B *Neisseria meningitidis* (MnB) factor H binding protein and implications for vaccine development," European Society for Paediatric Infectious Disease Symposium 2009, p. 505.
Anderson et al. (2009). "Development of a factor H binding protein vaccine for borad protection against invasive *Neisseria meningitidis* serogroup B (MnB) disease," 10th European Meningococcal Disease Society Congress 2009, p. 39.
Anderson et al. (2012). "Potential impact of the bivalent rLP2086 vaccine on *Neisseria meningitidis* invasive disease and carriage isolates in two adolescent populations," European Society for Paediatric Infectious Disease Symposium 2012, p. 807.
Anderson et al. (2013) "Potential impact of the bivalent rLP2086 vaccine on *Neisseria meningitidis* carriage and invasive serogroup B disease," Hum Vacc Immunotherap 9:471-9.
Appendix I to Statement of Grounds of Appeal filed by df-mp on Sep. 28, 2012, in relation to EP1645631, 1 pages.
Appendix II to Statement of Grounds of Appeal filed by df-mp on Sep. 28, 2012, in relation to EP1645631, 2 pages.
Beernick (Jul. 2010) "Impaired immungenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
Bentley et al. (2004). Identification of two immunologically distinct domains on the LP2086 outer membrane lipoprotein of *Neisseria meningitidis*, 14th International Pathogenic Neisseria Conference 2004, p. 144.
Bernfield L. et al. (Sep. 2002). "Identification of a novel vaccine candidate for group B *Neisseria meningitidis*," Thirteenth International Pathogenic Neisseria Conference, Norwegian Institute of Public Health, Oslo, Norway, pp. 116 and 124.
Bouvier et al. (1991). "A gene for a new lipoprotein in the dapA-purC interval of the *Escherichia coli* chromosome," J Bacteriol 173(17):5523-5531.
Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2(Suppl.):S1-S4.
Cantini et al. (Mar. 2006). "Solution Structure of the Immunodominant Domain of Protective Antigen GNA 1870 of *Neisseria meningitidis*," Journal of Biological Chemistry 281(11): 7220-7227.
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1>.
Cohn et al. (2010). "Potential Impact of Serogroup B Vaccines: Prevalence of candidate vaccine antigens among invasive *Neisseria meningitidis* isolates in the United States," 17th International Pathogenic Neisseria Conference 2010, p. 77.
Cordis, "Preparation of meningococcal antigens," posted online on Feb. 2, 2005, 2 pages.
Database accession No. NMB1994 (cf. XP2231040) (Tettelin et al.), uploaded Oct. 1, 2000.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by E. Richard Moxon dated Feb. 16, 2013, submitted in opposition proceedings for EP1645631, 5 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from *Neisseria meningitidis* serogroup B as a novel vaccine candidate," Vaccine 25:8420-8431.
Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic Neisseria Conference 2010, p. 130.
Facts and Submissions dated May 21, 2012, in relation to EP1645631, 30 pages.
Farley J. et al. (Sep. 2002). "Characterization, cloning and expression of different subfamilies of the ORF 2086 gene from *Neisseria meningitidis*," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-501.
Fletcher et al. (2004). "Vaccine Potential of the *Neisseria meningitidis* 2086 Lipoprotein," Infection and Immunity 72(4): 2088-2100.
Fontana et al. (2002). A genomic approach Abstract from the 13$^{th}$ International Pathogenic *Neisseria* Conference, Oslo, Norway, Sep. 1-6, 2002. p. 248.
Fraser et al. (1997). "Genomic sequence of a lyme disease spirochaete, *Borrelia burgdorferi*," Nature 390:580-586.
Fraser et al. (1998). "Complete genome sequence of *Treponema pallidum*, the syphilis spirochete," Science 281:375-388.
GenPept accession No. AAF42204, "hypothetical protein NMB1870 [*Neisseria meningitidis* MC58]," retrieved on Sep. 26, 2012, 2 pages.
Giuliani et al. (2006). "A universal vaccine for serogroup B meningococcus," PNAS 103(29):10834-10839.
Giuliani et al. (2010). "Measuring antigen-specific bactericidial responses to a multicomponent vaccine against serogroup B meningococcus," Vaccine 28:5023-5030.
Giuliani et al. (Feb. 2005). "The Region Comprising Amino Acids 100 to 255 of *Neisseria meningitidis* Lipoprotein GNA 1870 Elicits Bactericidal Antibodies," Infection and Immunity 73(2): 1151-1160.
Gold and Stormo (1987). "Translation Initiation", in *Escherichia con* and *Salmonella typhimurium*, Cellular and Molecular Biology, Ed. Neidhardt, pp. 1302-1307.

(56) References Cited

OTHER PUBLICATIONS

Gorringe et al. (2009). "16th International Pathogenic Neisseria Conference: recent progress towards effective meningococcal disease vaccines," Human Vaccines 5(2):53-56.

Grandi (2005). "Reverse vaccinology: a critical analysis," in Encyclopedia of Genetics, Genomics, Proteomics and Bioinformatics, pp. 1322-1326.

Granoff, DM. (2009). Relative importance of complement-mediated bactericidal and opsonic activity for protection against meningococcal disease. Vaccine 27(Supplement 2): B117-B125.

Harris et al. (2008). "Development and qualification of serum bactericidal assays for *Neisseria meningitidis* serogroup B," 16th International Pathogenic *Neisseria* Conference 2008, p. 268-269.

Harris et al. (2010). "Robustness of the Serum Bactericidal Activity (SBA) Assay for *Neisseria meningitidis* serogroup B," 17th International Pathogenic Neisseria Conference 2010, p. 169.

Harris et al. (2011) "Preclinical evidence for the potential of a bivalent fHBP vaccine to prevent *Neisseria meningitidis* serogroup C disease," Human Vaccines 7:1 (suppl) 1-7.

Hayashi and Wu, "Identification and characterization of lipid-modified proteins in bacteria," Chapter 10 in Lipid Modifications of Proteins: A Practical Approach, Hooper and Turner (eds.), published in 1992, 27 pages.

Hem et al. (1995). "Structure and properties of aluminum-containing adjuvants," Vaccine Design. Subunit and Adjuvant Approach, pp. 249-276.

Hodge et al. (2006). "Development of a luminex-based meningococcal rLP2086-specific human IgG assay," 15th International Pathogenic Neisseria Conference 2006, p. 113.

Hoiseth et al. (2008). "LP2086 and MLST distribution in epidemiologically relevant strains of serogroup B *Neisseria meningitidis*," 16th International Pathogenic Neisseria Conference 2008, p. 205.

Hou et al. (2005) "Protective antibody responses elicited by a meningococcal outer membrane vesicle vaccine with overexpressed genome-derived neisserial antigen 1870," J Infect Dis 192(4):580-90.

Hung et al. (2011). "The *Neisseria meningitidis* macrophage infectivity potentiator protein induces cross-strain serum bactericidal sctivity and is a potential serogroup B vaccine candidate," Infect Immun 79(9):3784-3791.

Jansen et al. (2008). "Bivalent recombinant LP2086 vaccine to provide broad protection against *Neiseria meningitidis* B disease: immunological correlates of protection and how to assess coverage against invasive MnB strains," 16th International Pathogenic Neisseria Conference 2008, p. 80-81.

Jansen et al. (2009). "Development of a bivalent factor H binding protein vaccine to broadly protect against invasive *Neisseria meningitides* serogroup B (MnB) disease," European Society for Paediatric Infectious Disease Symposium 2009, p. 311.

Jansen et al. (2010). "Estimating effectiveness for *Neisseria meningitidis* serogroup B (MnB) vaccine candidates composed of non-serogroup specific antigens," 17th International Pathogenic Neisseria Conference 2010, p. 37.

Jansen et al. (2011). "Monitoring the Breadth of Coverage of Meningococcal Vaccines: an Overview and Progress Update on the Pfizer Bivalent LP2086 Vaccine Program," 14th Annual Conference on Vaccine Research, 2011, p. 74.

JCVI-CMR website showing Z2491 Sanger sequence (http://cmr.jcvi.org/tigr-scripts/CMR/shared/Genomes.cgi and links). (2010).

Jiang et al. (2003). "Using rate of acid neutralization to characterize aluminum phosphate adjuvant," Pharma Dev Tech 8(4):349-356.

Jiang et al. (2006). "Serum IgG response induced by a bivalent recombinant LP2086 provides broad protection against serogroup B *Neisseria meningitidis*," 15th International Pathogenic Neisseria Conference 2006, p. 113.

Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.

Jiang et al., (2010) "Broad vaccine coverage predicted for a bivalent recombinant factor H binding protein based vaccine to prevent serogroup B meningococcal disease" Vaccine 28:6086-6093.

Johnson et al. (1999). "Analysis of the human Ig isotype response to lactoferrin binding protein A from *Neisseria meningitidis*," FEMS Immun. Med. Microbial. 25(4): 349-354.

Jones et al. (2009). "Generation of human serum complement lots that perform consistently for use in *Neisseria meningitidis* serogroup B (MnB) vaccine clinical trials," European Society for Paediatric Infectious Disease Symposium 2009, p. 566.

Juncker et al. (2003). "Prediction of lipoprotein signal peptides in gram-negative bacteria," Protein Sci 12:1652-1662.

Koeberling et al. (2007). "Improved immunogenicity of a H44/76 group B outer membrane vesicle vaccine with over-expressed genome-derived *Neisserial* antigen 1870," Vaccine 25(10):1912-1920.

Koeberling et al. (2009). "Meningococcal outer membrane vesicle vaccines derived from mutant strains engineered to express factor H binding proteins from antigenic variant groups 1 and 2," Clin Vac Immunol, 16(2):156-162.

Liebl et al. (1997). "Properties and gene structure of the *Thermotoga maritima* alpha-amylase AmyA, a putative lipoprotein of a hyperthermophilic bacterium," J Bacteriol 179(3):941-948.

Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, p. 271-272.

Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.

Marshall et al. (2012) "Safety and immunogenicity of a meningococcal B bivalent rLP2086 vaccine in healthy toddlers aged 18-36 months: a phase 1 randomized-controlled clinical trial," Ped Infect Dis J 31:1061-8.

Marshall et al. (2013) "A phase 2 open-label safety and immunogenicity study of a meningococcal B bivalent rLP2086 vaccine in healthy adults," Vaccine 31:1569-75.

Mascioni et al. (2008). "Determination of the domain and solution structure of rLP2086, a meningococcal vaccine candidate and human factor H binding protein," 16th International Pathogenic Neisseria Conference 2008, p. 77-78.

Mascioni et al. (2009) "Structural basis for the immunogenic properties of the meningococcal vaccine candidate LP2086," J Biol Chem 284:8738-46.

Mascioni et al. (2010) "NMR dynamics and antibody recognition of the meningococcal lipidated outer membrane protein LP2086 in micellar solution," Biochim Biophys Acta 1798:87-93.

Masignani V. (Mar. 17. 2003). "Vaccination against *Neisseria meningitidis* using three variants of the lipoprotein GNA1870," J. Exp. Med. 197(6):789-799.

McNeil et al. (2009) "Detection of LP2086 on the cell surface of *Neisseria meningitidis* and its accessibility in the presence of serogroup B capsular polysaccharide," Vaccine 27:3417-21.

McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.

McNeil et al. (2013) "Role of factor H binding protein in *Neisseria meningitidis* virulence and its potential as a vaccine candidate to broadly protect against meningococcal disease," Microbiol Mol Biol Rev 77:234.

Milagres et al. (1998). "Specificity of bactericidal antibody response to serogroup B meningococcal strains in Brazilian children after immunization with an outer membrane vaccine," Infection and Immun. 66(10): 4755-4781.

Munkley, et al. (1991). "Blocking of bactericidal killing of *Neisseria meningitidis* by antibodies directed against slacc 4 outer membrane proteins," Microbial Pathogenesis 11: 447-452.

(56) References Cited

OTHER PUBLICATIONS

Murphy et al. (2008). "Sequence diversity of vaccine candidate LP2086 in *Neisseria meningitidis* serogroup B strains causing invasive disease," 16th International Pathogenic Neisseria Conference 2008, p. 61.
Murphy et al. (2010). "Prevalence of Factor H Binding Protein (fHBP) Variants in *N. meningitidis* Carriage Isolates," 17th International Pathogenic Neisseria Conference 2010, p. 96.
Murphy et al., (2009) "Sequence diversity of the factor H binding protein vaccine candidate in epidemiologically relevant strains of serogroup B *Neisseria meningitidis*" J Infect Dis 200:379-389.
Nassif (2000). "A Furtive Pathogen Revealed," Science 287:1767-1768.
Notice of Opposition against European Patent EP 1645631, granted on Oct. 24, 2007. Opposition filed on Jul. 23, 2008. 20 pages.
Novartis (Jan. 22, 2013) "Novartis receives EU approval for Bexsero®, first vaccine to prevent the leading cause of life-threatening meningitis across Europe," Media Release, 3 pages.
Novartis (Oct. 9, 2008) "New Phase II data show Novartis investigational Meningitis B vaccine may also protect infants six months and older," Media Release, 4 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2012). "Design of meningococcal factor H binding protein mutant vaccines that do not bind human complement factor H," Infect Immun 80:2667-2677.
Parkhill, "Campylobacter jejuni genome sequence at the Sanger Centre," Post on BIOSCI/Bionet of May 8, 1998.
Patentees' Response to Opposition against European Patent EP 1645631, granted on Oct. 24, 2007. 13 pages.
Pettersson, et al. (2006). "Vaccine potential of the *Neisseria meningitidis* lactoferrin-binding proteins LbpA and LbpB," Vaccine 24(17):3545-3557.
Pillai et al. (2005) "Outer membrane protein (OMP) based vaccine for *Neisseria meningitidis* serogroup B," Vaccine 23(17-18):2206-2209.
Pizza et al. (2008) "Factor H-binding protein, a unique meningococcal vaccine antigen" Vaccine 26S:I46-8.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161.5. Oct. 28, 2009.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B *Neisseria meningitidis* (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent *Neisseria meningitidis* recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of *Neisseria meningitides*," Journal of Molecular Biology 386(1):97-108.
Schneider et al. (Apr. 16, 2009) "*Neisseria meningitidis* recruits factor H using protein mimicry of host carbohydrates," Nature 458(7240):890-893.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the mengococcus in vitro and in ex vivo and in vivo models of infection," Vaccine 28(12):2416-2427.
Sequence for "Putative Lipoprotein [*Neisseria Meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Sheldon et al. (2011). "Phase 1, Randomized, Open-Label, Study to Assess the Safety and Immunogenicity of Serogroup B *Neisseria meningitidis* (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of Erwinia chrysanthemi 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Tan et al. (2010). "Advances in the development of vaccines against *Neisseria meningitidis*," NEJM 362(16):1511-1520.
Telford et al. (2003). "Genomic and Proteomics in Vaccine Design", in *New Bacterial Vaccines*, edited by Ellis et al. Kleweur Academic/Plenum Publishers, USA. pp. 1-11.
The printed output from the NCBI open reading frame finder (Oct. 20, 2008), 12 pages.
TIGR website as of 1998, 8 pages.
United States Office Action mailed on Feb. 11, 2009, for U.S. Appl. No. 10/181,600, filed on Jan. 17, 2001, 5 pages.
United States Office Action mailed on Jul. 24, 2008, for U.S. Appl. No. 10/181,600, filed on Jan. 17, 2001, 23 pages.
United States Office Action mailed on Jul. 7, 2009, for U.S. Appl. No. 10/181,600, filed on Jan. 17, 2001, 23 pages.
U.S. Appl. No. 60/098,685, "*Neisseria* Spp, Polypeptide, Gene Sequence and Uses Thereof," filed Sep. 1, 1998.
von Heijne (1989). "The structure of signal peptides from bacterial lipoproteins," Protein Engineering 2(7):531-534.

(56) References Cited

OTHER PUBLICATIONS

Wang et al. (2010). "Prevalence and genetic diversity of candidate vaccine antigens among invasive *Neisseria meningitidis* isolates in the United States," 17th International Pathogenic Neisseria Conference 2010, p. 122.
Welsch et al. (2004). "Protective Activity of Monclonal Antibodies to Genome-Derived Neisserial Antigen 1870, a *Neisseria meningitidis* Candidate Vaccine," *The Journal of Immunology* 172: 5606-5615.
Welsch et al. (2007) "A novel mechanism for complement-mediated killing of encapsulated *Neisseria meningitidis* elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B *Neisseria meningitidis* in a murine nasal challenge model," 14th International Pathogenic Neisseria Conference 2004, p. 199.
Zhu et al. (2005) "Evaluation of recombinant lipidated P2086 protein as a vaccine candidate for group B *Neisseria meningitidis* in a murine nasal challenge model," Infect Immun 73(10):6838-45.
Zhu et al. (2006) "Intranasal immunization of mice with recombinant lipidated P2086 protein reduces nasal colonization of group B *Neisseria meningitidis*," Vaccine 24:5420-5.
Zhu et al. (2006). "Effective immunization strategy against group B *Neisseria meningitidis* using purified recombinant lipidated P2086 protein," 15th International Pathogenic Neisseria Conference 2006, p. 47.
Zlotnick et al. (2009). "Epidemiology of the serogroup B *Neisseria meningitidis* (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of *N. meningitidis*," 17th International Pathogenic Neisseria Conference 2010, p. 38.
Database UniProt (Oct. 1, 2000), "SubName: Full=Uncharacterized protein" retrieved from EBI, accession No. Q9JXV4 Database accession No. Q9JXV4.
Decision revoking the European Patent, filed in opposition against EP1976990, dated Nov. 11, 2013, 15 pages.
Experimental data: expression of NspA, '287' and '741' on 3 strains of bacteria, filed in opposition against EP1534326, dated Aug. 4, 2010. 2 pages.
Kovacs-Simon et al. (2011). "Lipoproteins of Bacterial Pathogens," Infect Immun 79(2):548-561.
Lewis et al. (2010). "The meningococcal vaccine candidate neisserial surface protein a (NspA) binds to factor H and enhances meningococcal resistance to complement," PLoS Pathogens 6(7):e1001027.
Liechti et al. (2012). "Outer membrane biogenesis in *Escherichia coli, Neisseria meningitidis*, and *Helicobacter pylori*: paradigm deviations in *H. pylori*," Front Cell and Infect Microbiol 2:article 29.
Lindblad, (2004). "Aluminium compounds for use in vaccines," Immunol Cell Biol.,82(5):497-505.
Madico et al. (2006). "The meningococcal vaccine candidate GNA1870 binds the complement regulatory protein factor H and enhances serum resistance," J Immunol 177(1):501-510.

Martin et al. (1998). "New Zealand epidemic of meningococcal disease identified by a strain with phenotype B:4:P1.4," JID 177:497-500.
Notice of Opposition filed May 24, 2012, filed in opposition against EP1976990, 19 pages.
Novartis (Jun. 9, 2011). "Novartis candidate vaccine Bexsero® shows significant potential in providing broad coverage against meningococcal serogroup B infections." Media Release, 6 pages.
Seib et al. (2011). "Characterization of Diverse Subvariants of the Meningococcal Factor H (fH) Binding Protein for Their Ability to Bind fH, To Mediate Serum Resistance, and To Induce Bactericidal Antibodies,"0 Infect Immun, 79(2):970-81.
U.S. Appl. No. 60/647,911, "GNA 1870-based vesicle vaccines for broad spectrum protection against diseases caused by *Neisseria meningitidis*," filed Jan. 27, 2005.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials,"Lancet 381:625-35.
Voulhoux and Tommassen (2002). "Transport of lipoproteins to the cell surfac in *Neisseria meningitidis*," 13th International Pathogenic Neisseria Conference 2002.
Welsch et al. (2002). "Genome-derived antigen (GNA) 2132 elicits protective serum antibodies to groups B and C *Neisseria meningitidis* strains," 13th International Pathogenic Neisseria Conferenece 2002, p. 25.
Written Submission to Oral Proceedings, filed in opposition against EP1976990, dated May 8, 2013, 11 pages.
Alignment of SEQ ID No. 19 of EP2327719 against SEQ ID Nos. 92, 94, 96, 98, 100, 102, 104, 106, and 108 of WO/2003/063766, filed in opposition against EP2327719, submitted May 20, 2015, 9 pages.
Alignment of SEQ ID No. 42 of EP2258716 against SEQ ID No. 41 of EP2258716, filed in opposition against EP2258716, submitted Apr. 16, 2015, 1 page.
Alignment of SEQ ID No: 42 of EP2258716 against SEQ ID Nos. 50, 52, 54, 56, 58, 60, 62, 64, 66, 68, 70, and 72 of WO/2003/063766, filed in opposition against EP2258716, submitted Apr. 16, 2015, 12 pages.
Beernink et al. (2011). "A meningococcal factor H binding protein mutant that eliminates factor H binding enhances protective antibody responses to vaccination," J Immunol, 186(6):3606-14.
Brendish and Read. (2015). "Neisseria meningitidis serogroup B bivalent factor H binding protein vaccine," Expert Rev. Vaccines, 14(4):493-503.
Donnelly et al. (2010). "Qualitative and quantitative assessment of meningococcal antigens to evaluate the potential strain coverage of protein-based vaccines," Proc Natl Aced Sci U S A, 107(45):19490-5.
Experimental Report, Submitted on Mar. 23, 2015, filed in relation to EP241 1048, 2 pages.
International Preliminary Report on Patentability mailed Jan. 13, 2012, for PCT/IB2010/002260, 10 pages.
International Search Report mailed Apr. 13, 2011, for PCT/IB2010/002260, 7 pages.
Notice of opposition, filed in opposition against EP2258716, dated Apr. 16, 2015, 12 pages.
Notice of opposition, filed in opposition against EP2327719, dated May 20, 2015, 14 pages.
Novartis internal data, filed in relation to EP1902726, submitted on Apr. 13, 2015, 1 page.
Patentee's response to notice of opposition, filed in opposition against EP1562983, dated Feb. 16, 2015, 9 pages.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Sandbu et al. (2007). "Immunogenicity and safety of a combination of two serogroup B meningococcal outer membrane vesicle vaccines," Clin Vaccine Immunol, 14(9):1062-9.
Statement of Grounds of Appeal, dated Mar. 23, 2015, filed in relation to EP241 1048, 8 pages.
Statement of grounds of appeal, filed in relation to EP1902726, dated Apr. 13, 2015, 9 pages.

(56) References Cited

OTHER PUBLICATIONS

Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
UniProt accession No. C0JF81, Murphy et al., Last modified on May 5, 2009. 4 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
Office Action, dated Apr. 6, 2015 for U.S. Appl. No. 13/367,289. 9 pages.
Response to Office Action, dated Sep. 9, 2014, for U.S. Appl. No. 13/367,289. 6 pages.
Office Action, dated Apr. 29, 2015 for U.S. Appl. No. 14/244,806. 6 pages.
Response to Office Action, dated Jun. 29, 2015 for U.S. Appl. No. 14/244,806. 37 pages.

* cited by examiner

*FIG. 3A*
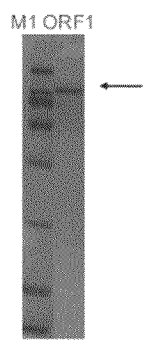
PURIFICATION
*FIG. 3B*
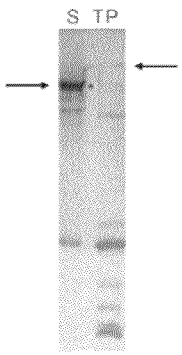
WESTERN BLOT
*FIG. 3C*
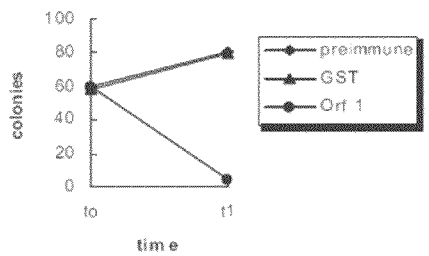
BACTERICIDAL ASSAY
*FIG. 3D*
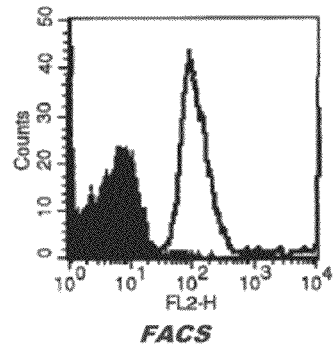
FACS
*FIG. 3E*
ELISA: POSITIVE

FIG. 4A
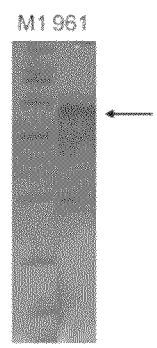
PURIFICATION
FIG. 4B
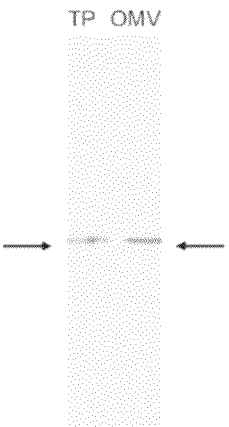
WESTERN BLOT
FIG. 4C
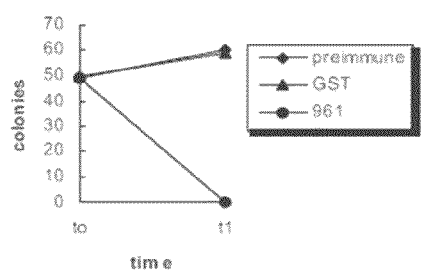
BACTERICIDAL ASSAY
FIG. 4D
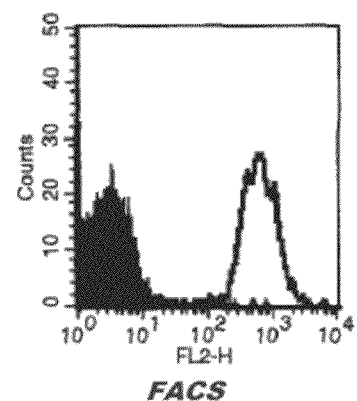
FACS
FIG. 4E
ELISA: POSITIVE

FIG. 7

```
            <A------------------------<Δ1-----------------
MC58    1   MFKRSVIAMACIFALSACGGGGGGSPDVKSADTLSKPAAPVVSEKETEAKEDAPQAGSQG
2996    1   MFERSVIAMACIFALSACGGGGGGSPDVKSADTLSKPAAPVVAEKETEVKEDAPQAGSQG

--------<Δ2--------------------------------
MC58   61   QGAPSAQGSQDMAAVSEENTGNGGAVTADNPKNEDEVAQNDMPQNAAGTDSSTPNHTPDP
2996   61   QGAPSTQGSQDMAAVSAENTGNGGAATTDKPKNEDEGPQNDMPQN...............

<Δ3--------
MC58  121   NMLAGNMENQATDAGESSQPANQPDMANAADGMQGDDPSAGGQNAGNTAAQGANQAGNNQ
2996  106   ...........................................SAESANQTGNNQ

--------------------A><B------
MC58  181   AAGSSDPIPASNPAPANGGSNFGRVDLANGVLIDGPSQNITLTHCKGDSCSGNNFLDEEV
2996  118   PADSSDSAPASNPAPANGGSNFGRVDLANGVLIDGPSQNITLTHCKGDSCNGDNLLDEEA

-B>
MC58  241   QLKSEFEKLSDADKISNYKKDGKNDKFVGLVADSVQMKGINQYIIFYKPK..PTSFARFR
2996  178   PSKSEFENLNESERIEKYKKDGKSDKFTNLVATAVQANGTNKYVIIYKDKSASSSARFR

<C---------
MC58  299   RSARSRRSLPAEMPLIPVNQADTLIVDGEAVSLTGHSGNIFAPEGNYRYLTYGAEKLPGG
2996  238   RSARSRRSLPAEMPLIPVNQADTLIVDGEAVSLTGHSGNIFAPEGNYRYLTYGAEKLPGG

MC58  359   SYALRVQGEPAKGEMLAGAAVYNGEVLHFHTENGRPYPTRGRFAAKVDFGSKSVDGIIDS
2996  298   SYALRVQGEPAKGEMLAGTAVYNGEVLHFHTENGRPYPTRGRFAAKVDFGSKSVDGIIDS

MC58  419   GDDLHMGTQKFKAAIDGNGFKGTWTENGSGDVSGKFYGPAGEEVAGKYSYRPTDAEKGGF
2996  358   GDDLHMGTQKFKAAIDGNGFKGTWTENGGGDVSGRFYGPAGEEVAGKYSYRPTDAEKGGF

--------C>
MC58  479   GVFAGKKEQD*
2996  418   GVFAGKKEQD*
```

FIG. 14A ΔG287-919
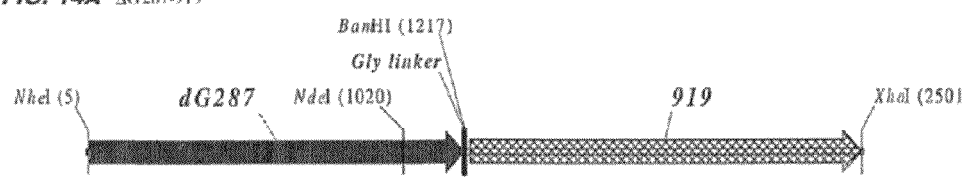
FIG. 14B ΔG287-953
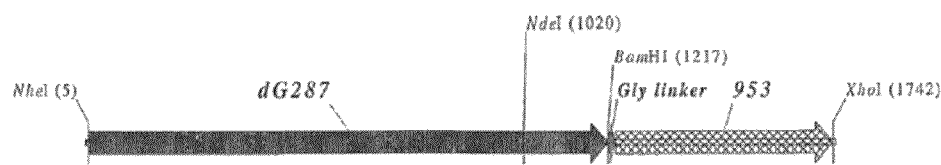
FIG. 14C ΔG287-961
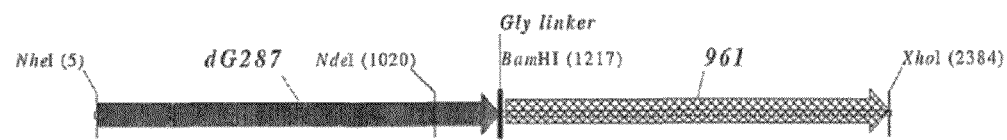

FIG. 14D ΔG287NZ-919
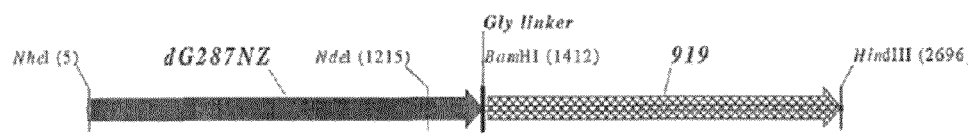
FIG. 14E ΔG287NZ-953
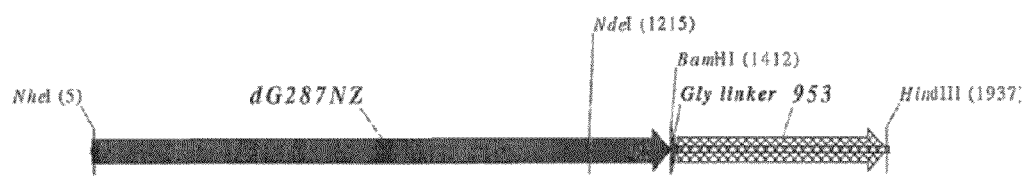
FIG. 14F ΔG287NZ-961
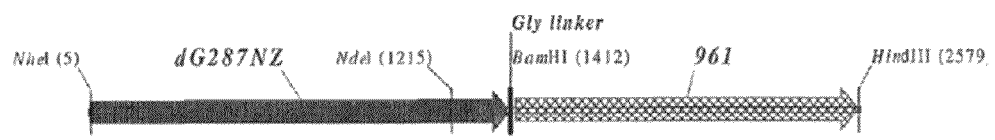

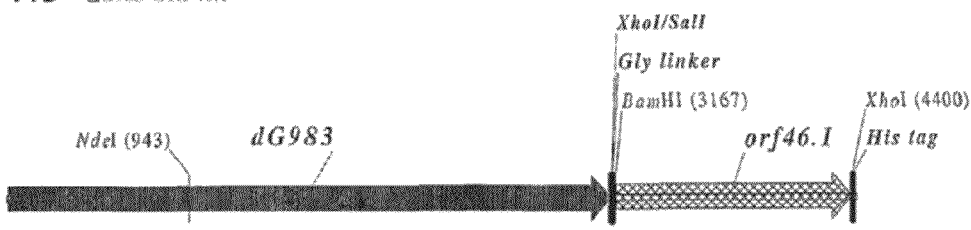
FIG. 14G  ΔG983-ORF46.1
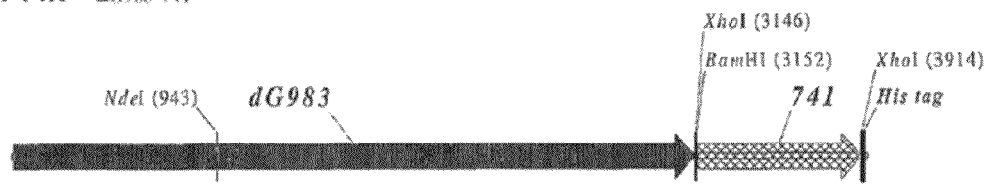
FIG. 14H  ΔG983-741
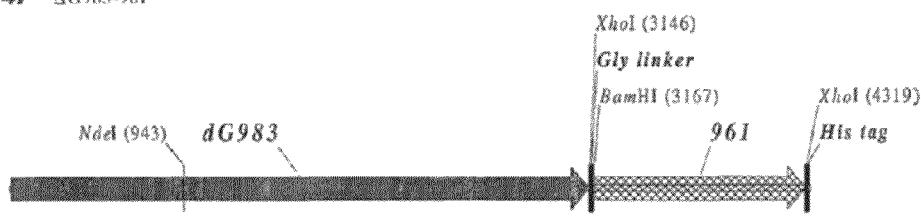
FIG. 14I  ΔG983-961

FIG. 14J ΔG983-961c
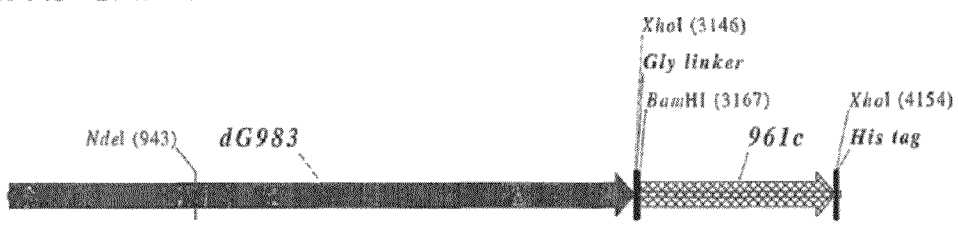
FIG. 14K ΔG741-961
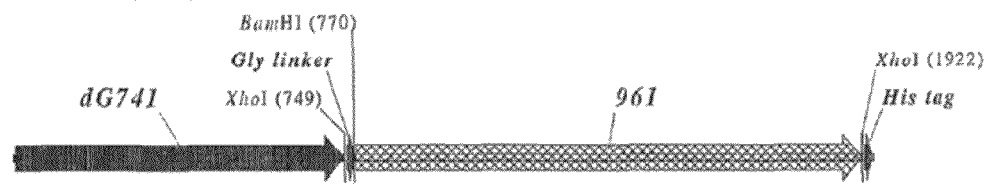
FIG. 14L ΔG741-961c
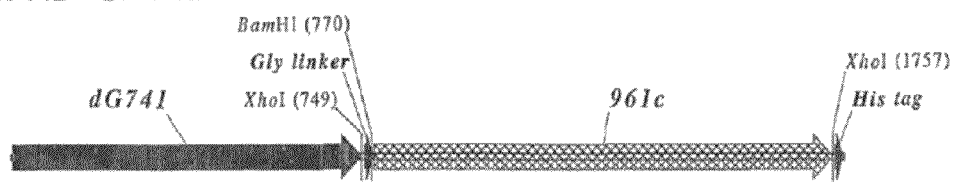

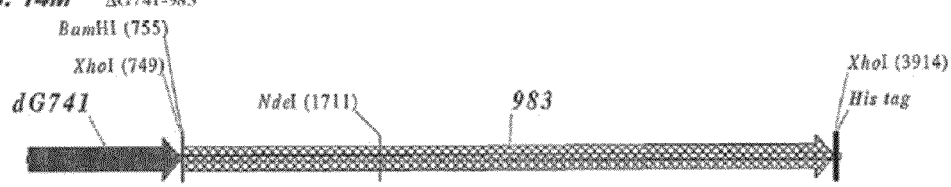
FIG. 14M ΔG741-983
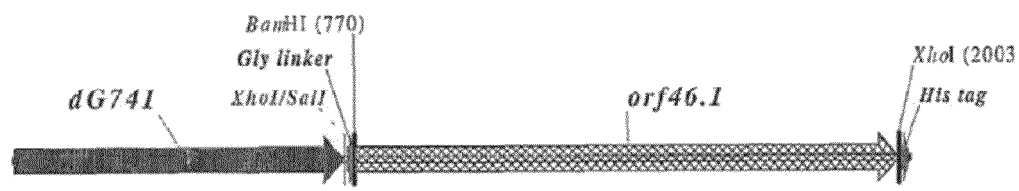
FIG. 14N ΔG741-ORF46.1
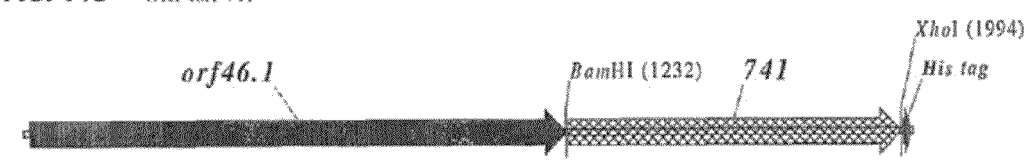
FIG. 14O ORF46.1-741

FIG. 14P  ORF46.1-961
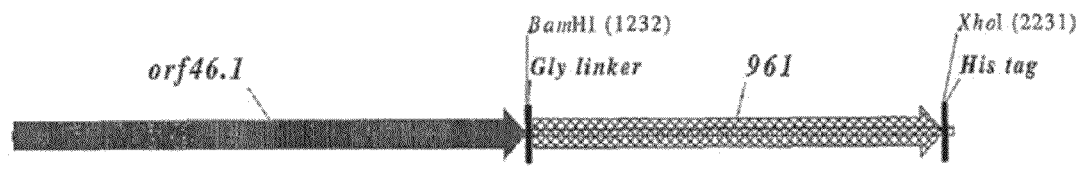
FIG. 14Q  ORF46.1-961c
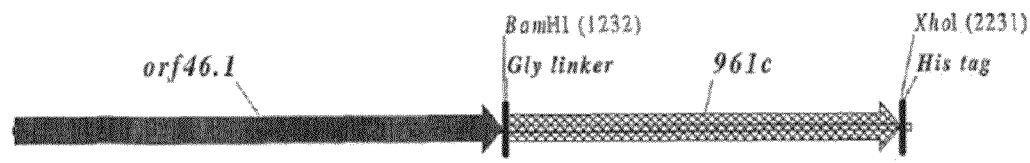
FIG. 14R  961-ORF46.1
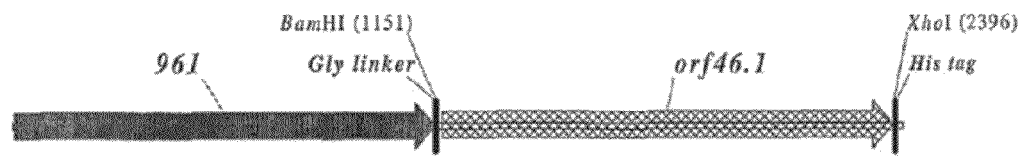

FIG. 14S 961-741
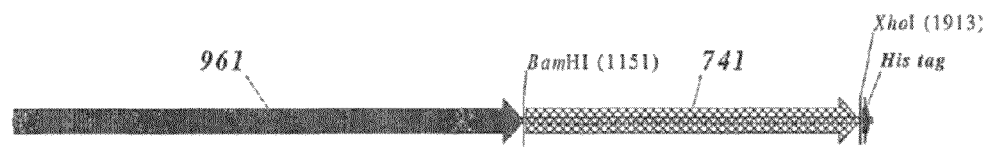
FIG. 14T 961-983
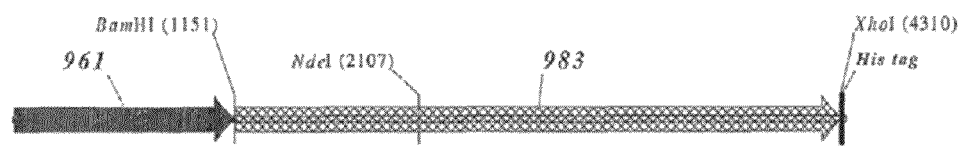
FIG. 14U 961c-ORF46.1
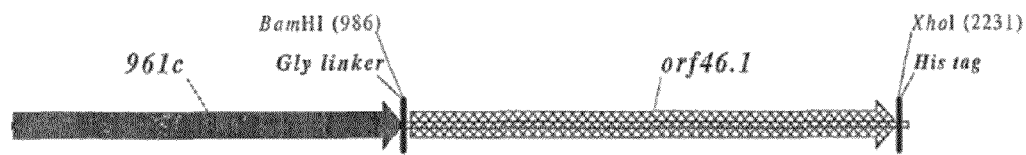

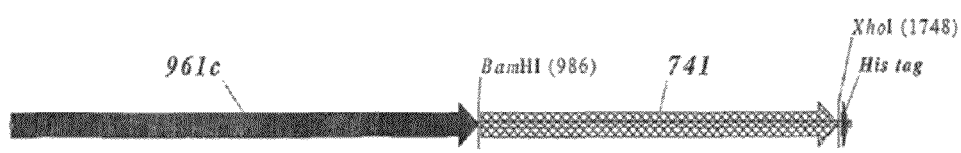
FIG. 14V  961c-741
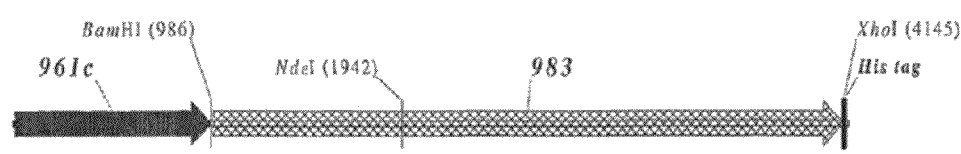
FIG. 14W  961c-983
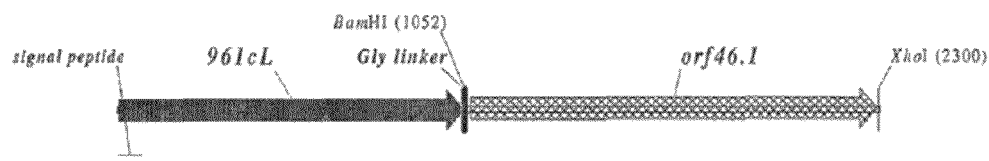
FIG. 14X  961cL-ORF46.1

FIG. 14Y 961cL-741
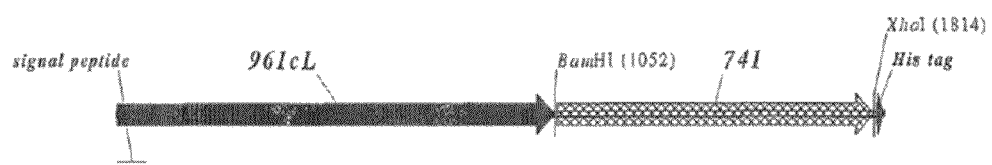
FIG. 14Z 961cL-983
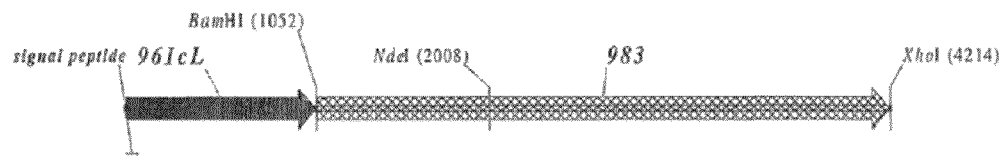

HETEROLOGOUS EXPRESSION OF NEISSERIAL PROTEINS

CROSS-REFERENCE TO RELATED APPLICATIONS

This application is a Continuation of U.S. application Ser. No. 14/244,806, filed Apr. 3, 2014; which is a Continuation of U.S. application Ser. No. 13/340,549, filed Dec. 29, 2011, now U.S. Pat. No. 8,703,914; which is a Divisional of U.S. application Ser. No. 12/825,210, filed Jun. 28, 2010, now U.S. Pat. No. 8,114,960; which is a Divisional of U.S. application Ser. No. 10/220,481, which claims an international filing date of Feb. 28, 2001, now U.S. Pat. No. 7,803,387; which is the National Phase of PCT Application No. PCT/IB2001/000452, filed Feb. 28, 2001; which claims the benefit of GB Application No. 0027675.8, filed Nov. 13, 2000; and GB Application No. 0004695.3, filed Feb. 28, 2000; all of which are incorporated herein by reference in their entirety.

TECHNICAL FIELD

This invention is in the field of protein expression. In particular, it relates to the heterologous expression of proteins from *Neisseria* (e.g. *N. gonorrhoeae* or, preferably, *N. meningitidis*).

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002099802SubSeqList.txt, date recorded: Oct. 9, 2014, size: 505 KB).

BACKGROUND

International patent applications WO99/24578, WO99/36544, WO99/57280 and WO00/22430 disclose proteins from *Neisseria meningitidis* and *Neisseria gonorrhoeae*. These proteins are typically described as being expressed in *E. coli* (i.e. heterologous expression) as either N-terminal GST-fusions or C-terminal His-tag fusions, although other expression systems, including expression in native *Neisseria*, are also disclosed.

It is an object of the present invention to provide alternative and improved approaches for the heterologous expression of these proteins. These approaches will typically affect the level of expression, the ease of purification, the cellular localisation of expression, and/or the immunological properties of the expressed protein.

DISCLOSURE

Nomenclature Herein

The 2166 protein sequences disclosed in WO99/24578, WO99/36544 and WO99/57280 are referred to herein by the following SEQ#numbers:

| Application | Protein sequences | SEQ# herein |
|---|---|---|
| WO99/24578 | Even SEQ IDs 2-892 | SEQ#s 1-446 |
| WO99/36544 | Even SEQ IDs 2-90 | SEQ#s 447-491 |
| WO99/57280 | Even SEQ IDs 2-3020 | SEQ#s 492-2001 |
| | Even SEQ IDs 3040-3114 | SEQ#s 2002-2039 |
| | SEQ IDs 3115-3241 | SEQ#s 2040-2166 |

In addition to this SEQ#numbering, the naming conventions used in WO99/24578, WO99/36544 and WO99/57280 are also used (e.g. 'ORF4', 'ORF40', 'ORF40-1' etc. as used in WO99/24578 and WO99/36544; 'm919', 'g919' and 'a919' etc. as used in WO99/57280).

The 2160 proteins NMB0001 to NMB2160 from Tettelin et al. [*Science* (2000) 287:1809-1815] are referred to herein as SEQ#s 2167-4326 [see also WO0/66791].

The term 'protein of the invention' as used herein refers to a protein comprising:
(a) one of sequences SEQ#s 1-4326; or
(b) a sequence having sequence identity to one of SEQ#s 1-4326; or
(c) a fragment of one of SEQ#s 1-4326.

The degree of 'sequence identity' referred to in (b) is preferably greater than 50% (eg. 60%, 70%, 80%, 90%, 95%, 99% or more). This includes mutants and allelic variants [e.g. see WO00/66741]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The 'fragment' referred to in (c) should comprise at least n consecutive amino acids from one of SEQ#s 1-4326 and, depending on the particular sequence, n is 7 or more (eg. 8, 10, 12, 14, 16, 18, 20, 25, 30, 35, 40, 50, 60, 70, 80, 90, 100 or more). Preferably the fragment comprises an epitope from one of SEQ#s 1-4326. Preferred fragments are those disclosed in WO00/71574 and WO01/04316.

Preferred proteins of the invention are found in *N. meningitidis* serogroup B.

Preferred proteins for use according to the invention are those of serogroup B *N. meningitidis* strain 2996 or strain 394/98 (a New Zealand strain). Unless otherwise stated, proteins mentioned herein are from *N. meningitidis* strain 2996. It will be appreciated, however, that the invention is not in general limited by strain. References to a particular protein (e.g. '287', '919' etc.) may be taken to include that protein from any strain.

Non-Fusion Expression

In a first approach to heterologous expression, no fusion partner is used, and the native leader peptide (if present) is used. This will typically prevent any 'interference' from fusion partners and may alter cellular localisation and/or post-translational modification and/or folding in the heterologous host.

Thus the invention provides a method for the heterologous expression of a protein of the invention, in which (a) no fusion partner is used, and (b) the protein's native leader peptide (if present) is used.

The method will typically involve the step of preparing an vector for expressing a protein of the invention, such that the first expressed amino acid is the first amino acid (methionine) of said protein, and last expressed amino acid is the last amino acid of said protein (i.e. the codon preceding the native STOP codon).

This approach is preferably used for the expression of the following proteins using the native leader peptide: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 936-1, 953, 961, 983, 989, Orf4, Orf7-1, Orf9-1, Orf23, Or25, Orf37, Orf38, Orf40, Orf40.1, Orf40.2, Orf72-1, Orf76-1, Orf85-2, Orf91, Orf97-1, Orf119, Orf143.1, NMB0109 and NMB2050.The suffix 'L' used herein in the name of a protein indicates expression in this manner using the native leader peptide.

Proteins which are preferably expressed using this approach using no fusion partner and which have no native leader peptide include: 008, 105, 117-1, 121-1, 122-1, 128-1, 148, 216, 243, 308, 593, 652, 726, 926, 982, Orf83-1 and Orf143-1.

Advantageously, it is used for the expression of ORF25 or ORF40, resulting in a protein which induces better anti-bactericidal antibodies than GST- or His-fusions.

This approach is particularly suited for expressing lipoproteins.

Leader-Peptide Substitution

In a second approach to heterologous expression, the native leader peptide of a protein of the invention is replaced by that of a different protein. In addition, it is preferred that no fusion partner is used. Whilst using a protein's own leader peptide in heterologous hosts can often localise the protein to its 'natural' cellular location, in some cases the leader sequence is not efficiently recognised by the heterologous host. In such cases, a leader peptide known to drive protein targeting efficiently can be used instead.

Thus the invention provides a method for the heterologous expression of a protein of the invention, in which (a) the protein's leader peptide is replaced by the leader peptide from a different protein and, optionally, (b) no fusion partner is used.

The method will typically involve the steps of: obtaining nucleic acid encoding a protein of the invention; manipulating said nucleic acid to remove nucleotides that encode the protein's leader peptide and to introduce nucleotides that encode a different protein's leader peptide. The resulting nucleic acid may be inserted into an expression vector, or may already be part of an expression vector. The expressed protein will consist of the replacement leader peptide at the N-terminus, followed by the protein of the invention minus its leader peptide.

The leader peptide is preferably from another protein of the invention (e.g. one of SEQ#s 1-4326), but may also be from an *E. coli* protein (e.g. the OmpA leader peptide) or an *Erwinia carotovora* protein (e.g. the PelB leader peptide), for instance.

A particularly useful replacement leader peptide is that of ORF4. This leader is able to direct lipidation in *E. coli*, improving cellular localisation, and is particularly useful for the expression of proteins 287, 919 and ΔG287. The leader peptide and N-terminal domains of 961 are also particularly useful.

Another useful replacement leader peptide is that of *E. coli* OmpA. This leader is able to direct membrane localisation of *E. coli*. It is particularly advantageous for the expression of ORF1, resulting in a protein which induces better anti-bactericidal antibodies than both fusions and protein expressed from its own leader peptide.

Another useful replacement leader peptide is MKKYLF-SAA. (SEQ ID NO:621) This can direct secretion into culture medium, and is extremely short and active. The use of this leader peptide is not restricted to the expression of Neisserial proteins—it may be used to direct the expression of any protein (particularly bacterial proteins).

Leader-Peptide Deletion

In a third approach to heterologous expression, the native leader peptide of a protein of the invention is deleted. In addition, it is preferred that no fusion partner is used.

Thus the invention provides a method for the heterologous expression of a protein of the invention, in which (a) the protein's leader peptide is deleted and, optionally, (b) no fusion partner is used.

The method will typically involve the steps of: obtaining nucleic acid encoding a protein of the invention; manipulating said nucleic acid to remove nucleotides that encode the protein's leader peptide. The resulting nucleic acid may be inserted into an expression vector, or may already be part of an expression vector. The first amino acid of the expressed protein will be that of the mature native protein.

This method can increase the levels of expression. For protein 919, for example, expression levels in *E. coli* are much higher when the leader peptide is deleted. Increased expression may be due to altered localisation in the absence of the leader peptide.

The method is preferably used for the expression of 919, ORF46, 961, 050-1, 760 and 287.

Domain-Based Expression

In a fourth approach to heterologous expression, the protein is expressed as domains. This may be used in association with fusion systems (e.g. GST or His-tag fusions).

Thus the invention provides a method for the heterologous expression of a protein of the invention, in which (a) at least one domain in the protein is deleted and, optionally, (b) no fusion partner is used.

The method will typically involve the steps of: obtaining nucleic acid encoding a protein of the invention; manipulating said nucleic acid to remove at least one domain from within the protein. The resulting nucleic acid may be inserted into an expression vector, or may already be part of an expression vector. Where no fusion partners are used, the first amino acid of the expressed protein will be that of a domain of the protein.

A protein is typically divided into notional domains by aligning it with known sequences in databases and then determining regions of the protein which show different alignment patterns from each other.

The method is preferably used for the expression of protein 287. This protein can be notionally split into three domains, referred to as A B & C (see FIG. 5). Domain B aligns strongly with IgA proteases, domain C aligns strongly with transferrin-binding proteins, and domain A shows no strong alignment with database sequences. An alignment of polymorphic forms of 287 is disclosed in WO00/66741.

Once a protein has been divided into domains, these can be (a) expressed singly (b) deleted from with the protein e.g. protein ABCD→ABD, ACD, BCD etc. or (c) rearranged e.g. protein ABC→ACB, CAB etc. These three strategies can be combined with fusion partners is desired.

ORF46 has also been notionally split into two domains—a first domain (amino acids 1-433) which is well-conserved between species and serogroups, and a second domain (amino acids 433-608) which is not well-conserved. The second domain is preferably deleted. An alignment of polymorphic forms of ORF46 is disclosed in WO00/66741.

Protein 564 has also been split into domains (FIG. 8), as have protein 961 (FIG. 12) and protein 502 (amino acids 28-167 of the MC58 protein).

Hybrid Proteins

In a fifth approach to heterologous expression, two or more (e.g. 3, 4, 5, 6 or more) proteins of the invention are expressed as a single hybrid protein. It is preferred that no non-Neisserial fusion partner (e.g. GST or poly-His) is used.

This offers two advantages. Firstly, a protein that may be unstable or poorly expressed on its own can be assisted by adding a suitable hybrid partner that overcomes the problem. Secondly, commercial manufacture is simplified—only one expression and purification need be employed in order to produce two separately-useful proteins.

Thus the invention provides a method for the simultaneous heterologous expression of two or more proteins of the invention, in which said two or more proteins of the invention are fused (i.e. they are translated as a single polypeptide chain).

The method will typically involve the steps of: obtaining a first nucleic acid encoding a first protein of the invention; obtaining a second nucleic acid encoding a second protein of the invention; ligating the first and second nucleic acids. The resulting nucleic acid may be inserted into an expression vector, or may already be part of an expression vector.

Preferably, the constituent proteins in a hybrid protein according to the invention will be from the same strain.

The fused proteins in the hybrid may be joined directly, or may be joined via a linker peptide e.g. via a poly-glycine linker (i.e. $G_n$ where n=3, 4, 5, 6, 7, 8, 9, 10 or more) or via a short peptide sequence which facilitates cloning. It is evidently preferred not to join a ΔG protein to the C-terminus of a poly-glycine linker.

The fused proteins may lack native leader peptides or may include the leader peptide sequence of the N-terminal fusion partner.

The method is well suited to the expression of proteins orf1, orf4, orf25, orf40, Orf46/46.1, orf83, 233, 287, 292L, 564, 687, 741, 907, 919, 953, 961 and 983.

The 42 hybrids indicated by 'X' in the following table of form $NH_2$-A-B—COOH are preferred:

| | B | | | | | | |
|---|---|---|---|---|---|---|---|
| A | $O_{RF}$46.1 | 287 | 741 | 919 | 953 | 961 | 983 |
| ORF46.1 | | X | X | X | X | X | X |
| 287 | X | | X | X | X | X | X |
| 741 | X | X | | X | X | X | X |
| 919 | X | X | X | | X | X | X |
| 953 | X | X | X | X | | X | X |
| 961 | X | X | X | X | X | | X |
| 983 | X | X | X | X | X | X | |

Preferred proteins to be expressed as hybrids are thus ORF46.1, 287, 741, 919, 953, 961 and 983. These may be used in their essentially full-length form, or poly-glycine deletions (ΔG) forms may be used (e.g. ΔG-287, ΔGTbp2, ΔG741, ΔG983 etc.), or truncated forms may be used (e.g. Δ1-287, Δ2-287 etc.), or domain-deleted versions may be used (e.g. 287B, 287C, 287BC, ORF46$_{1-433}$, ORF46$_{433-608}$, ORF46, 961c etc.).

Particularly preferred are: (a) a hybrid protein comprising 919 and 287; (b) a hybrid protein comprising 953 and 287; (c) a hybrid protein comprising 287 and ORF46.1; (d) a hybrid protein comprising ORF1 and ORF46.1; (e) a hybrid protein comprising 919 and ORF46.1; (f) a hybrid protein comprising ORF46.1 and 919; (g) a hybrid protein comprising ORF46.1, 287 and 919; (h) a hybrid protein comprising 919 and 519; and (i) a hybrid protein comprising ORF97 and 225. Further embodiments are shown in FIG. 14.

Where 287 is used, it is preferably at the C-terminal end of a hybrid; if it is to be used at the N-terminus, if is preferred to use a ΔG form of 287 is used (e.g. as the N-terminus of a hybrid with ORF46.1, 919, 953 or 961).

Where 287 is used, this is preferably from strain 2996 or from strain 394/98.

Where 961 is used, this is preferably at the N-terminus. Domain forms of 961 may be used.

Alignments of polymorphic forms of ORF46, 287, 919 and 953 are disclosed in WO00/66741. Any of these polymorphs can be used according to the present invention.

Temperature

In a sixth approach to heterologous expression, proteins of the invention are expressed at a low temperature.

Expressed Neisserial proteins (e.g. 919) may be toxic to *E. coli*, which can be avoided by expressing the toxic protein at a temperature at which its toxic activity is not manifested.

Thus the present invention provides a method for the heterologous expression of a protein of the invention, in which expression of a protein of the invention is carried out at a temperature at which a toxic activity of the protein is not manifested.

A preferred temperature is around 30° C. This is particularly suited to the expression of 919.

Mutations

As discussed above, expressed Neisserial proteins may be toxic to *E. coli*. This toxicity can be avoided by mutating the protein to reduce or eliminate the toxic activity. In particular, mutations to reduce or eliminate toxic enzymatic activity can be used, preferably using site-directed mutagenesis.

In a seventh approach to heterologous expression, therefore, an expressed protein is mutated to reduce or eliminate toxic activity.

Thus the invention provides a method for the heterologous expression of a protein of the invention, in which protein is mutated to reduce or eliminate toxic activity.

The method is preferably used for the expression of protein 907, 919 or 922. A preferred mutation in 907 is at Glu-117 (e.g. Glu→Gly); preferred mutations in 919 are at Glu-255 (e.g. Glu→Gly) and/or Glu-323 (e.g. Glu→Gly); preferred mutations in 922 are at Glu-164 (e.g. Glu→Gly), Ser-213 (e.g. Ser→Gly) and/or Asn-348 (e.g. Asn→Gly).

Alternative Vectors

In a eighth approach to heterologous expression, an alternative vector used to express the protein. This may be to improve expression yields, for instance, or to utilise plasmids that are already approved for GMP use.

Thus the invention provides a method for the heterologous expression of a protein of the invention, in which an alternative vector is used. The alternative vector is preferably pSM214, with no fusion partners. Leader peptides may or may not be included.

This approach is particularly useful for protein 953. Expression and localisation of 953 with its native leader peptide expressed from pSM214 is much better than from the pET vector.

pSM214 may also be used with: ΔG287, Δ2-287, Δ3-287, Δ4-287, Orf46.1, 961L, 961, 961(MC58), 961c, 961c-L, 919, 953 and ΔG287-Orf46.1.

Another suitable vector is pET-24b (Novagen; uses kanamycin resistance), again using no fusion partners. pET-24b is preferred for use with: ΔG287K, Δ2-287K, Δ3-287K, Δ4-287K, Orf46.1-K, Orf46A-K, 961-K (MC58), 961a-K, 961b-K, 961c-K, 961c-L-K, 961d-K, ΔG287-919-K, ΔG287-Orf46.1-K and ΔG287-961-K.

Multimeric Form

In a ninth approach to heterologous expression, a protein is expressed or purified such that it adopts a particular multimeric form.

This approach is particularly suited to protein 953. Purification of one particular multimeric form of 953 (the monomeric form) gives a protein with greater bactericidal activity than other forms (the dimeric form).

Proteins 287 and 919 may be purified in dimeric form.

Protein 961 may be purified in a 180 kDa oligomeric form (e.g. a tetramer).

Lipidation

In a tenth approach to heterologous expression, a protein is expressed as a lipidated protein.

Thus the invention provides a method for the heterologous expression of a protein of the invention, in which the protein is expressed as a lipidated protein.

This is particularly useful for the expression of 919, 287, ORF4, 406, 576-1, and ORF25. Polymorphic forms of 919, 287 and ORF4 are disclosed in WO00/66741.

The method will typically involve the use of an appropriate leader peptide without using an N-terminal fusion partner.

C-Terminal Deletions

In an eleventh approach to heterologous expression, the C-terminus of a protein of the invention is mutated. In addition, it is preferred that no fusion partner is used.

Thus the invention provides a method for the heterologous expression of a protein of the invention, in which (a) the protein's C-terminus region is mutated and, optionally, (b) no fusion partner is used.

The method will typically involve the steps of: obtaining nucleic acid encoding a protein of the invention; manipulating said nucleic acid to mutate nucleotides that encode the protein's C-terminus portion. The resulting nucleic acid may be inserted into an expression vector, or may already be part of an expression vector. The first amino acid of the expressed protein will be that of the mature native protein.

The mutation may be a substitution, insertion or, preferably, a deletion.

This method can increase the levels of expression, particularly for proteins 730, ORF29 and ORF46. For protein 730, a C-terminus region of around 65 to around 214 amino acids may be deleted; for ORF46, the C-terminus region of around 175 amino acids may be deleted; for ORF29, the C-terminus may be deleted to leave around 230-370 N-terminal amino acids.

Leader Peptide Mutation

In a twelfth approach to heterologous expression, the leader peptide of the protein is mutated. This is particularly useful for the expression of protein 919.

Thus the invention provides a method for the heterologous expression of a protein of the invention, in which the protein's leader peptide is mutated.

The method will typically involve the steps of: obtaining nucleic acid encoding a protein of the invention; and manipulating said nucleic acid to mutate nucleotides within the leader peptide. The resulting nucleic acid may be inserted into an expression vector, or may already be part of an expression vector.

Poly-Glycine Deletion

In a thirteenth approach to heterologous expression, polyglycine stretches in wild-type sequences are mutated. This enhances protein expression.

The poly-glycine stretch has the sequence $(Gly)_n$, where $n \geq 4$ (e.g. 5, 6, 7, 8, 9 or more). This stretch is mutated to disrupt or remove the $(Gly)_n$. This may be by deletion (e.g. CGGGGS (SEQ ID NO:622)→CGGGS (SEQ ID NO:623), CGGS (SEQ ID NO:624), CGS or CS), by substitution (e.g. CGGGGS (SEQ ID NO:622)→CGXGGS (SEQ ID NO:625), CGXXGS (SEQ ID NO:626), CGXGXS (SEQ ID NO:627) etc.), and/or by insertion (e.g. CGGGGS (SEQ ID NO:622)→CGGXGGS (SEQ ID NO:628), CGXGGGS (SEQ ID NO:629), etc.).

This approach is not restricted to Neisserial proteins—it may be used for any protein (particularly bacterial proteins) to enhance heterologous expression. For Neisserial proteins, however, it is particularly suitable for expressing 287, 741, 983 and Tbp2. An alignment of polymorphic forms of 287 is disclosed in WO00/66741.

Thus the invention provides a method for the heterologous expression of a protein of the invention, in which (a) a polyglycine stretch within the protein is mutated.

The method will typically involve the steps of: obtaining nucleic acid encoding a protein of the invention; and manipulating said nucleic acid to mutate nucleotides that encode a poly-glycine stretch within the protein sequence. The resulting nucleic acid may be inserted into an expression vector, or may already be part of an expression vector.

Conversely, the opposite approach (i.e. introduction of poly-glycine stretches) can be used to suppress or diminish expression of a given heterologous protein.

Heterologous Host

Whilst expression of the proteins of the invention may take place in the native host (i.e. the organism in which the protein is expressed in nature), the present invention utilises a heterologous host. The heterologous host may be prokaryotic or eukaryotic. It is preferably *E. coli*, but other suitable hosts include *Bacillus subtilis, Vibrio cholerae, Salmonella typhi, Salmonenna typhimurium, Neisseria meningitidis, Neisseria gonorrhoeae, Neisseria lactamica, Neisseria cinerea, Mycobateria* (e.g. *M. tuberculosis*), yeast etc.

Vectors etc.

As well as the methods described above, the invention provides (a) nucleic acid and vectors useful in these methods (b) host cells containing said vectors (c) proteins expressed or expressable by the methods (d) compositions comprising these proteins, which may be suitable as vaccines, for instance, or as diagnostic reagents, or as immunogenic compositions (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against Neisserial bacteria, and/or (3) a reagent which can raise antibodies against Neisserial bacteria and (g) a method of treating a patient, comprising administering to the patient a therapeutically effective amount of these compositions.

Sequences

The invention also provides a protein or a nucleic acid having any of the sequences set out in the following examples. It also provides proteins and nucleic acid having sequence identity to these. As described above, the degree of 'sequence identity' is preferably greater than 50% (eg. 60%, 70%, 80%, 90%, 95%, 99% or more).

Furthermore, the invention provides nucleic acid which can hybridise to the nucleic acid disclosed in the examples, preferably under "high stringency" conditions (eg. 65° C. in a 0.1×SSC, 0.5% SDS solution).

The invention also provides nucleic acid encoding proteins according to the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

BRIEF DESCRIPTION OF DRAWINGS

FIG. 3A-FIG. 3E show expression data for ORF1. FIG. 3A shows purification of ORF1.

FIG. 3B shows Western blot analysis. FIG. 3C shows the results of a bactericidal assay with ORF1. FIG. 3D shows FACS analysis. FIG. 3E shows the results of an ELISA assay.

FIG. 4A-FIG. 4E show expression data for protein 961. FIG. 4A shows purification of protein 961. FIG. 4B shows Western blot analysis. FIG. 4C shows the results of a bactericidal assay with protein 961. FIG. 4D shows FACS analysis. FIG. 4E shows the results of an ELISA assay.

FIG. 7 shows specific deletions within domain A of protein 287.

FIG. 10A shows results for control, phoC$_{wt}$, 9phoC, 9L1a, 9l1d, 9L1f, and 9S1e. FIG. 10B shows results for control, phoC$_{wt}$, 9phoC, 9S1b, 9S1c, and 9S1i.

FIG. 11A shows 730-C1.

FIG. 11B shows 730-C2.

FIG. 14A-FIG. 14Z show 26 hybrid proteins according to the invention. FIG. 14A shows ΔG287-919. FIG. 14B shows ΔG287-953. FIG. 14C shows ΔG287-961. FIG. 14D shows ΔG287NZ-919. FIG. 14E shows ΔG287NZ-953. FIG. 14F shows ΔG287NZ-961. FIG. 14G shows ΔG983-ORF46.1. FIG. 14H shows ΔG983-741. FIG. 14I shows ΔG983-961.FIG. 14J shows ΔG983-961c. FIG. 14K shows ΔG741-961. FIG. 14L shows ΔG741-961c. FIG. 14M shows ΔG741-983. FIG. 14N shows ΔG741-ORF46.1. FIG. 14O shows ORF46.1-741. FIG. 14P shows ORF46.1-961. FIG. 14Q shows ORF46.1-961c. FIG. 14R shows 961-ORF46.1. FIG. 14S shows 961-741. FIG. 14T shows 961-983. FIG. 14U shows 961c-ORF46.1. FIG. 14V shows 961c-741. FIG. 14W shows 961c-983. FIG. 14X shows 961cL-ORF46.1. FIG. 14Y shows 961cL-741. FIG. 14Z shows 961cL-983.

MODES FOR CARRYING OUT THE INVENTION

Example 1

919 and its Leader Peptide

Figure 1:
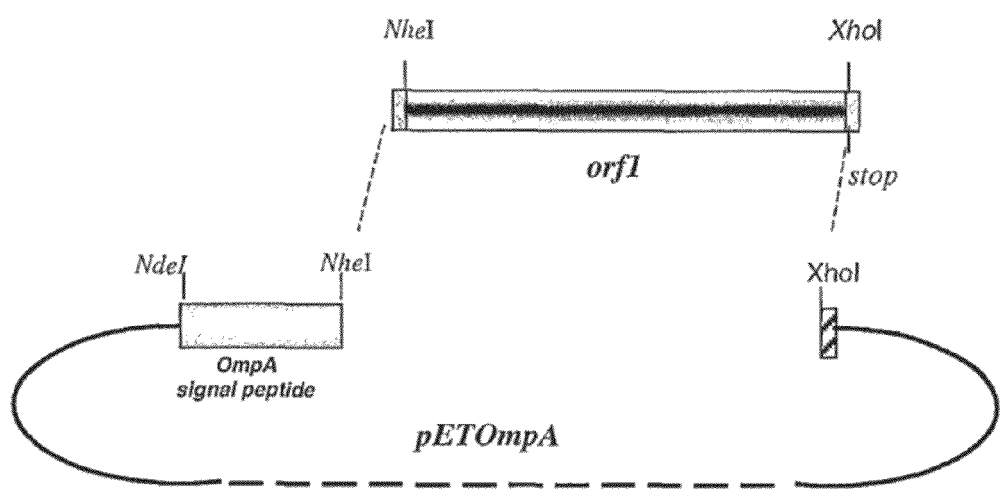
FIG. 1 shows a construct used to express orf1 protein using a heterologous leader peptide.

Protein 919 from *N. meningitidis* (serogroup B, strain 2996) has the following sequence (SEQ ID NO:1):

```
  1 MKKYLFRAAL YGIAAAILAA CQSKSIQTFP QPDTSVINGP DRPVGIPDPA

51 GTTVGGGGAV YTVVPHLSLP HWAAQDFAKS LQSFRLGCAN LKNRQGWQDV

101 CAQAFQTPVH SFQAKQFFER YFTPWQVAGN GSLAGTVTGY YEPVLKGDDR

151 RTAQARFPIY GIPDDFISVP LPAGLRSGKA LVRIRQTGKN SGTIDNTGGT

201 HTADLSRFPI TARTTAIKGR FEGSRFLPYH TRNQINGGAL DGKAPILGYA

251 EDPVELFFMH IQGSGRLKTP SGKYIRIGYA DKNEHPYVSI GRYMADKGYL

301 KLGQTSMQGI KAYMRQNPQR LAEVLGQNPS YIFFRELAGS SNDGPVGALG

351 TPLMGEYAGA VDRHYITLGA PLFVATAHPV TRKALNRLIM AQDTGSAIKG

401 AVRVDYFWGY GDEAGELAGK QKTTGYVWQL LPNGMKPEYR P*
```

The leader peptide is underlined.

The sequences of 919 from other strains can be found in FIGS. 7 and 18 of WO00/66741.

Example 2 of WO99/57280 discloses the expression of protein 919 as a His-fusion in *E. coli*. The protein is a good surface-exposed immunogen.

Three alternative expression strategies were used for 919:
1) 919 without its leader peptide (and without the mature N-terminal cysteine) and without any fusion partner ('919$^{untagged}$') (SEQ ID NO:2):

```
  1 QSKSIQTFP QPDTSVINGP DRPVGIPDPA GTTVGGGGAV YTVVPHLSLP

50 HWAAQDFAKS LQSFRLGCAN LKNRQGWQDV CAQAFQTPVH SFQAKQFFER

100 YFTPWQVAGN GSLAGTVTGY YEPVLKGDDR RTAQARFPIY GIPDDFISVP

150 LPAGLRSGKA LVRIRQTGKN SGTIDNTGGT HTADLSRFPI TARTTAIKGR

200 FEGSRFLPYH TRNQINGGAL DGKAPILGYA EDPVELFFMH IQGSGRLKTP

250 SGKYIRIGYA DKNEHPYVSI GRYMADKGYL KLGQTSMQGI KAYMRQNPQR

300 LAEVLGQNPS YIFFRELAGS SNDGPVGALG TPLMGEYAGA VDRHYITLGA
```

```
350 PLFVATAHPV TRKALNRLIM AQDTGSAIKG AVRVDYFWGY GDEAGELAGK

400 QKTTGYVWQL LPNGMKPEYR P*
```

The leader peptide and cysteine were omitted by designing the 5'-end amplification primer downstream from the predicted leader sequence.
2) 919 with its own leader peptide but without any fusion partner ('919L'); and
3) 919 with the leader peptide (MKTFFKTLSAAALALI-LAA (SEQ ID NO: 630)) from ORF4 ('919LOrf4') (SEQ ID NO:3).

```
  1 MKTFFKTLS AAALALILAA CQSKSIQTFP QPDTSVINGP DRPVGIPDPA

50 GTTVGGGGAV YTVVPHLSLP HWAAQDFAKS LQSFRLGCAN LKNRQGWQDV

100 CAQAFQTPVH SFQAKQFFER YFTPWQVAGN GSLAGTVTGY YEPVLKGDDR

150 RTAQARFPIY GIPDDFISVP LPAGLRSGKA LVRIRQTGKN SGTIDNTGGT

200 HTADLSRFPI TARTTAIKGR FEGSRFLPYH TRNQINGGAL DGKAPILGYA

250 EDPVELFFMH IQGSGRLKTP SGKYIRIGYA DKNEHPYVSI GRYMADKGYL

300 KLGQTSMQGI KSYMRQNPQR LAEVLGQNPS YIFFRELAGS SNDGPVGALG

350 TPLMGEYAGA VDRHYITLGA PLFVATAHPV TRKALNRLIM AQDTGSAIKG

400 AVRVDYFWGY GDEAGELAGK QKTTGYVWQL LPNGMKPEYR P*
```

To make this construct, the entire sequence encoding the ORF4 leader peptide was included in the 5'-primer as a tail (primer 919Lorf4 For). A NheI restriction site was generated by a double nucleotide change in the sequence coding for the ORF4 leader (no amino acid changes), to allow different genes to be fused to the ORF4 leader peptide sequence. A stop codon was included in all the 3'-end primer sequences.

All three forms of the protein were expressed and could be purified.

The '919L' and '919LOrf4' expression products were both lipidated, as shown by the incorporation of [3-H]-palmitate label. $919^{untagged}$ did not incorporate the $^3$H label and was located intracellularly.

919LOrf4 could be purified more easily than 919L. It was purified and used to immunise mice. The resulting sera gave excellent results in FACS and ELISA tests, and also in the bactericidal assay. The lipoprotein was shown to be localised in the outer membrane.

$919^{untagged}$ gave excellent ELISA titres and high serum bactericidal activity. FACS confirmed its cell surface location.

Example 2

919 and Expression Temperature

Growth of *E. coli* expressing the 919LOrf4 protein at 37° C. resulted in lysis of the bacteria. In order to overcome this problem, the recombinant bacteria were grown at 30° C. Lysis was prevented without preventing expression.

Example 3

Mutation of 907, 919 and 922

It was hypothesised that proteins 907, 919 and 922 are murein hydrolases, and more particularly lytic transglycosylases. Murein hydrolases are located on the outer membrane and participate in the degradation of peptidoglycan.

The purified proteins $919^{untagged}$, 919Lorf4, 919-His (i.e. with a C-terminus His-tag) and 922-His were thus tested for murein hydrolase activity [Ursinus & Holtje (1994) *J. Bact.* 176:338-343]. Two different assays were used, one determining the degradation of insoluble murein sacculus into soluble muropeptides and the other measuring breakdown of poly (MurNAc-GlcNAc)$_{n>30}$ glycan strands.

The first assay uses murein sacculi radiolabelled with meso-2,6-diamino-3,4,5-[$^3$H]pimelic acid as substrate. Enzyme (3-10 µg total) was incubated for 45 minutes at 37° C. in a total volume of 100 µl comprising 10 mM Tris-maleate (pH 5.5), 10 mM MgCl$_2$, 0.2% v/v Triton X-100 and [$^3$H] A$_2$pm labelled murein sacculi (about 10000 cpm). The assay mixture was placed on ice for 15 minutes with 100 l of 1% w/v N-acetyl-N,N,N-trimethylammonium for 15 minutes and precipitated material pelleted by centrifugation at 10000 g for 15 minutes. The radioactivity in the supernatant was measured by liquid scintillation counting. *E. coli* soluble lytic transglycosylase Slt70 was used as a positive control for the assay; the negative control comprised the above assay solution without enzyme.

All proteins except 919-His gave positive results in the first assay.

The second assay monitors the hydrolysis of poly(Mur-NAc-GlcNAc)glycan strands. Purified strands, poly(Mur-NAc-GlcNAc)$_{n>30}$ labelled with N-acetyl-D-1-[$^3$H]glucosamine were incubated with 3 µg of 919L in 10 mM Tris-maleate (pH 5.5), 10 mM MgCl$_2$ and 0.2% v/v Triton X-100 for 30 min at 37° C. The reaction was stopped by boiling for 5 minutes and the pH of the sample adjusted to about 3.5 by addition of 10 µl of 20% v/v phosphoric acid. Substrate and product were separated by reversed phase HPLC on a NUCLEOSIL® 300 C$_{18}$ column (an octadecyl modified silica phase for HPLC) as described by Harz et. al. [*Anal. Biochem.* (1990) 190:120-128]. The *E. coli* lytic transglycosylase Mlt A was used as a positive control in the assay. The negative control was performed in the absence of enzyme.

By this assay, the ability of 919LOrf4 to hydrolyse isolated glycan strands was demonstrated when anhydrodisaccharide subunits were separated from the oligosaccharide by HPLC.

Protein 919Lorf4 was chosen for kinetic analyses. The activity of 919Lorf4 was enhanced 3.7-fold by the addition of 0.2% v/v Triton X-100 in the assay buffer. The presence of Triton X-100 had no effect on the activity of 919$^{untagged}$. The effect of pH on enzyme activity was determined in Tris-Maleate buffer over a range of 5.0 to 8.0. The optimal pH for the reaction was determined to be 5.5. Over the temperature range 18° C. to 42° C., maximum activity was observed at 37° C. The effect of various ions on murein hydrolase activity was determined by performing the reaction in the presence of a variety of ions at a final concentration of 10 mM. Maximum activity was found with $Mg^{2+}$, which stimulated activity 2.1-fold, $Mn^{2+}$ and $Ca^{2+}$ also stimulated enzyme activity to a similar extent while the addition $Ni^{2+}$ and EDTA had no significant effect. In contrast, both $Fe^{2+}$ and $Zn^{2+}$ significantly inhibited enzyme activity.

The structures of the reaction products resulting from the digestion of unlabelled *E. coli* murein sacculus were analysed by reversed-phase HPLC as described by Glauner [*Anal. Biochem.* (1988) 172:451-464]. Murein sacculi digested with the muramidase Cellosyl were used to calibrate and standardise the Hypersil ODS column. The major reaction products were 1,6 anhydrodisaccharide tetra and tri peptides, demonstrating the formation of 1,6 anhydromuraminic acid intramolecular bond.

These results demonstrate experimentally that 919 is a murein hydrolase and in particular a member of the lytic transglycosylase family of enzymes. Furthermore the ability of 922-His to hydrolyse murein sacculi suggests this protein is also a lytic transglycosylase.

This activity may help to explain the toxic effects of 919 when expressed in *E. coli*.

In order to eliminate the enzymatic activity, rational mutagenesis was used. 907, 919 and 922 show fairly low homology to three membrane-bound lipidated murein lytic transglycosylases from *E. coli*:

919 (441aa) is 27.3% identical over 440aa overlap to *E. coli* MLTA (P46885);

922 (369aa) is 38.7% identical over 310aa overlap to *E. coli* MLTB (P41052); and 907-2 (207aa) is 26.8% identical over 149aa overlap to *E. coli* MLTC (P52066).

907-2 also shares homology with *E. coli* MLTD (P23931) and Slt70 (P03810), a soluble lytic transglycosylase that is located in the periplasmic space. No significant sequence homology can be detected among 919, 922 and 907-2, and the same is true among the corresponding MLTA, MLTB and MLTC proteins.

Crystal structures are available for Slt70 [1QTEA; 1QTEB; Thunnissen et al. (1995) *Biochemistry* 34:12729-12737] and for Slt35 [1LTM; 1QUS; 1QUT; van Asselt et al. (1999) *Structure Fold Des* 7:1167-80] which is a soluble form of the 40 kDa MLTB.

The catalytic residue (a glutamic acid) has been identified for both Slt70 and MLTB.

In the case of Slt70, mutagenesis studies have demonstrated that even a conservative substitution of the catalytic Glu505 with a glutamine (Gln) causes the complete loss of enzymatic activity. Although Slt35 has no obvious sequence similarity to Slt70, their catalytic domains shows a surprising similarity. The corresponding catalytic residue in MLTB is Glu162.

Another residue which is believed to play an important role in the correct folding of the enzymatic cleft is a well-conserved glycine (Gly) downstream of the glutamic acid. Recently, Terrak et al. [*Mol. Microbiol.* (1999) 34:350-64] have suggested the presence of another important residue which is an aromatic amino acid located around 70-75 residues downstream of the catalytic glutamic acid.

Sequence alignment of Slt70 (SEQ ID NO:5) with 907-2 (SEQ ID NO:4) and of MLTB (SEQ ID NO:7) with 922 (SEQ ID NO:6) were performed in order to identify the corresponding catalytic residues in the MenB antigens.

The two alignments in the region of the catalytic domain are reported below:

907-2/Slt70:

```
                    90         100        110       ▼120        130        140
907-2.pep    ERRRLLVNIQYESSRAG--LDTQIVLGLIEVESAFRQYAISGVGARGLMQVMPFWKNYIG
             ||   |    |  ::    :|  :  :::::  :  |||:    :  |  |||  |||||:||    ::
slty_ecoli   ERFPLAYNDLFKRYTSGKEIPQSYAMAIARQESAWNPKVKSPVGASGLMQIMPGTATHTV
                    480        490        500    ▲  510        520        530
                                                 GLU505
```

922/MLTB

```
                   150        160    ▼  170        180        190        200
922.pep      VAQKYGVPAELIVAVIGIETNYGKNTGSFRVADALATLGFDYPRRAGFFQKELVELLKLA
             : | ||||  |:||::||:||  :|:   |:  |:  ||||||:|:||||  :|:  ||    :|  :|
mltb_ecoli   AWQVYGVPPEIIVGIIGVETRWGRVMGKTRILDALATLSFNYPRRAEYFSGELETFLLMA
                   150        160   ▲   170        180        190        200
                                    GLU162

210        220        230        240        250        260
922.pep      KEEGGDVFAFKGSYAGAMGMPQFMPSSYRKWAVDYDGDGHRDIWGNVGDVAASVANYMKQ
             ::|     |  :  :||:||||||:  ||||||||:::|||::|||   ::|    |   |:  :||||:|
mltb_ecoli   RDEQDDPLNLKGSFAGAMGYGQFMPSSYKQYAVDFSGDGHINLWDPV-DAIGSVANYFKA
                   210        220        230        240        250        260
```

From these alignments, it results that the corresponding catalytic glutamate in 907-2 is Glu117, whereas in 922 is Glu164. Both antigens also share downstream glycines that could have a structural role in the folding of the enzymatic cleft (in bold), and 922 has a conserved aromatic residue around 70aa downstream (in bold).

In the case of protein 919, no 3D structure is available for its *E. coli* homologue MLTA, and nothing is known about a possible catalytic residue. Nevertheless, three amino acids in 919 (SEQ ID NO:8) are predicted as catalytic residues by alignment with MLTA (SEQ ID NO:9):
919/MLTA

```
                240        250    ▼   260        270        280        290
919.pep         ALDGKAPILGYAEDPVELFFMHIQGSGRLKTPSGKYIRI-GYADKNEHPYVSIGRYMADK
                ||:  |   ||:|::: :: |:|  :|||| :   :|:   :  :|| || | |||: : |:
mlta_ecoli.p    ALSDKY-ILAYSNSLMDNFIMDVQGSGYIDFGDGSPLNFFSYAGKNGHAYRSIGKVLIDR
                       170        180        190        200        210

300        310        320    ▼   330        340        ◊350    ◊
919.pep         GYLKLGQTSMQGIKSYMRQNPQ-RLAEVLGQNPSYIFFRELAGSSNDGPV-GALGTPLMG
                 :|   :  |||:|:  :  :  ::  |:|  ||||::||:    : :    ||  ||  ::||:|
mlta_ecoli.p    GEVKKEDMSMQAIRHWGETHSEAEVRELLEQNPSFVFFKPQSFA----PVKGASAVPLVG
                220        230        240        250        260        270

360 ▼      o          380        390        400    ◊◊410
919.pep         EYAGAVDRHYITLGAPLFVATAHPVTRKALN-----RLIMAQDTGSAIKGAVRVDYFWGY
                :  :  |  ||   |   |:  |::  :      |      ||::|  |:|:|||| :  |  : |
mlta_ecoli.p    RASVASDRSIIPPGTTLLAEVPLLDNNGKFNGQYELRLMVALDVGGAIKGQ-HFDIYQGI
                280        290        300        310        320        330

402        o
919.pep         GDEAGELAGKQKTTGYVWQLLP
                |  |||:  ||   :    |  ||| |
mlta_ecoli.p    GPEAGHRAGWYNHYGRVWVLKT
                340        350
```

The three possible catalytic residues are shown by the symbol ▼:

1) Glu255 (Asp in MLTA), followed by three conserved glycines (Gly263, Gly265 and Gly272) and three conserved aromatic residues located approximately 75-77 residues downstream. These downstream residues are shown by □.

2) Glu323 (conserved in MLTA), followed by 2 conserved glycines (Gly347 and Gly355) and two conserved aromatic residues located 84-85 residues downstream (Tyr406 or Phe407). These downstream residues are shown by ◊.

3) Asp362 (instead of the expected Glu), followed by one glycine (Gly 369) and a conserved aromatic residue (Trp428). These downstream residues are shown by ○.

Alignments of polymorphic forms of 919 are disclosed in WO00/66741.

Based on the prediction of catalytic residues, three mutants of the 919 and one mutant of 907, containing each a single amino acid substitution, have been generated. The glutamic acids in position 255 and 323 and the aspartic acids in position 362 of the 919 protein and the glutamic acid in position 117 of the 907 protein, were replaced with glycine residues using PCR-based SDM. To do this, internal primers containing a codon change from Glu or Asp to Gly were designed:

| Primers | SEQ ID NO | Sequences | Codon change |
|---|---|---|---|
| 919-E255 for | 10 | CGAAGACCCCGTCGgtCTTTTTTTTATG | GAA → Ggt |
| 919-E255 rev | 11 | GTGCATAAAAAAAGacCGACGGGGTCT | |
| 919-E323 for | 12 | AACGCCTCGCCGgtGTTTTGGGTCA | GAA → Ggt |
| 919-E323 rev | 13 | TTTGACCCAAAACacCGGCGAGGCG | |
| 919-D362 for | 14 | TGCCGGCGCAGTCGgtCGGCACTACA | GAC → Ggt |
| 919-D362 rev | 15 | TAATGTAGTGCCGacCGACTGCGCCG | |
| 907-E117 for | 16 | TGATTGAGGTGGgtAGCGCGTTCCG | GAA → Ggt |
| 907-E117 rev | 17 | GGCGGAACGCGCTacCCACCTCAAT | |

Underlined nucleotides code for glycine; the mutated nucleotides are in lower case.

To generate the 919-E255, 919-E323 and 919-E362 mutants, PCR was performed using 20 ng of the pET 919-LOrf4 DNA as template, and the following primer pairs:
1) Orf4L for/919-E255 rev
2) 919-E255 for/919L rev
3) Orf4L for/919-E323 rev
4) 919-E323 for/919L rev
5) Orf4L for/919-D362 rev
6) 919-D362 for/919L rev The second round of PCR was performed using the product of PCR 1-2, 3-4 or 5-6 as template, and as forward and reverse primers the "Orf4L for" and "919L rev" respectively.

For the mutant 907-E117, PCR have been performed using 200 ng of chromosomal DNA of the 2996 strain as template and the following primer pairs:
7) 907L for/907-E117 rev
8) 907-E117 for/907L rev The second round of PCR was performed using the products of PCR 7 and 8 as templates and the oligos "907L for" and "907L rev" as primers.

The PCR fragments containing each mutation were processed following the standard procedure, digested with NdeI and XhoI restriction enzymes and cloned into pET-21b+ vector. The presence of each mutation was confirmed by sequence analysis.

Mutation of Glu117 to Gly in 907 is carried out similarly, as is mutation of residues Glu164, Ser213 and Asn348 in 922.

The E255G mutant of 919 shows a 50% reduction in activity; the E323G mutant shows a 70% reduction in activity; the E362G mutant shows no reduction in activity.

Example 4

Multimeric Form

287-GST, 919$^{untagged}$ and 953-His were subjected to gel filtration for analysis of quaternary structure or preparative purposes. The molecular weight of the native proteins was estimated using either FPLC Superose 12 (H/R 10/30) or SUPERDEX™75 gel filtration columns (prepacked columns, Pharmacia). The buffers used for chromatography for 287, 919 and 953 were 50 mM Tris-HCQ (pH 8.0), 20 mM Bicine (pH 8.5) and 50 mM Bicine (pH 8.0), respectively. Additionally each buffer contained 150-200 mM NaCl and 10% v/v glycerol. Proteins. were dialysed against the appropriate buffer and applied in a volume of 200 μl. Gel filtration was performed with a flow rate of 0.5-2.0 ml/min and the eluate monitored at 280 nm. Fractions were collected and analysed by SDS-PAGE. Blue dextran 2000 and the molecular weight standards ribonuclease A, chymotrypsin A ovalbumin, albumin (Pharmacia) were used to calibrate the column. The molecular weight of the sample was estimated from a calibration curve of $K_{av}$ vs. log $M_T$ of the standards. Before gel filtration, 287-GST was digested with thrombin to cleave the GST moiety.

The estimated molecular weights for 287, 919 and 953-His were 73 kDa, 47 kDa and 43 kDa respectively. These results suggest 919 is monomeric while both 287 and 953 are principally dimeric in their nature. In the case of 953-His, two peaks were observed during gel filtration. The major peak (80%) represented a dimeric conformation of 953 while the minor peak (20%) had the expected size of a monomer. The monomeric form of 953 was found to have greater bactericidal activity than the dimer.

Example 5 pSM214 and pET24b Vectors 953 protein with its native leader peptide and no fusion partners was expressed from the pET vector and also from pSM214 [Velati Bellini et al. (1991) *J. Biotechnol.* 18, 177-192].

The 953 sequence was cloned as a full-length gene into pSM214 using the *E. coli* MM294-1 strain as a host. To do this, the entire DNA sequence of the 953 gene (from ATG to the STOP codon) was amplified by PCR using the following primers:

```
                                              (SEQ ID NO: 18)
953L for/2
CCGGAATTCTTATGAAAAAAATCATCTTCGCCGC Eco RI (SEQ ID NO: 19)
953L rev/2
GCCCAAGCTTTTATTGTTTGGCTGCCTCGATT Hind III
``` which contain EcoRI and HindIII restriction sites, respectively. The amplified fragment was digested with EcoRI and HindIII and ligated with the pSM214 vector digested with the same two enzymes. The ligated plasmid was transformed into *E. coli* MM294-1 cells (by incubation in ice for 65 minutes at 37° C.) and bacterial cells plated on LB agar containing 20 μg/ml of chloramphenicol.

Recombinant colonies were grown over-night at 37° C. in 4 ml of LB broth containing 20 μg/ml of chloramphenicol; bacterial cells were centrifuged and plasmid DNA extracted as and analysed by restriction with EcoRI and HindIII. To analyse the ability of the recombinant colonies to express the protein, they were inoculated in LB broth containing 20 μg/ml of chloramphenicol and let to grown for 16 hours at 37° C. Bacterial cells were centrifuged and resuspended in PBS. Expression of the protein was analysed by SDS-PAGE and Coomassie Blue staining.

Expression levels were unexpectedly high from the pSM214 plasmid.

Oligos used to clone sequences into pSM-214 vectors were as follows:

| | | | | | |
|---|---|---|---|---|---|
| Δ G287 (pSM-214) | Fwd | CCGG<u>AATTC</u>TTATG-TCGCCCGATGTTAAATCGGCGGA | SEQ ID NO: 20 | EcoRI |
| | Rev | GCCC<u>AAGCTT</u>-TCAATCCTGCTCTTTTTTGCCG | SEQ ID NO: 21 | HindIII |
| Δ2 287 (pSM-214) | Fwd | CCGG<u>AATTC</u>TTATG-AGCCAAGATATGGCGGCAGT | SEQ ID NO: 22 | EcoRI |
| | Rev | GCCC<u>AAGCTT</u>-TCAATCCTGCTCTTTTTTGCCG | SEQ ID NO: 23 | HindIII |
| Δ3 287 (pSM-214) | Fwd | CCGG<u>AATTC</u>TTATG-TCCGCCGAATCCGCAAATCA | SEQ ID NO: 24 | EcoRI |
| | Rev | GCCC<u>AAGCTT</u>-TCAATCCTGCTCTTTTTTGCCG | SEQ ID NO: 25 | HindIII |
| Δ4 287 (pSM-214) | Fwd | CCGG<u>AATTC</u>TTATG-GGAAGGGTTGATTTGGCTAATG | SEQ ID NO: 26 | EcoRI |
| | Rev | GCCC<u>AAGCTT</u>-TCAATCCTGCTCTTTTTTGCCG | SEQ ID NO: 27 | HindIII |

-continued

| | | | | |
|---|---|---|---|---|
| Orf46.1 (pSM-214) | Fwd | CCGGAATTCTTATG-TCAGATTTGGCAAACGATTCTT | SEQ ID NO: 28 | EcoRI |
| | Rev | GCCCAAGCTT-TTACGTATCATATTTCACGTGCTTC | SEQ ID NO: 29 | HindIII |
| ΔG 287-Orf46.1 (pSM-214) | Fwd | CCGGAATTCTTATG-TCGCCCGATGTTAAATCGGCGGA | SEQ ID NO: 30 | EcoRI |
| | Rev | GCCCAAGCTT-TTACGTATCATATTTCACGTGCTTC | SEQ ID NO: 31 | HindIII |
| 919 (pSM-214) | Fwd | CCGGAATTCTTATG-CAAAGCAAGAGCATCCAAACCT | SEQ ID NO: 32 | EcoRI |
| | Rev | GCCCAAGCTT-TTACGGGCGGTATTCGGGCT | SEQ ID NO: 33 | HindIII |
| 961L (pSM-214) | Fwd | CCGGAATTCATATG-AAACACTTTCCATCC | SEQ ID NO: 34 | EcoRI |
| | Rev | GCCCAAGCTT-TTACCACTCGTAATTGAC | SEQ ID NO: 35 | HindIII |
| 961 (pSM-214) | Fwd | CCGGAATTCATATG-GCCACAAGCGACGAC | SEQ ID NO: 36 | EcoRI |
| | Rev | GCCCAAGCTT-TTACCACTCGTAATTGAC | SEQ ID NO: 37 | HindIII |
| 961c L pSM-214 | Fwd | CCGGAATTCTTATG-AAACACTTTCCATCC | SEQ ID NO: 38 | EcoRI |
| | Rev | GCCCAAGCTT-TCAACCCACGTTGTAAGGTTG | SEQ ID NO: 39 | HindIII |
| 961c pSM-214 | Fwd | CCGGAATTCTTATG-GCCACAAACGACGACG | SEQ ID NO: 40 | EcoRI |
| | Rev | GCCCAAGCTT-TCAACCCACGTTGTAAGGTTG | SEQ ID NO: 41 | HindIII |
| 953 (pSM-214) | Fwd | CCGCAATTCTTATG-GCCACCTACAAAGTGGACGA | SEQ ID NO: 42 | EcoRI |
| | Rev | GCCCAAGCTT-TTATTGTTTGGCTGCCTCGATT | SEQ ID NO: 43 | HindIII |

These sequences were manipulated, cloned and expressed as described for 953L.

For the pET-24 vector, sequences were cloned and the proteins expressed in pET-24 as described below for pET21.

pET2 has the same sequence as pET-21, but with the kanamycin resistance cassette instead of ampicillin cassette.

Oligonucleotides used to clone sequences into pET-24b vector were:

| | | | | |
|---|---|---|---|---|
| ΔG 287 K | Fwd | CGCGGATCCGCTAGC-CCCGATGTTAAATCGGC § | SEQ ID NO: 44 | NheI |
| | Rev | CCCGCTCGAG-TCAATCCTGCTCTTTTTTGCC * | SEQ ID NO: 45 | XhoI |
| Δ2 287 K | Fwd | CGCGGATCCGCTAGC-CAAGATATGGCGGCAGT § | SEQ ID NO: 46 | NheI |
| Δ3 287 K | Fwd | CGCGGATCCGCTAGC-GCCGAATCCGCAAATCA § | SEQ ID NO: 47 | NheI |
| Δ4 287 K | Fwd | CGCGCTAGC-GGAAGGGTTGATTTGGCTAATGG § | SEQ ID NO: 48 | NheI |
| Orf46.1 K | Fwd | GGGAATTCCATATG-GGCATTTCCCGCAAAATATC | SEQ ID NO: 49 | NdeI |
| | Rev | CCCGCTCGAG-TTACGTATCATATTTCACGTGC | SEQ ID NO: 50 | XhoI |
| Orf46A K | Fwd | GGGAATTCCATATG-GGCATTTCCCGCAAAATATC | SEQ ID NO: 51 | NdeI |
| | Rev | CCCGCTCGAG-TTATTCTATGCCTTGTGCGGCAT | SEQ ID NO: 52 | XhoI |
| 961 K (MCS8) | Fwd | CGCGGATCCCATATG-GCCACAAGCGACGACGA | SEQ ID NO: 53 | NdeI |
| | Rev | CCCGCTCGAG-TTACCACTCGTAATTGAC | SEQ ID NO: 54 | XhoI |
| 961a K | Fwd | CGCGGATCCCATATG-GCCACAAACGACG | SEQ ID NO: 55 | NdeI |
| | Rev | CCCGCTCGAG-TCATTTAGCAATATTATCTTTGTTC | SEQ ID NO: 56 | XhoI |
| 961b K | Fwd | CGCGGATCCCATATG-AAAGCAAACAGTGCCGAC | SEQ ID NO: 57 | NdeI |
| | Rev | CCCGCTCGAG-TTACCACTCGTAATTGAC | SEQ ID NO: 58 | XhoI |
| 961c K | Fwd | CGCGGATCCCATATG-GCCACAAACGACG | SEQ ID NO: 59 | NdeI |
| | Rev | CCCGCTCGAG-TTAACCCACGTTGTAAGGT | SEQ ID NO: 60 | XhoI |
| 961cL K | Fwd | CGCGGATCCCATATG-ATGAAACACTTTCCATCC | SEQ ID NO: 61 | NdeI |
| | Rev | CCCGCTCGAG-TTAACCCACGTTGTAAGGT | SEQ ID NO: 62 | XhoI |
| 961d K | Fwd | CGCGGATCCCATATG-GCCACAAACGACG | SEQ ID NO: 63 | NdeI |
| | Rev | CCCGCTCGAG-TCAGTCTGACACTGTTTTATCC | SEQ ID NO: 64 | XhoI |
| ΔG 287-919 K | Fwd | CGCGGATCCGCTAGC-CCCGATGTTAAATCGGC | SEQ ID NO: 65 | NheI |
| | Rev | CCCGCTCGAG-TTACGGGCGGTATTCGG | SEQ ID NO: 66 | XhoI |
| ΔG 287-Orf46.1 K | Fwd | CGCGGATCCGCTAGC-CCCGATGTTAAATCGGC | SEQ ID NO: 67 | NheI |
| | Rev | CCCGCTCGAG-TTACGTATCATATTTCACGTGC | SEQ ID NO: 68 | XhoI |
| ΔG 287-961 K | Fwd | CGCGGATCCGCTAGC-CCCGATGTTAAATCGGC | SEQ ID NO: 69 | NheI |
| | Rev | CCCGCTCGAG-TTACCACTCGTAATTGAC | SEQ ID NO: 70 | XhoI |

* This primer was used as a Reverse primer for all the 287 forms.
§ Forward primers used in combination with the ΔG278 K reverse primer.

Example 6

ORF1 and its Leader Peptide

ORF1 from *N. meningitidis* (serogroup B, strain MC58) is predicted to be an outer membrane or secreted protein. It has the following sequence (SEQ ID NO:71):

```
   1 MKTTDKRTTE THRKAPKTGR IRFSPAYLAI CLSFGILPQA WAGHTYFGIN
  51 YQYYRDFAEN KGKFAVGAKD IEVYNKKGEL VGKSMTKAPM IDFSVVSRNG
 101 VAALVGDQYI VSVAHNGGYN NVDFGAEGRN PDQHRFTYKI VKRNNYKAGT
 151 KGHPYGGDYH MPRLHKFVTD AEPVEMTSYM DGRKYIDQNN YPDRVRIGAG
 201 RQYWRSDEDE PNERESSYHI ASAYSWLVGG NTFAQNGSGG GTVNLGSEKI
 251 KHSPYGFLPT GGSFGDSGSP MFIYDAQKQK WLINGVLQTG NPYIGKSNGF
 301 QLVRKDWFYD EIFAGDTHSV FYEPRQNGKY SFNDDNNGTG KINAKHEHNS
 351 LPNRLKTRTV QLFNVSLSET AREPVYHAAG GVNSYRPRLN NGENISFIDE
 401 GKGELILTSN INQGAGGLYF QGDFTVSPEN NETWQGAGVH ISEDSTVTWK
 451 VNGVANDRLS KIGKGTLHVQ AKGENQGSIS VGDGTVILDQ QADDKGKKQA
 501 FSEIGLVSGR GTVQLNADNQ FNPDKLYFGF RGGRLDLNGH SLSFERIQNT
 551 DEGAMIVNHN QDKESTVTIT GNKDIATTGN NNSLDSKKEI AYNGWFGEKD
 601 TTKTNGRLNL VYQPAAEDRT LLLSGGTNLN GNITQTNGKLFFSGRPTPHA
 651 YNHLNDHWSQ KEGIPRGEIV WDNDWINRTF KAENFQIKGG QAVVSRNVAK
 701 VKGDWHLSNH AQAVFGVAPH QSHTICTRSD WTGLTNCVEK TITDDKVIAS
 751 LTKTDISGNV DLADHAHLNL TGLATLNGNL SANGDTRYTV SHNATQNGNL
 801 SLVGNAQATF NQATLNGNTS ASGNASFNLS DHAVQNGSLT LSGNAKANVS
 851 HSALNGNVSL ADKAVFHFES SRFTGQISGG KDTALHLKDS EWTLPSGTEL
 901 GNLNLDNATI TLNSAYRHDA AGAQTGSATD APRRRSRRSR RSLLSVTPPT
 951 SVESRFNTLT VNGKLNGQGT FRFMSELFGY RSDKLKLAES SEGTYTLAVN
1001 NTGNEPASLE QLTVVEGKDN KPLSENLNFT LQNEHVDAGA WRYQLIRKDG
1051 EFRLHNPVKE QELSDKLGKA EAKKQAEKDN AQSLDALIAA GRDAVEKTES
1101 VAEPARQAGG ENVGIMQAEE EKKRVQADKD TALAKQREAE TRPATTAFPR
1151 ARRARRDLPQ LQPQPQPQPQ RDLISRYANS GLSEFSATLN SVFAVQDELD
1201 RVFAEDRRNA VWTSGIRDTK HYRSQDFRAY RQQTDLRQIG MQKNLGSGRV
1251 GILFSHNRTE NTFDDGIGNS ARLAHGAVFG QYGIDRFYIG ISAGAGFSSG
1301 SLSDGIGGKI RRRVLHYGIQ ARYRAGFGGF GIEPHIGATR YFVQKADYRY
1351 ENVNIATPGL AFNRYRAGIK ADYSFKPAQH ISITPYLSLS YTDAASGKVR
1401 TRVNTAVLAQ DFGKTRSAEW GVNAEIRGFT LSLHAAAAKG PQLEAQHSAG
1451 IKLGYRW*
```

The leader peptide is underlined.

A polymorphic form of ORF1 is disclosed in WO99/55 873.

Three expression strategies have been used for ORF1:

1) ORF1 using a His tag, following WO99/24578 (ORF1-His);

2) ORF1 with its own leader peptide but without any fusion partner ('ORF1L'); and 3) ORF1 with the leader peptide (MKKTAIAIAVALAG-FATVAQA (SEQ ID NO:72)) from *E. coli* OmpA ('Orf1LOmpA') (SEQ ID NO:73):

```
MKKTAIAIAVALAGFATVAQAASAGHTYFGINYQYYRDFAENKGKFAVGAKDIEVYNKKGELVGKSMTKAPMIDFSV
VSRNGVAALVGDQYIVSVAHNGGYNNVDFGAEGRNPDQHRFTYKIVKRNKYKAGTKGHPYGGDYHMPRLHKFVTDAE
PVEMTSYMDGRKYIDQNNYPDRVRIGAGRQYWRSDEDEPNNRESSYHIASAYSWLVGGYTFAQNGSGGGTVNLGSEK
IKHSPYGFLPTGGSFGDSGSPMFIYDAQKQKWLINGVLQTGNPYIGKSNGFQLVRKDWFYDEIFAGDTHSVFYEPRQ
NGKYSFNDDNNGTGKINAKHEHNSLPNRLKTRTVQLFNVSLSETAREFVYHAAGGVNSYRPRLNNGENISFIDEGKG
ELILTSNINQGAGGLYFQGDFTVSPENNETWQGAGVHISEDSTVTWKVNGVANDRLSKIGKGTLHVQAKGENQGSIS
VGDGTVILDQQADDKGKKQAFSEIGLVSGRGTVQLNADNQFNPDKLYFGFRGGRLDLNGHSLSFHRIQNTDEGAMIV
NHNQDKESTVTITGNKDIATTGNNNSLDSKKEIAYNGWFGEKDTTKTNGRLNLVYQPAAEDRTLLLSGGTNLNGNIT
QTNGKLFFSGRPTPHAYNHLNDHWSQKEGIPRGEIVWDNDWINRTFRAENFQKGGQAVVSRNVAKVKGDWHLSNHA
QAVFGVAPHQSHTICTRSDWTGLTNCVEKTITDDKVIASLTKTDISGNVDLADHAHLNLTGLATLNGNLSANGDTRY
TVSHNATQNGNLSLVGNAQATFNQATLNGNTSASGNASFNLSDHAVQNGSLTLSGNAKANVSHSALNGNVSLADKAV
FHFESSRPTGQISGGKDTALHLKDSEWTLPSGTELGNLNLDNATITLNSAYRHDAAGAQTGSATDAPRRRSRRSRRS
LLSVTPPTSVESRFNTLTVNGKLNGQGTFRFMSELFGYRSDKLKLAESSEGTYTLAVNNTGNEPASLEQLTVVEGKD
NKPLSENLNFTLQNEHVDAGAWRYQLIRKDGEFRLHNPVKEQELSDKLGKAEAKKQAEKDNAQSLDALIAAGRDAVE
KTESVAEPARQAGGENVGIMQAEEEKKRVQADKDTALAKQREAETRPATTAFPRARRARRDLPQLQPQPQPQPQRDL
ISRYANSGLSEFSATLNSVFAVQDELDRVFAEDRRNAVWTSGIRDTKHYRSQDFRAYRQQTDLRQIGMQKNLGSGRV
GILFSHNRTENTFDDGIGNSARLAHGAVFGQYGIDRFYIGISAGAGFSSGSLSDGIGGKIRRRVLHYGIQARYRAGF
GGFGIEPHIGATRYFVQKADYRYENVNIATPGLAFNRYRAGIKADYSFKPAQHISITPYLSLSYTDAASGKVRTRVN
TAVLAQDFGKTRSAEWGVNAEIKGFTLSLHAAAAKGPQLEAQHSAGIKLGYRW*
```

To make this construct, the clone pET911LOmpA (see below) was digested with the NheI and XhoI restriction enzymes and the fragment corresponding to the vector carrying the OmpA leader sequence was purified (pET-LOmpA). The ORF1 gene coding for the mature protein was amplified using the oligonucleotides ORF1-For and ORF1-Rev (including the NheI and XhoI restriction sites, respectively), digested with NheI and XzoI and ligated to the purified pETOmpA fragment (see FIG. 1). An additional AS dipeptide was introduced by the NheI site.

All three forms of the protein were expressed. The His-tagged protein could be purified and was confirmed as surface exposed, and possibly secreted (see FIG. 3). The protein was used to immunise mice, and the resulting sera gave excellent results in the bactericidal assay.

ORF1LOmpA was purified as total membranes, and was localised in both the inner and outer membranes. Unexpectedly, sera raised against ORF1LOmpA show even better ELISA and anti-bactericidal properties than those raised against the His-tagged protein.

ORF1L was purified as outer membranes, where it is localised.

Example 7

Protein 911 and its Leader Peptide

Protein 911 from *N. meningitidis* (serogroup B, strain MC58) has the following sequence (SEQ ID NO:74):

```
  1 MKKNILEFWV GLFVLIGAAA VAFLAFRVAG GAAFGGSDKT YAVYADFGDI
 51 GGLKVNAPVK SAGVLVGRVG AIGLDPKSYQ ARVRLDLDGK YQFSSDVSAQ
101 ILTSGLLGEQ YIGLQQGGDT ENLAAGDTIS VTSSAMVLEN LIGKFHTSFA
151 EKNADGGNAE KAAE*
```

The leader peptide is underlined.

Three expression strategies have been used for 911:

1) 911 with its own leader peptide but without any fusion partner ('911L');

2) 911 with the leader peptide from *E. coli* OmpA ('911LOmpA').

To make this construct, the entire sequence encoding the OmpA leader peptide was included in the 5'-primer as a tail (primer 911LOmpA Forward). A NheI restriction site was inserted between the sequence coding for the OmpA leader peptide and the 911 gene encoding the predicted mature protein (insertion of one amino acid, a serine), to allow the use of this construct to clone different genes downstream the OmpA leader peptide sequence.

3) 911 with the leader peptide (MKYLLPTAAAGLL-LAAQPAMA (SEQ ID NO:75)) from *Erwinia carotovora* PelB ('911LpelB').

To make this construct, the 5'-end PCR primer was designed downstream from the leader sequence and included the NcoI restriction site in order to have the 911 fused directly to the PelB leader sequence; the 3'-end primer included the STOP codon. The expression vector used was pET22b+ (Novagen), which carries the coding sequence for the PelB leader peptide. The NcoI site introduces an additional methionine after the PelB sequence.

All three forms of the protein were expressed. ELISA titres were highest using 911L, with 919LOmpA also giving good results.

Example 8

ORF46

The complete ORF46 protein from *N. meningitidis* (serogroup B, strain 2996) has the following sequence (SEQ ID NO:76):

```
  1 LGISRKISLI LSILAVCLPM HAHASDLAND SFIRQVLDRQ HFEPDGKYHL
 51 FGSRGELAER SGHIGLGKIQ SHQLGNLMIQ QAAIKGNIGY IVRFSDHGHE
101 VHSPFDNHAS HSDSDEAGSP VDGFSLYRIH WDGYEHHPAD GYDGPQGGGY
151 PAPKGARDIY SYDIKGVAQN IRLNLTDNRS TGQRLADRFH NAGSMLTQGV
201 GDGFKRATRY SPELDRSGNA AEAFNGTADI VKNIIGAAGE IVGAGDAVQG
251 ISEGSNIAVM HGLGLLSTEN KMARINDLAD MAQLKDYAAA AIRDWAVQNP
301 NAAQGIEAVS NIFMAAIPIK GIGAVRGKYG LGGITAHPIK RSQMGAIALP
351 KGKSAVSDNF ADAAYAKYPS PYHSRNIRSN LEQRYGKENI TSSTVPPSNM
401 KNVKLADQRH PKTGVPFDGK GFPNFEKHVK YDTKLDIQEL SGGGIPKAKP
451 VSDAKPRWEV DRKLNKLTTR EQVEKNVQEI RNGNKNSNFS QHAQLEREIN
501 KLKSADEINF ADGMGKFTDS MNDKAFSRLV KSVKENGFTN PVVEYVEING
551 KAYIVRGNNR VFAAEYLGRI HELKFKKVDF PVPNTSWKNP TDVLNESGNV
601 KRPRYRSK*
```

The leader peptide is underlined.

The sequences of ORF46 from other strains can be found in WO00/66741.

Three expression strategies have been used for ORF46:

1) ORF46 with its own leader peptide but without any fusion partner ('ORF46-2L');
2) ORF46 without its leader peptide and without any fusion partner ('ORF46-2'), with the leader peptide omitted by designing the 5'-end amplification primer downstream from the predicted leader sequence (SEQ ID NO:77):

```
  1 SDLANDSFIR QVLDRQHFEP DGKYHLFGSR GELAERSGHI GLGKIQSHQL
 51 GNLMIQQAAI KGNIGYIVRF SDHGHEVHSP FDNHASHSDS DEAGSPVDGF
101 SLYRIHWDGY EHHPADGYDG PQGGGYPAPK GARDIYSYDI KGVAQNIRLN
151 LTDNRSTGQR LADRFHNAGS MLTQGVGDGF KRATRYSPEL DRSGNAAEAF
201 NGTADIVKNI IGAAGEIVGA GDAVQGISEG SNIAVMHGLG LLSTENKMAR
251 INDLADMAQL KDYAAAAIRD WAVQNPNAAQ GIEAVSNIFM AAIPIKGIGA
301 VRGKYGLGGI TAHPIKRSQM GAIALPKGKS AVSDNFADAA YAKYPSPYHS
351 RNIRSNLEQR YGKENITSST VPPSNGKNVK LADQRHPKTG VPFDGKGFPN
401 FEKHVKYDTK LDIQELSGGG IPKAKPVSDA KPRWEVDRKL NKLTTREQVE
451 KNVQEIRNGN KNSNFSQHAQ LEREINKLKS ADEINFADGM GKFTDSMNDK
501 AFSRLVKSVK ENGFTNPVVE YVEINGKAYI VRGNNRVFAA EYLGRIHELK
551 FKKVDFPVPN TSWKNPTDVL NESGNVKRPRYRSK*
```

3) ORF46 as a truncated protein, consisting of the first 433 amino acids ('ORF46.1L'), constructed by designing PCR primers to amplify a partial sequence corresponding to aa 1-433.

A STOP codon was included in the 3'-end primer sequences.

ORF46-2L is expressed at a very low level to *E. coli*. Removal of its leader peptide (ORF46-2) does not solve this problem. The truncated ORF46.1L form (first 423 amino acids, which are well conserved between serogroups and species), however, is well-expressed and gives excellent results in ELISA test and in the bactericidal assay.

ORF46.1 has also been used as the basis of hybrid proteins. It has been fused with 287, 919, and ORF1. The hybrid proteins were generally insoluble, but gave some good ELISA and bactericidal results (against the homologous 2996 strain):

| Protein | ELISA | Bactericidal Ab |
|---|---|---|
| Orf1-Orf46.1-His | 850 | 256 |
| 919-Orf46.1-His | 12900 | 512 |
| 919-287-Orf46-His | n.d. | n.d. |
| Orf46.1-287His | 150 | 8192 |
| Orf46.1-919His | 2800 | 2048 |
| Orf46.1-287-919His | 3200 | 16384 |

For comparison, 'triple' hybrids of ORF46.1, 287 (either as a GST fusion, or in ΔG287 form) and 919 were constructed and tested against various strains (including the homologous 2996 strain) versus a simple mixture of the three antigens. FCA was used as adjuvant:

| | 2996 | BZ232 | MC58 | NGH38 | F6124 | BZ133 |
|---|---|---|---|---|---|---|
| Mixture | 8192 | 256 | 512 | 1024 | >2048 | >2048 |
| ORF46.1-287-919his | 16384 | 256 | 4096 | 8192 | 8192 | 8192 |
| ΔG287-919-ORF46.1his | 8192 | 64 | 4096 | 8192 | 8192 | 16384 |
| ΔG287-ORF46.1-919his | 4096 | 128 | 256 | 8192 | 512 | 1024 |

Again, the hybrids show equivalent or superior immunological activity.

Hybrids of two proteins (strain 2996) were compared to the individual proteins against various heterologous strains:

| | 1000 | MC58 | F6124 (MenA) |
|---|---|---|---|
| ORF46.1-His | <4 | 4096 | <4 |
| ORF1-His | 8 | 256 | 128 |
| ORF1-ORF46.1-His | 1024 | 512 | 1024 |

Again, the hybrid shows equivalent or superior immunological activity.

Example 9

Protein 961

The complete 961 protein from *N. meningitidis* (serogroup B, strain MC58) has the following sequence (SEQ ID NO:78):

```
  1 MSMKHFPAKV LTTAILATFC SGALAATSDD DVKKAATVAI VAAYNNGQEI
 51 NGFKAGETIY DIGEDGTITQ KDATAADVEA DDFKGLGLKK VVTNLTKTVN
101 ENKQNVDAKV KAAESEIEKL TTKLADTDAA LADTDAALDE TTNALNKLGE
151 NITTFAEETK TNIVKIDEKL EAVADTVDKH AEAFNDIADS LDETNTKADE
201 AVKTANEAKQ TAEETKQNVD AKVKAAETAA GKAEAAAGTA NTAADKAEAV
251 AAKVTDIKAD IATNKADIAK NSARIDSLDK NVANLRKETR QGLAEQAALS
301 GLFQPYNVGR FNVTAAVGGY KSESAVAIGT GFRFTENFAA KAGVAVGTSS
351 GSSANYHVGV NYEW*
```

The leader peptide is underlined.

Three approaches to 961 expression were used:

1) 961 using a GST fusion, following WO99/572810 ('GST961');
2) 961 with its own leader peptide but without any fusion partner ('961L'); and
3) 961 without its leader peptide and without any fusion partner. ('961$^{untagged}$'), with the leader peptide omitted by designing the 5'-end PCR primer downstream from the predicted leader sequence.

All three forms of the protein were expressed. The GST-fusion protein could be purified and antibodies against it confirmed that 961 is surface exposed (FIG. 4). The protein was used to immunise mice, and the resulting sera gave excellent results in the bactericidal assay. 961L could also be purified and gave very high ELISA titres.

Protein 961 appears to be phase variable. Furthermore, it is not found in all strains of *N. meningitidis*.

Example 10

Protein 287

Protein 287 from *N. meningitidis* (serogroup B, strain 2996) has the following sequence (SEQ ID NO:79):

```
  1 MFERSVIAMA CIFALSACGG GGGGSPDVKS ADTLSKPAAP VVAEKETEVK

51 EDAPQAGSQG QGAPSTQGSQ DMAAVSAENT GNGGAATTDK PKNEDEGPQN

101 DMPQNSAESA NQTGNNQPAD SSDSAPASNP APANGGSNFG RVDLANGVLI

151 DGPSQNITLT HCKGDSCNGD NLLDEEAPSK SEFENLNESE RIEKYKKDGK

201 SDKFTNLVAT AVQANGTNKY VIIYKDKSAS SSSARFRRSA RSRRSLPAEM

251 PLIPVNQADT LIVDGEAVSL TGHSGNIFAP EGNYRYLTYG AEKLPGGSYA

301 LRVQGEPAKG EMLAGTAVYN GEVLHFHTEN GRPYPTRGRF AAKVDFGSKS

351 VDGIIDSGDD LHMGTQKFKA AIDGNGFKGT WTENGGGDVS GRFYGPAGEE

401 VAGKYSYRPT DAEKGGFGVF AGKKEQD*
```

The leader peptide is shown underlined.

Figure 5:
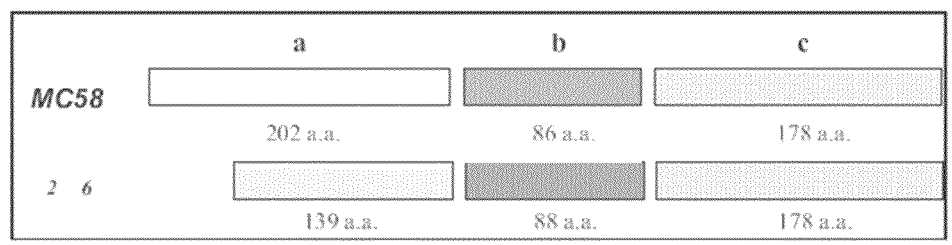
FIG. 5 shows domains of protein 287 and FIGS. 6 & 7 (SEQ ID NO:619 and 620) show deletions within domain A.

The sequences of 287 from other strains can be found in FIGS. 5 and 15 of WO00/66741.

Example 9 of WO99/57280 discloses the expression of 287 as a GST-fusion in *E. coli*.

A number of further approaches to expressing 287 in *E. coli* have been used, including:
1) 287 as a His-tagged fusion ('287-His');
2) 287 with its own leader peptide but without any fusion partner ('287L');
3) 287 with the ORF4 leader peptide and without any fusion partner ('287LOrf4'); and
4) 287 without its leader peptide and without any fusion partner ('287$^{untagged}$') (SEQ ID NO:80):

```
  1 CGGGGGGSPD VKSADTLSKP AAPVVAEKET EVKEDAPQAD SQGQGAPSTQ

51 GSQDMAAVSA ENTGNGGAAT TDKPKNEDEG PQNDMPQNSA ESANQTGNNQ

101 PADSSDSAPA SNPAPANGGS NFGRVDLANG VLIDGPSQNI TLTHCKGDSC

151 NGDNLLDEEA PSKSEFENLN ESERIEKYKK DGKSDKFTNL VATAVQANGT

201 NKYVIIYKDK SASSSSARFR RSARSRRSLP AEMPLIPVNQ ADTLIVDGEA

251 VSLTGHSGNI FAPEGNYRYL TYGAEKLPGG SYALRVQGEP AKGEMLAGTA

301 VYNGEVLHFH TENGRPYPTR GRFAAKVDFG SKSVDGIIDS GDDLHMGPQK

351 FKAAIDGNGF KGTWTENGGG DVSGRFYGPA GEEVAGKYSY RPTDAEKGGF

401 GVFAGKKEQD *
```

All these proteins could be expressed and purified.

'287L' and '287LOrf4' were confirmed as lipoproteins.

Figure 2:
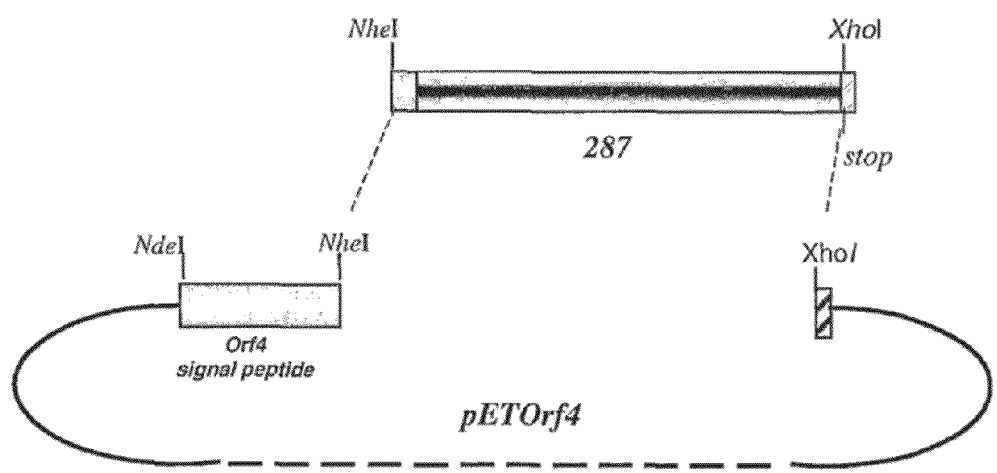
FIG. 2 shows a construct used to express 287 protein using a heterologous leader peptide.

As shown in FIG. 2, '287LOrf4' was constructed by digesting 919LOrf4 with NheI and XhoI. The entire ORF4 leader peptide was restored by the addition of a DNA sequence coding for the missing amino acids, as a tail, in the 5'-end primer (287LOrf4 for), fused to 287 coding sequence. The 287 gene coding for the mature protein was amplified using the oligonucleotides 287LOrf4 For and Rev (including the NheI and XhoI sites, respectively), digested with NheI and XhoI and ligated to the purified pBTOrf4 fragment.

Example 11

Further Non-Fusion Proteins with/without Native Leader Peptides

A similar approach was adopted for *E. coli* expression of further proteins from WO99/24578, WO99/36544 and WO99/57280.

The following were expressed without a fusion partner: 008, 105, 117-1, 121-1, 122-1, 128-1, 148, 216, 243, 308, 593, 652, 726, 982, and Orf143-1. Protein 117-1 was confirmed as surface-exposed by FACS and gave high ELISA titres.

The following were expressed with the native leader peptide but without a fusion partner: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 926, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1. These proteins are given the suffix 'L'.

His-tagged protein 760 was expressed with and without its leader peptide. The deletion of the signal peptide greatly increased expression levels. The protein could be purified most easily using 2M urea for solubilisation.

His-tagged protein 264 was well-expressed using its own signal peptide, and the 30 kDa protein gave positive Western blot results.

All proteins were successfully expressed.

The localisation of 593, 121-1, 128-1, 593, 726, and 982 in the cytoplasm was confirmed.

The localisation of 920-1L, 953L, ORF9-1L, ORF85-2L, ORF97-1L, 570L, 580L and 664L in the periplasm was confirmed.

The localisation of ORF40L in the outer membrane, and 008 and 519-1L in the inner membrane was confirmed. ORF25L, ORF4L, 406L, 576-1L were all confirmed as being localised in the membrane.

Protein 206 was found not to be a lipoprotein.

ORF25 and ORF40 expressed with their native leader peptides but without fusion partners, and protein 593 expressed without its native leader peptide and without a fusion partner, raised good anti-bactericidal sera. Surprisingly, the forms of ORF25 and ORF40 expressed without fusion partners and using their own leader peptides (i.e. 'ORF25L' and 'ORF40L') give better results in the bactericidal assay than the fusion proteins.

Proteins 920L and 953L were subjected to N-terminal sequencing, giving HRVWVETAH (SEQ ID NO:81) and ATYKVDEYHANARFAF (SEQ ID NO:82), respectively. This sequencing confirms that the predicted leader peptides were cleaved and, when combined with the periplasmic location, confirms that the proteins are correctly processed and localised by E. coli when expressed from their native leader peptides.

The N-terminal sequence of protein 519.1L localised in the inner membrane was MEFFIILLA (SEQ ID NO:83), indicating that the leader sequence is not cleaved. It may therefore function as both an uncleaved leader sequence and a transmembrane anchor in a manner similar to the leader peptide of PBP1 from N. gonorrhoeae [Ropp & Nicholas (1997) J. Bact. 179:2783-2787.].Indeed the N-terminal region exhibits strong hydrophobic character and is predicted by the Tmpred. program to be transmembrane.

Example 12

Lipoproteins

The incorporation of palmitate in recombinant lipoproteins was demonstrated by the method of Kraft et. al. [J. Bact. (1998) 180:3441-3447.]. Single colonies harbouring the plasmid of interest were grown overnight at 37° C. in 20 ml of LB/Amp (100 µg/ml) liquid culture. The culture was diluted to an $OD_{550}$ of 0.1 in 5.0 ml of fresh medium LB/Amp medium containing 5 µC/ml [$^3$H] palmitate (Amersham). When the $OD_{550}$ of the culture reached 0.4-0.8, recombinant lipoprotein was induced for 1 hour with IPTG (final concentration 1.0 mM). Bacteria were harvested by centrifugation in a bench top centrifuge at 2700 g for 15 min and washed twice with 1.0 ml cold PBS. Cells were resuspended in 120 µl of 20 mM Tris-HCl (pH 8.0), 1 mM EDTA, 1.0% w/v SDS and lysed by boiling for 10 min. After centrifugation at 13000 g for 10 min the supernatant was collected and proteins precipitated by the addition of 1.2 ml cold acetone and left for 1 hour at −20° C. Protein was pelleted by centrifugation at 13000 g for 10 min and resuspended in 20-50 µl (calculated to standardise loading with respect to the final O.D of the culture) of 1.0% w/v SDS. An aliquot of 15 µl was boiled with 5 µl of SDS-PAGE sample buffer and analysed by SDS-PAGE. After electrophoresis gels were fixed for 1 hour in 10% v/v acetic acid and soaked for 30 minutes in Amplify solution (Amersham). The gel was vacuum-dried under heat and exposed to Hyperfilm (Kodak) overnight −80° C.

Incorporation of the [$^3$H] palmitate label, confirming lipidation, was found for the following proteins: Orf4L, Orf25L, 287L, 287LOrf4, 406.L, 576L, 926L, 919L and 919LOrf4.

Example 13

Domains in 287

Based on homology of different regions of 287 to proteins that belong to different functional classes, it was split into three 'domains', as shown in FIG. 5. The second domain shows homology to IgA proteases, and the third domain shows homology to transferrin-binding proteins.

Each of the three 'domains' shows a different degree of sequence conservation between N. meningitidis strains—domain C is 98% identical, domain A is 83% identical, whilst domain B is only 71% identical. Note that protein 287 in strain MC58 is 61 amino acids longer than that of strain 2996. An alignment of the two sequences is shown in FIG. 7, and alignments for various strains are disclosed in WO00/66741 (see FIGS. 5 and 15 therein).

The three domains were expressed individually as C-terminal His-tagged proteins. This was done for the MC58 and 2996 strains, using the following constructs:

287a-MC58 (aa 1-202), 287b-MC58 (aa 203-288), 287c-MC58 (aa 311-488).

287a-2996 (aa 1-139), 287b-2996 (aa 140-225), 287c-2996 (aa 250-427).

To make these constructs, the stop codon sequence was omitted in the 3'-end primer sequence. The 5' primers included the NheI restriction site, and the 3' primers included a XhoI as a tail, in order to direct the cloning of each amplified fragment into the expression vector pET21b+ using NdeI-XhoI, NheI-XhoI, or NdeI-HindIII restriction sites.

All six constructs could be expressed, but 287b-MC8 required denaturation and refolding for solubilisation.

Deletion of domain A is described below ('Δ4 287-His').

Immunological data (serum bactericidal assay) were also obtained using the various domains from strain 2996, against the homologous and heterologous MenB strains, as well as MenA (F6124 strain) and MenC (BZ133 strain):

|  | 2996 | BZ232 | MC58 | NGH38 | 394/98 | MenA | MenC |
| --- | --- | --- | --- | --- | --- | --- | --- |
| 287-His | 32000 | 16 | 4096 | 4096 | 512 | 8000 | 16000 |
| 287(B)-His | 256 | — | — | — | — | 16 | — |
| 287(C)-His | 256 | — | 32 | 512 | 32 | 2048 | >2048 |
| 287(B-C)-His | 64000 | 128 | 4096 | 64000 | 1024 | 64000 | 32000 |

Using the domains of strain MC58, the following results were obtained:

|  | MC58 | 2996 | BZ232 | NGH38 | 394/98 | MenA | MenC |
| --- | --- | --- | --- | --- | --- | --- | --- |
| 287-His | 4096 | 32000 | 16 | 4096 | 512 | 8000 | 16000 |
| 287(B)-His | 128 | 128 | — | — | — | — | 128 |
| 287(C)-His | — | 16 | — | 1024 | — | 512 | — |
| 287(B-C)-His | 16000 | 64000 | 128 | 64000 | 512 | 64000 | >8000 |

Example 14

Deletions in 287

Figure 6:
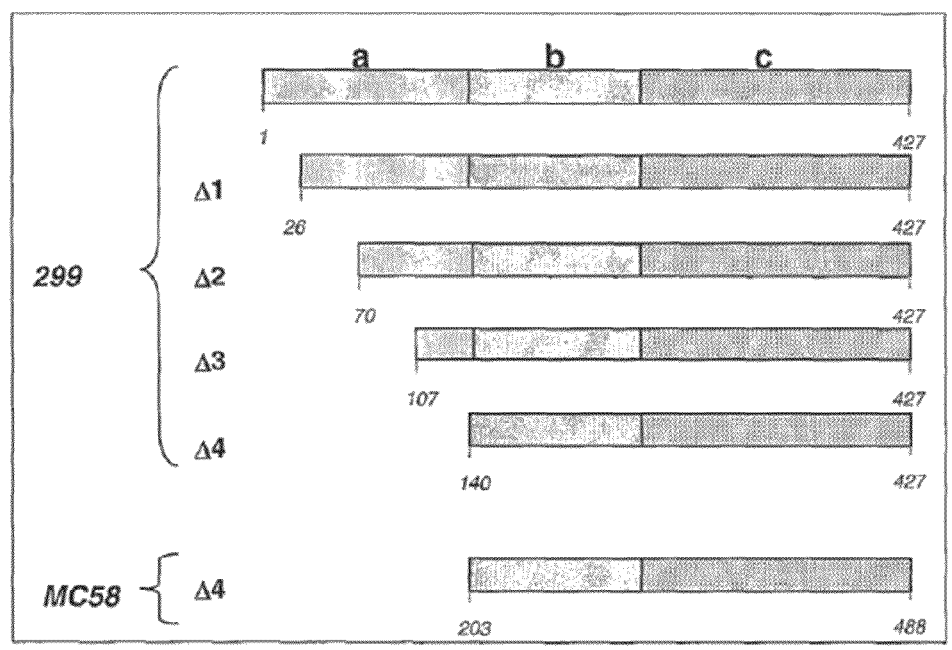
FIG. 6 shows deletions within domain A of protein 287.

As well as expressing individual domains, 287 was also expressed (as a C-terminal His-tagged protein) by making progressive deletions within the first domain. These Four deletion mutants of protein 287 from strain 2996 were used (FIG. 6):

1) '287-His', consisting of amino acids 18-427 (i.e. leader peptide deleted);
2) 'Δ1 287-His', consisting of amino acids 26-427;
3) 'Δ2 287-His', consisting of amino acids 70-427;
4) 'Δ3 287-His', consisting of amino acids 107-427; and
5) 'Δ4 287-His', consisting of amino acids 140-427 (=287-bc).

The 'Δ4' protein was also made for strain MC58 ('Δ4 287MC58-His'; aa 203-488).

The constructs were made in the same way as 287a/b/c, as described above.

All six constructs could be expressed and protein could be purified. Expression of 287-His was, however, quite poor.

Expression was also high when the C-terminal His-tags were omitted.

Immunological data (serum bactericidal assay) were also obtained using the deletion mutants, against the homologous (2996) and heterologous MenB strains, as well as MenA (F6124 strain) and MenC (BZ133 strain):

|  | 2996 | BZ232 | MC58 | NGH38 | 394/98 | MenA | MenC |
|---|---|---|---|---|---|---|---|
| 287-his | 32000 | 16 | 4096 | 4096 | 512 | 8000 | 16000 |
| Δ1 287-His | 16000 | 128 | 4096 | 4096 | 1024 | 8000 | 16000 |
| Δ2 287-His | 16000 | 128 | 4096 | >2048 | 512 | 16000 | >8000 |
| Δ3 287-His | 16000 | 128 | 4096 | >2048 | 512 | 16000 | >8000 |
| Δ4 287-His | 64000 | 128 | 4096 | 64000 | 1024 | 64000 | 32000 |

The same high activity for the Δ4 deletion was seen using the sequence from strain MC58.

As well as showing superior expression characteristics, therefore, the mutants are immunologically equivalent or superior.

Example 15

Poly-Glycine Deletions

The 'Δ1 287-His' construct of the previous example differs from 287-His and from '287$^{untagged}$' only by a short N-terminal deletion (GGGGGGS) (SEQ ID NO:631). Using an expression vector which replaces the deleted serine with a codon present in the Nhe cloning site, however, this amounts to a deletion only of $(Gly)_6$ (SEQ ID NO:632). Thus, the deletion of this $(Gly)_6$ sequence (SEQ ID NO:632) has been shown to have a dramatic effect on protein expression.

The protein lacking the N-terminal amino acids up to GGGGGG (SEQ ID NO: 632) is called 'ΔG 287'. In strain MC58, its sequence (leader peptide underlined) is (SEQ ID NO: 84):

➡ ΔG287
```
  1  MFKRSVIAMA CIFALSACGG GGGGSPDVKS ADTLSKPAAP VVSEKETEAK

51  EDAPQAGSQG QGAPSAQGSQ DMAAVSEENT GNGGAVTADN PKNEDEVAQN

101  DMPQNAAGTD SSTPNHTPDP NMLAGNMENQ ATDAGESSQP ANQPDMANAA

151  DGMQGDDPSA GGQNAGNTAA QGANQAGNNQ AAGSSDPIPA SNPAPANGGS

201  NFGRVDLANG VLIDGPSQNI TLTHCKGDSC SGNNFLDEEV QLKSEFEKLS

251  DADKISNYKK DGKNDKFVGL VADSVQMKGI NQYIIFYKPK PTSFARFRRS

301  ARSRRSLPAE MPLIPVNQAD TLIVDGEAVS LTGHSGNIFA PEGNYRYLTY

351  GAEKLPGGSY ALRVQGEPAK GEMLAGAAVY NGEVLHFHTE NGRPYPTRGR

401  FAAKVDFGSK SVDGIIDSGD DLHMGTQKFK AAIDGNGFKG TWTENGSGDV

451  SGKFYGPAGE EVAGKYSYRP TDAEKGGFGV FAGKKEQD*
```

ΔG287, with or without His-tag ('ΔG287-His' and 'ΔG287K', respectively), are expressed at very good levels in comparison with the '287-His' or '287$^{untagged}$'.

On the basis of gene variability data, variants of ΔG287-His were expressed in *E. coli* from a number of MenB strains, in particular from strains 2996, MC58, 1000, and BZ232. The results were also good.

It was hypothesised that poly-Gly deletion might be a general strategy to improve expression. Other MenB lipoproteins containing similar $(Gly)_n$ motifs (near the N-terminus, downstream of a cysteine) were therefore identified, namely Tbp2 (NMB0460) (SEQ ID NO:85), 741 (NMB 1870) (SEQ ID NO:86) and 983 (NMB1969) (SEQ ID NO:87):

TBP2 ➡ ΔGTbp2
```
  1  MNNPLVNQAA MVLPVFLLSA CLGGGGSFDL DSVDTEAPRP APKYQDVFSE

51  KPQAQKDQGG YGFAMRLKRR NWYPQAKEDE VKLDESDWEA TGLPDEPKEL

101  PKRQKSVIEK VETDSDNNIY SSPYLKPSNH QNGNTGNGIN QPKNQAKDYE

151  NFKYVYSGWF YKHAKREFNL KVEPKSAKNG DDGYIFYHGK EPSRQLPASG

201  KITYKGVWHF ATDTKKGQKF REIIQPSKSQ GDRYSGFSGD DGEEYSNKNK

251  STLTDGQEGY GFTSNLEVDF HNKKLTGKLI RNNANTDNNQ ATTTQYYSLE

301  AQVTGNRFNG KATATDKPQQ NSETKEHPFV SDSSSLSGGF FGPQGEELGF
```

```
-continued
351 RFLSDDQKVA VVGSAKTKDK PANGNTAAAS GGTDAAASNG AAGTSSENGK

401 LTTVLDAVEL KLGDKEVQKL DNFSNAAQLV VDGIMIPLLP EASESGNNQA

451 NQGTNGGTAF TRKFDHTPES DKKDAQAGTQ TNGAQTASNT AGDTNGKTKT

501 YEVEVCCSNL NYLKYGMLTR KNSKSAMQAG ESSSQADAKT EQVEQSMFLQ

551 GERTDEKEIP SEQNIVYRGS WYGYIANDKS TSWSGNASNA TSGNRAEFTV

601 NFADKKITGT LTADNRQEAT FTIDGNIKDN GFEGTAKTAE SGFDLDQSNT

651 TRTPKAYITD AKVQGGFYGP KAEELGGWFA YPGDKQTKNA TNASGNSSAT

701 VVFGAKRQQP VR*

741 ➤ ΔG741
  1 VNRTAFCCLS LTTALILTAC SSGGGGVAAD IGAGLADALT APLDHKDKGL

51 QSLTLDQSVR KNEKLKLAAQ GAEKTYGNGD SLNTGKLKND KVSRFDFIRQ

101 IEVDGQLITL ESGEFQVYKQ SHSALTAFQT EQIQDSEHSG KMVAKRQFRI

151 GDIAGEHTSF DKLPEGGRAT YRGTAFGSDD AGGKLTYTID FAAKQGNGKI

201 EHLKSPELNV DLAAADIKPD GKRHAVISGS VLYNQAEKGS YSLGIFGGKA

251 QEVAGSAEVK TVNGIRHIGL AAKQ*

983 ➤ ΔG983
  1 MRTTPTFPTK TFKPTAMALA VATTLSACLG GGGGGTSAPD FNAGGTGIGS

51 NSRATTAKSA AVSYAGIKNE MCKDRSMLCA GRDDVAVTDR DAKINAPPPN

101 LHTGDFPNPN DAYKNLINLK PAIEAGYTGR GVEVGIVDTG ESVGSISFPE

151 LYGRKEHGYN ENYKNYTAYM RKEAPEDGGG KDIEASFDDE AVIETEAKPT

201 DIRHVKEIGH IDLVSHIIGG RSVDGRPAGG IAPDATLHIN NTNDETKNEM

251 MVAAIRNAWV KLGERGVRIV NNSFGTTSRA GTADLFQIAN SEEQYRQALL

301 DYSGGDKTDE GIRLMQQSDY GNLSYHIRNK NNLFIFSTGN DAQAQPNTYA

351 LLPFYEKDAQ KGIITVAGVD RSGEKFKREM YGEPGTEPLE YGSNHCGITA

401 MWCLSAPYEA SVRFTRTNPI QIAGTSFSAP IVTGTAALLL QKYPWMSNDN

451 LRTTLLLTTAQ DIGAVGVDSK FGWGLLDAGK AMNGPASFPF GDFTADTKGT

501 SDIAYSFRND ISGTGGLIKK GGSQLQLHGN NTYTGKTIIE GGSLVLYGNN

551 KSDMRVETKG ALIYNGAASG GSLNSDGIVY LADTDQSGAN ETVHIKGSLQ

601 LDGKGTLYTR LGKLLKVDGT AIIGGKLYMS ARGKGAGYLN STGRRVPFLS

651 AAKIGQDYSF FTNIETDGGL LASLDSVEKT AGSEGDTLSY YVRRGNAART

701 ASAAAHSAPA GLKHAVEQGG SNLENLMVEL DASESSATPE TVETAAADRT

751 DMPGIRPYGA TFRAAAAVQH ANAADGVRIF NSLAATVYAD STAAHADMQG

801 RRLKAVSDGL DHNGTGLRVI AQTQQDGGTW EQGGVEGKMR GSTQTVGIAA

851 KTGENTTAAA TLGMGRSTWS ENSANAKTDS ISLFAGIRHD AGDIGYLKGL

901 FSYGRYKNSI SRSTGADEHA EGSVNGTLMQ LGALGGVNVP FAATGDLTVE

951 GGLRYDLLKQ DAFAEKGSAL GWSGNSLTEG TLVGLAGLKL SQPLSDKAVL

1001 FATAGVERDL NGRDYTVTGG FTGATAATGK TGARNMPHTR LVAGLGADVE

1051 FGNGWNGLAR YSYAGSKQYG NHSGRVGVGY RF*
```

Tbp2 and 741 genes were from strain MC58; 983 and 287 genes were from strain 2996. These were cloned in pET vector and expressed in *E. coli* without the sequence coding for their leader peptides or as "ΔG forms", both fused to a C-terminal His-tag. In each case, the same effect was seen—expression was good in the clones carrying the deletion of the poly-glycine stretch, and poor or absent if the glycines were present in the expressed protein:

| ORF | Express. | Purification | Bact. Activity |
|---|---|---|---|
| 287-His(2996) | +/− | + | + |
| '287^untagged'(2996) | +/− | nd | nd |
| ΔG287-His(2996) | + | + | + |
| ΔG287K(2996) | + | + | + |
| ΔG287-His(MC58) | + | + | + |
| ΔG287-His(1000) | + | + | + |
| ΔG287-His(BZ232) | + | + | + |
| Tbp2-His(MC58) | +/− | nd | nd |
| ΔGTbp2-His(MC58) | + | + | |
| 741-His(MC58) | +/− | nd | nd |
| ΔG741-His(MC58) | + | + | |
| 983-His (2996) | | | |
| ΔG983-His (2996) | + | + | |

Figure 13:
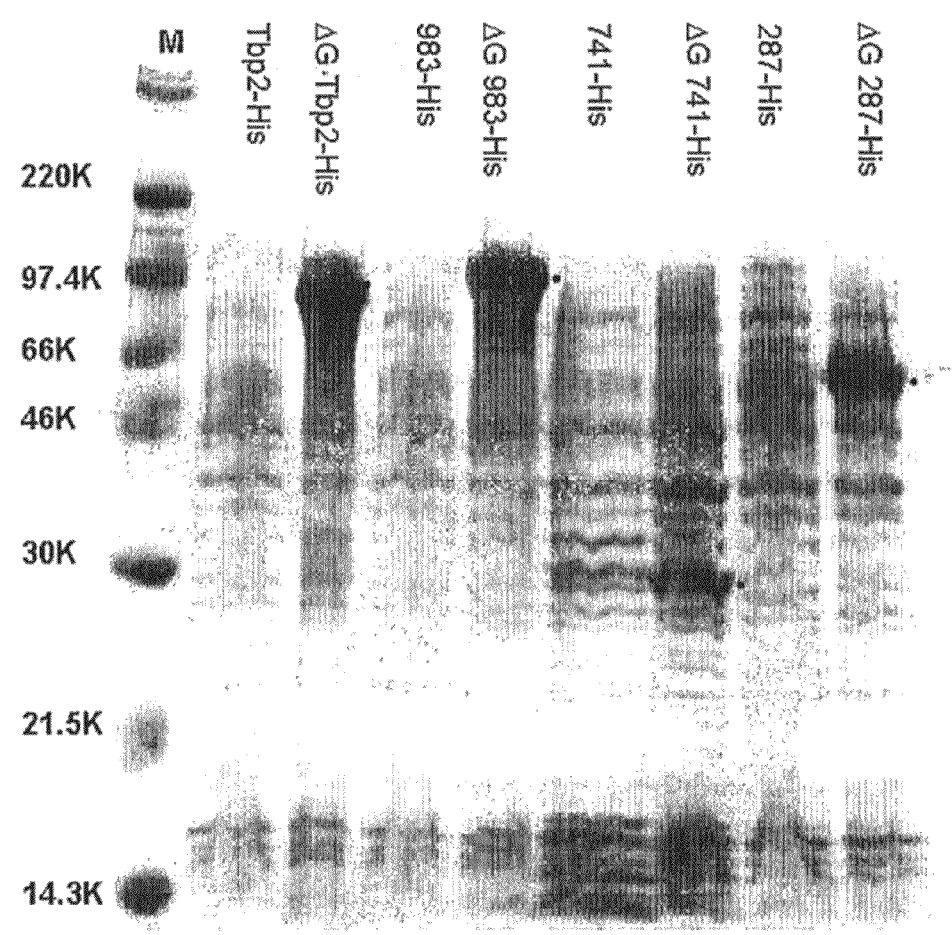
FIG. 13 shows SDS-PAGE of ΔG proteins. Dots show the main recombinant product.

SDS-PAGE of the proteins is shown in FIG. 13.

ΔG287 and Hybrids

ΔG287 proteins were made and purified for strains MC58, 1000 and BZ232. Each of these gave high ELISA titres and also serum bactericidal titres of >8192. ΔG287K, expressed from pET-24b, gave excellent titres in ELISA and the serum bactericidal assay. ΔG287-ORF46.1K may also be expressed in pET-24b.

ΔG287 was also fused directly in-frame upstream of 919 (SEQ ID NOS:88 and 89), 953 (SEQ ID NOS:90 and 91), 961 (SEQ ID NOS:92 and 93) (sequences shown below) and ORF46.1:

```
ΔG287-919
   1 ATGGCTAGCC CCGATGTTAA ATCGGCGGAC ACGCTGTCAA AACCGGCCGC
  51 TCCTGTTGTT GCTGAAAAAG AGACAGAGGT AAAAGAAGAT GCGCCACAGG
 101 CAGGTTCTCA AGGACAGGGC GCGCCATCCA CACAAGGCAG CCAAGATATG
 151 GCGGCAGTTT CGGCAGAAAA TACAGGCAAT GGCGGTGCGG CAACAACGGA
 201 CAAACCCAAA AATGAAGACG AGGGACCGCA AATGATATG CCGCAAAATT
 251 CCGCCGAATC CGCAAATCAA ACAGGGAACA ACCAACCCGC CGATTCTTCA
 301 GATTCCGCCC CCGCGTCAAA CCCTGCACCT GCGAATGGCG GTAGCAATTT
 351 TGGAAGGGTT GATTTGGCTA ATGGCGTTTT GATTGATGGG CCGTCGCAAA
 401 ATATAACGTT GACCCACTGT AAAGGCGATT CTTGTAATGG TGATAATTTA
 451 TTGGATGAAG AAGCACCGTC AAAATCAGAA TTTGAAAATT TAAATGAGTC
 501 TGAACGAATT GAGAAATATA AGAAAGATGG GAAAAGCGAT AAATTTACTA
 551 ATTTGGTTGC GACAGCAGTT CAAGCTAATG GAACTAACAA ATATGTCATC
 601 ATTTATAAAG ACAAGTCCGC TTCATCTTCA TCTGCGCGAT TCAGGCGTTC
 651 TGCACGGTCG AGGAGGTCGC TTCCTGCCGA GATGCCGCTA ATCCCCGTCA
 701 ATCAGGCGGA TACGCTGATT GTCGATGGGG AAGCGGTCAG CCTGACGGGG
 751 CATTCCGGCA ATATCTTCGC GCCCGAAGGG AATTACCGGT ATCTGACTTA
 801 CGGGGCGGAA AAATTGCCCG GCGGATCGTA TGCCCTCCGT GTGCAAGGCG
 851 AACCGGCAAA AGGCGAAATG CTTGCTGGCA CGGCCGTGTA CAACGGCGAA
 901 GTGCTGCATT TTCATACGGA AAACGGCCGT CCGTACCCGA CTAGAGGCAG
 951 GTTTGCCGCA AAAGTCGATT TCGGCAGCAA ATCTGTGGAC GGCATTATCG
1001 ACAGCGGCGA TGATTTGCAT ATGGGTACGC AAAAATTCAA AGCCGCCATC
1051 GATGGAAACG GCTTTAAGGG GACTTGGACG GAAAATGGCG GCGGGGATGT
1101 TTCCGGAAGG TTTTACGGCC CGGCCGGCGA GGAAGTGGCG GGAAAATACh
1151 GCTATCGCCC GACAGATGCG GAAAAGGGCG GATTCGGCGT GTTTGCCGGC
1201 AAAAAAGAGC AGGATGGATC CGGAGGAGGA GGATGCCAAA GCAAGAGCAT
1251 CCAAACCTTT CCGCAACCCG ACACATCCGT CATCAACGGC CCGGACCGGC
1301 CGGTCGGCAT CCCCGACCCC GCCGGAACGA CGGTCGGCGG CGGCGGGGCC
```

-continued

```
1351 GTCTATACCG TTGTACCGCA CCTGTCCCTG CCCCACTGGG CGGCGCAGGA

1401 TTTCGCCAAA AGCCTGCAAT CCTTCCGCCT CGGCTGCGCC AATTTGAAAA

1451 ACCGCCAAGG CTGGCAGGAT GTGTGCGCCC AAGCCTTTCA AACCCCCGTC

1501 CATTCCTTTC AGGCAAAACA GTTTTTTGAA CGCTATTTCA CGCCGTGGCA

1551 GGTTGCAGGC AACGGAAGCC TTGCCGGTAC GGTTACCGGC TATTACGAGC

1601 CGGTGCTGAA GGGCGACGAC AGGCGGACGG CACAAGCCCG CTTCCCGATT

1651 TACGGTATTC CCGACGATTT TATCTCCGTC CCCCTGCCTG CCGGTTTGCG

1701 GAGCGGAAAA GCCCTTGTCC GCATCAGGCA GACGGGAAAA AACAGCGGCA

1751 CAATCGACAA TACCGGCGGC ACACATACCG CCGACCTCTC CCGATTCCCC

1801 ATCACCGCGC GCACAACGGC AATCAAAGGC AGGTTTGAAG GAAGCCGCTT

1851 CCTCCCCTAC CACACGCGCA ACCAAATCAA CGGCGGCGCG CTTGACGGCA

1901 AAGCCCCGAT ACTCGGTTAC GCCGAAGACC CCGTCGAACT TTTTTTTATG

1951 CACATCCAAG GCTCGGGCCG TCTGAAAACC CCGTCCGGCA AATACATCCG

2001 CATCGGCTAT GCCGACAAAA ACGAACATCC CTACGTTTCC ATCGGACGCT

2051 ATATGGCGGA CAAAGGCTAC CTCAAGCTCG GCACACCTC GATGCAGGGC

2101 ATCAAAGCCT ATATGCGGCA AAATCCGCAA CGCCTCGCCG AAGTTTTGGG

2151 TCAAAACCCC AGCTATATCT TTTTCCGCGA GCTTGCCGGA AGCAGCAATG

2201 ACGGTCCCGT CGGCGCACTG GGCACGCCGT TGATGGGGGA ATATGCCGGC

2251 GCAGTCGACC GGCACTACAT TACCTTGGGC GCGCCCTTAT TTGTCGCCAC

2301 CGCCCATCCG GTTACCCGCA AAGCCCTCAA CCGCCTGATT ATGGCGCAGG

2351 ATACCGGCAG CGCGATTAAA GGCGCGGTGC GCGTGGATTA TTTTTGGGGA

2401 TACGGCGACG AAGCCGGCGA ACTTGCCGGC AAACAGAAAA CCACGGGTTA

2451 CGTCTGGCAG CTCCTACCCA ACGGTATGAA GCCCGAATAC CGCCCGTAAC

2501 TCGAG

1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GCQSKSIQTF PQPDTSVING PDRPVGIPDP AGTTVGGGGA

451 VYTVVPHLSL PHWAAQDFAK SLQSFRLGCA NLKNRQGWQD VCAQAPQTPV

501 HSFQAKQFFE RYFTPWQVAG NGSLAGTVTG YYEPVLKGDD RRTAQARFPI

551 YGIPDDFISV PLPAGLRSGK ALVRIRQTGK NSGTIDNTGG THTADLSRFP

601 ITARTTAIKG RFEGSRFLPY HTRNQINGGA LDGKAPILGY AEDPVELFFM

651 HIQGSGRLKT PSGKYIRIGY ADKNEHPYVS IGRYMADKGY LKLGQTSMQG

701 IKAYMRQNPQ RLAEVLGQNP SYIFFRELAG SSNDGPVGAL GTPLMGEYAG

751 AVDRHYITLG APLFVATAHP VTRKALNRLI MAQDTGSAIK GAVRVDYFWG

801 YGDEAGELAG KQKTTGYVWQ LLPNGMKPEY RP*
```

-continued

ΔG287-953

```
   1 ATGGCTAGCC CCGATGTTAA ATCGGCGGAC ACGCTGTCAA AACCGGCCGC
  51 TCCTGTTGTT GCTGAAAAAG AGACAGAGGT AAAAGAAGAT GCCACACAGG
 101 CAGGTTCTCA AGGACAGGGC GCGCCATCCA CACAAGCCCG CCAAGATATG
 151 GCGGCAGTTT CGGCAGAAAA TACAGGCAAT GGCGGTGCGG CAACAACGGA
 201 CAAACCCAAA AATGAAGACG AGGGACCGCA AAATGATATG CCGCAAAATT
 251 CCGCCGAATC CGCAAATCAA ACAGGGAACA ACCAACCCGC CGATTCTTCA
 301 GATTCCGCCC CCGCGTCAAA CCCTGCACCT GCGAATGGCG GTAGCAATTT
 351 TGGAAGGGTT GATTTGGCTA ATGGCGTTTT GATTGATGGG CCGTCGCAAA
 401 ATATAACGTT GACCCACTGT AAAGGCGATT CTTGTAATGG TGATAATTTA
 451 TTGGATGAAG AAGCACCGTC AAAATCAGAA TTTGAAAATT TAAATGAGTC
 501 TGAACGAATT GAGAAATATA AGAAAGATGG GAAAAGCGAT AAATTTACTA
 551 ATTTGGTTGC GACAGCAGTT CAAGCTAATG GAACTAACAA ATATGTCATC
 601 ATTTATAAAG ACAAGTCCGC TTCATCTTCA TCTGCGCGAT TCAGGCGTTC
 651 TGCACGGTCG AGGAGGTCGC TTCCTGCCGA GATGCCGCTA ATCCCCGTCA
 701 ATCAGGCGGA TACGCTGATT GTCGATGGGG AAGCGGTCAG CCTGACGGGG
 751 CATTCCGGCA ATATCTTCGC GCCCGAAGGG AATTACCGGT ATCTGACTTA
 801 CGGGGCGGAA AAATTGCCCG GCGGATCGTA TGCCCTCCGT GTGCAAGGCG
 851 AACCGGCAAA AGGCGAAATG CTTGCTGGCA CGGCCGTGTA CAACGGCGAA
 901 GTGCTGCATT TCATACGGA AAACGGCCGT CCGTACCCGA CTAGAGGCAG
 951 GTTTGCCGCA AAAGTCGATT TCGGCAGCAA ATCTGTGGAC GGCATTATCG
1001 ACAGCGGCGA TGATTTGCAT ATGGGTACGC AAAAATTCAA AGCCGCCATC
1051 GATGGAAACG GCTTTAAGGG GACTTGGACG AAAATGGCG GCGGGGATGT
1101 TTCCGGAAGG TTTTACGGCC CGGCCGGCGA GGAAGTGGCG GGAAAATACA
1151 GCTATCGCCC GACAGATGCG GAAAAGGGCG GATTCGGCGT GTTTGCCGGC
1201 AAAAAGAGC AGGATGGATC CGGAGGAGGA GGAGCCACCT ACAAAGTGGA
1251 CGAATATCAC GCCAACGCCC GTTTCGCCAT CGACCATTTC AACACCAGCA
1301 CCAACGTCGG CGGTTTTTAC GGTCTGACCG GTTCCGTCGA GTTCGACCAA
1351 GCAAAACGCG ACGGTAAAAT CGACATCACC ATCCCCGTTG CCAACCTGCA
1401 AAGCGGTCAG CAACACTTTA CCGACCACCT GAAATCAGCC GGCATTATCG
1451 ATGCCGCCCA ATATCGGAC ATCCGCTTTG TTTCCACCAA ATTCAACTTC
1501 AACGGCAAAA AACTGGTTTC CGTTGACGGC AACCTGACCA TGCACGGCAA
1551 AACCGCCCCC GTCAAACTCA AGCCGAAAAA ATTCAACTGC TACCAAAGCC
1601 CGATGGCGAA AACCGAAGTT TGCGGCGGCG ACTTCAGCAC CACCATCGAC
1651 CGCACCAAAT GGGGCGTGGA CTACCTCGTT AACGTTGGTA TGACCAAAAG
1701 CGTCCGCATC GACATCCAAA TCGAGGCAGC CAAACAATAA CTCGAG
```

```
  1 MASPDVKSAD TLSKPAAPVV AEKETEVKED APQAGSQGQG APSTQGSQDM
 51 AAVSAENTGN GGAATTDKPK NEDEGPQNDM PQNSAESANQ TGNNQPADSS
101 DSAPASNPAP ANGGSNFGRV DLANGVLIDG PSQNITLTHC KGDSCNGDNL
```

-continued

```
151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GATYKVDEYH ANARFAIDHF NTSTNVGGFY GLTGSVEFDQ

451 AKRDGKIDIT IPVANLQSGS QHFTDHLKSA DIFDAAQYPD IRFVSTKFNF

501 NGKKLVSVDG NLTMHGKTAP VKLKAEKFNC YQSPMAKTEV CGGDFSTTID

551 RTKWGVDYLV NVGMTKSVRI DIQIEAAKQ*
```

ΔG287-961
```
   1 ATGGCTAGCC CCGATGTTAA ATCGGCGGAC ACGCTGTCAA AACCGGCCGC

51 TCCTGTTGTT GCTGAAAAAG AGACAGAGGT AAAAGAAGAT GCGCCACAGG

101 CAGGTTCTCA AGGACAGGGC GCGCCATCCA CACAAGGCAG CCAAGATATG

151 GCGGCAGTTT CGGCAGAAAA TACAGGCAAT GGCGGTGCGG CAACAACGGA

201 CAAACCCAAA AATGAAGACG AGGGACCGCA AAATGATATG CCGCAAAATT

251 CCGCCGAATC CGCAAATCAA ACAGGGAACA ACCAACCCGC CGATTCTTCA

301 GATTCCGCCC CCGCGTCAAA CCCTGCACCT GCGAATGGCG GTAGCAATTT

351 TGGAAGGGTT GATTTGGCTA ATGGCGTTTT GATTGATGGG CCGCGTCAAA

401 ATATAACGTT GACCCACTGT AAAGGCGATT CTTGTAATGG TGATAATTTA

451 TTGGATGAAG AAGCACCGTC AAAATCAGAA TTTGAAAATT TAAATGAGTC

501 TGAACGAATT GAGAAATATA AGAAAGATGG GAAAAGCGAT AAATTTACTA

551 ATTTGGTTGC GACAGCAGTT CAAGCTAATG GAACTAACAA ATATGTCATC

601 ATTTATAAAG ACAAGTCCGC TTCATCTTCA TCTGCGCGAT TCAGGCGTTC

651 TGCACGGTCG AGGAGGTCGC TTCCTGCCGA GATGCCGCTA ATCCCCGTCA

701 ATCAGGCGGA TACGCTGATT GTCGATGGGG AAGCGGTCAG CCTGACGGGG

751 CATTCCGGCA ATATCTTCGC GCCCGAAGGG AATTACCGGT ATCTGACTTA

801 CGGGGCGGAA AAATTGCCCG GCGGATCGTA TGCCCTCCGT GTGCAAGGCG

851 AACCGGCAAA AGGCGAAATG CTTGCTGGCA CGGCCGTGTA CAACGGCGAA

901 GTGCTGCATT TTCATACGGA AAACGGCCGT CCGTACCCGA CTAGAGGCAG

951 GTTTGCCGCA AAAGTCGATT TCGGCAGCAA ATCTGTGGAC GGCATTATCG

1001 ACAGCGGCGA TGATTTGCAT ATGGGTACGC AAAAATTCAA AGCCGCCATC

1051 GATGGAAACG GCTTTAAGGG GACTTGGACG GAAAATGGCG GCGGGGATGT

1101 TTCCGGAAGG TTTTACGGCC CGGCCGGCGA GGAAGTGGCG GGAAAATACA

1151 GCTATCGCCC GACAGATGCG GAAAAGGGCG GATTCGGCGT GTTTGCCGGC

1201 AAAAAGAGC AGGATGGATC CGGAGGAGGA GGAGCCACAA ACGACGACGA

1251 TGTTAAAAAA GCTGCCACTG TGGCCATTGC TGCTGCCTAC AACAATGCC

1301 AAAAATTCAA CGGTTTCAAA GCTGGAGAGA CCATCTACGA CATTGATGAA

1351 GACGGCACAA TTACCAAAAA AGACGCAACT GCAGCCGATG TTGAAGCCGA
```

-continued

```
1401 CGACTTTAAA GGTCTGGGTC TGAAAAAGT CGTGACTAAC CTGACCAAAA

1451 CCGTCAATGA AACAAACAA AACGTCGATG CCAAAGTAAA AGCTGCAGAA

1501 TCTGAAATAG AAAAGTTAAC AACCAAGTTA GCAGACACTG ATGCCGCTTT

1551 AGCAGATACT GATGCCGCTC TGGATGCAAC CACCAACGCC TTGAATAAAT

1601 TGGGAGAAAA TATAACGACA TTTGCTGAAG AGACTAAGAC AAATATCGTA

1651 AAAATTGATG AAAATTAGA AGCCGTGGCT GATACCGTCG ACAAGCATGC

1701 CGAAGCATTC AACGATATCG CCGATTCATT GGATGAAACC AACACTAAGG

1751 CAGACGAAGC CGTCAAAACC GCCAATGAAG CCAAACAGAC GGCCGAAGAA

1801 ACCAAACAAA ACGTCGATGC CAAAGTAAAA GCTGCAGAAA CTGCAGCAGG

1851 CAAAGCCGAA GCTGCCGCTG GCACAGCTAA TACTGCAGCC GACAAGGCCG

1901 AAGCTGTCGC TGCLAAAGTT ACCGACATCA AGCTGATAT CGCTACGAAC

1951 AAAGATAATA TTGCTAAAAA AGCAAACAGT GCCGACGTGT ACACCAGAGA

2001 AGAGTCTGAC AGCAAATTTG TCAGAATTGA TGGTCTGAAC GCTACTACCG

2051 AAAAATTGGA CACACGCTTG GCTGCCGCTG AAAAATCCAT TGCCGATCAC

2101 GATACTCGCC TGAACGGTTT GGATAAAACA GTGTCAGACC TGCGCAAAGA

2151 AACCCGCCAA GGCCTTGCAG AACAAGCCGC GCTCTCCGGT CTGTTCCAAC

2201 CTTACAACGT GGGTCGGTTC AATGTAACGG CTGCAGTCGG CGGCTACAAA

2251 TCCGAATCGG CAGTCGCCAT CGGTACCGGC TTCCGCTTTA CCGAAAACTT

2301 TGCCGCCAAA GCAGGCGTGG CAGTCGGCAC TTCGTCCGGT TCTTCCGCAG

2351 CCTACCATGT CGGCGTCAAT TACGAGTGGT AACTCGAG
```

```
  1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GATNDDDVKK AATVAIAAAY NNGQEINGFK AGETIYDIDE

451 DGTITKKDAT AADVEADDFK GLGLKKVVTN LTKTVNENKQ NVDAKVKAAE

501 SEIEKLTTKL ADTDAALADT DAALDATTNA LNKLGENITT FAEETKTNIV

551 KIDEKLEAVA DTVDKHAEAF NDIADSLDET NTKADEAVKT ANEAKQTAEE

601 TKQNVDAKVK AAETAAGKAE AAAGTANTAA DKAEAVAAKV TDIKADIATN

651 KDNIAKKANS ADVYTREESD SKFVRIDGLN ATTEKLDTRL ASAEKSIADH

701 DTRLNGLDKT VSDLRKETRQ GLAEQAALSG LFQPYNVGRF NVTAAVGGYK

751 SESAVAIGTG FRFTENFAAK AGVAVGTSSG SSAAYHVGVN YEW*
```

|  | ELISA | Bactericidal |
| --- | --- | --- |
| ΔG287-953-His | 3834 | 65536 |
| ΔG287-961-His | 108627 | 65536 |

The bactericidal. efficacy (homologous strain) of antibodies raised against the hybrid proteins was compared with antibodies raised against simple mixtures of the component antigens (using 287-GST) for 919 and ORF46.1:

|  | Mixture with 287 | Hybrid with ΔG287 |
| --- | --- | --- |
| 919 | 32000 | 128000 |
| ORF46.1 | 128 | 16000 |

Data for bactericidal activity against heterologous MenB strains and against serotypes A and C were also obtained:

|  | 919 | | ORF46.1 | |
| --- | --- | --- | --- | --- |
| Strain | Mixture | Hybrid | Mixture | Hybrid |
| NGH38 | 1024 | 32000 | — | 16384 |
| MC58 | 512 | 8192 | — | 512 |
| BZ232 | 512 | 512 | — | — |
| MenA (F6124) | 512 | 32000 | — | 8192 |
| MenC (C11) | >2048 | >2048 | — | — |
| MenC (BZ133) | >4096 | 64000 | — | 8192 |

The hybrid proteins with ΔG287 at the N-terminus are therefore immunologically superior to simple mixtures, with ΔG287-ORF46.1 being particularly effective, even against heterologous strains. ΔG287-ORF46.1K may be expressed in pET-24b.

The same hybrid proteins were made using New Zealand strain 394/98 rather than 2996:

```
ΔG287NZ-919 (SEQ ID NOS: 94 and 95)
   1 ATGGCTAGCC CCGATGTCAA GTCGGCGGAC ACGCTGTCAA AACCTGCCGC

51 CCCTGTTGTT TCTGAAAAAG AGACAGAGGC AAAGGAAGAT GCGCCACAGG

101 CAGGTTCTCA AGGACAGGGC GCGCCATCCG CACAAGGCGG TCAAGATATG

151 GCGGCGGTTT CGGAAGAAAA TACAGGCAAT GGCGGTGCGG CAGCAACGGA

201 CAAACCCAAA AATGAAGACG AGGGGGCGCA AAATGATATG CCGCAAAATG

251 CCGCCGATAC AGATAGTTTG ACACCGAATC ACACCCCGGC TTCGAATATG

301 CCGGCCGGAA ATATGGAAAA CCAAGCACCG GATGCCGGGG AATCGGAGCA

351 GCCGGCAAAC CAACCGGATA TGGCAAATAC GGCGGACGGA ATGCAGGGTG

401 ACGATCCGTC GGCAGGCGGG GAAAATGCCG GCAATACGGC TGCCCAAGGT

451 ACAAATCAAG CCGAAAACAA TCAAACCGCC GGTTCTCAAA ATCCTGCCTC

501 TTCAACCAAT CCTAGCGCCA CGAATAGCGG TGGTGATTTT GGAAGGACGA

551 ACGTGGGCAA TTCTGTTGTG ATTGACGGGC CGTCGCAAAA TATAACGTTG

601 ACCCACTGTA AAGGCGATTC TTGTAGTGGC AATAATTTCT TGGATGAAGA

651 AGTACAGCTA AAATCAGAAT TTGAAAAATT AAGTGATGCA GACAAAATAA

701 GTAATTACAA GAAAGATGGG AAGAATGACG GGAAGAATGA TAAATTTGTC

751 GGTTTGGTTG CCGATAGTGT GCAGATGAAG GGAATCAATC AATATATTAT

801 CTTTTATAAA CCTAAACCCA CTTCATTTGC GCGATTTAGG CGTTCTGCAC

851 GGTCGAGGCG GTCGCTTCCG GCCGAGATGC CGCTGATTCC CGTCAATCAG

901 GCGGATACGC TGATTGTCGA TGGGGAAGCG GTCAGCCTGA CGGGGCATTC

951 CGGCAATATC TTCGCGCCCG AAGGGAATTA CCGGTATCTG ACTTACGGGG

1001 CGGAAAAATT GCCCGGCGGA TCGTATGCCC TCCGTGTTCA AGGCGAACCT

1051 TCAAAAGGCG AAATGCTCGC GGGCACGGCA GTGTACAACG GCGAAGTGCT

1101 GCATTTTCAT ACGGAAAACG GCCGTCCGTC CCCGTCCAGA GGCAGGTTTG

1151 CCGCAAAAGT CGATTTCGGC AGCAAATCTG TGGACGGCAT TATCGACAGC

1201 GGCGATGGTT TGCATATGGG TACGCAAAAA TTCAAAGCCG CCATCGATGG

1251 AAACGGCTTT AAGGGGACTT GGACGGAAAA TGGCGGCGGG GATGTTTCCG

1301 GAAAGTTTTA CGGCCCGGCC GGCGAGGAAG TGGCGGGAAA ATACAGCTAT

1351 CGCCCAACAG ATGCGGAAAA GGGCGGATTC GGCGTGTTTG CCGGCAAAAA
```

-continued

```
1401 AGAGCAGGAT GGATCCGGAG GAGGAGGATG CCAAAGCAAG AGCATCCAAA
1451 CCTTTCCGCA ACCCGACACA TCCGTCATCA ACGGCCCGGA CCGGCCGGTC
1501 GGCATCCCCG ACCCCGCCGG AACGACGGTC GGCGGCGGCG GGGCCGTCTA
1551 TACCGTTGTA CCGCACCTGT CCCTGCCCCA CTGGGCGGCG CAGGATTTCG
1601 CCAAAAGCCT GCAATCCTTC CGCCTCGGCT GCGCCAATTT GAAAAACCGC
1651 CAAGGCTGGC AGGATGTGTG CGCCCAAGCC TTTCAAACCC CCGTCCATTC
1701 CTTTCAGGCA AAACAGTTTT TTGAACGCTA TTTCACGCCG TGGCAGGTTG
1751 CAGGCAACGG AAGCCTTGCC GGTACGGTTA CCGGCTATTA CGAGCCGGTG
1801 CTGAAGGGCG ACGACAGGCG GACGGCACAA GCCCGCTTCC CGATTTACGG
1851 TATTCCCGAC GATTTATCT CCGTCCCCCT GCCTGCCGGT TTGCGGAGCG
1901 GAAAAGCCCT TGTCCGCATC AGGCAGACGG GAAAAAACAG CGGCACAATC
1951 GACAATACCG GCGGCACACA TACCGCCGAC CTCTCCCGAT TCCCCATCAC
2001 CGCGCGCACA ACGGCAATCA AAGGCAGGTT TGAAGGAAGC CGCTTCCTCC
2051 CCTACCACAC GCGCAACCAA ATCAACGGCG GCGCGCTTGA CGGCAAAGCC
2101 CCGATACTCG GTTACGCCGA AGACCCCGTC GAACTTTTTT TTATGCACAT
2151 CCAAGGCTCG GGCCGTCTGA AAACCCCGTC CGGCAAATAC ATCCGCATCG
2201 GCTATGCCGA CAAAAACGAA CATCCCTACG TTTCCATCGG ACGCTATATG
2251 GCGGACAAAG CTACCTCAA GCTCGGGCAG ACCTCGATGC AGGGCATCAA
2301 AGCCTATATG CGGCAAAATC CGCAACGCCT CGCCGAAGTT TTGGGTCAAA
2351 ACCCCAGCTA TATCTTTTTC CGCGAGCTTG CCGGAAGCAG CAATGACGGT
2401 CCCGTCGGCG CACTGGGCAC GCCGTTGATG GGGGAATATG CCGGCGCAGT
2451 CGACCGGCAC TACATTACCT TGGGCGCGCC CTTATTTGTC GCCACCGCCC
2501 ATCCGGTTAC CCGCAAAGCC CTCAACCGCC TGATTATGGC GCAGGATACC
2551 GGCAGCGCGA TTAAAGGCGC GGTGCGCGTG GATTATTTTT GGGGATACGG
2601 CGACGAAGCC GGCGAACTTG CCGGCAAACA GAAAACCACG GGTTACGTCT
2651 GGCAGCTCCT ACCCAACGGT ATGAAGCCCG AATACCGCCC GTAAAAGCTT

1 MASPDVKSAD TLSKPAAPVV SEKETEAKED APQAGSQGQG APSAQGGQDM
 51 AAVSEENTGN GGAAATDKPR NEDEGAQNDM PQNAADTDSL TPNHTPASNM
101 PAGNMENQAP DAGESEQPAN QPDMANTADG MQGDDPSAGG ENAGNTAAQG
151 TNQAENNQTA GSQNPASSTN PSATNSGGDF GRTNVGNSVV IDGPSQNITL
201 THCKGDSCSG NNFLDEEVQL KSEFEKLSDA DKISNYKKDG KNDGKNDKFV
251 GLVADSVQMK GINQYIIFYK PKPTSFARFR RSARSRRSLP AEMPLIPVNQ
301 ADTLIVDGEA VSLTGHSGNI FAPEGNYRYL TYGAEKLPGG SYALRVQGEP
351 SKGEMLAGTA VYNGEVLHFH TENGRPSPSR GRFAAKVDFG SKSVDGIIDS
401 GDGLHMGTQK FKAAIDGNGF KGTWTENGGG DVSGKFYGPA GEEVAGKYSY
451 RPTDAEKGGF GVFAGKKEQD GSGGGGCQSK SIQTFPQPDT SVINGPDRPV
501 GIPDPAGTTV GGGGAVYTVV PHLSLPHWAA QDFAKSLQSF RLGCANLKNR
551 QGWQDVCAQA FQTPVHSFQA KQFFERYFTP WQVAGNGSLA GTVTGYYEPV
601 LKGDDRRTAQ ARFPIYGIPD DFISVPLPAG LRSGKALVRI RQTGKNSGTI
651 DNTGGTHTAD LSRFPITART TAIKGRFEGS RFLPYHTRNQ INGGALDGKA
701 PILGYAEDPV ELFFMHIQGS GRLKTPSGKY IRIGYADKNE HPYVSIGRYM
```

```
751 ADKGYLKLGQ TSMQGIKAYM RQNPQRLAEV LGQNPSYIFF RELAGSSNDG

801 PVGALGTPLM GEYAGAVDRH YITLGAPLFV ATAHPVTRKA LNRLIMAQDT

851 GSAIKGAVRV DYFWGYGDEA GELAGKQKTT GYVWQLLPNG MKPEYRP*
```

ΔG287NZ-953 (SEQ ID NOS: 96 and 97)

```
   1 ATGGCTAGCC CCGATGTCAA GTCGGCGGAC ACGCTGTCAA AACCTGCCGC

51 CCCTGTTGTT TCTGAAAAAG AGACAGAGGC AAAGGAAGAT GCGCCACAGG

101 CAGGTTCTCA AGGACAGGGC GCGCCATCCG CACAAGGCGG TCAAGATATG

151 GCGGCGGTTT CGGAAGAAAA TACAGGCAAT GGCGGTGCGG CAGCAACGGA

201 CAAACCCAAA AATGAAGACG AGGGGCGCA AAATGATATG CCGCAAAATG

251 CCGCCGATAC AGATAGTTTG ACACCGAATC ACACCCCGGC TTCGAATATG

301 CCGGCCGGAA ATATGGAAAA CCAAGGCTCG GATGCCGGGG AATCGGAGCA

351 GCCGGCAAAC CAACCGGATA TGCAAATAC GGCGGACGGA ATGCAGGGTG

401 ACGATCCGTC GGCAGGCGGG GAAAACCACG GCAATACGGC TGCCCAAGGT

451 ACAAATCAAG CCGAAAACAA TCAAACCGCC GGTTCTCAAA ATCCTGCCTC

501 TTCAACCAAT CCTAGCGCCA CGAATAGCGG TGGTGATTTT GGAAGGACGA

551 ACGTGGGCAA TTCTGTTGTG ATTGACGGGC CGTCGCAAAA TATAACGTTG

601 ACCCACTGTA AAGGCGATTC TTGTAGTGGC AATAATTTCT GGATGAAGA

651 AGTACAGCTA AAATCAGAAT TTGAAAAATT AAGTGATGCA GACAAAATAA

701 GTAATTACAA GAAAGATGGG AAGAATGACG GGAAGAATGA TAAATTTGTC

751 GGTTTGGTTG CCGATAGTGT GCAGATGAAG GGAATCAATC AATATATTAT

801 CTTTTATAAA CCTAAACCCA CTTCATTTGC GCGATTTAGG CGTTCTGCAC

851 GGTCGAGGCG GTCGCTTCCG GCCGAGATGC CGCTGATTCC CGTCAATCAG

901 GCGGATACGC TGATTGTCGA TGGGGAAGCG GTCAGCCTGA CGGGGCATTC

951 CGGCAATATC TTCGCGCCCG AAGGGAATTA CCGGTATCTG ACTTACGGGG

1001 CGGAAAAATT GCCCGGCGGA TCGTATGCCC TCCGTGTTCA AGGCGAACCT

1051 TCAAAAGGCG AAATGCTCGC GGGCACGGCA GTGTACAACG GCGAAGTGCT

1101 GCATTTTCAT ACGGAAAACG GCCGTCCGTC CCCGTCCAGA GGCAGGTTTG

1151 CCGCAAAAGT CGATTTCGGC AGCAAATCTG TGGACGGCAT TATCGACAGC

1201 GGCGATGGTT TGCATATGGG TACGCAAAAA TTCAAAGCCG CCATCGATGG

1251 AAACGGCTTT AAGGGGACTT GGACGGAAAA TGGCGGCGGG GATGTTTCCG

1301 GAAAGTTTTA CGGCCCGGCC GGCGAGGAAG TGGCGGGAAA ATACAGCTAT

1351 CGCCCAACAG ATGCGGAAAA GGGCGGATTC GGCGTGTTTG CCGGCAAAAA

1401 AGAGCAGGAT GGATCCGGAG GAGGAGGAGC CACCTACAAA GTGGACGAAT

1451 ATCACGCCAA CGCCCGTTTC GCCATCGACC ATTTCAACAC CAGCACCAAC

1501 GTCGGCGGTT TTTACGGTCT GACCGGTTCC GTCGAGTTCG ACCAAGCAAA

1551 ACGCGACGGT AAAATCGACA TCACCATCCC CGTTGCCAAC CTGCAAAGCG

1601 GTTCGCAACA CTTTACCGAC CACCTGAAAT CAGCCGACAT CTTCGATGCC

1651 GCCCAATATC CGGACATCCG CTTTGTTTCC ACCAAATTCA ACTTCAACGG

1701 CAAAAAACTG GTTTCCGTTG ACGGCAACCT GACCATGCAC GGCAAAACCG

1751 CCCCCGTCAA ACTCAAAGCC GAAAAATTCA ACTGCTACCA AAGCCCGATG

1801 GCGAAAACCG AAGTTTGCGG CGGCGACTTC AGCACCACCA TCGACCGCAC
```

-continued

```
1851 CAAATGGGGC GTGGACTACC TCGTTAACGT TGGTATGACC AAAAGCGTCC
1901 GCATCGACAT CCAAATCGAG GCAGCCAAAC AATAAAAGCT T

1 MASPDVKSAD TLSKPAAPVV SEKETEAKED APQAGSQGQG APSAQGGQDM
  51 AAVSEENTGN GGAAATDKPK NEDEGAQNDM PQNAADTDSL TPNHTPASNM
 101 PAGNMENQAP DAGESEQPAN QPDMANTADG MQGDDPSAGG ENAGNTAAQG
 151 TNQAENNQTA GSQNPASSTN PSATNSGGDF GRTNVGNSVV IDGPSQNITL
 201 THCKGDSCSG NNFLDEEVQL KSEFEKLSDA DKISNYKKDG KNDGKNDKFV
 251 GLVADSVQMK GINQYIIFYK PKPTSFARFR RSARSRRSLP AEMPLIPVNQ
 301 ADTLIVDGEA VSLTGHSGNI FAPEGNYRYL TYGAEKLPGG SYALRVQGEP
 351 SKGEMLAGTA VYNGEVLHFH TENGRPSPSR GRFAAKVDFG SKSVDGIIDS
 401 GDGLHMGTQK FKAAIDGNGF KGTWTENGGG DVSGKFYGPA GEEVAGKYSY
 451 RPTDAEKGGF GVFAGKKEQD GSGGGGATYK VDEYHANARF AIDHFNTSTN
 501 VGGFYGLTGS VEFDQAKRDG KIDITIPVAN LQSGSQHFTD HLKSADIFDA
 551 AQYPDIRFVS TKFNFNGKKL VSVDGNLTMH GKTAPVKLKA EKFNCYVSPM
 601 AKTEVCGGDF STTIDRTKWG VDYLVNVGMT KSVRIDIQIE AAKQ*
```

ΔG287NZ-961 (SEQ ID NOS: 98 and 99)

```
   1 ATGGCTAGCC CCGATGTCAA GTCGGCGGAC ACGCTGTCAA AACCTGCCGC
  51 CCCTGTTGTT TCTGAAAAAG AGACAGAGGC AAAGGAAGAT GCGCCACAGG
 101 CAGGTTCTCA AGGACAGGGC GCGCCATCCG CACAAGGCGG TCAAGATATG
 151 GCGGCGGTTT CGGAAGAAAA TACAGGCAAT GGCGGTGCGG CAGCAACGGA
 201 CAAACCCAAA AATGAAGACG AGGGGGCGCA AAATGATATG CCGCAAAATG
 251 CCGCCGATAC AGATAGTTTG ACACCGAATC ACACCCCGGC TTCGAATATG
 301 CCGGCCGGAA ATATGGAAAA CCAAGCACCG GATGCCGGGG AATCGGAGCA
 351 GCCGGCAAAC CAACCGGATA TGGCAAATAC GGCGGACGGA ATGCAGGGTG
 401 ACGATCCGTC GGCAGGCGGG GAAAATGCCG GCAATACGGC TGCCCAAGGT
 451 ACAAATCAAG CCGAAAACAA TCAAACCGCC GGTTCTCAAA ATCCTGCCTC
 501 TTCAACCAAT CCTAGCGCCA CGAATAGCGG TGGTGATTTT GGAAGGACGA
 551 ACGTGGGCAA TTCGTTGTGT ATTGACGGGC CGTCGCAAAA TATAACGTTG
 601 ACCCACTGTA AAGGCGATTC TTGTAGTGGC AATAATTTCT TGGATGAAGA
 651 AGTACAGCTA AAATCAGAAT TTGAAAAATT AAGTGATGCA GAAAAATTCA
 701 GTAATTACAA GAAAGATGGG AAGAATGACG GAAGAATGA TAAATTTGTC
 751 GGTTTGGTTG CCGATAGTGT GCAGATGAAG GGAATCAATC AATATATTAT
 801 CTTTTATAAA CCTAAACCCA CTTCATTTGC GCGATTTAGG CGTTCTGCAC
 851 GGTCGAGGCG GTCGCTTCCG GCCGAGATGC CGCTGATTCC CGTCAATCAG
 901 GCGGATACGC TGATTGTCGA TGGGGAAGCG GTCAGCCTGA CGGGGCATTC
 951 CGGCAATATC TTCGCGCCCG AAGGGAATTA CCGGTATCTG ACTTACGGGG
1001 CGGAAAAATT GCCCGGCGGA TCGTATGCCC TCCGTGTTCA ACGGCAACCT
1051 TCAAAGGCG AAATGCTCGC GGGCACGGCA GTGTACAACG GCGAAGTGCT
1101 GCATTTTCAT ACGGAAAACG GCCGTCCGTC CCCGTCCAGA GGCAGGTTTG
1151 CCGCAAAAGT CGATTTCGGC AGCAAATCTG TGGACGGCAT TATCGACAGC
1201 GGCGATGGTT TGCATATGGG TACGCAAAAA TTCAAAGCCG CCATCGATGG
```

```
1251 AAACGGCTTT AAGGGGACTT GGACGGAAAA TGGCGGCGGG GATGTTTCCG

1301 GAAAGTTTTA CGGCCCGGCC GGCGAGGAAG TGGCGGGAAA ATACAGCTAT

1351 CGCCCAACAG ATGCGGAAAA GGGCGGATTC GGCGTGTTTG CCGGCAAAAA

1401 AGAGCAGGAT GGATCCGGAG GAGGAGGAGC ACAAACGAC GACGATGTTA

1451 AAAAGCTGC CACTGTGGCC ATTGCTGCTG CCTACAACAA TGGCCAAGAA

1501 ATCAACGGTT TCAAAGCTGG AGAGACCATC TACGACATTG ATGAAGACGG

1551 CACAATTACC AATGAAGACG CAACTGCAGC CGATGTTGAA GCCGACGACT

1601 TTAAAGGTCT GGGTCTGAAA AAGTCGTGA CTAACCTGAC CAAAACCGTC

1651 AATGAAAACA AACAAACGT CGATGCCAAA GTAAAAGCTG CAGAATCTGA

1701 AATAGAAAAG TTAACAACCA AGTTAGCAGA CACTGATGCC GCTTTAGCAG

1751 ATACTGATGC CGCTCTGGAT GCAACCACCA ACGCCTTGAA TAAATTGGGA

1801 GAAAATATAA CGACATTTGC TGAAGAGACT AAGACAAATA TCGTAAAAAT

1851 TGATGAAAAA TTAGAAGCCG TGGCAAATAC CGTCGACAAG CATGCCGAAG

1901 CATTCAACGA TATCGCCGAT TCATTGGATG AAACCAACAC TAAGGCAGAC

1951 GAAGCCGTCA AAACCGCCAA TGAAGCCAAA CAGACGGCCG AAGAAACCAA

2001 ACAAAACGTC GATGCCAAAG TAAAAGCTGC AGAAACTGCA GCAGGCAAAG

2051 CCGAAGCTGC CGCTGGCACA GCTAATACTG CAGCCGACAA GGCCGAAGCT

2101 GTCGCTGCAA AAGTTACCGA CATCAAAGCT GATATCGCTA CGAACAAAGA

2151 TAATATTGCT AAAAAAGCAA ACAGTGCCGA CGTGTACACC AGAGAAGAGT

2201 CTGACAGCAA ATTTGTCAGA ATTGATGGTC TGAACGCTAC TACCGAAAAA

2251 TTGGACACAC GCTTGGCTTC TGCTGAAAAA TCCATTGCCG ATCACGATAC

2301 TCGCCTGAAC GGTTTGGATA AACAGTGTC AGACCTGCGC AAAGAAACCC

2351 GCCAAGGCCT TGCTGAAAAA GCCGCGCTCT CCGGTCTGTT CCAACCTTAC

2401 AACGTGGGTC GGTTCAATGT AACGGCTGCA GTCGGCGGCT ACAAATCCGA

2451 ATCGGCAGTC GCCATCGGTA CCGGCTTCCG CTTTACCGAA AACTTTGCCG

2501 CCAAAGCAGG CGTGGCAGTC GGCACTTCGT CCGGTTCTTC CGCAGCCTAC

2551 CATGTCGGCG TCAATTACGA GTGGTAAAAG CTT

1 MASPDVKSAD TLSKPAAPVV SEKETEAKED APQAGSQGQG APSAQGGQDM

51 AAVSEENTGN GGAAATDKPK NEDEGAQNDM PQNAADTDSL TPNHTPASNM

101 PAGNMENQAP DAGESEQPAN QPDMANTADG MQGDDPSAGG ENAGNTAAQG

151 TNQAENNQTA GSQMPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQMK GINQYIIFYK PKPTSFARFR RSARSRRSLP AEMPLIPVNQ

301 ADTLIVDGEA VSLTGHSGNI FAPEGNYRYL TYGAEKLPGG SYALRVQGEP

351 SKGEMLAGTA VYNGEVLHFH TENGRPSPSR GRFAAKVDFG SKSVDGIIDS

401 GDGLHMGTQK FKAAIDGNGF KGTWTENGGG DVSGKFYGPA GEEVAGKYSY

451 RPTDAEKGGF GVFAGKKEQD GSGGGGATND DDVKKAATVA IAAAYNNGQE

501 INGFKAGETI YDIDEDGTIT KKDATAADVE ADDFKGLGLK KVVTNLTKTV

551 NENKQNVDAK VKAAESEIEK LTTKLADTDA ALADTDAALD ATTNALNKLG

601 ENITTFAEET KTNIVKIDEK LEAVADTVDK HAEAFNDIAD SLDETNTKAD

651 EAVKTANEAK QTAEETKQNV DAKVKAAETA AGKAEAAAGT ANTAADKAEA
```

```
701 VAAKVTDIKA DIATNKDNIA KKANSADVYT REESDSKFVR IDGLNATTEK

751 LDTRLASAEK SIADHDTRLN GLDKTVSDLR KETRQGLAEQ AALSGLFQPY

801 NVGRFNVTAA VGGYKSESAV AIGTGFRFTE NFAAKAGVAV GTSSGSSAAY

851 HVGVNYEW*
```

ΔG983 and Hybrids

Bactericidal titres generated in response to ΔG983 (His-fusion) were measured against various strains, including the homologous 2996 strain:

|  | 2996 | NGH38 | BZ133 |
|---|---|---|---|
| ΔG983 | 512 | 128 | 128 |

ΔG983 was also expressed as a hybrid, with ORF46.1 (SEQ ID NOS: 100 and 101), 741 (SEQ ID NOS: 102 and 103), 961 (SEQ ID NOS: 104 and 105) or 961 c(SEQ ID NOS: 106 and 107) at its C-terminus:

```
ΔG983-OR746.1
   1 ATGACTTCTG CGCCCGACTT CAATGCAGGC GGTACCGGTA TCGGCAGCAA

51 CAGCAGAGCA ACAACAGCGA ATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGG TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAGTCGCAG

1001 GCGTAGACCG CAGTGGAGAA AAGTTCAAAC GGGAAATGTA TGGAGAACCG

1051 GGTACAGAAC CGCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC

1201 ACGGCGGCTC TGCTGCTGCA GAAATACCCG TGGATGAGCA ACGACAACCT

1251 GCGTACCACG TTGCTGACGA CGGCTCAGGA CATCGGTGCA GTCGGCGTGG
```

-continued

```
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AAGGTACATC
1401 CGATATTGCC TACTCCTTCC GTAACGACAT TTCAGGCACG GGCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGCAGCA GGCAAGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GGCGTGGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
2251 GCTACCGTCT ATGCCGACAG TACCGCCGCC CATGCCGATA TGCAGGGACG
2301 CCGCCTGAAA GCCGTATCGG ACGGGTTGGA CCACAACGGC ACGGGTCTGC
2351 GCGTCATCGC GCAAACCCAA CAGGACGGTG AACGTGGGA CAGGGCGGT
2401 GTTGAAGGCA AAATGCGCGG CAGTACCCAA ACCGTCGGCA TTGCCGCGAA
2451 AACCGGCGAA AATACGACAG CAGCCGCCAC ACTGGGCATG GGACGCAGCA
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG
2701 GGCGGTGTCA ACGTTCCGTT TGCCGCAACG GGAGATTTGA CGGTCGAAGG
2751 CGGTCTGCGC TACGACCTGC TCAAACAGGA TGCATTCGCC GAAAAAGGCA
2801 GTGCTTTGGG CTGGAGCGGC AACAGCCTCA CTGAAGGCAC GCTGGTCGGA
2851 CTCGCGGGTC TGAAGCTGTC GCAACCCTTG AGCGATAAAG CCGTCCTGTT
2901 TGCAACGGCG GGCGTGGAAC GCGACCTGAA CGGACGCGAC TACACGGTAA
2951 CGGGCGGCTT TACCGGCGCG ACTGCAGCAA CCGGCAAGAC GGGGGCACGC
3001 AATATGCCGC ACACCCGTCT GGTTGCCGGC CTGGGCGCGG ATGTCGAATT
3051 CGGCAACGGC TGGAACGGCT TGGCACGTTA CAGCTACGCC GGTTCCAAAC
3101 AGTACGGCAA CCACAGCGGA CGAGTCGGCG TAGGCTACCG GTTCCTCGAC
3151 GGTGGCGGAG GCACTGGATC CTCAGATTTG GCAAACGATT CTTTTATCCG
3201 GCAGGTTCTC GACCGTCAGC ATTTCGAACC CGACGGGAAA TACCACCTAT
3251 TCGGCAGCAG GGGGGAACTT GCCGAGCGCA GCGGCCATAT CGGATTGGGA
3301 AAAATACAAA GCCATCAGTT GGGCAACCTG ATGATTCAAC AGGCGGCCAT
```

```
-continued
3351 TAAAGGAAAT ATCGGCTACA TTGTCCGCTT TTCCGATCAC GGGCACGAAG

3401 TCCATTCCCC CTTCGACAAC CATGCCTCAC ATTCCGATTC TGATGAAGCC

3451 GGTAGTCCCG TTGACGGATT TAGCCTTTAC CGCATCCATT GGGACGGATA

3501 CGAACACCAT CCCGCCGACG GCTATGACGG GCCACAGGGC GGCGGCTATC

3551 CCGCTCCCAA AGGCGCGAGG GATATATACA GCTACGACAT AAAAGGCGTT

3601 GCCCAAAATA TCCGCCTCAA CCTGACCGAC AACCGCAGCA CCGGACAACG

3651 GCTTGCCGAC CGTTTCCACA ATGCCGGTAG TATGCTGACG CAAGGAGTAG

3701 GCGACGGATT CAAACGCGCC ACCCGATACA GCCCCGAGCT GGACAGATCG

3751 GGCAATGCCG CCGAAGCCTT CAACGGCACT GCAGATATCG TTAAAAACAT

3801 CATCGGCGCG GCAGGAGAAA TTGTCGGCGC AGGCGATGCC GTGCAGGGCA

3851 TAAGCGAAGG CTCAAACATT GCTGTCATGC ACGGCTTGGG TCTGCTTTCC

3901 ACCGAAAACA AGATGGCGCG CATCAAOGAT TTGGCAGATA TGGCGCAACT

3951 CAAAGACTAT GCCGCAGCAG CCATCCGCGA TTGGGCAGTC AAAACCCCA

4001 ATGCCGCACA AGGCATAGAA GCCGTCAGCA ATATCTTTAT GGCAGCCATC

4051 CCCATCAAAG GGATTGGAGC TGTTCGGGGA AAATACGGCT TGGGCGGCAT

4101 CACGGCACAT CCTATCAAGC GGTCGCAGAT GGGCGCGATC GCATTGCCGA

4151 AAGGGAAATC CGCCGTCAGC GACAATTTTG CCGATGCGGC ATACGCCAAA

4201 TACCCGTCCC CTTACCATTC CCGAAATATC CGTTCAAACT TGGAGCAGCG

4251 TTACGGCAAA GAAAACATCA CCTCCTCAAC CGTGCCGCCG TCAAACGGCA

4301 AAAATGTCAA ACTGGCAGAC CAACGCCACC CGAAGACAGG CGTACCGTTT

4351 GACGGTAAAG GGTTTCCGAA TTTTGAGAAG CACGTGAAAT ATGATACGCT

4401 CGAGCACCAC CACCACCACC ACTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GODYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG
```

-continued

```
 951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLD

1051 GGGGTGSSDL ANDSFIRQVL DRQHFEPDGK YHLFGSRGEL AERSGHIGLG

1101 KIQSHQLGNL MIQQAAIKGN IGYIVRFSDH GHEVHSPFDN HASHSDSDEA

1151 GSPVDGFSLY RIHWDGYEHH PADGYDGPQG GGYPAPKGAR DITSYDIKGV

1201 AQNIRLNLTD NRSTGQRLAD RFHNAGSMLT QGVGDGFKRA TRYSPELDRS

1251 GNAAEAFNGT ADIVKNIIGA AGEIVGAGDA VQGISEGSNI AVMHGLGLLS

1301 TENKMARIND LADMAQLKDY AAAAIRDWAV QNPNAAQGIE AVSNIFMAAI

1351 PIKGIGAVRG KYGLGGITAH PIKRSQMGAI ALPKGKSAVS DNFADAAYAK

1401 YPSPYHSRNI RSNLEQRYGK ENITSSTVPP SNGKNVKLAD QRHPKTGVPF

1451 DGKGFPNFEK HVKYDTLEHH HHHH*
```

ΔG983-741
```
   1 ATGACTTCTG CGCCCGACTT CAATGCAGGC GGTACCGGTA TCGGCAGCAA

51 CAGCAGAGCA ACAACAGCGA ATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTACCGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGG TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAGTCGCAG

1001 GCGTAGACCG CAGTGGAGAA AAGTTCAAAC GGGAAATGTA TGGAGAACCG

1051 GGTACAGAAC GCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC

1201 ACGGCGGCTC TGCTGCTGCA GAAATACCCG TGGATGAGCA ACGACAACCT

1251 GCGTACCACG TTGCTGACGA CGGCTCAGGA CATCGGTGCA GTCGGCGTGG

1301 ACAGCAAGTT CGGCTGGGGA CTGCTGGATG CGGGTAAGGC CATGAACGGA

1351 CCCGCGTCCT TTCCGTTCGG CGACTTTACC GCCGATACGA AAGGTACATC

1401 CGATATTGCC TACTCCTTCC GTAACGACAT TTCAGGCACG GGCGGCCTGA
```

```
                         -continued
1451 TCAAAAAAGG CGGCAGCCAA CTGCAACTGC ACGGCAACAA CACCTATACG

1501 GGCAAAACCA TTATCGAAGG CGGTTCGCTG GTGTTGTACG GCAACAACAA

1551 ATCGGATATG CGCGTCGAAA CCAAAGGTGC GCTGATTTAT AACGGGCGG

1601 CATCCGGCGG CAGCCTGAAC AGCGACGGCA TTGTCTATCT GGCAGATACC

1651 GACCAATCCG GCGCAAACGA AACCGTACAC ATCAAAGGCA GTCTGCAGCT

1701 GGACGGCAAA GGTACGCTGT ACACACGTTT GGGCAAACTG CTGAAAGTGG

1751 ACGGTACGGC GATTATCGGC GGCAAGCTGT ACATGTCGGC ACGCGGCAAG

1801 GGGGCAGGCT ATCTCAACAG TACCGGACGA CGTGTTCCCT TCCTGAGTGC

1851 CGCCAAAATC GGGCAGGATT ATTCTTTCTT CACAAACATC GAAACCGACG

1901 GCGGCCTGCT GGCTTCCCTC GACAGCGTCG AAAAAACAGC GGGCAGTGAA

1951 GGCGACACGC TGTCCTATTA TGTCCGTCGC GGCAATGCGG CACGGACTGC

2001 TTCGGCAGCG GCACATTCCG CGCCCGCCGG TCTGAAACAC GCCGTAGAAC

2051 AGGGCGGCAG CAATCTGGAA AACCTGATGG TCGAACTGGA TGCCTCCGAA

2101 TCATCCGCAA CACCCGAGAC GGTTGAAACT GCGGCAGCCG ACCGCACAGA

2151 TATGCCGGGC ATCCGCCCCT ACGGCGCAAC TTTCCGCGCA GCGGCAGCCG

2201 TACAGCATGC GAATGCCGCC GACGGTGTAC GCATCTTCAA CAGTCTCGCC

2251 GCTACCGTCT ATGCCGACAG TACCGCCGCC CATGCCGATA TGCAGGGACG

2301 CCGCCTGAAA GCCGTATCGG ACGGGTTGGA CCACAACGGC ACGGGTCTGC

2351 GCGTCATCGC GCAAACCCAA CAGGACGGTG GAACGTGGGA ACAGGGCGGT

2401 GTTGAAGGCA AAATGCGCGG CAGTACCCAA ACCGTCGGCA TTGCCGCGAA

2451 AACCGGCGAA AATACGACAG CAGCCGCCAC ACTGGGCATG GGACGCAGCA

2501 CATGGAGCGA AAACAGTGCA AATGCAAAAA CCGACAGCAT TAGTCTGTTT

2551 GCAGGCATAC GGCACGATGC GGGCGATATC GGCTATCTCA AAGGCCTGTT

2601 CTCCTACGGA CGCTACAAAA ACAGCATCAG CCGCAGCACC GGTGCGGACG

2651 AACATGCGGA AGGCAGCGTC AACGGCACGC TGATGCAGCT GGGCAAACTG

2701 GGCGGTGTCA ACGTTCCGTT TGCCGCAACG GGAGATTTGA CGGTCGAAGG

2751 CGGTCTGCGC TACGACCTGC TCAAACAGGA TGCATTCGCC GAAAAAGGCA

2801 GTGCTTTGGG CTGGAGCGGC AACAGCCTCA CTGAAGGCAC GCTGGTCGGA

2851 CTCGCGGGTC TGAAGCTGTC GCAACCCTTG AGCGATAAAG CCGTCCTGTT

2901 TGCAACGGCG GGCGTGGAAC GCGACCTGAA CGGACGCGAC TACACGGTAA

2951 CGGGCGGCTT TACCGGCGCG ACTGCAGCAA CCGGCAAGAC GGGGGCACGC

3001 AATATGCCGC ACACCCGTCT GGTTGCCGGC CTGGGCGCGG ATGTCGAATT

3051 CCACAACGGC TGGAACGGCT TGGCACGTTA CAGCTACGCC GGTTCCAAAC

3101 AGTACGGCAA CCACAGCGGA CGAGTCGGCG TAGGCTACCG GTTCCTCGAG

3151 GGATCCGGAG GGGGTGGTGT CGCCGCCGAC ATCGGTGCGG GGCTTGCCGA

3201 TGCACTAACC GCACCGCTCG ACCATAAAGA CAAAGGTTTG CAGTCTTTGA

3251 CGCTGGATCA GTCCGTCAGG AAAAACGAGA AACTGAAGCT GGCGGCACAA

3301 GGTGCGGAAA AAACTTATGG AAACGGTGAC AGCCTCAATA CGGGCAAATT

3351 GAAGAACGAC AAGGTCAGCC GTTTCGACTT TATCCGCCAA ATCGAAGTGG

3401 ACGGGCAGCT CATTACCTTG GAGAGTGGAG AGTTCCAAGT ATACAAACAA

3451 AGCCATTCCG CCTTAACCGC CTTTCAGACC GAGCAAATAC AAGATTCGGA
```

-continued

```
3501 GCATTCCGGG AAGATGGTTG CGAAACGCCA GTTCAGAATC GGCGACATAG

3551 CGGGCGAACA TACATCTTTT GACAAGCTTC CCGAAGGCGG CAGGGCGACA

3601 TATCGCGGGA CGGCGTTCGG TTCAGACGAT GCCGGCGGAA AACTGACCTA

3651 CACCATAGAT TTCGCCGCCA AGCAGGGAAA CGGCAAAATC GAACATTTGA

3701 AATCGCCAGA ACTCAATGTC GACCTGGCCG CCGCCGATAT CAAGCCGGAT

3751 GGAAAACGCC ATGCCGTCAT CAGCGGTTCC GTCCTTTACA ACCAAGCCGA

3801 GAAAGGCAGT TACTCCCTCG GTATCTTTGG CGGAAAAGCC CAGGAAGTTG

3851 CCGGCAGCGC GGAAGTGAAA ACCGTAAACG GCATACGCCA TATCGGCCTT

3901 GCCGCCAAGC AACTCGAGCA CCACCACCAC CACCACTGA
```

```
   1 MTSAPDFNAG GTGIGSNSRA TTAKSAAVSY AGIKNEMCKD RSMLCAGRDD

51 VAVTDRDAKI NAPPPNLHTG DFPNPNDAYK NLINLRPAIE AGYTGRGVEV

101 GIVDTGESVG SISFPELYGR KEHGYNENYK NYTAYMRKEA PEDGGGKDIE

151 ASFDDEAVIR TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLRGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GSGGGGVAAD IGAGLADALT APLDHKDKGL QSLTLDQSVR KNEKLRLAAQ

1101 GAEKTYGNGD SLNTGKLKND KVSRFDFIRQ IEVDGQLITL ESGEFQVYKQ

1151 SHSALTAFQT EQIQDSEHSG KMVAKRQFRI GDIAGEHTSF DKLPEGGRAT

1201 YRGTAFGSDD AGGKLTYTID FAAKQGNGKI EHLKSPELNV DLAAADIKPD

1251 GKRHAVISGS VLYNQAEKGS YSLGIFGGKA QEVAGSAEVK TVNGIRHIGL

1301 AAKQLEHHHH HH*
```

ΔG983-961

```
   1 ATGACTTCTG CGCCCGACTT CAATGCAGGC GGTACCGGTA TCGGCAGCAA

51 CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT
```

-continued

```
 201 GCATACCGGA GACTTTCCAA ACCCAAATGA CGCATACAAG AATTTGATCA
 251 ACCTCAAACC TGCAATTGAA GCAGGCTATA CAGGACGCGG GGTAGAGGTA
 301 GGTATCGTCG ACACAGGCGA ATCCGTCGGC AGCATATCCT TTCCCGAACT
 351 GTATGGCAGA AAAGAACACG GCTATAACGA AAATTACAAA AACTATACGG
 401 CGTATATGCG GAAGGAAGCG CCTGAAGACG GAGGCGGTAA AGACATTGAA
 451 GCTTCTTTCG ACGATGAGGC CGTTATAGAG ACTGAAGCAA AGCCGACGGA
 501 TATCCGCCAC GTAAAAGAAA TCGGACACAT CGATTTGGTC TCCCATATTA
 551 TTGGCGGGCG TTCCGTGGAC GGCAGACCTG CAGGCGGTAT TGCGCCCGAT
 601 GCGACGCTAC ACATAATGAA TACGAATGAT GAAACCAAGA ACGAAATGAT
 651 GGTTGCAGCC ATCCGCAATG CATGGGTCAA GCTGGGCGAA CGTGGCGTGC
 701 GCATCGTCAA TAACAGTTTT GGAACAACAT CGAGGGCAGG CACTGCCGAC
 751 CTTTTCCAAA TAGCCAATTC GGAGGAGCAG TACCGCCAAG CGTTGCTCGA
 801 CTATTCCGGC GGTGATAAAA CAGACGAGGG TATCCGCCTG ATGCAACAGA
 851 GCGATTACGG CAACCTGTCC TACCACATCC GTAATAAAAA CATGCTTTTC
 901 ATCTTTTCGA CAGGCAATGA CGCACAAGCT CAGCCCAACA CATATGCCCT
 951 ATTGCCATTT TATGAAAAAG ACGCTCAAAA AGGCATTATC ACAGTCGCAG
1001 GCGTAGACCG CAGTGGAGAA AAGTTCAAAC GGGAAATGTA TGGAGAACCG
1051 GGTACAGAAC CGCTTGAGTA TGGCTCCAAC CATTGCGGAA TTACTGCCAT
1101 GTGGTGCCTG TCGGCACCCT ATGAAGCAAG CGTCCGTTTC ACCCGTACAA
1151 ACCCGATTCA AATTGCCGGA ACATCCTTTT CCGCACCCAT CGTAACCGGC
1201 ACGGCGGCTC TGCTGCTGCA GAAATACCCG TGGATGAGCA ACGACAACCT
1251 GCGTACCACG TTGCTGACGA CGGCTCAGGA CATCGGTGCA GTCGGCGTGG
1301 ACAGCAAGTT CGGCTGGGGA CTGCTGGATG CGGGTAAGGC CATGAACGGA
1351 CCCGCGTCQT TTCCGTTCGG CGACTTTACC GCCGATACGA AAGGTACATC
1401 CGATATTGCC TACTCCTTCC GTAACGACAT TTCAGGCACG GGCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
```

-continued

```
2251 GCTACCGTCT ATGCCGACAG TACCGCCGCC CATGCCGATA TGCAGGGACG

2301 CCGCCTGAAA GCCGTATCGG ACGGGTTGGA CCACAACGGC ACGGGTCTGC

2351 GCGTCATCGC GCAAACCCAA CAGGACGGTG AACGTGGGA ACAGGGCGGT

2401 GTTGAAGGCA AAATGCGCGG CAGTACCCAA ACCGTCGGCA TTGCCGCGAA

2451 AACCGGCGAA AATACGACAG CAGCCGCCAC ACTGGGCATG GGACGCAGCA

2501 CATGGAGCGA AAACAGTGCA AATGCAAAAA CCGACAGCAT TAGTCTGTTT

2551 GCAGGCATAC GGCACGATGC GGGCGATATC GGCTATCTCA AAGGCCTGTT

2601 CTCCTACGGA CGCTACAAAA ACAGCATCAG CCGCAGCACC GGTGCGGACG

2651 AACATGCGGA AGGCAGCGTC AACGGCACGC TGATGCAGCT GGGCGCACTG

2701 GGCGGTGTCA ACGTTCCGTT TGCCGCAACG GGAGATTTGA CGGTCGAAGG

2751 CGGTCTGCGC TACGACCTGC TCAAACAGGA TGCATTCGCC GAAAAAGGCA

2801 GTGCTTTGGG CTGGAGCGGC AACAGCCTCA CTGAAGGCAC GCTGGGCGAA

2851 CTCGCGGGTC TGAAGCTGTC GCAACCCTTG AGCGATAAAG CCGTCCTGTT

2901 TGCAACGGCG GGCGTGGAAC GCGACCTGAA CGGACGCGAC TACACGGTAA

2951 CGGGCGGCTT TACCGGCGCG ACTGCAGCAA CCGGCAAGAC GGGGGCACGC

3001 AATATGCCGC ACACCCGTCT GGTTGCCGGC CTGGGCGCGG ATGTCGAATT

3051 CGGCAACGGC TGGAACGGCT TGGCACGTTA CAGCTACGCC GGTTCCAAAC

3101 AGTACGGCAA CCACAGCGGA CGAGTCGGCG TAGGCTACCG GTTCCTCGAG

3151 GGTGGCGGAG GCACTGGATC CGCCACAAAC GACGACGATG TTAAAAAAGC

3201 TGCCACTGTG GCCATTGCTG CTGCCTACAA CAATGGCCAA GAAATCAACG

3251 GTTTCAAAGC TGGAGAGACC ATCTACGACA TTGATGAAGA CGGCACAATT

3301 ACCAAAAAAG ACGCAACTGC AGCCGATGTT GAAGCCGACG ACTTTAAAGG

3351 TCTGGGTCTG AAAAAAGTCG TGACTAACCT GACCAAAACC GTCAATGAAA

3401 ACAAACAAAA CGTCGATGCC AAAGTAAAAG CTGCAGAATC TGAAATAGAA

3451 AAGTTAACAA CCAAGTTAGC AGACACTGAT GCCGCTTTAG CAGATACTGA

3501 TGCCGCTCTG GATGCAACCA CCAACGCCTT GAATAAATTG GGAGAAAATA

3551 TAACGACATT TGCTGAAGAG ACTAAGACAA ATATCGTAAA AATTGATGAA

3601 AAATTAGAAG CCGTGGCTGA TACCGTCGAC AAGCATGCCG AAGCATTCAA

3651 CGATATCGCC GATTCATTGG ATGAAACCAA CACTAAGGCA GACGAAGCCG

3701 TCAAAACCGC CAATGAAGCC AAACAGACGG CCGAAGAAAC CAAACAAAAC

3751 GTCGATGCCA AGTAAAAGC TGCAGAAACT GCAGCAGGCA AAGCCGAAGC

3801 TGCCGCTGGC ACAGCTAATA CTGCAGCCGA CAAGGCCGAA GCTGTCGCTG

3851 CAAAAGTTAC CGACATCAAA GCTGATATCG CTACGAACAA AGATAATATT

3901 GCTAAAAAAG CAAACAGTGC CGACGTGTAC ACCAGAGAAG AGTCTGACAG

3951 CAAATTTGTC AGAATTGATG GTCTGAACGC TACTACCGAA AAATTGGACA

4001 CACGCTTGGC TTCTGCTGAA AAATCCATTG CCGATCACGA TACTCGCCTG

4051 AACGGTTTGG ATAAAACAGT GTCAGACCTG CGCAAAGAAA CCCGCCAAGG

4101 CCTTGCAGAA CAAGCCGCGC TCTCCGGTCT GTTCCAACCT TACAACGTGG

4151 GTCGGTTCAA TGTAACGGCT GCAGTCGGCG GCTACAAATC CGAATCGGCA

4201 GTCGCCATCG GTACCGGCTT CCGCTTTACC GAAAACTTTG CCGCCAAAGC
```

-continued

```
4251 AGGCGTGGCA GTCGGCACTT CGTCCGGTTC TTCCGCAGCC TACCATGTCG

4301 GCGTCAATTA CGAGTGGCTC GAGCACCACC ACCACCACCA CTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVC SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HcGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAVQHANAA DGVRIFNSLA

751 ATVYADSTAA HADMQGRRLK AVSDGLDHNG TGLRVIAQTQ QDGGTWEQGG

801 VEGEERGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVKTANEA KQTAEETKQN

1251 VDAKVKAAET AAGEAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGRFNVTA AVGGYKSESA

1401 VAIGTGFRFT ENFAAKAGVA VGTSSGSSAA YHVGVNYEWL EHHHHHH*
```

ΔG983-961c

```
   1 ATGACTTCTG CGCCCGACTT CAATGCAGGC GGTACCGGTA TCGGCAGCAA

51 CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAGAACACG GCTATAACGA AAATTACAAA AACTATACGG

401 CGTATATGCG GAAGGAAGCG CCTGAAGACG GAGGCGGTAA AGACATTGAA
```

-continued

```
 451 GCTTCTTTCG ACGATGAGGC CGTTATAGAG ACTGAAGCAA AGCCGACGGA

501 TATCCGCCAC GTAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGG TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAGTCGCAG

1001 GCGTAGACCG CAGTGGAGAA AAGTTCAAAC GGGAAATGTA TGGAGAACCG

1051 GGTACAGAAC CGCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC

1201 ACGGCGGCTC TGCTGCTGCA GAAATACCCG TGGATGAGCA ACGACAACCT

1251 GCGTACCACG TTGCTGACGA CGGCTCAGGA CATCGGTGCA GTCGGCGTGG

1301 ACAGCAAGTT CGGCTGGGGA CTGCTGGATG CGGGTAAGGC CATGAACGGA

1351 CCCGCGTCCT TTCCGTTCGG CGACTTTACC GCCGATACGA AAGGTACATC

1401 CGATATTGCC TACTCCTTCC GTAACGACAT TTCAGGCACG GGCGGCCTGA

1451 TCAAAAAAGG CGGCAGCCAA CTGCAACTGC ACGGCAACAA CACCTATACG

1501 GGCAAAACCA TTATCGAAGG CGGTTCGCTG GTGTTGTACG GCAACAACAA

1551 ATCGGATATG CGCGTCGAAA CCAAAGGTGC GCTGATTTAT AACGGGGCGG

1601 CATCCGGCGG CAGCCTGAAC AGCGACGGCA TTGTCTATCT GGCAGATACC

1651 GACCAATCCG GCGCAAACGA AACCGTACAC ATCAAAGGCA GTCTGCAGCT

1701 GGACGGCAAA GGTACGCTGT ACACACGTTT GGGCAAACTG CTGAAAGTGG

1751 ACGGTACGGC GATTATCGGC GGCAAGCTGT ACATGTCGGC ACGCGGCAAG

1801 GGGGCAGGCT ATCTCAACAG TACCGGACGA CGTGTTCCCT TCCTGAGTGC

1851 CGCCACAAAC GGGCAGGATT ATTCTTTCTT CACAAACATC GAAACCGACG

1901 GCGGCCTGCT GGCTTCCCTC GACAGCGTCG AAAAAACAGC GGGCAGTGAA

1951 GGCGACACGC TGTCCTATTA TGTCCGTCGC GGCAATGCGG CACGGACTGC

2001 TTCGGCAGCG GCACATTCCG CGCCCGCCGG TCTGAAACAC GCCGTAGAAC

2051 AGGGCGGCAG CAATCTGGAA AACCTGATGG TCGAACTGGA TGCCTCCGAA

2101 TCATCCGCAA CACCCGAGAC GGTTGAAACT GCGGCAGCCG ACCGCACAGA

2151 TATGCCGGGC ATCCGCCCCT ACGGCGCAAC TTTCCGCGCA GCGGCAGCCG

2201 TACAGCATGC GAATGCCGCC GACGGTGTAC GCATCGTCAA CAGTCTCGCC

2251 GCTACCGTCT ATGCCGACAG TACCGCCGCC CATGCCGATA TGCAGGGACG

2301 CCGCCTGAAA GCCGTATCGG ACGGGTTGGA CCACAACGGC ACGGGTCTGC

2351 GCGTCATCGC GCAAACCCAA CAGGACGGTG AACGTGGGA ACAGGGCGGT

2401 GTTGAAGGCA AATGCGCGG CAGTACCCAA ACCGTCGGCA TTGCCGCGAA

2451 AACCGGCGAA AATACGACAG CAGCCGCCAC ACTGGGCATG GGACGCAGCA
```

-continued

```
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG
2701 GGCGGTGTCA ACGTTCCGTT TGCCGCAACG GGAGATTTGA CGGTCGAAGG
2751 CGGTCTGCGC TACGACCTGC TCAAACAGGA TGCATTCGCC GAAAAAGGCA
2801 GTGCTTTGGG CTGGAGCGGC AACAGCCTCA CTGAAGGCAC GCTGGTCGGA
2851 CTCGCGGGTC TGAAGCTGTC GCAACCCTTG AGCGATAAAG CCGTCCTGTT
2901 TGCAACGGCG GGCGTGGAAC GCGACCTGAA CGGACGCGAC TACACGGTAA
2951 CGGGCGGCTT TACCGGCGCG ACTGCAGCAA CCGGCAAGAC GGGGGCACGC
3001 AATATGCCGC ACACCCGTCT GGTTGCCGGC CTGGGCGCGG ATGTCGAATT
3051 CGGCAACGGC TGGAACGGCT TGGCACGTTA CAGCTACGCC GGTTCCAAAC
3101 AGTACGGCAA CCACAGCGGA CGAGTCGGCG TAGGCTACCG GTTCCTCGAG
3151 GGTGGCGGAG GCACTGGATC CGCCACAAAC GACGACGATG TTAAAAAAGC
3201 TGCCACTGTG GCCATTGCTG CTGCCTACAA CAATGGCCAA GAAATCAACG
3251 GTTTCAAAGC TGGAGAGACC ATCTACGACA TTGATGAAGA CGGCACAATT
3301 ACCAAAAAAG ACGAACTGC AGCCGATGTT GAAGCCGACG ACTTTAAAGG
3351 TCTGGGTCTG AAAAAAGTCG TGACTAACCT GACCAAAACC GTCAATGAAA
3401 ACAAACAAAA CGTCGATGCC AAAGTAAAAG CTGCAGAATC TGAAATAGAA
3451 AAGTTAACAA CCAAGTTAGC AGACACTGAT GCCGCTTTAG CAGATACTGA
3501 TGCCGCTCTG GATGCAACCA CCAACGCCTT GAATAAATTG GGAGAAAATA
3551 TAACGACATT TGCTGAAGAG ACTAAGACAA ATATCGTAAA AATTGATGAA
3601 AAATTAGAAG CCGTGGCTGA TACCGTCGAC AAGCATGCCG AAGCATTCAA
3651 CGATATCGCC GATTCATTGG ATGAAACCAA CACTAAGGCA GACGAAGCCG
3701 TCAAAACCGC CAATGAAGCC AAACAGACGG CCGAAGAAAC CAAACAAAAC
3751 GTCGATGCCA AGTAAAAGC TGCAGAAACT GCAGCAGGCA AAGCCGAAGC
3801 TGCCGCTGGC ACAGCTAATA CTGCAGCCGA CAAGGCCGAA GCTGTCGCTG
3851 CAAAAGTTAC CGACATCAAA GCTGATATCG CTACGAACAA AGATAATATT
3901 GCTAAAAAAG CAAACAGTGC CGACGTGTAC ACCAGAGAAG AGTCTGACAG
3951 CAAATTTGTC AGAATTGATG GTCTGAACGC TACTACCGAA AAATTGGACA
4001 CACGCTTGGC TTCTGCTGAA AAATCCATTG CCGATCACGA TACTCGCCTG
4051 AACGGTTTGG ATAAAACAGT GTCAGACCTG CGCAAAGAAA CCCGCCAAGG
4101 CCTTGCAGAA CAAGCCGCGC TCTCCGGTCT GTTCCAACCT TACAACGTGG
4151 GTCTCGAGCA CCACCACCAC CACCACTGA
```

```
   1 MTSAPDFNAG GTGIGSNSRA TTAKSAAVSY AGIKNEMCKD RSMLCAGRDD
  51 VAVTDRDAKI NAPPPNLHTG DFPNPNDAYK NLINLEPAIE AGYTGRGVEV
 101 GIVDTGESVG SISFPELYGR KEHGYNENYK NYTAYMRKEA PEDGGGKDIE
 151 ASFDDEAVIE TEAKPTDIRH VKSIGHIDLV SHIIGGRSVD GRPAGGIAPD
 201 ATLHIMNTND ETKNEMMVAA IRNAWVKLGE RGVRIVNNSF GTTSRAGTAD
 251 LFQIANSEEQ YRQALLDYSG GDKTDEGIRL MQQSDYGNLS YHIRNKNMLF
 301 IFSTGNDAQA QPNTYALLPF YEKDAQKGII TVAGVDRSGE KFKREMYGEP
```

```
-continued
351 GTEPLEYGSN HCGITAMNCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVETANEA KQTAEETKQN

1251 VDAKVKAAET AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGLEHHHH HH*
```

ΔG741 and Hybrids

Bactericidal titres generated in response to ΔG741 (His-fusion) were measured against various strains, including the homologous 2996 strain:

|  | 2996 | MC58 | NGH38 | F6124 | BZ133 |
|---|---|---|---|---|---|
| ΔG741 | 512 | 131072 | >2048 | 16384 | >2048 |

As can be seen, the ΔG741-induced anti-bactericidal titre is particularly high against heterologous strain MC58.

ΔG741 was also fused directly in-frame upstream of proteins 961 (SEQ ID NOS:108 and 109), 961c, (SEQ ID NOS:110 and 111), 983 (SEQ ID NOS:112 and 113) and ORF46.1 (SEQ ID NOS:114 and 115):

```
ΔG741-961
   1 ATGGTCGCCG CCGACATCGG TGCGGGGCTT GCCGATGCAC TAACCGCACC

51 GCTCGACCAT AAAGACAAAG GTTTGCAGTC TTTGACGCTG ATCAGTCCG

101 TCAGGAAAAA CGAGAAACTG AAGCTGGCGG CACAAGGTGC GGAAAAAACT

151 TATGGAAACG GTGACAGCCT CAATACGGGC AAATTGAAGA ACGACAAGGT

201 CAGCCGTTTC GACTTTATCC GCCAAATCGA AGTGGACGGG CAGCTCATTA

251 CCTTGGAGAG TGGAGAGTTC CAAGTATACA AACAAAGCCA TTCCGCCTTA

301 ACCGCCTTTC AGACCGAGCA AATACAAGAT TCGGAGCATT CCGGGAAGAT

351 GGTTGCGAAA CGCCAGTTCA GAATCGGCGA CATAGCGGGC GAACATACAT

401 CTTTTGACAA GCTTCCCGAA GGCGGCAGGG CGACATATCG CGGGACGGCG

451 TTCGGTTCAG ACGATGCCGG CGGAAAACTG ACCTACACCA TAGATTTCGC

501 CGCCAAGCAG GGAAACGGCA AAATCGAACA TTTGAAATCG CCAGAACTCA

551 ATGTCGACCT GGCCGCCGCC GATATCAAGC CGGATGGAAA ACGCCATGCC
```

-continued

```
 601   GTCATCAGCG GTTCCGTCCT TTACAACCAA GCCGAGAAAG GCAGTTACTC
 651   CCTCGGTATC TTTGGCGGAA AAGCCCAGGA AGTTGCCGGC AGCGCGGAAG
 701   TGAAAACCGT AAACGGCATA CGCCATATCG GCCTTGCCGC AAGCAACTC
 751   GAGGGTGGCG GAGGCACTGG ATCCGCCACA AACGACGACG ATGTTAAAAA
 801   AGCTGCCACT GTGGCCATTG CTGCTGCCTA CAACAATGGC CAAGAAATCA
 851   ACGGTTTCAA AGCTGGAGAG ACCATCTACG ACATTGATGA AGACGGCACA
 901   ATTACCAAAA AAGACGCAAC TGCAGCCGAT GTTGAAGCCG ACGACTTTAA
 951   AGGTCTGGGT CTGAAAAAAG TCGTGACTAA CCTGACCAAA ACCGTCAATG
1001   AAAACAAACA AAACGTCGAT GCCAAAGTAA AAGCTGCAGA ATCTGAAATA
1051   GAAAAGTTAA CAACCAAGTT AGCAGACACT GATGCCGCTT TAGCAGATAC
1101   TGATGCCGCT CTGGATGCAA CCACCAACGC CTTGAATAAA TTGGGAGAAA
1151   ATATAACGAC ATTTGCTGAA GAGACTAAGA CAAATATCGT AAAAATTGAT
1201   GAAAAATTAG AAGCCGTGGC TGATACCGTC GACAAGCATG CCGAAGCATT
1251   CAACGATATC GCCGATTCAT GGATGAAAC CAACACTAAG GCAGACGAAG
1301   CCGTCAAAAC CGCCAATGAA GCCAAACAGA CGGCCGAAGA AACCAAACAA
1351   AACGTCGATG CCAAAGTAAA AGCTGCAGAA ACTGCAGCAG GCAAAGCCGA
1401   AGCTGCCGCT GGCACAGCTA ATACTGCAGC CGACAAGGCC GAAGCTGTCG
1451   CTGCAAAAGT TACCGACATC AAAGCTGATA TCGCTACGAA CAAAGATAAT
1501   ATTGCTAAAA AAGCAAACAG TGCCGACGTG TACACCAGAG AAGAGTCTGA
1551   CAGCAAATTT GTCAGAATTG ATGGTCTGAA CGCTACTACC GAAAAATTGG
1601   ACACACGCTT GGCTTCTGCT GAAAAATCCA TTGCCGATCA CGATACTCGC
1651   CTGAACGGTT TGGATAAAAC AGTGTCAGAC CTGCGCAAAG AAACCCGCCA
1701   AGGCCTTGCA GAACAAGCCG CGCTCTCCGG TCTGTTCCAA CCTTACAACG
1751   TGGGTCGGTT CAATGTAACG GCTGCAGTCG GCGGCTACAA ATCCGAATCG
1801   GCAGTCGCCA TCGGTACCGG CTTCCGCTTT ACCGAAAACT TTGCCGCCAA
1851   AGCAGGCGTG GCAGTCGGCA CTTCGTCCGG TTCTTCCGCA GCCTACCATG
1901   TCGGCGTCAA TTACGAGTGG CTCGAGCACC ACCACCACCA CCACTGA
   1   MVAADIGAGL ADALTAPLDH KDKGLQSLTL DQSVRKNEKL KLAAQGAEKT
  51   YGNGDSLNTG KLKNDKVSRF DFIRQIEVDG QLITLESGEF QVYKQSHSAL
 101   TAFQTEQIQD SEHSGKHVAK RQFRIGDIAG EHTSFDKLPE GGRATYRGTA
 151   FGSDDAGGKL TYTIDFAAKQ GNGKIEHLKS PELNVDLAAA DIKPDGKRHA
 201   VISGSVLYNQ AEKGSYSLGI FGGKAQEVAG SAEVKTVNGI RHIGLAAKQL
 251   EGGGGTGSAT NDDDVKKAAT VAIAAAYNNG QEINGFKAGE TIYDIDEDGT
 301   ITKKDATAAD VEADDFKGLG LKKVVTNLTK TVNENKQNVD AKVKAAESEI
 351   EKLTTKLADT DAALADTDAA LDATTNALNK LGENITTFAE ETKTNIVKID
 401   EKLEAVADTV DKHAEAFNDI ADSLDETNTK ADEAVKTANE AKQTAEETKQ
 451   NVDAKVKAAE TAAGKAEAAA GTANTAADKA EAVAAKVTDI KADIATNKDN
 501   IAKKANSADV YTREESDSKF VRIDGLNATT EKLDTRLASA EKSIADHDTR
 551   LNGLDKTVSD LRKETRQGLA EQAALSGLFQ PYNVGRFNVT AAVGGYKSES
 601   AVAIGTGFRF TENFAAKAGV AVGTSSGSSA AYHVGVNYEW LEEHHHHH*
```

ΔG741-961c
```
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAACAAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAGAAAG GCAGTTACTC
 651 CCTCGGTATC TTTGGCGGAA AGCCCAGGA AGTTGCCGGC AGCGCGGAAG
 701 TGAAAACCGT AAACGGCATA CGCCATATCG GCCTTGCCGC CAAGCAACTC
 751 GAGGGTGGCG GAGGCACTGG ATCCGCCACA AACGACGACG ATGTTAAAAA
 801 AGCTGCCACT GTGGCCATTG CTGCTGCCTA CAACAATGGC CAAGAAATCA
 851 ACGGTTTCAA AGCTGGAGAG ACCATCTACG ACATTGATGA AGACGGCACA
 901 ATTACCAAAA AAGACGCAAC TGCAGCCGAT GTTGAAGCCG ACGACTTTAA
 951 AGGTCTGGGT CTGAAAAAAG TCGTGACTAA CCTGACCAAA ACCGTCAATG
1001 AAAACAAACA AAACGTCGAT GCCAAAGTAA AAGCTGCAGA ATCTGAAATA
1051 GAAAAGTTAA CAACCAAGTT AGCAGACACT GATGCCGCTT TAGCAGATAC
1101 TGATGCCGCT CTGGATGCAA CCACCAACGC CTTGAATAAA TTGGGAGAAA
1151 ATATAACGAC ATTTGCTGAA GAGACTAAGA CAAATATCGT AAAAATTGAT
1201 GAAAAATTAG AAGCCGTGGC TGATACCGTC GACAAGCATG CCGAAGCATT
1251 CAACGATATC GCCGATTCAT TGGATGAAAC CAACACTAAG GCAGACGAAG
1301 CCGTCAAAAC CGCCAATGAA GCCAAATCGA CGGCCGAAGA AACCAAACAA
1351 AACGTCGATG CCAAAGTAAA AGCTGCAGAA ACTGCAGCAG CAAAGCCGA
1401 AGCTGCCGCT GGCACAGCTA ATACTGCAGC CGACAAGGCC GAAGCTGTCG
1451 CTGCAAAAGT TACCGACATC AAAGCTGATA TCGCTACGAA CAAAGATAAT
1501 ATTGCTAAAA AGCAAACAG TGCCGACGTG TACACCAGAG AAGAGTCTGA
1551 CAGCAAATTT GTCAGAATTG ATGGTCTGAA CGCTACTACC GAAAAATTGG
1601 ACACACGCTT GGCTTCTGCT GAAAATCCA TTGCCGATCA CGATACTCGC
1651 CTGAACGGTT TGGATAAAAC AGTGTCAGAC CTGCGCAAAG AAACCCGCCA
1701 AGGCCTTGCA GAACAAGCCG CGCTCTCCGG TCTGTTCCAA CCTTACAACG
1751 TGGGTCTCGA GCACCACCAC CACCACCACT GA

1 MVAADIGAGL ADALTAPLDH KDKGLQSLTL DQSVRKNEKL KLAAQGAEKT
  51 YGNGDSLNTG KLKNDKVSRF DFIRQIEVDG QLITLESGEF QVYKQSHSAL
 101 TAFQTEQIQD SEHSGKMVAK RQFRIGDIAG EHTSFDKLPE GGRATYRGTA
 151 FGSDDAGGKL TYTIDFAAKQ GNGKIEHLKS PELNVDLAAA DIKPDGKRHA
```

```
201  VISGSVLYNQ AEKGSYSLGI FGGKAQEVAG SAEVKTVNGI RHIGLAAKQL

251  EGGGGTGSAT NDDDVKKAAT VAIAAAYNNG QEINGFKAGE TIYDIDEDGT

301  ITKKDATAAD VEADDFKGLG LKKVVTNLTK TVNENKQNVD AKVKAAESEI

351  EKLTTKLADT DAALADTDAA LDATTNALNK LGENITTFAE ETKTNIVKID

401  EKLEAVADTV DKHAEAFNDI ADSLDETNTK ADEAVKTANE AKQTAEETKQ

451  NVDAKVKAAE TAAGKAEAAA GTANTAADKA EAVAAKVTDI KADIATNKDN

501  IAKKANSADV YTREESDSKF VRIDGLNATT EKLDTRLASA EKSIADHDTR

551  LNGLDKTVSD LRKETRQGLA EQAALSGLFQ PYNVGLEHHH HHH*
```

ΔG741-983
```
   1 ATGGTCGCCG CCGACATCGG TGCGGGCTT GCCGATGCAC TAACCGCACC

51 GCTCGACCAT AAAGACAAAG GTTTGCAGTC TTTGACGCTG GATCAGTCCG

101 TCAGGAAAAA CGAGAAACTG AAGCTGGCGG CACAAGGTGC GGAAAAAACT

151 TATGGAAACG GTGACAGCCT CAATACGGGC AAATTGAAGA ACGACAAGGT

201 CAGCCGTTTC GACTTTATCC GCCAAATCGA AGTGGACGGG CAGCTCATTA

251 CCTTGGAGAG TGGAGAGTTC AAGTATACA AACAAAGCCA TTCCGCCTTA

301 ACCGCCTTTC AGACCGAGCA ATACAAGAT TCGGAGCATT CCGGGAAGAT

351 GGTTGCGAAA CGCCAGTTCA GAATCGGCGA CATAGCGGGC GAACATACAT

401 CTTTTGACAA GCTTCCCGAA GGCGGCAGGG CGACATATCG CGGGACGGCG

451 TTCGGTTCAG ACGATGCCGG CGGAAAACTG ACCTACACCA TAGATTTCGC

501 CGCCAAGCAG GGAAACGGCA AAATCGAACA TTTGAAATCG CAAGAAATCA

551 ATGTCGACCT GGCCGCCGCC GATATCAAGC CGGATGGAAA ACGCCATGCC

601 GTCATCAGCG GTTCCGTCCT TTACAACCAA GCCGAGAAAG GCAGTTACTC

651 CCTCGGTATC TTTGGCGGAA AAGCCCAGGA AGTTGCCGGC AGCGCGGANG

701 TGAAAACCGT AAACGGCATA CGCCATATCG GCCTTGCCGC CAAGCAACTC

751 GAGGGATCCG GCGGAGGCGG CACTTCTGCG CCCGACTTCA ATGCAGGCGG

801 TACCGGTATC GGCAGCAACA GCAGAGCAAC AACAGCGAAA TCAGCAGCAG

851 TATCTTACGC CGGTATCAAG AACGAAATGT GCAAAGACAG AAGCATGCTC

901 TGTGCCGGTC GGGATGACGT TGCGGTTACA GACAGGGATG CCAAAATCAA

951 TGCCCCCCCC CCGAATCTGC ATACCGGAGA CTTTCCAAAC CCAAATGACG

1001 CATACAAGAA TTTGATCAAC CTCAAACCTG CAATTGAAGC AGGCTATACA

1051 GGACGCGGGG TAGAGGTAGG TATCGTCGAC ACAGGCGAAT CCGTCGGCAG

1101 CATATCCTTT CCCGAACTGT ATGGCAGAAA AGAACACGGC TATAACGAAA

1151 ATTACCAAAA CTATACGGCG TATATGCGGA AGGAAGCGCC TGAAGACGGA

1201 GGCGGTAAAG ACATTGAAGC TTCTTTCGAC GATGAGGCCG TTATAGAGAC

1251 TGAAGCAAAG CCGACGGATA TCCGCCACGT AAAAGAAATC GGACACATCG

1301 ATTTGGTCTC CCATATTATT GGCGGGCGTT CCGTGGACGG CAGACCTGCA

1351 GGCGGTATTG CGCCCGATGC GACGCTACAC ATAATGAATA CGAATGATGA

1401 AACCAAGAAC GAAATGATGG TTGCAGCCAT CCGCAATGCA TGGGTCAAGC

1451 TGGGCGAACG TGGCGTGCGC ATCGTCAATA ACAGTTTTGG AACAACATCG

1501 AGGGCAGGCA CTGCCGACCT TTTCCAAATA GCCAATTCGG AGGAGCAGTA

1551 CCGCCAAGCG TTGCTCGACT ATTCCGGCGG TGATAAAACA GACGAGGGTA
```

-continued

```
1601  TCCGCCTGAT GCAACAGAGC GATTACGGCA ACCTGTCCTA CCACATCCGT

1651  AATAAAAACA TGCTTTTCAT CTTTTCGACA GGCAATGACG CACAAGCTCA

1701  GCCCAACACA TATGCCCTAT TGCCATTTTA TGAAAAGAC GCTCAAAAAG

1751  GCATTATCAC AGTCGCAGGC GTAGACCGCA GTGGAGAAAA GTTCAAACGG

1801  GAAATGTATG GAGAACCGGG TACAGAACCG CTTGAGTATG GCTCCAACCA

1851  TTGCGGAATT ACTGCCATGT GGTGCCTGTC GGCACCCTAT GAAGCAAGCG

1901  TCCGTTTCAC CCGTACAAAC CCGATTCAAA TTGCCGGAAC ATCCTTTTCC

1951  GCACCCATCG TAACCGGCAC GGCGGCTCTG CTGCTGCAGA AATACCCGTG

2001  GATGAGCAAC GACAACCTGC GTACCACGTT GCTGACGACG GCTCAGGACA

2051  TCGGTGCAGT CGGCGTGGAC AGCAAGTTCG GCTGGGGACT GCTGGATGCG

2101  GGTAAGGCCA TGAACGGACC CGCGTCCTTT CCGTTCGGCG ACTTTACCGC

2151  CGATACGAAA GGTACATCCG ATATTGCCTA CTCCTTCCGT AACGACATTT

2201  CAGGCACGGG CGGCCTGATC AAAAAAGGCG GCAGCCAACT GCAACTGCAC

2251  GGCAACAACA CCTATACGGG CAAAACCATT ATCGAAGGCG GTTCGCTGGT

2301  GTTGTACGGC AACAACAAAT CGGATATGCG CGTCGAAACC AAAGGTGCGC

2351  TGATTTATAA CGGGGCGGCA TCCGGCGGCA GCCTGAACAG CGACGGCATT

2401  GTCTATCTGG CAGATACCGA CCAATCCGGC GCAAACGAAA CCGTACACAT

2451  CAAAGGCAGT CTGCAGCTGG ACGGCAAAGG TACGCTGTAC ACACGTTTGG

2501  GCAAACTGCT GAAAGTGGAC GGTACGGCGA TTATCGGCGG CAAGCTGTAC

2551  ATGTCGGCAC GCGGCAAGGG GGCAGGCTAT CTCAACAGTA CCGGACGACG

2601  TGTTCCCTTC CTGAGTGCCG CCAAAATCGG GCAGGATTAT TCTTTCTTCA

2651  CAAACATCGA AACCGACGGC GGCCTGCTGG CTTCCCTCGA CAGCGTCGAA

2701  AAAACAGCGG GCAGTGAAGG CGACACGCTG TCCTATTATG TCCGTCGCGG

2751  CAATGCGGCA CGGACTGCTT CGGCAGCGGC ACATTCCGCG CCCGCCGGTC

2801  TGAAACACGC CGTAGAACAG GGcGGCAGCA ATCTGGAAAA CCTGATGGTC

2851  GAACTGGATG CCTCCGAATC ATCCGCAACA CCCGAGACGG TTGAAACTGC

2901  GGCAGCCGAC CGCACAGATA TGCCGGGCAT CCGCCCCTAC GGCGCAACTT

2951  TCCGCGCAGC GGCAGCCGTA CAGCATGCGA ATGCCGCCGA CGGTGTACGC

3001  ATCTTCAACA GTCTCGCCGC TACCGTCTAT GCCGACAGTA CCGCCGCCCA

3051  TGCCGATATG CAGGGACGCC GCCTGAAAGC CGTATCGGAC GGGTTGGACC

3101  ACAACGGCAC GGGTCTGCGC GTCATCGCGC AAACCCAACA GGACGGTGGA

3151  ACGTGGGAAC AGGGCGGTGT TGAAGGCAAA ATGCGCGGCA GTACCCAAAC

3201  CGTCGGCATT GCCGCGAAAA CCGGCGAAAA TACGACAGCA GCCGCCACAC

3251  TGGGCATGGG ACGCAGCACA TGGAGCGAAA ACAGTGCAAA TGCAAAAACC

3301  GACAGCATTA GTCTGTTTGC AGGCATACGG CACGATGCGG GCGATATCGG

3351  CTATCTCAAA GGCCTGTTCT CCTACGGACG CTACAAAAAC AGCATCAGCC

3401  GCAGCACCGG TGCGGACGAA CATGCGGAAG CAGCGTCAA CGGCACGCTG

3451  ATGCAGCTGG GCGCACTGGG CGGTGTCAAC GTTCCGTTTG CCGCAACGGG

3501  AGATTTGACG GTCGAAGGCG GTCTGCGCTA CGACCTGCTC AAACAGGATG

3551  CATTCGCCGA AAAAGGCAGT GCTTTGGGCT GGAGCGGcAA CAGCCTCACT

3601  GAAGGCACGC TGGTCGGACT CGCGGGTCTG AAGCTGTCGC AACCCTTGAG
```

```
3651  CGATAAAGCC GTCCTGTTTG CAACGGCGGG CGTGGAAcGC GACCTGAACG

3701  GACGCGACTA CACGGTAACG GGCGGCTTTA CCGGCGCGAC TGCAGCAACC

3751  GGCAAGACGG GGGCACGCAA TATGCCGCAC ACCCGTCTGG TTGCCGGCCT

3801  GGGCGCGGAT GTCGAATTCG GCAACGGCTG GAACGGCTTG GCACGTTACA

3851  GCTACGCCGG TTCCAAACAG TACGGCAACC ACAGCGGACG AGTCGGCGTA

3901  GGCTACCGGT TCCTCGAGCA CCACCACCAC CACCACTGA

1  MVAADIGAGL ADALTAPLDH KDKGLQSLTL DQSVRKNEKL KLAAQGAEKT

51  YGNGDSLNTG KLKNDKVSRF DFIRQIEVDG QLITLESGEF QVYKQSHSAL

101  TAFQTEQIQD SEHSGKMVAK RQFRIGDIAG EHTSFDKLPE GGRATYRGTA

151  FGSDDAGGKL TYTIDFAAKQ GNGKIEHLKS PELNVDLAAA DIKPDGKRHA

201  VISGSVLYNQ AEKGSYSLGI FGGKAQEVAG SAEVKTVNGI RHIGLAAKQL

251  EGSGGGGTSA PDFNAGGTGI GSNSRATTAK SAAVSYAGIK NEMCKDRSML

301  CAGRDDVAVT DRDAKINAPP PNLHTGDFPN PNDAYKNLIN LKPAIEAGYT

351  GRGVEVGIVD TGESVGSISF PELYGRKEHG YNENYKNYTA YMRKEAPEDG

401  GGKDIEASFD DEAVIETEAK PTDIRHVKEI GHIDLVSHII GGRSVDGRPA

451  GGIAPDATLH IMNTNDETKN EMMVAAIRNA WVKLGERGVR IVNNSFGTTS

501  RAGTADLFQI ANSEEQYRQA LLDYSGGDKT DEGIRLMQQS DYGNLSYHIR

551  NKNMLFIFST GNDAQAQPNT YALLPFYEKD AQKGIITVAG VDRSGEKFKR

601  EMYGEPGTEP LEYGSNHCGI TAMWCLSAPY EASVRFTRTN PIQIAGTSFS

651  APIVTGTAAL LLQKYPWMSN DNLRTTLLTT AQDIGAVGVD SKFGWGLLDA

701  GKAMNGPASF PFGDFTADTK GTSDIAYSFR NDISGTGGLI KKGGSQLQLH

751  GNNTYTGKTI IEGGSLVLYG NNKSDMRVET KGALIYNGAA SGGSLNSDGI

801  VYLADTDQSG ANETVHIKGS LQLDGKGTLY TRLGKLLKVD GTAIIGGKLY

851  MSARGKGAGY LNSTGRRVPF LSAAKIGQDY SFFTNIETDG GLLASLDSVE

901  KTAGSEGDTL SYYVRRGNAA RTASAAAHSA PAGLKHAVEQ GGSNLENLMV

951  ELDASESSAT PETVETAAAD RTDMPGIRPY GATFRAAAAV QHANAADGVR

1001  IFNSLAATVY ADSTAAHADM QGRRLKAVSD GLDHNGTGLR VIAQTQQDGG

1051  TWEQGGVEGK MRGSTQTVGI AAKTGENTTA AATLGMGRST WSENSANAKT

1101  DSISLFAGIR HDAGDIGYLK GLFSYGRYKN SISRSTGADE HAEGSVNGTL

1151  MQLGALGGVN VPFAATGDLT VEGGLRYDLL KQDAFAEKGS ALGWSGNSLT

1201  EGTLVGLAGL KLSQPLSDKA VLFATAGVER DLNGRDYTVT GGFTGATAAT

1251  GKTGARNMPH TRLVAGLGAD VEFGNGWNGL ARYSYAGSKQ YGNHSGRVGV

1301  GYRFLEHHHH HH*

ΔG741-ORF46.1
   1  ATGGTCGCCG CCGACATCGG TGCGGGGCTT GCCGATGCAC TAACCGCACC

51  GCTCGACCAT AAAGACAAAG GTTTGCAGTC TTTGACGCTG GATCAGTCCG

101  TCAGGAAAAA CGAGAAACTG AAGCTGGCGG CACAAGGTGC GGAAAAAACT

151  TATGGAAACG GTGACAGCCT CAATACGGGC AAATCGAACA ACGACAAGGT

201  CAGCCGTTTC GACTTTATCC GCCAAATCGA AGTGGACGGG CAGCTCATTA

251  CCTTGGAGAG TGGAGAGTTC CAAGTATACA AACAAAGCCA TTCCGCCTTA

301  ACCGCCTTTC AGACCGAGCA AATACAAGAT TCGGAGCATT CCGGGAAGAT
```

```
-continued
 351  GGTTGCGAAA CGCCAGTTCA GAATCGGCGA CATAGCGGGC GAACATACAT
 401  CTTTTGACAA GCTTCCCGAA GGCGGCAGGG CGACATATCG CGGGACGGCG
 451  TTCGGTTCAG ACGATGCCGG CGGAAAACTG ACCTACACCA TAGATTTCGC
 501  CGCCAAGCAG GGAAACGGCA AAATCGAACA TTTGAAATCG CCAGAACTCA
 551  ATGTCGACCT GGCCGCCGCC GATATCAAGC CGGATGGAAA ACGCCATGCC
 601  GTCATCAGCG GTTCCGTCCT TTACAACCAA GCCGAGAAAG GCAGTTACTC
 651  CCTCGGTATC TTTGGCGGAA AAGCCCAGGA AGTTGCCGGC AGCGCGGAAG
 701  TGAAAACCGT AAACGGCATA CGCCATATCG GCCTTGCCGC CAAGCAACTC
 751  GACGGTGGCG GAGGCACTGG ATCCTCAGAT TTGGCAAACG ATTCTTTTAT
 801  CCGGCAGGTT CTCGACCGTC AGCATTTCGA ACCCGACGGG AAATACCACC
 851  TATTCGGCAG CAGGGGGGAA CTTGCCGAGC GCAGCGGCCA TATCGGATTG
 901  GGAAAAATAC AAAGCCATCA GTTGGGCAAC CTGATGATTC AACAGGCGGC
 951  CATTAAAGGA AATATCGGCT ACATTGTCCG CTTTTCCGAT CACGGGCACG
1001  AAGTCCATTC CCCCTTCGAC AACCATGCCT CACATTCCGA TTCTGATGAA
1051  GCCGGTAGTC CCGTTGACGG ATTTAGCCTT TACCGCATCC ATTGGGACGG
1101  ATACGAACAC CATCCCGCCG ACGGCTATGA CGGGCCACAG GGCGGCGGCT
1151  ATCCCGCTCC CAAAGGCGCG AGGGATATAT ACAGCTACGA CATAAAAGGC
1201  GTTGCCCAAA ATATCCGCCT CAACCTGACC GACAACCGCA GCACCGGACA
1251  ACGGCTTGCC GACCGTTTCC ACAATGCCGG TAGTATGCTG ACGCAAGGAG
1301  TAGGCGACGG ATTCAAACGC GCCACCCGAT ACAGCCCCGA GCTGGACAGA
1351  TCGGGCAATG CCGCCGAAGC CTTCAACGGC ACTGCAGATA TCGTTAAAAA
1401  CATCATCGGC GCGGCAGGAG AAATTGTCGG CGCAGGCGAT GCCGTGCAGG
1451  GCATAAGCGA AGGCTCAAAC ATTGCTGTCA TGCACGGCTT GGGTCTGCTT
1501  TCCACCGAAA ACAAGATGGC GCGCATCAAC GATTTGGCAG ATATGGCGCA
1551  ACTCAAAGAC TATGCCGCAG CAGCCATCCG CGATTGGGCA GTCCAAAACC
1601  CCAATGCCGC ACAAGGCATA GAAGCCGTCA GCAATATCTT TATGGCAGCC
1651  ATCCCCATCA AGGGATTGG AGCTGTTCGG GGAAAATACG GCTTGGGCGG
1701  CATCACGGCA CATCCTATCA AGCGGTCGCA GATGGGCGCG ATCGCATTGC
1751  CGAAAGGGAA ATCCGCCGTC AGCGACAATT TGCCGATGC GGCATACGCC
1801  AAATACCCGT CCCCTTACCA TTCCCGAAAT ATCCGTTCAA ACTTGGAGCA
1851  GCGTTACGGC AAAGAAAACA TCACCTCCTC AACCGTGCCG CCGTCAAACG
1901  GCAAAAATGT CAAACTGGCA GACCAACGCC ACCCGAAGAC AGGCGTACCG
1951  TTTGACGGTA AAGGGTTTCC GAATTTTGAG AAGCACGTGA AATATGATAC
2001  GCTCGAGCAC CACCACCACC ACCACTGA 1  MVAADIGAGL ADALTAPLDH KDKGLQSLTL DQSVRKNEKL KLAAQGAEKT
  51  YGNGDSLNTG KLKNDKVSRF DFIRQIEVDG QLITLESGEF QVYKQSHSAL
 101  TAFQTEQIQD SEHSGKMVAK RQFRIGDIAG EHTSFDKLPE GGRARYAGTA
 151  FGSDDAGGKL TYTIDFAAKQ GNGKIEHLKS PELNVDLAAA DIKPDGKRHA
 201  VISGSVLYNQ AEKGSYSLGI FGGKAQEVAG SAEVKTVNGI RHIGLAAKQL
 251  DGGGTGSSD LANDSFIRQV LDRQHFEPDG KYHLFGSRGE LAERSGHIGL
 301  GKIQSHQLGN LMIQQAAIKG NIGYIVRFSD HGHEVHSPFD NHASHSDSDE
```

```
351  AGSPVDGFSL  YRIHWDGYEH  HPADGYDGPQ  GGGYPAPKGA  RDIYSYDIKG

401  VAQNIRLNLT  DNRSTGQRLA  DRFHNAGSML  TQGVGDGFKR  ATRYSPELDR

451  SGNAAEAFNG  TADIVKNIIG  AAGEIVGAGD  AVQGISEGSN  IAVMHGLGLL

501  STENKMARIN  DLADMAQLKD  YAAAAIRDWA  VQNPNAAQGI  EAVSNIFMAA

551  IPIKGIGAVR  GKYGLGGITA  HPIKRSQMGA  IALPKGKSAV  SDNFADANYA

601  KYPSPYHSRN  IRSNLEQRYG  KENITSSTVP  PSNGXNVKLA  DQRHPKTGVP

651  FDGKGFPNFE  KHVKYDTLEH  HHHHH*
```

Example 16

C-Terminal Fusions ('Hybrids') with 287/ΔG287

According to the invention, hybrids of two proteins A & B may be either NH$_2$-A-B—COOH or NH$_2$—B-A-COOH. The effect of this difference was investigated using protein 287 either C-terminal (in '287-His' form) or N-terminal (in ΔG287 form—sequences shown above) to 919, 953 and ORF46.1. A panel of strains was used, including homologous strain 2996. FCA was used as adjuvant:

|  | 287 & 919 | | 287 & 953 | | 287 & ORF46.1 | |
|---|---|---|---|---|---|---|
| Strain | ΔG287-919 | 919-287 | ΔG287-953 | 953-287 | ΔG287-46.1 | 46.1-287 |
| 2996 | 128000 | 16000 | 65536 | 8192 | 16384 | 8192 |
| BZ232 | 256 | 128 | 128 | <4 | <4 | <4 |
| 1000 | 2048 | <4 | <4 | <4 | <4 | <4 |
| MC58 | 8192 | 1024 | 16384 | 1024 | 512 | 128 |
| NGH38 | 32000 | 2048 | >2048 | 4096 | 16384 | 4096 |
| 394/98 | 4096 | 32 | 256 | 128 | 128 | 16 |
| MenA (F6124) | 32000 | 2048 | >2048 | 32 | 8192 | 1024 |
| ManC (BZ133) | 64000 | >8192 | >8192 | <16 | 8192 | 2048 |

Better bactericidal titres are generally seen with 287 at the N-terminus (in the ΔG form)

When fused to protein 961 [NH$_2$-ΔG287-961-COOH—sequence shown above], the resulting protein is insoluble and must be denatured and renatured for purification. Following renaturation, around 50% of the protein was found to remain insoluble. The soluble and insoluble proteins were compared, and much better bactericidal titres were obtained with the soluble protein (FCA as adjuvant):

|  | 2996 | BZ232 | MC58 | NGH38 | F6I24 | BZ133 |
|---|---|---|---|---|---|---|
| Soluble | 65536 | 128 | 4096 | >2048 | >2048 | 4096 |
| Insoluble | 8192 | <4 | <4 | 16 | n.d. | n.d. |

Titres with the insoluble form were, however, improved by using alum adjuvant instead:

| Insoluble | 32768 | 128 | 4096 | >2048 | >2048 | 2048 |
|---|---|---|---|---|---|---|

Example 17

N-Terminal Fusions ('Hybrids') to 287

Expression of protein 287 as full-length with a C-terminal His-tag, or without its leader peptide but with a C-terminal His-tag, gives fairly low expression levels. Better expression is achieved using a N-terminal GST-fusion.

As an alternative to using GST as an N-terminal fusion partner, 287 was placed at the C-terminus of protein 919 ('919-287'), of protein 953 ('953-287'), and of proteins ORF46.1 ('ORF46.1-287'). In both cases, the leader peptides were deleted, and the hybrids were direct in-frame fusions.

To generate the 953-287 hybrid, the leader peptides of the two proteins were omitted by designing the forward primer downstream from the leader of each sequence; the stop codon sequence was omitted in the 953 reverse primer but included in the 287 reverse primer. For the 953 gene, the 5' and the 3' primers used for amplification included a NdeI and a BamHI restriction sites respectively, whereas for the amplification of the 287 gene the 5' and the 3' primers included a BamHI and a XhoI restriction sites respectively. In this way a sequential directional cloning of the two genes in pET21b+, using NdeI-BamHI (to clone the first gene) and subsequently BamHI-XhoI (to clone the second gene) could be achieved.

The 919-287 hybrid was obtained by cloning the sequence coding for the mature portion of 287 into the XhoI site at the 3'-end of the 919-His clone in pET21b+. The primers used for amplification of the 287 gene were designed for introducing a SalI restriction site at the 5'- and a XhoI site at the 3'- of the PCR fragment. Since the cohesive ends produced by the SalI and XhoI restriction enzymes are compatible, the 287 PCR product digested with SalI-XhoI could be inserted in the pET21b-919 clone cleaved with XhoI.

The ORF46.1-287 hybrid was obtained similarly.

The bactericidal efficacy (homologous strain) of antibodies raised against the hybrid proteins was compared with antibodies raised against simple mixtures of the component antigens:

|  | Mixture with 287 | Hybrid with 287 |
|---|---|---|
| 919 | 32000 | 16000 |
| 953 | 8192 | 8192 |
| ORF46.1 | 128 | 8192 |

Data for bactericidal activity against heterologous MenB strains and against serotypes A and C were also obtained for 919-287 and 953-287:

|  | 919 | | 953 | | ORF46.1 | |
|---|---|---|---|---|---|---|
| Strain | Mixture | Hybrid | Mixture | Hybrid | Mixture | Hybrid |
| MC58 | 512 | 1024 | 512 | 1024 | — | 1024 |
| NGH38 | 1024 | 2048 | 2048 | 4096 | — | 4096 |
| BZ232 | 512 | 128 | 1024 | 16 | — | — |
| MenA (F6124) | 512 | 2048 | 2048 | 32 | — | 1024 |
| MenC (C11) | >2048 | n.d. | >2048 | n.d. | — | n.d. |
| MenC (BZ133) | >4096 | >8192 | >4096 | <16 | — | 2048 |

Hybrids of ORF46.1 and 919 were also constructed. Best results (four-fold higher titre) were achieved with 919 at the N-terminus.

Hybrids 919-519His, ORF97-225His and 225-ORF97His were also tested. These gave moderate ELISA fitres and bactericidal antibody responses.

Example 18

The Leader Peptide from ORF4

As shown above, the leader peptide of ORF4 can be fused to the mature sequence of other proteins (e.g. proteins 287 and 919). It is able to direct lipidation in *E. coli*.

Example 19

Domains in 564

Figure 8:
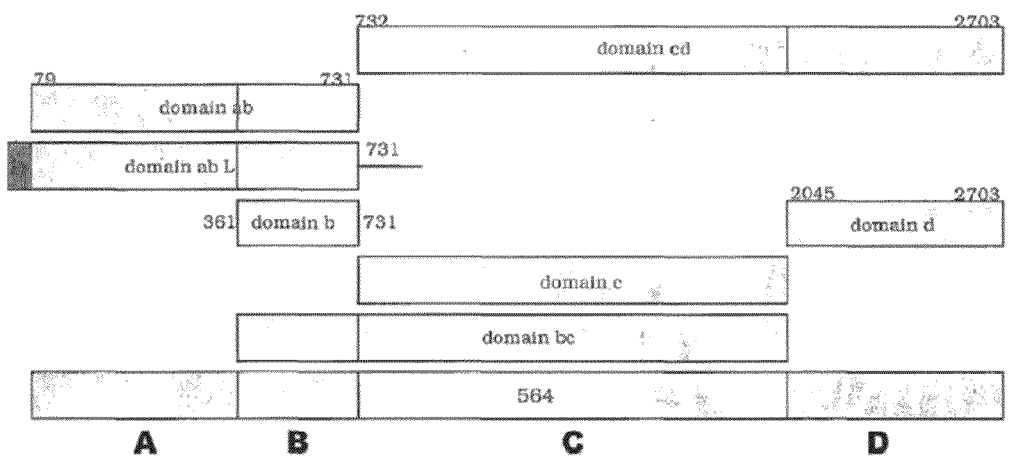
FIG. 8 shows domains of protein 564.

The protein '564' is very large (2073aa), and it is difficult to clone and express it in complete form. To facilitate expression, the protein has been divided into four domains, as shown in FIG. 8 (according to the MC58 sequence):

| Domain | A | B | C | D |
|---|---|---|---|---|
| Amino Acids | 79-360 | 361-731 | 732-2044 | 2045-2073 |

These domains show the following homologies:
Domain A shows homology to other bacterial toxins:

| gb|AAG03431.1|AE004443_9 | probable hemagglutinin [*Pseudomonas aeruginosa*] (38%) |
| gb|AAC31981.1|(139897) | HecA [*Pectobacterium chrysanthemi*] (45%) |
| emb|CAA36409.1|(X52156) | filamentous hemagglutinin [*Bordetella pertussis*] (31%) |
| gb|AAC79757.1|(AF057695) | large supernatant protein1 [*Haemophilus ducreyi*] (26%) |
| gb|AAA25657.1|(M30186) | HpmA precursor [*Proteus mirabilis*] (29%) |

Domain B shows no homology, and is specific to 564.
Domain C shows homology to:

| gb|AAF84995.1|AE004032 | HA-like secreted protein [*Xylella fastidiosa*] (33%) |
| gb|AAG05850.1|AE004673 | hypothetical protein [*Pseudomonas aeruginosa*] (27%) |
| gb|AAF68414.1.AF237928 | putative FHA [*Pasteurella multocisida*] (23%) |
| gb|AAC79757.1|(AF057695) | large supernatant protein1 [*Haemophilus ducreyi*] (23%) |
| pir||S21010 | FHA B precursor [*Bordetella pertussis*] (20%) |

Domain D shows homology to other bacterial toxins:

| gb|AAF84995.1|AE004032_14 | HA-like secreted protein [*Xylella fastidiosa*] (29%) |

Using the MC58 strain sequence, good intracellular expression of 564ab was obtained in the form of GST-fusions (no purification) and his-tagged protein; this domain-pair was also expressed as a lipoprotein, which showed moderate expression in the outer membrane/supernatant fraction.

The b domain showed moderate intracellular expression when expressed as a his-tagged product (no purification), and good expression as a GST-fusion.

The c domain showed good intracellular expression as a GST-fusion, but was insoluble. The d domain showed moderate intracellular expression as a his-tagged product (no purification). The cd protein domain-pair showed moderate intracellular expression (no purification) as a GST-fusion.

Good bactericidal assay titres were observed using the c domain and the be pair.

Example 20

The 919 Leader Peptide

Figure 9:
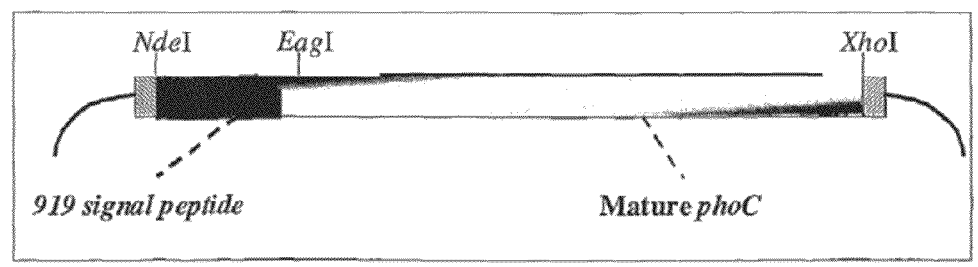
FIG. 9 shows the PhoC reporter gene driven by the 919 leader peptide.

The 20mer leader peptide (SEQ ID NO:633) from 919 is discussed in example 1 above:
MKKYLFRAAL YGIAAAILAA As shown in example 1, deletion of this leader improves heterologous expression, as does substitution with the ORF4 leader peptide. The influence of the 919 leader on expression was investigated by fusing the coding sequence to the PhoC reporter gene from *Morganella morganii* [Thaller et al. (1994) *Microbiology* 140:1341-1350]. The construct (SEQ ID NO:116) was cloned in the pET21-b plasmid between the NdeI and XhoI sites (FIG. 9):

```
  1 MKKYLFRAAL YGIAAAILAA AIPAGNDATT KPDLYYLKNE QAIDSLKLLP

51 PPPEVGSIQF LNDQAMYEKG RMLRNTERGK QAQADADLAA GGVATAFSGA

101 FGYPITEKDS PELYKLLTNM IEDAGDLATR SAKEHYNRIR PFAFYGTETC

151 NTKDQKKLST NGSYPSGHTS IGWATALVLA EVNPANQDAI LERGYQLGQS

201 RVICGYHWQS DVDAARIVGS AAVATLHSDP AFQAQLAKAK QEFAQKSQK*
```

The level of expression of PhoC from this plasmid is >200-fold lower than that found for the same construct but containing the native PhoC signal peptide. The same result was obtained even after substitution of the T7 promoter with the *E. coli* Plac promoter. This means that the influence of the 919 leader sequence on expression does not depend on the promoter used.

In order to investigate if the results observed were due to some peculiarity of the 919 signal peptide nucleotide sequence (secondary structure formation, sensitivity to RNAases, etc.) or to protein instability induced by the presence of this signal peptide, a number of mutants were generated. The approach used was a substitution of nucleotides of the 919 signal peptide sequence by cloning synthetic linkers containing degenerate codons. In this way, mutants were obtained with nucleotide and/or amino acid substitutions.

Two different linkers were used, designed to produce mutations in two different regions of the 919 signal peptide sequence, in the first 19 base pairs (L1) (SEQ ID NO:117) and between bases 20-36 (S1) (SEQ ID NO:118).

L1: 5' T ATG AAa/g TAc/t c/tTN TTt/c a/cGC GCC GCC CTG TAC GGC ATC GCC GCC GCC ATC CTC GCC GCC GCG ATC CC 3'

S1: 5' T ATG AAA AAA TAC CTA TTC CGa/g GCN GCN c/tTa/g TAc/t GGc/g ATC GCC GCC GCC ATC CTC GCC GCC GCG ATC CC 3'

The alignment of some of the mutants obtained is given below.

L1 Mutants:

```
                                                   (SEQ ID NO: 119)
9L1-a
ATGAAGAAGTACCTTTTCAGCGCCGCC~~~~~~~~~~~~~~~~~~~~~~~~~~~~~~~~

(SEQ ID NO: 120)
9L1-e
ATGAAAAAATACTTTTTCCGCGCCGCC~~~~~~~~~~~~~~~~~~~~~~~~~~~~~~~~

(SEQ ID NO: 121)
9L1-d
ADGAAAAAATACTTTTTCCGCGCCGCC~~~~~~~~~~~~~~~~~~~~~~~~~~~~~~~~

(SEQ ID NO: 122)
9L1-f
ATGAAAAAATATCTCTTTAGCGCCGCCCTGTACGGCATCGCCGCCGCCATCCTCGCCGCC (SEQ ID NO: 123)
919sp
ATGAAAAAATACCTATTCCGCGCCGCCCTGTACGGCATCGCCGCCGCCATCCTCGCCGCC (SEQ ID NO: 124)
9L1a
MKKYLFSAA~~~~~~~~~~~

(SEQ ID NO: 125)
9L1e
MKKYFFRAA~~~~~~~~~~~

(SEQ ID NO: 126)
9L1d
MKKYFFRAA~~~~~~~~~~~

(SEQ ID NO: 127)
9L1f
MKKYLFSAALYGIAAAILAA (SEQ ID NO: 128)
919sp
MKKYLFRAALYGIAAAILAA  (i.e. native signal peptide)
```

S1 Mutants:

```
(SEQ ID NO: 129)
9S1-e
ATGAAAAAATACCTATTC.................ATCGCCGCCGCCATCCTCGCCGCC (SEQ ID NO: 130)
9S1-c
ATGAAAAAATACCTATTCCGAGCTGCCCAATACGGCATCGCCGCCGCCATCCTCGCCGCC (SEQ ID NO: 131)
9S1-b
ATGAAAAAATACCTATTCCGGGCCGCCCAATACGGCATCGCCGCCGCCATCCTCGCCGCC (SEQ ID NO: 132)
931-i
ATGAAAAAATACCTATTCCGGGCGGCTTTGTACGGGATCGCCGCCGCCATCCTCGCCGCC
```

(SEQ ID NO: 123)
919sp
ATGAAAAAATACCTATTCCGCGCCGCCCTGTACGGCATCGCCGCCGCCATCCTCGCCGCC (SEQ ID NO: 133)
9S1e
MKKYLF......IAAAILAA (SEQ ID NO: 134)
9S1c
MKKYLFRAAQYGIAAAILAA (SEQ ID NO: 135)
9S1b
MKKYLFRAAQYGIAAAILAA (SEQ ID NO: 136)
9S1i
MKKYLFRAALYGIAAAILAA (SEQ ID NO: 128)
919sp
MKKYLFRAALYGIAAAILAA

As shown in the sequences alignments, most of the mutants analysed contain in-frame deletions which were unexpectedly produced by the host cells.

Figure 10A:
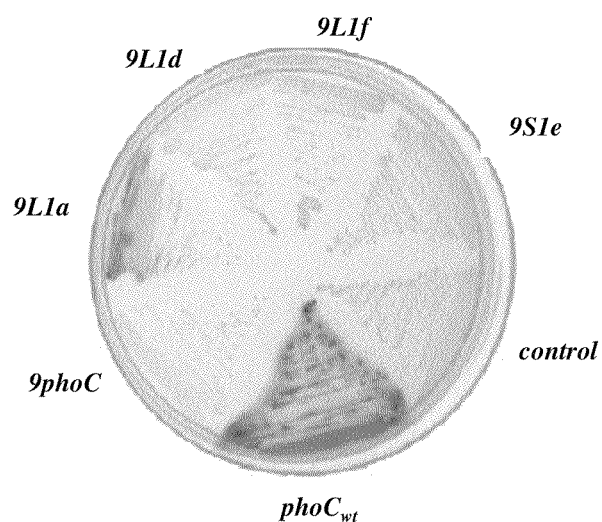
FIG. 10A-FIG. 10B show the results obtained using mutants of the 919 leader peptide driving the PhoC reporter.
Figure 10B:
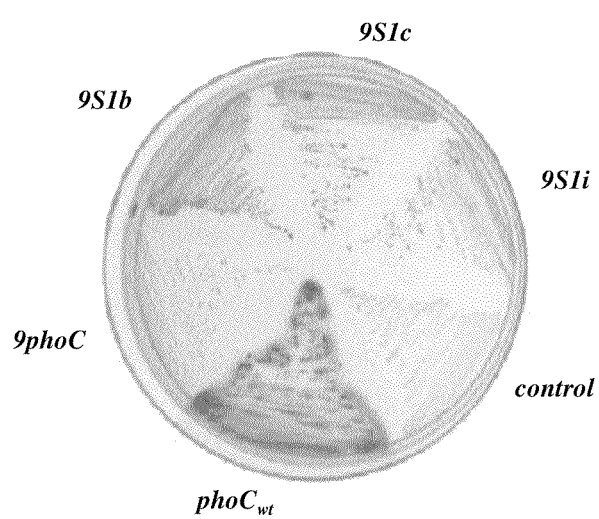

Selection of the mutants was performed by transforming *E. coli* BL21(DE3) cells with DNA prepared from a mixture of L1 and S1 mutated clones. Single transformants were screened for high PhoC activity by streaking them onto LB plates containing 100 µg/ml ampicillin, 50 µg/ml methyl green, 1 mg/ml PDP (phenolphthaleindiphosphate). On this medium PhoC-producing cells become green (FIG. 10).

A quantitative analysis of PhoC produced by these mutants was carried out in liquid medium using pNPP as a substrate for PhoC activity. The specific activities measured in cell extracts and supernatants of mutants grown in liquid medium for 0, 30, 90, 180 min. were:

Cell Extracts

|         | 0      | 30     | 90     | 180    |
|---------|--------|--------|--------|--------|
| control | 0.00   | 0.00   | 0.00   | 0.00   |
| 9phoC   | 1.11   | 1.11   | 3.33   | 4.44   |
| 9S1e    | 102.12 | 111.00 | 149.85 | 172.05 |
| 9L1a    | 206.46 | 111.00 | 94.35  | 83.25  |
| 9L1d    | 5.11   | 4.77   | 4.00   | 3.11   |
| 9L1f    | 27.75  | 94.35  | 82.14  | 36.63  |
| 9S1b    | 156.51 | 111.00 | 72.15  | 28.86  |
| 9S1c    | 72.15  | 33.30  | 21.09  | 14.43  |
| 9S1i    | 156.51 | 83.25  | 55.50  | 26.64  |
| phoCwt  | 194.25 | 180.93 | 149.85 | 142.08 |

Supernatants

|         | 0     | 30    | 90    | 180    |
|---------|-------|-------|-------|--------|
| control | 0.00  | 0.00  | 0.00  | 0.00   |
| 9phoC   | 0.33  | 0.00  | 0.00  | 0.00   |
| 9S1e    | 0.11  | 0.22  | 0.44  | 0.89   |
| 9L1a    | 4.88  | 5.99  | 5.99  | 7.22   |
| 9L1d    | 0.11  | 0.11  | 0.11  | 0.11   |
| 9L1f    | 0.11  | 0.22  | 0.11  | 0.11   |
| 9S1b    | 1.44  | 1.44  | 1.44  | 1.67   |
| 9S1c    | 0.44  | 0.78  | 0.56  | 0.67   |
| 9S1i    | 0.22  | 0.44  | 0.22  | 0.78   |
| phoCwt  | 34.41 | 43.29 | 87.69 | 177.60 |

Some of the mutants produce high amounts of PhoC and in particular, mutant 9L1a can secrete PhoC in the culture medium. This is noteworthy since the signal peptide sequence of this mutant is only 9 amino acids long. This is the shortest signal peptide described to date.

Example 21

C-Terminal Deletions of Maf-Related Proteins

MafB-related proteins include 730, ORF46 and ORF29.

The 730 protein from MC58 has the following sequence (SEQ ID NO:137):

```
  1 VKPLRRLTNL LAACAVAAAA LIQPALAADL AQDPFITDNA QRQHYEPGGK

51 YHLFGDPRGS VSDRTGKINV IQDYTHQMGN LLIQQANING TIGYHTRFSG

101 HGHEEHAPFD NHAADSASEE KGNVDEGFTV YRLNWEGHEH HPADAYDGPK

151 GGNYPKPTGA RDEYTYHVNG TARSIKLNPT DTRSIRQRIS DNYSNLGSNF

201 SDRADEANRK MFEHNAKLDR WGNSMEFING VAAGALNPFI SAGEALGIGD

251 ILYGTRYAID KAAMRNIAPL PAEGKFAVIG GLGSVAGFEK NTREAVDRWI

301 QENPNAAETV EAVFNVAAAA KVAKLAKAAK PGKAAVSGDF ADSYKKKLAL

351 SDSARQLYQN AKYREALDIH YEDLIRRKTD GSSKFINGRE IDAVTNDALI
```

```
                                   -continued
401 QAKRTISAID KPKNFLNQKN RKQIKATIEA ANQQGKRAEF WFKYGVHSQV

451 KSYIESKGGI VKTGLGD*
```

The leader peptide is underlined.

730 shows similar features to ORF46 (see example 8 above):
- as for Orf46, the conservation of the 730 sequence among MenB, MenA and gonococcus is high (>80%) only for the N-terminal portion. The C-terminus, from ~340, is highly divergent.
- its predicted secondary structure contains a hydrophobic segment spanning the central region of the molecule (aa. 227-247).
- expression of the full-length gene in E. coli gives very low yields of protein. Expression from tagged or untagged constructs where the signal peptide sequence has been omitted has a toxic effect on the host cells. In other words, the presence of the full-length mature protein in the cytoplasm is highly toxic for the host cell while its translocation to the periplasm (mediated by the signal peptide) has no detectable effect on cell viability. This "intracellular toxicity" of 730 is particularly high since clones for expression of the leaderless 730 can only be obtained at very low frequency using a recA genetic background (E. coli strains: HB101 for cloning; HMS174(DE3) for expression).

To overcome this toxicity, a similar approach was used for 730 as described in example 8 for ORF46. Four C-terminal truncated forms were obtained, each of which is well expressed. All were obtained from intracellular expression of His-tagged leaderless 730.

Form A consists of the N-terminal hydrophilic region of the mature protein (aa. 28-226). This was purified as a soluble His-tagged product, having a higher-than-expected MW.

Form B extends to the end of the region conserved between serogroups (aa. 28-340). This was purified as an insoluble His-tagged product.

Figure 11A:
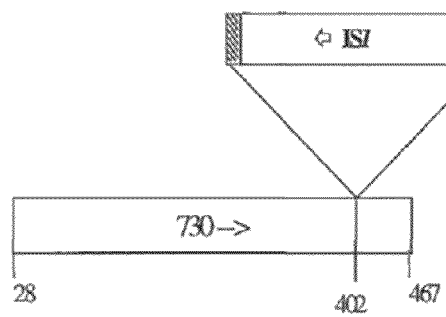
FIG. 11A-FIG. 11B show insertion mutants of protein 730.
Figure 11B:
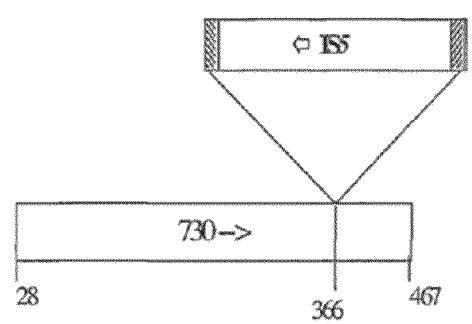

The C-terminal truncated forms named C1 and C2 were obtained after screening for clones expressing high levels of 730-His clones in strain HMS174(DE3). Briefly, the pET21b plasmid containing the His-tagged sequence coding for the full-length mature 730 protein was used to transform the recA strain HMS174(DE3). Transformants were obtained at low frequency which showed two phenotypes: large colonies and very small colonies. Several large and small colonies were analysed for expression of the 730-His clone. Only cells from large colonies over-expressed a protein recognised by anti-730A antibodies. However the protein over-expressed in different clones showed differences in molecular mass. Sequencing of two of the clones revealed that in both cases integration of an E. coli IS sequence had occurred within the sequence coding for the C terminal region of 730. The two integration events have produced in-frame fusion with 1 additional codon in the case of C1, and 12 additional codons in the case of C2 (FIG. 11). The resulting "mutant" forms of 730 have the following sequences:

```
730-C1 (due to an IS1 insertion-FIG. 11A) (SEQ ID NO: 138)
  1 MADLAQDPFI TDNAQRQHYE PGGKYHLFGD PRGSVSDRTG KINVIQDYTH

51 QMGNLLIQQA NINGTIGYHT RFSGHGHEEH APFDNHAADS ASEEKGNVDE

101 GFTVYRLNWE GHEHHPADAY DGPKGGNYPR PTGARDEYTY HVNGTARSIK

151 LNPTDTRSIR QRISDNYSNL GSNFSDRADE ANRKMFEHNA KLDRWGNSME

201 FINGVAAGAL NPFISAGEAL GIGDILYGTR YAIDKAAMRN IAPLPAEGEF

251 AVIGGLGSVA GFEKNTREAV DRWIQENPNA AETVEAVFNV AAAAKVAKLA

301 KAAKPGKAAV SGDFADSYKK KLALSDSARQ LYQNAKYREA LDIHYEDLIR

351 RKTDGSSKFI NGREIDAVTN DALIQAR*
```

The additional amino acid produced by the insertion is underlined.

```
730-C2 (due to an IS5 insertion-FIG. 11B) (SEQ ID NO: 139)
  1 MADLAQDPFI TDNAQRQHYE PGGKYHLFGD PRGSVSDRTG KINVIQDYTH

51 QMGNLLIQQA NINGTIGYHT RFSGHGHEEH APFDNHAADS ASEEKGNVDE

101 GFTVYRLNWE GHEHHPADAY DGPKGGNYPK PTGARDEYTY HVNGTARSIK

151 LNPTDTRSIR QRISDNYSNL GSNFSDRADE ANRKMFEHNA KLDRWGNSME

201 FINGVAAGAL NPFISAGEAL GIGDILYGTR YAIDKAAMRN IAPLPAEGKF

251 AVIGGLGSVA GFEKNTREAV DRWIQENPNA AETVEAVFNV AAAAKVAKLA

301 KAAKPGKAAV SGDFADSYKK KLALSDSARQ LYQNAKYREA LGKVRISGEI

351 LLG*
```

The additional amino acids produced by the insertion are underlined.

In conclusion, intracellular expression of the 730-C1 form gives very high level of protein and has no toxic effect on the host cells, whereas the presence of the native C-terminus is toxic. These data suggest that the "intracellular toxicity" of 730 is associated with the C-terminal 65 amino acids of the protein.

Equivalent truncation of ORF29 to the first 231 or 368 amino acids has been performed, using expression with or without the leader peptide (amino acids 1-26; deletion gives cytoplasmic expression) and with or without a His-tag.

Example 22

Domains in 961

Figure 12:
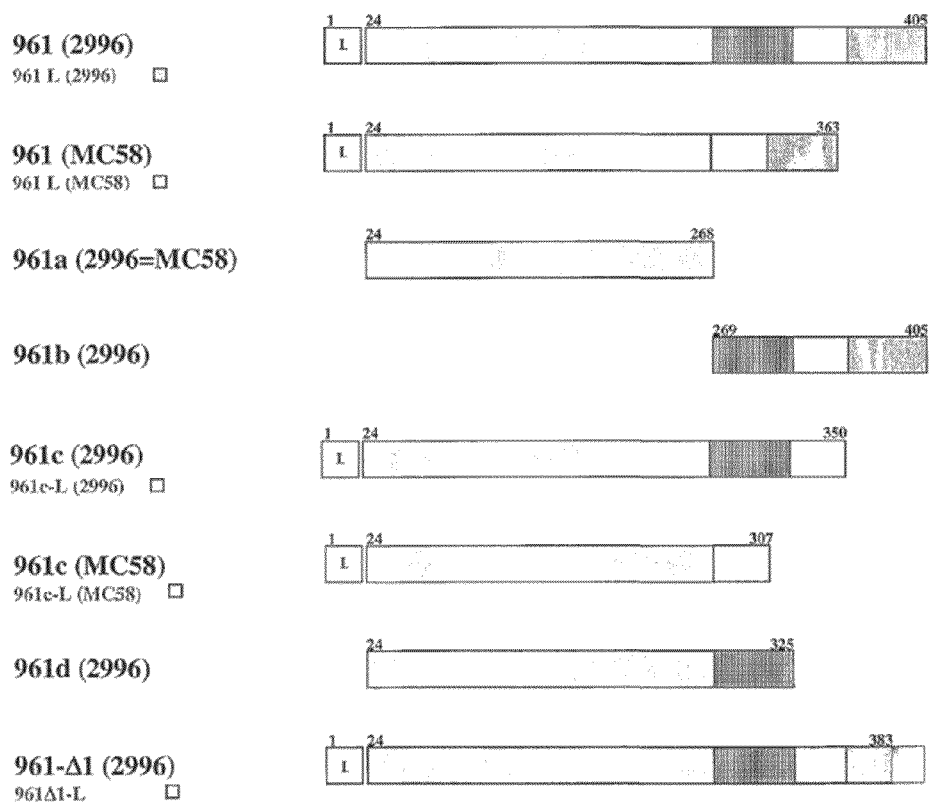
FIG. 12 shows domains of protein 961.

As described in example 9 above, the GST-fusion of 961 was the best-expressed in *E. coli*. To improve expression, the protein was divided into domains (FIG. 12).

The domains of 961 were designed on the basis of YadA (an adhesin produced by *Yersinia* which has been demonstrated to be an adhesin localized on the bacterial surface that forms oligomers that generate surface projection [Hoiczyk et al. (2000) *EMBO J.* 19:5989-99]) and are: leader peptide, head domain, coiled-coil region (stalk), and membrane anchor domain.

These domains were expressed with or without the leader peptide, and optionally fused either to C-terminal His-tag or to N-terminal GST. *E. coli* clones expressing different domains of 961 were analyzed by SDS-PAGE and western blot for the production and localization of the expressed protein, from over-night (o/n) culture or after 3 hours induction with IPTG. The results were:

| | Total lysate (Western Blot) | Periplasm (Western Blot) | Supernatant (Western Blot) | OMV SDS-PAGE |
|---|---|---|---|---|
| 961 (o/n) | − | − | − | |
| 961 (IPTG) | +/− | − | − | |
| 961-L (o/n) | + | − | − | + |
| 961-L (IPTG) | + | − | − | + |
| 961c-L (o/n) | − | − | − | |
| 961c-L (IPTG) | + | + | + | |
| 961Δ$_1$-L (o/n) | − | − | − | |
| 961Δ$_1$-L (IPTG) | + | − | − | + |

The results show that in *E. coli*:

961-L is highly expressed and localized on the outer membrane. By western blot analysis two specific bands have been detected: one at ~45 kDa (the predicted molecular weight) and one at ~180 kDa, indicating that 961-L can form oligomers. Additionally, these aggregates are more expressed in the over-night culture (without IPTG induction). OMV preparations of this clone were used to immunize mice and serum was obtained. Using over-night culture (predominantly by oligomeric form) the serum was bactericidal; the IPTG-induced culture (predominantly monomeric) was not bactericidal.

961Δ$_1$-L (with a partial deletion in the anchor region) is highly expressed and localized on the outer membrane, but does not form oligomers;

the 961c-L (without the anchor region) is produced in soluble form and exported in the supernatant.

Titres in ELISA and in the serum bactericidal assay using His-fusions were as follows:

| | ELISA | Bactericidal |
|---|---|---|
| 961a (aa 24-268) | 24397 | 4096 |
| 961b (aa 269-405) | 7763 | 64 |
| 961c-L | 29770 | 8192 |
| 961c (2996) | 30774 | >65536 |
| 961c (MC58) | 33437 | 16384 |
| 961d | 26069 | >65536 |

*E. coli* clones expressing different forms of 961 (961, 961-L, 961Δ$_1$-L and 961c-L) were used to investigate if the 961 is an adhesin (c.f. YadA). An adhesion assay was performed using (a) the human epithelial cells and (b) *E. coli* clones after either over-night culture or three hours IPTG induction. 961-L grown over-night (961Δ$_1$-L) and IPTG-induced 961c-L (the clones expressing protein on surface) adhere to human epithelial cells.

961c was also used in hybrid proteins (see above). As 961 and its domain variants direct efficient expression, they are ideally suited as the N-terminal portion of a hybrid protein.

Example 23

Further Hybrids

Further hybrid proteins of the invention are shown below (see also FIG. 14). These are advantageous when compared to the individual proteins:

```
ORF46.1-741 (SEQ ID NOs: 140 and 141)
  1 ATGTCAGATT TGGCAAACGA TTCTTTTATC CGGCAGGTTC TCGACCGTCA

51 GCATTTCGAA CCCGACGGGA AATACCACCT ATTCGGCAGC AGGGGGGAAC

101 TTGCCGAGCG CAGCGGCCAT ATCGGATTGG GAAAAATACA AAGCCATCAG

151 TTGGGCAACC TGATGATTCA ACAGGCGGCC ATTAAAGGAA ATATCGGCTA

201 CATTGTCCGC TTTTCCGATC ACGGGCACGA AGTCCATTCC CCCTTCGACA

251 ACCATGCCTC ACATTCCGAT TCTGATGAAG CCGGTAGTCC CGTTGACGGA

301 TTTAGCCTTT ACCGCATCCA TTGGGACGGA TACGAACACC ATCCCGCCGA

351 CGGCTATGAC GGGCCACAGG GCGGCGGCTA TCCCGCTCCC AAAGGCGCGA

401 GGGATATATA CAGCTACGAC ATAAAAGGCG TTGCCCAAAA TATCCGCCTC

451 AACCTGACCG ACAACCGCAG CACCGGACAA CGGCTTGCCG ACCGCATCCA
```

```
 501 CAATGCCGGT AGTATGCTGA CGCAAGGAGT AGGCGACGGA TTCAAACGCG
 551 CCACCCGATA CAGCCCCGAG CTGGACAGAT CGGGCAATGC CGCCGAAGCC
 601 TTCAACGGCA CTGCAGATAT CGTTAAAAAC ATCATCGGCG CGGCAGGAGA
 651 AATTGTCGGC GCAGGCGATG CCGTGCAGGG CATAAGCGAA GGCTCAAACA
 701 TTGCTGTCAT GCACCGCTCG GGTCTGCTTT CCACCGAAAA CAAGATGGCG
 751 CGCATCAACG ATTTGGCAGA TATGGCGCAA CTCAAAGACT ATGCCGCAGC
 801 AGCCATCCGC GATTGGGCAG TCCAAAACCC CAATGCCGCA CAAGGCATAG
 851 AAGCCGTCAG CAATATCTTT ATGGCAGCCA TCCCCATCAA AGGGATTGGA
 901 GCTGTTCGGG GAAAATACGG CTTGGGCGGC ATCACGGCAC ATCCTATCAA
 951 GCGGTCGCAG ATGGGCGCGA TCGCATTGCC GAAAGGGAAA TCCGCCGTCA
1001 GCGACAATTT TGCCGATGCG GCATACGCCA AATACCCGTC CCCTTACCAT
1051 TCCCGAAATA TCCGTTCAAA CTTGGAGCAG CGTTACGGCA AGAAAAACAT
1101 CACCTCCTCA ACCGTGCCGC CGTCAAACGG CAAAAATGTC AAACTGGCAG
1151 ACCAACGCCA CCCGAAGACA GGCGTACCGT TTGACGGTAA AGGGTTTCCG
1201 AATTTTGAGA AGCACGTGAA ATATGATACG GGATCCGGAG GGGGTGGTGT
1251 CGCCGCCGAC ATCGGTGCGG GGCTTGCCGA TGCACTAACC GCACCGCTCG
1301 ACCATAAAGA CAAGGTTTG CAGTCTTTGA CGCTGGATCA GTCCGTCAGG
1351 AAAAACGAGA AACTGAAGCT GGCGGCACAA GGTGCGGAAA AAACTTATGG
1401 AAACGGTGAC AGCCTCAATA CGGGCAAATT GAAGAACGAC AAGGTCAGCC
1451 GTTTCGACTT TATCCGCCAA ATCGAAGTGG ACGGGCAGCT CATTACCTTG
1501 GAGAGTGGAG AGTTCCAAGT ATACAAACAA AGCCATTCCG CCTTAACCGC
1551 CTTTCAGACC GAGCAAATAC AAGATTCGGA GCATTCCGGG AAGATGGTTG
1601 CGAAACGCCA GTTCAGAATC GGCGACTAG CGGGCGAACA TACATCTTTT
1651 GACAAGCTTC CCGAAGGCGG CAGGGCGACA TATCGCGGGA CGGCGTTCGG
1701 TTCAGACGAT GCCGGCGGAA AACTGACCTA CACCATAGAT TTCGCCGCCA
1751 AGCAGGGAAA CGGCAAAATC GAACATTTGA ATCGCCAGA ACTCAATGTC
1801 GACCTGGCCG CCGCCGATAT CAAGCCGGAT GGAAAACGCC ATGCCGTCAT
1851 CAGCGGTTCC GTCCTTTACA ACCAAGCCGA GAAAGGCAGT TACTCCCTCG
1901 GTATCTTTGG CGGAAAAGCC CAGGAAGTTG CCGGCAGCGC GGAAGTGAAA
1951 ACCGTAAACG GCATACGCCA TATCGGCCTT GCCGCCAAGC AACTCGAGCA
2001 CCACCACCAC CACCACTGA
   1 MSDLANDSFI RQVLDRQHFE PDGKYHLFGS RGELAERSGH IGLGKIQSHQ
  51 LGNLMIQQAA IKGNIGYIVR FSDHGHEVHS PFDNHASHSD SDEAGSPVDG
 101 FSLYRIHWDG YEHHPADGYD GPQGGGYPAP KGARDIYSYD IKGVAQNIRL
 151 NLTDNRSTGQ RLADRFHNAG SMLTQGVGDG FKRATRYSPE LDRSGNAAEA
 201 FNGTADIVKN IIGAAGEIVG AGDAVQGISE GSNIAVMHGL GLLSTENKMA
 251 RINDLADMAQ LKDYAAAAIR DWAVQNPNAA QGIEAVSNIF MAAIPIKGIG
 301 AVRGKYGLGG ITAHPIKRSQ MGAIALPKGK SAVSDNFADA AYAKYPSPYH
 351 SRNIRSNLEQ RYGKENITSS TVPPSNGKNV KLADQRHPKT GVPFDGKGFP
 401 NFEKHVKYDT GSGGGGVAAD IGAGLADALT APLDHKDKGL QSLTLDQSVR
 451 KNEKLKLAAQ GAEKTYGNGD SLNTGKLKND KVSRFDFIRQ IEVDGQLITL
```

-continued

```
501 ESGEFQVYKQ SHSALTAFQT EQIQDSEHSG KMVAKRQFRI GDIAGEHTSF

551 DKLPEGGRAT YRGTAFGSDD AGGKLTYTID FAAKQGNGKI EHLKSPELNV

601 DLAAADIKPD GKRHAVISGS VLYNQAEKGS YSLGIFGGKA QEVAGSAEVK

651 TVNGIRHIGL AAKQLEHHHH HH*
```

ORF46.1-961 (SEQ ID NOs: 142 and 143)
```
   1 ATGTCAGATT TGGCAAACGA TTCTTTTATC CGGCAGGTTC TCGACCGTCA

51 GCATTTCGAA CCCGACGGGA AATACCACCT ATTCGGCAGC AGGGGGGAAC

101 TTGCCGAGCG CAGCGGCCAT ATCGGATTGG GAAAAATACA AAGCCATCAG

151 TTGGGCAACC TGATGATTCA ACAGGCGGCC ATTAAAGGAA ATATCGGCTA

201 CATTGTCCGC TTTTCCGATC ACGGGCACGA AGTCCATTCC CCCTTCGACA

251 ACCATGCCTC ACATTCCGAT TCTGATGAAG CCGGTAGTCC CGTTGACGGA

301 TTTAGCCTTT ACCGCATCCA TTGGGACGGA TACGAACACC ATCCCGCCGA

351 CGGCTATGAC GGGCCACAGG GCGGCGGCTA TCCCGCTCCC AAAGGCGCGA

401 GGGATATATA CAGCTACGAC ATAAAAGGCG TTGCCCAAAA TATCCGCCTC

451 AACCTGACCG ACAACCGCAG CACCGGACAA CGGCTTGCCG ACCGTTTCCA

501 CAATGCCGGT AGTATGCTGA CGCAAGGAGT AGGCGACGGA TTCAAACGCG

551 CCACCCGATA CAGCCCCGAG CTGGACAGAT CGGGCAATGC CGCCGAAGCC

601 TTCAACGGCA CTGCAGATAT CGTTAAAAAC ATCATCGGCG CGGCAGGAGA

651 AATTGTCGGC GCAGGCGATG CCGTGCAGGG CATAAGCGAA GGCTCAAACA

701 TTGCTGTCAT GCACGGCTTG GGTCTGCTTT CCACCGAAAA CAAGATGGCG

751 CGCATCAACG ATTTGGCAGA TATGGCGCAA CTCAAAGACT ATGCCGCAGC

801 AGCCATCCGC GATTGGGCAG TCCAAAACCC CAATGCCGCA CAAGGCATAG

851 AAGCCGTCAG CAATATCTTT ATGGCAGCCA TCCCCATCAA AGGGATTGGA

901 GCTGTTCGGG AAAATACGG CTTGGGCGGC ATCACGGCAC ATCCTATCAA

951 GCGGTCGCAG ATGGGCGCGA TCGCATTGCC GGAAGTGAAA TCCGCCGTCA

1001 GCGACAATTT TGCCGATGCG GCATACGCCA ATACCCGTC CCCTTACCAT

1051 TCCCGAAATA TCCGTTCAAA CTTGGAGCAG CGTTACGGCA AGAAAAACAT

1101 CACCTCCTCA ACCGTGCCGC CGTCAAACGG CAAAAATGTC AAACTGGCAG

1151 ACCAACGCCA CCCGAAGACA GGCGTACCGT TGACGGTAA AGGGTTTCCG

1201 AATTTTGAGA AGCACGTGAA ATATGATACG GGATCCGGAG GAGGAGGAGC

1251 CACAAACGAC GACGATGTTA AAAAGCTGC CACTGTGGCC ATTGCTGCTG

1301 CCTACAACAA TGGCCAAGAA ATCAACGGTT TCAAAGCTGG AGAGACCATC

1351 TACGACATTG ATGAAGACGG CACAATTACC AAAAAGACG CAACTGCAGC

1401 CGATGTTGAA GCCGACGACT TTAAAGGTCT GGGTCTGAAA AAGTCGTGA

1451 CTAACCTGAC CAAAACCGTC AATGAAAACA AACAAACGT CGATGCCAAA

1501 GTAAAAGCTG CAGAATCTGA AATAGAAAAG TTAACAACCA AGTTAGCAGA

1551 CACTGATGCC GCTTTAGCAG ATACTGATGC CGCTCTGGAT GCAACCACCA

1601 ACGCCTTGAA TAAATTGGGA GAAAATATAA CGACATTTGC TGAAGAGACT

1651 AAGACAAATA TCGTAAAAAT TGATGAAAAA TTAGAAGCCG TGGCTGATAC

1701 CGTCGACAAG CATGCCGAAG CATTCAACGA TATCGCCGAT TCATTGGATG

1751 AAACCAACAC TAAGGCAGAC GAAGCCGTCA AAACCGCCAA TGAAGCCAAA
```

-continued
```
1801 CAGACGGCCG AAGAAACCAA ACAAAACGTC GATGCCAAAG TAAAAGCTGC

1851 AGAAACTGCA GCAGGCAAAG CCGAAGCTGC CGCTGGCACA GCTAATACTG

1901 CAGCCGACAA GGCCGAAGCT GTCGCTGCAA AAGTTACCGA CATCAAAGCT

1951 GATATCGCTA CGAACAAAGA TAATATTGCT AAAAAAGCAA ACAGTGCCGA

2001 CGTGTACACC AGAGAAGAGT CTGACAGCAA ATTTGTCAGA ATTGATGGTC

2051 TGAACGCTAC TACCGAAAAA TTGGACACAC GCTTGGCTTC TGCTGAAAAA

2101 TCCATTGCCG ATCACGATAC TCGCCTGAAC GGTTTGGATA AACAGTGTC

2151 AGACCTGCGC AAAGAAACCC GCCAAGGCCT TGCAGAACAA GCCGCGCTCT

2201 CCGGTCTGTT CCAACCTTAC AACGTGGGTC GGTTCAATGT AACGGCTGCA

2251 GTCGGCGGCT ACAANTCCGA ATCGGCAGTC GCCATCGGTA CCGGCTTCCG

2301 CTTTACCGAA AACTTTGCCG CCAAAGCAGG CGTGGCAGTC GGCACTTCGT

2351 CCGGTTCTTC CGCAGCCTAC CATGTCGGCG TCAATTACGA GTGGCTCGAG

2401 CACCACCACC ACCACCACTG A
```

```
   1 MSDLANDSFI RQVLDRQHFE PDGKYHLFGS RGELAERSGH IGLGKIQSHQ

51 LGNLMIQQAA IKGNIGYIVR FSDHGHEVHS PFDNHASHSD SDEAGSPVDG

101 FSLYRIHWDG YEHHPADGYD GPQGGGYPAP KGARDIYSYD IKGVAQNIRL

151 NLTDNRSTGQ RLADRFHNAG SMLTQGVGDG FKRATRYSPE LDRSGNAAEA

201 FNGTADIVKN IIGAAGEIVG AGDAVQGISE GSNIAVMHGL GLLSTENKMA

251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDKGFP

401 NFEKHVKYDT GSGGGGATND DDVKKAATVA IAAAYNNGQE INGFKAGETI

451 YDIDEDGTIT KKDATAADVE ADDFKGLGLK KVVTNLTKTV NENKQNVDAK

501 VKAAESEIEK LTTKLADTDA ALADTDAALD ATTNALNKLG ENITTFAEET

551 KTNIVKIDEK LEAVADTVDK HAEAFNDIAD SLDETNTKAD EAVKTANEAK

601 QTAEETKQNV DAKVKAAETA AGKAEAAAGT ANTAADKAEA VAAKVTDIKA

651 DIATNKDNIA KKANSADVYT REESDSKFVR IDGLNATTEK LDTRLASAEK

701 SIADHDTRLN GLDKTVSDLR KETRQGLAEQ AALSGLFQPY NVGRFNVTAA

751 VGGYKSESAV AIGTGFRFTE NFAAKAGVAV GTSSGSSAAY HVGVNYEWLE

801 HHHHHH*
```

ORF46.1-961c (SEQ ID NOs: 144 and 145)
```
   1 ATGTCAGATT TGGCAAACGA TTCTTTTATC CGGCAGGTTC TCGACCGTCA

51 GCATTTCGAA CCCGACGGGA ATACCACCT ATTCGGCAGC AGGGGGGAAC

101 TTGCCGAGCG CAGCGGCCAT ATCGGATTGG GAAAAATACA AAGCCATCAG

151 TTGGGCAACC TGATGATTCA ACAGGCGGCC ATTAAAGGAA ATATCGGCTA

201 CATTGTCCGC TTTTCCGATC ACGGGCACGA AGTCCATTCC CCCTTCGACA

251 ACCATGCCTC ACATTCCGAT TCTGATGAAG CCGGTAGTCC CGTTGACGGA

301 TTTAGCCTTT ACCGCATCCA TTGGGACGGA TACGAACACC ATCCCGCCGA

351 CGGCTATGAC GGGCCACAGG GCGGCGGCTA TCCCGCTCCC AAAGGCGCGA

401 GGGATATATA CAGCTACGAC ATAAAAGGCG TTGCCCAAAA TATCCGCCTC

451 AACCTGACCG ACAACCGCAG CACCGGACAA CGGCTTGCCG ACCGTTTCCA
```

-continued

```
 501 CAATGCCGGT AGTATGCTGA CGCAAGGAGT AGGCGACGGA TTCAAACGCG
 551 CCACCCGATA CAGCCCCGAG CTGGACAGAT CGGGCAATGC CGCCGAAGCC
 601 TTCAACGGCA CTGCAGATAT CGTTAAAAAC ATCATCGGCG CGGCAGGAGA
 651 AATTGTCGGC GCAGGCGATG CCGTGCAGGG CATAAGCGAA GGCTCAAACA
 701 TTGCTGTCAT GCACGGCTTG GGTCTGCTTT CCACCGAAAA CAAGATGGCG
 751 CGCATCAACG ATTTGGCAGA TATGGCGCAA CTCAAAGACT ATGCCGCAGC
 801 AGCCATCCGC GATTGGGCAG TCCAAAACCC CAATGCCGCA CAAGGCATAG
 851 AAGCCATCAG CAATATCTTT ATGGCAGCCA TCCCCATCAA AGGGATTGGA
 901 GCTGTTCGGG GAAAATACGG CTTGGGCGGC ATCACGGCAC ATCCTATCAA
 951 GCGGTCGCAG ATGGGCGCGA TCGCATTGCC GAAAGGGAAA TCCGCCGTCA
1001 GCGACAATTT TGCCGATGCG GCATACGCCA ATACCCGTC CCCTTACCAT
1051 TCCCGAAATA TCCGTTCAAA CTTGGAGCAG CGTTACGGCA AGAAAAACAT
1101 CACCTCCTCA ACCGTGCCGC CGTCAAACGG CAAAATGTC AAACTGGCAG
1151 ACCAACGCCA CCCGAAGACA GGCGTACCGT TTGACGGTAA AGGGTTTCCG
1201 AATTTTGAGA AGCACGTGAA ATATGATACG GGATCCGGAG GAGGAGGAGC
1251 CACAAACGAC GACGATGTTA AAAAGCTGC CACTGTGGCC ATTGCTGCTG
1301 CCTACAACAA TGGCCAAGAA ATCAACGGTT TCAAAGCTGG AGAGACCATC
1351 TACGACATTG ATGAAGACGG CACAATTACC AAAAAGACG CAACTGCAGC
1401 CGATGTTGAA GCCGACGACT TTAAAGGTCT GGGTCTGAAA AAAGTCGTGA
1451 CTAACCTGAC CAAAACCGTC AATGAAAACA ACAAAACGT CGATGCCAAA
1501 GTAAAAGCTG CAGAATCTGA AATAGAAAAG TTAACAACCA AGTTAGCAGA
1551 CACTGATGCC GCTTTAGCAG ATACTGATGC CGCTCTGGAT GCAACCACCA
1601 ACGCCTTGAA TAAATTGGGA GAAAATATAA CGACATTTGC TGAAGAGACT
1651 AAGACAAATA TCGTAAAAAT TGATGAAAAA TTAGAAGCCG TGGCTGATAC
1701 CGTCGACAAG CATGCCGAAG CATTCAACGA TATCGCCGAT TCATTGGATG
1751 AAACCAACAC TAAGGCAGAC GAAGCCGTCA AAACCGCCAA TGAAGCCAAA
1801 CAGACGGCCG AAGAAACCAA ACAAAACGTC GATGCCAAAG TAAAAGCTGC
1851 AGAAACTGCA GCAGGCAAAG CCGAAGCTGC CGCTGGCACA GCTAATACTG
1901 CAGCCGACAA GGCCGAAGCT GTCGCTGCAA AAGTTACCGA CATCAAAGCT
1951 GATATCGCTA CGAACAAAGA TAATATTGCT AAAAAAGCAA ACAGTGCCGA
2001 CGTGTACACC AGAGAAGAGT CTGACAGCAA ATTTGTCAGA ATTGATGGTC
2051 TGAACGCTAC TACCGAAAAA TTGGACACAC GCTTGGCTTC TGCTGAAAAA
2101 TCCATTGCCG ATCACGATAC TCGCCTGAAC GGTTTGGATA AACAGTGTC
2151 AGACCTGCGC AAAGAAACCC GCCAAGGCCT TGCAGAACAA GCCGCGCTCT
2201 CCGGTCTGTT CCAACCTTAC AACGTGGGTC TCGAGCACCA CCACCACCAC
2251 CACTGA
```

```
  1 MSDLANDSFI RQVLDRQHFE PDGKYKLFGS RGELAERSGH IGLGKIQSHQ
 51 LGNLMIQQAA IKGNIGYIVR FSDHGHEVHS PFDNHASHSD SDEAGSPVDG
101 FSLYRIHWDG YEHHPADGYD GPQGGGYPAP KGARDIYSYD IKGVAQNIRL
151 NLTDNRSTGQ RLADRFHNAG SMLTQGVGDG FKRATRYSPE LDRSGNAAEA
201 FNGTADIVKN IIGAAGEIVG AGDAVQGISE GSNIAVMHGL GLLSTENKMA
```

-continued

```
251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGATND DDVKKAATVA IAAAYNNGQE INGFKAGETI

451 YDIDEDGTIT KKDATAADVE ADDFKGLGLK KVVTNLTKTV NENKQNVDAK

501 VKAAESEIEK LTTKLADTDA ALADTDAALD ATTNALNKLG ENITTFAEET

551 KTNIVKIDEK LEAVADTVDK HAEAFNDIAD SLDETNTKAD EAVKTANEAK

601 QTAEETKQNV DAKVKAAETA AGKAEAAAGT ANTAADKAEA VAAKVTDIKA

651 DIATNKDNIA KKANSADVYT REESDSKFVR IDGLNATTEK LDTRLASAEK

701 SIADHDTRLN GLDKTVSDLR KETRQGLAEQ AALSGLFQPY NVGLEHHHHH

751 H*
```

961-ORF46.1 (SEQ ID NOs: 146 and 147)
```
   1 ATGGCCACAA ACGACGACGA TGTTAAAAAA GCTGCCACTG TGGCCATTGC

51 TGCTGCCTAC AACAATGGCC AAGAAATCAA CGGATTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA ACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTCGGTTC AATGTAACGG

1001 CTGCAGTCGG CGOCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGAGG AGGAGGATCA GATTTGGCAA ACGATTCTTT TATCCGGCAG

1201 GTTCTCGACC GTCAGCATTT CGAACCCGAC GGGAAATACC ACCTATTCGG

1251 CAGCAGGGGG GAACTTGCCG AGCGCAGCGG CCATATCGGA TTGGGAAAAA

1301 TACAAAGCCA TCAGTTGGGC AACCTGATGA TTCAACAGGC GGCCATTAAA

1351 GGAAATATCG GCTACATTGT CCGCTTTTCC GATCACGGGC ACGAAGTCCA

1401 TTCCCCCTTC GACAACCATG CCTCACATTC CGATTCTGAT GAAGCCGGTA
```

-continued

```
1451 GTCCCGTTGA CGGATTTAGC CTTTACCGCA TCCATTGGGA CGGATACGAA

1501 CACCATCCCG CCGACGGCTA TGACGGGCCA CAGGGCGGCG GCTATCCCGC

1551 TCCCAAAGGC GCGAGGGATA TATACAGCTA CGACATAAAA GGCGTTGCCC

1601 AAAATATCCG CCTCAACCTG ACCGACAACC GCAGCACCGG ACAACGGCTT

1651 GCCGACCGTT TCCACAATGC CGGTAGTATG CTGACGCAAG GAGTAGGCGA

1701 CGGATTCAAA CGCGCCACCC GATACAGCCC CGAGCTGGAC AGATCGGGCA

1751 ATGCCGCCGA AGCCTTCAAC GGCACTGCAG ATATCGTTAA AACATCATC

1801 GGCGCGGCAG GAGAAATTGT CGGCGCAGGC GATGCCGTGC AGGGCATAAG

1851 CGAAGGCTCA ACATTGCTG TCATGCACGG CTTGGGTCTG CTTTCCACCG

1901 AAAACAAGAT GGCGCGCATC AACGATTTGG CAGATATGGC GCAACTCAAA

1951 GACTATGCCG CAGCAGCCAT CCGCGATTGG GCAGTCCAAA ACCCCAATGC

2001 CGCACAAGGC ATAGAAGCCG TCAGCAATAT CTTTATGGCA GCCATCCCCA

2051 TCAAAGGGAT TGGAGCTGTT CGGGGAAAAT ACGGCTTGGG CGGCATCACG

2101 GCACATCCTA TCAAGCGGTC GCAGATGGGC GCGATCGCAT TGCCGAAAGG

2151 GAAATCCGCC GTCAGCGACA ATTTTGCCGA TGCGGCATAC GCCAAATACC

2201 CGTCCCCTTA CCATTCCCGA AATATCCGTT CAAACTTGGA GCAGCGTTAC

2251 GGCAAAGAAA ACATCACCTC CTCAACCGTG CCGCCGTCAA CGGCAAAAA

2301 TGTCAAACTG GCAGACCAAC GCCACCCGAA GACAGGCGTA CCGTTTGACG

2351 GTAAGGGTT TCCGAATTTT GAGAAGCACG TGAAATATGA TACGCTCGAG

2401 CACCACCACC ACCACCACTG A

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDEHAEAF NDIADSLDET NTKADEAVKT ANEAKQTAEE TYQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGS DLANDSFIRQ

401 VLDRQHFEPD GKEHLFGSRG ELAERSGHIG LGKIQSHQLG NLMIQQAAIK

451 GNIGYIVRFS DHGHEVHSPF DNHASHSDSD EAGSPVDGFS LYRIHWDGYE

501 HHPADGYDGP QGGGYPAPKG ARDIYSYDEK GVAQNIRLNL TDNRSTGQRL

551 ADRFHNAGSM LTQGVGDGFK RATRYSPELD RSGNAAEAFN GTADIVKNII

601 GAAGEIVGAG DAVQGISEGS NIAVMHGLGL LSTENKMARI NDLADMAQLK

651 DYAAAAIRDW AVQNPNAAQG IEAVSNIFMA AIPIKGIGAV RGKYGLGGIT

701 AHPIKRSQMG AIALPKGKSA VSDNFADAAY AKYPSPYHSR NIRSNLEQRY

751 GKENITSSTV PPSNGKNVKL ADQRHPKTGV PFDGKGFPNF EKHVKYDTLE

801 HHHHHH*

961-741 (SEQ ID NOs: 148 and 149)
   1 ATGGCCACAA ACGACGACGA TGTTAAAAAA GCAGACACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT
```

-continued

```
 151 GCAGCCGATG TTGAAGCCGA CGACTTTAAA GGTCTGGGTC TGAAAAAAGT
 201 CGTGACTAAC CTGACCAAAA CCGTCAATGA AAACAAACAA AACGTCGATG
 251 CCAAAGTAAA AGCTGCAGAA TCTGAAATAG AAAAGTTAAC AACCAAGTTA
 301 GCAGACACTG ATGCCGCTTT AGCAGATACT GATGCCGCTC TGGATGCAAC
 351 CACCAACGCC TTGAATAAAT TGGGAGAAAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG GCACAGCTAA
 651 TACTGCAGCC GACTATGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
 951 GCTCTCCGGT CTGTTCCAAC CTTACAACGT GGGTCGGTTC AATGTAACGG
1001 CTGCAGTCGG CGGCTACAAA TCCGAATCGG CAGTCGCCAT CGGTACCGGC
1051 TTCCGCTTTA CCGAAAACTT TGCCGCCAAA GCAGGCGTGG CAGTCGGCAC
1101 TTCGTCCGGT TCTTCCGCAG CCTACCATGT CGGCGTCAAT TACGAGTGGG
1151 GATCCGGAGG GGGTGGTGTC GCCGCCGACA TCGGTGCGGG GCTTGCCGAT
1201 GCACTAACCG CACCGCTCGA CCATAAAGAC AAAGGTTTGC AGTCTTTGAC
1251 GCTGGATCAG TCCGTCAGGA AAAACGAGAA ACTGAAGCTG GCGGCACAAG
1301 GTGCGGAAAA AACTTATGGA AACGGTGACA GCCTCAATAC GGGCAAATTG
1351 AAGAACGACA AGGTCAGCCG TTTCGACTTT ATCCGCCAAA TCGAAGTGGA
1401 CGGGCAGCTC ATTACCTTGG AGAGTGGAGA GTTCCAAGTA TACAAACAAA
1451 GCCATTCCGC CTTAACCGCC TTTCAGACCG AGCAAATACA AGATTCGGAG
1501 CATTCCGGGA AGATGGTTGC GAAACGCCAG TTCAGAATCG GCGACATAGC
1551 GGGCGAACAT ACATCTTTTG ACAAGCATGC CGAAGGCGGC AGGGCGACAT
1601 ATCGCGGGAC GGCGTTCGGT TCAGACGATG CCGGCGGAAA ACTGACCTAC
1651 ACCATAGATT TCGCCGCCAA GCAGGGAAAC GGCAAAATCG AACATTTGAA
1701 ATCGCCAGAA CTCAATGTCG ACCTGGCCGC CGCCGATATC AAGCCGGATG
1751 GAAAACGCCA TGCCGTCATC AGCGGTTCCG TCCTTTACAA CCAAGCCGAG
1801 AAAGGCAGTT ACTCCCTCGG TATCTTTGGC GGAAAAGCCC AGGAAGTTGC
1851 CGGCAGCGCG GAAGTGAAAA CCGTAAACGG CATACGCCAT ATCGGCCTTG
1901 CCGCCAAGCA ACTCGAGCAC CACCACCACC ACCACTGA

1 MATNDDDVKK AATVAIAAAY NNGQEINGFK AGETIYDIDE DGTITKKDAT
  51 AADVEADDFK GLGLKKVVTN LTKTVNENKQ NVDAKVKAAE SEIEKLTTKL
 101 ADTDAALADT DAALDATTNA LNKLGENITT FAEETKTNIV KIDEKLEAVA
 151 DTVDKHAEAF NDIADSLDET NTKADEAVKT ANEAKQTAEE TKQNVDAKVK
 201 AAETAAGKAE AAAGTANTAA DKAEAVAAKV TDIKADIATN KDNIAKKANS
```

-continued

```
251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGV AADIGAGLAD

401 ALTAPLDHKD KGLQSLTLDQ SVRKNEKLKL AAQGAEKTYG NGDSLNTGKL

451 KNDKVSRFDF IRQIEVDGQL ITLESGEFQV YKQSHSALTA FQTEQIQDSE

501 HSGKMVAKRQ FRIGDIAGEH TSFDKLPEGG RATYRGTAFG SDDAGGKLTY

551 TIDFAAKQGN GKIEHLKSPE LNVDLAAADI KPDGKRHAVI SGSVLYNQAE

601 KGSYSLGIFG GKAQEVAGSA EVKTVNGIRH IGLAAKQLEH HHHHH*
```

961-983 (SEQ ID NOs: 150 and 151)

```
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT GGGAGAAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTCCACCC CACAAGGCCG AAGCTGTCCC TCCAAAACTT ACCOACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAAGGCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTCGGTTC AATGTAACGG

1001 CTGCAGTCGG CGGCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGCGG AGGCGGCACT TCTGCGCCCG ACTTCAATGC AGGCGGTACC

1201 GGTATCGGCA GCAACAGCAG AGCAACAACA GCGAAATCAG CAGCAGTATC

1251 TTACGCCGGT ATCAAGAACG AAATGTGCAA AGACAGAAGC ATGCTCTGTG

1301 CCGGTCGGGA TGACGTTGCG GTTACAGACA GGGATGCCAA AATCAATGCC

1351 CCCCCCCGA ATCTGCATAC CGGAGACTTT CCAAACCCAA ATGACGCATA

1401 CAAGAATTTG ATCAACCTCA AACCTGCAAT TGAAGCAGGC TATACAGGAC

1451 GCGGGGTAGA GGTAGGTATC GTCGACACAG GCGAATCCGT CGGCAGCATA

1501 TCCTTTCCCG AACTGTATGG CAGAAAAGAA CACGGCTATA CGAAAATTA

1551 CAAAAACTAT ACGGCGTATA TGCGGAAGGA AGCGCCTGAA GACGGAGGCG
```

-continued

```
1601 GTAAAGACAT TGAAGCTTCT TTCGACGATG AGGCCGTTAT AGAGACTGAA

1651 GCAAAGCCGA CGGATATCCG CCACGTAAAA GAAATCGGAC ACATCGATTT

1701 GGTCTCCCAT ATTATTGGCG GGCGTTCCGT GGACGGCAGA CCTGCAGGCG

1751 GTATTGCGCC CGATGCGACG CTACACATAA TGAATACGAA TGATGAAACC

1801 AAGAACGAAA TGATGGTTGC AGCCATCCGC AATGCATGGG TCAAGCTGGG

1851 CGAACGTGGC GTGCGCATCG TCAATAACAG TTTTGGAACA ACATCGAGGG

1901 CAGGCACTGC CGACCTTTTC CAAATAGCCA ATTCGGAGGA GCAGTACCGC

1951 CAAGCGTTGC TCGACTATTC CGGCGGTGAT AAAACAGACG AGGGTATCCG

2001 CCTGATGCAA CAGAGCGATT ACGGCAACCT GTCCTACCAC ATCCGTAATA

2051 AAAACATGCT TTTCATCTTT TCGACAGGCA ATGACGCACA AGCTCAGCCC

2101 AACACATATG CCCTATTGCC ATTTTATGAA AAAGACGCTC AAAAAGGCAT

2151 TATCACAGTC GCAGGCGTAG ACCGCAGTGG AGAAAAGTTC AAACGGGAAA

2201 TGTATGGAGA ACCGGGTACA GAACCGCTTG AGTATGGCTC CAACCATTGC

2251 GGAATTACTG CCATGTGGTG CCTGTCGGCA CCCTATGAAG CAAGCGTCCG

2301 TTTCACCCGT ACAAACCCGA TTCAAATTGC CGGAACATCC TTTTCCGCAC

2351 CCATCGTAAC CGGCACGGCG GCTCTGCTGC TGCAGAAATA CCCGTGGATG

2401 AGCAACGACA ACCTGCGTAC CACGTTGCTG ACGACGGCTC AGGACATCGG

2451 TGCAGTCGGC GTGGACAGCA AGTTCGGCTG GGACTGCTG GATGCGGGTA

2501 AGGCCATGAA CGGACCCGCG TCCTTTCCGT TCGGCGACTT TACCGCCGAT

2551 ACGAAAGGTA CATCCGATAT TGCCTACTCC TTCCGTAACG ACATTTCAGG

2601 CACGGGCGGC CTGATCAAAA AAGGCGGCAG CCAACTGCAA CTGCACGGCA

2651 ACAACACCTA TGGGCAAA ACCATTATCG AAGGCGGTTC GCTGGTGTTG

2701 TACGGCAACA ACAAATCGGA TATGCGCGTC GAAACCAAAG GTGCGCTGAT

2751 TTATAACGGG GCGGCATCCG GCGGCAGCCT GAACAGCGAC GGCATTGTCT

2801 ATCTGGCAGA TACCGACCAA TCCGGCGCAA ACGAAACCGT ACACATCAAA

2851 GGCAGTCTGC AGCTGGACGG CAAAGGTACG CTGTACACAC GTTTGGGCAA

2901 ACTGCTGAAA GTGGACGGTA CGGCGATTAT CGGCGGCAAG CTGTACATGT

2951 CGGCACGCGG CAAGGGGGCA GGCTATCTCA ACAGTACCGG ACGACGTGTT

3001 CCCTTCCTGA GTGCCGCCAA AATCGGGCAG GATTATTCTT TCTTCACAAA

3051 CATCGAAACC GACGGCGGCC TGCTGGCTTC CCTCGACAGC GTCGAAAAAA

3101 CAGCGGGCAG TGAAGGCGAC ACGCTGTCCT ATTATGTCCG TCGCGGCAAT

3151 GCGGCACGGA CTGCTTCGGC AGCGGCACAT TCCGCGCCCG CCGGTCTGAA

3201 ACACGCCGTA GAACAGGGCG GCAGCAATCT GGAAAACCTG ATGGTCGAAC

3251 TGGATGCCTC CGAATCATCC GCAACACCCG AGACGGTTGA AACTGCGGCA

3301 GCCGACCGCA CAGATATGCC GGGCATCCGC CCCTACGGCG CAACTTTCCG

3351 CGCAGCGGCA GCCGTACAGC ATGCGAATGC CGCCGACGGT GTACGCATCT

3401 TCAACAGTCT CGCCGCTACC GTCTATGCCG ACAGTACCGC CGCCCATGCC

3451 GATATGCAGG GACGCCGCCT GAAAGCCGTA TCGGACGGGT TGGACCACAA

3501 CGGCACGGGT CTGCGCGTCA TCGCGCAAAC CCAACAGGAC GGTGGAACGT

3551 GGGAACAGGG CGGTGTTGAA GGCAAAATGC GCGGCAGTAC CCAAACCGTC

3601 GGCATTGCCG CGAAAACCGG CGAAAATACG ACAGCAGCCG CCACACTGGG
```

```
-continued
3651 CATGGGACGC AGCACATGGA GCGAAAACAG TGCAAATGCA AAAACCGACA

3701 GCATTAGTCT GTTTGCAGGC ATACGGCACG ATGCGGGCGA TATCGGCTAT

3751 CTCAAAGGCC TGTTCTCCTA CGGACGCTAC AAAAACAGCA TCAGCCGCAG

3801 CACCGGTGCG GACGAACATG CGGAAGGCAG CGTCAACGGC ACGCTGATGC

3851 AGCTGGGCGC ACTGGGCGGT GTCAACGTTC CGTTTGCCGC AACGGGAGAT

3901 TGAACGGACG AAGGCGGTCT GCGCTACGAC CTGCTCAAAC AGGATGCATT

3951 CGCCGAAAAA GGCAGTGCTT TGGGCTGGAG CGGCAACAGC CTCACTGAAG

4001 GCACGCTGGT CGGACTCGCG GGTCTGAAGC TGTCGCAACC CTTGAGCGAT

4051 AAAGCCGTCC TGTTTGCAAC GGCGGGCGTG GAACGCGACC TGAACGGACG

4101 CGACTACACG GTAACGGGCG GCTTTACCGG CGCGACTGCA GCAACCGGCA

4151 AGACGGGGGC ACGCAATATG CCGCACACCC GTCTGGTTGC CGGCCTGGGC

4201 GCGGATGTCG AATTCGGCAA CGGCTGGAAC GGCTTGGCAC GTTACAGCTA

4251 CGCCGGTTCC AAACAGTACG GAAACCAAAG CGGACGAGTC GGCGTAGGCT

4301 ACCGGTTCCT CGAGCACCAC CACCACCACC ACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGT SAPDFNAGGT

401 GIGSNSRATT AKSAAVSYAG IKNEMCKDRS MLCAGRDDVA VTDRDAKINA

451 PPPNLHTGDF PNPNDAYKNL INLKPAIEAG YTGRGVEVGI VDTGESVGSI

501 SFPELYGRKE HGYNENYKNY TAYMRKEAPE DGGGKDIEAS FDDEAVIETE

551 AKPTDIRHVK EIGHIDLVSH IIGGRSVDGR PAGGIAPDAT LHIMNTNDET

601 KNEMMVAAIR NAWVKLGERG VRIVNNSFGT TSRAGTADLF QIANSEEQYR

651 QALLDYSGGD KTDEGIRLMQ QSDYGNLSYH IRNKNMLFIF STGNDAQAQP

701 NTYALLPFYE KDAQKGIITV AGVDRSGEKF KREMYGEPGT EPLEYGSNHC

751 GITAMWCLSA PYEASVRFTR TNPIQIAGTS FSAPIVTGTA ALLLQKYPWM

801 SNDNLRTTLL TTAQDIGAVG VDSKFGWGLL DAGKAMNGPA SFPFGDFTAD

851 TKGTSDIAYS FRNDISGTGG LIKKGGSQLQ LHGNNTYTGK TIIEGGSLVL

901 YGNNKSDMRV ETKGALIYNG AASGGSLNSD GIVYLADTDQ SGANETVHIK

951 GSLQLDGKGT LYTRLGKLLK VDGTAIIGGK LYMSARGKGA GYLNSTGRRV

1001 PFLSAAKIGQ DYSFFTNIET DGGLLASLDS VEKTAGSEGD TLSYYVRRGN

1051 AARTASAAAH SAPAGLKHAV EQGGSNLENL MVELDASESS ATPETVETAA

1101 ADRTDMPGIR PYGATFRAAA AVQHANAADG VRIFNSLAAT VYADSTAAHA

1151 DMOGRRLEAV SDGLDENGTG LRVIAQTQQD GGTWEQGGVE GKMRGSTQTV

1201 GIAAKTGENT TAAATLGMGR STWSENSANA KTDSISLFAG IRHDAGDIGY

1251 LKGLFSYGRY KNSISRSTGA DEHAEGSVNG TLMQLGALGG VNVPFAATGD

1301 LTVEGGLRYD LLKQDAFAEK GSALGWSGNS LTEGTLVGLA GLKLSQPLSD
```

```
1351 KAVLFATAGV ERDLNGRDYT VTGGFTGATA ATGKTGARNM PHTRLVAGLG

1401 ADVEFGNGWN GLARYSYAGS KQYGNHSGRV GVGYRFLEHH HHHH*

961c-ORF46.1 (SEQ ID NOs: 152 and 153)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCTGCCGCTG TTGAAGCCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATGTCA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGAAAAAAGT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATGTCA CACACCCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTGGATCC GGAGGAGGAG

1001 GATCAGATTT GGCAAACGAT TCTTTTATCC GGCAGGTTCT CGACCGTCAG

1051 CATTTCGAAC CCGACGGGAA ATACCACCTA TTGGGCGGCA GGGGGGAACT

1101 TGCCGAGCGC AGCGGCCATA TCGGATTGGG AAAAATACAA AGCCATCAGT

1151 TGGGCAACCT GATGATTCAA CAGGCGGCCA TTAAAGGAAA TATCGGCTAC

1201 ATTGTCCGCT TTTCCGATCA CGGGCACGAA GTCCATTCCC CCTTCGACAA

1251 CCATGCCTCA CATTCCGATT CTGATGAAGC CGGTAGTCCC GTTGACCGAT

1301 TTAGCCTTTA CCGCATCCAT TGGGACGGAT ACGAACACCA TCCCGCCGAC

1351 GGCTATGACG GCCACAGGG CGGCGGCTAT CCCGCTCCCA AAGGCGCGAG

1401 GGATATATAC AGCTACGACA TAAAAGGCGT TGCCCAAAAT ATCCGCCTCA

1451 ACCTGACCGA CAACCGCAGC ACCGGACAAC GGCTTGCCGA CCGTTTCCAC

1501 AATGCCGGTA GTATGCTGAC GCAAGGAGTA GGCGACGGAT TCAAACGCGC

1551 CACCCGATAC AGCCCCGAGc TGGACAGATC GGGCAATGCC GCCGAAGCCT

1601 TCAACGGCAC TGCAGATATC GTTAAAAACA TCATCGGCGC GGCAGGAGAA

1651 ATTGTCGGCG CAGGCGATGC CGTGCAGGGC ATAAGCGAAG GCTCAAACAT

1701 TGCTGTCATG CACGGCTTGG GTCTGCTTTC CACCGAAAAC AAGATGGCGC

1751 GCATCAACGA TTTGGCAGAT ATGGCGCAAC TCAAAGACTA TGcCGCAGCA

1801 GCCATCCGCG ATTGGGCAGT CCAAAACCCC AATGCCGCAC AAGGCATAGA

1851 AGCCGTCAGC AATATCTTTA TGGCAGCCAT CCCCATCAAA GGGATTGGAG
```

-continued

```
1901 CTGTTCGGGG AAAATACGGC TTGGGCGGCA TCACGGCACA TCCTATCAAG

1951 CGGTCGCAGA TGGGCGCGAT CGCATTGCCG AAAGGGAAAT CCGCCGTCAG

2001 CGACAATTTT GCCGATGCGG CATACGCCAA ATACCCGTCC CCTTACCATT

2051 CCCGAAATAT CCGTTCAAAC TTGGAGCAGC GTTACGGCAA AGAAAACATC

2101 ACCTCCTCAA CCGTGCCGCC GTCAAACGGC AAAAATGTCA AACTGGCAGA

2151 CCAACGCCAC CCGAAGACAG GCGTACCGTT TGACGGTAAA GGGTTTCCGA

2201 ATTTTGAGAA GCACGTGAAA TATGATACGC TCGAGCACCA CCACCACCAC

2251 CACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGGS GGGGSDLAND SFIRQVLDRQ

351 HFEPDGKYHL FGSRGELAER SGHIGLGKIQ SHQLGNLMIQ QAAIKGNIGY

401 IVRFSDHGNE VHSPFDNHAS HSDSDEAGSP VDGFSLYRIH WDGYEHHPAD

451 GYDGPQGGGY PAPKGARDIY SYDIKGVAQN IRLNLTDNRS TGQRLADRFH

501 NAGSMLTQGV GDGFKRATRY SPELDRSGNA AEAFNGTADI VKNIIGAAGE

551 IVGAGDAVQG ISEGSNIAVM HGLGLLSTEN KMARINDLAD MAQLKDYAAA

601 AIRDWAVQNP NAAQGIEAVS NIFNAAIPIK GIGAVRGKYG LGGITAHPIK

651 RSQMGAIALP KGKSAVSDNF ADAAYAKYPS PYHSRNIRSN LEQRYGKENI

701 TSSTVPPSNG KNVKLADQRH PKTGVPFDGK GFPNFEKHVK YDTLEHHHHH

751 H*

961c-741 (SEQ ID NOs: 154 and 155)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA ACGGCACAA TTACCAAAAA GACGCAACT

151 GCAGCCGATG TTGAAGCCGA CGACTTLAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGAAAAAAGT ACCGACATCA

701 AAGCTGATAT CGCTACGAAc AAAGATAATA TTGCTAAAAA AGCAAACAGT

751 GCCGACGTGT ACACCAGAGA AGAGTCTGAC AGCAAATTTG TCAGAATTGA
```

-continued

```
 801 TGGTCTGAAC GCTACTACCG AAAAATTAGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTGGATCC GGAGGGGGTG

1001 GTGTCGCCGC CGACATCGGT GCGGGGCTTG CCGATGCACT AACCGCACCG

1051 CTCGACCATA AAGACAAAGG TTTGCAGTCT TTGACGCTGG ATCAGTCCGT

1101 CAGGAAAAAC GAGAAACTGA AGCTGGCGGC ACAAGGTGCG GAAAAAACTT

1151 ATGGAAACGG TGACAGCCTC AATACGGGCA AATTGAAGAA CGACAAGGTC

1201 AGCCGTTTCG ACTTTATCCG CCAAATCGAA GTGGACGGGC AGCTCATTAC

1251 CTTGGAGAGT GGAGAGTTCC AAGTATACAA ACAAAGCCAT TCCGCCTTAA

1301 CCGCCTTTCA GACCGAGCAA ATACAAGATT CGAAGCATTC CGGGAAGATG

1351 GTTGCGAAAC GCCAGTTCAG AATCGGCGAC ATAGCGGGCG AACATACATC

1401 TTTTGACAAG CTTCCCGAAG GTGGACGGGC GACATATCGC GGGACGGCGT

1451 TCGGTTCAGA CGATGCCGGC GGAAAACTGA CCTACACCAT AGATTTCGCC

1501 GCCAAGCAGG GAAACGGCAA AATCGAACAT TTGAAATCGC CAGAACTCAA

1551 TGTCGACCTG GCCGCCGCCG ATATCAAGCC GGATGGAAAA CGCCATGCCG

1601 TCATCAGCGG TTCCGTCCTT TACAACCAAG CCGAGAAAGG CAGTTACTCC

1651 CTCGGTATCT TTGGCGGAAA AGCCCAGGAA GTTGCCGGCA GCGCGGAAGT

1701 GAAAACCGTA AACGGCATAC GCCATATCGG CCTTGCCGCC AAGCAACTCG

1751 AGCACCACCA CCACCACCAC TGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGGS GGGGVAADIG AGLADALTAP

351 LDHKDKGLQS LTLDQSVRKN EKLKLAAQGA EKTYGNGDSL NTGKLKNDKV

401 SRFDFIRQIE VDGQLITLES GEFQVYKQSH SALTAFQTEQ IQDSEHSGKM

451 VAKRQFRIGD IAGEHTSFDK LPEGGRATYR GTAFGSDDAG GKLTYTIDFA

501 AKQGNGKIEH LKSPELNVDL AAADIKPDGK RHAVISGSVL YNQAEKGSYS

551 LGIFGGKAQE VAGSAEVKTV NGIRHIGLAA KQLEHHHHHH *

961c-983 (SEQ ID NOS: 156 and 157)
   1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG
```

-continued

```
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG CACAGCTAA
 651 TACTGCAGCC GACAAGGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
 951 GCTCTCCGGT CTGTTCCAAC CTTACAACGT GGGTGGATCC GGCGGAGGCG
1001 GCACTTCTGC GCCCGACTTC AATGCAGGCG GTACCGGTAT CGGCAGCAAC
1051 AGCAGAGCAA CAACAGCGAA ATCAGCAGCA GTATCTTACG CCGGTATCAA
1101 GAACGAAATG TGCAAAGACA GAAGCATGCT CTGTGCCGGT CGGGATGACG
1151 TTGCGGTTAC AGACAGGGAT GCCAAAATCA ATGCCCCCCC CCCGAATCTG
1201 CATACCGGAG ACTTTCCAAA CCCAAATGAC GCATACAAGA ATTTGATCAA
1251 CCTCAAACCT GCAATTGAAG CAGGCTATAC AGGACGCGGG GTAGAGGTAG
1301 GTATCGTCGA CACAGGCGAA TCCGTCGGCA GCATATCCTT TCCCGAACTG
1351 TATGGCAGAA AAGAACACGG CTATAACGAA AATTACAAAA ACTATACGGC
1401 GTATATGCGG AAGGAAGCGC CTGAAGACGG AGGCGGTAAA GACATTGAAG
1451 CTTCTTTCGA CGATGAGGCC GTTATAGAGA CTGAAGCAAA GCCGACGGAT
1501 ATCCGCCACG TAAAAGAAAT CGGACACATC GATTTGGTCT CCCATATTAT
1551 TGGCGGGCGT TCCGTGGACG GCAGACCTGC AGGCGGTATT GCGCCCGATG
1601 CGACGCTACA CATAATGAAT ACGAATGATG AAACCAAGAA CGAAATGATG
1651 GTTGCAGCCA TCCGCAATGC ATGGGTCAAG CTGGGCGAAC GTGGCGTGCG
1701 CATCGTCAAT AACAGTTTTG GAACAACATC GAGGGCAGGC ACTGCCGACC
1751 TTTTCCAAAT AGCCAATTCG GAGGAGCAGT ACCGCCAAGC GTTGCTCGAC
1801 TATTCCGGCG GTGATAAAAC AGACGAGGGT ATCCGCCTGA TGCAACAGAG
1851 CGATTACGGC AACCTGTCCT ACCACATCCG TAATAAAAAC ATGCTTTTCA
1901 TCTTTTCGAC AGGCAATGAC GCACAAGCTC AGCCCAACAC ATATGCCCTA
1951 TTGCCATTTT ATGAAAAAGA CGCTCAAAAA GGCATTATCA CAGTCGCAGG
2001 CGTAGACCGC AGTGGAGAAA AGTTCAAACG GGAAATGTAT GGAGAACCGG
2051 GTACAGAACC GCTTGAGTAT GGCTCCAACC ATTGCGGAAT TACTGCCATG
2101 TGGTGCCTGT CGGCACCCTA TGAAGCAAGC GTCCGTTTCA CCCGTACAAA
2151 CCCGATTCAA ATTGCCGGAA CATCCTTTTC CGCACCCATC GTAACCGGCA
2201 CGGCGGCTCT GCTGCTGCAG AAATACCCGT GGATGAGCAA CGACAACCTG
2251 CGTACCACGT TGCTGACGAC GGCTCAGGAC ATCGGTGCAG TCGGCGTGGA
2301 CAGCAAGTTC GGCTGGGGAC TGCTGGATGC GGGTAAGGCC ATGAACGGAC
2351 CCGCGTCCTT TCCGTTCGGC GACTTTACCG CCGATACGAA AGGTACATCC
2401 GATATTGCCT ACTCCTTCCG TAACGACATT TCAGGCACGG GCGGCCTGAT
```

```
2451 CAAAAAAGGC GGCAGCCAAC TGCAACTGCA CGGCAACAAC ACCTATACGG

2501 GCAAAACCAT TATCGAAGGC GGTTCGCTGG TGTTGTACGG CAACAACAAA

2551 TCGGATATGC GCGTCGAAAC CAAAGGTGCG CTGATTTATA CGGGGCGGC

2601 ATCCGGCGGC AGCCTGAACA GCGACGGCAT TGTCTATCTG GCAGATACCG

2651 ACCAATCCGG CGCAAACGAA ACCGTACACA TCAAAGGCAG TCTGCAGCTG

2701 GACGGCAAAG GTACGCTGTA CACACGTTTG GCAAACTGC TGAAAGTGGA

2751 CGGTACGGCG ATTATCGGCG GCAAGCTGTA CATGTCGGCA CGCGGCAAGG

2801 GGGCAGGCTA TCTCAACAGT ACCGGACGAC GTGTTCCCTT CCTGAGTGCC

2851 GCCAAAATCG GCAGGATTA TTCTTTCTTC ACAAACATCG AAACCGACGG

2901 CGGCCTGCTG GCTTCCCTCG ACAGCGTCGA AAAACAGCG GCAGTGAAG

2951 GCGACACGCT GTCCTATTAT GTCCGTCGCG GCAATGCGGC ACGGACTGCT

3001 TCGGCAGCGG CACATTCCGC GCCCGCCGGT CTGAAACACG CCGTAGAACA

3051 GGGCGGCAGC AATCTGGAAA ACCTGATGGT CGAACTGGAT GCCTCCGAAT

3101 CATCCGCAAC ACCCGAGACG GTTGAAACTG CGGCAGCCGA CCGCACAGAT

3151 ATGCCGGGCA TCCGCCCCTA CGGCGCAACT TTCCGCGCAG CGGCAGCCGT

3201 ACAGCATGCG AATGCCGCCG ACGGTGTACG CATCTTCAAC AGTCTCGCCG

3251 CTACCGTCTA TGCCGACAGT ACCGCCGCCC ATGCCGATAT GCAGGGACGC

3301 CGCCTGAAAG CCGTATCGGA CGGGTTGGAC CACAACGGCA CGGGTCTGCG

3351 CGTCATCGCG CAAACCCAAC AGGACGGTGG AACGTGGGAA CAGGGCGGTG

3401 TTGAAGGCAA AATGCGCGGC AGTACCCAAA CCGTCGGCAT TGCCGCGAAA

3451 ACCGGCGAAA ATACGACAGC AGCCGCCACA CTGGGCATGG GACGCAGCAC

3501 ATGGAGCGAA AACAGTGCAA ATGCAAAAAC CGACAGCATT AGTCTGTTTG

3551 CAGGCATACG GCACGATGCG GGCGATATCG GCTATCTCAA AGGCCTGTTC

3601 TCCTACGGAC GCTACAAAAA CAGCATCAGC CGCAGCACCG GTGCGGACGA

3651 ACATGCGGAA GGCAGGATTA ACGGCACGCT GATGCAGCTG GGCGCACTGG

3701 GCGGTGTCAA CGTTCCGTTT GCCGCAACGG AGATTTGAC GGTCGAAGGC

3751 GGTCTGCGCT ACGACCTGCT CAAACAGGAT GCATTCGCCG AAAAAGGCAG

3801 TGCTTTGGGC TGGAGCGGCA ACAGCCTCAC TGAAGGCACG CTGGTCGGAC

3851 TCGCGGGTCT GAAGCTGTCG CAACCCTTGA GCGATAAAGC CGTCCTGTTT

3901 GCAACGGCGG GCGTGGAACG CGACCTGAAC GGACGCGACT ACACGGTAAC

3951 GGGCGGCTTT ACCGGCGCGA CTGCAGCAAC CGGCAAGACG GGGCACGCA

4001 ATATGCCGCA CACCCGTCTG GTTGCCGGCC TGGGCGCGGA TGTCGAATTC

4051 GGCAACGGCT GGAACGGCTT GGCACGTTAC AGCTACGCCG GTTCCAAACA

4101 GTACGGCAAC CACAGCGGAC GAGTCGGCGT AGGCTACCGG TTCCTCGAGC

4151 ACCACCACCA CCACCACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIRADIATN KDNIAKKANS

251 ADVYTREESD SKFVRIDGLN ATTEKLDTRL ASAEKSIADH DTRLNGLDKT
```

```
 301 VSDLRKETRQ GLAEQAALSG LFQPYNVGGS GGGGTSAPDF NAGGTGIGSN

351 SRATTAKSAA VSYAGIKNEM CKDRSMLCAG RDDVAVTDRD AKINAPPPNL

401 HTGDFPNPND AYKNLINLKP AIEAGYTGRG VEVGIVDTGE SVGSISFPEL

451 YGRKEHGYNE NYRNYTAYMR KEAPEDGGGK DIEASFDDEA VIETEAKPTD

501 IRHVKEIGHI DLVSHIIGGR SVDGRPAGGI APDATLHIMN TNDETKNEMM

551 VAAIRNAWVK LGERGVRIVN NSFGTTSRAG TADLFQIANS EEQYRQALLD

601 YSGGDKTDEG IRLMQQSDYG NLSYHIRNKN MLFIFSTGND AQAQPNTYAL

651 LPFYEKDAQK GIITVAGVDR SGEKFKREMY GEPGTEPLEY GSNHCGITAM

701 WCLSAFYEAS VRFTRTNPIQ IAGTSFSAPI VTGTAALLLQ KYPWMSNDNL

751 RTTLLTTAQD IGAVGVDSKF GWGLLDAGKA MNGPASFPFG DFTADTKGTS

801 DIAYSFRNDI SGTGGLIKKG GSQLQLHGNN TYTGKTIIEG GSLVLYGNNK

851 SDMRVETKGA LIYNGAASGG SLNSDGIVYL ADTDQSGANE TVHIKGSLQL

901 DGKGTLYTRL GKLLKVDGTA IIGGKLYMSA RGKGAGYLNS TGRRVPFLSA

951 AKIGQDYSFF TNIETDGGLL ASLDSVEKTA GSEGDTLSYY VRRGNAARTA

1001 SAAAHSAPAG LRHAVEQGGS NLENLMVELD ASESSATPET VETAAADRTD

1051 MPGIRPYGAT FRAAAAVQHA NAADGVRIFN SLAATVYADS TAAHADMQGR

1101 RLKAVSDGLD HNGTGLRVIA QTQQDGGTWE QGGVEGKMRG STQTVGIAAK

1151 TGENTTAAAT LGMGRSTWSE NSANAKTDSI SLFAGIRHDA GDIGYLKGLF

1201 SYGRYKNSIS RSTGADEHAE GSVNGTLMQL GALGGVNVPF AATGDLTVEG

1251 GLRYDLLKQD AFAEKGSALG WSGNSLTEGT LVGLAGLKLS QPLSDKAVLF

1301 ATAGVERDLN GRDYTVTGGF TGATAATGKT GARNMPHTRL VAGLGADVEF

1351 GNGWNGLARY SYAGSKQYGN HSGRVGVGYR FLEHHHHHH*

961cL-ORF46.1 (SEQ ID NOS: 158 and 159)
   1 ATGAAACACT TCCATCCAA AGTACTGACC ACAGCCATCC TTGCCACTTT

51 CTGTAGCGGC GCACTGGCAG CCACAAACGA CGACGATGTT AAAAAAGCTG

101 CCACTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAGAC GCAACTGCAG CCGATGTTGA AGCCGACGAC TTTAAAGGTC

251 TGGGTCTGAA AAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA TAAATTGGG AGAAAATATA

451 ACGACATTTG CTGAAGAGAC TAAGACAAAT ATCGTAAAAA TTGATGAAAA

501 ATTAGAAGCC GTGGCTGATA CCGTCGACAA GCATGCCGAA GCATTCAACG

551 ATATCGCCGA TTCATTGGAT GAAACCAACA CTAAGGCAGA CGAAGCCGTC

601 AAAACCGCCA ATGAAGCCAA ACAGACGGCC GAAGAAACCA AACAAAACGT

651 CGATGCCAAA GTAAAAGCTG CAGAAACTGC AGCAGGCAAA GCCGAAGCTG

701 CCGCTGGCAC AGCTAATACT GCAGCCGACA AGGCCGAAGC TGTCGCTGCA

751 AAAGTTACCG ACATCAAAGC TGATATCGCT ACGAACAAAG ATAATATTGC

801 TAAAAAGCA AACAGTGCCG ACGTGTACAC CAGAGAAGAG TCTGACAGCA

851 AATTTGTCAG AATTGATGGT CTGAACGCTA CTACCGAAAA ATTGGACACA
```

```
 901 CGCTTGGCTT CTGCTGAAAA ATCCATTGCC GATCACGATA CTCGCCTGAA

951 CGGTTTGGAT AAAACAGTGT CAGACCTGCG CAAAGAAACC CGCCAAGGCC

1001 TTGCAGAACA AGCCGCGCTC TCCGGTCTGT TCCAACCTTA CAACGTGGGT

1051 GGATCCGGAG GAGGAGGATC AGATTTGGCA AACGATTCTT TTATCCGGCA

1101 GGTTCTCGAC CGTCAGCATT TCGAACCCGA CGGGAAATAC CACCTATTCG

1151 GCAGCAGGGG GGAACTTGCC GAGCGCAGCG GCCATATCGG ATTGGGAAAA

1201 ATACAAASCC ATCAGTTGGG CAACCTGATG ATTCAACAGG CGGCCATTAA

1251 AGGAAATATC GGCTACATTG TCCGCTTTTC CGATCACGGG CACGAAGTCC

1301 ATTCCCCCTT CGACAACCAT GCCTCACATT CCGATTCTGA TGAAGCCGGT

1351 AGTCCCGTTG ACGGATTTAG CCTTTACCGC ATCCATTGGG ACGGATACGA

1401 ACACCATCCC GCCGACGGCT ATGACGGGCC ACAGGGCGGC GGCTATCCCG

1451 CTCCCAAAGG CGCGAGGGAT ATATACAGCT ACGACATAAA AGGCGTTGCC

1501 CAAAATATCC GCCTCAACCT GACCGACAAC CGCAGCACCG GACAACGGCT

1551 TGCCGACCGT TTCCACAATG CCGGTAGTAT GCTGACGCAA GGAGTAGGCG

1601 ACGGATTCAA ACGCGCCACC CGATACAGCC CCGAGCTGGA CAGATCGGGC

1651 AATGCCGCCG AAGCCTTCAA CGGCACTGCA GATATCGTTA AAAACATCAT

1701 CGGCGCGGCA GGAGAAATTG TCGGCGCAGG CGATGCCGTG CAGGGCATAA

1751 GCGAAGGCTC AAACATTGCT GTCATGCACG GCTTGGGTCT GCTTTCCACC

1801 GAAAACAAGA TGGCGCGCAT CAACGATTTG CAGATATGG CGCAACTCAA

1851 AGACTATGCC GCAGCAGCCA TCCGCGATTG GCAGTCCAA AACCCCAATG

1901 CCGCACAAGG CATAGAAGCC GTCAGCAATA TCTTTATGGC AGCCATCCCC

1951 ATCAAAGGGA TTGGAGCTGT TCGGGGAAAA TACGGCTTGG GCGGCATCAC

2001 GGCACATCCT ATCAAGCGGT CGCAGATGGG CGCGATCGCA TTGCCGAAAG

2051 GGAAATCCGC CGTCAGCGAC AATTTTGCCG ATGCGGCATA CGCCAAATAC

2101 CCGTCCCCTT ACCATTCCCG AAATATCCGT TCAAACTTGG AGCAGCGTTA

2151 CGGCAAAGAA AACATCACCT CCTCAACCGT GCCGCCGTCA AACGGCAAAA

2201 ATGTCAAACT GGCAGACCAA CGCCACCCGA AGACAGGCGT ACCGTTTGAC

2251 GGTAAAGGGT TTCCGAATTT TGAGAAGCAC GTGAAATATG ATACGTAACT

2301 CGAG

1 MKNFPSKVLT TAILATFCSG ALAATMDDDV KKAATVAIAA AYNNGQEING

51 FKAGETIYDI DEDGTITKKD ATAADVEADD FKGLGLKKVV TNLTKTVNEN

101 KQNVDARVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGK AEAAAGTANT AADKAEAVAA

251 KVTDIKADIA TNKDNIAKKA NSADVYTREE SDSRFVRIDG LNATTERLDT

301 RLASAEKSIA DHDTRLNGLD KTVSDLRKET RQGLAEQAAL SGLFQPYNVG

351 GSGGGGSDLA NDSFIRQVLD RQHFEPDGKY HLFGSRGELA ERSGHIGLGR

401 IQSHQLGNLM IQQAAIKGNI GYIVRFSDHG HEVHSPFDNH ASHSDSDEAG

451 SPVDGFSLYR IHWDGYEHHP ADGYDGAQGG GYPAPKGARD IYSYDIKGVA

501 QNIRLNLTDN RSTGQRLADR FHNAGSMLTQ GVGDGFKRAT RYSPELDRSG

551 NAAEAFNGTA DIVKNIIGAA GEIVGAGDAV QGISEGSNIA VMHGLGLLST
```

-continued

601 ENKMARINDL ADMAQLKDYA AAAIRDWAVQ NPNAAQGIEA VSNIFMAAIP

651 IKGIGAVRGK YGLGGITAHP IKRSQMGAIA LPKGKSAVSD NFADAAYAKY

701 PSPYHSRNIR SNLEQRYGKE NITSSTVPPS NGKNVKLADQ RHPKTGVPFD

751 GKGFPNFEKH VRYDT*

961cL-741 (SEQ ID NOS: 160 and 161)
   1 ATGAAACACT TCCATCCAA AGTACTGACC ACAGCCATCC TTGCCACTTT

51 CTGTAGCGGC GCACTGGCAG CCACAAACGA CGACGATGTT AAAAAAGCTG

101 CCACTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAAGAC GCAACTGCAG CCGATGTTGA AGCCGACGAC TTTAAAGGTC

251 TGGGTCTGAA AAAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA ATAAATTGGG AGAAAATATA

451 ACGACATTTG CTGAAGAGAC TAAGACAAAT ATCGTAAAAA TTGATGAAAA

501 ATTAGAAGCC GTGGCTGATA CCGTCGACAA GCATGCCGAA GCATTCAACG

551 ATATCGCCGA TTCATTGGAT GAAACCAACA CTAAGGCAGA CGAAGCCGTC

601 AAAACCGCCA ATGAAGCCAA ACAGACGGCC GAAGAAACCA AACAAAACGT

651 CGATGCCAAA GTAAAAGCTG CAGAAACTGC AGCAGGCAAA GCCGAAGCTG

701 CCGCTGGCAC AGCTAATACT GCAGCCGACA AGGCCGAAGC TGTCGCTGCA

751 AAAGTTACCG ACATCAAAGC TGATATCGCT ACGAACAAAG ATAATATTGC

801 TAAAAAGCA ACAGTGCCG ACGTGTACAC CAGAGAAGAG TCTGACAGCA

851 AATTTGTCAG AATTGATGGT CTGAACGCTA CTACCGAAAA ATTGGACACA

901 CGCTTGGCTT CTGCTGAAAA ATCCATTGCC GATCACGATA CTCGCCTGAA

951 CGGTTTGGAT AAAACAGTGT CAGACCTGCG CAAAGAAACC CGCCAAGGCC

1001 TTGCAGAACA AGCCGCGCTC TCCGGTCTGT TCCAACCTTA CAACGTGGGT

1051 GGATCCGGAG GGGGTGGTGT CGCCGCCGAC ATCGGTGCGG GGCTTGCCGA

1101 TGCACTAACC GCACCGCTCG ACCATAAAGA CAAAGGTTTG CAGTCTTTGA

1151 CGCTGGATCA GTCCGTCAGG AAAAACGAGA AACTGAAGCT GGCGGCACAA

1201 GGTGCGGAAA AAACTTATGG AAACGGTGAC AGCCTCAATA CGGGCAAATT

1251 GAAGAACGAC AAGGTCAGCC GTTTCGACTT TATCCGCCAA ATCGAAGTGG

1301 ACGGGCAGCT CATTACCTTG GAGAGTGGAG AGTTCCAAGT ATACAAACAA

1351 AGCCATTCCG CCTTAACCGC CTTTCAGACC GAGCAAATAC AAGATTCGGA

1401 GGATCCGGAG AAGATGGTTG CGAAACGCCA GTTCAGAATC GGCGACATAG

1451 CGGGCGAACA TACATCTTTT GACAAGCTTC CGAAGGCGG CAGGGCGACA

1501 TATCGCGGGA CGGCGTTCGG TTCAGACGAT GCCGGCGGAA AACTGACCTA

1551 CACCATAGAT TTCGCCGCCA AGCAGGGAAA CGGCAAAATC GAACATTTGA

1601 AATCGCCAGA ACTCAATGTC GACCTGGCCG CCGCCGATAT CAAGCCGGAT

1651 GGAAAACGCC ATGCCGTCAT CAGCGGTTCC GTCCTTTACA ACCAAGCCGA

1701 GAAAGGCAGT TACTCCCTCG GTATCTTTGG CGGAAAAGCC CAGGAAGTTG

```
-continued
1751 CCGGCAGCGC GGAAGTGAAA ACCGTAAACG GCATACGCCA TATCGGCCTT

1801 GCCGCCAAGC AACTCGAGCA CCACCACCAC CACCACTGA

1 MKHFPSKVLT TAILATFCSG ALAATNDDDV KKAATVAIAA AYNNGQEING

51 FKAGETIYDI DEDGTITKKD ATAADVEADD FKGLGLKKVV TNLTKTVNEN

101 KQNVDAKVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGE AEAAAGTANT AADKAEAVAA

251 KVTDIKADIA TNKDNIAKKA NSADVYTREE SDSKFVRIDG LNATTEKLDT

301 RLASAEKSIA DHDTRLNGLD KTVSDLRKET RQGLAEQAAL SGLFQPYNVG

351 GSGGGGVAAD IGAGLADALT APLDHKDKGL QSLTLDQSVR KNEKLKLAAQ

401 GAEKTYGNGD SLNTGKLKND KVSRFDFIRQ IEVDGQLITL ESGEFQVYKQ

451 SHSALTAFQT EQIQDSEHSG KMVAKRQFRI GDIAGEHTSF DKLPEGGRAT

501 YRGTAFGSDD AGGKLTYTID FAAKQGNGKI EHLKSPELNV DLAAADIKPD

551 GKRHAVISGS VLYNQAEKGS YSLGIFGGKA QEVAGSAEVK TVNGIRHIGL

601 AAKQLEHHHH HH*

961cL-983 (SEQ ID NOS: 162 and 163)
   1 ATGAAACACT TTCCATCCAA AGTACTGACC ACAGCCATCC TTGCCACTTT

51 CTGTAGCGGC GCACTGGCAG CCACAAACGA CGACGATGTT AAAAAAGCTG

101 CCACTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAAGAC GCAACTGCAG CCGATGTTGA AGCCGACGAC TTTAAAGGTC

251 TGGGTCTGAA AAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA ATAAATTGGG AGAAAATATA

451 ACGACATTTG CTGAAGAGAC TAAGACAAAT ATCGTAAAAA TTGATGAAAA

501 ATTAGAAGCC GTGGCTGATA CCGTCGACAA GCATGCCGAA GCATTCAACG

551 ATATCGCCGA TTCATTGGAT GAAACCAACA CTAAGGCAGA CGAAGCCGTC

601 AAAACCGCCA ATGAAGCCAA ACAGACGGCC GAAGAAACCA AACAAAACGT

651 CGATGCCAAA GTAAAAGCTG CAGAAACTGC AGCAGGCAAA GCCGAAGCTG

701 CCGCTGGCAC AGCTAATACT GCAGCCGACA AGGCCGAAGC TGTCGCTGCA

751 AAAGTTACCG ACATCAAAGC TGATATCGCT ACGAACAAAG ATAATATTGC

801 TAAAAAAGCA ACAGTGCCG ACGTGTACAC CAGAGAAGAG TCTGACAGCA

851 AATTTGTCAG AATTGATGGT CTGAACGCTA CTACCGAAAA ATTGGACACA

901 CGCTTGGCTT CTGCTGAAAA ATCCATTGCC GATCACGATA CTCGCCTGAA

951 CGGTTGGGAT AAAACAGTGT CAGACCTGCG CAAAGAAACC CGCCAAGGCC

1001 TTGCAGAACA AGCCGCGCTC TCCGGTCTGT TCCAACCTTA CAACGTGGGT

1051 GGATCCGGCG GAGGCGGCAC TTCTGCGCCC GACTTCAATG CAGGCGGTAC

1101 CGGTATCGGC AGCAACAGCA GAGCAACAAC AGCGAAATCA GCAGCAGTAT

1151 CTTACGCCGG TATCAAGAAC GAAATGTGCA AGACAGAAG CATGCTCTGT

1201 GCCGGTCGGG ATGACGTTGC GGTTACAGAC AGGGATGCCA AAATCAATGC
```

-continued

```
1251 CCCCCCCCCG AATCTGCATA CCGGAGACTT TCCAAACCCA AATGACGCAT

1301 ACAAGAATTT GATCAACCTC AAACCTGCAA TTGAAGCAGG CTATACAGGA

1351 CGCGGGGTAG AGGTAGGTAT CGTCGACACA GGCGAATCCG TCGGCAGCAT

1401 ATCCTTTCCC GAACTGTATG GCAGAAAAGA ACACGGCTAT AACGAAAATT

1451 ACAAAAACTA TACGGCGTAT ATGCGGAAGG AAGCGCCTGA AGACGGAGGC

1501 GGTAAAGACA TTGAAGCTTC TTTCGACGAT GAGGCCGTTA TAGAGACTGA

1551 AGCAAAGCCG ACGGATATCC GCCACGTAAA AGAAATCGGA CACATCGATT

1601 TGGTCTCCCA TATTATTGGC GGGCGTTCCG TGGACGGCAG ACCTGCAGGC

1651 GGTATTGCGC CCGATGCGAC GCTACACATA ATGAATACGA ATGATGAAAC

1701 CAAGAACGAA ATGATGGTTG CAGCCATCCG CAATGCATGG GTCAAGCTGG

1751 GCGAACGTGG CGTGCGCATC GTCAATAACA GTTTIGGAAC AACATCGAGG

1801 GCAGGCACTG CCGACCTTTT CCAAATAGCC AATTCGGAGG AGCAGTACCG

1851 CCAAGCGTTG CTCGACTATT CCGGCGGTGA TAAAACAGAC GAGGGTATCC

1901 GCCTGATGCA ACAGAGCGAT TACGGCAACC TGTCCTACCA CATCCGTAAT

1951 AAAAACATGC TTTTCATCTT TTCGACAGGC AATGACGCAC AAGCTCAGCC

2001 CAACACATAT GCCCTATTGC CATTTTATGA AAAAGACGCT CAAAAAGGCA

2051 TTATCACAGT CGCAGGCGTA GACCGCAGTG GAGAAAAGTT CAAACGGGAA

2101 ATGTATGGAG AACCGGGTAC AGAACCGCTT GAGTATGGCT CCAACCATTG

2151 CGGAATTACT GCCATGTGGT GCCTGTCGGC ACCCTATGAA GCAAGCGTCC

2201 GTTTCACCCG TACAAACCCG ATTCAAATTG CCGGAACATC CTTTTCCGCA

2251 CCCATCGTAA CCGGCACGGC GGCTCTGCTG CTGCAGAAAT ACCCGTGGAT

2301 GAGCAACGAC AACCTGCGTA CCACGTTGCT GACGACGGCT CAGGACATCG

2351 GTGCAGTCGG CGTGGACAGC AAGTTCGGCT GGGGACTGCT GGATGCGGGT

2401 AAGGCCATGA ACGGACCCGC GTCCTTTCCG TTCGGCGACT TTACCGCCGA

2451 TACGAAAGGT ACATCCGATA TTGCCTACTC CTTCCGTAAC GACATTTCAG

2501 GCACGGGCGG CCTGATCAAA AAAGGCGGCA GCCAACTGCA ACTGCACGGC

2551 AACAACACCT ATACGGGCAA AACCATTATC GAAGGCGGTT CGCTGGTGTT

2601 GTACGGCAAC AACAAATCGG ATATGCGCGT CGAAACCAAA GGTGCGCTGA

2651 TTTATAACGG GGCGGCATCC GGCGGCAGCC TGAACAGCGA CGGCATTGTC

2701 TATCTGGCAG ATACCGACCA ATCCGGCGCA AACGAAACCG TACACATCAA

2751 AGGCAGTCTG CAGCTGGACG GCAAAGGTAC GCTGTACACA CGTTTGGGCA

2801 AACTGCTGAA AGTGGACGGT ACGGCGATTA TCGGCGGCAA GCTGTACATG

2851 TCGGCACGCG GCAAGGGGGC AGGCTATCTC AACAGTACCG GACGACGTGT

2901 TCCCTTCCTG AGTGCCGCCA AAATCGGGCA GGATTATTCT TTCTTCACAA

2951 ACATCGAAAC CGACGGCGGC CTGCTGGCTT CCCTCGACAG CGTCGAAAAA

3001 ACAGCGGGCA GTGAAGGCGA CACGCTGTCC TATTATGTCC GTCGCGGCAA

3051 TGCGGCACGG ACTGCTTCGG CAGCGGCACA TTCCGCGCCC GCCGGTCTGA

3101 AACACGCCGT AGAACAGGGC GGCAGCAATC TGGAAAACCT GATGGTCGAA

3151 CTGGATGCCT CCGAATCATC CGCAACACCC GAGACGGTTG AAACTGCGGC

3201 AGCCGACCGC ACAGATATGC CGGGCATCCG CCCCTACGGC GCAACTTTCC

3251 GCGCAGCGGC AGCCGTACAG CATGCGAATG CCGCCGACGG TGTACGCATC
```

-continued

```
3301 TTCAACAGTC TCGCCGCTAC CGTCTATGCC GACAGTACCG CCGCCCATGC
3351 CGATATGCAG GGACGCCGCC TGAAAGCCGT ATCGGACGGG TTGGACCACA
3401 ACGGCACGGG TCTGCGCGTC ATCGCGCAAA CCCAACAGGA CGGTGGAACG
3451 TGGGAACAGG GCGGTGTTGA AGGCAAAATG CGCGGCAGTA CCCAAACCGT
3501 CGGCATTGCC GCGAAAACCG GCGAAAATAC GACAGCAGCC GCCACACTGG
3551 GCATGGGACG CAGCACATGG AGCGAAAACA GTGCAAATGC AAAAACCGAC
3601 AGCATTAGTC TGPPTGCAGG CATACGGCAC GATGCGGGCG ATATCGGCTA
3651 TCTCAAAGGC CTGTTCTCCT ACGGACGCTA CAAAAACAGC ATCAGCCGCA
3701 GCACCGGTGC GGACGAACAT GCGGAAGGCA GCGTCAACGG CACGCTGATG
3751 CAGCTGGGCG CACTGGGCGG TGTCAACGTT CCGTPPGCCG CAACGGGAGA
3801 TTTGACGGTC GAAGGCGGTC TGCGCTACGA CCTGCTCAAA CAGGATGCAT
3851 TCGCCGAAAA AGGCAGTGCT TTGGGCTGGA GCGGCAACAG CCTCACTGAA
3901 GGCACGCTGG TCGGACTCGC GGGTCTGAAG CTUTCGCAAC CCTTGAGCGA
3951 TAAAGCCGTC CTGTTTGCAA CGGCGGGCGT GGAACGCGAC CTGAACGGAC
4001 GCGACTACAC GGTAACGGGC GGCTTTACCG GCGCGACTGC AGCAACCGGC
4051 AAGACGGGGG CACGCAATAT GCCGCACACC CGTCTGGTTG CCGGCCTGGG
4101 CGCGGATGTC GAATTCGGCA ACGGCTGGAA CGGCTTGGCA CGTTACAGCT
4151 ACGCCGGTTC CAAACAGTAC GGCAACCACA GCGGACGAGT CGGCGTAGGC
4201 TACCGGTTCT GACTCGAG

1 MKHFPSKVLT TAILATFCSG ALAATNDDDV KKAATVAIAA AYNEGQEING
  51 FKAGETIYDI DEDGTITKKD ATAADVEADD FKGLGLKKVV TNLTKTVNEN
 101 KQNVDAKVKA AESEIEKLTT KLADTDAALA DTDAALDATT NALNKLGENI
 151 TTFAEETKTN IVKIDEKLEA VADTVDKHAE AFNDIADSLD ETNTKADEAV
 201 KTANEAKQTA EETKQNVDAK VKAAETAAGK AEAAAGTANT AADKAEAVAA
 251 KVTDIKADIA TNKDNIAKKA NSADVYTREE SDSKFVRIDG LNATTEKLDT
 301 RLASAEKSIA DHDTRLNGLD KTVSDLRKET RQGLAEQAAL SGLFQPYNVG
 351 GSGGGGTSAP DFNAGGTGIG SNSRATTAKS AAVSYAGIKN EMCKDRSMLC
 401 AGRDDVAVTD RDAKINAPPP NLHTGDFPNP NDAYKNLINL KPAIEAGYTG
 451 RGVEVGIVDT GESVGSISFP ELYGRKEHGY NENYKNYTAY MRKEAPEDGG
 501 GKDIEASFDD EAVIETEAKP TDIRHVKEIG HIDLVSHIIG GRSVDGRPAG
 551 GIAPDATLHI MNTNDETKNE MMVAAIRNAW VKLGERGVRI VNNSFGTTSR
 601 AGTADLFQIA NSEEQYRQAL LDYSGGDKTD EGIRLMQQSD YGNLSYHIRN
 651 KNMLFIFSTG NDAQAQPNTY ALLPFYEKDA QKGIITVAGV DRSGEKFKRE
 701 MYGEPGTEPL EYGSNHCGIT AMWCLSAPYE ASVRFTRTNP IQIAGTSFSA
 751 PIVTGTAALL LQKYPWMSND NLRTTLLTTA QDIGAVGVDS KFGWGLLDAG
 801 KAMNGPASFP FGDFTADTKG TSDIAYSFRN DISGTGGLIK KGGSQLQLHG
 851 NNTYTGRTII EGGSLVLYGN NKSDMRVETK GALIYNGAAS GGSLNSDGIV
 901 YLADTDQSGA NETVHIKGSL QLDGKGTLYT RLGKLLKVDG TAIIGGKLYM
 951 SARGRGAGYL NSTGRRVPFL SAAKIGQDYS FFTNIETDGG LLASLDSVEK
1001 TAGSEGDTLS YYVRRGNAAR TASAAAHSAP AGLKHAVEQG GSNLENLMVE
1051 LDASESSATP ETVETAAADR TDMPGIRPYG ATFRAAAAVQ HANAADGVRI
```

```
                           -continued
1101 FNSLAATVYA DSTAAHADMQ GRRLKAVSDG LDHNGTGLRV IAQTQQDGGT

1151 WEQGGVEGKM RGSTQTVGIA AKTGENTTAA ATLGMGRSTW SENSANAKTD

1201 SISLFAGIRH DAGDIGYLKG LFSYGRYKNS ISRSTGADEH AEGSVNGTLM

1251 QLGALGGVNV PFAATGDLTV EGGLRYDLLK QDAFAEKGSA LGWSGNSLTE

1301 GTLVGLAGLK LSQPLSDKAV LFATAGVERD LNGRDYTVTG GFTGATAATG

1351 KTGARNMPHT RLVAGLGADV EFGNGWNGLA RYSYAGSKQY GNHSGRVGVG

1401 YRF*
```

It will be understood that the invention has been described by way of example only and modifications may be made whilst remaining within the scope and spirit of the invention. For instance, the use of proteins from other strains is envisaged [e.g. see WO00/66741 for polymorphic sequences for ORF4, ORF40, ORF46, 225, 235, 287, 519, 726, 919 and 953].

EXPERIMENTAL DETAILS

FPLC Protein Purification

The following table summarises the FPLC protein purification that was used:

| Protein | PI | Column | Buffer | pH | Protocol |
| --- | --- | --- | --- | --- | --- |
| 121.1<sup>untagged</sup> | 623 | Mono Q | Tris | 8.0 | A |
| 128.1<sup>untagged</sup> | 5.04 | Mono Q | Bis-Tris propane | 6.5 | A |
| 406.1L | 7.75 | Mono Q | Diethanolamine | 9.0 | B |
| 576.1L | 5.63 | Mono Q | Tris | 7.5 | B |
| 593<sup>untagged</sup> | 8.79 | Mono S | Hepes | 7.4 | A |
| 726<sup>untagged</sup> | 4.95 | Hi-trap S | Bis-Tris | 6.0 | A |
| 919<sup>untagged</sup> | 10.5(-leader) | Mono S | Bicine | 8.5 | C |
| 919Lorf4 | 10.4(-leader) | Mono S | Tris | 8.0 | B |
| 920L | 6.92(-leader) | Mono Q | Diethanolamine | 8.5 | A |
| 953L | 7.56(-leader) | Mono S | MES | 6.6 | D |
| 982<sup>untagged</sup> | 4.73 | Mono Q | Bis-Tris propane | 6.5 | A |
| 919-287 | 6.58 | Hi-trap Q | Tris | 8.0 | A |
| 953-287 | 4.92 | Mono Q | Bis-Tris propane | 6.2 | A |

Buffer solutions included 20-120 mM NaCl, 5.0 mg/ml CHAPS and 10% v/v glycerol. The dialysate was centrifuged at 13000 g for 20 min and applied to either a mono Q or mono S FPLC ion-exchange resin. Buffer and ion exchange resins were chosen according to the pI of the protein of interest and the recommendations of the FPLC protocol manual [Pharmacia: *FPLC Ion Exchange and Chromatofocussing; Principles and Methods*. Pharmacia Publication]. Proteins were eluted using a step-wise NaCl gradient. Purification was analysed by SDS-PAGE and protein concentration determined by the Bradford method.

The letter in the 'protocol' column refers to the following:

FPLC-A: Clones 121.1, 128.1, 593, 726, 982, periplasmic protein 920L and hybrid proteins 919-287, 953-287 were purified from the soluble fraction of *E. coli* obtained after disruption of the cells. Single colonies harbouring the plasmid of interest were grown overnight at 37° C. in 20 ml of LB/Amp (100 μg/ml) liquid culture. Bacteria were diluted 1:30 in 1.0 L of fresh medium and grown at either 30° C. or 37° C. until the OD$_{550}$ reached 0.6-08. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. For cytosolic proteins (121.1, 128.1, 593, 726 and 982) and periplasmic protein 920L, bacteria were resuspended in 25 ml of PBS containing complete protease inhibitor (Boehringer-Mannheim). Cells were lysed by sonication using a Branson SONIFIER® 450 (ultrasonic cell disruption/homogenizer). Disrupted cells were centrifuged at 8000 g for 30 min to sediment unbroken cells and inclusion bodies and the supernatant taken to 35% v/v saturation by the addition of 3.9 M $(NH_4)_2SO_4$. The precipitate was sedimented at 8000 g for 30 minutes. The supernatant was taken to 70% v/v saturation by the addition of 3.9 M $(NH_4)_2SO_4$ and the precipitate collected as above. Pellets containing the protein of interest were identified by SDS-PAGE and dialysed against the appropriate ion-exchange buffer (see below) for 6 hours or overnight. The periplasmic fraction from *E. coli* expressing 953L was prepared according to the protocol of Evans et. al. [*Infect. Immun.* (1974) 10:1010-1017] and dialysed against the appropriate ion-exchange buffer. Buffer and ion exchange resin were chosen according to the pI of the protein of interest and the recommendations of the FPLC protocol manual (Pharmacia). Buffer solutions included 20 mM NaCl, and 10% (v/v) glycerol. The dialysate was centrifuged at 13000 g for 20 min and applied to either a mono Q or mono S FPLC ion-exchange resin. Buffer and ion exchange resin were chosen according to the pI of the protein of interest and the recommendations of the FPLC protocol manual (Pharmacia). Proteins were eluted from the ion-exchange resin using either step-wise or continuous NaCl gradients. Purification was analysed by SDS-PAGE and protein concentration determined by Bradford method. Cleavage of the leader peptide of periplasmic proteins was demonstrated by sequencing the NH$_2$-terminus (see below).

FPLC-B: These proteins were purified from the membrane fraction of *E. coli*. Single colonies harbouring the plasmid of interest were grown overnight at 37° C. in 20 ml of LB/Amp (100 μg/ml) liquid culture. Bacteria were diluted 1:30 in 1.0 L of fresh medium. Clones 406.1L and 919LOrf4 were grown at 30° C. and Orf25L and 576.1L at 37° C. until the OD$_{550}$ reached 0.6-0.8. In the case of 919LOrf4, growth at 30° C. was essential since expression of recombinant protein at 37° C. resulted in lysis of the cells. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed at 4° C. Bacteria were resuspended in 25 ml of PBS containing complete protease inhibitor (Boehringer-Mannheim) and lysed by osmotic shock with 2-3 passages through a French Press. Unbroken cells were removed by centrifugation at 5000 g for 15 min and membranes precipitated by centrifugation at 100000 g (Beckman Ti50, 38000 rpm) for 45 minutes. A Dounce homogenizer was used to re-suspend the membrane pellet in 7.5 ml of 20 mM Tris-HCl (pH 8.0), 1.0 M NaCl and complete protease inhibitor. The suspension was mixed for 2-4 hours, centrifuged at 100000 g for 45 min and the pellet resuspended in 7.5 ml of 20 mM Tris-HCl (pH 8.0), 1.0M NaCl, 5.0 mg/ml CHAPS, 10% (v/v) glycerol and complete protease inhibitor. The solution was mixed overnight, centrifuged at 100000 g for 45 minutes and the supernatant dialysed for 6 hours against an appropriately selected buffer. In the case of Orf25.L, the pellet obtained after CHAPS extraction was found to contain the recombinant protein. This fraction, without further purification, was used to immunise mice.

FPLC-C: Identical to FPLC-A, but purification was from the soluble fraction obtained after permeabilising $E.\ coli$ with polymyxin B, rather than after cell disruption.

FPLC-D: A single colony harbouring the plasmid of interest was grown overnight at 37° C. in 20 ml of LB/Amp (100 µg/ml) liquid culture. Bacteria were diluted 1:30 in 1.0 L of fresh medium and grown at 30° C. until the $OD_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. Cells were resuspended in 20 mM Bicine (pH 8.5), 20 mM NaCl, 10% (v/v) glycerol, complete protease inhibitor (Boehringer-Mannheim) and disrupted using a Branson SONIFIER® 450 (ultrasonic cell disruption/homogenizer). The sonicate was centrifuged at 8000 g for 30 min to sediment unbroken cells and inclusion bodies. The recombinant protein was precipitated from solution between 35% v/v and 70% v/v saturation by the addition of 3.9M $(NH_4)_2SO_4$. The precipitate was sedimented at 8000 g for 30 minutes, resuspended in 20 mM Bicine (pH 8.5), 20 mM NaCl, 10% (v/v) glycerol and dialysed against this buffer for 6 hours or overnight. The dialysate was centrifuged at 13000 g for 20 min and applied to the FPLC resin. The protein was eluted from the column using a step-wise NaCl gradients. Purification was analysed by SDS-PAGE and protein concentration determined by Bradford method.

Cloning Strategy and Oligonucleotide Design

Genes coding for antigens of interest were amplified by PCR, using oligonucleotides designed on the basis of the genomic sequence of $N.\ meningitidis$ B MC58. Genomic DNA from strain 2996 was always used as a template in PCR reactions, unless otherwise specified, and the amplified fragments were cloned in the expression vector pET21b+ (Novagen) to express the protein as C-terminal His-tagged product, or in pET-24b+(Novagen) to express the protein in 'untagged' form (e.g. ΔG 287K).

Where a protein was expressed without a fusion partner and with its own leader peptide (if present), amplification of the open reading frame (ATG to STOP codons) was performed.

Where a protein was expressed in 'untagged' form, the leader peptide was omitted by designing the 5'-end amplification primer downstream from the predicted leader sequence.

The melting temperature of the primers used in PCR depended on the number and type of hybridising nucleotides in the whole primer, and was determined using the formulae:

$T_{m1} = 4(G+C) + 2(A+T)$ (tail excluded)

$T_{m2} = 64.9 + 0.41(\% \ GC) - 600/N$ (whole primer)

The melting temperatures of the selected oligonucleotides were usually 65-70° C. for the whole oligo and 50-60° C. for the hybridising region alone.

Oligonucleotides were synthesised using a Perkin Elmer 394 DNA/RNA Synthesizer, eluted from the columns in 2.0 ml $NH_4OH$, and deprotected by 5 hours incubation at 56° C. The oligos were precipitated by addition of 0.3M Na-Acetate and 2 volumes ethanol. The samples were centrifuged and the pellets resuspended in water.

| | | Sequences | SEQ ID NO | Restriction site |
|---|---|---|---|---|
| Orf1L | Fwd | CGCGGATCCGCTAGC-AAAACAACCGACAAACGG | 164 | NheI |
| | Rev | CCCGCTCGAG-TTACCAGCGTAGCCTA | 165 | XhoI |
| Orf1 | Fwd | CTAGCTAGC-GGACACACTTATTCGGCATC | 166 | NheI |
| | Rev | CCCGCTCGAG-TTACCAGCGTAGCCTAATTTG | 167 | XhoI |
| Orf1OmpA | Fwd | | 168 | NdeI-(NheI) |
| | Rev | CCCGCTCGAG- | | XhoI |
| Orf4L | Fwd | CGCGGATCCCATATG-AAAACCTTCTTCAAAACC | 169 | NdeI |
| | Rev | CCCGCTCGAG-TTATTTGGCTGCGCCTTC | 170 | XhoI |
| Orf7-1L | Fwd | GCGGCCATTAAT-ATGTTGAGAAAATTGTTGAAAATGG | 171 | AseI |
| | Rev | GGGGCCTCGAG-TTATTTTTCAAAATATATTGC | 172 | XhoI |
| Orf9-1L | Fwd | GCGGCCATATG-TTACCTAACCGTTTCAAAATGT | 173 | NdeI |
| | Rev | GCGGGCCTCGAG-TTATTTCCGAGGTTTTCGGG | 174 | XhoI |
| Orf23L | Fwd | CGCGGATCCCATATG-ACACGCTTCAAATATTC | 175 | NdeI |
| | Rev | CCCGCTCGAG-TTATTTAAACCGATAGGTAAA | 176 | XhoI |
| Orf25L | Fwd | CGCGGATCCCATATG-GGCCAGGGAAGAACCGC | 177 | NdeI |
| | Rev | GCCAAGCTT-ATCGATGGAATAGCCGCG | 178 | HindIII |
| Orf29-1 His | Fwd | CGCGGATCCGCTAGC-AACGGTTTGGATGCCCG | 179 | NheI |
| | Rev | CCCGCTCGAG-TTTGTCTAAGTTCCTGATAT | 180 | XhoI |
| | | CCCGCTCGAG-ATTCCCACCTGCCATC | 181 | |
| Orf29-1 b-His (MC58) | Fwd | CGCGGATCCGCTAGC-ATGAATTTGCCTATTCAAAAAT | 182 | NheI |
| | Rev | CCCGCTCGAG-TTAATTCCCACCTGCCATC | 183 | XhoI |
| Orf29-1 b-L (MC58) | Fwd | CGCGGATCCGCTAGC-ATGAATTTGCCTATTCAAAAAT | 184 | NheI |
| | Rev | CCCGCTCGAG-TTGGACGATGCCGCGA | 185 | XhoI |
| Orf29-1 c-His (MC58) | Fwd | CGCGGATCCGCTAGC-ATGAATTTGCCTATTCAAAAAT | 186 | NheI |
| | Rev | CCCGCTCGAG-TTATTGGACGATGCCCGC | 187 | XhoI |
| Orf29-1 c-L | Fwd | CGCGGATCCCATATG-TATCGCAAACTGATTGC | 188 | NdeI |
| | Rev | CCCGCTCGAG-CTAATCGATGGAATAGCC | 189 | XhoI |
| Orf37L | Fwd | CGCGGATCCCATATG-AAACAGACAGTCAAATG | 190 | NdeI |
| | Rev | CCCGCTCGAG-TCAATAACCCGCCTTCAG | 191 | XhoI |
| Orf38L | Fwd | CGCGGATCCCATATG-TTACGTTTGACTGCTTTAGCCGTATGCACC | 192 | NdeI |
| | Rev | CCCGCTCGAG-TTATTTTGCCGCGTTAAAAGCGTCGGCAAC | 193 | XhoI |

-continued

| | | Sequences | SEQ ID NO | Restriction site |
|---|---|---|---|---|
| Orf40L | Fwd | CGCGGATCCCATATG-AACAAATATACCGCAT | 194 | NdeI |
| | Rev | CCCGCTCGAG-TTACCACTGATAACCGAC | 195 | XhoI |
| Orf40.2-His | Fwd | CGCGGATCCCATATG-ACCGATGACGACGATTTAT | 196 | NdeI |
| | Rev | GCCCAAGCTT-CCACTGATAACCGACAGA | 197 | HindIII |
| Orf40.2L | Fwd | CGCGGATCCCATATG-AACAAATATACCGCAT | 198 | NdeI |
| | Rev | GCCAAGCTT-TTACCACTGATAACCGAC | 199 | HindIII |
| Orf46-2L | Fwd | GGGAATTCCATATG-GGCATTTCCCGCAAAATATC | 200 | NdeI |
| | Rev | CCCGCTCGAG-TTATTTACTCCTATAACGAGGTCTCTTAAC | 201 | XhoI |
| Orf46-2 | Fwd | GGGAATTCCATATG-TCAGATTTGGCAAACGATTCTT | 202 | NdeI |
| | Rev | CCCGCTCGAG-TTATTTACTCCTATAACGAGGTCTCTTAAC | 203 | XhoI |
| Orf46.1L | Fwd | GGGAATTCCATATG-GGCATTTCCCGCAAAATATC | 204 | NdeI |
| | Rev | CCCGCTCGAG-TTACGTATCATATTTCACGTGC | 205 | XhoI |
| orf46.(His-GST) | Fwd | GGGAATTCCATATGCACGTGAAATATGATACGAAG | 206 | NdeI |
| | Rev | CCCGCTCGAGTTTACTCCTATAACGAGGTCTCTTAAC | 207 | XhoI |
| rf46.1-His | Fwd | GGGAATTCCATATGTCAGATTTGGCAAACGATTCTT | 208 | NdeI |
| | Rev | CCCGCTCGAGCGTATCATATTTCACGTGC | 209 | XhoI |
| orf46.2-His | Fwd | GGGAATTCCATATGTCAGATTTGGCAAACGATTCTT | 210 | NdeI |
| | Rev | CCCGCTCGAG-TTACTCCTATAACGAGGTCTCTTAAC | 211 | XhoI |
| Orf65-1-(His/GST) (MC58) | Fwd | CGCGGATCCCATATG-CAAAATGCGTTCAAAATCCC | 212 | BamHI-NdeI |
| | Rev | CGCGGATCCCATATG-AACAAATATACCGCAT | 213 | XhoI |
| | | CCCGCTCGAG-TTTGCTTTCGATAGAACGG | 214 | |
| Orf72-1L | Fwd | GCGGCCATATG-GTCATAAAATACAAATTTGAA | 215 | NdeI |
| | Rev | GCGGCCTCGAG-TTAGCCTGGACCTTTGCAAATT | 216 | XhoI |
| Orf76-1L | Fwd | GCGGCCATATG-AAACAGAAAAAAACCGCTG | 217 | NdeI |
| | Rev | GCGGCCTCGAG-TTACGGTTTGACACCGTTTTC | 218 | XhoI |
| Orf83.1L | Fwd | CGCGGATCCCATATG-AAAACCCTGCTCCTC | 219 | NdeI |
| | Rev | CCCGCTCGAG-TTATCCTCCTTTGCCGC | 220 | XhoI |
| Orf85-2L | Fwd | GCGGCCATATG-GCAAAAATGATGAAATGGG | 221 | NdeI |
| | Rev | GCGGCCTCGAG-TTATCGGCGCGGGGCC | 222 | XhoI |
| Orf91L (MC58) | Fwd | GCGGCCATATGAAAAAATCCTCCCTCATCA | 223 | NdeI |
| | Rev | GCGGCCTCGAGTTATTTGCCCGCCGTTTTTGGC | 224 | XhoI |
| Orf91-His (MC58) | Fwd | GCGGCCATATGCCCCTGCCGACGCGTAAG | 225 | NdeI |
| | Rev | GCGGCCTCGAGTTTGCCGCCGTTTTTGGCTTTC | 226 | XhoI |

-continued

| | | Sequences | SEQ ID NO | Restriction site |
|---|---|---|---|---|
| Orf97-1L | Fwd<br>Rev | GCGGCCATATG-AAACACATACTCCCCTGA<br>GCGGCCTCGAG-TTATTCGCCTACGGTTTTTG | 227<br>228 | NdeI<br>XhoI |
| Orf119L (MC58) | Fwd<br>Rev | GCGGCCATATGATTACATCGTACTGTTTC<br>GCGGCCTCGAGTTAGGAGAACAGGCGCAATGC | 229<br>230 | NdeI<br>XhoI |
| Orf119-His (MC58) | Fwd<br>Rev | GCGGCCATATGTACAACATGTATCAGAAAAC<br>GCGGCCTCGAGGGAGAACAGGCGCAATGCG | 231<br>232 | NdeI<br>XhoI |
| Orf137.1 (His-GST) (MC58) | Fwd<br>Rec | CGCGGATCCGCTAGCTGCGGCACGGCGGG<br>CCCGCTCGAGATAACGTATGCCGCCAG | 233<br>234 | BamHI-NheI<br>XhoI |
| Orf143-1L | Fwd<br>Rev | CGCGGATCCCATATG-GAATCAACACTTTCAC<br>CCCGCTCGAG-TTACACGCGGTTGCTGT | 235<br>236 | NdeI<br>XhoI |
| 008 | Fwd<br>Rev | CGCGGATCCCATATG-AACAACAGAGACATTTTG<br>CCCGCTCGAG-TTACCTGTCCGGTAAAAG | 237<br>238 | NdeI<br>XhoI |
| 050-1 (48) | Fwd<br>Rev | CGCGGATCCGCTAGC-ACCGTCATCAAACAGGAA<br>CCCGCTCGAG-TCAAGATTCGACGGGGA | 239<br>240 | NheI<br>XhoI |
| 105 | Fwd<br>Rev | CGCGGATCCCATATG-TCCGCAAACGAATACG<br>CCCGCTCGAG-TCAGTGTTCTGCCAGTTT | 241<br>242 | NdeI<br>XhoI |
| 111L | Fwd<br>Rev | CGCGGATCCCATATG-CCGTCTGAAACACG<br>CCCGCTCGAG-TTAGCGGAGCAGTTTTTC | 243<br>244 | NdeI<br>XhoI |
| 117-1 | Fwd<br>Rev | CGCGGATCCCATATG-ACCGCCATCAGCC<br>CCCGCTCGAG-TTAAAGCCGGGTAACGC | 245<br>246 | NdeI<br>XhoI |
| 121-1 | Fwd<br>Rev | GCGGCCATATG-GAAACACAGCTTTACATCGG<br>GCGGCCTCGAG-TCAATAATATATCCCGCG | 247<br>248 | NdeI<br>XhoI |
| 122-1 | Fwd<br>Rev | GCGGCCATATG-ATTAAAATCCGCAATATCC<br>GCGGCCTCGAG-TTAAATCTTGGTAGATTGGATTTGG | 249<br>250 | NdeI<br>XhoI |
| 128-1 | Fwd<br>Rev | GCGGCCATATG-ACTGACAACGCACTGCTCC<br>GCGGCCTCGAG-TCAGACCGCGTTGTCGAAAC | 251<br>252 | NdeI<br>XhoI |
| 148 | Fwd<br>Rev | CGCGGATCCCATATG-GCGTTAAAAACATCAAA<br>CCCGCTCGAG-TCAGCCCTTCATACAGC | 253<br>254 | NdeI<br>XhoI |
| 149.1L (MC58) | Fwd<br>Rev | GCGGCCATTAATGCACAAACTTACACTTCAAACC<br>GCGGCCTCGAGTTAAAACTTCACGTTCACGCCG | 255<br>256 | AseI<br>XhoI |
| 149.1-His (MC58) | Fwd<br>Rev | GCGGCCATTAATGCATGAAACTGAGCAATCGTGG<br>GCGGCCTCGAGAAACTTCACGTTCACCCGCCGGTAAA | 257<br>258 | AseI<br>XhoI |

-continued

| | | Sequences | SEQ ID NO | Restriction site |
|---|---|---|---|---|
| 205 (His-GST) (MC58) | Fwd<br>Rev | CGCGGATCCCATATGGGCAAATCCGAAAATACG<br>CCCGCTCGAGATAATGGCGCGCGCGG | 259<br>260 | BamHI-NdeI<br>XhoI |
| 206L | Fwd<br>Rev | CGCGGATCCCATATG-TTTCCCCCGACAA<br>CCCGCTCGAG-TCATTCTGTAAAAAAGTATG | 261<br>262 | NdeI<br>XhoI |
| 214 (His-GST) (MC58) | Fwd<br>Rev | CGCGGATCCCATATGCTTCAAAGCGACAGCAG<br>CCCGCTCGAGTTCGGATTTTTGCGTACTC | 263<br>264 | BamHI-NdeI<br>XhoI |
| 216 | Fwd<br>Rev | CGCGGATCCCATATG-GCAATGGCAGAAAACG<br>CCCGCTCGAG-CTATACAATCCGTGCCG | 265<br>266 | NdeI<br>XhoI |
| 225-1L | Fwd<br>Rev | CGCGGATCCCATATG-GATTCTTTTTTCAAACC<br>CCCGCTCGAG-TCAGTTCAGAAAGCGGG | 267<br>268 | NdeI<br>XhoI |
| 235L | Fwd<br>Rev | CGCGGATCCCATATG-AAACCTTTGATTTTAGG<br>CCCGCTCGAG-TTATTTGGGCTGCTCTTC | 269<br>270 | NdeI<br>XhoI |
| 243 | Fwd<br>Rev | CGCGGATCCCATATG-GTAATCGTCTGGTTG<br>CCCGCTCGAG-CTACGACTTGGTTACCG | 271<br>272 | NdeI<br>XhoI |
| 247-1L | Fwd<br>Rev | GCGGCCATATG-AGACCTAAAATGCTAAAGCTAC<br>GCGGCCTCGAG-TCAAAGTGTTCTGTTTGCGC | 273<br>274 | NdeI<br>XhoI |
| 264-His | Fwd<br>Rev | GCGGCCATATG-TTGACTTTAACCCGAAAAA<br>GCGGCCTCGAG-GCCGGCGGTCAATACCGCCCGAA | 275<br>276 | NdeI<br>XhoI |
| 270 (His-GST) (MC58) | Fwd<br>Rev | CGCGGATCCCATATGGCGCAATGCGATTTGAC<br>CCCGCTCGAGTTCGGCGGTAAATGCCG | 277<br>278 | BamHI-NdeI<br>XhoI |
| 274L | Fwd<br>Rev | GCGGCCATATG-GCGGGGCCGATTTTTGT<br>GCGGCCTCGAG-TTATTTGCTTTCAGTATTATTG | 279<br>280 | NdeI<br>XhoI |
| 283L | Fwd<br>Rev | GCGGCCATATG-AACTTTGCTTTATCCGTCA<br>GCGGCCTCGAG-TTAACGCAGTATTTGTTTAC | 281<br>282 | NdeI<br>XhoI |
| 285-His | Fwd<br>Rev | CGCGGATCCCATATGGGGTTTGCGCTTCGGGC<br>GCCAAGCTTTTTCTTTGCCGTTTCCG | 283<br>284 | BamHI<br>HindIII |
| 286-His (MC58) | Fwd<br>Rev | CGCGGATCCCATATG-GCCGACCTTTCCGAAAA<br>CCCGCTCGAG-GAAGCGCGTTCCCAAGC | 285<br>286 | NdeI<br>XhoI |
| 286L (MC58) | Fwd<br>Rev | CGCGGATCCCATATG-CACGACACCCGTAC<br>CCCGCTCGAG-TTAGAAGCGCGTTCCAA | 287<br>288 | NdeI<br>XhoI |
| 287L | Fwd<br>Rev | CTAGCTAGC-TTTAAACCAGCGTAATCGCAATGG<br>CCCGCTCGAG-TCAATCCTGCTCTTTTTGCC | 289<br>290 | NheI<br>XhoI |

-continued

| | | Sequences | SEQ ID NO | Restriction site |
|---|---|---|---|---|
| 287 | Fwd | CTAGCTAGC-GGGGGCGGCGGTGGCG | 291 | NheI |
| | Rev | CCCGCTCGAG-TCAATCCTGCTCTTTTTGCC | 292 | XhoI |
| 287LOrf4 | Fwd | CTAGCTAGCGCTCATCCTCGCCGCC-TGCGGGGGCGCGGT | 293 | NheI |
| | Rev | CCCGCTCGAG-TCAATCCTGCTCTTTTTGCC | 294 | XhoI |
| 287-fu | Fwd | CGGGGATCC-GGGGGCGGCGGTGGCG | 295 | BamHI |
| | Rev | CCCGCTCGAG-TCAATCCTGCTCTTTTTGCC | 296 | XhoI |
| 287-His | Fwd | CTAGCTAGC-GGGGGCGGCGGTGGCG | 297 | NheI |
| | Rev | CCCGCTCGAG-ATCCTGCTCTTTTTGCC * | 298 | XhoI |
| 287-His (2996) | Fwd | CTAGCTAGC-TGCGCTGGGCGCGGTGGCG | 299 | NheI |
| | Rev | CCCGCTCGAG-ATCCTGCTCTTTTTGCC | 300 | XhoI |
| Δ1 287-His | Fwd | CGCGGATCCGCTAGC-CCCGATGTTAAATCGGC | 301 | NheI |
| Δ2 287-His | Fwd | CGCGGATCCGCTAGC-CAAGATATGGCGGCAGT | 302 | NheI |
| Δ3 287-His | Fwd | CGCGGATCCGCTAGC-GCCGAATCCGCAAATCA | 303 | NheI |
| Δ4 287-His | Fwd | CGCGCTAGC-GGAAGGGTTGATTTGGCTAATGG | 304 | NheI |
| Δ4 287MC58-His | Fwd | CGCGCTAGC-GGAAGGGTTGATTTGGCTAATGG | 305 | NheI |
| 287a-His | Fwd | CGCCATATG-TTTAAACGCAGCGTAATCGC | 306 | NdeI |
| | Rev | CCCGCTCGAG-AAAATTGCTACCGCCATTCGCAGG | 307 | XhoI |
| 287b-His | Fwd | CGCCATATG-GGAAGGGTTGATTTGGCTAATGG | 308 | NdeI |
| 287b-2996-His | Rev | CCCGCTCGAG-CTTGTCTTTATAAATGATGACATATTTG | 309 | XhoI |
| 287b-MC58-His | Rev | CCCGCTCGAG-TTTATAAAAGATAATATATTGATTGATTCC | 310 | XhoI |
| 287c-2996-His | Fwd | CGCGCTAGC-ATGCCCGCTGATTCCCGTCAATC * | 311 | NheI |
| '287untagged' (2996) | Fwd | CTAGCTAGC-GGGGGCGGCGGTGGCG | 312 | NheI |
| | Rev | CCCGCTCGAG-TCAATCCTGCTCTTTTTGCC | 313 | XhoI |
| ΔG287-His * | Fwd | CGCGGATCCGCTAGC-CCCGATGTTAAATCGGC | 314 | NheI |
| | Rev | CCCGCTCGAG-ATCCTGCTCTTTTTGCC | 315 | XhoI |

-continued

| | | Sequences | SEQ ID NO | Restriction site |
|---|---|---|---|---|
| ΔG287K (2996) | Fwd | CGCGGATCCGCTAGC-CCCGATGTTAAATCGGC | 316 | NheI |
| | Rev | CCCGCTCGAG-TCAATCCTGCTCTTTTTGCC | 317 | XhoI |
| ΔG 287-L | Fwd | CGCGGATCCGCTAGC-TTTGAACGCAGTGTGATTGCAATGGCTTGTATTTTTGCC CTTTCAGCCTGT TCGCCCGATGTTAAATCGGCG | 318 | NheI |
| | Rev | CCCGCTCGAG-TCAATCCTGCTCTTTTTGCC | 319 | XhoI |
| ΔG 287-Orf4L | Fwd | CGCGGATCCGCTAGC-AAAACCTTCTTCAAAACCCTTTCCGCCGCCGCACTCGCG CTCATCCTCGCCGCCTGC TCGCCCGATGTTAAATCG | 320 | NheI |
| | Rev | CCCGCTCGAG-TCAATCCTGCTCTTTTTGCC | 321 | XhoI |
| 292L | Fwd | CGCGGATCCCATATG-AAAACCAAGTTAATCAAA | 322 | NdeI |
| | Rev | CCCGCTCGAG-TTATTGATTTTTGCGGATGA | 323 | XhoI |
| 308-1 | Fwd | CGCGGATCCCATATG-TTAAATCGGGTATTTTATC | 324 | NdeI |
| | Rev | CCCGCTCGAG-TTAATCCGCCATTCCCTG | 325 | XhoI |
| 401L | Fwd | GCGGCCATATG-AAATTACAACAATTGGCTG | 326 | NdeI |
| | Rev | GCGGCCTCGAG-TTACCTTACGTTTTCAAAG | 327 | XhoI |
| 406L | Fwd | CGCGGATCCCATATG-CAAGCACGGCTGCT | 328 | NdeI |
| | Rev | CCCGCTCGAG-TCAAGGTTGTCCTTGTCTA | 329 | XhoI |
| 502-1L | Fwd | CGCGGATCCCATATG-ATGAAACCGCACAAC | 330 | NdeI |
| | Rev | CCCGCTCGAG-TCAGTTGCTCAACACGTC | 331 | XhoI |
| 502-A (His-GST) | Fwd | CGCGGATCCCATATGTAGAGCGCGCTTAAGCA | 332 | BamHI-NdeI |
| | Rev | CCCGCTCGAGAGCTGCATGGCGGCG | 333 | XhoI |
| 503-1L | Fwd | CGCGGATCCCATATG-GCACGGTCGTTATAC | 334 | NdeI |
| | Rev | CCCGCTCGAG-CTACCGCGCATTCCTG | 335 | XhoI |
| 519-1L | Fwd | GCGGCCATATG-GAATTTTCATTATCTTGTT | 336 | NdeI |
| | Rev | GCGGCCTCGAG-TTATTTGGCGGTTTTGCTGC | 337 | XhoI |
| 525-1L | Fwd | GCGGCCATATG-AAGTATGTCCGGTTATTTTC | 338 | NdeI |
| | Rev | GCGGCCTCGAG-TTATCGGCTTGTGCAACGG | 339 | XhoI |
| 529-(His/GST) (MC58) | Fwd | CGCGGATCCGCTAGC-TCCGGCAGCAAAACCGA | 340 | Bam HI-NheI |
| | Rev | GCCAAGCTT-ACGCAGTTCGGAATGGAG | 341 | HindIII |
| 552L | Fwd | GCCGCCATATGTTGAATATTAAACTGAAAACCTTG | 342 | NdeI |
| | Rev | GCGCCCTCGAGTTATTTCTGATGCCTTTTCCC | 343 | XhoI |

-continued

| | | Sequences | SEQ ID NO | Restriction site |
|---|---|---|---|---|
| 556L | Fwd | GCCGCCATATGACAATAAGACCAAACTG | 344 | NdeI |
| | Rev | GCCGCCTCGAGTTAACGGTGCGGACGTTTC | 345 | XhoI |
| 557L | Fwd | CGCGGATCCCATATG-AACAAACTGTTTCTTAC | 346 | NdeI |
| | Rev | CCCGCTCGAG-TCATTCCGCCTTCAGAAA | 347 | XhoI |
| 564ab-(His/GST) (MC58) | Fwd | CGCGGATCCCATATG-CAAGGTATCGTTGCCGACAAATCCCACCT | 348 | BamHI-NdeI |
| | Rev | CCCGCTCGAG-AGCTAATTGTGCTTGGTTTGCAGATAGGAGTT | 349 | XhoI |
| 564abL (MC58) | Fwd | CGCGGATCCCATATG-AACCCGACCCTGTACAAAGTTGTATTTAACAAACATC | 350 | NdeI |
| | Rev | CCCGCTCGAG-TTAAGCTAATTGTGCTTGGTTTGCAGATAGGAGTT | 351 | XhoI |
| 564b-(His/GST) (MC58) | Fwd | CGCGGATCCCATATG-ACGGGAGAAAATCATGCGGTTTCACTTCATG | 352 | BamHI-NdeI |
| | Rev | CCCGCTCGAG-AGCTAATTGTGCTTGGTTTGCAGATAGGAGTT | 353 | XhoI |
| 564c-(His/GST) (MC58) | Fwd | CGCGGATCCCATATG-GTTTCAGACGGCCTATACAACCAACATGTGAAATT | 354 | BamHI-NdeI |
| | Rev | CCCGCTCGAG-GCGGTAACTGCCGCTTGCACTGAATCCGTAA | 355 | XhoI |
| 564bc-(His/GST) (MC58) | Fwd | CGCGGATCCCATATG-ACGGGAGAAAATCATGCGGTTTCACTTCATG | 356 | BamHI-NdeI |
| | Rev | CCCGCTCGAG-GCGGTAACTGCCGCTTGCACTGAATCCGTAA | 357 | XhoI |
| 564d-(His/GST) (MC58) | Fwd | CGCGGATCCCATATG-CAAAGCAAAGTCAAAGCAGACCATGCCTCCGTAA | 358 | BamHI-NdeI |
| | Rev | CCCGCTCGAG-TCTTTTCCTTTCAATTATAACTTTAGTAGTTCAATTTTG GTCCCC | 359 | XhoI |
| 564cd-(His/GST) (MC58) | Fwd | CGCGGATCCCATATG-GTTTCAGACGGCCTATACAACCAACATGTGAAATT | 360 | BamHI-NdeI |
| | Rev | CCCGCTCGAG-TCTTTTCCTTTCAATTATAACTTTAGTAGTTCAATTTTG GTCCCC | 361 | XhoI |
| 570L | Fwd | GCGGCCATATG-ACCCGTTTGACCCGCG | 362 | NdeI |
| | Rev | GCGGCCTCGAG-TCAGCGGGCGTTCATTCTT | 363 | XhoI |
| 576-1L | Fwd | CGCGGATCCCATATG-AACACCATTTTCAAAATC | 364 | NdeI |
| | Rev | CCCGCTCGAG-TTAATTACTTTTTGATGTCG | 365 | XhoI |
| 580L | Fwd | GCGGCCATATG-GATTCGCCCAAGGTCGG | 366 | NdeI |
| | Rev | GCGGCCTCGAG-CTACACTTCCCCCGAAGTGG | 367 | XhoI |
| 583L | Fwd | CGCGGATCCCATATG-ATAGTTGACCAAAGCC | 368 | NdeI |
| | Rev | CCCGCTCGAG-TTATTTTTCCGATTTTTCGG | 369 | XhoI |
| 593 | Fwd | GCGGCCATATG-CTTGAACTGAACGACT | 370 | NdeI |
| | Rev | GCGGCCTCGAG-TCAGCGGAACGCGGACGATT | 371 | XhoI |

-continued

| | | Sequences | SEQ ID NO | Restriction site |
|---|---|---|---|---|
| 650 (His-GST) (MC58) | Fwd | CGCGGATCCCATATGTCCAAACTCAAAACCATCG | 372 | BamHI-NdeI |
| | Rev | CCCGCTCGAGGCTTCCAATCAGTTTGACC | 373 | XhoI |
| 652 | Fwd | GCGGCCATATG-AGCGCAATCGTTGATATTTC | 374 | NdeI |
| | Rev | GCGGCCTCGAG-TTATTTGCCCAGTTGGTAGAATG | 375 | XhoI |
| 664L | Fwd | GCGGCCATATG-GTGATACATCCGACTACTTC | 376 | NdeI |
| | Rev | GCGGCCTCGAG-TCAAAATCGAGTTTTACACCA | 377 | XhoI |
| 726 | Fwd | GCGGCCATATG-ACCATCTATTTCAAAAACGG | 378 | NdeI |
| | Rev | GCGGCCTCGAG-TCAGCCGATGTTTAGCGTCCATT | 379 | XhoI |
| 741-His (MC58) | Fwd | CGCGGATCCCATATG-AGCAGCGGAGGGGGTG | 380 | NdeI |
| | Rev | CCCGCTCGAG-TTGCTTGGCGGCAAGGC | 381 | XhoI |
| ΔG741-His (MC58) | Fwd | CGCGGATCCCATATG-GTCGCCGCCCGACATCG | 382 | NdeI |
| | Rev | CCCGCTCGAG-TTGCTTGGCGGCAAGGC | 383 | XhoI |
| 686-2-(His/GST) (MC58) | Fwd | CGCGGATCCCATATG-GGCGGTTCGAAGGCG | 384 | BamHI-NdeI |
| | Rev | CCCGCTCGAG-TTGAACACTGATGTCTTTTCCGA | 385 | XhoI |
| 719-(His/GST) (MC58) | Fwd | CGCGGATCCGCTAGC-AAACTCTGTTGGTGTTAAC | 386 | BamHI-NheI |
| | Rev | CCCGCTCGAG-TTGACCCGCTCCACGG | 387 | XhoI |
| 730-His (MC58) | Fwd | CGCGCCATATGGCGGACTTGGCGCAAGACCC | 388 | NdeI |
| | Rev | GCGGCCCTCGAGATCTCCTAAACCTGTTTTAACAATGCCG | 389 | XhoI |
| 730A-His (MC58) | Fwd | GCGGGATCCATATGGCGGACTTGGCGCAAGACCC | 390 | NdeI |
| | Rev | GCGGCCTCGAGCTCCATGCTGTTGCCCCAGC | 391 | XhoI |
| 730B-His (MC58) | Fwd | GCGGCCATATGGCGGACTTGGCGCAAGACCC | 392 | NdeI |
| | Rev | GCGGCCTCGAGAAAATCCCCCGCTAACCGAG | 393 | XhoI |
| 741-His (MC58) | Fwd | CGCGGATCCCATATG-AGCAGCGGAGGGGGTG | 394 | NdeI |
| | Rev | CCCGCTCGAG-TTGCTTGGCGGCAAGGC | 395 | XhoI |
| ΔG741-His (MC58) | Fwd | CGCGGATCCCATATG-GTCGCCGCCCGACATCG | 396 | NdeI |
| | Rev | CCCGCTCGAG-TTGCTTGGCGGCAAGGC | 397 | XhoI |
| 743 (His-GST) | Fwd | CGCGGATCCCATATGACGGTGTTGTGCCTGTT | 398 | BamHI-NdeI |
| | Rev | CCCGCTCGAGCTTACGGATCAAATTGACG | 399 | XhoI |
| 757 (His-GST) (MC58) | Fwd | CGCGGATCCCATATGGGCAGCCAATCTGAAGAA | 400 | BamHI-NdeI |
| | Rev | CCCGCTCGAGCTCAGCTTTTGCCGTCAA | 401 | XhoI |

-continued

| | | Sequences | SEQ ID NO | Restriction site |
|---|---|---|---|---|
| 759-His/GST (MC58) | Fwd | CGCGGATCCGCTAGC-TACTCATCCATTGTCCGC | 402 | BamHI-NheI |
| | Rev | CCCGCTCGAG-CCAGTTGTAGCCTATTTTG | 403 | XhoI |
| 759L (MC58) | Fwd | CGCGGATCCGCTAGC-ATGCGCTTCACACACAC | 404 | NheI |
| | Rev | CCCGCTCGAG-TTACCAGTTGTAGCCTATTT | 405 | XhoI |
| 760-His | Fwd | GCCGCCATATGCACAAACGGAAGGTTTGGAA | 406 | NdeI |
| | Rev | GCCGCCTCGAGAAAACTGTAACGCAGGTTTGCCGTC | 407 | XhoI |
| 769-His (MC58) | Fwd | GCGGCCATATGGAAGAAACACCGGCGAACCG | 408 | NdeI |
| | Rev | GCGGCCTCGAGGAACGTTTTATTAAACTCGAC | 409 | XhoI |
| 907L | Fwd | GCGGCCATATG-AGAAAACCGACCGATACCCTA | 410 | NdeI |
| | Rev | GCGGCCTCGAG-TCAACGCCACTGCCAGCGGTTG | 411 | XhoI |
| 911L | Fwd | CGCGGATCCCATATG-AAGAAGAACATATTGGAATTTGGGTCGGACTG | 412 | NdeI |
| | Rev | CCCGCTCGAG-TTATTCGGCGGCTTTTCCGCATTGCCG | 413 | XhoI |
| 911LOmpA | Fwd | GGGAATTCCATATGAAAAAAGACAGCTATCGCGATTGCA GTGGCACTGGCTGGTTTCGCTACCGTAGCGCAGGCCGC TAGC-GCTTTCCGGTGGCCGGGTGC | 414 | NdeI-(NheI) |
| | Rev | CCCGCTCGAG-TTATTCGGCGGCTTTTTCCGCATTGCCG | 415 | XhoI |
| 911LPelB | Fwd | CATGCCATGG-CTTTCCGGCTGGCCGGCGGTGC | 416 | NcoI |
| | Rev | CCCGCTCGAG-TTATTCGGCGGCTTTTTCCGCATTGCCG | 417 | XhoI |
| 913-His/GST (MC58) | Fwd | CGCGGATCCCATATG-TTTGCCGAAAACCCGCC | 418 | BamHI-NdeI |
| | Rev | CCCGCTCGAG-AGGTTGTGTTCCAGGTTG | 419 | XhoI |
| 913L (MC58) | Fwd | CGCGGATCCCATATG-AAAAAAACCCGCCTATG | 420 | NdeI |
| | Rev | CCCGCTCGAG-TTAAGGTTGTGTTCCAGG | 421 | XhoI |
| 919L | Fwd | CGCGGATCCCATATG-AAAAAATACCTATTCCGC | 422 | NdeI |
| | Rev | CCCGCTCGAG-TTACGGGCGGTATTCGG | 423 | XhoI |
| 919 | Fwd | CGCGGATCCCATATG-CAAAGCAAGAGCATCCAAA | 424 | NdeI |
| | Rev | CCCGCTCGAG-TTACGGCGGTATTCGG | 425 | XhoI |
| 919L Orf4 | Fwd | GGGAATTCCATATGAAAAACTTCTTCAAAACCCTTTCCG CCGCCGCGCTAGCGCTCATCCTCGCCGCC-TGCCAAAGCAAGAGCATC | 426 | NdeI-(NheI) |
| | Rev | CCCGCTCGAG-TTACGGGCGGTATTCGGGCTTCATACCG | 427 | XhoI |
| (919)-287fusion | Fwd | CGCGGATCCGTCGAC-TGTGGGGGCGCGGTGGC | 428 | SalI |
| | Rev | CCCGCTCGAG-TCAATCCTGCTCTTTTTTGCC | 429 | XhoI |

| | | Sequences | SEQ ID NO | Restriction site |
|---|---|---|---|---|
| 920-1L | Fwd | GCGGCCATATG-AAGAAAACATTGACACTGC | 430 | NdeI |
| | Rev | GCGGCCTCGAG-TTAATGGTGCGAATGACCGAT | 431 | XhoI |
| 925-His/GST (MC58) *GATE* | Fwd | ggggacaagtacaaaaaagcaggtTGCGGCAAGGATGCCGG | 432 | attB1 |
| | Rev | ggggaccactagtacaagaaagctgggtCTAAAGCAACAATGCCGG | 433 | attB2 |
| 926L | Fwd | CGCGGATCCCATATG-AAACACACCGTATCC | 434 | NdeI |
| | Rev | CCCGCTCGAG-TTATCTCGTGCGCGCC | 435 | XhoI |
| 927.2-(His/GST) (MC58) | Fwd | CGCGGATCCCATATG-AGCCCGGCGCCGATT | 436 | BamHI-NdeI |
| | Rev | CCCGCTCGAG-TTTTTGTGCCGTCAGCG | 437 | XhoI |
| 932-His/GST (MC58) *GATE* | Fwd | ggggacaagtttgtacaaaaaagcaggctTGTTCGTTTGGGGGATTTAAACCAAACCAAATC | 438 | attB1 |
| 935 (MC58) | For | CGCGGATCCCATATGGCGGATGCGCCCGCG | 439 | BamHI-NdeI |
| | Rev | CCCGCTCGAGAAACCGCCAATCCGCC | 440 | XhoI |
| 936-1L | Rev | ggggaccactagtacaagaaagagggtTCATTTTGTTTTTCCTTCTTCTCGAGGCCATT | 441 | attB2 |
| 953L | Fwd | CGCGGATCCCATATG-AAACCCAAACCGCAC | 442 | NdeI |
| | Rev | CCCGCTCGAG-TCAGCGTTGGACGTAGT | 443 | XhoI |
| 953-fa | Fwd | GGGAATTCCATATG-AAAAAAATCATCTTCGCCG | 444 | NdeI |
| | Rev | CCCGCTCGAG-TTATTGTTTGGCTGCCTCGAT | 445 | XhoI |
| 954 (His-GST) (MC58) | Fwd | GGGAATTCCATATG-GCCACTTACAAAGTGGACG | 446 | NdeI |
| | Rev | CGGGGATCC-TTGTTTGGCTGCCTCGATTTG | 447 | BamHI |
| 958-His/GST (MC58) *GATE* | Fwd | CGCGGATCCCATATGCCAAGAACAATCGCAGAAAG | 448 | BamHI-NdeI |
| | Rev | CCCGCTCGAGTTTTTTCGGCAAATTGGCTT | 449 | XhoI |
| 961L | Fwd | ggggacaagtttgtacaaaaaagcaggctGCCGATGCCGTTGCGG | 450 | attB1 |
| | Rev | ggggaccactttgtacaagaaagctgggcTCAGGGTCGTTGTTGCG | 451 | attB2 |
| 961 | Fwd | CGCGGATCCCATATG-AAACACTTTCCATCC | 452 | NdeI |
| | Rev | CCCGCTCGAG-TTACCACTCGTAATTGAC | 453 | XhoI |
| 961 c (His/GST) | Fwd | CGGATCCCATATG-GCCACAAGCGACGAC | 454 | NdeI |
| | Rev | CCCGCTCGAG-TTACCACTCGTAATTGAC | 455 | XhoI |
| | Fwd | CGCGGATCCCATATG-GCCACAAACGACG | 456 | BamHI-NdeI |
| | Rev | CCCGCTCGAG-ACCCACGTTGTAAGGTTG | 457 | XhoI |

-continued

| | | Sequences | SEQ ID NO | Restriction site |
|---|---|---|---|---|
| 961 c-(His/GST) (MC58) | Fwd | CGCGGATCCCATATG-GCCACAAGCGACGACGA | 458 | BamHI-NdeI |
| | Rev | CCCGCTCGAG-ACCCACGTTGTAAGTTG | 459 | XhoI |
| 961 c-L | Fwd | CGCGGATCCCATATG-ATGAAACACTTTCCATCC | 460 | NdeI |
| | Rev | CCCGCTCGAG-TTAACCACGTTGTAAGGT | 461 | XhoI |
| 961 c-L (MC58) | Fwd | CGCGGATCCCATATG-ATGAAACACTTTCCATCC | 462 | NdeI |
| | Rev | CCCGCTCGAG-TTAACCCACGTTGTAAGGT | 463 | XhoI |
| 961 d (His/GST) | Fwd | CGCGGATCCCATATG-GCCACAAACGACG | 464 | BamHI-NdeI |
| | Rev | CCCGCTCGAG-GTCTGACACTGTTTTATCC | 465 | XhoI |
| 961 Δ1-L | Fwd | CGCGGATCCCATATG-ATGAAACACTTTCCATCC | 466 | NdeI |
| | Rev | CCCGCTCGAG-TTATGCTTTGGCGCAAAG | 467 | XhoI |
| fu 961-. . . | Fwd | CGCGGATCCCATATG-GCCACAAAACGACGAC | 468 | NdeI |
| | Rev | CGCGGATCC-CCACTCGTAATTGACGCC | 469 | BamHI |
| fu 961-. . . (MC58) | Fwd | CGCGGATCCCATATG-GCCACAAOCGACGAC | 470 | NdeI |
| | Rev | CGCGGATCC-CCACTCGTAATTGACGCC | 471 | BamHI |
| fu 961 c-. . . | Fwd | CGCGGATCCCATATG-GCCACAAACGACGAC | 472 | NdeI |
| | Rev | CGCGGATCC-ACCCACGTTGTAAGGTTG | 473 | BamHI |
| fu 961 c-L . . . | Fwd | CGCGGATCCCATATG-ATGAAACACTTTCCATCC | 474 | NdeI |
| | Rev | CGCGGATCC-ACCCACTTTGTAAGGTTG | 475 | BamHI |
| fu (961)-741 (MC58)-His | Fwd | CGCGGATCC-GGAGGGGTGGTGTCG | 476 | BamHI |
| | Rev | CCCGCTCGAG-TTGCTTGGCGCAAGGC | 477 | XhoI |
| fu (961)-983-His | Fwd | CGCGGATCC-GGCGGAGGCGGCACTT | 478 | BamHI |
| | Rev | CCCGCTCGAG-GAACCGGTAGCCTACG | 479 | XhoI |
| fu (961)-Orf46.1-His | Fwd | CGCGGATCCGGTGGTGGT-TCAGATTTGGCAAACGATTC | 480 | BamHI |
| | Rev | CCCGCTCGAG-CGTATCATATTTCACGTGC | 481 | XhoI |
| fu (961 c-L)-741 (MC58) | Fwd | CGCGGATCC-GGAGGGGTGGTGTCG | 482 | BamHI |
| | Rev | CCCGCTCGAG-TTATTGCTTGGCGGCAAG | 483 | XhoI |
| fu (961e-L)-983 | Fwd | CGCGGATCC-GGCGGAGGCGGCACTT | 484 | BamHI |
| | Rev | CCCGCTCGAG-TCAGAACCGGTAGCCTAC | 485 | XhoI |
| fu (961c-L)-Orf46.1 | Fwd | CGCGGATCCGGTGGTGGT-TCAGATTTGGCAAACGATTC | 486 | BamHI |
| | Rev | CCCGCTCGAG-TTACGTATCATATTTCACGTGC | 487 | XhoI |

-continued

| | | Sequences | SEQ ID NO | Restriction site |
|---|---|---|---|---|
| 961-(His/GST) (MC58) | Fwd | CGCGGATCCCATATG-GCCACAAGCGACGACG | 488 | BamHI-NdeI |
| | Rev | CCCGCTCGAG-CCACTCGTAATTGACGCC | 489 | XhoI |
| 961 Δ1-His | Fwd | CGCGGATCCCATATG-GCCACAAACGACGAC | 490 | NdeI |
| | Rev | CCCGCTCGAG-TGCTTTGGCGCAAAGTT | 491 | XhoI |
| 961a-(His/GST) | Fwd | CGCGGATCCCATATG-GCCACAAACGACGAC | 492 | BamHI-NdeI |
| | Rev | CCCGCTCGAG-TTTAGCAATATTATCTTTGTTCGTAGC | 493 | XhoI |
| 961b-(His/GST) | Fwd | CGCGGATCCCATATG-AAAGCAAACCGTGCCGA | 494 | BamHI-NdeI |
| | Rev | CCCGCTCGAG-CCACTCGTAATTGACGCC | 495 | XhoI |
| 961-His/GST GATE | Fwd | ggggacaagtttgtacaaaaaagcaggctCGAGCCACAAACGACGACG ATGTTAAAAAAGC | 496 | attB1 |
| | Rev | gggaccactttgtacaagaaagctgggtTTACCACTCGTAATTGACGC CGACATGGTAGG | 497 | attB2 |
| 982 | Fwd | GCGGCCATATG-GCAGCAAAAGACGTACAGTT | 498 | NdeI |
| | Rev | GCGGCCTCGAG-TTACATCATGCCGCCCATACCA | 499 | XhoI |
| 983-His (2996) | Fwd | CGCGGATCCGCTAGC-TTAGGCGGCGGCGGAG | 500 | NheI |
| | Rev | CCCGCTCGAG-GAACCGGTAGCCTACG | 501 | XhoI |
| ΔG983-His (2996) | Fwd | CCCCTAGCTAGC-ACTTCTGCGCCCGACTT | 502 | NheI |
| | Rev | CCCGCTCGAG-GAACCGGTAGCCTACG | 503 | XhoI |
| 983-His | Fwd | CGCGGATCCGCTAGC-TTAGGCGGCGGCGGAG | 504 | NheI |
| | Rev | CCCGCTCGAG-GAACCGGTAGCCTACG | 505 | XhoI |
| ΔG983-His | Fwd | CGCGGATCCGCTAGC-ACTTCTGCGCCCGACTT | 506 | NheI |
| | Rev | CCCGCTCGAG-GAACCGGTAGCCTACG | 507 | XhoI |
| 983L | Fwd | CGCGGATCCGCTAGC-CGAACGACCCCCAACCTTCCCTACAAAAACTTTCAA | 508 | NheI |
| | Rev | CCCGCTCGAG-TCAGAACCGACGTGCCAAGCCGTTC | 509 | XhoI |
| 987-His (MC58) | Fwd | GCGCCATATGCCCCACTGAAGAACGACG | 510 | NdeI |
| | Rev | GCCGCCTCGAGTAATAAACCTTCTATGGCGAGCAG | 511 | XhoI |
| 989-(His/GST) (MC58) | Fwd | CGCGGATCCCATATG-TCCGTCCACGCATCCG | 512 | BamHI-NdeI |
| | Rev | CCCGCTCGAG-TTTGAATTTGTAGGTGTATTG | 513 | XhoI |
| 989L (MC58) | Fwd | CGCGGATCCCATATG-ACCCCTTCCGCACT | 514 | NdeI |
| | Rev | CCCGCTCGAG-TTATTTGAATTTGTAGGTGTAT | 515 | XhoI |
| CrgA-His (MC58) | Fwd | CGCGGATCCCATATG-AAAACCAATTCAGAAGAA | 513 | NdeI |
| | Rev | CCCGCTCGAG-TCCAGAGATTGTTTCC | 517 | XhoI |

| | | Sequences | SEQ ID NO | Restriction site |
|---|---|---|---|---|
| PilC1-ES (MC58) | Fwd | GATGCCCGAAGGGCGGG | 518 | |
| | Rev | GCCCAAGCTT-TCAGAAGAAGACTTCACGC | 519 | |
| PilC1-His (MC58) | Fwd | CGCGGATCCCATATG-CAAACCCATAAATACGCTATT | 520 | NdeI |
| | Rev | GCCCAAGCTT-GAAGAAGACTTCACGCCAG | 521 | HindIII |
| Δ1PilC1-His (MC58) | Fwd | CGCGGATCCCATATG-GTCTTTTTCGACAATACCGA | 522 | NdeI |
| | Rev | GCCCAAGCTT- | 523 | HindIII |
| PilC1L (MC58) | Fwd | CGCGGATCCCATATG-AATAAAACTTTAAAAGGCGG | 524 | NdeI |
| | Rev | GCCCAAGCTT-TCAGAAGAAGACTTCACGC | 525 | HindIII |
| ΔGTbp2-His (MC58) | Fwd | CGCGAATCCCATATG-TTCGATCTTGATTCTGTCGA | 526 | NdeI |
| | Rev | CCCGCTCGAG-TCGCACAGGCTGTTGGCG | 527 | XhoI |
| Tbp2-His (MC58) | Fwd | CGCGGATCCCATATG-TTGGGCGGAGGCGGCAG | 528 | NdeI |
| | Rev | CCCGCTCGAG-TCGCACAGGCTGTTGGCG | 529 | XhoI |
| Tbp2-His (MC58) | Fwd | CGCGAATCCCATATG-TTGGGCGGAGGCGGCAG | 530 | NdeI |
| | Rev | CCCGCTCGAG-TCGCACAGGCTGTTGGCG | 531 | XhoI |
| NMB0109-(His/GST) (MC58) | Fwd | CGCGGATCCCATATG-GCAAATTTGGAGGTGCGC | 532 | BamHI-NdeI |
| | Rev | CCCGCTCGAG-TTCGAGCGGTTGAAGC | 533 | XhoI |
| NMB0109L (MC58) | Fwd | CGCGGATCCCATATG-CAACGTCGTATTATAACCC | 534 | NdeI |
| | Rev | CCCGCTCGAG-TTATTCGGAGCGGTTGAAG | 535 | XhoI |
| NMB0207-(His/GST) (MC58) | Fwd | CGCGGATCCCATATG-GGCATCAAAGTCGCCATCAACGGCTAC | 536 | BamHI-NdeI |
| | Rev | CCCGCTCGAG-TTTGAGCGGGCGCACTTCAAGTCCG | 537 | XhoI |
| NMB0462-(His/GST) (MC58) | Fwd | CGCGGATCCCATATG-GGCGGCAGCGAAAAAAAC | 538 | BamHI-NdeI |
| | Rev | CCCGCTCGAG-GTTGGTGCCGACTTTGAT | 539 | XhoI |
| NMB0623-(His/GST) (MC58) | Fwd | CGCGGATCCCATATG-GGCGGCGGAAGCGATA | 540 | BamHI-NdeI |
| | Rev | CCCGCTCGAG-TTTGCCCGCTTTGAGCC | 541 | XhoI |
| NMB0625 (His-GST) (MC58) | Fwd | CGCGGATCCCATATGGGCAAATCCGAAAATACG | 542 | BamHI-NdeI |
| | Rev | CCCGCTCGAGCATCCCGTACTGTTTCG | 543 | XhoI |
| NMB0634 (His/GST) (MC58) | Fwd | ggggacaagtttgtacaaaaaagcaggctCCGACATTACCGTGTACAAC GGCCAACAAGAA | 544 | attB1 |
| | Rev | ggggaccactagtacaagaaagctggtCTTATTTCATACCGGCTTGCT CAAGCAGCCGG | 545 | attB2 |

-continued

| | | Sequences | SEQ ID NO | Restriction site |
|---|---|---|---|---|
| NMB0776-His/GST (MC58) | Fwd | ggggacaagtttgtacaaaaaagcaggctGATACGGTGTTTTCCTGTAA AACGACAACAA | 546 | attB1 |
| | Rev | ggggaccactttgtacaagaaagcggtCTAGGAAAAATCGTCATCGT TGAAATTCGCC | 547 | attB2 |
| NMB1115-His/GST (MC58) | Fwd | ggggacaagtttgtacaaaaaagcaggctATGCACCCCATCGAAACC | 548 | attB1 |
| | Rev | ggggaccactttgtacaagaaagcggtCTAGTCTTGCAGTGCCTC | 549 | attB2 |
| NMB1343- (His/GST) (MC58) | Fwd | CGCGGATCCCATATG-GGAAATTCTTATATAGAGGCATTAG | 550 | BamHI-NdeI |
| | Rev | CCCGCTCGAG-GTTAATTTCTATCAACTCTTTAGCAATAAT | 551 | XhoI |
| NMB1369 (His-GST (MC58) | Fwd | CGCGGATCCCATATGGCCTGCCAAGACGACA | 552 | BamHI-NdeI |
| | Rev | CCCGCTCGAGCCGCCTCCTGCCGAAA | 553 | XhoI |
| NMB1551 (His-GST) (MC58) | Fwd | CGCGGATCCCATATGGCAGAGATCTGTTGATAA | 554 | BamHI-NdeI |
| | Rev | CCCGCTCGAGCGGTTTTCCGCCCAATG | 555 | XhoI |
| NMB1899 (His-GST) (MC58) | Fwd | CGCGGATCCCATATGCAGCCGATACGGTC | 556 | BamHI-NdeI |
| | Rev | CCCGCTCGAGAATCACTTCCAACACAAAT | 557 | XhoI |
| NMB2050- (His/GST) (MC58) | Fwd | CGCGGATCCCATATG-TGGTTGCTGATGAAGGGC | 558 | BamHI-NdeI |
| | Rev | CCCGCTCGAG-GACTGCTTCATCTTCTGC | 559 | XhoI |
| NMB2050L | Fwd | CGCGGATCCCATATG-GAACTGATGACTGTTTTGC | 560 | NdeI |
| | Rev | CCCGCTCGAG-TCAGACTGCTTCATCTTCT | 561 | XhoI |
| NMB2159- (His/GST) (MC58) | Fwd | CGCGGATCCCATATG-AGCATTAAAGTAGCGATTAACGGTTTCGGC | 562 | BamHI-NdeI |
| | Rev | CCCGCTCGAG-GATTTTCCTGCGAAGTATTCCAAAGTGCG | 563 | XhoI |
| fu-ΔG287-His | Fwd | CGCGGATCCGCTAGC-CCCGATGTTAAATCGGC | 564 | NheI |
| | Rev | CGGGGATCC-ATCCTGCTCTTTTTTGCCGG | 565 | BamHI |
| fu-(ΔG287)-919-His | Fwd | CGCGGATCCGGTGGTGGT-CAAAGCAAGAGCATCCAAACC | 566 | BamHI |
| | Rev | CCCAAGCTT-TTCGGGCGGGTATTCGGGCTTC | 567 | HindIII |
| fu-(ΔG287)-953-His | Fwd | CGCGGATCCGGTGGTGGT-GCCACCTACAAAGTGGAC | 568 | BamHI |
| | Rev | GCCCAAGCTT-TTGTTTGGCTGCCTCGAT | 569 | HindIII |
| fu-(ΔG287)-961-His | Fwd | CGCGGATCCGGTGGTGGT-ACAAGCGACCACG | 570 | BamHI |
| | Rev | GCCCAAGCTT-CCACTCGTAATTGACGCC | 571 | HindIII |
| fu-(ΔG287)-Orf46.1-His | Fwd | CGCGGATCCGGTGGTGGT-TCAGATTTGGCAAACGATTC | 572 | BamHI |
| | Rev | CCCAAGCTT-CGTATCATATTTCACGTGC | 573 | HindIII |

-continued

| | | Sequences | SEQ ID NO | Restriction site |
|---|---|---|---|---|
| fu-(ΔG287-919)-Orf46.1-His | Fwd | CCCAAGCTTGGTGGTGGTGGTGGT-TCAGATTTGGCAAACGATTC | 574 | HindIII |
| | Rev | CCCGCTCGAG-CGTATCATATTTCACGTGC | 575 | XhoI |
| fu-(ΔG287-Orf46.1)-919-His | Fwd | CCCAAGCTTGGTGGTGGTGGTGGT-CAAAGCAAGAGCATCCAAACC | 576 | HindII |
| | Rev | CCCGCTCGAG-CGGGCCGGTATTCGGGCTT | 577 | XhoI |
| fu ΔG287 (394.98) | Fwd | CGCGGATCCGCTAGC-CCCGATGTTAAATCGGC | 578 | NheI |
| | Rev | CGGGGATCC-ATCCTGCTCTTTTTGCCGG | 579 | BamHI |
| fu Orf1-(Orf46.1)-His | Fwd | CGCGGATCCGCTAGC-GGACACACTTATTTCGGCATC | 580 | NheI |
| | Rev | CGCGGATCC-CCAGCGGTAGCCTAATTGAT | 581 | |
| fu (Orf1)-Orf46.1-His | Fwd | CGCGGATCCGGTGGTGGT-TCAGATTTGGCAAACGATTC | 582 | BamHI |
| | Rev | CCCAAGCTT-CGTATCATATTTCACGTGC | 583 | HindIII |
| fu (919)-Orf46.1-His | Fwd1 | GCGGCGTCGACGGTGGCGGAGGCACTGGATCCTCAG | 584 | SalI |
| | Fwd2 | GGAGGCACTGGATCCTCAGATTTGGCAAACGATTC | 585 | |
| | Rev | CCCGCTCGAG-CGTATCATATTTCACGTGC | 586 | XhoI |
| Fu orf46- | Fwd | GGAATTCCATATGTCAGATTTGGCAAACGATTC | 587 | NdeI |
| | Rev | CGCGGATCCGTATCATATTTCACGTGC | 588 | BamHI |
| Fu (orf46)-287-His | Fwd | CGGGGATCCGGGGCGGCGGTGGCG | 589 | BamHI |
| | Rev | CCCAAGCTTATCCTGCTCTTTTTGCCGG | 590 | HindIII |
| Fu (orf46)-919-His | Fwd | CGCGGATCCGGTGGTGGTCAAAGCAAGAGCATCCAAACC | 591 | BamHI |
| | Rev | CCCAAGCTTCGGGCGGTATTCGGGCTTC | 592 | HindIII |
| Fu (orf46-919)-287-His | Fwd | CCCCAAGCTTGGGGCGGCGGTGGCG | 593 | HindIII |
| | Rev | CCCGCTCGAGATCCTGCTCTTTTTGCCGGC | 594 | XhoI |
| Fu (orf46-287)-919-His | Fwd | CCCAAGCTTGGTGGTGGTGGTGGTCAAAGCAAGAGCATCCAAACC | 595 | HindIII |
| | Rev | CCCGCTCGAGCGGGCCGGTATTCGGGCTT | 596 | XhoI |
| (ΔG741)-961c-His | Fwd1 | GGAGGCACTGGATCCGCAGCCACAAACGACGACGA | 597 | XhoI |
| | Fwd2 | GCGGCCTCGAG-GGTGCGGAGGCACTGGATCCGCGAG | 598 | |
| | Rev | CCCGCTCGAG-ACCCAGCTTGTAAGGTTG | 599 | XhoI |
| (ΔG741)-961-His | Fwd1 | GGAGGCACTGGATCCGCAGCCACAAACGACGACGA | 600 | XhoI |
| | Fwd2 | GCGGCCTCGAG-GGTGCGGAGGCACTGGATCCGCGAG | 601 | |
| | Rev | CCCGCTCGAG-CCACTCGTAATTGACGCC | 602 | XhoI |
| (ΔG741)-983-His | Fwd | GCGGCCTCGAG-GGATCCGGCGGCCGAGGCGGCACTTCTCCG | 603 | XhoI |
| | Rev | CCCGCTCGAG-GAACCGGTAGCCTACG | 604 | XhoI |

-continued

| | | Sequences | SEQ ID NO | Restriction site |
|---|---|---|---|---|
| (ΔG741)-orf46.1-His | Fwd1 | GGAGGCACTGGATCCTCAGATTTGGCAAACGATTC | 605 | SalI |
| | Fwd2 | GCGGCGTCGACGGTGGCGGAGGCACTGGATCCTCAGA | 606 | |
| | Rev | CCCGCTCGAG-CGTATCATATTTCACGTGC | 607 | XhoI |
| (ΔG983)-741 (MC58)-His | Fwd | GCGGCCTTCGAG-GGATCCGAGGGGGTGGTGTCGCC | 608 | XhoI |
| | Rev | CCCGCTCGAG-TTGCTTGGCGGCAAG | 609 | XhoI |
| (ΔG983)-961c-His | Fwd1 | GGAGGCACTGGATCCGCCAGCCACAAACGACGACGA | 610 | XhoI |
| | Fwd2 | GCGGCCTCGAG-GGTGGCGGAGGCACTGGATCCGCAG | 611 | |
| | Rev | CCCGCTCGAG-ACCCAGCTTGTAAGGTTG | 612 | XhoI |
| (ΔG983)-961-His | Fwd1 | GGAGGCACTGGATCCGCCAGCCACAAACGACGACGA | 613 | XhoI |
| | Fwd2 | GCGGCCTCGAG-GGTGGCGGAGGCACTGGATCCGCAG | 614 | |
| | Rev | CCCGCTCGAG-CCACTCGTAATTGACGCC | 615 | XhoI |
| (ΔG983)-orf46.1-His | Fwd1 | GGAGGCACTGGATCCTCAGATTTGGCAAACGATTC | 616 | SalI |
| | Fwd2 | GCGGCGTCGACGGTGGCGGAGGCACTGGATCCTCAGA | 617 | |
| | Rev | CCCGCTCGAG-CGTATCATATTTCACGTGC | 618 | XhoI |

* This primer was used as a Reverse primer for all the C terminal fusions of 287 to the His-tag
$ Forward primers used in combination with the 287-His Reverse primer.
NB-All PCR reactions use strain 2996 unless otherwise specified (e.g. strain MC58)

In all constructs starting with an ATG not followed by a unique NheI site, the ATG codon is part of the NdeI site used for cloning. The constructs made using NheI as a cloning site at the 5' end (e.g. all those containing 287 at the N-terminus) have two additional codons (GCT AGC) fused to the coding sequence of the antigen.

Preparation of Chromosomal DNA Templates

*N. meningitidis* strains 2996, MC58, 394.98, 1000 and BZ232 (and others) were grown to exponential phase in 100 ml of GC medium, harvested by centrifugation, and resuspended in 5 ml buffer (20% w/v sucrose, 50 mM Tris-HCl, 50 mM EDTA, pH8). After 10 minutes incubation on ice, the bacteria were lysed by adding 10 ml of lysis solution (50 mM NaCl, 1% Na-Sarkosyl, 50 µg/ml Proteinase K), and the suspension incubated at 37° C. for 2 hours. Two phenol extractions (equilibrated to pH 8) and one $CHCl_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading $OD_{260}$.

PCR Amplification

The standard PCR protocol was as follows: 200 ng of genomic DNA from 2996, MC581000, or BZ232 strains or 10 ng of plasmid DNA preparation of recombinant clones were used as template in the presence of 40 1M of each oligonucleotide primer, 400-800 M dNTPs solution, 1×PCR buffer (including 1.5 mM $MgCl_2$), 2.5 units TaqI DNA polymerase (using Perkin-Elmer AMPLITAQ® DNA Polymerase kit, Boerhingher Mannheim EXPAND™ Long Template kit).

After a preliminary 3 minute incubation of the whole mix at 95° C., each sample underwent a two-step amplification: the first 5 cycles were performed using the hybridisation temperature that excluded the restriction enzyme tail of the primer ($T_{m1}$). This was followed by 30 cycles according to the hybridisation temperature calculated for the whole length oligos ($T_{m2}$). Elongation times, performed at 68° C. or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

Digestion of PCR Fragments and of the Cloning Vectors

The purified DNA corresponding to the amplified fragment was digested with the appropriate restriction enzymes for cloning into pET-21b+, pET22b+ or pET-24b+. Digested fragments were purified using the QIAquick PCR purification kit (following the manufacturer's instructions) and eluted with either $H_2O$ or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

Cloning

The fragments corresponding to each gene, previously digested and purified, were ligated into pET21b+, pET22b+ or pET-24b+. A molar ratio of 3:1 fragment/vector was used with T4 DNA ligase in the ligation buffer supplied by the manufacturer.

Recombinant plasmid was transformed into competent *E. coli* DH5 or HB101 by incubating the ligase reaction solution and bacteria for 40 minutes on ice, then at 37° C. for 3 minutes. This was followed by the addition of 800 µl LB broth and incubation at 37° C. for 20 minutes. The cells were centrifuged at maximum speed in an Eppendorf microfuge, resuspended in approximately 200 µl of the supernatant and plated onto LB ampicillin (100 mg/ml) agar.

Screening for recombinant clones was performed by growing randomly selected colonies overnight at 37° C. in 4.0 ml of LB broth+100 µg/ml ampicillin. Cells were pelleted and plasmid DNA extracted using the Qiagen QIAprep Spin Miniprep Kit, following the manufacturer's instructions. Approximately 1 µg of each individual miniprep was digested with the appropriate restriction enzymes and the digest loaded onto a 1-1.5% agarose gel (depending on the expected insert size), in parallel with the molecular weight marker (1 kb DNA Ladder, GIBCO®). Positive clones were selected on the basis of the size of insert.

Expression

After cloning each gene into the expression vector, recombinant plasmids were transformed into *E. coli* strains suitable for expression of the recombinant protein. 1 µl of each construct was used to transform *E. coli* BL21-DE3 as described above. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, to give an $OD_{600}$ between 0.1 and 0.2. The flasks were incubated at 30° C. or at 37° C. in a gyratory water bath shaker until $OD_{600}$ indicated exponential growth suitable for induction of expression (0.4-0.8 OD). Protein expression was induced by addition of 1.0 mM IPTG. After 3 hours incubation at 30° C. or 37° C. the $OD_{600}$ was measured and expression examined. 1.0 ml of each sample was centrifuged in a microfuge, the pellet resuspended in PBS and analysed by SDS-PAGE and Coomassie Blue staining.

Gateway Cloning and Expression

Sequences labelled GATE were cloned and expressed using the GATEWAY Cloning Technology (GIBCO®-BRL). Recombinational cloning (RC) is based on the recombination reactions that mediate the integration and excision of phage into and from the *E. coli* genome, respectively. The integration involves recombination of the attP site of the phage DNA within the attB site located in the bacterial genome (BP reaction) and generates an integrated phage genome flanked by attL and attR sites. The excision recombines attL and attR sites back to attP and attB sites (LR reaction). The integration reaction requires two enzymes [the phage protein Integrase (Int) and the bacterial protein integration host factor (IHF)] (BP clonase). The excision reaction requires Int, IHF, and an additional phage enzyme, Excisionase (Xis) (LR clonase). Artificial derivatives of the 25-bp bacterial attB recombination site, referred to as B1 and B2, were added to the 5' end of the primers used in PCR reactions to amplify Neisserial ORFs. The resulting products were BP cloned into a "Donor vector" containing complementary derivatives of the phage attP recombination site (P1 and P2) using BP clonase. The resulting "Entry clones" contain ORFs flanked by derivatives of the attL site (L1 and L2) and were subcloned into expression "destination vectors" which contain derivatives of the attL-compatible attR sites (R1 and R2) using LR clonase. This resulted in "expression clones" in which ORFs are flanked by B1 and B2 and fused in frame to the GST or His N terminal tags.

The *E. coli* strain used for GATEWAY expression is BL21-SI. Cells of this strain are induced for expression of the T7 RNA polymerase by growth in medium containing salt (0.3 M NaCl).

Note that this system gives N-terminus His tags.

Preparation of Membrane Proteins.

Fractions composed principally of either inner, outer or total membrane were isolated in order to obtain recombinant proteins expressed with membrane-localisation leader sequences. The method for preparation of membrane fractions, enriched for recombinant proteins, was adapted from Filip et. al. [*J. Bact.* (1973) 115:717-722] and Davies et. al. [*J.*

*Immunol. Meth.* (1990) 143:215-225]. Single colonies harbouring the plasmid of interest were grown overnight at 37° C. in 20 ml of LB/Amp (100 µg/ml) liquid culture. Bacteria were diluted 1:30 in 1.0 L of fresh medium and grown at either 30° C. or 37° C. until the $OD_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. and resuspended in 20 ml of 20 mM Tris-HCl (pH 7.5) and complete protease inhibitors (Boehringer-Mannheim). All subsequent procedures were performed at 4° C. or on ice.

Cells were disrupted by sonication using a Branson SONIFIER® 450 (ultrasonic cell disruption/homogenizer) and centrifuged at 5000 g for 20 min to sediment unbroken cells and inclusion bodies. The supernatant, containing membranes and cellular debris, was centrifuged at 50000 g (Beckman Ti50, 29000 rpm) for 75 min, washed with 20 mM Bis-tris propane (pH 6.5), 1.0 M NaCl, 10% (v/v) glycerol and sedimented again at 50000 g for 75 minutes. The pellet was resuspended in 20 mM Tris-HCl (pH 7.5), 2.0% (v/v) Sarkosyl, complete protease inhibitor (1.0 mM EDTA, final concentration) and incubated for 20 minutes to dissolve inner membrane. Cellular debris was pelleted by centrifugation at 5000 g for 10 min and the supernatant centrifuged at 75000 g for 75 minutes (Beckman Ti50, 33000 rpm). Proteins 008L and 519L were found in the supernatant suggesting inner membrane localisation. For these proteins both inner and total membrane fractions (washed with NaCl as above) were used to immunise mice. Outer membrane vesicles obtained from the 75000 g pellet were washed with 20 mM Tris-HCl (pH 7.5) and centrifuged at 75000 g for 75 minutes or overnight. The OMV was finally resuspended in 500 µl of 20 mM Tris-HCl (pH 7.5), 10% v/v glycerol. Orf1L and Orf40L were both localised and enriched in the outer membrane fraction which was used to immunise mice. Protein concentration was estimated by standard Bradford Assay (Bio-Rad), while protein concentration of inner membrane fraction was determined with the DC protein assay (Bio-Rad). Various fractions from the isolation procedure were assayed by SDS-PAGE.

Purification of his-Tagged Proteins

Various forms of 287 were cloned from strains 2996 and MC58. They were constructed with a C-terminus His-tagged fusion and included a mature form (aa 18-427), constructs with deletions (Δ1, Δ2, Δ3 and Δ4) and clones composed of either B or C domains. For each clone purified as a His-fusion, a single colony was streaked and grown overnight at 37° C. on a LB/Amp (100 µg/ml) agar plate. An isolated colony from this plate was inoculated into 20 ml of LB/Amp (100 µg/ml) liquid medium and grown overnight at 37° C. with shaking. The overnight culture was diluted 1:30 into 1.0 L LB/Amp (100 µg/ml) liquid medium and allowed to grow at the optimal temperature (30 or 37° C.) until the $OD_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of either (i) cold buffer A (300 mM NaCl, 50 mM phosphate buffer, 10 mM imidazole, pH 8.0) for soluble proteins or (ii) buffer B (10 mM Tris-HCl, 100 mM phosphate buffer, pH 8.8 and, optionally, 8M urea) for insoluble proteins. Proteins purified in a soluble form included 287-His, Δ1, Δ2, Δ3 and Δ4287-His, Δ4287MC58-His, 287c-His and 287cMC58-His. Protein 287bMC58-His was insoluble and purified accordingly. Cells were disrupted by sonication on ice four times for 30 sec at 40 W using a Branson SONIFIER® 450 (ultrasonic cell disruption/homogenizer) and centrifuged at 13000×g for 30 min at 4° C. For insoluble proteins, pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants for both soluble and insoluble preparations were mixed with 150 µl $Ni^{2+}$-resin (previously equilibrated with either buffer A or buffer B, as appropriate) and incubated at room temperature with gentle agitation for 30 min. The resin was Chelating SEPHAROSE™ Fast Flow (IMAC medium, Pharmacia), prepared according to the manufacturer's protocol. The batch-wise preparation was centrifuged at 700 g for 5 min at 4° C. and the supernatant discarded. The resin was washed twice (batch-wise) with 10 ml buffer A or B for 10 min, resuspended in 1.0 ml buffer A or B and loaded onto a disposable column. The resin continued to be washed with either (i) buffer A at 4° C. or (ii) buffer B at room temperature, until the $OD_{280}$ of the flow-through reached 0.02-0.01. The resin was further washed with either (i) cold buffer C (300 mM NaCl, 50 mM phosphate buffer, 20 mM imidazole, pH 8.0) or (ii) buffer D (10 mM Tris-HCl, 100 mM phosphate buffer, pH 6.3 and, optionally, 8M urea) until $OD_{280}$ of the flow-through reached 0.02-0.01. The His-fusion protein was eluted by addition of 700 µl of either (i) cold elution buffer A (300 mM NaCl, 50 mM phosphate buffer, 250 mM imidazole, pH 8.0) or (ii) elution buffer B (10 mM Tris-HCl, 100 mM phosphate buffer, pH 4.5 and, optionally, 8M urea) and fractions collected until the $OD_{280}$ indicated all the recombinant protein was obtained. 20 µl aliquots of each elution fraction were analysed by SDS-PAGE. Protein concentrations were estimated using the Bradford assay.

Renaturation of Denatured his-Fusion Proteins.

Denaturation was required to solubilize 287bMC8, so a renaturation step was employed prior to immunisation. Glycerol was added to the denatured fractions obtained above to give a final concentration of 10% v/v. The proteins were diluted to 200 µg/ml using dialysis buffer I (10% v/v glycerol, 0.5M arginine, 50 mM phosphate buffer, 5.0 mM reduced glutathione, 0.5 mM oxidised glutathione, 2.0M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

$$\text{Protein(mg/ml)} = (1.55 \times OD_{280}) - (0.76 \times OD_{260})$$

Amino Acid Sequence Analysis.

Automated sequence analysis of the $NH_2$-terminus of proteins was performed on a Beckman sequencer (LF 3000) equipped with an on-line phenylthiohydantoin-amino acid analyser (System Gold) according to the manufacturer's recommendations.

Immunization

Balb/C mice were immunized with antigens on days 0, 21 and 35 and sera analyzed at day 49.

Sera Analysis—ELISA

The acapsulated MenB M7 and the capsulated strains were plated on chocolate agar plates and incubated overnight at 37° C. with 5% $CO_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 4000 rpm. The supernatant was discarded and bacteria were washed twice with PBS, resuspended in PBS containing 0.025% formaldehyde, and incubated for 1 hour at 37° C. and then overnight at 4° C. with stirring. 100 µl bacterial cells were added to each well of a 96 well Greiner plate and incubated overnight at 4° C. The wells were then washed three times with PBT washing buffer (0.1% TWEEN®-20 (Polysorbate 20, Sigma Aldrich) in PBS). 200 µl of saturation buffer (2.7% polyvinylpyrrolidone 10 in water) was added to each well and the plates incubated for 2 hours at 37° C. Wells were washed three times with PBT. 200 µl of diluted sera (Dilution buffer: 1% BSA, 0.1% TWEEN®-20 (Polysorbate 20, Sigma Aldrich), 0.1% $NaN_3$ in PBS) were added to each well and the plates incubated for 2 hours at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100µl of substrate buffer for HRP (25 ml of citrate buffer pH5, 10 mg of O-phenildiamine and 10 µl of $H_2SO_2$) were added to each well and the plates were left at room temperature for 20 minutes. 100 µl 12.5% $H_2SO_4$ was added to each well and $OD_{490}$ was followed. The ELISA titers were calculated arbitrarily as the dilution of sera which gave an $OD_{490}$ value of 0.4 above the level of preimmune sera. The ELISA was considered positive when the dilution of sera with $OD_{490}$ of 0.4 was higher than 1:400.

Sera Analysis—FACS Scan Bacteria Binding Assay

The acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA in PBS, 0.4% $NaN_3$) and centrifuged for 5 minutes at 4000 rpm. Cells were resuspended in blocking buffer to reach $OD_{620}$ of 0.05. 100 µl bacterial cells were added to each well of a COSTAR®96 well plate. 100 µl of diluted (1:100, 1:200, 1:400) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated $F(ab)_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan (Laser Power 15 mW) setting were: FL2 on; FSC-H threshold: 92; FSC PMT Voltage: E 01; SSC PMT: 474; Amp. Gains 6.1; FL-2 PMT: 586; compensation values: 0.

Sera Analysis—Bactericidal Assay

*N. meningitidis* strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 10 mM $MgCl_2$, 10 mM $CaCl_2$ and 0.5% (w/v) BSA (assay buffer) at the working dilution of $10^5$ CFU/ml. The total volume of the final reaction mixture was 50 µl with 25 µl of serial two fold dilution of test serum, 12.5 µl of bacteria at the working dilution, 12.5 µl of baby rabbit complement (final concentration 25%).

Controls included bacteria incubated with complement serum, immune sera incubated with bacteria and with complement inactivated by heating at 56° C. for 30'. Immediately after the addition of the baby rabbit complement, 10 µl of the controls were plated on Mueller-Hinton agar plates using the tilt method (time 0). The 96-wells plate was incubated for 1 hour at 37° C. with rotation. 7 µl of each sample were plated on Mueller-Hinton agar plates as spots, whereas 10 µl of the controls were plated on Mueller-Hinton agar plates using the tilt method (time 1). Agar plates were incubated for 18 hours at 37 degrees and the colonies corresponding to time 0 and time 1 were counted.

Sera Analysis—Western Blots

Purified proteins (500 ng/lane), outer membrane vesicles (5 µg) and total cell extracts (25 µg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: *N. meningitidis* strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson SONIFIER®3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilise the inner membranes. The suspension was centrifuged at 10000 g for 10 minutes to remove aggregates, the supernatant was further centrifuged at 50000 g for 3 hours. The pellet, containing the outer membranes was washed in PBS and resuspended in the same buffer. Protein concentration was measured by the D.C. Bio-Rad Protein assay (Modified Lowry method), using BSA as a standard.

Total cell extracts were prepared as follows: *N. meningitidis* strain 2996 was grown overnight on a GC plate, harvested with a loop and resuspended in 1 ml of 20 mM Tris-HCl. Heat inactivation was performed at 56° C. for 30 minutes.

961 Domain Studies

Cellular Fractions Preparation Total lysate, periplasm, supernatant and OMV of *E. coli* clones expressing different domains of 961 were prepared using bacteria from over-night cultures or after 3 hours induction with IPTG. Briefly, the periplasm were obtained suspending bacteria in saccarose 25% and Tris 50 mM (pH 8) with polimixine 100 µg/ml. After 1 hr at room temperature bacteria were centrifuged at 13000 rpm for 15 min and the supernatant were collected. The culture supernatant were filtered with 0.2 µm and precipitated with TCA 50% in ice for two hours. After centrifugation (30 min at 13000 rp) pellets were rinsed twice with ethanol 70% and suspended in PBS. The OMV preparation was performed as previously described. Each cellular fraction were analyzed in SDS-PAGE or in Western Blot using the polyclonal antiserum raised against GST-961.

Adhesion Assay Chang epithelial cells (Wong-Kilbourne derivative, clone 1-5c-4, human conjunctiva) were maintained in DMEM (GIBCO®) supplemented with 10% heat-inactivated FCS, 15 mM L-glutamine and antibiotics.

For the adherence assay, sub-confluent culture of Chang epithelial cells were rinsed with PBS and treated with trypsin-EDTA (GIBCO®), to release them from the plastic support. The cells were then suspended in PBS, counted and dilute in PBS to $5 \times 10^5$ cells/ml.

Bacteria from over-night cultures or after induction with IPTG, were pelleted and washed twice with PBS by centrifuging at 13000 for 5 min. Approximately $2-3 \times 10^8$ (cfu) were incubated with 0.5 mg/ml FITC (Sigma) in 1 ml buffer containing 50 mM NaHCO$_3$ and 100 mM NaCl pH 8, for 30 min at room temperature in the dark. FITC-labeled bacteria were wash 2-3 times and suspended in PBS at $1-1.5 \times 10^9$/ml. 200 μl of this suspension ($2-3 \times 10^8$) were incubated with 200 μl ($1 \times 10^5$) epithelial cells for 30 min a 37° C. Cells were than centrifuged at 2000 rpm for 5 min to remove non-adherent bacteria, suspended in 200 μl of PBS, transferred to FACScan tubes and read

We claim:

1. A method of expressing an *E. coli* lipidated protein comprising
   a) providing an *E. coli* host cell containing a nucleic acid encoding a heterologous leader peptide operably linked to a coding sequence for the protein, wherein the protein comprises i) a sequence having greater than 80% sequence identity to SEQ ID NO: 634; or ii) a fragment of at least 14 consecutive amino acids from SEQ ID NO: 634, wherein the *E. coli* host cell is capable of lipidating the protein and the heterologous leader peptide directs lipidation in the *E. coli* host cell;
   b) expressing of the protein under conditions where the protein is lipidated at an N-terminal cysteine.

2. The method of claim 1, wherein the protein comprises (i).

3. The method of claim 2, wherein the sequence has greater than 90% sequence identity to SEQ ID NO: 634.

4. The method of claim 2 further comprising c) isolating the *E. coli* lipidated protein from the *E. coli* host cell.

5. The method of claim 4 further comprising d) formulating an immunogenic composition with the *E. coli* lipidated protein isolated from the *E. coli* host cell.

6. The method of claim 5, wherein the immunogenic composition further comprises an alum adjuvant.

7. The method of claim 1, wherein the protein comprises (ii).

8. The method of claim 7, wherein the fragment includes 20 or more contiguous amino acids from SEQ ID NO: 634.

9. The method of claim 8, wherein the fragment includes 50 or more contiguous amino acids from SEQ ID NO: 634.

10. The method of claim 8 further comprising c) isolating the *E. coli* lipidated protein from the *E. coli* host cell.

11. The method of claim 10 further comprising d) formulating an immunogenic composition with the *E. coli* lipidated protein isolated from the *E. coli* host cell.

12. The method of claim 11, wherein the immunogenic composition further comprises an alum adjuvant.

* * * * *

SEQUENCE LISTING

```
<160> NUMBER OF SEQ ID NOS: 634

<210> SEQ ID NO 1
<211> LENGTH: 441
<212> TYPE: PRT
<213> ORGANISM: Neisseria meningitidis

<400> SEQUENCE: 1

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285
```

```
Ser Ile Gly Arg Tyr Met Ala Asp Lys Gly Tyr Leu Lys Leu Gly Gln
        290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
                435                 440

<210> SEQ ID NO 2
<211> LENGTH: 420
<212> TYPE: PRT
<213> ORGANISM: Neisseria meningitidis

<400> SEQUENCE: 2

Gln Ser Lys Ser Ile Gln Thr Phe Pro Gln Pro Asp Thr Ser Val Ile
1               5                   10                  15

Asn Gly Pro Asp Arg Pro Val Gly Ile Pro Asp Pro Ala Gly Thr Thr
                20                  25                  30

Val Gly Gly Gly Gly Ala Val Tyr Thr Val Val Pro His Leu Ser Leu
            35                  40                  45

Pro His Trp Ala Ala Gln Asp Phe Ala Lys Ser Leu Gln Ser Phe Arg
50                  55                  60

Leu Gly Cys Ala Asn Leu Lys Asn Arg Gln Gly Trp Gln Asp Val Cys
65                  70                  75                  80

Ala Gln Ala Phe Gln Thr Pro Val His Ser Phe Gln Ala Lys Gln Phe
                85                  90                  95

Phe Glu Arg Tyr Phe Thr Pro Trp Gln Val Ala Gly Asn Gly Ser Leu
                100                 105                 110

Ala Gly Thr Val Thr Gly Tyr Tyr Glu Pro Val Leu Lys Gly Asp Asp
            115                 120                 125

Arg Arg Thr Ala Gln Ala Arg Phe Pro Ile Tyr Gly Ile Pro Asp Asp
        130                 135                 140

Phe Ile Ser Val Pro Leu Pro Ala Gly Leu Arg Ser Gly Lys Ala Leu
145                 150                 155                 160

Val Arg Ile Arg Gln Thr Gly Lys Asn Ser Gly Thr Ile Asp Asn Thr
                165                 170                 175

Gly Gly Thr His Thr Ala Asp Leu Ser Arg Phe Pro Ile Thr Ala Arg
            180                 185                 190

Thr Thr Ala Ile Lys Gly Arg Phe Glu Gly Ser Arg Phe Leu Pro Tyr
        195                 200                 205

His Thr Arg Asn Gln Ile Asn Gly Gly Ala Leu Asp Gly Lys Ala Pro
210                 215                 220
```

```
Ile Leu Gly Tyr Ala Glu Asp Pro Val Glu Leu Phe Phe Met His Ile
225                 230                 235                 240

Gln Gly Ser Gly Arg Leu Lys Thr Pro Ser Gly Lys Tyr Ile Arg Ile
            245                 250                 255

Gly Tyr Ala Asp Lys Asn Glu His Pro Tyr Val Ser Ile Gly Arg Tyr
        260                 265                 270

Met Ala Asp Lys Gly Tyr Leu Lys Leu Gly Gln Thr Ser Met Gln Gly
        275                 280                 285

Ile Lys Ala Tyr Met Arg Gln Asn Pro Gln Arg Leu Ala Glu Val Leu
290                 295                 300

Gly Gln Asn Pro Ser Tyr Ile Phe Phe Arg Glu Leu Ala Gly Ser Ser
305                 310                 315                 320

Asn Asp Gly Pro Val Gly Ala Leu Gly Thr Pro Leu Met Gly Glu Tyr
                325                 330                 335

Ala Gly Ala Val Asp Arg His Tyr Ile Thr Leu Gly Ala Pro Leu Phe
                340                 345                 350

Val Ala Thr Ala His Pro Val Thr Arg Lys Ala Leu Asn Arg Leu Ile
            355                 360                 365

Met Ala Gln Asp Thr Gly Ser Ala Ile Lys Gly Ala Val Arg Val Asp
370                 375                 380

Tyr Phe Trp Gly Tyr Gly Asp Glu Ala Gly Glu Leu Ala Gly Lys Gln
385                 390                 395                 400

Lys Thr Thr Gly Tyr Val Trp Gln Leu Leu Pro Asn Gly Met Lys Pro
                405                 410                 415

Glu Tyr Arg Pro
            420

<210> SEQ ID NO 3
<211> LENGTH: 440
<212> TYPE: PRT
<213> ORGANISM: Artificial Sequence
<220> FEATURE:
<223> OTHER INFORMATION: Synthetic construct

<400> SEQUENCE: 3

Met Lys Thr Phe Phe Lys Thr Leu Ser Ala Ala Ala Leu Ala Leu Ile
1               5                   10                  15

Leu Ala Ala Cys Gln Ser Lys Ser Ile Gln Thr Phe Pro Gln Pro Asp
            20                  25                  30

Thr Ser Val Ile Asn Gly Pro Asp Arg Pro Val Gly Ile Pro Asp Pro
        35                  40                  45

Ala Gly Thr Thr Val Gly Gly Gly Ala Val Tyr Thr Val Val Pro
50                  55                  60

His Leu Ser Leu Pro His Trp Ala Ala Gln Asp Phe Ala Lys Ser Leu
65                  70                  75                  80

Gln Ser Phe Arg Leu Gly Cys Ala Asn Leu Lys Asn Arg Gln Gly Trp
            85                  90                  95

Gln Asp Val Cys Ala Gln Ala Phe Gln Thr Pro Val His Ser Phe Gln
            100                 105                 110

Ala Lys Gln Phe Phe Glu Arg Tyr Phe Thr Pro Trp Gln Val Ala Gly
            115                 120                 125

Asn Gly Ser Leu Ala Gly Thr Val Thr Gly Tyr Tyr Glu Pro Val Leu
        130                 135                 140

Lys Gly Asp Asp Arg Arg Thr Ala Gln Ala Arg Phe Pro Ile Tyr Gly
145                 150                 155                 160
```

```
Ile Pro Asp Asp Phe Ile Ser Val Pro Leu Pro Ala Gly Leu Arg Ser
                165                 170                 175

Gly Lys Ala Leu Val Arg Ile Arg Gln Thr Gly Lys Asn Ser Gly Thr
            180                 185                 190

Ile Asp Asn Thr Gly Gly Thr His Thr Ala Asp Leu Ser Arg Phe Pro
        195                 200                 205

Ile Thr Ala Arg Thr Thr Ala Ile Lys Gly Arg Phe Glu Gly Ser Arg
    210                 215                 220

Phe Leu Pro Tyr His Thr Arg Asn Gln Ile Asn Gly Gly Ala Leu Asp
225                 230                 235                 240

Gly Lys Ala Pro Ile Leu Gly Tyr Ala Glu Asp Pro Val Glu Leu Phe
                245                 250                 255

Phe Met His Ile Gln Gly Ser Gly Arg Leu Lys Thr Pro Ser Gly Lys
            260                 265                 270

Tyr Ile Arg Ile Gly Tyr Ala Asp Lys Asn Glu His Pro Tyr Val Ser
        275                 280                 285

Ile Gly Arg Tyr Met Ala Asp Lys Gly Tyr Leu Lys Leu Gly Gln Thr
    290                 295                 300

Ser Met Gln Gly Ile Lys Ser Tyr Met Arg Gln Asn Pro Gln Arg Leu
305                 310                 315                 320

Ala Glu Val Leu Gly Gln Asn Pro Ser Tyr Ile Phe Phe Arg Glu Leu
                325                 330                 335

Ala Gly Ser Ser Asn Asp Gly Pro Val Gly Ala Leu Gly Thr Pro Leu
            340                 345                 350

Met Gly Glu Tyr Ala Gly Ala Val Asp Arg His Tyr Ile Thr Leu Gly
        355                 360                 365

Ala Pro Leu Phe Val Ala Thr Ala His Pro Val Thr Arg Lys Ala Leu
    370                 375                 380

Asn Arg Leu Ile Met Ala Gln Asp Thr Gly Ser Ala Ile Lys Gly Ala
385                 390                 395                 400

Val Arg Val Asp Tyr Phe Trp Gly Tyr Gly Asp Glu Ala Gly Glu Leu
                405                 410                 415

Ala Gly Lys Gln Lys Thr Thr Gly Tyr Val Trp Gln Leu Leu Pro Asn
            420                 425                 430

Gly Met Lys Pro Glu Tyr Arg Pro
        435                 440

<210> SEQ ID NO 4
<211> LENGTH: 58
<212> TYPE: PRT
<213> ORGANISM: Artificial Sequence
<220> FEATURE:
<223> OTHER INFORMATION: Neisseria meningitidis

<400> SEQUENCE: 4

Glu Arg Arg Arg Leu Leu Val Asn Ile Gln Tyr Glu Ser Ser Arg Ala
1               5                   10                  15

Gly Leu Asp Thr Gln Ile Val Leu Gly Leu Ile Glu Val Glu Ser Ala
            20                  25                  30

Phe Arg Gln Tyr Ala Ile Ser Gly Val Gly Ala Arg Gly Leu Met Gln
        35                  40                  45

Val Met Pro Phe Trp Lys Asn Tyr Ile Gly
    50                  55

<210> SEQ ID NO 5
```

```
<211> LENGTH: 60
<212> TYPE: PRT
<213> ORGANISM: Artificial Sequence
<220> FEATURE:
<223> OTHER INFORMATION: Escherichia coli

<400> SEQUENCE: 5

Glu Arg Phe Pro Leu Ala Tyr Asn Asp Leu Phe Lys Arg Tyr Thr Ser
1               5                   10                  15

Gly Lys Glu Ile Pro Gln Ser Tyr Ala Met Ala Ile Ala Arg Gln Glu
            20                  25                  30

Ser Ala Trp Asn Pro Lys Val Lys Ser Pro Val Gly Ala Ser Gly Leu
        35                  40                  45

Met Gln Ile Met Pro Gly Thr Ala Thr His Thr Val
    50                  55                  60

<210> SEQ ID NO 6
<211> LENGTH: 120
<212> TYPE: PRT
<213> ORGANISM: Artificial Sequence
<220> FEATURE:
<223> OTHER INFORMATION: Neisseria meningitidis

<400> SEQUENCE: 6

Val Ala Gln Lys Tyr Gly Val Pro Ala Glu Leu Ile Val Ala Val Ile
1               5                   10                  15

Gly Ile Glu Thr Asn Tyr Gly Lys Asn Thr Gly Ser Phe Arg Val Ala
            20                  25                  30

Asp Ala Leu Ala Thr Leu Gly Phe Asp Tyr Pro Arg Arg Ala Gly Phe
        35                  40                  45

Phe Gln Lys Glu Leu Val Glu Leu Leu Lys Leu Ala Lys Glu Glu Gly
    50                  55                  60

Gly Asp Val Phe Ala Phe Lys Gly Ser Tyr Ala Gly Ala Met Gly Met
65                  70                  75                  80

Pro Gln Phe Met Pro Ser Ser Tyr Arg Lys Trp Ala Val Asp Tyr Asp
                85                  90                  95

Gly Asp Gly His Arg Asp Ile Trp Gly Asn Val Gly Asp Val Ala Ala
            100                 105                 110

Ser Val Ala Asn Tyr Met Lys Gln
        115                 120

<210> SEQ ID NO 7
<211> LENGTH: 119
<212> TYPE: PRT
<213> ORGANISM: Artificial Sequence
<220> FEATURE:
<223> OTHER INFORMATION: Escherichia coli

<400> SEQUENCE: 7

Ala Trp Gln Val Tyr Gly Val Pro Pro Glu Ile Ile Val Gly Ile Ile
1               5                   10                  15

Gly Val Glu Thr Arg Trp Gly Arg Val Met Gly Lys Thr Arg Ile Leu
            20                  25                  30

Asp Ala Leu Ala Thr Leu Ser Phe Asn Tyr Pro Arg Arg Ala Glu Tyr
        35                  40                  45

Phe Ser Gly Glu Leu Glu Thr Phe Leu Leu Met Ala Arg Asp Glu Gln
    50                  55                  60

Asp Asp Pro Leu Asn Leu Lys Gly Ser Phe Ala Gly Ala Met Gly Tyr
65                  70                  75                  80
```

```
Gly Gln Phe Met Pro Ser Ser Tyr Lys Gln Tyr Ala Val Asp Phe Ser
                85                  90                  95

Gly Asp Gly His Ile Asn Leu Trp Asp Pro Val Asp Ala Ile Gly Ser
            100                 105                 110

Val Ala Asn Tyr Phe Lys Ala
        115

<210> SEQ ID NO 8
<211> LENGTH: 194
<212> TYPE: PRT
<213> ORGANISM: Artificial Sequence
<220> FEATURE:
<223> OTHER INFORMATION: Neisseria meningitidis

<400> SEQUENCE: 8

Ala Leu Asp Gly Lys Ala Pro Ile Leu Gly Tyr Ala Glu Asp Pro Val
1               5                   10                  15

Glu Leu Phe Phe Met His Ile Gln Gly Ser Gly Arg Leu Lys Thr Pro
                20                  25                  30

Ser Gly Lys Tyr Ile Arg Ile Gly Tyr Ala Asp Lys Asn Glu His Pro
            35                  40                  45

Tyr Val Ser Ile Gly Arg Tyr Met Ala Asp Lys Gly Tyr Leu Lys Leu
        50                  55                  60

Gly Gln Thr Ser Met Gln Gly Ile Lys Ser Tyr Met Arg Gln Asn Pro
65                  70                  75                  80

Gln Arg Leu Ala Glu Val Leu Gly Gln Asn Pro Ser Tyr Ile Phe Phe
                85                  90                  95

Arg Glu Leu Ala Gly Ser Ser Asn Asp Gly Pro Val Gly Ala Leu Gly
            100                 105                 110

Thr Pro Leu Met Gly Glu Tyr Ala Gly Ala Val Asp Arg His Tyr Ile
        115                 120                 125

Thr Leu Gly Ala Pro Leu Phe Val Ala Thr Ala His Pro Val Thr Arg
    130                 135                 140

Lys Ala Leu Asn Arg Leu Ile Met Ala Gln Asp Thr Gly Ser Ala Ile
145                 150                 155                 160

Lys Gly Ala Val Arg Val Asp Tyr Phe Trp Gly Tyr Gly Asp Glu Ala
                165                 170                 175

Gly Glu Leu Ala Gly Lys Gln Lys Thr Thr Gly Tyr Val Trp Gln Leu
            180                 185                 190

Leu Pro

<210> SEQ ID NO 9
<211> LENGTH: 196
<212> TYPE: PRT
<213> ORGANISM: Escherichia coli

<400> SEQUENCE: 9

Ala Leu Ser Asp Lys Tyr Ile Leu Ala Tyr Ser Asn Ser Leu Met Asp
1               5                   10                  15

Asn Phe Ile Met Asp Val Gln Gly Ser Gly Tyr Ile Asp Phe Gly Asp
                20                  25                  30

Gly Ser Pro Leu Asn Phe Phe Ser Tyr Ala Gly Lys Asn Gly His Ala
            35                  40                  45

Tyr Arg Ser Ile Gly Lys Val Leu Ile Asp Arg Gly Glu Val Lys Lys
        50                  55                  60

Glu Asp Met Ser Met Gln Ala Ile Arg His Trp Gly Leu Thr His Ser
65                  70                  75                  80
```

Glu Ala Glu Val Arg Glu Leu Leu Gln Asn Pro Ser Phe Val Phe
            85                  90                  95

Phe Lys Pro Gln Ser Phe Ala Pro Val Lys Gly Ala Ser Ala Val Pro
        100                 105                 110

Leu Val Gly Arg Ala Ser Val Ala Ser Asp Arg Ser Ile Ile Pro Pro
        115                 120                 125

Gly Thr Thr Leu Leu Ala Glu Val Pro Leu Leu Asp Asn Asn Gly Lys
130                 135                 140

Phe Asn Gly Gln Tyr Glu Leu Arg Leu Met Val Ala Leu Asp Val Gly
145                 150                 155                 160

Gly Ala Ile Lys Gly Gln His Phe Asp Ile Tyr Gln Gly Ile Gly Pro
                165                 170                 175

Glu Ala Gly His Arg Ala Gly Trp Tyr Asn His Tyr Gly Arg Val Trp
            180                 185                 190

Val Leu Lys Thr
        195

<210> SEQ ID NO 10
<211> LENGTH: 28
<212> TYPE: DNA
<213> ORGANISM: Artificial Sequence
<220> FEATURE:
<223> OTHER INFORMATION: Synthetic construct

<400> SEQUENCE: 10
cgaagacccc gtcggtcttt tttttatg                                  28

<210> SEQ ID NO 11
<211> LENGTH: 28
<212> TYPE: DNA
<213> ORGANISM: Artificial Sequence
<220> FEATURE:
<223> OTHER INFORMATION: Synthetic construct

<400> SEQUENCE: 11
gtgcataaaa aaaagaccga cggggtct                                  28

<210> SEQ ID NO 12
<211> LENGTH: 25
<212> TYPE: DNA
<213> ORGANISM: Artificial Sequence
<220> FEATURE:
<223> OTHER INFORMATION: Synthetic construct

<400> SEQUENCE: 12
aacgcctcgc cggtgttttg ggtca                                     25

<210> SEQ ID NO 13
<211> LENGTH: 25
<212> TYPE: DNA
<213> ORGANISM: Artificial Sequence
<220> FEATURE:
<223> OTHER INFORMATION: Synthetic construct

<400> SEQUENCE: 13
tttgacccaa acaccggcg aggcg                                      25

<210> SEQ ID NO 14
<211> LENGTH: 26
<212> TYPE: DNA
<213> ORGANISM: Artificial Sequence
<220> FEATURE:

<223> OTHER INFORMATION: Synthetic construct

<400> SEQUENCE: 14
tgccggcgca gtcggtcggc actaca                                        26

<210> SEQ ID NO 15
<211> LENGTH: 26
<212> TYPE: DNA
<213> ORGANISM: Artificial Sequence
<220> FEATURE:
<223> OTHER INFORMATION: Synthetic construct

<400> SEQUENCE: 15
taatgtagtg ccgaccgact gcgccg                                        26

<210> SEQ ID NO 16
<211> LENGTH: 25
<212> TYPE: DNA
<213> ORGANISM: Artificial Sequence
<220> FEATURE:
<223> OTHER INFORMATION: Synthetic construct

<400> SEQUENCE: 16
tgattgaggt gggtagcgcg ttccg                                         25

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
ggcggaacgc gctacccacc tcaat                                         25

<210> SEQ ID NO 18
<211> LENGTH: 34
<212> TYPE: DNA
<213> ORGANISM: Artificial Sequence
<220> FEATURE:
<223> OTHER INFORMATION: Synthetic construct

<400> SEQUENCE: 18
ccggaattct tatgaaaaaa atcatcttcg ccgc                               34

<210> SEQ ID NO 19
<211> LENGTH: 32
<212> TYPE: DNA
<213> ORGANISM: Artificial Sequence
<220> FEATURE:
<223> OTHER INFORMATION: Synthetic construct

<400> SEQUENCE: 19
gcccaagctt ttattgtttg gctgcctcga tt                                 32

<210> SEQ ID NO 20
<211> LENGTH: 37
<212> TYPE: DNA
<213> ORGANISM: Artificial Sequence
<220> FEATURE:
<223> OTHER INFORMATION: Synthetic construct

<400> SEQUENCE: 20
ccggaattct tatgtcgccc gatgttaaat cggcgga                            37

```
<210> SEQ ID NO 21
<211> LENGTH: 32
<212> TYPE: DNA
<213> ORGANISM: Artificial Sequence
<220> FEATURE:
<223> OTHER INFORMATION: Synthetic construct

<400> SEQUENCE: 21
gcccaagctt tcaatcctgc tcttttttgc cg                                    32

<210> SEQ ID NO 22
<211> LENGTH: 34
<212> TYPE: DNA
<213> ORGANISM: Artificial Sequence
<220> FEATURE:
<223> OTHER INFORMATION: Synthetic construct

<400> SEQUENCE: 22
ccggaattct tatgagccaa gatatggcgg cagt                                  34

<210> SEQ ID NO 23
<211> LENGTH: 32
<212> TYPE: DNA
<213> ORGANISM: Artificial Sequence
<220> FEATURE:
<223> OTHER INFORMATION: Synthetic construct

<400> SEQUENCE: 23
gcccaagctt tcaatcctgc tcttttttgc cg                                    32

<210> SEQ ID NO 24
<211> LENGTH: 34
<212> TYPE: DNA
<213> ORGANISM: Artificial Sequence
<220> FEATURE:
<223> OTHER INFORMATION: Synthetic construct

<400> SEQUENCE: 24
ccggaattct tatgtccgcc gaatccgcaa atca                                  34

<210> SEQ ID NO 25
<211> LENGTH: 32
<212> TYPE: DNA
<213> ORGANISM: Artificial Sequence
<220> FEATURE:
<223> OTHER INFORMATION: Synthetic construct

<400> SEQUENCE: 25
gcccaagctt tcaatcctgc tcttttttgc cg                                    32

<210> SEQ ID NO 26
<211> LENGTH: 36
<212> TYPE: DNA
<213> ORGANISM: Artificial Sequence
<220> FEATURE:
<223> OTHER INFORMATION: Synthetic construct

<400> SEQUENCE: 26
ccggaattct tatgggaagg gttgatttgg ctaatg                                36

<210> SEQ ID NO 27
<211> LENGTH: 32
<212> TYPE: DNA
<213> ORGANISM: Artificial Sequence
<220> FEATURE:
<223> OTHER INFORMATION: Synthetic construct
```

```
<400> SEQUENCE: 27
gcccaagctt tcaatcctgc tcttttttgc cg                              32

<210> SEQ ID NO 28
<211> LENGTH: 36
<212> TYPE: DNA
<213> ORGANISM: Artificial Sequence
<220> FEATURE:
<223> OTHER INFORMATION: Synthetic construct

<400> SEQUENCE: 28
ccggaattct tatgtcagat ttggcaaacg attctt                          36

<210> SEQ ID NO 29
<211> LENGTH: 35
<212> TYPE: DNA
<213> ORGANISM: Artificial Sequence
<220> FEATURE:
<223> OTHER INFORMATION: Synthetic construct

<400> SEQUENCE: 29
gcccaagctt ttacgtatca tatttcacgt gcttc                           35

<210> SEQ ID NO 30
<211> LENGTH: 37
<212> TYPE: DNA
<213> ORGANISM: Artificial Sequence
<220> FEATURE:
<223> OTHER INFORMATION: Synthetic construct

<400> SEQUENCE: 30
ccggaattct tatgtcgccc gatgttaaat cggcgga                         37

<210> SEQ ID NO 31
<211> LENGTH: 35
<212> TYPE: DNA
<213> ORGANISM: Artificial Sequence
<220> FEATURE:
<223> OTHER INFORMATION: Synthetic construct

<400> SEQUENCE: 31
gcccaagctt ttacgtatca tatttcacgt gcttc                           35

<210> SEQ ID NO 32
<211> LENGTH: 36
<212> TYPE: DNA
<213> ORGANISM: Artificial Sequence
<220> FEATURE:
<223> OTHER INFORMATION: Synthetic construct

<400> SEQUENCE: 32
ccggaattct tatgcaaagc aagagcatcc aaacct                          36

<210> SEQ ID NO 33
<211> LENGTH: 30
<212> TYPE: DNA
<213> ORGANISM: Artificial Sequence
<220> FEATURE:
<223> OTHER INFORMATION: Synthetic construct

<400> SEQUENCE: 33
gcccaagctt ttacgggcgg tattcgggct                                 30

<210> SEQ ID NO 34
<211> LENGTH: 29
```

<212> TYPE: DNA
<213> ORGANISM: Artificial Sequence
<220> FEATURE:
<223> OTHER INFORMATION: Synthetic construct

<400> SEQUENCE: 34
ccggaattca tatgaaacac tttccatcc                                29

<210> SEQ ID NO 35
<211> LENGTH: 28
<212> TYPE: DNA
<213> ORGANISM: Artificial Sequence
<220> FEATURE:
<223> OTHER INFORMATION: Synthetic construct

<400> SEQUENCE: 35
gcccaagctt ttaccactcg taattgac                                 28

<210> SEQ ID NO 36
<211> LENGTH: 29
<212> TYPE: DNA
<213> ORGANISM: Artificial Sequence
<220> FEATURE:
<223> OTHER INFORMATION: Synthetic construct

<400> SEQUENCE: 36
ccggaattca tatggccaca agcgacgac                                29

<210> SEQ ID NO 37
<211> LENGTH: 28
<212> TYPE: DNA
<213> ORGANISM: Artificial Sequence
<220> FEATURE:
<223> OTHER INFORMATION: Synthetic construct

<400> SEQUENCE: 37
gcccaagctt ttaccactcg taattgac                                 28

<210> SEQ ID NO 38
<211> LENGTH: 29
<212> TYPE: DNA
<213> ORGANISM: Artificial Sequence
<220> FEATURE:
<223> OTHER INFORMATION: Synthetic construct

<400> SEQUENCE: 38
ccggaattct tatgaaacac tttccatcc                                29

<210> SEQ ID NO 39
<211> LENGTH: 31
<212> TYPE: DNA
<213> ORGANISM: Artificial Sequence
<220> FEATURE:
<223> OTHER INFORMATION: Synthetic construct

<400> SEQUENCE: 39
gcccaagctt tcaacccacg ttgtaaggtt g                             31

<210> SEQ ID NO 40
<211> LENGTH: 30
<212> TYPE: DNA
<213> ORGANISM: Artificial Sequence
<220> FEATURE:
<223> OTHER INFORMATION: Synthetic construct

<400> SEQUENCE: 40

```
ccggaattct tatggccaca aacgacgacg                                    30

<210> SEQ ID NO 41
<211> LENGTH: 31
<212> TYPE: DNA
<213> ORGANISM: Artificial Sequence
<220> FEATURE:
<223> OTHER INFORMATION: Synthetic construct

<400> SEQUENCE: 41
gcccaagctt tcaacccacg ttgtaaggtt g                                  31

<210> SEQ ID NO 42
<211> LENGTH: 34
<212> TYPE: DNA
<213> ORGANISM: Artificial Sequence
<220> FEATURE:
<223> OTHER INFORMATION: Synthetic construct

<400> SEQUENCE: 42
ccggaattct tatggccacc tacaaagtgg acga                               34

<210> SEQ ID NO 43
<211> LENGTH: 32
<212> TYPE: DNA
<213> ORGANISM: Artificial Sequence
<220> FEATURE:
<223> OTHER INFORMATION: Synthetic construct

<400> SEQUENCE: 43
gcccaagctt ttattgtttg gctgcctcga tt                                 32

<210> SEQ ID NO 44
<211> LENGTH: 32
<212> TYPE: DNA
<213> ORGANISM: Artificial Sequence
<220> FEATURE:
<223> OTHER INFORMATION: Synthetic construct

<400> SEQUENCE: 44
cgcggatccg ctagccccga tgttaaatcg gc                                 32

<210> SEQ ID NO 45
<211> LENGTH: 31
<212> TYPE: DNA
<213> ORGANISM: Artificial Sequence
<220> FEATURE:
<223> OTHER INFORMATION: Synthetic construct

<400> SEQUENCE: 45
cccgctcgag tcaatcctgc tcttttttgc c                                  31

<210> SEQ ID NO 46
<211> LENGTH: 32
<212> TYPE: DNA
<213> ORGANISM: Artificial Sequence
<220> FEATURE:
<223> OTHER INFORMATION: Synthetic construct

<400> SEQUENCE: 46
cgcggatccg ctagccaaga tatggcggca gt                                 32

<210> SEQ ID NO 47
<211> LENGTH: 32
<212> TYPE: DNA
<213> ORGANISM: Artificial Sequence
```

```
<220> FEATURE:
<223> OTHER INFORMATION: Synthetic construct

<400> SEQUENCE: 47
cgcggatccg ctagcgccga atccgcaaat ca                                32

<210> SEQ ID NO 48
<211> LENGTH: 32
<212> TYPE: DNA
<213> ORGANISM: Artificial Sequence
<220> FEATURE:
<223> OTHER INFORMATION: Synthetic construct

<400> SEQUENCE: 48
cgcgctagcg aagggttga tttggctaat gg                                 32

<210> SEQ ID NO 49
<211> LENGTH: 34
<212> TYPE: DNA
<213> ORGANISM: Artificial Sequence
<220> FEATURE:
<223> OTHER INFORMATION: Synthetic construct

<400> SEQUENCE: 49
gggaattcca tatgggcatt tcccgcaaaa tatc                              34

<210> SEQ ID NO 50
<211> LENGTH: 32
<212> TYPE: DNA
<213> ORGANISM: Artificial Sequence
<220> FEATURE:
<223> OTHER INFORMATION: Synthetic construct

<400> SEQUENCE: 50
cccgctcgag ttacgtatca tatttcacgt gc                                32

<210> SEQ ID NO 51
<211> LENGTH: 34
<212> TYPE: DNA
<213> ORGANISM: Artificial Sequence
<220> FEATURE:
<223> OTHER INFORMATION: Synthetic construct

<400> SEQUENCE: 51
gggaattcca tatgggcatt tcccgcaaaa tatc                              34

<210> SEQ ID NO 52
<211> LENGTH: 33
<212> TYPE: DNA
<213> ORGANISM: Artificial Sequence
<220> FEATURE:
<223> OTHER INFORMATION: Synthetic construct

<400> SEQUENCE: 52
cccgctcgag ttattctatg ccttgtgcgg cat                               33

<210> SEQ ID NO 53
<211> LENGTH: 32
<212> TYPE: DNA
<213> ORGANISM: Artificial Sequence
<220> FEATURE:
<223> OTHER INFORMATION: Synthetic construct

<400> SEQUENCE: 53
cgcggatccc atatggccac aagcgacgac ga                                32
```

<210> SEQ ID NO 54
<211> LENGTH: 28
<212> TYPE: DNA
<213> ORGANISM: Artificial Sequence
<220> FEATURE:
<223> OTHER INFORMATION: Synthetic construct

<400> SEQUENCE: 54
cccgctcgag ttaccactcg taattgac                                    28

<210> SEQ ID NO 55
<211> LENGTH: 28
<212> TYPE: DNA
<213> ORGANISM: Artificial Sequence
<220> FEATURE:
<223> OTHER INFORMATION: Synthetic construct

<400> SEQUENCE: 55
cgcggatccc atatggccac aaacgacg                                    28

<210> SEQ ID NO 56
<211> LENGTH: 35
<212> TYPE: DNA
<213> ORGANISM: Artificial Sequence
<220> FEATURE:
<223> OTHER INFORMATION: Synthetic construct

<400> SEQUENCE: 56
cccgctcgag tcatttagca atattatctt tgttc                            35

<210> SEQ ID NO 57
<211> LENGTH: 33
<212> TYPE: DNA
<213> ORGANISM: Artificial Sequence
<220> FEATURE:
<223> OTHER INFORMATION: Synthetic construct

<400> SEQUENCE: 57
cgcggatccc atatgaaagc aaacagtgcc gac                              33

<210> SEQ ID NO 58
<211> LENGTH: 28
<212> TYPE: DNA
<213> ORGANISM: Artificial Sequence
<220> FEATURE:
<223> OTHER INFORMATION: Synthetic construct

<400> SEQUENCE: 58
cccgctcgag ttaccactcg taattgac                                    28

<210> SEQ ID NO 59
<211> LENGTH: 28
<212> TYPE: DNA
<213> ORGANISM: Artificial Sequence
<220> FEATURE:
<223> OTHER INFORMATION: Synthetic construct

<400> SEQUENCE: 59
cgcggatccc atatggccac aaacgacg                                    28

<210> SEQ ID NO 60
<211> LENGTH: 29
<212> TYPE: DNA
<213> ORGANISM: Artificial Sequence
<220> FEATURE:
<223> OTHER INFORMATION: Synthetic construct

```
<400> SEQUENCE: 60
cccgctcgag ttaacccacg ttgtaaggt                                          29

<210> SEQ ID NO 61
<211> LENGTH: 33
<212> TYPE: DNA
<213> ORGANISM: Artificial Sequence
<220> FEATURE:
<223> OTHER INFORMATION: Synthetic construct

<400> SEQUENCE: 61
cgcggatccc atatgatgaa acactttcca tcc                                     33

<210> SEQ ID NO 62
<211> LENGTH: 29
<212> TYPE: DNA
<213> ORGANISM: Artificial Sequence
<220> FEATURE:
<223> OTHER INFORMATION: Synthetic construct

<400> SEQUENCE: 62
cccgctcgag ttaacccacg ttgtaaggt                                          29

<210> SEQ ID NO 63
<211> LENGTH: 28
<212> TYPE: DNA
<213> ORGANISM: Artificial Sequence
<220> FEATURE:
<223> OTHER INFORMATION: Synthetic construct

<400> SEQUENCE: 63
cgcggatccc atatggccac aaacgacg                                           28

<210> SEQ ID NO 64
<211> LENGTH: 32
<212> TYPE: DNA
<213> ORGANISM: Artificial Sequence
<220> FEATURE:
<223> OTHER INFORMATION: Synthetic construct

<400> SEQUENCE: 64
cccgctcgag tcagtctgac actgttttat cc                                      32

<210> SEQ ID NO 65
<211> LENGTH: 32
<212> TYPE: DNA
<213> ORGANISM: Artificial Sequence
<220> FEATURE:
<223> OTHER INFORMATION: Synthetic construct

<400> SEQUENCE: 65
cgcggatccg ctagccccga tgttaaatcg gc                                      32

<210> SEQ ID NO 66
<211> LENGTH: 27
<212> TYPE: DNA
<213> ORGANISM: Artificial Sequence
<220> FEATURE:
<223> OTHER INFORMATION: Synthetic construct

<400> SEQUENCE: 66
cccgctcgag ttacgggcgg tattcgg                                            27

<210> SEQ ID NO 67
```

<211> LENGTH: 32
<212> TYPE: DNA
<213> ORGANISM: Artificial Sequence
<220> FEATURE:
<223> OTHER INFORMATION: Synthetic construct

<400> SEQUENCE: 67
cgcggatccg ctagccccga tgttaaatcg gc        32

<210> SEQ ID NO 68
<211> LENGTH: 32
<212> TYPE: DNA
<213> ORGANISM: Artificial Sequence
<220> FEATURE:
<223> OTHER INFORMATION: Synthetic construct

<400> SEQUENCE: 68
cccgctcgag ttacgtatca tatttcacgt gc        32

<210> SEQ ID NO 69
<211> LENGTH: 32
<212> TYPE: DNA
<213> ORGANISM: Artificial Sequence
<220> FEATURE:
<223> OTHER INFORMATION: Synthetic construct

<400> SEQUENCE: 69
cgcggatccg ctagccccga tgttaaatcg gc        32

<210> SEQ ID NO 70
<211> LENGTH: 28
<212> TYPE: DNA
<213> ORGANISM: Artificial Sequence
<220> FEATURE:
<223> OTHER INFORMATION: Synthetic construct

<400> SEQUENCE: 70
cccgctcgag ttaccactcg taattgac        28

<210> SEQ ID NO 71
<211> LENGTH: 1457
<212> TYPE: PRT
<213> ORGANISM: Neisseria meningitidis

<400> SEQUENCE: 71

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn

```
            130                 135                 140
Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560
```

```
Gln Asp Lys Glu Ser Thr Val Thr Ile Thr Gly Asn Lys Asp Ile Ala
            565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
            595                 600                 605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
            645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
            675                 680                 685

Gly Gly Gln Ala Val Val Ser Arg Asn Val Ala Lys Val Lys Gly Asp
            690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
            725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
            805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
            885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Arg Ser Arg Arg Ser Leu Leu
            930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
            965                 970                 975
```

```
Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
            995                 1000                1005

Leu Glu Gln Leu Thr Val Val Glu Gly Lys Asp Asn Lys Pro Leu Ser
        1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Phe Arg Leu His Asn
            1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
        1075                1080                1085

Ala Ala Gly Arg Asp Ala Val Glu Lys Thr Glu Ser Val Ala Glu Pro
        1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
            1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln Pro Gln
            1155                1160                1165

Pro Gln Arg Asp Leu Ile Ser Arg Tyr Ala Asn Ser Gly Leu Ser Glu
        1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
            1205                1210                1215

Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
        1380                1385                1390

Asp Ala Ala Ser Gly Lys Val Arg Thr Arg Val Asn Thr Ala Val Leu
```

```
                  1395                1400                1405

Ala Gln Asp Phe Gly Lys Thr Arg Ser Ala Glu Trp Gly Val Asn Ala
            1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
                1445                1450                1455

Trp

<210> SEQ ID NO 72
<211> LENGTH: 21
<212> TYPE: PRT
<213> ORGANISM: Escherichia coli

<400> SEQUENCE: 72

Met Lys Lys Thr Ala Ile Ala Ile Ala Val Ala Leu Ala Gly Phe Ala
1               5                   10                  15

Thr Val Ala Gln Ala
            20

<210> SEQ ID NO 73
<211> LENGTH: 1439
<212> TYPE: PRT
<213> ORGANISM: Artificial Sequence
<220> FEATURE:
<223> OTHER INFORMATION: Synthetic construct

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Ser Ala Gly His Thr Tyr Phe Gly Ile Asn
            20                  25                  30

Tyr Gln Tyr Tyr Arg Asp Phe Ala Glu Asn Lys Gly Lys Phe Ala Val
        35                  40                  45

Gly Ala Lys Asp Ile Glu Val Tyr Asn Lys Lys Gly Glu Leu Val Gly
    50                  55                  60

Lys Ser Met Thr Lys Ala Pro Met Ile Asp Phe Ser Val Val Ser Arg
65                  70                  75                  80

Asn Gly Val Ala Ala Leu Val Gly Asp Gln Tyr Ile Val Ser Val Ala
                85                  90                  95

His Asn Gly Gly Tyr Asn Asn Val Asp Phe Gly Ala Glu Gly Arg Asn
            100                 105                 110

Pro Asp Gln His Arg Phe Thr Tyr Lys Ile Val Lys Arg Asn Asn Tyr
        115                 120                 125

Lys Ala Gly Thr Lys Gly His Pro Tyr Gly Gly Asp Tyr His Met Pro
    130                 135                 140

Arg Leu His Lys Phe Val Thr Asp Ala Glu Pro Val Glu Met Thr Ser
145                 150                 155                 160

Tyr Met Asp Gly Arg Lys Tyr Ile Asp Gln Asn Asn Tyr Pro Asp Arg
                165                 170                 175

Val Arg Ile Gly Ala Gly Arg Gln Tyr Trp Arg Ser Asp Glu Asp Glu
            180                 185                 190

Pro Asn Asn Arg Glu Ser Ser Tyr His Ile Ala Ser Ala Tyr Ser Trp
        195                 200                 205

Leu Val Gly Gly Asn Thr Phe Ala Gln Asn Gly Ser Gly Gly Thr
    210                 215                 220
```

```
Val Asn Leu Gly Ser Glu Lys Ile Lys His Ser Pro Tyr Gly Phe Leu
225                 230                 235                 240

Pro Thr Gly Gly Ser Phe Gly Asp Ser Gly Ser Pro Met Phe Ile Tyr
            245                 250                 255

Asp Ala Gln Lys Gln Lys Trp Leu Ile Asn Gly Val Leu Gln Thr Gly
        260                 265                 270

Asn Pro Tyr Ile Gly Lys Ser Asn Gly Phe Gln Leu Val Arg Lys Asp
    275                 280                 285

Trp Phe Tyr Asp Glu Ile Phe Ala Gly Asp Thr His Ser Val Phe Tyr
290                 295                 300

Glu Pro Arg Gln Asn Gly Lys Tyr Ser Phe Asn Asp Asp Asn Asn Gly
305                 310                 315                 320

Thr Gly Lys Ile Asn Ala Lys His Glu His Asn Ser Leu Pro Asn Arg
                325                 330                 335

Leu Lys Thr Arg Thr Val Gln Leu Phe Asn Val Ser Leu Ser Glu Thr
            340                 345                 350

Ala Arg Glu Pro Val Tyr His Ala Ala Gly Val Asn Ser Tyr Arg
        355                 360                 365

Pro Arg Leu Asn Asn Gly Glu Asn Ile Ser Phe Ile Asp Glu Gly Lys
    370                 375                 380

Gly Glu Leu Ile Leu Thr Ser Asn Ile Asn Gln Gly Ala Gly Gly Leu
385                 390                 395                 400

Tyr Phe Gln Gly Asp Phe Thr Val Ser Pro Glu Asn Asn Glu Thr Trp
                405                 410                 415

Gln Gly Ala Gly Val His Ile Ser Glu Asp Ser Thr Val Thr Trp Lys
            420                 425                 430

Val Asn Gly Val Ala Asn Asp Arg Leu Ser Lys Ile Gly Lys Gly Thr
        435                 440                 445

Leu His Val Gln Ala Lys Gly Glu Asn Gln Gly Ser Ile Ser Val Gly
    450                 455                 460

Asp Gly Thr Val Ile Leu Asp Gln Gln Ala Asp Asp Lys Gly Lys Lys
465                 470                 475                 480

Gln Ala Phe Ser Glu Ile Gly Leu Val Ser Gly Arg Gly Thr Val Gln
                485                 490                 495

Leu Asn Ala Asp Asn Gln Phe Asn Pro Asp Lys Leu Tyr Phe Gly Phe
            500                 505                 510

Arg Gly Gly Arg Leu Asp Leu Asn Gly His Ser Leu Ser Phe His Arg
        515                 520                 525

Ile Gln Asn Thr Asp Glu Gly Ala Met Ile Val Asn His Asn Gln Asp
    530                 535                 540

Lys Glu Ser Thr Val Thr Ile Thr Gly Asn Lys Asp Ile Ala Thr Thr
545                 550                 555                 560

Gly Asn Asn Asn Ser Leu Asp Ser Lys Lys Glu Ile Ala Tyr Asn Gly
                565                 570                 575

Trp Phe Gly Glu Lys Asp Thr Thr Lys Thr Asn Gly Arg Leu Asn Leu
            580                 585                 590

Val Tyr Gln Pro Ala Ala Glu Asp Arg Thr Leu Leu Leu Ser Gly Gly
        595                 600                 605

Thr Asn Leu Asn Gly Asn Ile Thr Gln Thr Asn Gly Lys Leu Phe Phe
    610                 615                 620

Ser Gly Arg Pro Thr Pro His Ala Tyr Asn His Leu Asn Asp His Trp
625                 630                 635                 640

Ser Gln Lys Glu Gly Ile Pro Arg Gly Glu Ile Val Trp Asp Asn Asp
```

```
                    645                 650                 655
Trp Ile Asn Arg Thr Phe Lys Ala Glu Asn Phe Gln Ile Lys Gly Gly
                660                 665                 670

Gln Ala Val Val Ser Arg Asn Val Ala Lys Val Lys Gly Asp Trp His
            675                 680                 685

Leu Ser Asn His Ala Gln Ala Val Phe Gly Val Ala Pro His Gln Ser
        690                 695                 700

His Thr Ile Cys Thr Arg Ser Asp Trp Thr Gly Leu Thr Asn Cys Val
705                 710                 715                 720

Glu Lys Thr Ile Thr Asp Asp Lys Val Ile Ala Ser Leu Thr Lys Thr
                725                 730                 735

Asp Ile Ser Gly Asn Val Asp Leu Ala Asp His Ala His Leu Asn Leu
            740                 745                 750

Thr Gly Leu Ala Thr Leu Asn Gly Asn Leu Ser Ala Asn Gly Asp Thr
        755                 760                 765

Arg Tyr Thr Val Ser His Asn Ala Thr Gln Asn Gly Asn Leu Ser Leu
    770                 775                 780

Val Gly Asn Ala Gln Ala Thr Phe Asn Gln Ala Thr Leu Asn Gly Asn
785                 790                 795                 800

Thr Ser Ala Ser Gly Asn Ala Ser Phe Asn Leu Ser Asp His Ala Val
                805                 810                 815

Gln Asn Gly Ser Leu Thr Leu Ser Gly Asn Ala Lys Ala Asn Val Ser
            820                 825                 830

His Ser Ala Leu Asn Gly Asn Val Ser Leu Ala Asp Lys Ala Val Phe
        835                 840                 845

His Phe Glu Ser Ser Arg Phe Thr Gly Gln Ile Ser Gly Gly Lys Asp
    850                 855                 860

Thr Ala Leu His Leu Lys Asp Ser Glu Trp Thr Leu Pro Ser Gly Thr
865                 870                 875                 880

Glu Leu Gly Asn Leu Asn Leu Asp Asn Ala Thr Ile Thr Leu Asn Ser
                885                 890                 895

Ala Tyr Arg His Asp Ala Ala Gly Ala Gln Thr Gly Ser Ala Thr Asp
            900                 905                 910

Ala Pro Arg Arg Arg Ser Arg Arg Ser Arg Ser Leu Leu Ser Val
        915                 920                 925

Thr Pro Pro Thr Ser Val Glu Ser Arg Phe Asn Thr Leu Thr Val Asn
    930                 935                 940

Gly Lys Leu Asn Gly Gln Gly Thr Phe Arg Phe Met Ser Glu Leu Phe
945                 950                 955                 960

Gly Tyr Arg Ser Asp Lys Leu Lys Leu Ala Glu Ser Ser Glu Gly Thr
                965                 970                 975

Tyr Thr Leu Ala Val Asn Asn Thr Gly Asn Glu Pro Ala Ser Leu Glu
            980                 985                 990

Gln Leu Thr Val Val Glu Gly Lys Asp Asn Lys Pro Leu Ser Glu Asn
        995                 1000                1005

Leu Asn Phe Thr Leu Gln Asn Glu His Val Asp Ala Gly Ala Trp Arg
    1010                1015                1020

Tyr Gln Leu Ile Arg Lys Asp Gly Glu Phe Arg Leu His Asn Pro Val
1025                1030                1035                1040

Lys Glu Gln Glu Leu Ser Asp Lys Leu Gly Lys Ala Glu Ala Lys Lys
                1045                1050                1055

Gln Ala Glu Lys Asp Asn Ala Gln Ser Leu Asp Ala Leu Ile Ala Ala
            1060                1065                1070
```

Gly Arg Asp Ala Val Glu Lys Thr Glu Ser Val Ala Glu Pro Ala Arg
            1075                1080                1085

Gln Ala Gly Gly Glu Asn Val Gly Ile Met Gln Ala Glu Glu Lys
    1090                1095                1100

Lys Arg Val Gln Ala Asp Lys Asp Thr Ala Leu Ala Lys Gln Arg Glu
1105                1110                1115                1120

Ala Glu Thr Arg Pro Ala Thr Thr Ala Phe Pro Arg Ala Arg Arg Ala
            1125                1130                1135

Arg Arg Asp Leu Pro Gln Leu Gln Pro Gln Pro Gln Pro Gln
            1140                1145                1150

Arg Asp Leu Ile Ser Arg Tyr Ala Asn Ser Gly Leu Ser Glu Phe Ser
            1155                1160                1165

Ala Thr Leu Asn Ser Val Phe Ala Val Gln Asp Glu Leu Asp Arg Val
            1170                1175                1180

Phe Ala Glu Asp Arg Arg Asn Ala Val Trp Thr Ser Gly Ile Arg Asp
1185                1190                1195                1200

Thr Lys His Tyr Arg Ser Gln Asp Phe Arg Ala Tyr Arg Gln Gln Thr
            1205                1210                1215

Asp Leu Arg Gln Ile Gly Met Gln Lys Asn Leu Gly Ser Gly Arg Val
            1220                1225                1230

Gly Ile Leu Phe Ser His Asn Arg Thr Glu Asn Thr Phe Asp Asp Gly
            1235                1240                1245

Ile Gly Asn Ser Ala Arg Leu Ala His Gly Ala Val Phe Gly Gln Tyr
            1250                1255                1260

Gly Ile Asp Arg Phe Tyr Ile Gly Ile Ser Ala Gly Ala Gly Phe Ser
1265                1270                1275                1280

Ser Gly Ser Leu Ser Asp Gly Ile Gly Gly Lys Ile Arg Arg Arg Val
            1285                1290                1295

Leu His Tyr Gly Ile Gln Ala Arg Tyr Arg Ala Gly Phe Gly Gly Phe
            1300                1305                1310

Gly Ile Glu Pro His Ile Gly Ala Thr Arg Tyr Phe Val Gln Lys Ala
            1315                1320                1325

Asp Tyr Arg Tyr Glu Asn Val Asn Ile Ala Thr Pro Gly Leu Ala Phe
            1330                1335                1340

Asn Arg Tyr Arg Ala Gly Ile Lys Ala Asp Tyr Ser Phe Lys Pro Ala
1345                1350                1355                1360

Gln His Ile Ser Ile Thr Pro Tyr Leu Ser Leu Ser Tyr Thr Asp Ala
            1365                1370                1375

Ala Ser Gly Lys Val Arg Thr Arg Val Asn Thr Ala Val Leu Ala Gln
            1380                1385                1390

Asp Phe Gly Lys Thr Arg Ser Ala Glu Trp Gly Val Asn Ala Glu Ile
            1395                1400                1405

Lys Gly Phe Thr Leu Ser Leu His Ala Ala Ala Lys Gly Pro Gln
            1410                1415                1420

Leu Glu Ala Gln His Ser Ala Gly Ile Lys Leu Gly Tyr Arg Trp
1425                1430                1435

<210> SEQ ID NO 74
<211> LENGTH: 164
<212> TYPE: PRT
<213> ORGANISM: Neisseria meningitidis

<400> SEQUENCE: 74

Met Lys Lys Asn Ile Leu Glu Phe Trp Val Gly Leu Phe Val Leu Ile

```
1               5                   10                  15
Gly Ala Ala Ala Val Ala Phe Leu Ala Phe Arg Val Ala Gly Gly Ala
                20                  25                  30
Ala Phe Gly Gly Ser Asp Lys Thr Tyr Ala Val Tyr Ala Asp Phe Gly
                35                  40                  45
Asp Ile Gly Gly Leu Lys Val Asn Ala Pro Val Lys Ser Ala Gly Val
            50                  55                  60
Leu Val Gly Arg Val Gly Ala Ile Gly Leu Asp Pro Lys Ser Tyr Gln
65                  70                  75                  80
Ala Arg Val Arg Leu Asp Leu Asp Gly Lys Tyr Gln Phe Ser Ser Asp
                85                  90                  95
Val Ser Ala Gln Ile Leu Thr Ser Gly Leu Leu Gly Glu Gln Tyr Ile
                100                 105                 110
Gly Leu Gln Gln Gly Gly Asp Thr Glu Asn Leu Ala Ala Gly Asp Thr
                115                 120                 125
Ile Ser Val Thr Ser Ser Ala Met Val Leu Glu Asn Leu Ile Gly Lys
            130                 135                 140
Phe Met Thr Ser Phe Ala Glu Lys Asn Ala Asp Gly Gly Asn Ala Glu
145                 150                 155                 160
Lys Ala Ala Glu

<210> SEQ ID NO 75
<211> LENGTH: 21
<212> TYPE: PRT
<213> ORGANISM: Erwinia carotovora

<400> SEQUENCE: 75

Met Lys Tyr Leu Leu Pro Thr Ala Ala Ala Gly Leu Leu Leu Ala Ala
1               5                   10                  15

Gln Pro Ala Met Ala
                20

<210> SEQ ID NO 76
<211> LENGTH: 608
<212> TYPE: PRT
<213> ORGANISM: Neisseria meningitidis

<400> SEQUENCE: 76

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
                20                  25                  30

Ile Arg Gln Val Leu Asp Arg Gln His Phe Glu Pro Asp Gly Lys Tyr
                35                  40                  45

His Leu Phe Gly Ser Arg Gly Glu Leu Ala Glu Arg Ser Gly His Ile
            50                  55                  60

Gly Leu Gly Lys Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
                100                 105                 110

Asp Ser Asp Glu Ala Gly Ser Pro Val Asp Gly Phe Ser Leu Tyr Arg
                115                 120                 125

Ile His Trp Asp Gly Tyr Glu His Pro Ala Asp Gly Tyr Asp Gly
            130                 135                 140
```

```
Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
            165                 170                 175

Asp Asn Arg Ser Thr Gly Gln Arg Leu Ala Asp Arg Phe His Asn Ala
        180                 185                 190

Gly Ser Met Leu Thr Gln Gly Val Gly Asp Gly Phe Lys Arg Ala Thr
    195                 200                 205

Arg Tyr Ser Pro Glu Leu Asp Arg Ser Gly Asn Ala Ala Glu Ala Phe
210                 215                 220

Asn Gly Thr Ala Asp Ile Val Lys Asn Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
    290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Ile Thr Ala
                325                 330                 335

His Pro Ile Lys Arg Ser Gln Met Gly Ala Ile Ala Leu Pro Lys Gly
            340                 345                 350

Lys Ser Ala Val Ser Asp Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Ile Pro Lys Ala
        435                 440                 445

Lys Pro Val Ser Asp Ala Lys Pro Arg Trp Glu Val Asp Arg Lys Leu
    450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
            500                 505                 510

Gly Met Gly Lys Phe Thr Asp Ser Met Asn Asp Lys Ala Phe Ser Arg
        515                 520                 525

Leu Val Lys Ser Val Lys Glu Asn Gly Phe Thr Asn Pro Val Val Glu
    530                 535                 540

Tyr Val Glu Ile Asn Gly Lys Ala Tyr Ile Val Arg Gly Asn Asn Arg
545                 550                 555                 560
```

Val Phe Ala Ala Glu Tyr Leu Gly Arg Ile His Glu Leu Lys Phe Lys
            565                 570                 575

Lys Val Asp Phe Pro Val Pro Asn Thr Ser Trp Lys Asn Pro Thr Asp
        580                 585                 590

Val Leu Asn Glu Ser Gly Asn Val Lys Arg Pro Arg Tyr Arg Ser Lys
        595                 600                 605

<210> SEQ ID NO 77
<211> LENGTH: 584
<212> TYPE: PRT
<213> ORGANISM: Artificial Sequence
<220> FEATURE:
<223> OTHER INFORMATION: Neisseria meningitidis

<400> SEQUENCE: 77

Ser Asp Leu Ala Asn Asp Ser Phe Ile Arg Gln Val Leu Asp Arg Gln
1               5                   10                  15

His Phe Glu Pro Asp Gly Lys Tyr His Leu Phe Gly Ser Arg Gly Glu
            20                  25                  30

Leu Ala Glu Arg Ser Gly His Ile Gly Leu Gly Lys Ile Gln Ser His
        35                  40                  45

Gln Leu Gly Asn Leu Met Ile Gln Gln Ala Ala Ile Lys Gly Asn Ile
    50                  55                  60

Gly Tyr Ile Val Arg Phe Ser Asp Gly His Glu Val His Ser Pro
65                  70                  75                  80

Phe Asp Asn His Ala Ser His Ser Asp Ser Asp Glu Ala Gly Ser Pro
                85                  90                  95

Val Asp Gly Phe Ser Leu Tyr Arg Ile His Trp Asp Gly Tyr Glu His
            100                 105                 110

His Pro Ala Asp Gly Tyr Asp Gly Pro Gln Gly Gly Tyr Pro Ala
        115                 120                 125

Pro Lys Gly Ala Arg Asp Ile Tyr Ser Tyr Asp Ile Lys Gly Val Ala
    130                 135                 140

Gln Asn Ile Arg Leu Asn Leu Thr Asp Asn Arg Ser Thr Gly Gln Arg
145                 150                 155                 160

Leu Ala Asp Arg Phe His Asn Ala Gly Ser Met Leu Thr Gln Gly Val
                165                 170                 175

Gly Asp Gly Phe Lys Arg Ala Thr Arg Tyr Ser Pro Glu Leu Asp Arg
            180                 185                 190

Ser Gly Asn Ala Ala Glu Ala Phe Asn Gly Thr Ala Asp Ile Val Lys
        195                 200                 205

Asn Ile Ile Gly Ala Ala Gly Glu Ile Val Gly Ala Gly Asp Ala Val
    210                 215                 220

Gln Gly Ile Ser Glu Gly Ser Asn Ile Ala Val Met His Gly Leu Gly
225                 230                 235                 240

Leu Leu Ser Thr Glu Asn Lys Met Ala Arg Ile Asn Asp Leu Ala Asp
                245                 250                 255

Met Ala Gln Leu Lys Asp Tyr Ala Ala Ala Ile Arg Asp Trp Ala
            260                 265                 270

Val Gln Asn Pro Asn Ala Ala Gln Gly Ile Glu Ala Val Ser Asn Ile
        275                 280                 285

Phe Met Ala Ala Ile Pro Ile Lys Gly Ile Gly Ala Val Arg Gly Lys
    290                 295                 300

Tyr Gly Leu Gly Gly Ile Thr Ala His Pro Ile Lys Arg Ser Gln Met
305                 310                 315                 320

-continued

```
Gly Ala Ile Ala Leu Pro Lys Gly Lys Ser Ala Val Ser Asp Asn Phe
                325                 330                 335

Ala Asp Ala Ala Tyr Ala Lys Tyr Pro Ser Pro Tyr His Ser Arg Asn
            340                 345                 350

Ile Arg Ser Asn Leu Glu Gln Arg Tyr Gly Lys Glu Asn Ile Thr Ser
        355                 360                 365

Ser Thr Val Pro Pro Ser Asn Gly Lys Asn Val Lys Leu Ala Asp Gln
    370                 375                 380

Arg His Pro Lys Thr Gly Val Pro Phe Asp Gly Lys Gly Phe Pro Asn
385                 390                 395                 400

Phe Glu Lys His Val Lys Tyr Asp Thr Lys Leu Asp Ile Gln Glu Leu
                405                 410                 415

Ser Gly Gly Gly Ile Pro Lys Ala Lys Pro Val Ser Asp Ala Lys Pro
            420                 425                 430

Arg Trp Glu Val Asp Arg Lys Leu Asn Lys Leu Thr Thr Arg Glu Gln
        435                 440                 445

Val Glu Lys Asn Val Gln Glu Ile Arg Asn Gly Asn Lys Asn Ser Asn
    450                 455                 460

Phe Ser Gln His Ala Gln Leu Glu Arg Glu Ile Asn Lys Leu Lys Ser
465                 470                 475                 480

Ala Asp Glu Ile Asn Phe Ala Asp Gly Met Gly Lys Phe Thr Asp Ser
                485                 490                 495

Met Asn Asp Lys Ala Phe Ser Arg Leu Val Lys Ser Val Lys Glu Asn
            500                 505                 510

Gly Phe Thr Asn Pro Val Val Glu Tyr Val Gly Ile Asn Gly Lys Ala
        515                 520                 525

Tyr Ile Val Arg Gly Asn Asn Arg Val Phe Ala Ala Glu Tyr Leu Gly
    530                 535                 540

Arg Ile His Glu Leu Lys Phe Lys Lys Val Asp Phe Pro Val Pro Asn
545                 550                 555                 560

Thr Ser Trp Lys Asn Pro Thr Asp Val Leu Asn Glu Ser Gly Asn Val
                565                 570                 575

Lys Arg Pro Arg Tyr Arg Ser Lys
            580
```

<210> SEQ ID NO 78
<211> LENGTH: 364
<212> TYPE: PRT
<213> ORGANISM: Neisseria meningitidis

<400> SEQUENCE: 78

```
Met Ser Met Lys His Phe Pro Ala Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110
```

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
        130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 79
<211> LENGTH: 427
<212> TYPE: PRT
<213> ORGANISM: Neisseria meningitidis

<400> SEQUENCE: 79

Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser

```
                  115                 120                 125
Asn Pro Ala Pro Ala Asn Gly Gly Ser Asn Phe Gly Arg Val Asp Leu
        130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
        210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285

Tyr Gly Ala Glu Lys Leu Pro Gly Gly Ser Tyr Ala Leu Arg Val Gln
        290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
        355                 360                 365

Lys Ala Ala Ile Asp Gly Asn Gly Phe Lys Gly Thr Trp Thr Glu Asn
        370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
            420                 425

<210> SEQ ID NO 80
<211> LENGTH: 410
<212> TYPE: PRT
<213> ORGANISM: Artificial Sequence
<220> FEATURE:
<223> OTHER INFORMATION: Neisseria meningitidis

<400> SEQUENCE: 80

Cys Gly Gly Gly Gly Gly Ser Pro Asp Val Lys Ser Ala Asp Thr
1               5                   10                  15

Leu Ser Lys Pro Ala Ala Pro Val Val Ala Glu Lys Glu Thr Glu Val
                20                  25                  30

Lys Glu Asp Ala Pro Gln Ala Gly Ser Gln Gly Gln Gly Ala Pro Ser
            35                  40                  45

Thr Gln Gly Ser Gln Asp Met Ala Ala Val Ser Ala Glu Asn Thr Gly
```

```
            50                  55                  60
Asn Gly Gly Ala Ala Thr Thr Asp Lys Pro Lys Asn Glu Asp Glu Gly
 65                  70                  75                  80

Pro Gln Asn Asp Met Pro Gln Asn Ser Ala Glu Ser Ala Asn Gln Thr
                 85                  90                  95

Gly Asn Asn Gln Pro Ala Asp Ser Ser Asp Ser Ala Pro Ala Ser Asn
            100                 105                 110

Pro Ala Pro Ala Asn Gly Gly Ser Asn Phe Gly Arg Val Asp Leu Ala
        115                 120                 125

Asn Gly Val Leu Ile Asp Gly Pro Ser Gln Asn Ile Thr Leu Thr His
130                 135                 140

Cys Lys Gly Asp Ser Cys Asn Gly Asp Asn Leu Leu Asp Glu Glu Ala
145                 150                 155                 160

Pro Ser Lys Ser Glu Phe Glu Asn Leu Asn Ser Glu Arg Ile Glu
                165                 170                 175

Lys Tyr Lys Lys Asp Gly Lys Ser Asp Lys Phe Thr Asn Leu Val Ala
            180                 185                 190

Thr Ala Val Gln Ala Asn Gly Thr Asn Lys Tyr Val Ile Ile Tyr Lys
        195                 200                 205

Asp Lys Ser Ala Ser Ser Ser Ala Arg Phe Arg Arg Ser Ala Arg
210                 215                 220

Ser Arg Arg Ser Leu Pro Ala Glu Met Pro Leu Ile Pro Val Asn Gln
225                 230                 235                 240

Ala Asp Thr Leu Ile Val Asp Gly Glu Ala Val Ser Leu Thr Gly His
                245                 250                 255

Ser Gly Asn Ile Phe Ala Pro Glu Gly Asn Tyr Arg Tyr Leu Thr Tyr
            260                 265                 270

Gly Ala Glu Lys Leu Pro Gly Gly Ser Tyr Ala Leu Arg Val Gln Gly
        275                 280                 285

Glu Pro Ala Lys Gly Glu Met Leu Ala Gly Thr Ala Val Tyr Asn Gly
290                 295                 300

Glu Val Leu His Phe His Thr Glu Asn Gly Arg Pro Tyr Pro Thr Arg
305                 310                 315                 320

Gly Arg Phe Ala Ala Lys Val Asp Phe Gly Ser Lys Ser Val Asp Gly
                325                 330                 335

Ile Ile Asp Ser Gly Asp Asp Leu His Met Gly Thr Gln Lys Phe Lys
            340                 345                 350

Ala Ala Ile Asp Gly Asn Gly Phe Lys Gly Thr Trp Thr Glu Asn Gly
        355                 360                 365

Gly Gly Asp Val Ser Gly Arg Phe Tyr Gly Pro Ala Gly Glu Glu Val
370                 375                 380

Ala Gly Lys Tyr Ser Tyr Arg Pro Thr Asp Ala Glu Lys Gly Gly Phe
385                 390                 395                 400

Gly Val Phe Ala Gly Lys Lys Glu Gln Asp
                405                 410

<210> SEQ ID NO 81
<211> LENGTH: 9
<212> TYPE: PRT
<213> ORGANISM: Artificial Sequence
<220> FEATURE:
<223> OTHER INFORMATION: Neisseria meningitidis

<400> SEQUENCE: 81

His Arg Val Trp Val Glu Thr Ala His
```

```
<210> SEQ ID NO 82
<211> LENGTH: 16
<212> TYPE: PRT
<213> ORGANISM: Artificial Sequence
<220> FEATURE:
<223> OTHER INFORMATION: Neisseria meningitidis

<400> SEQUENCE: 82

Ala Thr Tyr Lys Val Asp Glu Tyr His Ala Asn Ala Arg Phe Ala Phe
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: Neisseria meningitidis

<400> SEQUENCE: 83

Met Glu Phe Phe Ile Ile Leu Leu Ala
1               5

<210> SEQ ID NO 84
<211> LENGTH: 488
<212> TYPE: PRT
<213> ORGANISM: Artificial Sequence
<220> FEATURE:
<223> OTHER INFORMATION: Neisseria meningitidis

<400> SEQUENCE: 84

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
        210                 215                 220
```

-continued

```
Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
            245                 250                 255

Asn Tyr Lys Lys Asp Gly Lys Asn Asp Lys Phe Val Gly Leu Val Ala
        260                 265                 270

Asp Ser Val Gln Met Lys Gly Ile Asn Gln Tyr Ile Ile Phe Tyr Lys
    275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485
```

```
<210> SEQ ID NO 85
<211> LENGTH: 712
<212> TYPE: PRT
<213> ORGANISM: Artificial Sequence
<220> FEATURE:
<223> OTHER INFORMATION: Neisseria meningitidis

<400> SEQUENCE: 85
```

```
Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Asp Thr Glu Ala Pro Arg Pro Ala Pro Lys Tyr Gln Asp Val Phe
        35                  40                  45

Ser Glu Lys Pro Gln Ala Gln Leu Asp Gln Gly Gly Tyr Gly Phe Ala
    50                  55                  60

Met Arg Leu Lys Arg Arg Asn Trp Tyr Pro Gln Ala Lys Glu Asp Glu
65                  70                  75                  80

Val Lys Leu Asp Glu Ser Asp Trp Glu Ala Thr Gly Leu Pro Asp Glu
                85                  90                  95
```

```
Pro Lys Glu Leu Pro Lys Arg Gln Lys Ser Val Ile Glu Lys Val Glu
            100                 105                 110

Thr Asp Ser Asp Asn Asn Ile Tyr Ser Ser Pro Tyr Leu Lys Pro Ser
            115                 120                 125

Asn His Gln Asn Gly Asn Thr Gly Asn Gly Ile Asn Gln Pro Lys Asn
            130                 135                 140

Gln Ala Lys Asp Tyr Glu Asn Phe Lys Tyr Val Tyr Ser Gly Trp Phe
145                 150                 155                 160

Tyr Lys His Ala Lys Arg Glu Phe Asn Leu Lys Val Glu Pro Lys Ser
                165                 170                 175

Ala Lys Asn Gly Asp Asp Gly Tyr Ile Phe Tyr His Gly Lys Glu Pro
            180                 185                 190

Ser Arg Gln Leu Pro Ala Ser Gly Lys Ile Thr Tyr Lys Gly Val Trp
            195                 200                 205

His Phe Ala Thr Asp Thr Lys Lys Gly Gln Lys Phe Arg Glu Ile Ile
            210                 215                 220

Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
                245                 250                 255

Gln Glu Gly Tyr Gly Phe Thr Ser Asn Leu Glu Val Asp Phe His Asn
            260                 265                 270

Lys Lys Leu Thr Gly Lys Leu Ile Arg Asn Asn Ala Asn Thr Asp Asn
            275                 280                 285

Asn Gln Ala Thr Thr Thr Gln Tyr Tyr Ser Leu Glu Ala Gln Val Thr
            290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Ser Leu
                325                 330                 335

Ser Gly Gly Phe Phe Gly Pro Gln Gly Glu Glu Leu Gly Phe Arg Phe
            340                 345                 350

Leu Ser Asp Asp Gln Lys Val Ala Val Val Gly Ser Ala Lys Thr Lys
            355                 360                 365

Asp Lys Pro Ala Asn Gly Asn Thr Ala Ala Ala Ser Gly Gly Thr Asp
            370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
            435                 440                 445

Gln Ala Asn Gln Gly Thr Asn Gly Gly Thr Ala Phe Thr Arg Lys Phe
            450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
            500                 505                 510
```

```
Leu Lys Tyr Gly Met Leu Thr Arg Lys Asn Ser Lys Ser Ala Met Gln
        515                 520                 525

Ala Gly Glu Ser Ser Ser Gln Ala Asp Ala Lys Thr Glu Gln Val Glu
    530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710
```

<210> SEQ ID NO 86
<211> LENGTH: 274
<212> TYPE: PRT
<213> ORGANISM: Artificial Sequence
<220> FEATURE:
<223> OTHER INFORMATION: Neisseria meningitidis

<400> SEQUENCE: 86

```
Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160
```

```
Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 87
<211> LENGTH: 1082
<212> TYPE: PRT
<213> ORGANISM: Artificial Sequence
<220> FEATURE:
<223> OTHER INFORMATION: Neisseria meningitidis

<400> SEQUENCE: 87

Met Arg Thr Thr Pro Thr Phe Pro Thr Lys Thr Phe Lys Pro Thr Ala
1               5                   10                  15

Met Ala Leu Ala Val Ala Thr Thr Leu Ser Ala Cys Leu Gly Gly Gly
            20                  25                  30

Gly Gly Gly Thr Ser Ala Pro Asp Phe Asn Ala Gly Gly Thr Gly Ile
        35                  40                  45

Gly Ser Asn Ser Arg Ala Thr Thr Ala Lys Ser Ala Ala Val Ser Tyr
    50                  55                  60

Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
        115                 120                 125

Gly Arg Gly Val Glu Val Gly Ile Val Asp Thr Gly Glu Ser Val Gly
    130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Gly Lys Asp Ile Glu Ala Ser Phe Asp Asp Glu Ala Val
            180                 185                 190

Ile Glu Thr Glu Ala Lys Pro Thr Asp Ile Arg His Val Lys Glu Ile
        195                 200                 205

Gly His Ile Asp Leu Val Ser His Ile Ile Gly Gly Arg Ser Val Asp
    210                 215                 220

Gly Arg Pro Ala Gly Gly Ile Ala Pro Asp Ala Thr Leu His Ile Met
225                 230                 235                 240

Asn Thr Asn Asp Glu Thr Lys Asn Glu Met Met Val Ala Ala Ile Arg
```

```
            245                 250                 255
Asn Ala Trp Val Lys Leu Gly Glu Arg Gly Val Arg Ile Val Asn Asn
            260                 265                 270

Ser Phe Gly Thr Thr Ser Arg Ala Gly Thr Ala Asp Leu Phe Gln Ile
            275                 280                 285

Ala Asn Ser Glu Glu Gln Tyr Arg Gln Ala Leu Leu Asp Tyr Ser Gly
            290                 295                 300

Gly Asp Lys Thr Asp Glu Gly Ile Arg Leu Met Gln Gln Ser Asp Tyr
305                 310                 315                 320

Gly Asn Leu Ser Tyr His Ile Arg Asn Lys Asn Met Leu Phe Ile Phe
            325                 330                 335

Ser Thr Gly Asn Asp Ala Gln Ala Gln Pro Asn Thr Tyr Ala Leu Leu
            340                 345                 350

Pro Phe Tyr Glu Lys Asp Ala Gln Lys Gly Ile Ile Thr Val Ala Gly
            355                 360                 365

Val Asp Arg Ser Gly Glu Lys Phe Lys Arg Glu Met Tyr Gly Glu Pro
            370                 375                 380

Gly Thr Glu Pro Leu Glu Tyr Gly Ser Asn His Cys Gly Ile Thr Ala
385                 390                 395                 400

Met Trp Cys Leu Ser Ala Pro Tyr Glu Ala Ser Val Arg Phe Thr Arg
            405                 410                 415

Thr Asn Pro Ile Gln Ile Ala Gly Thr Ser Phe Ser Ala Pro Ile Val
            420                 425                 430

Thr Gly Thr Ala Ala Leu Leu Leu Gln Lys Tyr Pro Trp Met Ser Asn
            435                 440                 445

Asp Asn Leu Arg Thr Thr Leu Leu Thr Thr Ala Gln Asp Ile Gly Ala
            450                 455                 460

Val Gly Val Asp Ser Lys Phe Gly Trp Gly Leu Leu Asp Ala Gly Lys
465                 470                 475                 480

Ala Met Asn Gly Pro Ala Ser Phe Pro Phe Gly Asp Phe Thr Ala Asp
            485                 490                 495

Thr Lys Gly Thr Ser Asp Ile Ala Tyr Ser Phe Arg Asn Asp Ile Ser
            500                 505                 510

Gly Thr Gly Gly Leu Ile Lys Lys Gly Gly Ser Gln Leu Gln Leu His
            515                 520                 525

Gly Asn Asn Thr Tyr Thr Gly Lys Thr Ile Glu Gly Gly Ser Leu
            530                 535                 540

Val Leu Tyr Gly Asn Asn Lys Ser Asp Met Arg Val Glu Thr Lys Gly
545                 550                 555                 560

Ala Leu Ile Tyr Asn Gly Ala Ala Ser Gly Gly Ser Leu Asn Ser Asp
            565                 570                 575

Gly Ile Val Tyr Leu Ala Asp Thr Asp Gln Ser Gly Ala Asn Glu Thr
            580                 585                 590

Val His Ile Lys Gly Ser Leu Gln Leu Asp Gly Lys Gly Thr Leu Tyr
            595                 600                 605

Thr Arg Leu Gly Lys Leu Leu Lys Val Asp Gly Thr Ala Ile Ile Gly
            610                 615                 620

Gly Lys Leu Tyr Met Ser Ala Arg Gly Lys Gly Ala Gly Tyr Leu Asn
625                 630                 635                 640

Ser Thr Gly Arg Arg Val Pro Phe Leu Ser Ala Ala Lys Ile Gly Gln
            645                 650                 655

Asp Tyr Ser Phe Phe Thr Asn Ile Glu Thr Asp Gly Gly Leu Leu Ala
            660                 665                 670
```

```
Ser Leu Asp Ser Val Glu Lys Thr Ala Gly Ser Glu Gly Asp Thr Leu
            675                 680                 685

Ser Tyr Tyr Val Arg Arg Gly Asn Ala Ala Arg Thr Ala Ser Ala Ala
    690                 695                 700

Ala His Ser Ala Pro Ala Gly Leu Lys His Ala Val Glu Gln Gly Gly
705                 710                 715                 720

Ser Asn Leu Glu Asn Leu Met Val Glu Leu Asp Ala Ser Glu Ser Ser
                725                 730                 735

Ala Thr Pro Glu Thr Val Glu Thr Ala Ala Asp Arg Thr Asp Met
                740                 745                 750

Pro Gly Ile Arg Pro Tyr Gly Ala Thr Phe Arg Ala Ala Ala Val
            755                 760                 765

Gln His Ala Asn Ala Ala Asp Gly Val Arg Ile Phe Asn Ser Leu Ala
    770                 775                 780

Ala Thr Val Tyr Ala Asp Ser Thr Ala Ala His Ala Asp Met Gln Gly
785                 790                 795                 800

Arg Arg Leu Lys Ala Val Ser Asp Gly Leu Asp His Asn Gly Thr Gly
                805                 810                 815

Leu Arg Val Ile Ala Gln Thr Gln Gln Asp Gly Gly Thr Trp Glu Gln
            820                 825                 830

Gly Gly Val Glu Gly Lys Met Arg Gly Ser Thr Gln Thr Val Gly Ile
    835                 840                 845

Ala Ala Lys Thr Gly Glu Asn Thr Thr Ala Ala Thr Leu Gly Met
850                 855                 860

Gly Arg Ser Thr Trp Ser Glu Asn Ser Ala Asn Ala Lys Thr Asp Ser
865                 870                 875                 880

Ile Ser Leu Phe Ala Gly Ile Arg His Asp Ala Gly Asp Ile Gly Tyr
                885                 890                 895

Leu Lys Gly Leu Phe Ser Tyr Gly Arg Tyr Lys Asn Ser Ile Ser Arg
            900                 905                 910

Ser Thr Gly Ala Asp Glu His Ala Glu Gly Ser Val Asn Gly Thr Leu
    915                 920                 925

Met Gln Leu Gly Ala Leu Gly Gly Val Asn Val Pro Phe Ala Ala Thr
930                 935                 940

Gly Asp Leu Thr Val Glu Gly Gly Leu Arg Tyr Asp Leu Leu Lys Gln
945                 950                 955                 960

Asp Ala Phe Ala Glu Lys Gly Ser Ala Leu Gly Trp Ser Gly Asn Ser
                965                 970                 975

Leu Thr Glu Gly Thr Leu Val Gly Leu Ala Gly Leu Lys Leu Ser Gln
            980                 985                 990

Pro Leu Ser Asp Lys Ala Val Leu Phe Ala Thr Ala Gly Val Glu Arg
    995                 1000                1005

Asp Leu Asn Gly Arg Asp Tyr Thr Val Thr Gly Gly Phe Thr Gly Ala
    1010                1015                1020

Thr Ala Ala Thr Gly Lys Thr Gly Ala Arg Asn Met Pro His Thr Arg
1025                1030                1035                1040

Leu Val Ala Gly Leu Gly Ala Asp Val Glu Phe Gly Asn Gly Trp Asn
                1045                1050                1055

Gly Leu Ala Arg Tyr Ser Tyr Ala Gly Ser Lys Gln Tyr Gly Asn His
            1060                1065                1070

Ser Gly Arg Val Gly Val Gly Tyr Arg Phe
    1075                1080
```

<210> SEQ ID NO 88
<211> LENGTH: 2505
<212> TYPE: DNA
<213> ORGANISM: Artificial Sequence
<220> FEATURE:
<223> OTHER INFORMATION: Synthetic construct

<400> SEQUENCE: 88

| | | | | | |
|---|---|---|---|---|---|
| atggctagcc | ccgatgttaa | atcggcggac | acgctgtcaa | aaccggccgc | tcctgttgtt | 60 |
| gctgaaaaag | agacagaggt | aaaagaagat | gcgccacagg | caggttctca | aggacagggc | 120 |
| gcgccatcca | cacaaggcag | ccaagatatg | gcggcagttt | cggcagaaaa | tacaggcaat | 180 |
| ggcggtgcgg | caacaacgga | caaacccaaa | aatgaagacg | agggaccgca | aaatgatatg | 240 |
| ccgcaaaatt | ccgccgaatc | cgcaaatcaa | acagggaaca | accaacccgc | cgattcttca | 300 |
| gattccgccc | ccgcgtcaaa | ccctgcacct | gcgaatggcg | gtagcaattt | tggaagggtt | 360 |
| gatttggcta | atggcgtttt | gattgatggg | ccgtcgcaaa | atataacgtt | gacccactgt | 420 |
| aaaggcgatt | cttgtaatgg | tgataattta | ttggatgaag | aagcaccgtc | aaaatcagaa | 480 |
| tttgaaaatt | taaatgagtc | tgaacgaatt | gagaaatata | agaaagatgg | gaaaagcgat | 540 |
| aaatttacta | atttggttgc | gacagcagtt | caagctaatg | gaactaacaa | atatgtcatc | 600 |
| atttataaag | acaagtccgc | ttcatcttca | tctgcgcgat | tcaggcgttc | tgcacggtcg | 660 |
| aggaggtcgc | ttcctgccga | gatgccgcta | atccccgtca | atcaggcgga | tacgctgatt | 720 |
| gtcgatgggg | aagcggtcag | cctgacgggg | cattccggca | atatcttcgc | gcccgaaggg | 780 |
| aattaccggt | atctgactta | cggggcgaa | aaattgcccg | gcggatcgta | tgccctccgt | 840 |
| gtgcaaggcg | aaccggcaaa | aggcgaaatg | cttgctggca | cggccgtgta | caacggcgaa | 900 |
| gtgctgcatt | ttcatacgga | aaacggccgt | ccgtacccga | ctagaggcag | gtttgccgca | 960 |
| aaagtcgatt | tcggcagcaa | atctgtggac | ggcattatcg | acagcggcga | tgatttgcat | 1020 |
| atgggtacga | aaaaattcaa | agccgccatc | gatggaaacg | gctttaaggg | gacttggacg | 1080 |
| gaaaatggcg | gcggggatgt | tccggaagg | ttttacggcc | cggccggcga | ggaagtggcg | 1140 |
| ggaaaataca | gctatcgccc | gacagatgcg | gaaaagggcg | gattcggcgt | gtttgccggc | 1200 |
| aaaaaagagc | aggatggatc | cggaggagga | ggatgccaaa | gcaagagcat | ccaaaccttt | 1260 |
| ccgcaacccg | acacatccgt | catcaacggc | ccggaccggc | cggtcggcat | ccccgacccc | 1320 |
| gccggaacga | cggtcggcgg | cggcggggcc | gtctataccg | ttgtaccgca | cctgtccctg | 1380 |
| ccccactggg | cggcgcagga | tttcgccaaa | agcctgcaat | ccttccgcct | cggctgcgcc | 1440 |
| aatttgaaaa | accgccaagg | ctggcaggat | gtgtgcgccc | aagcctttca | aaccccgtc | 1500 |
| cattcctttc | aggcaaaaca | gttttttgaa | cgctatttca | cgccgtggca | ggttgcaggc | 1560 |
| aacggaagcc | ttgccggtac | ggttaccggc | tattacgagc | cggtgctgaa | gggcgacgac | 1620 |
| aggcggacgg | cacaagcccg | cttcccgatt | tacggtattc | ccgacgattt | tatctccgtc | 1680 |
| ccctgcctg | ccggtttgcg | gagcggaaaa | gcccttgtcc | gcatcaggca | gacgggaaaa | 1740 |
| aacagcggca | caatcgacaa | taccggcggc | acacataccg | ccgacctctc | ccgattcccc | 1800 |
| atcaccgcgc | gcacaacggc | aatcaaaggc | aggtttgaag | aagccgcctt | cctcccctac | 1860 |
| cacacgcgca | accaaatcaa | cggcggcgcg | cttgacggca | agccccgat | actcggttac | 1920 |
| gccgaagacc | ccgtcgaact | ttttttatg | cacatccaag | gctcgggccg | tctgaaaacc | 1980 |
| ccgtccggca | aatacatccg | catcggctat | gccgacaaaa | acgaacatcc | ctacgtttcc | 2040 |
| atcggacgct | atatggcgga | caaaggctac | ctcaagctcg | gcagacctc | gatgcagggc | 2100 |

```
atcaaagcct atatgcggca aaatccgcaa cgcctcgccg aagttttggg tcaaaacccc   2160
agctatatct ttttccgcga gcttgccgga agcagcaatg acggtcccgt cggcgcactg   2220
ggcacgccgt tgatggggga atatgccggc gcagtcgacc ggcactacat taccttgggc   2280
gcgcccttat ttgtcgccac cgcccatccg gttacccgca aagccctcaa ccgcctgatt   2340
atggcgcagg ataccggcag cgcgattaaa ggcgcggtgc gcgtggatta ttttggggga   2400
tacggcgacg aagccggcga acttgccggc aaacagaaaa ccacggggtta cgtctggcag   2460 ctcctaccca acggtatgaa gcccgaatac cgcccgtaac tcgag              2505
```

<210> SEQ ID NO 89
<211> LENGTH: 832
<212> TYPE: PRT
<213> ORGANISM: Artificial Sequence
<220> FEATURE:
<223> OTHER INFORMATION: Synthetic construct

<400> SEQUENCE: 89

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285
```

-continued

```
Glu Met Leu Ala Gly Thr Ala Val Tyr Asn Gly Glu Val Leu His Phe
290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Asp Val Ser
        355                 360                 365

Gly Arg Phe Tyr Gly Pro Ala Gly Glu Val Ala Gly Lys Tyr Ser
370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Cys Gln Ser Lys Ser
                405                 410                 415

Ile Gln Thr Phe Pro Gln Pro Asp Thr Ser Val Ile Asn Gly Pro Asp
                420                 425                 430

Arg Pro Val Gly Ile Pro Asp Pro Ala Gly Thr Thr Val Gly Gly Gly
                435                 440                 445

Gly Ala Val Tyr Thr Val Val Pro His Leu Ser Leu Pro His Trp Ala
450                 455                 460

Ala Gln Asp Phe Ala Lys Ser Leu Gln Ser Phe Arg Leu Gly Cys Ala
465                 470                 475                 480

Asn Leu Lys Asn Arg Gln Gly Trp Gln Asp Val Cys Ala Gln Ala Phe
                485                 490                 495

Gln Thr Pro Val His Ser Phe Gln Ala Lys Gln Phe Phe Glu Arg Tyr
                500                 505                 510

Phe Thr Pro Trp Gln Val Ala Gly Asn Gly Ser Leu Ala Gly Thr Val
            515                 520                 525

Thr Gly Tyr Tyr Glu Pro Val Leu Lys Gly Asp Arg Arg Thr Ala
530                 535                 540

Gln Ala Arg Phe Pro Ile Tyr Gly Ile Pro Asp Asp Phe Ile Ser Val
545                 550                 555                 560

Pro Leu Pro Ala Gly Leu Arg Ser Gly Lys Ala Leu Val Arg Ile Arg
                565                 570                 575

Gln Thr Gly Lys Asn Ser Gly Thr Ile Asp Asn Thr Gly Gly Thr His
                580                 585                 590

Thr Ala Asp Leu Ser Arg Phe Pro Ile Thr Ala Arg Thr Thr Ala Ile
            595                 600                 605

Lys Gly Arg Phe Glu Gly Ser Arg Phe Leu Pro Tyr His Thr Arg Asn
610                 615                 620

Gln Ile Asn Gly Gly Ala Leu Asp Gly Lys Ala Pro Ile Leu Gly Tyr
625                 630                 635                 640

Ala Glu Asp Pro Val Glu Leu Phe Phe Met His Ile Gln Gly Ser Gly
                645                 650                 655

Arg Leu Lys Thr Pro Ser Gly Lys Tyr Ile Arg Ile Gly Tyr Ala Asp
                660                 665                 670

Lys Asn Glu His Pro Tyr Val Ser Ile Gly Arg Tyr Met Ala Asp Lys
                675                 680                 685

Gly Tyr Leu Lys Leu Gly Gln Thr Ser Met Gln Gly Ile Lys Ala Tyr
690                 695                 700

Met Arg Gln Asn Pro Gln Arg Leu Ala Glu Val Leu Gly Gln Asn Pro
```

```
                705                 710                 715                 720
Ser Tyr Ile Phe Phe Arg Glu Leu Ala Gly Ser Ser Asn Asp Gly Pro
                    725                 730                 735

Val Gly Ala Leu Gly Thr Pro Leu Met Gly Glu Tyr Ala Gly Ala Val
                740                 745                 750

Asp Arg His Tyr Ile Thr Leu Gly Ala Pro Leu Phe Val Ala Thr Ala
                    755                 760                 765

His Pro Val Thr Arg Lys Ala Leu Asn Arg Leu Ile Met Ala Gln Asp
        770                 775                 780

Thr Gly Ser Ala Ile Lys Gly Ala Val Arg Val Asp Tyr Phe Trp Gly
785                 790                 795                 800

Tyr Gly Asp Glu Ala Gly Glu Leu Ala Gly Lys Gln Lys Thr Thr Gly
                    805                 810                 815

Tyr Val Trp Gln Leu Leu Pro Asn Gly Met Lys Pro Glu Tyr Arg Pro
                820                 825                 830

<210> SEQ ID NO 90
<211> LENGTH: 1746
<212> TYPE: DNA
<213> ORGANISM: Artificial Sequence
<220> FEATURE:
<223> OTHER INFORMATION: Synthetic construct

<400> SEQUENCE: 90
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaaccgc cgattcttca     300
gattccgccc ccgcgtcaaa ccctgcacct gcgaatggcg gtagcaattt tggaagggtt     360
gatttggcta atgcgttttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg gaaaagcgat     540
aaatttacta atttggttgc gacagcagtt caagctaatg gaactaacaa atatgtcatc     600
atttataaag acaagtccgc ttcatcttca tctgcgcgat tcaggcgttc tgcacggtcg     660
aggaggtcgc ttcctgccga gatgccgcta atccccgtca atcaggcgga tacgctgatt     720
gtcgatgggg aagcggtcag cctgacgggg cattccggca atatcttcgc gcccgaaggg     780
aattaccggt atctgactta cggggcggaa aaattgcccg gcggatcgta tgccctccgt     840
gtgcaaggca aaccggcaaa aggcgaaatg cttgctggca cggccgtgta acggcgaa      900
gtgctgcatt tcatacgga aaacggccgt ccgtacccga ctagaggcag gtttgccgca     960
aaagtcgatt tcggcagcaa atctgtggac ggcattatcg acagcggcga tgatttgcat    1020
atgggtacgc aaaaaattcaa agccgccatc gatggaaacg gctttaaggg gacttggacg    1080
gaaaatggcg gcggggatgt ttccggaagg ttttacggcc cggccggcga ggaagtggcg    1140
ggaaaataca gctatcgccc gacagatgcg gaaaagggcg gattcggcgt gtttgccggc    1200
aaaaaagagc aggatggatc cggaggagga ggagccacct acaaagtgga cgaatatcac    1260
gccaacgccc gtttcgccat cgaccatttt aacaccagca ccaacgtcgg cggtttttac    1320
ggtctgaccg gttccgtcga gttcgaccaa gcaaaacgcg acggtaaaat cgacatcacc    1380
```

-continued

```
atccccgttg ccaacctgca aagcggttcg caacacttta ccgaccacct gaaatcagcc      1440
gacatcttcg atgccgccca atatccggac atccgctttg tttccaccaa attcaacttc      1500
aacggcaaaa aactggtttc cgttgacggc aacctgacca tgcacggcaa aaccgccccc      1560
gtcaaactca aagccgaaaa attcaactgc taccaaagcc cgatggcgaa accgaagtt       1620 tgcggcggcg acttcagcac caccatcgac cgcaccaaat ggggcgtgga ctacctcgtt      1680
aacgttggta tgaccaaaag cgtccgcatc gacatccaaa tcgaggcagc caaacaataa      1740
ctcgag                                                                1746
```

<210> SEQ ID NO 91
<211> LENGTH: 579
<212> TYPE: PRT
<213> ORGANISM: Artificial Sequence
<220> FEATURE:
<223> OTHER INFORMATION: Synthetic construct

<400> SEQUENCE: 91

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
```

```
                290                 295                 300
His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
                340                 345                 350

Asn Gly Phe Lys Gly Thr Trp Thr Glu Asn Gly Gly Asp Val Ser
            355                 360                 365

Gly Arg Phe Tyr Gly Pro Ala Gly Glu Val Ala Gly Lys Tyr Ser
370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Ala Thr Tyr Lys Val
                405                 410                 415

Asp Glu Tyr His Ala Asn Ala Arg Phe Ala Ile Asp His Phe Asn Thr
                420                 425                 430

Ser Thr Asn Val Gly Gly Phe Tyr Gly Leu Thr Gly Ser Val Glu Phe
                435                 440                 445

Asp Gln Ala Lys Arg Asp Gly Lys Ile Asp Ile Thr Ile Pro Val Ala
                450                 455                 460

Asn Leu Gln Ser Gly Ser Gln His Phe Thr Asp His Leu Lys Ser Ala
465                 470                 475                 480

Asp Ile Phe Asp Ala Ala Gln Tyr Pro Asp Ile Arg Phe Val Ser Thr
                485                 490                 495

Lys Phe Asn Phe Asn Gly Lys Lys Leu Val Ser Val Asp Gly Asn Leu
                500                 505                 510

Thr Met His Gly Lys Thr Ala Pro Val Lys Leu Lys Ala Glu Lys Phe
                515                 520                 525

Asn Cys Tyr Gln Ser Pro Met Ala Lys Thr Glu Val Cys Gly Gly Asp
                530                 535                 540

Phe Ser Thr Thr Ile Asp Arg Thr Lys Trp Gly Val Asp Tyr Leu Val
545                 550                 555                 560

Asn Val Gly Met Thr Lys Ser Val Arg Ile Asp Ile Gln Ile Glu Ala
                565                 570                 575

Ala Lys Gln
```

<210> SEQ ID NO 92
<211> LENGTH: 2388
<212> TYPE: DNA
<213> ORGANISM: Artificial Sequence
<220> FEATURE:
<223> OTHER INFORMATION: Synthetic construct

<400> SEQUENCE: 92

```
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa atgaagacg agggaccgca aaatgatatg     240
ccgcaaaatt ccgccgaatc cgcaaatcaa acagggaaca accaaccgc cgattcttca     300 gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
```

```
aaaggcgatt cttgtaatgg tgataattta ttggatgaag aagcaccgtc aaaatcagaa     480
tttgaaaatt taaatgagtc tgaacgaatt gagaaatata agaaagatgg gaaaagcgat     540
aaatttacta atttggttgc gacagcagtt caagctaatg gaactaacaa atatgtcatc     600
atttataaag acaagtccgc ttcatcttca tctgcgcgat tcaggcgttc tgcacggtcg     660
aggaggtcgc ttcctgccga gatgccgcta atccccgtca atcaggcgga tacgctgatt     720
gtcgatgggg aagcggtcag cctgacgggg cattccggca atatcttcgc gcccgaaggg     780
aattaccggt atctgactta cggggcggaa aaattgcccg gcggatcgta tgccctccgt     840
gtgcaaggcg aaccggcaaa aggcgaaatg cttgctggca cggccgtgta caacggcgaa     900
gtgctgcatt tcatacgga  aaacggccgt ccgtacccga ctagaggcag gtttgccgca     960
aaagtcgatt tcggcagcaa atctgtggac ggcattatcg acagcggcga tgatttgcat    1020
atgggtacgc aaaaattcaa agccgccatc gatggaaacg ctttaaggg gacttggacg     1080 gaaaatggcg gcggggatgt tccggaagg  ttttacggcc cggccggcga ggaagtggcg    1140
ggaaaataca gctatcgccc gacagatgcg gaaaagggcg gattcggcgt gtttgccggc    1200 aaaaagagc  aggatggatc cggaggagga ggagccacaa acgacgacga tgttaaaaaa    1260
gctgccactg tggccattgc tgctgcctac aacaatggcc aagaaatcaa cggttttcaaa   1320 gctggagaga ccatctacga cattgatgaa gacggcacaa ttaccaaaaa agacgcaact    1380
gcagccgatg ttgaagccga cgactttaaa ggtctgggtc tgaaaaaagt cgtgactaac    1440
ctgaccaaaa ccgtcaatga aaacaaacaa acgtcgatg  ccaaagtaaa agctgcagaa    1500
tctgaaatag aaaagttaac aaccaagtta gcagacactg atgccgcttt agcagatact    1560
gatgccgctc tggatgcaac caccaacgcc ttgaataaat tgggagaaaa tataacgaca    1620
tttgctgaag agactaagac aaatatcgta aaaattgatg aaaaattaga agccgtggct    1680
gataccgtcg acaagcatgc cgaagcattc aacgatatcg ccgattcatt ggatgaaacc    1740
aacactaagg cagacgaagc cgtcaaaacc gccaatgaag ccaaacagac ggccgaagaa    1800
accaaacaaa acgtcgatgc caaagtaaaa gctgcagaaa ctgcagcagg caaagccgaa    1860
gctgccgctg gcacagctaa tactgcagcc gacaaggccg aagctgtcgc tgcaaaagtt    1920
accgacatca agctgatat  cgctacgaac aaagataata ttgctaaaaa agcaaacagt    1980
gccgacgtgt acaccagaga agagtctgac agcaaatttg tcagaattga tggtctgaac    2040
gctactaccg aaaaattgga cacacgcttg gcttctgctg aaaaatccat tgccgatcac    2100
gatactcgcc tgaacggttt ggataaaaca gtgtcagacc tgcgcaaaga aacccgccaa    2160
ggccttgcag aacaagccgc gctctccggt ctgttccaac cttacaacgt gggtcggttc    2220
aatgtaacgg ctgcagtcgg cggctacaaa tccgaatcgg cagtcgccat cggtaccggc    2280
ttccgcttta ccgaaaactt tgccgccaaa gcaggcgtgg cagtcggcac ttcgtccggt    2340
tcttccgcag cctaccatgt cggcgtcaat tacgagtggt aactcgag               2388
```

<210> SEQ ID NO 93
<211> LENGTH: 793
<212> TYPE: PRT
<213> ORGANISM: Artificial Sequence
<220> FEATURE:
<223> OTHER INFORMATION: Synthetic construct

<400> SEQUENCE: 93

```
Met Ala Ser Pro Asp Val Lys Ser Ala Asp Thr Leu Ser Lys Pro Ala
1               5                   10                  15
```

Ala Pro Val Val Ala Glu Lys Glu Thr Glu Val Lys Glu Asp Ala Pro
                20                  25                  30

Gln Ala Gly Ser Gln Gly Gln Gly Ala Pro Ser Thr Gln Gly Ser Gln
            35                  40                  45

Asp Met Ala Ala Val Ser Ala Glu Asn Thr Gly Asn Gly Gly Ala Ala
50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Ala Thr Asn Asp Asp
                405                 410                 415

Asp Val Lys Lys Ala Ala Thr Val Ala Ile Ala Ala Tyr Asn Asn
            420                 425                 430

Gly Gln Glu Ile Asn Gly Phe Lys Ala Gly Glu Thr Ile Tyr Asp Ile

```
                435              440              445
        Asp Glu Asp Gly Thr Ile Thr Lys Lys Asp Ala Thr Ala Ala Asp Val
        450              455              460

Glu Ala Asp Asp Phe Lys Gly Leu Gly Leu Lys Lys Val Val Thr Asn
        465              470              475              480

Leu Thr Lys Thr Val Asn Glu Asn Lys Gln Asn Val Asp Ala Lys Val
                         485              490              495

Lys Ala Ala Glu Ser Glu Ile Glu Lys Leu Thr Thr Lys Leu Ala Asp
                    500              505              510

Thr Asp Ala Ala Leu Ala Asp Thr Asp Ala Ala Leu Asp Ala Thr Thr
            515              520              525

Asn Ala Leu Asn Lys Leu Gly Glu Asn Ile Thr Thr Phe Ala Glu Glu
        530              535              540

Thr Lys Thr Asn Ile Val Lys Ile Asp Glu Lys Leu Glu Ala Val Ala
        545              550              555              560

Asp Thr Val Asp Lys His Ala Glu Ala Phe Asn Asp Ile Ala Asp Ser
                         565              570              575

Leu Asp Glu Thr Asn Thr Lys Ala Asp Glu Ala Val Lys Thr Ala Asn
                    580              585              590

Glu Ala Lys Gln Thr Ala Glu Thr Lys Gln Asn Val Asp Ala Lys
                595              600              605

Val Lys Ala Ala Glu Thr Ala Ala Gly Lys Ala Glu Ala Ala Gly
        610              615              620

Thr Ala Asn Thr Ala Ala Asp Lys Ala Glu Ala Val Ala Ala Lys Val
        625              630              635              640

Thr Asp Ile Lys Ala Asp Ile Ala Thr Asn Lys Asp Asn Ile Ala Lys
                         645              650              655

Lys Ala Asn Ser Ala Asp Val Tyr Thr Arg Glu Glu Ser Asp Ser Lys
                    660              665              670

Phe Val Arg Ile Asp Gly Leu Asn Ala Thr Thr Glu Lys Leu Asp Thr
                675              680              685

Arg Leu Ala Ser Ala Glu Lys Ser Ile Ala Asp His Asp Thr Arg Leu
            690              695              700

Asn Gly Leu Asp Lys Thr Val Ser Asp Leu Arg Lys Glu Thr Arg Gln
        705              710              715              720

Gly Leu Ala Glu Gln Ala Ala Leu Ser Gly Leu Phe Gln Pro Tyr Asn
                         725              730              735

Val Gly Arg Phe Asn Val Thr Ala Ala Val Gly Gly Tyr Lys Ser Glu
                    740              745              750

Ser Ala Val Ala Ile Gly Thr Gly Phe Arg Phe Thr Glu Asn Phe Ala
                755              760              765

Ala Lys Ala Gly Val Ala Val Gly Thr Ser Ser Gly Ser Ser Ala Ala
            770              775              780

Tyr His Val Gly Val Asn Tyr Glu Trp
        785              790

<210> SEQ ID NO 94
<211> LENGTH: 2700
<212> TYPE: DNA
<213> ORGANISM: Artificial Sequence
<220> FEATURE:
<223> OTHER INFORMATION: Synthetic construct

<400> SEQUENCE: 94
atggctagcc ccgatgtcaa gtcggcggac acgctgtcaa aacctgccgc ccctgttgtt      60
```

```
tctgaaaaag agacagaggc aaaggaagat gcgccacagg caggttctca aggacagggc    120
gcgccatccg cacaaggcgg tcaagatatg gcggcggttt cggaagaaaa tacaggcaat    180
ggcggtgcgg cagcaacgga caaacccaaa aatgaagacg aggggcgca aaatgatatg     240 ccgcaaaatg ccgccgatac agatagtttg acaccgaatc acaccccggc ttcgaatatg    300
ccggccggaa atatggaaaa ccaagcaccg gatgccgggg aatcggagca gccggcaaac    360
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgc tgattgtcga tggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaaggcg aaatgctcgc gggcacggca   1080
gtgtacaacg gcgaagtgct gcattttcat acggaaaacg gccgtccgtc cccgtccaga   1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260 aagggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggatg ccaaagcaag   1440
agcatccaaa cctttccgca acccgacaca tccgtcatca acggcccgga ccggccggtc   1500
ggcatccccg accccgccgg aacgacggtc ggcggcggcg gggccgtcta taccgttgta   1560
ccgcacctgt ccctgcccca ctgggcggcg caggatttcg ccaaaagcct gcaatccttc   1620
cgcctcggct gcgccaattt gaaaaaccgc caaggctggc aggatgtgtg cgcccaagcc   1680
tttcaaaccc ccgtccattc ctttcaggca aaacagtttt ttgaacgcta tttcacgccg   1740
tggcaggttg caggcaacgg aagccttgcc ggtacggtta ccggctatta cgagccggtg   1800
ctgaagggcg acgacaggcg gacggcacaa gcccgcttcc cgatttacgg tattcccgac   1860
gattttatct ccgtcccccct gcctgccggt ttgcggagcg aaaagcccct tgtccgcatc   1920
aggcagacgg gaaaaaacag cggcacaatc gacaataccg gcggcacaca taccgccgac   1980
ctctcccgat tccccatcac cgcgcgcaca acggcaatca aggcaggtt tgaaggaagc    2040 cgcttcctcc cctaccacac gcgcaaccaa atcaacggcg gcgcgcttga cggcaaagcc   2100
ccgatactcg gttacgccga agaccccgtc gaactttttt ttatgcacat ccaaggctcg   2160
ggccgtctga aaacccgtc cggcaaatac atccgcatcg gctatgccga caaaaacgaa   2220
catccctacg tttccatcgg acgctatatg gcggacaaag gctacctcaa gctcgggcag   2280
acctcgatgc agggcatcaa agcctatatg cggcaaaatc gcaacgcct cgccgaagtt   2340 ttgggtcaaa accccagcta tatcttttt cgcgagcttg ccggaagcag caatgacggt   2400
```

-continued

```
cccgtcggcg cactgggcac gccgttgatg ggggaatatg ccggcgcagt cgaccggcac   2460
tacattacct tgggcgcgcc cttatttgtc gccaccgccc atccggttac ccgcaaagcc   2520
ctcaaccgcc tgattatggc gcaggatacc ggcagcgcga ttaaaggcgc ggtgcgcgtg   2580 gattatttt gggatacgg cgacgaagcc ggcgaacttg ccggcaaaca gaaaaccacg    2640
ggttacgtct ggcagctcct acccaacggt atgaagcccg aataccgccc gtaaaagctt   2700
```

<210> SEQ ID NO 95
<211> LENGTH: 897
<212> TYPE: PRT
<213> ORGANISM: Artificial Sequence
<220> FEATURE:
<223> OTHER INFORMATION: Synthetic construct

<400> SEQUENCE: 95

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320
```

```
Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
            355                 360                 365

Phe His Thr Glu Asn Gly Arg Pro Ser Pro Ser Arg Gly Arg Phe Ala
        370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Glu Val Ala Gly Lys Tyr
            435                 440                 445

Ser Tyr Arg Pro Thr Asp Ala Glu Lys Gly Gly Phe Gly Val Phe Ala
        450                 455                 460

Gly Lys Lys Glu Gln Asp Gly Ser Gly Gly Gly Cys Gln Ser Lys
465                 470                 475                 480

Ser Ile Gln Thr Phe Pro Gln Pro Asp Thr Ser Val Ile Asn Gly Pro
                485                 490                 495

Asp Arg Pro Val Gly Ile Pro Asp Pro Ala Gly Thr Thr Val Gly Gly
                500                 505                 510

Gly Gly Ala Val Tyr Thr Val Val Pro His Leu Ser Leu Pro His Trp
            515                 520                 525

Ala Ala Gln Asp Phe Ala Lys Ser Leu Gln Ser Phe Arg Leu Gly Cys
        530                 535                 540

Ala Asn Leu Lys Asn Arg Gln Gly Trp Gln Asp Val Cys Ala Gln Ala
545                 550                 555                 560

Phe Gln Thr Pro Val His Ser Phe Gln Ala Lys Gln Phe Phe Glu Arg
                565                 570                 575

Tyr Phe Thr Pro Trp Gln Val Ala Gly Asn Gly Ser Leu Ala Gly Thr
                580                 585                 590

Val Thr Gly Tyr Tyr Glu Pro Val Leu Lys Gly Asp Asp Arg Arg Thr
            595                 600                 605

Ala Gln Ala Arg Phe Pro Ile Tyr Gly Ile Pro Asp Asp Phe Ile Ser
        610                 615                 620

Val Pro Leu Pro Ala Gly Leu Arg Ser Gly Lys Ala Leu Val Arg Ile
625                 630                 635                 640

Arg Gln Thr Gly Lys Asn Ser Gly Thr Ile Asp Asn Thr Gly Gly Thr
                645                 650                 655

His Thr Ala Asp Leu Ser Arg Phe Pro Ile Thr Ala Arg Thr Thr Ala
                660                 665                 670

Ile Lys Gly Arg Phe Glu Gly Ser Arg Phe Leu Pro Tyr His Thr Arg
            675                 680                 685

Asn Gln Ile Asn Gly Gly Ala Leu Asp Gly Lys Ala Pro Ile Leu Gly
        690                 695                 700

Tyr Ala Glu Asp Pro Val Glu Leu Phe Phe Met His Ile Gln Gly Ser
705                 710                 715                 720

Gly Arg Leu Lys Thr Pro Ser Gly Lys Tyr Ile Arg Ile Gly Tyr Ala
                725                 730                 735
```

```
Asp Lys Asn Glu His Pro Tyr Val Ser Ile Gly Arg Tyr Met Ala Asp
            740                 745                 750

Lys Gly Tyr Leu Lys Leu Gly Gln Thr Ser Met Gln Gly Ile Lys Ala
        755                 760                 765

Tyr Met Arg Gln Asn Pro Gln Arg Leu Ala Glu Val Leu Gly Gln Asn
    770                 775                 780

Pro Ser Tyr Ile Phe Phe Arg Glu Leu Ala Gly Ser Ser Asn Asp Gly
785                 790                 795                 800

Pro Val Gly Ala Leu Gly Thr Pro Leu Met Gly Glu Tyr Ala Gly Ala
                805                 810                 815

Val Asp Arg His Tyr Ile Thr Leu Gly Ala Pro Leu Phe Val Ala Thr
            820                 825                 830

Ala His Pro Val Thr Arg Lys Ala Leu Asn Arg Leu Ile Met Ala Gln
        835                 840                 845

Asp Thr Gly Ser Ala Ile Lys Gly Ala Val Arg Val Asp Tyr Phe Trp
    850                 855                 860

Gly Tyr Gly Asp Glu Ala Gly Glu Leu Ala Gly Lys Gln Lys Thr Thr
865                 870                 875                 880

Gly Tyr Val Trp Gln Leu Leu Pro Asn Gly Met Lys Pro Glu Tyr Arg
                885                 890                 895

Pro
```

<210> SEQ ID NO 96
<211> LENGTH: 1941
<212> TYPE: DNA
<213> ORGANISM: Artificial Sequence
<220> FEATURE:
<223> OTHER INFORMATION: Synthetic construct

<400> SEQUENCE: 96

```
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
gcgccatccg cacaaggcgg tcaagatatg gcggcggttt cggaagaaaa tacaggcaat     180
ggcggtgcgg cagcaacgga caaacccaaa aatgaagacg agggggcgca aaatgatatg     240
ccgcaaaatg ccgccgatac agatagtttg acaccgaatc acaccccggc ttcgaatatg     300
ccggccggaa atatggaaaa ccaagcaccg gatgccgggg aatcggagca gccggcaaac     360
caaccggata tggcaaatac ggcggacgga atgcagggtg acgatccgtc ggcaggcggg     420
gaaaatgccg gcaatacggc tgcccaaggt acaaatcaag ccgaaaacaa tcaaaccgcc     480
ggttctcaaa atcctgcctc ttcaaccaat cctagcgcca cgaatagcgg tggtgatttt     540
ggaaggacga acgtgggcaa ttctgttgtg attgacgggc gtcgcaaaa tataacgttg       600
acccactgta aaggcgattc ttgtagtggc aataatttct tggatgaaga agtacagcta     660
aaatcagaat ttgaaaaatt aagtgatgca gacaaaataa gtaattacaa gaaagatggg     720
aagaatgacg ggaagaatga taaatttgtc ggtttggttg ccgatagtgt gcagatgaag     780
ggaatcaatc aatatattat ctttttataaa cctaaaccca cttcatttgc gcgatttagg     840
cgttctgcac ggtcgaggcg gtcgcttccg gccgagatgc cgctgattcc cgtcaatcag     900
gcggatacgc tgattgtcga tggggaagcg gtcagcctga cggggcattc cggcaatatc     960
ttcgcgcccg aagggaatta ccggtatctg acttacgggg cggaaaaatt gccggcgga    1020
tcgtatgccc tccgtgttca aggcgaacct tcaaaaggcg aaatgctcgc gggcacggca    1080
gtgtacaacg gcgaagtgct gcattttcat acggaaaacg gccgtccgtc cccgtccaga    1140
```

-continued

```
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggagc cacctacaaa   1440
gtggacgaat atcacgccaa cgcccgtttc gccatcgacc atttcaacac cagcaccaac   1500
gtcggcggtt tttacggtct gaccggttcc gtcgagttcg accaagcaaa acgcgacggt   1560
aaaatcgaca tcaccatccc cgttgccaac ctgcaaagcg gttcgcaaca ctttaccgac   1620
cacctgaaat cagccgacat cttcgatgcc gcccaatatc cggacatccg ctttgtttcc   1680
accaaattca acttcaacgg caaaaaactg gtttccgttg acggcaacct gaccatgcac   1740
ggcaaaaccg cccccgtcaa actcaaagcc gaaaaattca actgctacca aagcccgatg   1800
gcgaaaaccg aagtttgcgg cggcgacttc agcaccacca tcgaccgcac caaatggggc   1860
gtggactacc tcgttaacgt tggtatgacc aaaagcgtcc gcatcgacat ccaaatcgag   1920
gcagccaaac aataaaagct t                                             1941
```

<210> SEQ ID NO 97
<211> LENGTH: 644
<212> TYPE: PRT
<213> ORGANISM: Artificial Sequence
<220> FEATURE:
<223> OTHER INFORMATION: Synthetic construct

<400> SEQUENCE: 97

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
        50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
```

-continued

```
                210                 215                 220
Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
                260                 265                 270

Pro Thr Ser Phe Ala Arg Phe Arg Arg Ser Ala Arg Ser Arg Arg Ser
                275                 280                 285

Leu Pro Ala Glu Met Pro Leu Ile Pro Val Asn Gln Ala Asp Thr Leu
                290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
                355                 360                 365

Phe His Thr Glu Asn Gly Arg Pro Ser Pro Ser Arg Gly Arg Phe Ala
                370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
                450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
                500                 505                 510

Phe Asp Gln Ala Lys Arg Asp Gly Lys Ile Asp Ile Thr Ile Pro Val
                515                 520                 525

Ala Asn Leu Gln Ser Gly Ser Gln His Phe Thr Asp His Leu Lys Ser
530                 535                 540

Ala Asp Ile Phe Asp Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
                610                 615                 620

Val Asn Val Gly Met Thr Lys Ser Val Arg Ile Asp Ile Gln Ile Glu
625                 630                 635                 640
```

Ala Ala Lys Gln

<210> SEQ ID NO 98
<211> LENGTH: 2583
<212> TYPE: DNA
<213> ORGANISM: Artificial Sequence
<220> FEATURE:
<223> OTHER INFORMATION: Synthetic construct

<400> SEQUENCE: 98

| | | | | | |
|---|---|---|---|---|---|
| atggctagcc | ccgatgtcaa | gtcggcggac | acgctgtcaa | aacctgccgc | ccctgttgtt | 60 |
| tctgaaaaag | agacagaggc | aaaggaagat | gcgccacagg | caggttctca | aggacagggc | 120 |
| gcgccatccg | cacaaggcgg | tcaagatatg | gcggcggttt | cggaagaaaa | tacaggcaat | 180 |
| ggcggtgcgg | cagcaacgga | caaacccaaa | aatgaagacg | aggggcgca | aaatgatatg | 240 |
| ccgcaaaatg | ccgccgatac | agatagtttg | acaccgaatc | acaccccggc | ttcgaatatg | 300 |
| ccggccggaa | atatggaaaa | ccaagcaccg | gatgccgggg | aatcggagca | gccggcaaac | 360 |
| caaccggata | tggcaaatac | ggcggacgga | atgcagggtg | acgatccgtc | ggcaggcggg | 420 |
| gaaaatgccg | gcaatacggc | tgcccaaggt | acaaatcaag | ccgaaaacaa | tcaaaccgcc | 480 |
| ggttctcaaa | atcctgcctc | ttcaaccaat | cctagcgcca | cgaatagcgg | tggtgatttt | 540 |
| ggaaggacga | acgtgggcaa | ttctgttgtg | attgacgggc | cgtcgcaaaa | tataacgttg | 600 |
| acccactgta | aaggcgattc | ttgtagtggc | aataatttct | tggatgaaga | agtacagcta | 660 |
| aaatcagaat | ttgaaaaatt | aagtgatgca | gacaaaataa | gtaattacaa | gaaagatggg | 720 |
| aagaatgacg | ggaagaatga | taaatttgtc | ggtttggttg | ccgatagtgt | gcagatgaag | 780 |
| ggaatcaatc | aatatattat | cttttataaa | cctaaaccca | cttcatttgc | gcgatttagg | 840 |
| cgttctgcac | ggtcgaggcg | gtcgcttccg | gccgagatgc | cgctgattcc | cgtcaatcag | 900 |
| gcggatacgc | tgattgtcga | tggggaagcg | gtcagcctga | cggggcattc | cggcaatatc | 960 |
| ttcgcgcccg | aagggaatta | ccggtatctg | acttacgggg | cggaaaaatt | gcccggcgga | 1020 |
| tcgtatgccc | tccgtgttca | aggcgaacct | tcaaaaggcg | aaatgctcgc | gggcacggca | 1080 |
| gtgtacaacg | gcgaagtgct | gcattttcat | acggaaaacg | gccgtccgtc | cccgtccaga | 1140 |
| ggcaggtttg | ccgcaaaagt | cgatttcggc | agcaaatctg | tggacggcat | tatcgacagc | 1200 |
| ggcgatggtt | tgcatatggg | tacgcaaaaa | ttcaagccg | ccatcgatgg | aaacggcttt | 1260 |
| aaggggactt | ggacggaaaa | tggcggcggg | gatgtttccg | gaaagtttta | cggcccggcc | 1320 |
| ggcgaggaag | tggcgggaaa | atacagctat | cgcccaacag | atgcggaaaa | gggcggattc | 1380 |
| ggcgtgtttg | ccggcaaaaa | agagcaggat | ggatccggag | gaggaggagc | cacaaacgac | 1440 |
| gacgatgtta | aaaagctgc | cactgtggcc | attgctgctg | cctacaacaa | tggccaagaa | 1500 |
| atcaacggtt | tcaaagctgg | agagaccatc | tacgacattg | atgaagacgg | cacaattacc | 1560 |
| aaaaaagacg | caactgcagc | cgatgttgaa | gccgacgact | ttaaaggtct | gggtctgaaa | 1620 |
| aaagtcgtga | ctaacctgac | caaaaccgtc | aatgaaaaca | acaaaacgt | cgatgccaaa | 1680 |
| gtaaagctg | cagaatctga | aatagaaaag | ttaacaacca | agttagcaga | cactgatgcc | 1740 |
| gctttagcag | atactgatgc | cgctctggat | gcaaccacca | acgccttgaa | taattggga | 1800 |
| gaaaatataa | cgacatttgc | tgaagagact | aagacaaata | tcgtaaaaat | tgatgaaaaa | 1860 |
| ttagaagccg | tggctgatac | cgtcgacaag | catgccgaag | cattcaacga | tatcgccgat | 1920 |
| tcattggatg | aaaccaacac | taaggcagac | gaagccgtca | aaaccgccaa | tgaagccaaa | 1980 |

```
cagacggccg aagaaaccaa acaaaacgtc gatgccaaag taaaagctgc agaaactgca    2040
gcaggcaaag ccgaagctgc cgctggcaca gctaatactg cagccgacaa ggccgaagct    2100
gtcgctgcaa aagttaccga catcaaagct gatatcgcta cgaacaaaga taatattgct    2160
aaaaaagcaa acagtgccga cgtgtacacc agagaagagt ctgacagcaa atttgtcaga    2220
attgatggtc tgaacgctac taccgaaaaa ttggacacac gcttggcttc tgctgaaaaa    2280
tccattgccg atcacgatac tcgcctgaac ggtttggata aaacagtgtc agacctgcgc    2340
aaagaaaccc gccaaggcct tgcagaacaa gccgcgctct ccggtctgtt ccaaccttac    2400
aacgtgggtc ggttcaatgt aacggctgca gtcggcggct acaaatccga atcggcagtc    2460
gccatcggta ccggcttccg ctttaccgaa aactttgccg ccaaagcagg cgtggcagtc    2520
ggcacttcgt ccggttcttc cgcagcctac catgtcggcg tcaattacga gtggtaaaag    2580
ctt                                                                  2583
```

<210> SEQ ID NO 99
<211> LENGTH: 858
<212> TYPE: PRT
<213> ORGANISM: Artificial Sequence
<220> FEATURE:
<223> OTHER INFORMATION: Synthetic construct

<400> SEQUENCE: 99

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255
```

```
Val Gln Met Lys Gly Ile Asn Gln Tyr Ile Ile Phe Tyr Lys Pro Lys
            260                 265                 270

Pro Thr Ser Phe Ala Arg Phe Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
            355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Asn Asp
465                 470                 475                 480

Asp Asp Val Lys Lys Ala Ala Thr Val Ala Ile Ala Ala Ala Tyr Asn
                485                 490                 495

Asn Gly Gln Glu Ile Asn Gly Phe Lys Ala Gly Glu Thr Ile Tyr Asp
            500                 505                 510

Ile Asp Glu Asp Gly Thr Ile Thr Lys Lys Asp Ala Thr Ala Ala Asp
        515                 520                 525

Val Glu Ala Asp Asp Phe Lys Gly Leu Gly Leu Lys Lys Val Val Thr
    530                 535                 540

Asn Leu Thr Lys Thr Val Asn Glu Asn Lys Gln Asn Val Asp Ala Lys
545                 550                 555                 560

Val Lys Ala Ala Glu Ser Glu Ile Glu Lys Leu Thr Thr Lys Leu Ala
                565                 570                 575

Asp Thr Asp Ala Ala Leu Ala Asp Thr Asp Ala Ala Leu Asp Ala Thr
            580                 585                 590

Thr Asn Ala Leu Asn Lys Leu Gly Glu Asn Ile Thr Thr Phe Ala Glu
        595                 600                 605

Glu Thr Lys Thr Asn Ile Val Lys Ile Asp Glu Lys Leu Glu Ala Val
    610                 615                 620

Ala Asp Thr Val Asp Lys His Ala Glu Ala Phe Asn Asp Ile Ala Asp
625                 630                 635                 640

Ser Leu Asp Glu Thr Asn Thr Lys Ala Asp Glu Ala Val Lys Thr Ala
                645                 650                 655

Asn Glu Ala Lys Gln Thr Ala Glu Glu Thr Lys Gln Asn Val Asp Ala
            660                 665                 670
```

```
Lys Val Lys Ala Ala Glu Thr Ala Ala Gly Lys Ala Glu Ala Ala Ala
            675                 680                 685

Gly Thr Ala Asn Thr Ala Ala Asp Lys Ala Glu Ala Val Ala Ala Lys
    690                 695                 700

Val Thr Asp Ile Lys Ala Asp Ile Ala Thr Asn Lys Asp Asn Ile Ala
705                 710                 715                 720

Lys Lys Ala Asn Ser Ala Asp Val Tyr Thr Arg Glu Glu Ser Asp Ser
                725                 730                 735

Lys Phe Val Arg Ile Asp Gly Leu Asn Ala Thr Thr Glu Lys Leu Asp
            740                 745                 750

Thr Arg Leu Ala Ser Ala Glu Lys Ser Ile Ala Asp His Asp Thr Arg
        755                 760                 765

Leu Asn Gly Leu Asp Lys Thr Val Ser Asp Leu Arg Lys Glu Thr Arg
    770                 775                 780

Gln Gly Leu Ala Glu Gln Ala Ala Leu Ser Gly Leu Phe Gln Pro Tyr
785                 790                 795                 800

Asn Val Gly Arg Phe Asn Val Thr Ala Ala Val Gly Gly Tyr Lys Ser
                805                 810                 815

Glu Ser Ala Val Ala Ile Gly Thr Gly Phe Arg Phe Thr Glu Asn Phe
            820                 825                 830

Ala Ala Lys Ala Gly Val Ala Val Gly Thr Ser Ser Gly Ser Ser Ala
        835                 840                 845

Ala Tyr His Val Gly Val Asn Tyr Glu Trp
    850                 855
```

<210> SEQ ID NO 100
<211> LENGTH: 4425
<212> TYPE: DNA
<213> ORGANISM: Artificial Sequence
<220> FEATURE:
<223> OTHER INFORMATION: Synthetic construct

<400> SEQUENCE: 100

```
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180
aatgccccccc cccgaatct gcataccgga gactttccaa acccaaatga cgcatacaag     240
aatttgatca acctcaaacc tgcaattgaa gcaggctata caggacgcgg ggtagaggta     300
ggtatcgtcg acacaggcga atccgtcggc agcatatcct ttcccgaact gtatggcaga     360
aaagaacacg gctataacga aaattacaaa aactatacgg cgtatatgcg gaaggaagcg     420
cctgaagacg gaggcggtaa agacattgaa gcttctttcg acgatgaggc cgttatagag     480
actgaagcaa agccgacgga tatccgccac gtaaaagaaa tcggacacat cgatttggtc     540
tcccatatta ttggcgggcg ttccgtggac ggcagacctg caggcggtat tgcgcccgat     600
gcgacgctac acataatgaa tacgaatgat gaaaccaaga acgaaatgat ggttgcagcc     660
atccgcaatg catgggtcaa gctgggcgaa cgtggcgtgc gcatcgtcaa taacagtttt     720
ggaacaacat cgagggcagg cactgccgac cttttccaaa tagccaattc ggaggagcag     780
taccgccaag cgttgctcga ctattccggc ggtgataaaa cagacgaggg tatccgcctg     840
atgcaacaga gcgattacgg caacctgtcc taccacatcc gtaataaaaa catgcttttc     900
atcttttcga caggcaatga cgcacaagct cagcccaaca catatgccct attgccattt     960
tatgaaaaag acgctcaaaa aggcattatc acagtcgcag gcgtagaccg cagtgagaa    1020
```

-continued

```
aagttcaaac gggaaatgta tggagaaccg ggtacagaac cgcttgagta tggctccaac      1080
cattgcggaa ttactgccat gtggtgcctg tcggcaccct atgaagcaag cgtccgtttc      1140
acccgtacaa acccgattca aattgccgga acatccttt  ccgcacccat cgtaaccggc      1200
acggcggctc tgctgctgca gaaatacccg tggatgagca acgacaacct gcgtaccacg      1260
ttgctgacga cggctcagga catcggtgca gtcggcgtgg acagcaagtt cggctgggga      1320
ctgctggatg cgggtaaggc catgaacgga cccgcgtcct ttccgttcgg cgactttacc      1380
gccgatacga aagtacatc  cgatattgcc tactccttcc gtaacgacat ttcaggcacg      1440
ggcggcctga tcaaaaaagg cggcagccaa ctgcaactgc acggcaacaa cacctatacg      1500
ggcaaaacca ttatcgaagg cggttcgctg gtgttgtacg gcaacaacaa atcggatatg      1560
cgcgtcgaaa ccaaaggtgc gctgatttat aacggggcgg catccggcgg cagcctgaac      1620
agcgacggca ttgtctatct ggcagatacc gaccaatccg gcgcaaacga aaccgtacac      1680
atcaaaggca gtctgcagct ggacggcaaa ggtacgctgt acacgcgttt gggcaaactg      1740
ctgaaagtgg acggtacggc gattatcggc ggcaagctgt acatgtcggc acgcggcaag      1800
ggggcaggct atctcaacag taccggacga cgtgttccct tcctgagtgc cgccaaaatc      1860
gggcaggatt attcttttctt cacaaacatc gaaaccgacg gcggcctgct ggcttccctc      1920
gacagcgtcg aaaaaacagc gggcagtgaa ggcgacacgc tgtcctatta tgtccgtcgc      1980
ggcaatgcgg cacggactgc ttcggcagcg gcacattccg cgcccgccgg tctgaaacac      2040
gccgtagaac agggcggcag caatctgaaa aacctgatgg tcgaactgga tgcctccgaa      2100
tcatccgcaa caccccgagac ggttgaaact gcggcagccg accgcacaga tatgccgggc      2160
atccgcccct acgcgcaac  tttccgcgca cggcagccg  tacagcatgc gaatgccgcc      2220
gacggtgtac gcatcttcaa cagtctcgcc gctaccgtct atgccgacag taccgccgcc      2280
catgccgata tgcagggacg ccgcctgaaa gccgtatcgg acgggttgga ccacaacggc      2340
acgggtctgc gcgtcatcgc gcaaacccaa caggacggtg gaacgtggga acagggcggt      2400
gttgaaggca aaatgcgcgg cagtacccaa accgtcggca ttgccgcgaa aaccggcgaa      2460
aatacgacag cagccgccac actgggcatg ggacgcagca catggagcga aaacagtgca      2520
aatgcaaaaa ccgacagcat tagtctgttt gcaggcatac ggcacgatgc gggcgatatc      2580
ggctatctca aaggcctgtt ctcctacgga cgctacaaaa acagcatcag ccgcagcacc      2640
ggtgcggacg aacatgcgga aggcagcgtc aacggcacgc tgatgcagct gggcgcactg      2700
gcggtgtca  acgttccgtt tgccgcaacg ggagatttga cggtcgaagg cggtctgcgc      2760
tacgacctgc tcaaacagga tgcattcgcc gaaaaaggca gtgctttggg ctggagcggc      2820
aacagcctca ctgaaggcac gctggtcgga ctcgcgggtc tgaagctgtc gcaacccttg      2880
agcgataaag ccgtcctgtt tgcaacggcg ggcgtggaac gcgacctgaa cggacgcgac      2940
tacacggtaa cgggcggctt taccggcgcg actgcagcaa ccggcaagac gggggcacgc      3000
aatatgccgc acacccgtct ggttgccggc ctgggcgcgg atgtcgaatt cggcaacggc      3060
tggaacggct tggcacgtta cagctacgcc ggttccaaac agtacggcaa ccacagcgga      3120
cgagtcggcg taggctaccg gttcctcgac ggtggcggag gcactggatc ctcagatttg      3180
gcaaacgatt cttttatccg gcaggttctc gaccgtcagc atttcgaacc cgacgggaaa      3240
taccacctat tcggcagcag gggggaactt gccgagcgca gcggccatat cggattggga      3300
aaaatacaaa gccatcagtt gggcaacctg atgattcaac aggcggccat taaaggaaat      3360
```

```
atcggctaca ttgtccgctt ttccgatcac gggcacgaag tccattcccc cttcgacaac    3420
catgcctcac attccgattc tgatgaagcc ggtagtcccg ttgacggatt tagcctttac    3480
cgcatccatt gggacggata cgaacaccat cccgccgacg gctatgacgg ccacagggc     3540 ggcggctatc ccgctcccaa aggcgcgagg gatatataca gctacgacat aaaaggcgtt    3600
gcccaaaata tccgcctcaa cctgaccgac aaccgcagca ccggacaacg gcttgccgac    3660
cgtttccaca atgccggtag tatgctgacg caaggagtag gcgacggatt caaacgcgcc    3720
acccgataca gccccgagct ggacagatcg ggcaatgccg ccgaagcctt caacggcact    3780
gcagatatcg ttaaaaacat catcggcgcg caggagaaa ttgtcggcgc aggcgatgcc     3840
gtgcagggca taagcgaagg ctcaaacatt gctgtcatgc acggcttggg tctgctttcc    3900
accgaaaaca agatggcgcg catcaacgat ttggcagata tggcgcaact caaagactat    3960
gccgcagcag ccatccgcga ttgggcagtc caaaacccca atgccgcaca aggcatagaa    4020
gccgtcagca atatctttat ggcagccatc cccatcaaag ggattggagc tgttcgggga    4080
aaatacggct tgggcggcat cacggcacat cctatcaagc ggtcgcagat gggcgcgatc    4140
gcattgccga aagggaaatc cgccgtcagc gacaattttg ccgatgcggc atacgccaaa    4200
tacccgtccc cttaccattc ccgaaatatc cgttcaaact tggagcagcg ttacggcaaa    4260
gaaaacatca cctcctcaac cgtgccgccg tcaaacggca aaaatgtcaa actggcagac    4320
caacgccacc cgaagacagg cgtaccgttt gacggtaaag ggtttccgaa ttttgagaag    4380
cacgtgaaat atgatacgct cgagcaccac caccaccacc actga                    4425
```

<210> SEQ ID NO 101
<211> LENGTH: 1474
<212> TYPE: PRT
<213> ORGANISM: Artificial Sequence
<220> FEATURE:
<223> OTHER INFORMATION: Synthetic construct

<400> SEQUENCE: 101

Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

```
Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
```

```
                  595                 600                 605
Gly Arg Arg Val Pro Phe Leu Ser Ala Ala Lys Ile Gly Gln Asp Tyr
610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
                660                 665                 670

Ser Ala Pro Ala Gly Leu Lys His Ala Val Glu Gln Gly Gly Ser Asn
                675                 680                 685

Leu Glu Asn Leu Met Val Glu Leu Asp Ala Ser Glu Ser Ser Ala Thr
690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
                740                 745                 750

Val Tyr Ala Asp Ser Thr Ala Ala His Ala Asp Met Gln Gly Arg Arg
                755                 760                 765

Leu Lys Ala Val Ser Asp Gly Leu Asp His Asn Gly Thr Gly Leu Arg
770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Thr Leu Gly Met Gly Arg
                820                 825                 830

Ser Thr Trp Ser Glu Asn Ser Ala Asn Ala Lys Thr Asp Ser Ile Ser
                835                 840                 845

Leu Phe Ala Gly Ile Arg His Asp Ala Gly Asp Ile Gly Tyr Leu Lys
850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Thr Gly Asp
                900                 905                 910

Leu Thr Val Glu Gly Gly Leu Arg Tyr Asp Leu Leu Lys Gln Asp Ala
                915                 920                 925

Phe Ala Glu Lys Gly Ser Ala Leu Gly Trp Ser Gly Asn Ser Leu Thr
                930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
                980                 985                 990

Ala Thr Gly Lys Thr Gly Ala Arg Asn Met Pro His Thr Arg Leu Val
                995                 1000                1005

Ala Gly Leu Gly Ala Asp Val Glu Phe Gly Asn Gly Trp Asn Gly Leu
                1010                1015                1020
```

-continued

```
Ala Arg Tyr Ser Tyr Ala Gly Ser Lys Gln Tyr Gly Asn His Ser Gly
1025                1030                1035                1040

Arg Val Gly Val Gly Tyr Arg Phe Leu Asp Gly Gly Gly Thr Gly
            1045                1050                1055

Ser Ser Asp Leu Ala Asn Asp Ser Phe Ile Arg Gln Val Leu Asp Arg
1060                1065                1070

Gln His Phe Glu Pro Asp Gly Lys Tyr His Leu Phe Gly Ser Arg Gly
            1075                1080                1085

Glu Leu Ala Glu Arg Ser Gly His Ile Gly Leu Gly Lys Ile Gln Ser
1090                1095                1100

His Gln Leu Gly Asn Leu Met Ile Gln Gln Ala Ala Ile Lys Gly Asn
1105                1110                1115                1120

Ile Gly Tyr Ile Val Arg Phe Ser Asp His Gly His Glu Val His Ser
                1125                1130                1135

Pro Phe Asp Asn His Ala Ser His Ser Asp Ser Asp Glu Ala Gly Ser
                1140                1145                1150

Pro Val Asp Gly Phe Ser Leu Tyr Arg Ile His Trp Asp Gly Tyr Glu
            1155                1160                1165

His His Pro Ala Asp Gly Tyr Asp Gly Pro Gln Gly Gly Gly Tyr Pro
    1170                1175                1180

Ala Pro Lys Gly Ala Arg Asp Ile Tyr Ser Tyr Asp Ile Lys Gly Val
1185                1190                1195                1200

Ala Gln Asn Ile Arg Leu Asn Leu Thr Asp Asn Arg Ser Thr Gly Gln
                1205                1210                1215

Arg Leu Ala Asp Arg Phe His Asn Ala Gly Ser Met Leu Thr Gln Gly
            1220                1225                1230

Val Gly Asp Gly Phe Lys Arg Ala Thr Arg Tyr Ser Pro Glu Leu Asp
            1235                1240                1245

Arg Ser Gly Asn Ala Ala Glu Ala Phe Asn Gly Thr Ala Asp Ile Val
    1250                1255                1260

Lys Asn Ile Ile Gly Ala Ala Gly Glu Ile Val Gly Ala Gly Asp Ala
1265                1270                1275                1280

Val Gln Gly Ile Ser Glu Gly Ser Asn Ile Ala Val Met His Gly Leu
                1285                1290                1295

Gly Leu Leu Ser Thr Glu Asn Lys Met Ala Arg Ile Asn Asp Leu Ala
                1300                1305                1310

Asp Met Ala Gln Leu Lys Asp Tyr Ala Ala Ala Ala Ile Arg Asp Trp
        1315                1320                1325

Ala Val Gln Asn Pro Asn Ala Ala Gln Gly Ile Glu Ala Val Ser Asn
            1330                1335                1340

Ile Phe Met Ala Ala Ile Pro Ile Lys Gly Ile Gly Ala Val Arg Gly
1345                1350                1355                1360

Lys Tyr Gly Leu Gly Gly Ile Thr Ala His Pro Ile Lys Arg Ser Gln
                1365                1370                1375

Met Gly Ala Ile Ala Leu Pro Lys Gly Lys Ser Ala Val Ser Asp Asn
            1380                1385                1390

Phe Ala Asp Ala Ala Tyr Ala Lys Tyr Pro Ser Pro Tyr His Ser Arg
        1395                1400                1405

Asn Ile Arg Ser Asn Leu Glu Gln Arg Tyr Gly Lys Glu Asn Ile Thr
    1410                1415                1420

Ser Ser Thr Val Pro Pro Ser Asn Gly Lys Asn Val Lys Leu Ala Asp
1425                1430                1435                1440
```

```
Gln Arg His Pro Lys Thr Gly Val Pro Phe Asp Gly Lys Gly Phe Pro
            1445                1450                1455

Asn Phe Glu Lys His Val Lys Tyr Asp Thr Leu Glu His His His His
            1460                1465                1470

His His

<210> SEQ ID NO 102
<211> LENGTH: 3939
<212> TYPE: DNA
<213> ORGANISM: Artificial Sequence
<220> FEATURE:
<223> OTHER INFORMATION: Synthetic construct

<400> SEQUENCE: 102
atgacttctg cgcccgactt caatgcaggc ggtaccggta tcggcagcaa cagcagagca      60
acaacagcga aatcagcagc agtatcttac gccggtatca gaacgaaat gtgcaaagac      120 agaagcatgc tctgtgccgg tcgggatgac gttgcggtta cagacaggga tgccaaaatc     180 aatgccccc cccgaatct gcataccgga gactttccaa acccaaatga cgcatacaag      240
aatttgatca acctcaaacc tgcaattgaa gcaggctata caggacgcgg gtagaggta     300 ggtatcgtcg acacaggcga atccgtcggc agcatatcct ttcccgaact gtatggcaga    360
aaagaacacg gctataacga aaattacaaa actatacgg cgtatatgcg aaggaagcg     420 cctgaagacg gaggcggtaa agacattgaa gcttctttcg acgatgaggc cgttatagag    480
actgaagcaa agccgacgga tatccgccac gtaaagaaa tcggacacat cgatttggtc    540
tcccatatta ttggcgggcg ttccgtggac ggcagacctg caggcggtat tgcgcccgat    600
gcgacgctac acataatgaa tacgaatgat gaaaccaaga cgaaatgat ggttgcagcc    660 atccgcaatg catgggtcaa gctgggcgaa cgtggcgtgc gcatcgtcaa taacagtttt    720
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg gtacagaac cgcttgagta tggctccaac   1080
cattgcggaa ttactgccat gtggtgcctg tcggcaccct atgaagcaag cgtccgtttc    1140
acccgtacaa acccgattca aattgccgga acatcctttt ccgcacccat cgtaaccggc    1200
acggcggctc tgctgctgca gaaataccg tggatgagca cgacaacct gcgtaccacg     1260 ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aagtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg tgttgtacg gcaacaacaa atcggatatg    1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
```

```
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acgcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg aacgtgggga cagggcggt    2400
gttgaaggca aaatgcgcgg cagtacccaa ccgtcggca ttgccgcgaa aaccggcgaa    2460
aatacgacag cagccgccac actgggcatg ggacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggatccggag ggggtggtgt cgccgccgac    3180
atcggtgcgg ggcttgccga tgcactaacc gcaccgctcg accataaaga caaaggtttg    3240
cagtctttga cgctggatca gtccgtcagg aaaaacgaga aactgaagct ggcggcacaa    3300
ggtgcggaaa aaacttatgg aaacggtgac agcctcaata cgggcaaatt gaagaacgac    3360
aaggtcagcc gtttcgactt tatccgccaa atcgaagtgg acgggcagct cattaccttg    3420
gagagtggag agttccaagt atacaaacaa agccattccg ccttaaccgc ctttcagacc    3480
gagcaaatac aagattcgga gcattccggg aagatggttg cgaaacgcca gttcagaatc    3540
ggcgacatag cgggcgaaca tacatctttt gacaagcttc ccgaaggcgg cagggcgaca    3600
tatcgcggga cggcgttcgg ttcagacgat gccggcggaa aactgaccta caccatagat    3660
ttcgccgcca agcagggaaa cggcaaaatc gaacatttga atcgccaga actcaatgtc    3720
gacctggccg ccgccgatat caagccggat ggaaaacgcc atgccgtcat cagcggttcc    3780
gtcctttaca accaagccga gaaggcagt tactccctcg gtatctttgg cggaaaagcc    3840
caggaagttg ccggcagcgc ggaagtgaaa accgtaaacg gcatacgcca tatcggcctt    3900
gccgccaagc aactcgagca ccaccaccac caccactga                          3939
```

<210> SEQ ID NO 103
<211> LENGTH: 1312
<212> TYPE: PRT
<213> ORGANISM: Artificial Sequence
<220> FEATURE:
<223> OTHER INFORMATION: Synthetic construct

```
<400> SEQUENCE: 103

Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415
```

```
Leu Arg Thr Thr Leu Leu Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala His Ala Asp Met Gln Gly Arg Arg
        755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Thr Leu Gly Met Gly Arg
            820                 825                 830
```

```
Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
            915                 920                 925

Phe Ala Glu Lys Gly Ser Ala Leu Gly Trp Ser Gly Asn Ser Leu Thr
            930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
                980                 985                 990

Ala Thr Gly Lys Thr Gly Ala Arg Asn Met Pro His Thr Arg Leu Val
            995                 1000                1005

Ala Gly Leu Gly Ala Asp Val Glu Phe Gly Asn Gly Trp Asn Gly Leu
            1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Ser Gly Gly Gly
                1045                1050                1055

Val Ala Ala Asp Ile Gly Ala Gly Leu Ala Asp Ala Leu Thr Ala Pro
            1060                1065                1070

Leu Asp His Lys Asp Lys Gly Leu Gln Ser Leu Thr Leu Asp Gln Ser
            1075                1080                1085

Val Arg Lys Asn Glu Lys Leu Lys Leu Ala Ala Gln Gly Ala Glu Lys
            1090                1095                1100

Thr Tyr Gly Asn Gly Asp Ser Leu Asn Thr Gly Lys Leu Lys Asn Asp
1105                1110                1115                1120

Lys Val Ser Arg Phe Asp Phe Ile Arg Gln Ile Glu Val Asp Gly Gln
                1125                1130                1135

Leu Ile Thr Leu Glu Ser Gly Glu Phe Gln Val Tyr Lys Gln Ser His
                1140                1145                1150

Ser Ala Leu Thr Ala Phe Gln Thr Glu Gln Ile Gln Asp Ser Glu His
                1155                1160                1165

Ser Gly Lys Met Val Ala Lys Arg Gln Phe Arg Ile Gly Asp Ile Ala
            1170                1175                1180

Gly Glu His Thr Ser Phe Asp Lys Leu Pro Glu Gly Arg Ala Thr
1185                1190                1195                1200

Tyr Arg Gly Thr Ala Phe Gly Ser Asp Ala Gly Lys Leu Thr
                1205                1210                1215

Tyr Thr Ile Asp Phe Ala Ala Lys Gln Gly Asn Gly Lys Ile Glu His
                1220                1225                1230

Leu Lys Ser Pro Glu Leu Asn Val Asp Leu Ala Ala Asp Ile Lys
            1235                1240                1245

Pro Asp Gly Lys Arg His Ala Val Ile Ser Gly Ser Val Leu Tyr Asn
```

```
                    1250              1255                 1260
        Gln Ala Glu Lys Gly Ser Tyr Ser Leu Gly Ile Phe Gly Gly Lys Ala
        1265              1270               1275                1280

Gln Glu Val Ala Gly Ser Ala Glu Val Lys Thr Val Asn Gly Ile Arg
                           1285               1290                1295

His Ile Gly Leu Ala Ala Lys Gln Leu Glu His His His His His His
                    1300              1305                 1310

<210> SEQ ID NO 104
<211> LENGTH: 4344
<212> TYPE: DNA
<213> ORGANISM: Artificial Sequence
<220> FEATURE:
<223> OTHER INFORMATION: Synthetic construct

<400> SEQUENCE: 104
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180
aatgcccccc ccccgaatct gcataccgga gactttccaa acccaaatga cgcatacaag     240
aatttgatca acctcaaacc tgcaattgaa gcaggctata caggacgcgg ggtagaggta     300
ggtatcgtcg acacaggcga atccgtcggc agcatatcct ttcccgaact gtatggcaga     360
aaagaacacg gctataacga aaattacaaa actatacgg cgtatatgcg aaggaagcg      420 cctgaagacg gaggcggtaa agacattgaa gcttctttcg acgatgaggc cgttatagag     480
actgaagcaa agccgacgga tatccgccac gtaaaagaaa tcggacacat cgatttggtc     540
tcccatatta ttggcggggcg ttccgtggac ggcagacctg caggcggtat tgcgcccgat     600
gcgacgctac acataatgaa tacgaatgat gaaaccaaga cgaaatgat ggttgcagcc      660 atccgcaatg catgggtcaa gctgggcgaa cgtggcgtgc gcatcgtcaa taacagtttt     720
ggaacaacat cgagggcagg cactgccgac cttttccaaa tagccaattc ggaggagcag     780
taccgccaag cgttgctcga ctattccggc ggtgataaaa cagacgaggg tatccgcctg     840
atgcaacaga gcgattacgg caacctgtcc taccacatcc gtaataaaaa catgcttttc     900
atcttttcga caggcaatga cgcacaagct cagcccaaca catatgccct attgccattt     960
tatgaaaaag acgctcaaaa aggcattatc acagtcgcag gcgtagaccg cagtggagaa    1020
aagttcaaac gggaaatgta tggagaaccg ggtacagaac gcttgagta tggctccaac     1080 cattgcggaa ttactgccat gtggtgcctg tcggcaccct atgaagcaag cgtccgtttc     1140
acccgtacaa acccgattca aattgccgga acatccttt ccgcacccat cgtaaccggc     1200
acggcggctc tgctgctgca gaaataccccg tggatgagca cgacaacct gcgtaccacg    1260 ttgctgacga cggctcagga catcggtgca gtcggcgtgg acagcaagtt cggctgggga    1320
ctgctggatg cgggtaaggc catgaacgga cccgcgtcc ttccgttcgg cgactttacc     1380
gccgatacga aaggtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg gtgttgtacg gcaacaacaa atcggatatg    1560
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
```

-continued

```
ctgaaagtgg acggtacggc gattatcggc ggcaagctgt acatgtcggc acgcggcaag      1800
ggggcaggct atctcaacag taccggacga cgtgttccct tcctgagtgc cgccaaaatc      1860
gggcaggatt attctttctt cacaaacatc gaaaccgacg gcggcctgct ggcttccctc      1920
gacagcgtcg aaaaaacagc gggcagtgaa ggcgacacgc tgtcctatta tgtccgtcgc      1980
ggcaatgcgg cacggactgc ttcggcagcg gcacattccg cgcccgccgg tctgaaacac      2040
gccgtagaac agggcggcag caatctggaa aacctgatgg tcgaactgga tgcctccgaa      2100
tcatccgcaa cacccgagac ggttgaaact gcggcagccg accgcacaga tatgccgggc      2160
atccgcccct acgcgcaac tttccgcgca gcggcagccg tacagcatgc gaatgccgcc      2220
gacggtgtac gcatcttcaa cagtctcgcc gctaccgtct atgccgacag taccgccgcc      2280
catgccgata tgcagggacg ccgcctgaaa gccgtatcgg acgggttgga ccacaacggc      2340
acgggtctgc gcgtcatcgc gcaaacccaa caggacggtg aacgtggga acagggcggt      2400 gttgaaggca aaatgcgcgg cagtacccaa accgtcggca ttgccgcgaa aaccggcgaa      2460
aatacgacag cagccgccac actgggcatg ggacgcagca catggagcga aaacagtgca      2520
aatgcaaaaa ccgacagcat tagtctgttt gcaggcatac ggcacgatgc gggcgatatc      2580
ggctatctca aaggcctgtt ctcctacgga cgctacaaaa acagcatcag ccgcagcacc      2640
ggtgcggacg aacatgcgga aggcagcgtc aacggcacgc tgatgcagct gggcgcactg      2700
ggcggtgtca acgttccgtt tgccgcaacg ggagatttga cggtcgaagg cggtctgcgc      2760
tacgacctgc tcaaacagga tgcattcgcc gaaaaaggca gtgctttggg ctggagcggc      2820
aacagcctca ctgaaggcac gctggtcgga ctcgcgggtc tgaagctgtc gcaacccttg      2880
agcgataaag ccgtcctgtt tgcaacggcg ggcgtggaac gcgacctgaa cggacgcgac      2940 tacacgtaa cgggcggctt taccggcgcg actgcagcaa ccgcaagac gggggcacgc      3000 aatatgccgc acacccgtct ggttgccggc ctgggcgcgg atgtcgaatt cggcaacggc      3060
tggaacggct tggcacgtta cagctacgcc ggttccaaac agtacggcaa ccacagcgga      3120
cgagtcggcg taggctaccg gttcctcgag ggtggcggag gcactggatc cgccacaaac      3180
gacgacgatg ttaaaaaagc tgccactgtg gccattgctg ctgcctacaa caatggccaa      3240
gaaatcaacg gtttcaaagc tggagagacc atctacgaca ttgatgaaga cggcacaatt      3300
accaaaaaag acgcaactgc agccgatgtt gaagccgacg acttttaaagg tctgggtctg      3360 aaaaaagtcg tgactaacct gaccaaaacc gtcaatgaaa acaaacaaaa cgtcgatgcc      3420
aaagtaaaag ctgcagaatc tgaaatagaa aagttaacaa ccaagttagc agacactgat      3480
gccgctttag cagatactga tgccgctctg gatgcaacca ccaacgcctt gaataaattg      3540
ggagaaaata taacgacatt tgctgaagag actaagacaa atatcgtaaa aattgatgaa      3600
aaattagaag ccgtggctga taccgtcgac aagcatgccg aagcattcaa cgatatcgcc      3660
gattcattgg atgaaaccaa cactaaggca gacgaagccg tcaaaccgc caatgaagcc      3720 aaacagacgg ccgaagaaac caaacaaaac gtcgatgcca agtaaaaagc tgcagaaact      3780
gcagcaggca agccgaagc tgccgctggc acagctaata ctgcagccga caaggccgaa      3840
gctgtcgctg caaagttac cgacatcaaa gctgatatcg ctacgaacaa agataatatt      3900
gctaaaaaag caaacagtgc cgacgtgtac accagagaag agtctgacag caaatttgtc      3960
agaattgatg gtctgaacgc tactaccgaa aaattggaca cacgcttggc ttctgctgaa      4020
aaatccattg ccgatcacga tactcgcctg aacggtttgg ataaaacagt gtcagacctg      4080
cgcaaagaaa cccgccaagg ccttgcagaa caagccgcgc tctccggtct gttccaacct      4140
```

-continued

```
tacaacgtgg gtcggttcaa tgtaacggct gcagtcggcg gctacaaatc cgaatcggca    4200
gtcgccatcg gtaccggctt ccgctttacc gaaaactttg ccgccaaagc aggcgtggca    4260
gtcggcactt cgtccggttc ttccgcagcc taccatgtcg gcgtcaatta cgagtggctc    4320
gagcaccacc accaccacca ctga                                           4344
```

<210> SEQ ID NO 105
<211> LENGTH: 1447
<212> TYPE: PRT
<213> ORGANISM: Artificial Sequence
<220> FEATURE:
<223> OTHER INFORMATION: Synthetic construct

<400> SEQUENCE: 105

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320
```

-continued

```
Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
690                 695                 700

Pro Glu Thr Val Glu Thr Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
```

```
              740                 745                 750
Val Tyr Ala Asp Ser Thr Ala Ala His Ala Asp Met Gln Gly Arg Arg
            755                 760                 765

Leu Lys Ala Val Ser Asp Gly Leu Asp His Asn Gly Thr Gly Leu Arg
            770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                    805                 810                 815

Lys Thr Gly Glu Asn Thr Thr Ala Ala Ala Thr Leu Gly Met Gly Arg
                    820                 825                 830

Ser Thr Trp Ser Glu Asn Ser Ala Asn Ala Lys Thr Asp Ser Ile Ser
                    835                 840                 845

Leu Phe Ala Gly Ile Arg His Asp Ala Gly Asp Ile Gly Tyr Leu Lys
                    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                    885                 890                 895

Leu Gly Ala Leu Gly Gly Val Asn Val Pro Phe Ala Ala Thr Gly Asp
                    900                 905                 910

Leu Thr Val Glu Gly Gly Leu Arg Tyr Asp Leu Leu Lys Gln Asp Ala
                    915                 920                 925

Phe Ala Glu Lys Gly Ser Ala Leu Gly Trp Ser Gly Asn Ser Leu Thr
                    930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                    965                 970                 975

Asn Gly Arg Asp Tyr Thr Val Thr Gly Gly Phe Thr Gly Ala Thr Ala
                    980                 985                 990

Ala Thr Gly Lys Thr Gly Ala Arg Asn Met Pro His Thr Arg Leu Val
                    995                 1000                1005

Ala Gly Leu Gly Ala Asp Val Glu Phe Gly Asn Gly Trp Asn Gly Leu
            1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
                    1045                1050                1055

Ser Ala Thr Asn Asp Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
            1075                1080                1085

Glu Thr Ile Tyr Asp Ile Asp Glu Asp Gly Thr Ile Thr Lys Lys Asp
            1090                1095                1100

Ala Thr Ala Ala Asp Val Glu Ala Asp Phe Lys Gly Leu Gly Leu
1105                1110                1115                1120

Lys Lys Val Val Thr Asn Leu Lys Thr Val Asn Glu Asn Lys Gln
                    1125                1130                1135

Asn Val Asp Ala Lys Val Lys Ala Ala Glu Ser Glu Ile Glu Lys Leu
            1140                1145                1150

Thr Thr Lys Leu Ala Asp Thr Asp Ala Ala Leu Ala Asp Thr Asp Ala
            1155                1160                1165
```

Ala Leu Asp Ala Thr Thr Asn Ala Leu Asn Lys Leu Gly Glu Asn Ile
     1170                1175                1180

Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
            1205                1210                1215

Asn Asp Ile Ala Asp Ser Leu Asp Glu Thr Asn Thr Lys Ala Asp Glu
        1220                1225                1230

Ala Val Lys Thr Ala Asn Glu Ala Lys Gln Thr Ala Glu Glu Thr Lys
    1235                1240                1245

Gln Asn Val Asp Ala Lys Val Lys Ala Ala Glu Thr Ala Ala Gly Lys
1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
            1285                1290                1295

Lys Asp Asn Ile Ala Lys Lys Ala Asn Ser Ala Asp Val Tyr Thr Arg
        1300                1305                1310

Glu Glu Ser Asp Ser Lys Phe Val Arg Ile Asp Gly Leu Asn Ala Thr
    1315                1320                1325

Thr Glu Lys Leu Asp Thr Arg Leu Ala Ser Ala Glu Lys Ser Ile Ala
1330                1335                1340

Asp His Asp Thr Arg Leu Asn Gly Leu Asp Lys Thr Val Ser Asp Leu
1345                1350                1355                1360

Arg Lys Glu Thr Arg Gln Gly Leu Ala Glu Gln Ala Ala Leu Ser Gly
            1365                1370                1375

Leu Phe Gln Pro Tyr Asn Val Gly Arg Phe Asn Val Thr Ala Ala Val
        1380                1385                1390

Gly Gly Tyr Lys Ser Glu Ser Ala Val Ala Ile Gly Thr Gly Phe Arg
    1395                1400                1405

Phe Thr Glu Asn Phe Ala Ala Lys Ala Gly Val Ala Val Gly Thr Ser
1410                1415                1420

Ser Gly Ser Ser Ala Ala Tyr His Val Gly Val Asn Tyr Glu Trp Leu
1425                1430                1435                1440

Glu His His His His His His
            1445

<210> SEQ ID NO 106
<211> LENGTH: 4179
<212> TYPE: DNA
<213> ORGANISM: Artificial Sequence
<220> FEATURE:
<223> OTHER INFORMATION: Synthetic construct

<400> SEQUENCE: 106
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180
aatgcccccc ccccgaatct gcataccgga gactttccaa acccaaatga cgcatacaag     240
aatttgatca acctcaaacc tgcaattgaa gcaggctata caggacgcgg ggtagaggta     300
ggtatcgtcg acacaggcga atccgtcggc agcatatcct ttcccgaact gtatggcaga     360
aaagaacacg gctataacga aaattacaaa aactatacgg cgtatatgcg gaaggaagcg     420

```
cctgaagacg gaggcggtaa agacattgaa gcttctttcg acgatgaggc cgttatagag      480
actgaagcaa agccgacgga tatccgccac gtaaaagaaa tcggacacat cgatttggtc      540
tcccatatta ttggcgggcg ttccgtggac ggcagacctg caggcggtat tgcgcccgat      600
gcgacgctac acataatgaa tacgaatgat gaaaccaaga acgaaatgat ggttgcagcc      660
atccgcaatg catgggtcaa gctgggcgaa cgtggcgtgc gcatcgtcaa taacagtttt      720
ggaacaacat cgagggcagg cactgccgac cttttccaaa tagccaattc ggaggagcag      780
taccgccaag cgttgctcga ctattccggc ggtgataaaa cagacgaggg tatccgcctg      840
atgcaacaga gcgattacgg caacctgtcc taccacatcc gtaataaaaa catgcttttc      900 atctttcga caggcaatga cgcacaagct cagcccaaca catatgccct attgccattt       960
tatgaaaaag acgctcaaaa aggcattatc acagtcgcag gcgtagaccg cagtggagaa      1020
aagttcaaac gggaaatgta tggagaaccg ggtacagaac cgcttgagta tggctccaac      1080
cattgcggaa ttactgccat gtggtgcctg tcggcaccct atgaagcaag cgtccgtttc      1140
acccgtacaa acccgattca aattgccgga acatccttt ccgcacccat cgtaaccggc       1200
acggcggctc tgctgctgca gaaatacccg tggatgagca cgacaacct gcgtaccacg       1260 ttgctgacga cggctcagga catcggtgca gtcggcgtgg acagcaagtt cggctgggga      1320
ctgctggatg cgggtaaggc catgaacgga cccgcgtcct ttccgttcgg cgactttacc      1380
gccgatacga aggtacatc cgatattgcc tactccttcc gtaacgacat tcaggcacg        1440 ggcggcctga tcaaaaaagg cggcagccaa ctgcaactgc acggcaacaa cacctatacg      1500
ggcaaaacca ttatcgaagg cggttcgctg gtgttgtacg caacaacaa atcggatatg       1560 cgcgtcgaaa ccaaaggtgc gctgatttat aacggggcgg catccggcgg cagcctgaac      1620
agcgacggca ttgtctatct ggcagatacc gaccaatccg cgcaaacga aaccgtacac       1680 atcaaaggca gtctgcagct ggacggcaaa ggtacgctgt acacgtttt gggcaaactg       1740 ctgaaagtgg acgtacggc gattatcggc ggcaagctgt acatgtcggc acgcggcaag       1800
ggggcaggct atctcaacag taccggacga cgtgttccct tcctgagtgc cgccaaaatc      1860
gggcaggatt attctttctt cacaaacatc gaaaccgacg gcggcctgct ggcttccctc      1920
gacagcgtcg aaaaaacagc gggcagtgaa ggcgacacgc tgtcctatta tgtccgtcgc      1980
ggcaatgcgg cacggactgc ttcggcagcg gcacattccg cgcccgccgg tctgaaacac      2040
gccgtagaac agggcggcag caatctggaa aacctgatgg tcgaactgga tgcctccgaa      2100
tcatccgcaa cacccgagac ggttgaaact gcggcagccg accgcacaga tatgccgggc      2160
atccgcccct acggcgcaac tttccgcgca gcggcagccg tacagcatgc gaatgccgcc      2220
gacggtgtac gcatcttcaa cagtctcgcc gctaccgtct atgccgacag taccgccgcc      2280
catgccgata tgcagggacg ccgcctgaaa gccgtatcgg acgggttgga ccacaacggc      2340
acgggtctgc gcgtcatcgc gcaaacccaa caggacggtg aacgtgggga cagggcggt       2400 gttgaaggca aaatgcgcgg cagtacccaa accgtcggca ttgccgcgaa aaccggcgaa      2460
aatacgacag cagccgccac actgggcatg gacgcagca catggagcga aaacagtgca      2520
aatgcaaaaa ccgacagcat tagtctgttt gcaggcatac ggcacgatgc gggcgatatc      2580
ggctatctca aaggcctgtt ctcctacgga cgctacaaaa acagcatcag ccgcagcacc      2640
ggtgcggacg aacatgcgga aggcagcgtc aacggcacgc tgatgcagct gggcgcactg      2700
ggcggtgtca acgttccgtt tgccgcaacg ggagatttga cggtcgaagg cggtctgcgc      2760
tacgacctgc tcaaacagga tgcattcgcc gaaaaaggca gtgctttggg ctggagcggc      2820
```

```
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acaccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaccgc caatgaagcc    3720 aaacagacgg ccgaagaaac caaacaaaac gtcgatgcca agtaaaagc tgcagaaact    3780 gcagcaggca agccgaagc tgccgctggc acagctaata ctgcagccga caaggccgaa    3840
gctgtcgctg caaaagttac cgacatcaaa gctgatatcg ctacgaacaa agataatatt    3900
gctaaaaaag caaacagtgc cgacgtgtac accagagaag agtctgacag caaatttgtc    3960
agaattgatg gtctgaacgc tactaccgaa aaattggaca cacgcttggc ttctgctgaa    4020
aaatccattg ccgatcacga tactcgcctg aacggtttgg ataaaacagt gtcagacctg    4080
cgcaaagaaa cccgccaagg ccttgcagaa caagccgcgc tctccggtct gttccaacct    4140
tacaacgtgg gtctcgagca ccaccaccac caccactga                          4179
```

<210> SEQ ID NO 107
<211> LENGTH: 1392
<212> TYPE: PRT
<213> ORGANISM: Artificial Sequence
<220> FEATURE:
<223> OTHER INFORMATION: Synthetic construct

<400> SEQUENCE: 107

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
```

```
              115                 120                 125
Tyr Lys Asn Tyr Thr Ala Tyr Met Arg Lys Glu Ala Pro Glu Asp Gly
        130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540
```

```
Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
                580                 585                 590

Leu Tyr Met Ser Ala Arg Gly Lys Gly Ala Gly Tyr Leu Asn Ser Thr
                595                 600                 605

Gly Arg Arg Val Pro Phe Leu Ser Ala Lys Ile Gly Gln Asp Tyr
610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
                660                 665                 670

Ser Ala Pro Ala Gly Leu Lys His Ala Val Glu Gln Gly Gly Ser Asn
                675                 680                 685

Leu Glu Asn Leu Met Val Glu Leu Asp Ala Ser Glu Ser Ser Ala Thr
690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
                740                 745                 750

Val Tyr Ala Asp Ser Thr Ala Ala His Ala Asp Met Gln Gly Arg Arg
                755                 760                 765

Leu Lys Ala Val Ser Asp Gly Leu Asp His Asn Gly Thr Gly Leu Arg
                770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
                820                 825                 830

Ser Thr Trp Ser Glu Asn Ser Ala Asn Ala Lys Thr Asp Ser Ile Ser
                835                 840                 845

Leu Phe Ala Gly Ile Arg His Asp Ala Gly Asp Ile Gly Tyr Leu Lys
                850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
                900                 905                 910

Leu Thr Val Glu Gly Gly Leu Arg Tyr Asp Leu Leu Lys Gln Asp Ala
                915                 920                 925

Phe Ala Glu Lys Gly Ser Ala Leu Gly Trp Ser Gly Asn Ser Leu Thr
                930                 935                 940

Glu Gly Thr Leu Val Gly Leu Ala Gly Leu Lys Leu Ser Gln Pro Leu
945                 950                 955                 960
```

-continued

```
Ser Asp Lys Ala Val Leu Phe Ala Thr Ala Gly Val Glu Arg Asp Leu
            965                 970                 975

Asn Gly Arg Asp Tyr Thr Val Thr Gly Gly Phe Thr Gly Ala Thr Ala
        980                 985                 990

Ala Thr Gly Lys Thr Gly Ala Arg Asn Met Pro His Thr Arg Leu Val
    995                 1000                1005

Ala Gly Leu Gly Ala Asp Val Glu Phe Gly Asn Gly Trp Asn Gly Leu
1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
            1045                1050                1055

Ser Ala Thr Asn Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
        1075                1080                1085

Glu Thr Ile Tyr Asp Ile Asp Glu Asp Gly Thr Ile Thr Lys Lys Asp
        1090                1095                1100

Ala Thr Ala Ala Asp Val Glu Ala Asp Phe Lys Gly Leu Gly Leu
1105                1110                1115                1120

Lys Lys Val Val Thr Asn Leu Thr Lys Thr Val Asn Glu Asn Lys Gln
            1125                1130                1135

Asn Val Asp Ala Lys Val Lys Ala Ala Glu Ser Glu Ile Glu Lys Leu
        1140                1145                1150

Thr Thr Lys Leu Ala Asp Thr Asp Ala Ala Leu Ala Asp Thr Asp Ala
            1155                1160                1165

Ala Leu Asp Ala Thr Thr Asn Ala Leu Asn Lys Leu Gly Glu Asn Ile
    1170                1175                1180

Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
            1205                1210                1215

Asn Asp Ile Ala Asp Ser Leu Asp Glu Thr Asn Thr Lys Ala Asp Glu
        1220                1225                1230

Ala Val Lys Thr Ala Asn Glu Ala Lys Gln Thr Ala Glu Glu Thr Lys
    1235                1240                1245

Gln Asn Val Asp Ala Lys Val Lys Ala Ala Glu Thr Ala Ala Gly Lys
        1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
            1285                1290                1295

Lys Asp Asn Ile Ala Lys Lys Ala Asn Ser Ala Asp Val Tyr Thr Arg
        1300                1305                1310

Glu Glu Ser Asp Ser Lys Phe Val Arg Ile Asp Gly Leu Asn Ala Thr
    1315                1320                1325

Thr Glu Lys Leu Asp Thr Arg Leu Ala Ser Ala Glu Lys Ser Ile Ala
1330                1335                1340

Asp His Asp Thr Arg Leu Asn Gly Leu Asp Lys Thr Val Ser Asp Leu
1345                1350                1355                1360

Arg Lys Glu Thr Arg Gln Gly Leu Ala Glu Gln Ala Ala Leu Ser Gly
            1365                1370                1375

Leu Phe Gln Pro Tyr Asn Val Gly Leu Glu His His His His His His
```

<210> SEQ ID NO 108
<211> LENGTH: 1947
<212> TYPE: DNA
<213> ORGANISM: Artificial Sequence
<220> FEATURE:
<223> OTHER INFORMATION: Synthetic construct

<400> SEQUENCE: 108

| | | | | | |
|---|---|---|---|---|---|
| atggtcgccg | ccgacatcgg | tgcggggctt | gccgatgcac | taaccgcacc | gctcgaccat | 60 |
| aaagacaaag | gtttgcagtc | tttgacgctg | gatcagtccg | tcaggaaaaa | cgagaaactg | 120 |
| aagctggcgg | cacaaggtgc | ggaaaaaact | tatggaaacg | gtgacagcct | caatacgggc | 180 |
| aaattgaaga | acgacaaggt | cagccgtttc | gactttatcc | gccaaatcga | agtggacggg | 240 |
| cagctcatta | ccttggagag | tggagagttc | caagtataca | aacaaagcca | ttccgcctta | 300 |
| accgcctttc | agaccgagca | aatacaagat | tcggagcatt | ccggaagat | ggttgcgaaa | 360 |
| cgccagttca | gaatcggcga | catagcgggc | gaacatacat | cttttgacaa | gcttcccgaa | 420 |
| ggcggcaggg | cgacatatcg | cgggacggcg | ttcggttcag | acgatgccgg | cggaaaactg | 480 |
| acctacacca | tagatttcgc | cgccaagcag | ggaaacggca | aaatcgaaca | tttgaaatcg | 540 |
| ccagaactca | atgtcgacct | ggccgccgcc | gatatcaagc | cggatggaaa | acgccatgcc | 600 |
| gtcatcagcg | gttccgtcct | ttacaaccaa | gccgagaaag | cagttactc | cctcggtatc | 660 |
| tttggcggaa | agcccagga | agttgccggc | agcgcggaag | tgaaaaccgt | aaacggcata | 720 |
| cgccatatcg | gccttgccgc | caagcaactc | gagggtggcg | gaggcactgg | atccgccaca | 780 |
| aacgacgacg | atgttaaaaa | agctgccact | gtggccattg | ctgctgccta | caacaatggc | 840 |
| caagaaatca | acgtttcaa | agctggagag | accatctacg | acattgatga | agacggcaca | 900 |
| attaccaaaa | aagacgcaac | tgcagccgat | gttgaagccg | acgactttaa | aggtctgggt | 960 |
| ctgaaaaaag | tcgtgactaa | cctgaccaaa | accgtcaatg | aaaacaaaca | aaacgtcgat | 1020 |
| gccaaagtaa | aagctgcaga | atctgaaata | gaaaagttaa | caaccaagtt | agcagacact | 1080 |
| gatgccgctt | tagcagatac | tgatgccgct | ctggatgcaa | ccaccaacgc | cttgaataaa | 1140 |
| ttgggagaaa | atataacgac | atttgctgaa | gagactaaga | caaatatcgt | aaaaattgat | 1200 |
| gaaaaattag | aagccgtggc | tgataccgtc | gacaagcatg | ccgaagcatt | caacgatatc | 1260 |
| gccgattcat | ggatgaaac | caacactaag | gcagacgaag | ccgtcaaaac | cgccaatgaa | 1320 |
| gccaaacaga | cggccgaaga | aaccaaacaa | aacgtcgatg | ccaaagtaaa | agctgcagaa | 1380 |
| actgcagcag | gcaaagccga | agctgccgct | ggcacagcta | atactgcagc | cgacaaggcc | 1440 |
| gaagctgtcg | ctgcaaaagt | taccgacatc | aaagctgata | tcgctacgaa | caaagataat | 1500 |
| attgctaaaa | aagcaaacag | tgccgacgtg | tacaccagag | aagagtctga | cagcaaattt | 1560 |
| gtcagaattg | atggtctgaa | cgctactacc | gaaaaattgg | acacacgctt | ggcttctgct | 1620 |
| gaaaaatcca | ttgccgatca | cgatactcgc | ctgaacggtt | tggataaaac | agtgtcagac | 1680 |
| ctgcgcaaag | aaacccgcca | aggccttgca | gaacaagccg | cgctctccgg | tctgttccaa | 1740 |
| ccttacaacg | tgggtcggtt | caatgtaacg | gctgcagtcg | gcggctacaa | atccgaatcg | 1800 |
| gcagtcgcca | tcggtaccgg | cttccgcttt | accgaaaact | tgccgccaa | gcaggcgtg | 1860 |
| gcagtcggca | cttcgtccgg | ttcttccgca | gcctaccatg | tcggcgtcaa | ttacgagtgg | 1920 |
| ctcgagcacc | accaccacca | ccactga | | | | 1947 |

-continued

```
<210> SEQ ID NO 109
<211> LENGTH: 648
<212> TYPE: PRT
<213> ORGANISM: Artificial Sequence
<220> FEATURE:
<223> OTHER INFORMATION: Synthetic construct

<400> SEQUENCE: 109
```

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Thr
                245                 250                 255

Gly Ser Ala Thr Asn Asp Asp Val Lys Lys Ala Ala Thr Val Ala
            260                 265                 270

Ile Ala Ala Ala Tyr Asn Asn Gly Gln Glu Ile Asn Gly Phe Lys Ala
        275                 280                 285

Gly Glu Thr Ile Tyr Asp Ile Asp Glu Asp Gly Thr Ile Thr Lys Lys
    290                 295                 300

Asp Ala Thr Ala Ala Asp Val Glu Ala Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Glu Ser Glu Ile Glu Lys
            340                 345                 350

Leu Thr Thr Lys Leu Ala Asp Thr Asp Ala Ala Leu Ala Asp Thr Asp
        355                 360                 365

Ala Ala Leu Asp Ala Thr Thr Asn Ala Leu Asn Lys Leu Gly Glu Asn

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
            405                 410                 415

Phe Asn Asp Ile Ala Asp Ser Leu Asp Glu Thr Asn Thr Lys Ala Asp
            420                 425                 430

Glu Ala Val Lys Thr Ala Asn Glu Ala Lys Gln Thr Ala Glu Glu Thr
            435                 440                 445

Lys Gln Asn Val Asp Ala Lys Val Lys Ala Ala Glu Thr Ala Ala Gly
        450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
            515                 520                 525

Thr Thr Glu Lys Leu Asp Thr Arg Leu Ala Ser Ala Glu Lys Ser Ile
            530                 535                 540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Arg Phe Asn Val Thr Ala Ala
            580                 585                 590

Val Gly Gly Tyr Lys Ser Glu Ser Ala Val Ala Ile Gly Thr Gly Phe
            595                 600                 605

Arg Phe Thr Glu Asn Phe Ala Ala Lys Ala Gly Val Ala Val Gly Thr
            610                 615                 620

Ser Ser Gly Ser Ser Ala Ala Tyr His Val Gly Val Asn Tyr Glu Trp
625                 630                 635                 640

Leu Glu His His His His His His
            645

<210> SEQ ID NO 110
<211> LENGTH: 1782
<212> TYPE: DNA
<213> ORGANISM: Artificial Sequence
<220> FEATURE:
<223> OTHER INFORMATION: Synthetic construct

<400> SEQUENCE: 110

```
atggtcgccg ccgacatcgg tgcggggctt gccgatgcac taaccgcacc gctcgaccat      60
aaagacaaag gtttgcagtc tttgacgctg atcagtccg tcaggaaaaa cgagaaactg     120
aagctggcgg cacaaggtgc ggaaaaaact tatggaaacg gtgacagcct caatacgggc     180
aaattgaaga cgacaaggt cagccgtttc gactttatcc gccaaatcga agtggacggg     240
cagctcatta ccttggagag tggagagttc aagtataca aacaaagcca ttccgcctta     300
accgcctttc agaccgagca aatacaagat tcggagcatt ccggaagat ggttgcgaaa     360 cgccagttca gaatcggcga catagcgggc gaacatatac tttttgacaa gcttcccgaa     420
ggcggcaggg cgacatatcg cgggacggcg ttcggttcag acgatgccgg cggaaaactg     480
```

```
acctacacca tagatttcgc cgccaagcag ggaaacggca aaatcgaaca tttgaaatcg    540
ccagaactca atgtcgacct ggccgccgcc gatatcaagc cggatggaaa acgccatgcc    600
gtcatcagcg gttccgtcct ttacaaccaa gccgagaaag gcagttactc cctcggtatc    660
tttggcggaa aagcccagga agttgccggc agcgcgaaag tgaaaaccgt aaacggcata    720
cgccatatcg gccttgccgc caagcaactc gagggtggcg gaggcactgg atccgccaca    780
aacgacgacg atgttaaaaa agctgccact gtggccattg ctgctgccta acaatggc     840 caagaaatca acggtttcaa agctggagag accatctacg acattgatga agacggcaca    900
attaccaaaa aagacgcaac tgcagccgat gttgaagccg acgactttaa aggtctgggt    960
ctgaaaaaag tcgtgactaa cctgaccaaa accgtcaatg aaaacaaaca aaacgtcgat   1020
gccaaagtaa aagctgcaga atctgaaata gaaaagttaa caaccaagtt agcagacact   1080
gatgccgctt tagcagatac tgatgccgct ctggatgcaa ccaccaacgc cttgaataaa   1140
ttgggagaaa atataacgac atttgctgaa gagactaaga caaatatcgt aaaaattgat   1200
gaaaaattag aagccgtggc tgataccgtc gacaagcatg ccgaagcatt caacgatatc   1260
gccgattcat tggatgaaac caacactaag gcagacgaag ccgtcaaaac cgccaatgaa   1320
gccaaacaga cggccgaaga accaaacaa acgtcgatg ccaaagtaaa agctgcagaa   1380
actgcagcag gcaaagccga agctgccgct ggcacagcta atactgcagc cgacaaggcc   1440
gaagctgtcg ctgcaaaagt taccgacatc aaagctgata tcgctacgaa caagataat   1500 attgctaaaa agcaaacag tgccgacgtg tacaccagag aagagtctga cagcaaattt   1560
gtcagaattg atggtctgaa cgctactacc gaaaaattgg acacacgctt ggcttctgct   1620
gaaaaatcca ttgccgatca cgatactcgc ctgaacggtt tggataaaac agtgtcagac   1680
ctgcgcaaaa aaacccgcca aggccttgca gaacaagccg cgctctccgg tctgttccaa   1740
ccttacaacg tgggtctcga gcaccaccac caccaccact ga                      1782
```

<210> SEQ ID NO 111
<211> LENGTH: 593
<212> TYPE: PRT
<213> ORGANISM: Artificial Sequence
<220> FEATURE:
<223> OTHER INFORMATION: Synthetic construct

<400> SEQUENCE: 111

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
```

```
                130                 135                 140
Thr Tyr Arg Gly Thr Ala Phe Gly Ser Asp Asp Ala Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
                180                 185                 190

Lys Pro Asp Gly Lys Arg His Ala Val Ile Ser Gly Ser Val Leu Tyr
                195                 200                 205

Asn Gln Ala Glu Lys Gly Ser Tyr Ser Leu Gly Ile Phe Gly Gly Lys
                210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Thr
                245                 250                 255

Gly Ser Ala Thr Asn Asp Asp Val Lys Lys Ala Ala Thr Val Ala
                260                 265                 270

Ile Ala Ala Ala Tyr Asn Asn Gly Gln Glu Ile Asn Gly Phe Lys Ala
                275                 280                 285

Gly Glu Thr Ile Tyr Asp Ile Asp Glu Asp Gly Thr Ile Thr Lys Lys
                290                 295                 300

Asp Ala Thr Ala Ala Asp Val Glu Ala Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Ala Glu Ser Glu Ile Glu Lys
                340                 345                 350

Leu Thr Thr Lys Leu Ala Asp Thr Asp Ala Ala Leu Ala Asp Thr Asp
                355                 360                 365

Ala Ala Leu Asp Ala Thr Thr Asn Ala Leu Asn Lys Leu Gly Glu Asn
                370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
                420                 425                 430

Glu Ala Val Lys Thr Ala Asn Glu Ala Lys Gln Thr Ala Glu Glu Thr
                435                 440                 445

Lys Gln Asn Val Asp Ala Lys Val Lys Ala Ala Glu Thr Ala Ala Gly
                450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
                500                 505                 510

Arg Glu Glu Ser Asp Ser Lys Phe Val Arg Ile Asp Gly Leu Asn Ala
                515                 520                 525

Thr Thr Glu Lys Leu Asp Thr Arg Leu Ala Ser Ala Glu Lys Ser Ile
                530                 535                 540

Ala Asp His Asp Thr Arg Leu Asn Gly Leu Asp Lys Thr Val Ser Asp
545                 550                 555                 560
```

Leu Arg Lys Glu Thr Arg Gln Gly Leu Ala Glu Gln Ala Ala Leu Ser
            565                 570                 575

Gly Leu Phe Gln Pro Tyr Asn Val Gly Leu Glu His His His His
            580                 585                 590

His

<210> SEQ ID NO 112
<211> LENGTH: 3939
<212> TYPE: DNA
<213> ORGANISM: Artificial Sequence
<220> FEATURE:
<223> OTHER INFORMATION: Synthetic construct

<400> SEQUENCE: 112

| | | | | | |
|---|---|---|---|---|---|
| atggtcgccg | ccgacatcgg | tgcggggctt | gccgatgcac | taaccgcacc | gctcgaccat | 60 |
| aaagacaaag | gtttgcagtc | tttgacgctg | gatcagtccg | tcaggaaaaa | cgagaaactg | 120 |
| aagctggcgg | cacaaggtgc | ggaaaaaact | tatggaaacg | gtgacagcct | caatacgggc | 180 |
| aaattgaaga | acgacaaggt | cagccgtttc | gactttatcc | gccaaatcga | agtggacggg | 240 |
| cagctcatta | ccttggagag | tggagagttc | aagtataca | aacaaagcca | ttccgcctta | 300 |
| accgcctttc | agaccgagca | aatacaagat | tcggagcatt | ccgggaagat | ggttgcgaaa | 360 |
| cgccagttca | gaatcggcga | catagcgggc | gaacatacat | cttttgacaa | gcttcccgaa | 420 |
| ggcggcaggg | cgacatatcg | cgggacggcg | ttcggttcag | acgatgccgg | cggaaaactg | 480 |
| acctacacca | tagatttcgc | cgccaagcag | ggaaacggca | aaatcgaaca | tttgaaatcg | 540 |
| ccagaactca | atgtcgacct | ggccgccgcc | gatatcaagc | cggatggaaa | acgccatgcc | 600 |
| gtcatcagcg | gttccgtcct | ttacaaccaa | gccgagaaag | gcagttactc | cctcggtatc | 660 |
| tttggcggaa | aagcccagga | agttgccggc | agcgcggaag | tgaaaaccgt | aaacggcata | 720 |
| cgccatatcg | gccttgccgc | caagcaactc | gagggatccg | gcggaggcgg | cacttctgcg | 780 |
| cccgacttca | atgcaggcgg | taccggtatc | ggcagcaaca | gcagagcaac | aacagcgaaa | 840 |
| tcagcagcag | tatcttacgc | cggtatcaag | aacgaaatgt | gcaaagacag | aagcatgctc | 900 |
| tgtgccggtc | gggatgacgt | tgcggttaca | gacagggatg | ccaaaatcaa | tgcccccccc | 960 |
| ccgaatctgc | ataccggaga | cttttccaaac | ccaaatgacg | catacaagaa | tttgatcaac | 1020 |
| ctcaaacctg | caattgaagc | aggctataca | ggacgcgggg | tagaggtagg | tatcgtcgac | 1080 |
| acaggcgaat | ccgtcggcag | catatccttt | cccgaactgt | atggcagaaa | agaacacggc | 1140 |
| tataacgaaa | attacaaaaa | ctatacggcg | tatatgcgga | aggaagcgcc | tgaagacgga | 1200 |
| ggcggtaaag | acattgaagc | ttctttcgac | gatgaggccg | ttatagagac | tgaagcaaag | 1260 |
| ccgacggata | tccgccacgt | aaaagaaatc | ggacacatcg | atttggtctc | ccatattatt | 1320 |
| ggcgggcgtt | ccgtggacgg | cagacctgca | ggcggtattg | cgcccgatgc | gacgctacac | 1380 |
| ataatgaata | cgaatgatga | aaccaagaac | gaaatgatgg | ttgcagccat | ccgcaatgca | 1440 |
| tgggtcaagc | tgggcgaacg | tggcgtgcgc | atcgtcaata | acagttttgg | aacaacatcg | 1500 |
| agggcaggca | ctgccgacct | tttccaaata | gccaattcgg | aggagcagta | ccgccaagcg | 1560 |
| ttgctcgact | attccggcgg | tgataaaaca | gacgagggta | tccgcctgat | gcaacagagc | 1620 |
| gattacggca | acctgtccta | ccacatccgt | aataaaaaca | tgcttttcat | cttttcgaca | 1680 |
| ggcaatgacg | cacaagctca | gcccaacaca | tatgccctat | tgccattta | tgaaaaagac | 1740 |
| gctcaaaaag | gcattatcac | agtcgcaggc | gtagaccgca | gtggagaaaa | gttcaaacgg | 1800 |

```
gaaatgtatg gagaaccggg tacagaaccg cttgagtatg gctccaacca ttgcggaatt    1860
actgccatgt ggtgcctgtc ggcaccctat gaagcaagcg tccgtttcac ccgtacaaac    1920
ccgattcaaa ttgccggaac atccttttcc gcacccatcg taaccggcac ggcggctctg    1980
ctgctgcaga ataccccgtg gatgagcaac gacaacctgc gtaccacgtt gctgacgacg    2040
gctcaggaca tcggtgcagt cggcgtggac agcaagttcg gctgggact gctggatgcg     2100
ggtaaggcca tgaacggacc cgcgtccttt ccgttcggcg actttaccgc cgatacgaaa    2160
ggtacatccg atattgccta ctccttccgt aacgacattt caggcacggg cggcctgatc    2220
aaaaaaggcg gcagccaact gcaactgcac ggcaacaaca cctatacggg caaaaccatt    2280
atcgaaggcg gttcgctggt gttgtacggc aacaacaaat cggatatgcg cgtcgaaacc    2340
aaaggtgcgc tgatttataa cggggcggca tccggcggca gcctgaacag cgacggcatt    2400
gtctatctgg cagataccga ccaatccggc gcaaacgaaa ccgtacacat caaaggcagt    2460
ctgcagctgg acggcaaagg tacgctgtac acacgtttgg gcaaactgct gaaagtggac    2520
ggtacggcga ttatcggcgg caagctgtac atgtcggcac gcgcaagggg ggcaggctat    2580
ctcaacagta ccggacgacg tgttcccttc ctgagtgccg ccaaaatcgg gcaggattat    2640
tctttcttca caaacatcga aaccgacggc ggcctgctgg cttccctcga cagcgtcgaa    2700
aaaacagcgg gcagtgaagg cgacacgctg tcctattatg tccgtcgcgg caatgcggca    2760
cggactgctt cggcagcggc acattccgcg cccgccggtc tgaaacacgc cgtagaacag    2820
ggcggcagca atctggaaaa cctgatggtc gaactggatg cctccgaatc atccgcaaca    2880
cccgagacgt tgaaactgc ggcagccgac cgcacagata tgccgggcat ccgcccctac     2940
ggcgcaactt ccgcgcagc ggcagccgta cagcatgcga atgccgccga cggtgtacgc     3000
atcttcaaca gtctcgccgc taccgtctat gccgacagta ccgccgccca tgccgatatg    3060
cagggacgcc gcctgaaagc cgtatcggac gggttggacc acaacggcac gggtctgcgc    3120
gtcatcgcgc aaacccaaca ggacggtgga acgtgggaac agggcggtgt tgaaggcaaa    3180
atgcgcggca gtacccaaac cgtcggcatt gccgcgaaaa ccggcgaaaa tacgacagca    3240
gccgccacac tgggcatggg acgcagcaca tggagcgaaa acagtgcaaa tgcaaaaacc    3300
gacagcatta gtctgtttgc aggcatacgg cacgatgcgg gcgatatcgg ctatctcaaa    3360
ggcctgttct cctacggacg ctacaaaaac agcatcagcc gcagcaccgg tgcggacgaa    3420
catgcggaag gcagcgtcaa cggcacgctg atgcagctgg gcgcactggg cggtgtcaac    3480
gttccgtttg ccgcaacggg agatttgacg gtcgaaggcg gtctgcgcta cgacctgctc    3540
aaacaggatg cattcgccga aaaaggcagt gctttgggct ggagcggcaa cagcctcact    3600
gaaggcacgc tggtcggact cgcgggtctg aagctgtcgc aacccttgag cgataaagcc    3660
gtcctgtttg caacggcggg cgtggaacgc gacctgaacg gacgcgacta cacggtaacg    3720
ggcggcttta ccgcgcgac tgcagcaacc ggcaagacgg gggcacgcaa tatgccgcac     3780
acccgtctgg ttgccggcct gggcgcggat gtcgaattcg gcaacggctg gaacggcttg    3840
gcacgttaca gctacgccgg ttccaaacag tacggcaacc acagcggacg agtcggcgta    3900
ggctaccggt tcctcgagca ccaccaccac caccactga                           3939
```

<210> SEQ ID NO 113
<211> LENGTH: 1312
<212> TYPE: PRT
<213> ORGANISM: Artificial Sequence
<220> FEATURE:
<223> OTHER INFORMATION: Synthetic construct

<400> SEQUENCE: 113

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Ser Gly Gly Gly
                245                 250                 255

Gly Thr Ser Ala Pro Asp Phe Asn Ala Gly Gly Thr Gly Ile Gly Ser
            260                 265                 270

Asn Ser Arg Ala Thr Thr Ala Lys Ser Ala Ala Val Ser Tyr Ala Gly
        275                 280                 285

Ile Lys Asn Glu Met Cys Lys Asp Arg Ser Met Leu Cys Ala Gly Arg
    290                 295                 300

Asp Asp Val Ala Val Thr Asp Arg Asp Ala Lys Ile Asn Ala Pro Pro
305                 310                 315                 320

Pro Asn Leu His Thr Gly Asp Phe Pro Asn Pro Asn Asp Ala Tyr Lys
                325                 330                 335

Asn Leu Ile Asn Leu Lys Pro Ala Ile Glu Ala Gly Tyr Thr Gly Arg
            340                 345                 350

Gly Val Glu Val Gly Ile Val Asp Thr Gly Glu Ser Val Gly Ser Ile
        355                 360                 365

Ser Phe Pro Glu Leu Tyr Gly Arg Lys Glu His Gly Tyr Asn Glu Asn
    370                 375                 380

Tyr Lys Asn Tyr Thr Ala Tyr Met Arg Lys Glu Ala Pro Glu Asp Gly
385                 390                 395                 400

Gly Gly Lys Asp Ile Glu Ala Ser Phe Asp Asp Glu Ala Val Ile Glu
```

```
                    405                 410                 415
Thr Glu Ala Lys Pro Thr Asp Ile Arg His Val Lys Glu Ile Gly His
            420                 425                 430

Ile Asp Leu Val Ser His Ile Ile Gly Gly Arg Ser Val Asp Gly Arg
            435                 440                 445

Pro Ala Gly Gly Ile Ala Pro Asp Ala Thr Leu His Ile Met Asn Thr
            450                 455                 460

Asn Asp Glu Thr Lys Asn Glu Met Met Val Ala Ala Ile Arg Asn Ala
465                 470                 475                 480

Trp Val Lys Leu Gly Glu Arg Gly Val Arg Ile Val Asn Asn Ser Phe
            485                 490                 495

Gly Thr Thr Ser Arg Ala Gly Thr Ala Asp Leu Phe Gln Ile Ala Asn
            500                 505                 510

Ser Glu Glu Gln Tyr Arg Gln Ala Leu Leu Asp Tyr Ser Gly Gly Asp
            515                 520                 525

Lys Thr Asp Glu Gly Ile Arg Leu Met Gln Gln Ser Asp Tyr Gly Asn
            530                 535                 540

Leu Ser Tyr His Ile Arg Asn Lys Asn Met Leu Phe Ile Phe Ser Thr
545                 550                 555                 560

Gly Asn Asp Ala Gln Ala Gln Pro Asn Thr Tyr Ala Leu Leu Pro Phe
            565                 570                 575

Tyr Glu Lys Asp Ala Gln Lys Gly Ile Ile Thr Val Ala Gly Val Asp
            580                 585                 590

Arg Ser Gly Glu Lys Phe Lys Arg Glu Met Tyr Gly Glu Pro Gly Thr
            595                 600                 605

Glu Pro Leu Glu Tyr Gly Ser Asn His Cys Gly Ile Thr Ala Met Trp
            610                 615                 620

Cys Leu Ser Ala Pro Tyr Glu Ala Ser Val Arg Phe Thr Arg Thr Asn
625                 630                 635                 640

Pro Ile Gln Ile Ala Gly Thr Ser Phe Ser Ala Pro Ile Val Thr Gly
            645                 650                 655

Thr Ala Ala Leu Leu Leu Gln Lys Tyr Pro Trp Met Ser Asn Asp Asn
            660                 665                 670

Leu Arg Thr Thr Leu Leu Thr Thr Ala Gln Asp Ile Gly Ala Val Gly
            675                 680                 685

Val Asp Ser Lys Phe Gly Trp Gly Leu Leu Asp Ala Gly Lys Ala Met
            690                 695                 700

Asn Gly Pro Ala Ser Phe Pro Phe Gly Asp Phe Thr Ala Asp Thr Lys
705                 710                 715                 720

Gly Thr Ser Asp Ile Ala Tyr Ser Phe Arg Asn Asp Ile Ser Gly Thr
            725                 730                 735

Gly Gly Leu Ile Lys Lys Gly Gly Ser Gln Leu Gln Leu His Gly Asn
            740                 745                 750

Asn Thr Tyr Thr Gly Lys Thr Ile Ile Glu Gly Gly Ser Leu Val Leu
            755                 760                 765

Tyr Gly Asn Asn Lys Ser Asp Met Arg Val Glu Thr Lys Gly Ala Leu
            770                 775                 780

Ile Tyr Asn Gly Ala Ala Ser Gly Gly Ser Leu Asn Ser Asp Gly Ile
785                 790                 795                 800

Val Tyr Leu Ala Asp Thr Asp Gln Ser Gly Ala Asn Glu Thr Val His
            805                 810                 815

Ile Lys Gly Ser Leu Gln Leu Asp Gly Lys Gly Thr Leu Tyr Thr Arg
            820                 825                 830
```

-continued

```
Leu Gly Lys Leu Leu Lys Val Asp Gly Thr Ala Ile Ile Gly Gly Lys
        835                 840                 845
Leu Tyr Met Ser Ala Arg Gly Lys Gly Ala Gly Tyr Leu Asn Ser Thr
    850                 855                 860
Gly Arg Arg Val Pro Phe Leu Ser Ala Ala Lys Ile Gly Gln Asp Tyr
865                 870                 875                 880
Ser Phe Phe Thr Asn Ile Glu Thr Asp Gly Gly Leu Leu Ala Ser Leu
                885                 890                 895
Asp Ser Val Glu Lys Thr Ala Gly Ser Glu Gly Asp Thr Leu Ser Tyr
                900                 905                 910
Tyr Val Arg Arg Gly Asn Ala Ala Arg Thr Ala Ser Ala Ala His
                915                 920                 925
Ser Ala Pro Ala Gly Leu Lys His Ala Val Glu Gln Gly Gly Ser Asn
            930                 935                 940
Leu Glu Asn Leu Met Val Glu Leu Asp Ala Ser Glu Ser Ser Ala Thr
945                 950                 955                 960
Pro Glu Thr Val Glu Thr Ala Ala Asp Arg Thr Asp Met Pro Gly
                    965                 970                 975
Ile Arg Pro Tyr Gly Ala Thr Phe Arg Ala Ala Ala Val Gln His
                980                 985                 990
Ala Asn Ala Ala Asp Gly Val Arg Ile Phe Asn Ser Leu Ala Ala Thr
            995                 1000                1005
Val Tyr Ala Asp Ser Thr Ala Ala His Ala Asp Met Gln Gly Arg Arg
        1010                1015                1020
Leu Lys Ala Val Ser Asp Gly Leu Asp His Asn Gly Thr Gly Leu Arg
1025                1030                1035                1040
Val Ile Ala Gln Thr Gln Gln Asp Gly Gly Thr Trp Glu Gln Gly Gly
                1045                1050                1055
Val Glu Gly Lys Met Arg Gly Ser Thr Gln Thr Val Gly Ile Ala Ala
            1060                1065                1070
Lys Thr Gly Glu Asn Thr Thr Ala Ala Ala Thr Leu Gly Met Gly Arg
        1075                1080                1085
Ser Thr Trp Ser Glu Asn Ser Ala Asn Ala Lys Thr Asp Ser Ile Ser
        1090                1095                1100
Leu Phe Ala Gly Ile Arg His Asp Ala Gly Asp Ile Gly Tyr Leu Lys
1105                1110                1115                1120
Gly Leu Phe Ser Tyr Gly Arg Tyr Lys Asn Ser Ile Ser Arg Ser Thr
                1125                1130                1135
Gly Ala Asp Glu His Ala Glu Gly Ser Val Asn Gly Thr Leu Met Gln
            1140                1145                1150
Leu Gly Ala Leu Gly Gly Val Asn Val Pro Phe Ala Thr Gly Asp
        1155                1160                1165
Leu Thr Val Glu Gly Gly Leu Arg Tyr Asp Leu Leu Lys Gln Asp Ala
        1170                1175                1180
Phe Ala Glu Lys Gly Ser Ala Leu Gly Trp Ser Gly Asn Ser Leu Thr
1185                1190                1195                1200
Glu Gly Thr Leu Val Gly Leu Ala Gly Leu Lys Leu Ser Gln Pro Leu
                1205                1210                1215
Ser Asp Lys Ala Val Leu Phe Ala Thr Ala Gly Val Glu Arg Asp Leu
            1220                1225                1230
Asn Gly Arg Asp Tyr Thr Val Thr Gly Gly Phe Thr Gly Ala Thr Ala
        1235                1240                1245
```

```
Ala Thr Gly Lys Thr Gly Ala Arg Asn Met Pro His Thr Arg Leu Val
    1250                1255                1260

Ala Gly Leu Gly Ala Asp Val Glu Phe Gly Asn Gly Trp Asn Gly Leu
1265                1270                1275                1280

Ala Arg Tyr Ser Tyr Ala Gly Ser Lys Gln Tyr Gly Asn His Ser Gly
            1285                1290                1295

Arg Val Gly Val Gly Tyr Arg Phe Leu Glu His His His His His
            1300                1305                1310
```

<210> SEQ ID NO 114
<211> LENGTH: 2028
<212> TYPE: DNA
<213> ORGANISM: Artificial Sequence
<220> FEATURE:
<223> OTHER INFORMATION: Synthetic construct

<400> SEQUENCE: 114

| | | | | | |
|---|---|---|---|---|---|
| atggtcgccg | ccgacatcgg | tgcggggctt | gccgatgcac | taaccgcacc | gctcgaccat | 60 |
| aaagacaaag | gtttgcagtc | tttgacgctg | gatcagtccg | tcaggaaaaa | cgagaaactg | 120 |
| aagctggcgg | cacaaggtgc | ggaaaaaact | tatggaaacg | gtgacagcct | caatacgggc | 180 |
| aaattgaaga | cgacaaggt | cagccgtttc | gactttatcc | gccaaatcga | agtggacggg | 240 |
| cagctcatta | ccttggagag | tggagagttc | caagtataca | aacaaagcca | ttccgcctta | 300 |
| accgcctttc | agaccgagca | aatacaagat | tcggagcatt | ccgggaagat | ggttgcgaaa | 360 |
| cgccagttca | gaatcggcga | catagcgggc | gaacatacat | cttttgacaa | gcttcccgaa | 420 |
| ggcggcaggg | cgacatatcg | cgggacggcg | ttcggttcag | acgatgccgg | cggaaaactg | 480 |
| acctacacca | tagatttcgc | cgccaagcag | ggaaacggca | aaatcgaaca | tttgaaatcg | 540 |
| ccagaactca | atgtcgacct | ggccgccgcc | gatatcaagc | cggatggaaa | acgccatgcc | 600 |
| gtcatcagcg | gttccgtcct | ttacaaccaa | gccgagaaag | gcagttactc | cctcggtatc | 660 |
| tttggcggaa | aagcccagga | agttgccggc | agcgcgaag | tgaaaaccgt | aaacggcata | 720 |
| cgccatatcg | gccttgccgc | caagcaactc | gacggtggcg | gaggcactgg | atcctcagat | 780 |
| ttggcaaacg | attcttttat | ccggcaggtt | ctcgaccgtc | agcatttcga | acccgacggg | 840 |
| aaataccacc | tattcggcag | caggggggaa | cttgccgagc | gcagcggcca | tatcggattg | 900 |
| ggaaaaatac | aaagccatca | gttgggcaac | ctgatgattc | aacaggcggc | cattaaagga | 960 |
| aatatcggct | acattgtccg | ctttccgat | cacgggcacg | aagtccattc | ccccttcgac | 1020 |
| aaccatgcct | cacattccga | ttctgatgaa | gccgtagtc | ccgttgacgg | atttagcctt | 1080 |
| taccgcatcc | attgggacgg | atacgaacac | catcccgccg | acggctatga | cgggccacag | 1140 |
| ggcggcggct | atcccgctcc | caaggcgcg | agggatatat | acagctacga | cataaaaggc | 1200 |
| gttgcccaaa | atatccgcct | caacctgacc | gacaaccgca | gcaccggaca | acggcttgcc | 1260 |
| gaccgttttcc | acaatgccgg | tagtatgctg | acgcaaggag | taggcgacgg | attcaaacgc | 1320 |
| gccacccgat | acagccccga | gctggacaga | tcgggcaatg | ccgccgaagc | cttcaacggc | 1380 |
| actgcagata | tcgttaaaaa | catcatcggc | gcggcaggag | aaattgtcgg | cgcaggcgat | 1440 |
| gccgtgcagg | gcataagcga | aggctcaaac | attgctgtca | tgcacggctt | gggtctgctt | 1500 |
| tccaccgaaa | acaagatggc | gcgcatcaac | gatttggcag | atatggcgca | actcaaagac | 1560 |
| tatgccgcag | cagccatccg | cgattgggca | gtccaaaacc | ccaatgccgc | acaaggcata | 1620 |
| gaagccgtca | gcaatatctt | tatggcagcc | atccccatca | aagggattgg | agctgttcgg | 1680 |
| ggaaaatacg | gcttgggcgg | catcacggca | catcctatca | gcggtcgca | gatgggcgcg | 1740 |

```
atcgcattgc cgaaagggaa atccgccgtc agcgacaatt ttgccgatgc ggcatacgcc   1800
aaatacccgt ccccttacca ttcccgaaat atccgttcaa acttggagca gcgttacggg   1860
aaagaaaaca tcacctcctc aaccgtgccg ccgtcaaacg gcaaaaatgt caaactggca   1920
gaccaacgcc acccgaagac aggcgtaccg tttgacggta aagggtttcc gaattttgag   1980
aagcacgtga aatatgatac gctcgagcac caccaccacc accactga                2028
```

```
<210> SEQ ID NO 115
<211> LENGTH: 675
<212> TYPE: PRT
<213> ORGANISM: Artificial Sequence
<220> FEATURE:
<223> OTHER INFORMATION: Synthetic construct

<400> SEQUENCE: 115
```

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Asp Gly Gly Gly Gly Thr
                245                 250                 255

Gly Ser Ser Asp Leu Ala Asn Asp Ser Phe Ile Arg Gln Val Leu Asp
            260                 265                 270

Arg Gln His Phe Glu Pro Asp Gly Lys Tyr His Leu Phe Gly Ser Arg
        275                 280                 285

Gly Glu Leu Ala Glu Arg Ser Gly His Ile Gly Leu Gly Lys Ile Gln
    290                 295                 300

Ser His Gln Leu Gly Asn Leu Met Ile Gln Gln Ala Ala Ile Lys Gly
```

```
            305                 310                 315                 320
        Asn Ile Gly Tyr Ile Val Arg Phe Ser Asp His Gly His Glu Val His
                        325                 330                 335

Ser Pro Phe Asp Asn His Ala Ser His Ser Asp Ser Asp Glu Ala Gly
                        340                 345                 350

Ser Pro Val Asp Gly Phe Ser Leu Tyr Arg Ile His Trp Asp Gly Tyr
                        355                 360                 365

Glu His His Pro Ala Asp Gly Tyr Asp Gly Pro Gln Gly Gly Gly Tyr
                        370                 375                 380

Pro Ala Pro Lys Gly Ala Arg Asp Ile Tyr Ser Tyr Asp Ile Lys Gly
        385                 390                 395                 400

Val Ala Gln Asn Ile Arg Leu Asn Leu Thr Asp Asn Arg Ser Thr Gly
                        405                 410                 415

Gln Arg Leu Ala Asp Arg Phe His Asn Ala Gly Ser Met Leu Thr Gln
                        420                 425                 430

Gly Val Gly Asp Gly Phe Lys Arg Ala Thr Arg Tyr Ser Pro Glu Leu
                        435                 440                 445

Asp Arg Ser Gly Asn Ala Ala Glu Ala Phe Asn Gly Thr Ala Asp Ile
                        450                 455                 460

Val Lys Asn Ile Ile Gly Ala Ala Gly Glu Ile Val Gly Ala Gly Asp
        465                 470                 475                 480

Ala Val Gln Gly Ile Ser Glu Gly Ser Asn Ile Ala Val Met His Gly
                        485                 490                 495

Leu Gly Leu Leu Ser Thr Glu Asn Lys Met Ala Arg Ile Asn Asp Leu
                        500                 505                 510

Ala Asp Met Ala Gln Leu Lys Asp Tyr Ala Ala Ala Ile Arg Asp
                        515                 520                 525

Trp Ala Val Gln Asn Pro Asn Ala Ala Gln Gly Ile Glu Ala Val Ser
                        530                 535                 540

Asn Ile Phe Met Ala Ala Ile Pro Ile Lys Gly Ile Gly Ala Val Arg
        545                 550                 555                 560

Gly Lys Tyr Gly Leu Gly Gly Ile Thr Ala His Pro Ile Lys Arg Ser
                        565                 570                 575

Gln Met Gly Ala Ile Ala Leu Pro Lys Gly Lys Ser Ala Val Ser Asp
                        580                 585                 590

Asn Phe Ala Asp Ala Ala Tyr Ala Lys Tyr Pro Ser Pro Tyr His Ser
                        595                 600                 605

Arg Asn Ile Arg Ser Asn Leu Glu Gln Arg Tyr Gly Lys Glu Asn Ile
                        610                 615                 620

Thr Ser Ser Thr Val Pro Pro Ser Asn Gly Lys Asn Val Lys Leu Ala
        625                 630                 635                 640

Asp Gln Arg His Pro Lys Thr Gly Val Pro Phe Asp Gly Lys Gly Phe
                        645                 650                 655

Pro Asn Phe Glu Lys His Val Lys Tyr Asp Thr Leu Glu His His His
                        660                 665                 670

His His His
                675

<210> SEQ ID NO 116
<211> LENGTH: 249
<212> TYPE: PRT
<213> ORGANISM: Artificial Sequence
<220> FEATURE:
<223> OTHER INFORMATION: Synthetic construct
```

<400> SEQUENCE: 116

Met Lys Lys Tyr Leu Phe Arg Ala Ala Leu Tyr Gly Ile Ala Ala Ala
1               5                   10                  15

Ile Leu Ala Ala Ala Ile Pro Ala Gly Asn Asp Ala Thr Thr Lys Pro
            20                  25                  30

Asp Leu Tyr Tyr Leu Lys Asn Glu Gln Ala Ile Asp Ser Leu Lys Leu
        35                  40                  45

Leu Pro Pro Pro Pro Glu Val Gly Ser Ile Gln Phe Leu Asn Asp Gln
    50                  55                  60

Ala Met Tyr Glu Lys Gly Arg Met Leu Arg Asn Thr Glu Arg Gly Lys
65                  70                  75                  80

Gln Ala Gln Ala Asp Ala Asp Leu Ala Ala Gly Val Ala Thr Ala
                85                  90                  95

Phe Ser Gly Ala Phe Gly Tyr Pro Ile Thr Glu Lys Asp Ser Pro Glu
            100                 105                 110

Leu Tyr Lys Leu Leu Thr Asn Met Ile Glu Asp Ala Gly Asp Leu Ala
        115                 120                 125

Thr Arg Ser Ala Lys Glu His Tyr Met Arg Ile Arg Pro Phe Ala Phe
    130                 135                 140

Tyr Gly Thr Glu Thr Cys Asn Thr Lys Asp Gln Lys Lys Leu Ser Thr
145                 150                 155                 160

Asn Gly Ser Tyr Pro Ser Gly His Thr Ser Ile Gly Trp Ala Thr Ala
                165                 170                 175

Leu Val Leu Ala Glu Val Asn Pro Ala Asn Gln Asp Ala Ile Leu Glu
            180                 185                 190

Arg Gly Tyr Gln Leu Gly Gln Ser Arg Val Ile Cys Gly Tyr His Trp
        195                 200                 205

Gln Ser Asp Val Asp Ala Ala Arg Ile Val Gly Ser Ala Ala Val Ala
    210                 215                 220

Thr Leu His Ser Asp Pro Ala Phe Gln Ala Gln Leu Ala Lys Ala Lys
225                 230                 235                 240

Gln Glu Phe Ala Gln Lys Ser Gln Lys
                245

<210> SEQ ID NO 117
<211> LENGTH: 66
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(66)
<223> OTHER INFORMATION: n = A, T/U, G or C

<400> SEQUENCE: 117
tatgaartay ytnttymgcg ccgccctgta cggcatcgcc gccgccatcc tcgccgccgc    60
gatccc                                                               66

<210> SEQ ID NO 118
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(69)
<223> OTHER INFORMATION: n = A, T/U, G or C

```
<400> SEQUENCE: 118
tatgaaaaaa tacctattcc grgcngcnyt rtayggsatc gccgccgcca tcctcgccgc    60
cgcgatccc                                                            69

<210> SEQ ID NO 119
<211> LENGTH: 27
<212> TYPE: DNA
<213> ORGANISM: Artificial Sequence
<220> FEATURE:
<223> OTHER INFORMATION: Synthetic construct

<400> SEQUENCE: 119
atgaagaagt accttttcag cgccgcc                                        27

<210> SEQ ID NO 120
<211> LENGTH: 27
<212> TYPE: DNA
<213> ORGANISM: Artificial Sequence
<220> FEATURE:
<223> OTHER INFORMATION: Synthetic construct

<400> SEQUENCE: 120
atgaaaaaat acttttccg cgccgcc                                         27

<210> SEQ ID NO 121
<211> LENGTH: 27
<212> TYPE: DNA
<213> ORGANISM: Artificial Sequence
<220> FEATURE:
<223> OTHER INFORMATION: Synthetic construct

<400> SEQUENCE: 121
atgaaaaaat acttttccg cgccgcc                                         27

<210> SEQ ID NO 122
<211> LENGTH: 60
<212> TYPE: DNA
<213> ORGANISM: Artificial Sequence
<220> FEATURE:
<223> OTHER INFORMATION: Synthetic construct

<400> SEQUENCE: 122
atgaaaaaat atctctttag cgccgccctg tacggcatcg ccgccgccat cctcgccgcc    60

<210> SEQ ID NO 123
<211> LENGTH: 60
<212> TYPE: DNA
<213> ORGANISM: Artificial Sequence
<220> FEATURE:
<223> OTHER INFORMATION: Synthetic construct

<400> SEQUENCE: 123
atgaaaaaat acctattccg cgccgccctg tacggcatcg ccgccgccat cctcgccgcc    60

<210> SEQ ID NO 124
<211> LENGTH: 9
<212> TYPE: PRT
<213> ORGANISM: Artificial Sequence
<220> FEATURE:
<223> OTHER INFORMATION: Synthetic construct

<400> SEQUENCE: 124

Met Lys Lys Tyr Leu Phe Ser Ala Ala
1               5
```

<210> SEQ ID NO 125
<211> LENGTH: 9
<212> TYPE: PRT
<213> ORGANISM: Artificial Sequence
<220> FEATURE:
<223> OTHER INFORMATION: Synthetic construct

<400> SEQUENCE: 125

Met Lys Lys Tyr Phe Phe Arg Ala Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic construct

<400> SEQUENCE: 126

Met Lys Lys Tyr Phe Phe Arg Ala Ala
1               5

<210> SEQ ID NO 127
<211> LENGTH: 20
<212> TYPE: PRT
<213> ORGANISM: Artificial Sequence
<220> FEATURE:
<223> OTHER INFORMATION: Synthetic construct

<400> SEQUENCE: 127

Met Lys Lys Tyr Leu Phe Ser Ala Ala Leu Tyr Gly Ile Ala Ala Ala
1               5                   10                  15

Ile Leu Ala Ala
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic construct

<400> SEQUENCE: 128

Met Lys Lys Tyr Leu Phe Arg Ala Ala Leu Tyr Gly Ile Ala Ala Ala
1               5                   10                  15

Ile Leu Ala Ala
            20

<210> SEQ ID NO 129
<211> LENGTH: 42
<212> TYPE: DNA
<213> ORGANISM: Artificial Sequence
<220> FEATURE:
<223> OTHER INFORMATION: Synthetic construct

<400> SEQUENCE: 129
atgaaaaaat acctattcat cgccgccgcc atcctcgccg cc                         42

<210> SEQ ID NO 130
<211> LENGTH: 60
<212> TYPE: DNA
<213> ORGANISM: Artificial Sequence
<220> FEATURE:
<223> OTHER INFORMATION: Synthetic construct

```
<400> SEQUENCE: 130
atgaaaaaat acctattccg agctgcccaa tacggcatcg ccgccgccat cctcgccgcc    60

<210> SEQ ID NO 131
<211> LENGTH: 60
<212> TYPE: DNA
<213> ORGANISM: Artificial Sequence
<220> FEATURE:
<223> OTHER INFORMATION: Synthetic construct

<400> SEQUENCE: 131
atgaaaaaat acctattccg ggccgcccaa tacggcatcg ccgccgccat cctcgccgcc    60

<210> SEQ ID NO 132
<211> LENGTH: 60
<212> TYPE: DNA
<213> ORGANISM: Artificial Sequence
<220> FEATURE:
<223> OTHER INFORMATION: Synthetic construct

<400> SEQUENCE: 132
atgaaaaaat acctattccg ggcggctttg tacgggatcg ccgccgccat cctcgccgcc    60

<210> SEQ ID NO 133
<211> LENGTH: 14
<212> TYPE: PRT
<213> ORGANISM: Artificial Sequence
<220> FEATURE:
<223> OTHER INFORMATION: Synthetic construct

<400> SEQUENCE: 133

Met Lys Lys Tyr Leu Phe Ile Ala Ala Ala Ile Leu Ala Ala
1               5                   10

<210> SEQ ID NO 134
<211> LENGTH: 20
<212> TYPE: PRT
<213> ORGANISM: Artificial Sequence
<220> FEATURE:
<223> OTHER INFORMATION: Synthetic construct

<400> SEQUENCE: 134

Met Lys Lys Tyr Leu Phe Arg Ala Ala Gln Tyr Gly Ile Ala Ala Ala
1               5                   10                  15

Ile Leu Ala Ala
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic construct

<400> SEQUENCE: 135

Met Lys Lys Tyr Leu Phe Arg Ala Ala Gln Tyr Gly Ile Ala Ala Ala
1               5                   10                  15

Ile Leu Ala Ala
            20

<210> SEQ ID NO 136
<211> LENGTH: 20
<212> TYPE: PRT
<213> ORGANISM: Artificial Sequence
<220> FEATURE:
```

<223> OTHER INFORMATION: Synthetic construct

<400> SEQUENCE: 136

Met Lys Lys Tyr Leu Phe Arg Ala Ala Leu Tyr Gly Ile Ala Ala Ala
1               5                   10                  15

Ile Leu Ala Ala
            20

<210> SEQ ID NO 137
<211> LENGTH: 467
<212> TYPE: PRT
<213> ORGANISM: Artificial Sequence
<220> FEATURE:
<223> OTHER INFORMATION: Neisseria meningitidis

<400> SEQUENCE: 137

Val Lys Pro Leu Arg Arg Leu Thr Asn Leu Leu Ala Ala Cys Ala Val
1               5                   10                  15

Ala Ala Ala Ala Leu Ile Gln Pro Ala Leu Ala Ala Asp Leu Ala Gln
            20                  25                  30

Asp Pro Phe Ile Thr Asp Asn Ala Gln Arg Gln His Tyr Glu Pro Gly
        35                  40                  45

Gly Lys Tyr His Leu Phe Gly Asp Pro Arg Gly Ser Val Ser Asp Arg
    50                  55                  60

Thr Gly Lys Ile Asn Val Ile Gln Asp Tyr Thr His Gln Met Gly Asn
65                  70                  75                  80

Leu Leu Ile Gln Gln Ala Asn Ile Asn Gly Thr Ile Gly Tyr His Thr
                85                  90                  95

Arg Phe Ser Gly His Gly His Glu Glu His Ala Pro Phe Asp Asn His
            100                 105                 110

Ala Ala Asp Ser Ala Ser Glu Glu Lys Gly Asn Val Asp Glu Gly Phe
        115                 120                 125

Thr Val Tyr Arg Leu Asn Trp Glu Gly His Glu His His Pro Ala Asp
    130                 135                 140

Ala Tyr Asp Gly Pro Lys Gly Gly Asn Tyr Pro Lys Pro Thr Gly Ala
145                 150                 155                 160

Arg Asp Glu Tyr Thr Tyr His Val Asn Gly Thr Ala Arg Ser Ile Lys
                165                 170                 175

Leu Asn Pro Thr Asp Thr Arg Ser Ile Arg Gln Arg Ile Ser Asp Asn
            180                 185                 190

Tyr Ser Asn Leu Gly Ser Asn Phe Ser Asp Arg Ala Asp Glu Ala Asn
        195                 200                 205

Arg Lys Met Phe Glu His Asn Ala Lys Leu Asp Arg Trp Gly Asn Ser
    210                 215                 220

Met Glu Phe Ile Asn Gly Val Ala Ala Gly Leu Asn Pro Phe Ile
225                 230                 235                 240

Ser Ala Gly Glu Ala Leu Gly Ile Gly Asp Ile Leu Tyr Gly Thr Arg
                245                 250                 255

Tyr Ala Ile Asp Lys Ala Ala Met Arg Asn Ile Ala Pro Leu Pro Ala
            260                 265                 270

Glu Gly Lys Phe Ala Val Ile Gly Gly Leu Gly Ser Val Ala Gly Phe
        275                 280                 285

Glu Lys Asn Thr Arg Glu Ala Val Asp Arg Trp Ile Gln Glu Asn Pro
    290                 295                 300

Asn Ala Ala Glu Thr Val Glu Ala Val Phe Asn Val Ala Ala Ala Ala
305                 310                 315                 320

Lys Val Ala Lys Leu Ala Lys Ala Ala Lys Pro Gly Lys Ala Val
                325                 330                 335

Ser Gly Asp Phe Ala Asp Ser Tyr Lys Lys Leu Ala Leu Ser Asp
            340                 345                 350

Ser Ala Arg Gln Leu Tyr Gln Asn Ala Lys Tyr Arg Glu Ala Leu Asp
        355                 360                 365

Ile His Tyr Glu Asp Leu Ile Arg Arg Lys Thr Asp Gly Ser Ser Lys
370                 375                 380

Phe Ile Asn Gly Arg Glu Ile Asp Ala Val Thr Asn Asp Ala Leu Ile
385                 390                 395                 400

Gln Ala Lys Arg Thr Ile Ser Ala Ile Asp Lys Pro Lys Asn Phe Leu
                405                 410                 415

Asn Gln Lys Asn Arg Lys Gln Ile Lys Ala Thr Ile Glu Ala Ala Asn
            420                 425                 430

Gln Gln Gly Lys Arg Ala Glu Phe Trp Phe Lys Tyr Gly Val His Ser
        435                 440                 445

Gln Val Lys Ser Tyr Ile Glu Ser Lys Gly Gly Ile Val Lys Thr Gly
    450                 455                 460

Leu Gly Asp
465

<210> SEQ ID NO 138
<211> LENGTH: 377
<212> TYPE: PRT
<213> ORGANISM: Artificial Sequence
<220> FEATURE:
<223> OTHER INFORMATION: Synthetic construct

<400> SEQUENCE: 138

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
            20                  25                  30

Gly Ser Val Ser Asp Arg Thr Gly Lys Ile Asn Val Ile Gln Asp Tyr
        35                  40                  45

Thr His Gln Met Gly Asn Leu Leu Ile Gln Gln Ala Asn Ile Asn Gly
    50                  55                  60

Thr Ile Gly Tyr His Thr Arg Phe Ser Gly His Gly His Glu Glu His
65                  70                  75                  80

Ala Pro Phe Asp Asn His Ala Ala Asp Ser Ala Ser Glu Glu Lys Gly
                85                  90                  95

Asn Val Asp Glu Gly Phe Thr Val Tyr Arg Leu Asn Trp Glu Gly His
            100                 105                 110

Glu His His Pro Ala Asp Ala Tyr Asp Gly Pro Lys Gly Gly Asn Tyr
        115                 120                 125

Pro Lys Pro Thr Gly Ala Arg Asp Glu Tyr Thr Tyr His Val Asn Gly
    130                 135                 140

Thr Ala Arg Ser Ile Lys Leu Asn Pro Thr Asp Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190

Asp Arg Trp Gly Asn Ser Met Glu Phe Ile Asn Gly Val Ala Ala Gly
        195                 200                 205

```
Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Ala Val Ile Gly Gly Leu
                245                 250                 255

Gly Ser Val Ala Gly Phe Glu Lys Asn Thr Arg Glu Ala Val Asp Arg
                260                 265                 270

Trp Ile Gln Glu Asn Pro Asn Ala Ala Glu Thr Val Glu Ala Val Phe
            275                 280                 285

Asn Val Ala Ala Ala Lys Val Ala Lys Leu Ala Lys Ala Ala Lys
            290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Asp Ile His Tyr Glu Asp Leu Ile Arg Arg Lys
                340                 345                 350

Thr Asp Gly Ser Ser Lys Phe Ile Asn Gly Arg Glu Ile Asp Ala Val
                355                 360                 365

Thr Asn Asp Ala Leu Ile Gln Ala Arg
    370                 375

<210> SEQ ID NO 139
<211> LENGTH: 353
<212> TYPE: PRT
<213> ORGANISM: Artificial Sequence
<220> FEATURE:
<223> OTHER INFORMATION: Synthetic construct

<400> SEQUENCE: 139

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
            20                  25                  30

Gly Ser Val Ser Asp Arg Thr Gly Lys Ile Asn Val Ile Gln Asp Tyr
        35                  40                  45

Thr His Gln Met Gly Asn Leu Leu Ile Gln Ala Asn Ile Asn Gly
    50                  55                  60

Thr Ile Gly Tyr His Thr Arg Phe Ser Gly His Gly His Glu His
65                  70                  75                  80

Ala Pro Phe Asp Asn His Ala Ala Asp Ser Ala Ser Glu Glu Lys Gly
                85                  90                  95

Asn Val Asp Glu Gly Phe Thr Val Tyr Arg Leu Asn Trp Glu Gly His
            100                 105                 110

Glu His His Pro Ala Asp Ala Tyr Asp Gly Pro Lys Gly Asn Tyr
        115                 120                 125

Pro Lys Pro Thr Gly Ala Arg Asp Glu Tyr Thr Tyr His Val Asn Gly
    130                 135                 140

Thr Ala Arg Ser Ile Lys Leu Asn Pro Thr Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190
```

```
Asp Arg Trp Gly Asn Ser Met Glu Phe Ile Asn Gly Val Ala Ala Gly
        195                 200                 205

Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Val Ile Gly Gly Leu
                245                 250                 255

Gly Ser Val Ala Gly Phe Glu Lys Asn Thr Arg Glu Ala Val Asp Arg
                260                 265                 270

Trp Ile Gln Glu Asn Pro Asn Ala Ala Glu Thr Val Glu Ala Val Phe
                275                 280                 285

Asn Val Ala Ala Ala Lys Val Ala Lys Leu Ala Lys Ala Ala Lys
    290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Gly Lys Val Arg Ile Ser Gly Ile Leu Leu
                340                 345                 350

Gly
```

<210> SEQ ID NO 140
<211> LENGTH: 2019
<212> TYPE: DNA
<213> ORGANISM: Artificial Sequence
<220> FEATURE:
<223> OTHER INFORMATION: Synthetic construct

<400> SEQUENCE: 140

```
atgtcagatt tggcaaacga ttctttatc cggcaggttc tcgaccgtca gcatttcgaa      60
cccgacggga ataccacct attcggcagc agggggaaac ttgccgagcg cagcggccat     120
atcggattgg gaaaatataca aagccatcag ttgggcaacc tgatgattca acaggcggcc     180
attaaggaa atatcggcta cattgtccgc ttttccgatc acgggcacga agtccattcc     240
cccttcgaca accatgcctc acattccgat tctgatgaag ccggtagtcc cgttgacgga     300
tttagccttt accgcatcca ttgggacgga tacgaacacc atcccgccga cggctatgac     360
gggccacagg gcggcggcta tcccgctccc aaaggcgcga gggatatata cagctacgac     420
ataaaaggcg ttgcccaaaa tatccgcctc aacctgaccg caaccgcag caccggacaa     480
cggcttgccg accgtttcca caatgccggt agtatgctga cgcaaggagt aggcgacgga     540
ttcaaacgcg ccacccgata cagccccgag ctggacagat cggcaatgc cgccgaagcc     600
ttcaacggca ctgcagatat cgttaaaaac atcatcggcg cggcaggaga aattgtcggc     660
gcaggcgatg ccgtgcaggg cataagcgaa ggctcaaaca ttgctgtcat gcacggcttg     720
ggtctgcttt ccaccgaaaa caagatggcg cgcatcaacg atttggcaga tatggcgcaa     780
ctcaaagact atgccgcagc agccatccgc gattgggcag tccaaaaccc caatgccgca     840
caaggcatag aagccgtcag caatatcttt atggcagcca tccccatcaa agggattgga     900
gctgttcggg gaaaatacgg cttgggcggc atcacggcac atcctatcaa gcggtcgcag     960
atgggcgcga tcgcattgcc gaaagggaaa tccgccgtca gcgacaattt tgccgatgcg    1020
gcatacgcca ataccgtc cccttaccat tcccgaaata tccgttcaaa cttggagcag    1080
```

```
cgttacggca aagaaaacat cacctcctca accgtgccgc cgtcaaacgg caaaatgtc    1140 aaactggcag accaacgcca cccgaagaca ggcgtaccgt ttgacggtaa agggtttccg    1200
aattttgaga agcacgtgaa atatgatacg ggatccggag ggggtggtgt cgccgccgac    1260
atcggtgcgg ggcttgccga tgcactaacc gcaccgctcg accataaaga caaaggtttg    1320
cagtctttga cgctggatca gtccgtcagg aaaaacgaga aactgaagct ggcggcacaa    1380
ggtgcggaaa aaacttatgg aaacggtgac agcctcaata cgggcaaatt gaagaacgac    1440
aaggtcagcc gtttcgactt tatccgccaa atcgaagtgg acgggcagct cattaccttg    1500
gagagtggag agttccaagt atacaaacaa agccattccg ccttaaccgc ctttcagacc    1560
gagcaaatac aagattcgga gcattccggg aagatggttg cgaaacgcca gttcagaatc    1620
ggcgacatag cgggcgaaca tacatctttt gacaagcttc ccgaaggcgg cagggcgaca    1680
tatcgcggga cggcgttcgg ttcagacgat gccggcggaa aactgaccta caccatagat    1740
ttcgccgcca gcagggaaa cggcaaaatc gaacatttga atcgccaga actcaatgtc    1800 gacctggccg ccgccgatat caagccggat ggaaaacgcc atgccgtcat cagcggttcc    1860
gtcctttaca accaagccga gaaggcagt tactccctcg gtatctttgg cggaaaagcc    1920
caggaagttg ccggcagcgc ggaagtgaaa accgtaaacg gcatacgcca tatcggcctt    1980
gccgccaagc aactcgagca ccaccaccac caccactga                          2019
```

<210> SEQ ID NO 141
<211> LENGTH: 672
<212> TYPE: PRT
<213> ORGANISM: Artificial Sequence
<220> FEATURE:
<223> OTHER INFORMATION: Synthetic construct

<400> SEQUENCE: 141

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
```

-continued

```
                195                 200                 205
Lys Asn Ile Ile Gly Ala Ala Gly Glu Ile Val Gly Ala Gly Asp Ala
    210                 215                 220
Val Gln Gly Ile Ser Glu Gly Ser Asn Ile Ala Val Met His Gly Leu
225                 230                 235                 240
Gly Leu Leu Ser Thr Glu Asn Lys Met Ala Arg Ile Asn Asp Leu Ala
                245                 250                 255
Asp Met Ala Gln Leu Lys Asp Tyr Ala Ala Ala Ile Arg Asp Trp
            260                 265                 270
Ala Val Gln Asn Pro Asn Ala Ala Gln Gly Ile Glu Ala Val Ser Asn
        275                 280                 285
Ile Phe Met Ala Ala Ile Pro Ile Lys Gly Ile Gly Ala Val Arg Gly
    290                 295                 300
Lys Tyr Gly Leu Gly Ile Thr Ala His Pro Ile Lys Arg Ser Gln
305                 310                 315                 320
Met Gly Ala Ile Ala Leu Pro Lys Gly Lys Ser Ala Val Ser Asp Asn
                325                 330                 335
Phe Ala Asp Ala Ala Tyr Ala Lys Tyr Pro Ser Pro Tyr His Ser Arg
            340                 345                 350
Asn Ile Arg Ser Asn Leu Glu Gln Arg Tyr Gly Lys Glu Asn Ile Thr
        355                 360                 365
Ser Ser Thr Val Pro Pro Ser Asn Gly Lys Asn Val Lys Leu Ala Asp
    370                 375                 380
Gln Arg His Pro Lys Thr Gly Val Pro Phe Asp Gly Lys Gly Phe Pro
385                 390                 395                 400
Asn Phe Glu Lys His Val Lys Tyr Asp Thr Gly Ser Gly Gly Gly
                405                 410                 415
Val Ala Ala Asp Ile Gly Ala Gly Leu Ala Asp Ala Leu Thr Ala Pro
            420                 425                 430
Leu Asp His Lys Asp Lys Gly Leu Gln Ser Leu Thr Leu Asp Gln Ser
        435                 440                 445
Val Arg Lys Asn Glu Lys Leu Lys Leu Ala Ala Gln Gly Ala Glu Lys
    450                 455                 460
Thr Tyr Gly Asn Gly Asp Ser Leu Asn Thr Gly Lys Leu Lys Asn Asp
465                 470                 475                 480
Lys Val Ser Arg Phe Asp Phe Ile Arg Gln Ile Glu Val Asp Gly Gln
                485                 490                 495
Leu Ile Thr Leu Glu Ser Gly Glu Phe Gln Val Tyr Lys Gln Ser His
            500                 505                 510
Ser Ala Leu Thr Ala Phe Gln Thr Glu Gln Ile Gln Asp Ser Glu His
        515                 520                 525
Ser Gly Lys Met Val Ala Lys Arg Gln Phe Arg Ile Gly Asp Ile Ala
    530                 535                 540
Gly Glu His Thr Ser Phe Asp Lys Leu Pro Glu Gly Gly Arg Ala Thr
545                 550                 555                 560
Tyr Arg Gly Thr Ala Phe Gly Ser Asp Asp Ala Gly Gly Lys Leu Thr
                565                 570                 575
Tyr Thr Ile Asp Phe Ala Ala Lys Gln Gly Asn Gly Lys Ile Glu His
            580                 585                 590
Leu Lys Ser Pro Glu Leu Asn Val Asp Leu Ala Ala Ala Asp Ile Lys
        595                 600                 605
Pro Asp Gly Lys Arg His Ala Val Ile Ser Gly Ser Val Leu Tyr Asn
    610                 615                 620
```

```
Gln Ala Glu Lys Gly Ser Tyr Ser Leu Gly Ile Phe Gly Gly Lys Ala
625                 630                 635                 640

Gln Glu Val Ala Gly Ser Ala Glu Val Lys Thr Val Asn Gly Ile Arg
            645                 650                 655

His Ile Gly Leu Ala Ala Lys Gln Leu Glu His His His His His His
            660                 665                 670
```

<210> SEQ ID NO 142
<211> LENGTH: 2421
<212> TYPE: DNA
<213> ORGANISM: Artificial Sequence
<220> FEATURE:
<223> OTHER INFORMATION: Synthetic construct

<400> SEQUENCE: 142

| | |
|---|---:|
| atgtcagatt tggcaaacga ttcttttatc cggcaggttc tcgaccgtca gcatttcgaa | 60 |
| cccgacggga ataccacct attcggcagc agggggaac ttgccgagcg cagcggccat | 120 |
| atcggattgg gaaaaataca agccatcag ttgggcaacc tgatgattca acaggcggcc | 180 |
| attaaaggaa atatcggcta cattgtccgc ttttccgatc acgggcacga agtccattcc | 240 |
| cccttcgaca accatgcctc acattccgat tctgatgaag ccggtagtcc cgttgacgga | 300 |
| tttagccttt accgcatcca ttgggacgga tacgaacacc atcccgccga cggctatgac | 360 |
| gggccacagg gcggcggcta tcccgctccc aaaggcgcga gggatatata cagctacgac | 420 |
| ataaaaggcg ttgcccaaaa tatccgcctc aacctgaccg acaaccgcag caccggacaa | 480 |
| cggcttgccg accgtttcca caatgccggt agtatgctga cgcaaggagt aggcgacgga | 540 |
| ttcaaacgcg ccacccgata cagccccgag ctggacagat cgggcaatgc cgccgaagcc | 600 |
| ttcaacggca ctgcagatat cgttaaaaac atcatcggcg cggcaggaga aattgtcggc | 660 |
| gcaggcgatg ccgtgcaggg cataagcgaa ggctcaaaca ttgctgtcat gcacggcttg | 720 |
| ggtctgcttt ccaccgaaaa caagatggcg cgcatcaacg attggcagga tatgcgcaa | 780 |
| ctcaaagact atgccgcagc agccatccgc gattgggcag tccaaaaccc caatgccgca | 840 |
| caaggcatag aagccgtcag caatatcttt atggcagcca tccccatcaa agggattgga | 900 |
| gctgttcggg gaaaatacgg cttgggcggc atcacggcac atcctatcaa gcggtcgcag | 960 |
| atgggcgcga tcgcattgcc gaaagggaaa tccgccgtca gcgacaattt tgccgatgcg | 1020 |
| gcatacgcca aatacccgtc cccttaccat tcccgaaata tccgttcaaa cttggagcag | 1080 |
| cgttacggca agaaaacat cacctcctca accgtgccgc cgtcaaacgg caaaaatgtc | 1140 |
| aaactggcag accaacgcca cccgaagaca ggcgtaccgt ttgacggtaa agggtttccg | 1200 |
| aattttgaga agcacgtgaa atatgatacg ggatccggag gaggaggagc cacaaacgac | 1260 |
| gacgatgtta aaaagctgc cactgtggcc attgctgctg cctacaacaa tggccaagaa | 1320 |
| atcaacggtt tcaaagctgg agagaccatc tacgacattg atgaagacgg cacaattacc | 1380 |
| aaaaaagacg caactgcagc cgatgttgaa gccgacgact taaaggtct gggtctgaaa | 1440 |
| aaagtcgtga ctaacctgac caaaaccgtc aatgaaaaca acaaaacgt cgatgccaaa | 1500 |
| gtaaaagctg cagaatctga aatagaaaag ttaacaacca gttagcaga cactgatgcc | 1560 |
| gctttagcag atactgatgc cgctctggat gcaaccacca acgccttgaa taaattggga | 1620 |
| gaaaatataa cgacatttgc tgaagagact aagacaaata tcgtaaaaat tgatgaaaaa | 1680 |
| ttagaagccg tggctgatac cgtcgacaag catgccgaag cattcaacga tatcgccgat | 1740 |
| tcattggatg aaaccaacac taaggcagac gaagccgtca aaaccgccaa tgaagccaaa | 1800 |

```
cagacggccg aagaaaccaa acaaaacgtc gatgccaaag taaaagctgc agaaactgca    1860
gcaggcaaag ccgaagctgc cgctggcaca gctaatactg cagccgacaa ggccgaagct    1920
gtcgctgcaa aagttaccga catcaaagct gatatcgcta cgaacaaaga taatattgct    1980
aaaaaagcaa acagtgccga cgtgtacacc agagaagagt ctgacagcaa atttgtcaga    2040
attgatggtc tgaacgctac taccgaaaaa ttggacacac gcttggcttc tgctgaaaaa    2100
tccattgccg atcacgatac tcgcctgaac ggtttggata aacagtgtc agacctgcgc    2160 aaagaaaccc gccaaggcct tgcagaacaa gccgcgctct ccggtctgtt ccaaccttac    2220
aacgtgggtc ggttcaatgt aacgctgca gtcggcggct acaaatccga atcggcagtc    2280
gccatcggta ccggcttccg ctttaccgaa aactttgccg ccaaagcagg cgtggcagtc    2340
ggcacttcgt ccggttcttc cgcagcctac catgtcggcg tcaattacga gtggctcgag    2400
caccaccacc accaccactg a                                              2421
```

<210> SEQ ID NO 143
<211> LENGTH: 806
<212> TYPE: PRT
<213> ORGANISM: Artificial Sequence
<220> FEATURE:
<223> OTHER INFORMATION: Synthetic construct

<400> SEQUENCE: 143

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
```

-continued

```
                245                 250                 255
Asp Met Ala Gln Leu Lys Asp Tyr Ala Ala Ala Ile Arg Asp Trp
            260                 265                 270
Ala Val Gln Asn Pro Asn Ala Ala Gln Gly Ile Glu Ala Val Ser Asn
        275                 280                 285
Ile Phe Met Ala Ala Ile Pro Ile Lys Gly Ile Gly Ala Val Arg Gly
    290                 295                 300
Lys Tyr Gly Leu Gly Gly Ile Thr Ala His Pro Ile Lys Arg Ser Gln
305                 310                 315                 320
Met Gly Ala Ile Ala Leu Pro Lys Gly Lys Ser Ala Val Ser Asp Asn
                325                 330                 335
Phe Ala Asp Ala Ala Tyr Ala Lys Tyr Pro Ser Pro Tyr His Ser Arg
            340                 345                 350
Asn Ile Arg Ser Asn Leu Glu Gln Arg Tyr Gly Lys Glu Asn Ile Thr
        355                 360                 365
Ser Ser Thr Val Pro Pro Ser Asn Gly Lys Asn Val Lys Leu Ala Asp
    370                 375                 380
Gln Arg His Pro Lys Thr Gly Val Pro Phe Asp Gly Lys Gly Phe Pro
385                 390                 395                 400
Asn Phe Glu Lys His Val Lys Tyr Asp Thr Gly Ser Gly Gly Gly Gly
                405                 410                 415
Ala Thr Asn Asp Asp Val Lys Lys Ala Ala Thr Val Ala Ile Ala
            420                 425                 430
Ala Ala Tyr Asn Asn Gly Gln Glu Ile Asn Gly Phe Lys Ala Gly Glu
        435                 440                 445
Thr Ile Tyr Asp Ile Asp Glu Asp Gly Thr Ile Thr Lys Lys Asp Ala
    450                 455                 460
Thr Ala Ala Asp Val Glu Ala Asp Phe Lys Gly Leu Gly Leu Lys
465                 470                 475                 480
Lys Val Val Thr Asn Leu Thr Lys Thr Val Asn Glu Asn Lys Gln Asn
                485                 490                 495
Val Asp Ala Lys Val Lys Ala Ala Glu Ser Glu Ile Glu Lys Leu Thr
            500                 505                 510
Thr Lys Leu Ala Asp Thr Asp Ala Ala Leu Ala Asp Thr Asp Ala Ala
        515                 520                 525
Leu Asp Ala Thr Thr Asn Ala Leu Asn Lys Leu Gly Glu Asn Ile Thr
    530                 535                 540
Thr Phe Ala Glu Glu Thr Lys Thr Asn Ile Val Lys Ile Asp Glu Lys
545                 550                 555                 560
Leu Glu Ala Val Ala Asp Thr Val Asp Lys His Ala Glu Ala Phe Asn
                565                 570                 575
Asp Ile Ala Asp Ser Leu Asp Glu Thr Asn Thr Lys Ala Asp Glu Ala
            580                 585                 590
Val Lys Thr Ala Asn Glu Ala Lys Gln Thr Ala Glu Glu Thr Lys Gln
        595                 600                 605
Asn Val Asp Ala Lys Val Lys Ala Ala Glu Thr Ala Ala Gly Lys Ala
    610                 615                 620
Glu Ala Ala Ala Gly Thr Ala Asn Thr Ala Ala Asp Lys Ala Glu Ala
625                 630                 635                 640
Val Ala Ala Lys Val Thr Asp Ile Lys Ala Asp Ile Ala Thr Asn Lys
                645                 650                 655
Asp Asn Ile Ala Lys Lys Ala Asn Ser Ala Asp Val Tyr Thr Arg Glu
            660                 665                 670
```

```
Glu Ser Asp Ser Lys Phe Val Arg Ile Asp Gly Leu Asn Ala Thr Thr
            675                 680                 685

Glu Lys Leu Asp Thr Arg Leu Ala Ser Ala Glu Lys Ser Ile Ala Asp
        690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
                725                 730                 735

Phe Gln Pro Tyr Asn Val Gly Arg Phe Asn Val Thr Ala Ala Val Gly
            740                 745                 750

Gly Tyr Lys Ser Glu Ser Ala Val Ala Ile Gly Thr Gly Phe Arg Phe
        755                 760                 765

Thr Glu Asn Phe Ala Ala Lys Ala Gly Val Ala Val Gly Thr Ser Ser
770                 775                 780

Gly Ser Ser Ala Ala Tyr His Val Gly Val Asn Tyr Glu Trp Leu Glu
785                 790                 795                 800

His His His His His His
            805
```

<210> SEQ ID NO 144
<211> LENGTH: 2256
<212> TYPE: DNA
<213> ORGANISM: Artificial Sequence
<220> FEATURE:
<223> OTHER INFORMATION: Synthetic construct

<400> SEQUENCE: 144

```
atgtcagatt tggcaaacga ttcttttatc cggcaggttc tcgaccgtca gcatttcgaa      60
cccgacggga ataccacct attcggcagc agggggggaac ttgccgagcg cagcggccat     120
atcggattgg gaaaaataca agccatcag ttgggcaacc tgatgattca caggcggcc      180 attaaaggaa atatcggcta cattgtccgc ttttccgatc acgggcacga agtccattcc     240
cccttcgaca accatgcctc acattccgat tctgatgaag ccggtagtcc cgttacgga     300 tttagccttt accgcatcca ttgggacgga tacgaacacc atcccgccga cggctatgac     360
gggccacagg gcggcggcta ccccgctccc aaaggcgcga gggatatata cagctacgac    420
ataaaaggcg ttgcccaaaa tatccgcctc aacctgaccg acaaccgcag caccggacaa     480
cggcttgccg accgtttcca caatgccggt agtatgctga cgcaaggagt aggcgacgga     540
ttcaaacgcg ccacccgata cagccccgag ctggacagat cgggcaatgc cgccgaagcc     600
ttcaacggca ctgcagatat cgttaaaaac atcatcggcg cggcaggaga aattgtcggc     660
gcaggcgatg ccgtgcaggg cataagcgaa ggctcaaaca ttgctgtcat gcacggcttg     720
ggtctgcttt ccaccgaaaa caagatggcg cgcatcaacg atttggcaga tatggcgcaa    780
ctcaaagact atgccgcagc agccatccgc gattgggcag tccaaaaccc caatgccgca    840
caaggcatag aagccgtcag caatatcttt atggcagcca tccccatcaa agggattgga    900
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca ataccccgtc cccttaccat tcccgaaata tccgttcaaa cttggagcag   1080
cgttacggca agaaaacat cacctcctca accgtgccgc cgtcaaacgg caaaaatgtc   1140
aaactggcag accaacgcca cccgaagaca ggcgtaccgt tgacggtaa agggtttccg   1200 aattttgaga agcacgtgaa atatgatacg ggatccggag gaggaggagc cacaaacgac   1260
```

```
gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca acaaaacgt cgatgccaaa    1500 gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaccgccaa tgaagccaaa    1800 cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aacagtgtc agacctgcgc    2160 aaagaaaccc gccaaggcct tgcagaacaa gccgcgctct ccggtctgtt ccaaccttac   2220
aacgtgggtc tcgagcacca ccaccaccac cactga                             2256
```

<210> SEQ ID NO 145
<211> LENGTH: 751
<212> TYPE: PRT
<213> ORGANISM: Artificial Sequence
<220> FEATURE:
<223> OTHER INFORMATION: Synthetic construct

<400> SEQUENCE: 145

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
```

-continued

```
                180                 185                 190
    Arg Ser Gly Asn Ala Ala Glu Ala Phe Asn Gly Thr Ala Asp Ile Val
                    195                 200                 205
    Lys Asn Ile Ile Gly Ala Ala Gly Glu Ile Val Gly Ala Gly Asp Ala
                    210                 215                 220
    Val Gln Gly Ile Ser Glu Gly Ser Asn Ile Ala Val Met His Gly Leu
    225                 230                 235                 240
    Gly Leu Leu Ser Thr Glu Asn Lys Met Ala Arg Ile Asn Asp Leu Ala
                    245                 250                 255
    Asp Met Ala Gln Leu Lys Asp Tyr Ala Ala Ala Ile Arg Asp Trp
                    260                 265                 270
    Ala Val Gln Asn Pro Asn Ala Ala Gln Gly Ile Glu Ala Val Ser Asn
                    275                 280                 285
    Ile Phe Met Ala Ala Ile Pro Ile Lys Gly Ile Gly Ala Val Arg Gly
                    290                 295                 300
    Lys Tyr Gly Leu Gly Gly Ile Thr Ala His Pro Ile Lys Arg Ser Gln
    305                 310                 315                 320
    Met Gly Ala Ile Ala Leu Pro Lys Gly Lys Ser Ala Val Ser Asp Asn
                    325                 330                 335
    Phe Ala Asp Ala Ala Tyr Ala Lys Tyr Pro Ser Pro Tyr His Ser Arg
                    340                 345                 350
    Asn Ile Arg Ser Asn Leu Glu Gln Arg Tyr Gly Lys Glu Asn Ile Thr
                    355                 360                 365
    Ser Ser Thr Val Pro Pro Ser Asn Gly Lys Asn Val Lys Leu Ala Asp
    370                 375                 380
    Gln Arg His Pro Lys Thr Gly Val Pro Phe Asp Gly Lys Gly Phe Pro
    385                 390                 395                 400
    Asn Phe Glu Lys His Val Lys Tyr Asp Thr Gly Ser Gly Gly Gly
                    405                 410                 415
    Ala Thr Asn Asp Asp Asp Val Lys Lys Ala Ala Thr Val Ala Ile Ala
                    420                 425                 430
    Ala Ala Tyr Asn Asn Gly Gln Glu Ile Asn Gly Phe Lys Ala Gly Glu
                    435                 440                 445
    Thr Ile Tyr Asp Ile Asp Glu Asp Gly Thr Ile Thr Lys Lys Asp Ala
                    450                 455                 460
    Thr Ala Ala Asp Val Glu Ala Asp Phe Lys Gly Leu Gly Leu Lys
    465                 470                 475                 480
    Lys Val Val Thr Asn Leu Thr Lys Thr Val Asn Glu Asn Lys Gln Asn
                    485                 490                 495
    Val Asp Ala Lys Val Lys Ala Ala Glu Ser Glu Ile Glu Lys Leu Thr
                    500                 505                 510
    Thr Lys Leu Ala Asp Thr Asp Ala Leu Ala Asp Thr Asp Ala Ala
                    515                 520                 525
    Leu Asp Ala Thr Thr Asn Ala Leu Asn Lys Leu Gly Glu Asn Ile Thr
                    530                 535                 540
    Thr Phe Ala Glu Glu Thr Lys Thr Asn Ile Val Lys Ile Asp Glu Lys
    545                 550                 555                 560
    Leu Glu Ala Val Ala Asp Thr Val Asp Lys His Ala Glu Ala Phe Asn
                    565                 570                 575
    Asp Ile Ala Asp Ser Leu Asp Glu Thr Asn Thr Lys Ala Asp Glu Ala
                    580                 585                 590
    Val Lys Thr Ala Asn Glu Ala Lys Gln Thr Ala Glu Glu Thr Lys Gln
                    595                 600                 605
```

```
Asn Val Asp Ala Lys Val Lys Ala Ala Glu Thr Ala Ala Gly Lys Ala
            610                 615                 620
Glu Ala Ala Ala Gly Thr Ala Asn Thr Ala Ala Asp Lys Ala Glu Ala
625                 630                 635                 640
Val Ala Ala Lys Val Thr Asp Ile Lys Ala Asp Ile Ala Thr Asn Lys
                645                 650                 655
Asp Asn Ile Ala Lys Lys Ala Asn Ser Ala Asp Val Tyr Thr Arg Glu
                660                 665                 670
Glu Ser Asp Ser Lys Phe Val Arg Ile Asp Gly Leu Asn Ala Thr Thr
            675                 680                 685
Glu Lys Leu Asp Thr Arg Leu Ala Ser Ala Glu Lys Ser Ile Ala Asp
            690                 695                 700
His Asp Thr Arg Leu Asn Gly Leu Asp Lys Thr Val Ser Asp Leu Arg
705                 710                 715                 720
Lys Glu Thr Arg Gln Gly Leu Ala Glu Gln Ala Ala Leu Ser Gly Leu
                725                 730                 735
Phe Gln Pro Tyr Asn Val Gly Leu Glu His His His His His
                740                 745                 750
```

<210> SEQ ID NO 146
<211> LENGTH: 2421
<212> TYPE: DNA
<213> ORGANISM: Artificial Sequence
<220> FEATURE:
<223> OTHER INFORMATION: Synthetic construct

<400> SEQUENCE: 146

```
atggccacaa acgacgacga tgttaaaaaa gctgccactg tggccattgc tgctgcctac      60
aacaatggcc agaaatcaa cggtttcaaa gctggagaga ccatctcgca cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aaacaaacaa     240
aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat tgggagaaaa tataacgaca tttgctgaag agactaagac aaatatcgta     420
aaaattgatg aaaaattaga agccgtggct gataccgtcg acaagcatgc cgaagcattc     480
aacgatatcg ccgattcatt ggatgaaacc aacactaagg cagacgaagc cgtcaaaacc     540
gccaatgaag ccaaacagac ggccgaagaa ccaaacaaa acgtcgatgc caaagtaaaa     600
gctgcagaaa ctgcagcagg caaagccgaa gctgccgctg cacagctaa tactgcagcc     660
gacaaggccg aagctgtcgc tgcaaaagtt accgacatca agctgatat cgctacgaac     720
aaagataata ttgctaaaaa agcaaacagt gccgacgtgt acaccagaga gagtctgac      780
agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag aacaagccgc gctctccggt     960
ctgttccaac cttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggagg aggaggatca gatttggcaa acgattcttt tatccggcag    1200
gttctcgacc gtcagcattt cgaacccgac gggaaatacc acctattcgg cagcaggggg    1260
```

```
gaacttgccg agcgcagcgg ccatatcgga ttgggaaaaa tacaaagcca tcagttgggc    1320
aacctgatga ttcaacaggc ggccattaaa ggaaatatcg ctacattgt ccgcttttcc     1380 gatcacgggc acgaagtcca ttccccttc gacaaccatg cctcacattc cgattctgat     1440
gaagccggta gtcccgttga cggatttagc ctttaccgca tccattggga cggatacgaa    1500
caccatcccg ccgacggcta tgacgggcca cagggcggcg gctatcccgc tcccaaaggc    1560
gcgagggata tatacagcta cgacataaaa ggcgttgccc aaaatatccg cctcaacctg    1620
accgacaacc gcagcaccgg acaacggctt gccgaccgtt tccacaatgc cggtagtatg    1680
ctgacgcaag gagtaggcga cggattcaaa cgcgccaccc gatacagccc cgagctggac    1740
agatcgggca atgccgccga agccttcaac ggcactgcag atatcgttaa aaacatcatc    1800
ggcgcggcag gagaaattgt cggcgcaggc gatgccgtgc agggcataag cgaaggctca    1860
aacattgctg tcatgcacgg cttgggtctg ctttccaccg aaaacaagat ggcgcgcatc    1920
aacgatttgg cagatatggc gcaactcaaa gactatgccg cagcagccat ccgcgattgg    1980
gcagtccaaa accccaatgc cgcacaaggc atagaagccg tcagcaatat ctttatggca    2040
gccatcccca tcaaagggat tggagctgtt cggggaaaat acggcttggg cggcatcacg    2100
gcacatccta tcaagcggtc gcagatgggc gcgatcgcat tgccgaaagg gaaatccgcc    2160
gtcagcgaca ttttgccga tgcggcatac gccaaatacc cgtcccctta ccattcccga    2220
aatatccgtt caaacttgga gcagcgttac ggcaaagaaa acatcacctc ctcaaccgtg    2280
ccgccgtcaa acggcaaaaa tgtcaaactg cagaccaac gccacccgaa gacaggcgta    2340
ccgtttgacg gtaaagggtt tccgaatttt gagaagcacg tgaaatatga tacgctcgag    2400
caccaccacc accaccactg a                                              2421
```

<210> SEQ ID NO 147
<211> LENGTH: 806
<212> TYPE: PRT
<213> ORGANISM: Artificial Sequence
<220> FEATURE:
<223> OTHER INFORMATION: Synthetic construct

<400> SEQUENCE: 147

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
        50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
```

```
            145                 150                 155                 160
Asn Asp Ile Ala Asp Ser Leu Asp Glu Thr Asn Thr Lys Ala Asp Glu
            165                 170                 175
Ala Val Lys Thr Ala Asn Glu Ala Lys Gln Thr Ala Glu Glu Thr Lys
            180                 185                 190
Gln Asn Val Asp Ala Lys Val Lys Ala Ala Glu Thr Ala Ala Gly Lys
            195                 200                 205
Ala Glu Ala Ala Ala Gly Thr Ala Asn Thr Ala Ala Asp Lys Ala Glu
            210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
                260                 265                 270
Thr Glu Lys Leu Asp Thr Arg Leu Ala Ser Ala Glu Lys Ser Ile Ala
            275                 280                 285
Asp His Asp Thr Arg Leu Asn Gly Leu Asp Lys Thr Val Ser Asp Leu
            290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Arg Phe Asn Val Thr Ala Ala Val
                325                 330                 335
Gly Gly Tyr Lys Ser Glu Ser Ala Val Ala Ile Gly Thr Gly Phe Arg
                340                 345                 350
Phe Thr Glu Asn Phe Ala Ala Lys Ala Gly Val Ala Val Gly Thr Ser
            355                 360                 365
Ser Gly Ser Ser Ala Ala Tyr His Val Gly Val Asn Tyr Glu Trp Gly
            370                 375                 380
Ser Gly Gly Gly Ser Asp Leu Ala Asn Asp Ser Phe Ile Arg Gln
385                 390                 395                 400
Val Leu Asp Arg Gln His Phe Glu Pro Asp Gly Lys Tyr His Leu Phe
                405                 410                 415
Gly Ser Arg Gly Glu Leu Ala Glu Arg Ser Gly His Ile Gly Leu Gly
                420                 425                 430
Lys Ile Gln Ser His Gln Leu Gly Asn Leu Met Ile Gln Gln Ala Ala
            435                 440                 445
Ile Lys Gly Asn Ile Gly Tyr Ile Val Arg Phe Ser Asp His Gly His
450                 455                 460
Glu Val His Ser Pro Phe Asp Asn His Ala Ser His Ser Asp Ser Asp
465                 470                 475                 480
Glu Ala Gly Ser Pro Val Asp Gly Phe Ser Leu Tyr Arg Ile His Trp
                485                 490                 495
Asp Gly Tyr Glu His His Pro Ala Asp Gly Tyr Asp Gly Pro Gln Gly
                500                 505                 510
Gly Gly Tyr Pro Ala Pro Lys Gly Ala Arg Asp Ile Tyr Ser Tyr Asp
            515                 520                 525
Ile Lys Gly Val Ala Gln Asn Ile Arg Leu Asn Leu Thr Asp Asn Arg
            530                 535                 540
Ser Thr Gly Gln Arg Leu Ala Asp Arg Phe His Asn Ala Gly Ser Met
545                 550                 555                 560
Leu Thr Gln Gly Val Gly Asp Gly Phe Lys Arg Ala Thr Arg Tyr Ser
                565                 570                 575
```

```
Pro Glu Leu Asp Arg Ser Gly Asn Ala Ala Glu Ala Phe Asn Gly Thr
            580                 585                 590

Ala Asp Ile Val Lys Asn Ile Gly Ala Ala Gly Glu Ile Val Gly
        595                 600                 605

Ala Gly Asp Ala Val Gln Gly Ile Ser Glu Gly Ser Asn Ile Ala Val
    610                 615                 620

Met His Gly Leu Gly Leu Leu Ser Thr Glu Asn Lys Met Ala Arg Ile
625                 630                 635                 640

Asn Asp Leu Ala Asp Met Ala Gln Leu Lys Asp Tyr Ala Ala Ala
                645                 650                 655

Ile Arg Asp Trp Ala Val Gln Asn Pro Asn Ala Ala Gln Gly Ile Glu
        660                 665                 670

Ala Val Ser Asn Ile Phe Met Ala Ala Ile Pro Ile Lys Gly Ile Gly
        675                 680                 685

Ala Val Arg Gly Lys Tyr Gly Leu Gly Gly Ile Thr Ala His Pro Ile
        690                 695                 700

Lys Arg Ser Gln Met Gly Ala Ile Ala Leu Pro Lys Gly Lys Ser Ala
705                 710                 715                 720

Val Ser Asp Asn Phe Ala Asp Ala Ala Tyr Ala Lys Tyr Pro Ser Pro
                725                 730                 735

Tyr His Ser Arg Asn Ile Arg Ser Asn Leu Glu Gln Arg Tyr Gly Lys
                740                 745                 750

Glu Asn Ile Thr Ser Ser Thr Val Pro Pro Ser Asn Gly Lys Asn Val
            755                 760                 765

Lys Leu Ala Asp Gln Arg His Pro Lys Thr Gly Val Pro Phe Asp Gly
        770                 775                 780

Lys Gly Phe Pro Asn Phe Glu Lys His Val Lys Tyr Asp Thr Leu Glu
785                 790                 795                 800

His His His His His His
            805

<210> SEQ ID NO 148
<211> LENGTH: 1938
<212> TYPE: DNA
<213> ORGANISM: Artificial Sequence
<220> FEATURE:
<223> OTHER INFORMATION: Synthetic construct

<400> SEQUENCE: 148
atggccacaa cgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa    180
ggtctgggtc tgaaaaaagt cgtgactaac ctgaccaaaa ccgtcaatga aacaaacaa     240 aacgtcgatg ccaaagtaaa agctgcagaa tctgaaatag aaaagttaac aaccaagtta     300
gcagacactg atgccgcttt agcagatact gatgccgctc tggatgcaac caccaacgcc    360
ttgaataaat gggagaaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg cacagctaa tactgcagcc    660 gacaaggccg aagctgtcgc tgcaaaagtt accgacatca agctgatat cgctacgaac    720
```

```
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtcggttc aatgtaacgg ctgcagtcgg cggctacaaa   1020
tccgaatcgg cagtcgccat cggtaccggc ttccgcttta ccgaaaactt tgccgccaaa   1080
gcaggcgtgg cagtcggcac ttcgtccggt tcttccgcag cctaccatgt cggcgtcaat   1140
tacgagtggg gatccggagg gggtggtgtc gccgccgaca tcggtgcggg gcttgccgat   1200
gcactaaccg caccgctcga ccataaagac aaaggtttgc agtctttgac gctggatcag   1260
tccgtcagga aaaacgagaa actgaagctg gcggcacaag gtgcggaaaa aacttatgga   1320
aacggtgaca gcctcaatac gggcaaattg aagaacgaca aggtcagccg tttcgacttt   1380
atccgccaaa tcgaagtgga cgggcagctc attaccttgg agagtggaga gttccaagta   1440
tacaaacaaa gccattccgc cttaaccgcc tttcagaccg agcaaataca agattcggag   1500
cattccggga agatggttgc gaaacgccag ttcagaatcg cgacatagc gggcgaacat    1560 acatcttttg acaagcttcc cgaaggcggc agggcgacat atcgcgggac ggcgttcggt   1620
tcagacgatg ccggcggaaa actgacctac accatagatt tcgccgccaa gcagggaaac   1680
ggcaaaatcg aacatttgaa atcgccagaa ctcaatgtcg acctggccgc cgccgatatc   1740
aagccggatg gaaaacgcca tgccgtcatc agcggttccg tccttttacaa ccaagccgag   1800 aaaggcagtt actccctcgg tatctttggc ggaaaagccc aggaagttgc cggcagcgcg   1860
gaagtgaaaa ccgtaaacgg catacgccat atcggccttg ccgccaagca actcgagcac   1920
caccaccacc accactga                                                 1938
```

<210> SEQ ID NO 149
<211> LENGTH: 645
<212> TYPE: PRT
<213> ORGANISM: Artificial Sequence
<220> FEATURE:
<223> OTHER INFORMATION: Synthetic construct

<400> SEQUENCE: 149

```
Met Ala Thr Asn Asp Asp Val Lys Lys Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140
```

```
Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
            165                 170                 175

Ala Val Lys Thr Ala Asn Glu Ala Lys Gln Thr Ala Glu Glu Thr Lys
        180                 185                 190

Gln Asn Val Asp Ala Lys Val Lys Ala Glu Thr Ala Ala Gly Lys
        195                 200                 205

Ala Glu Ala Ala Ala Gly Thr Ala Asn Thr Ala Ala Asp Lys Ala Glu
        210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
            245                 250                 255

Glu Glu Ser Asp Ser Lys Phe Val Arg Ile Asp Gly Leu Asn Ala Thr
        260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
            325                 330                 335

Gly Gly Tyr Lys Ser Glu Ser Ala Val Ala Ile Gly Thr Gly Phe Arg
        340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
        370                 375                 380

Ser Gly Gly Gly Val Ala Ala Asp Ile Gly Ala Gly Leu Ala Asp
385                 390                 395                 400

Ala Leu Thr Ala Pro Leu Asp His Lys Asp Lys Gly Leu Gln Ser Leu
            405                 410                 415

Thr Leu Asp Gln Ser Val Arg Lys Asn Glu Lys Leu Lys Leu Ala Ala
        420                 425                 430

Gln Gly Ala Glu Lys Thr Tyr Gly Asn Gly Asp Ser Leu Asn Thr Gly
        435                 440                 445

Lys Leu Lys Asn Asp Lys Val Ser Arg Phe Asp Phe Ile Arg Gln Ile
450                 455                 460

Glu Val Asp Gly Gln Leu Ile Thr Leu Glu Ser Gly Glu Phe Gln Val
465                 470                 475                 480

Tyr Lys Gln Ser His Ser Ala Leu Thr Ala Phe Gln Thr Glu Gln Ile
            485                 490                 495

Gln Asp Ser Glu His Ser Gly Lys Met Val Ala Lys Arg Gln Phe Arg
        500                 505                 510

Ile Gly Asp Ile Ala Gly Glu His Thr Ser Phe Asp Lys Leu Pro Glu
        515                 520                 525

Gly Gly Arg Ala Thr Tyr Arg Gly Thr Ala Phe Gly Ser Asp Asp Ala
        530                 535                 540

Gly Gly Lys Leu Thr Tyr Thr Ile Asp Phe Ala Ala Lys Gln Gly Asn
545                 550                 555                 560
```

```
Gly Lys Ile Glu His Leu Lys Ser Pro Glu Leu Asn Val Asp Leu Ala
            565                 570                 575

Ala Ala Asp Ile Lys Pro Asp Gly Lys Arg His Ala Val Ile Ser Gly
        580                 585                 590

Ser Val Leu Tyr Asn Gln Ala Glu Lys Gly Ser Tyr Ser Leu Gly Ile
    595                 600                 605

Phe Gly Lys Ala Gln Glu Val Ala Gly Ser Ala Glu Val Lys Thr
610                 615                 620

Val Asn Gly Ile Arg His Ile Gly Leu Ala Ala Lys Gln Leu Glu His
625                 630                 635                 640

His His His His His
                645

<210> SEQ ID NO 150
<211> LENGTH: 4335
<212> TYPE: DNA
<213> ORGANISM: Artificial Sequence
<220> FEATURE:
<223> OTHER INFORMATION: Synthetic construct

<400> SEQUENCE: 150
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat tgggagaaaa tataacgaca tttgctgaag agactaagac aaatatcgta     420
aaaattgatg aaaaattaga gccgtggct gataccgtcg acaagcatgc cgaagcattc     480
aacgatatcg ccgattcatt ggatgaaacc aacactaagg cagacgaagc cgtcaaaacc     540
gccaatgaag ccaaacagac ggccgaagaa accaaacaaa acgtcgatgc caaagtaaaa     600
gctgcagaaa ctgcagcagg caaagccgaa gctgccgctg gcacagctaa tactgcagcc     660
gacaaggccg aagctgtcgc tgcaaaagtt accgacatca agctgatat cgctacgaac     720 aaagataata ttgctaaaaa agcaaacagt gccgacgtgt acaccagaga gagtctgac     780 agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag aacaagccgc gctctccggt     960
ctgttccaac cttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggcgg aggcggcact tctgcgcccg acttcaatgc aggcggtacc    1200
ggtatcggca gcaacagcag agcaacaaca gcgaaatcag cagcagtatc ttacgccggt    1260
atcaagaacg aaatgtgcaa agacagaagc atgctctgtg ccggtcggga tgacgttgcg    1320
gttacagaca gggatgccaa aatcaatgcc cccccccga atctgcatac cggagacttt    1380
ccaaacccaa atgacgcata caagaatttg atcaacctca acctgcaat gaagcaggc     1440 tatacaggac gcggggtaga ggtaggtatc gtcgacacag gcgaatccgt cggcagcata    1500
tcctttcccg aactgtatgg cagaaaagaa cacggctata acgaaaatta caaaaactat    1560
```

```
acggcgtata tgcggaagga agcgcctgaa gacggaggcg gtaaagacat tgaagcttct    1620
ttcgacgatg aggccgttat agagactgaa gcaaagccga cggatatccg ccacgtaaaa    1680
gaaatcggac acatcgattt ggtctcccat attattggcg ggcgttccgt ggacggcaga    1740
cctgcaggcg gtattgcgcc cgatgcgacg ctacacataa tgaatacgaa tgatgaaacc    1800
aagaacgaaa tgatggttgc agccatccgc aatgcatggg tcaagctggg cgaacgtggc    1860
gtgcgcatcg tcaataacag ttttggaaca acatcgaggg caggcactgc cgaccttttc    1920
caaatagcca attcggagga gcagtaccgc caagcgttgc tcgactattc cggcggtgat    1980
aaaacagacg agggtatccg cctgatgcaa cagagcgatt acggcaacct gtcctaccac    2040
atccgtaata aaaacatgct tttcatcttt tcgacaggca atgacgcaca agctcagccc    2100
aacacatatg ccctattgcc attttatgaa aaagacgctc aaaaaggcat tatcacagtc    2160
gcaggcgtag accgcagtgg agaaaagttc aaacgggaaa tgtatggaga accgggtaca    2220
gaaccgcttg agtatggctc caaccattgc ggaattactg ccatgtggtg cctgtcggca    2280
ccctatgaag caagcgtccg tttcacccgt acaaacccga ttcaaattgc cggaacatcc    2340 tttccgcac ccatcgtaac cggcacggcg gctctgctgc tgcagaaata cccgtggatg     2400
agcaacgaca acctgcgtac cacgttgctg acgacggctc aggacatcgg tgcagtcggc    2460
gtggacagca gttccggctg gggactgctg gatgcgggta aggccatgaa cggacccgcg    2520
tcctttccgt tcggcgactt taccgccgat acgaaaggta catccgatat tgcctactcc    2580
ttccgtaacg acatttcagg cacgggcggc ctgatcaaaa aaggcggcag ccaactgcaa    2640
ctgcacggca acaaccta tacgggcaaa accattatcg aaggcggttc gctggtgttg     2700
tacggcaaca caaatcgga tatgcgcgtc gaaaccaaag gtgcgctgat ttataacggg     2760
gcggcatccg gcggcagcct gaacagcgac ggcattgtct atctggcaga taccgaccaa    2820
tccggcgcaa acgaaaccgt acacatcaaa ggcagtctgc agctggacgg caaaggtacg    2880
ctgtacacac gtttgggcaa actgctgaaa gtggacggta cggcgattat cggcggcaag    2940
ctgtacatgt cggcacgcgg caaggggca ggctatctca acagtaccgg acgacgtgtt     3000
cccttcctga gtgccgccaa aatcgggcag gattattctt tcttcacaaa catcgaaacc    3060
gacggcggcc tgctggcttc cctcgacagc gtcgaaaaaa cagcgggcag tgaaggcgac    3120
acgctgtcct attatgtccg tcgcggcaat gcggcacgga ctgcttcggc agcggcacat    3180
tccgcgcccg ccggtctgaa acacgccgta gaacagggcg gcagcaatct ggaaaacctg    3240
atggtcgaac tggatgcctc cgaatcatcc gcaacacccg agacggttga aactgcggca    3300
gccgaccgca cagatatgcc gggcatccgc ccctacggcg caactttccg cgcagcggca    3360
gccgtacagc atgcgaatgc cgccgacggt gtacgcatct tcaacagtct cgccgctacc    3420
gtctatgccg acagtaccgc cgcccatgcc gatatgcagg gacgccgcct gaaagccgta    3480
tcggacgggt tggaccacaa cggcacgggt ctgcgcgtca tcgcgcaaac ccaacaggac    3540
ggtggaacgt gggaacaggg cggtgttgaa ggcaaaatgc gcggcagtac ccaaaccgtc    3600
ggcattgccg cgaaaaccgg cgaaaatacg acagcagccg ccacactggg catgggacgc    3660
agcacatgga gcgaaaacag tgcaaatgca aaaaccgaca gcattagtct gtttgcaggc    3720
atacggcacg atgcgggcga tatcggctat ctcaaaggcc tgttctccta cggacgctac    3780
aaaaacagca tcgccgcag caccggtgcg gacgaacatg cggaaggcag cgtcaacggc    3840
acgctgatgc agctgggcgc actgggcggt gtcaacgttc cgtttgccgc aacgggagat    3900
```

-continued

```
ttgacggtcg aaggcggtct gcgctacgac ctgctcaaac aggatgcatt cgccgaaaaa      3960
ggcagtgctt tgggctggag cggcaacagc ctcactgaag gcacgctggt cggactcgcg      4020
ggtctgaagc tgtcgcaacc cttgagcgat aaagccgtcc tgtttgcaac ggcgggcgtg      4080
gaacgcgacc tgaacggacg cgactacacg gtaacgggcg gctttaccgg cgcgactgca      4140
gcaaccggca agacgggggc acgcaatatg ccgcacaccc gtctggttgc cggcctgggc      4200
gcggatgtcg aattcggcaa cggctggaac ggcttggcac gttacagcta cgccggttcc      4260
aaacagtacg gcaaccacag cggacgagtc ggcgtaggct accggttcct cgagcaccac      4320
caccaccacc actga                                                       4335
```

<210> SEQ ID NO 151
<211> LENGTH: 1444
<212> TYPE: PRT
<213> ORGANISM: Artificial Sequence
<220> FEATURE:
<223> OTHER INFORMATION: Synthetic construct

<400> SEQUENCE: 151

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285
```

-continued

```
Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
    370                 375                 380

Ser Gly Gly Gly Thr Ser Ala Pro Asp Phe Asn Ala Gly Gly Thr
385                 390                 395                 400

Gly Ile Gly Ser Asn Ser Arg Ala Thr Thr Ala Lys Ser Ala Ala Val
            405                 410                 415

Ser Tyr Ala Gly Ile Lys Asn Glu Met Cys Lys Asp Arg Ser Met Leu
                420                 425                 430

Cys Ala Gly Arg Asp Asp Val Ala Val Thr Asp Arg Asp Ala Lys Ile
            435                 440                 445

Asn Ala Pro Pro Pro Asn Leu His Thr Gly Asp Phe Pro Asn Pro Asn
450                 455                 460

Asp Ala Tyr Lys Asn Leu Ile Asn Leu Lys Pro Ala Ile Glu Ala Gly
465                 470                 475                 480

Tyr Thr Gly Arg Gly Val Glu Val Gly Ile Val Asp Thr Gly Glu Ser
                485                 490                 495

Val Gly Ser Ile Ser Phe Pro Glu Leu Tyr Gly Arg Lys Glu His Gly
            500                 505                 510

Tyr Asn Glu Asn Tyr Lys Asn Tyr Thr Ala Tyr Met Arg Lys Glu Ala
        515                 520                 525

Pro Glu Asp Gly Gly Gly Lys Asp Ile Glu Ala Ser Phe Asp Asp Glu
    530                 535                 540

Ala Val Ile Glu Thr Glu Ala Lys Pro Thr Asp Ile Arg His Val Lys
545                 550                 555                 560

Glu Ile Gly His Ile Asp Leu Val Ser His Ile Ile Gly Gly Arg Ser
                565                 570                 575

Val Asp Gly Arg Pro Ala Gly Gly Ile Ala Pro Asp Ala Thr Leu His
            580                 585                 590

Ile Met Asn Thr Asn Asp Glu Thr Lys Asn Glu Met Met Val Ala Ala
        595                 600                 605

Ile Arg Asn Ala Trp Val Lys Leu Gly Glu Arg Gly Val Arg Ile Val
    610                 615                 620

Asn Asn Ser Phe Gly Thr Thr Ser Arg Ala Gly Thr Ala Asp Leu Phe
625                 630                 635                 640

Gln Ile Ala Asn Ser Glu Glu Gln Tyr Arg Gln Ala Leu Leu Asp Tyr
                645                 650                 655

Ser Gly Gly Asp Lys Thr Asp Glu Gly Ile Arg Leu Met Gln Gln Ser
            660                 665                 670

Asp Tyr Gly Asn Leu Ser Tyr His Ile Arg Asn Lys Asn Met Leu Phe
        675                 680                 685

Ile Phe Ser Thr Gly Asn Asp Ala Gln Ala Gln Pro Asn Thr Tyr Ala
    690                 695                 700
```

```
Leu Leu Pro Phe Tyr Glu Lys Asp Ala Gln Lys Gly Ile Ile Thr Val
705                 710                 715                 720

Ala Gly Val Asp Arg Ser Gly Glu Lys Phe Lys Arg Glu Met Tyr Gly
                725                 730                 735

Glu Pro Gly Thr Glu Pro Leu Glu Tyr Gly Ser Asn His Cys Gly Ile
            740                 745                 750

Thr Ala Met Trp Cys Leu Ser Ala Pro Tyr Glu Ala Ser Val Arg Phe
        755                 760                 765

Thr Arg Thr Asn Pro Ile Gln Ile Ala Gly Thr Ser Phe Ser Ala Pro
    770                 775                 780

Ile Val Thr Gly Thr Ala Ala Leu Leu Leu Gln Lys Tyr Pro Trp Met
785                 790                 795                 800

Ser Asn Asp Asn Leu Arg Thr Thr Leu Leu Thr Thr Ala Gln Asp Ile
                805                 810                 815

Gly Ala Val Gly Val Asp Ser Lys Phe Gly Trp Gly Leu Leu Asp Ala
            820                 825                 830

Gly Lys Ala Met Asn Gly Pro Ala Ser Phe Pro Phe Gly Asp Phe Thr
        835                 840                 845

Ala Asp Thr Lys Gly Thr Ser Asp Ile Ala Tyr Ser Phe Arg Asn Asp
    850                 855                 860

Ile Ser Gly Thr Gly Gly Leu Ile Lys Lys Gly Gly Ser Gln Leu Gln
865                 870                 875                 880

Leu His Gly Asn Asn Thr Tyr Thr Gly Lys Thr Ile Ile Glu Gly Gly
                885                 890                 895

Ser Leu Val Leu Tyr Gly Asn Asn Lys Ser Asp Met Arg Val Glu Thr
            900                 905                 910

Lys Gly Ala Leu Ile Tyr Asn Gly Ala Ala Ser Gly Gly Ser Leu Asn
        915                 920                 925

Ser Asp Gly Ile Val Tyr Leu Ala Asp Thr Asp Gln Ser Gly Ala Asn
    930                 935                 940

Glu Thr Val His Ile Lys Gly Ser Leu Gln Leu Asp Gly Lys Gly Thr
945                 950                 955                 960

Leu Tyr Thr Arg Leu Gly Lys Leu Leu Lys Val Asp Gly Thr Ala Ile
                965                 970                 975

Ile Gly Gly Lys Leu Tyr Met Ser Ala Arg Gly Lys Gly Ala Gly Tyr
            980                 985                 990

Leu Asn Ser Thr Gly Arg Arg Val Pro Phe Leu Ser Ala Ala Lys Ile
        995                 1000                1005

Gly Gln Asp Tyr Ser Phe Phe Thr Asn Ile Glu Thr Asp Gly Gly Leu
    1010                1015                1020

Leu Ala Ser Leu Asp Ser Val Glu Lys Thr Ala Gly Ser Glu Gly Asp
1025                1030                1035                1040

Thr Leu Ser Tyr Tyr Val Arg Arg Gly Asn Ala Ala Arg Thr Ala Ser
                1045                1050                1055

Ala Ala Ala His Ser Ala Pro Ala Gly Leu Lys His Ala Val Glu Gln
            1060                1065                1070

Gly Gly Ser Asn Leu Glu Asn Leu Met Val Glu Leu Asp Ala Ser Glu
        1075                1080                1085

Ser Ser Ala Thr Pro Glu Thr Val Glu Thr Ala Ala Ala Asp Arg Thr
    1090                1095                1100

Asp Met Pro Gly Ile Arg Pro Tyr Gly Ala Thr Phe Arg Ala Ala Ala
1105                1110                1115                1120

Ala Val Gln His Ala Asn Ala Ala Asp Gly Val Arg Ile Phe Asn Ser
```

Leu Ala Ala Thr Val Tyr Ala Asp Ser Thr Ala Ala His Ala Asp Met
       1140                1145                1150

Gln Gly Arg Arg Leu Lys Ala Val Ser Asp Gly Leu Asp His Asn Gly
   1155                1160                1165

Thr Gly Leu Arg Val Ile Ala Gln Thr Gln Gln Asp Gly Gly Thr Trp
   1170                1175                1180

Glu Gln Gly Gly Val Glu Gly Lys Met Arg Gly Ser Thr Gln Thr Val
1185                1190                1195                1200

Gly Ile Ala Ala Lys Thr Gly Glu Asn Thr Thr Ala Ala Ala Thr Leu
               1205                1210                1215

Gly Met Gly Arg Ser Thr Trp Ser Glu Asn Ser Ala Asn Ala Lys Thr
               1220                1225                1230

Asp Ser Ile Ser Leu Phe Ala Gly Ile Arg His Asp Ala Gly Asp Ile
               1235                1240                1245

Gly Tyr Leu Lys Gly Leu Phe Ser Tyr Gly Arg Tyr Lys Asn Ser Ile
               1250                1255                1260

Ser Arg Ser Thr Gly Ala Asp Glu His Ala Glu Gly Ser Val Asn Gly
1265                1270                1275                1280

Thr Leu Met Gln Leu Gly Ala Leu Gly Gly Val Asn Val Pro Phe Ala
               1285                1290                1295

Ala Thr Gly Asp Leu Thr Val Gly Gly Leu Arg Tyr Asp Leu Leu
               1300                1305                1310

Lys Gln Asp Ala Phe Ala Glu Lys Gly Ser Ala Leu Gly Trp Ser Gly
               1315                1320                1325

Asn Ser Leu Thr Glu Gly Thr Leu Val Gly Leu Ala Gly Leu Lys Leu
               1330                1335                1340

Ser Gln Pro Leu Ser Asp Lys Ala Val Leu Phe Ala Thr Ala Gly Val
1345                1350                1355                1360

Glu Arg Asp Leu Asn Gly Arg Asp Tyr Thr Val Thr Gly Gly Phe Thr
               1365                1370                1375

Gly Ala Thr Ala Ala Thr Gly Lys Thr Gly Ala Arg Asn Met Pro His
               1380                1385                1390

Thr Arg Leu Val Ala Gly Leu Gly Ala Asp Val Glu Phe Gly Asn Gly
               1395                1400                1405

Trp Asn Gly Leu Ala Arg Tyr Ser Tyr Ala Gly Ser Lys Gln Tyr Gly
               1410                1415                1420

Asn His Ser Gly Arg Val Gly Val Gly Tyr Arg Phe Leu Glu His His
1425                1430                1435                1440

His His His His

<210> SEQ ID NO 152
<211> LENGTH: 2256
<212> TYPE: DNA
<213> ORGANISM: Artificial Sequence
<220> FEATURE:
<223> OTHER INFORMATION: Synthetic construct

<400> SEQUENCE: 152
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact cagccgatg ttgaagccga cgactttaaa      180
ggtctgggtc tgaaaaaagt cgtgactaac ctgaccaaaa ccgtcaatga aaacaaacaa     240

```
aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg cacagctaa tactgcagcc     660 gacaaggccg aagctgtcgc tgcaaaagtt accgacatca agctgatat cgctacgaac     720 aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggaggaggag gatcagattt ggcaaacgat   1020
tcttttatcc ggcaggttct cgaccgtcag catttcgaac ccgacgggaa ataccaccta   1080
ttcggcagca ggggggaact tgccgagcgc agcggccata tcggattggg aaaaatacaa   1140
agccatcagt tgggcaacct gatgattcaa caggcggcca ttaaggaaa tatcggctac    1200 attgtccgct tttccgatca cgggcacgaa gtccattccc ccttcgacaa ccatgcctca   1260
cattccgatt ctgatgaagc cggtagtccc gttgacggat ttagccttta ccgcatccat   1320
tgggacggat acgaacacca tcccgccgac ggctatgacg gccacaggg cggcggctat    1380 cccgctccca aaggcgcgag ggatatatac agctacgaca taaaaggcgt tgcccaaaat   1440
atccgcctca acctgaccga caaccgcagc accggacaac ggcttgccga ccgtttccac   1500
aatgccggta gtatgctgac gcaaggagta ggcgacggat tcaaacgcgc cacccgatac   1560
agccccgagc tggacagatc gggcaatgcc gccgaagcct tcaacggcac tgcagatatc   1620
gttaaaaaca tcatcggcgc ggcaggagaa attgtcggcg caggcgatgc cgtgcagggc   1680
ataagcgaag gctcaaacat tgctgtcatg cacggcttgg gtctgctttc caccgaaaac   1740
aagatggcgc gcatcaacga tttggcagat atggcgcaac tcaaagacta tgccgcagca   1800
gccatccgcg attgggcagt ccaaaacccc aatgccgcac aaggcataga agccgtcagc   1860
aatatcttta tggcagccat ccccatcaaa gggattggag ctgttcgggg aaaatacggc   1920
ttgggcggca tcacggcaca tcctatcaag cggtcgcaga tgggcgcgat cgcattgccg   1980
aaagggaaat ccgccgtcag cgacaattt gccgatgcgg catacgccaa ataccgtcc    2040 ccttaccatt cccgaaatat ccgttcaaac ttggagcagc gttacggcaa agaaaacatc   2100
acctcctcaa ccgtgccgcc gtcaaacggc aaaaatgtca aactggcaga ccaacgccac   2160
ccgaagacag gcgtaccgtt tgacggtaaa gggtttccga ttttgagaa gcacgtgaaa    2220 tatgatacgc tcgagcacca ccaccaccac cactga                              2256
```

<210> SEQ ID NO 153
<211> LENGTH: 751
<212> TYPE: PRT
<213> ORGANISM: Artificial Sequence
<220> FEATURE:
<223> OTHER INFORMATION: Synthetic construct

<400> SEQUENCE: 153

Met Ala Thr Asn Asp Asp Val Lys Lys Ala Ala Thr Val Ala Ile

-continued

```
1               5                   10                  15
Ala Ala Ala Tyr Asn Asn Gly Gln Glu Ile Asn Gly Phe Lys Ala Gly
            20                  25                  30
Glu Thr Ile Tyr Asp Ile Asp Glu Asp Gly Thr Ile Thr Lys Lys Asp
            35                  40                  45
Ala Thr Ala Ala Asp Val Glu Ala Asp Phe Lys Gly Leu Gly Leu
    50                  55                  60
Lys Lys Val Val Thr Asn Leu Thr Lys Thr Val Asn Glu Asn Lys Gln
65                  70                  75                  80
Asn Val Asp Ala Lys Val Lys Ala Ala Glu Ser Glu Ile Glu Lys Leu
                85                  90                  95
Thr Thr Lys Leu Ala Asp Thr Asp Ala Ala Leu Ala Asp Thr Asp Ala
                100                 105                 110
Ala Leu Asp Ala Thr Thr Asn Ala Leu Asn Lys Leu Gly Glu Asn Ile
            115                 120                 125
Thr Thr Phe Ala Glu Glu Thr Lys Thr Asn Ile Val Lys Ile Asp Glu
            130                 135                 140
Lys Leu Glu Ala Val Ala Asp Thr Val Asp Lys His Ala Glu Ala Phe
145                 150                 155                 160
Asn Asp Ile Ala Asp Ser Leu Asp Glu Thr Asn Thr Lys Ala Asp Glu
                165                 170                 175
Ala Val Lys Thr Ala Asn Glu Ala Lys Gln Thr Ala Glu Thr Lys
                180                 185                 190
Gln Asn Val Asp Ala Lys Val Lys Ala Ala Glu Thr Ala Ala Gly Lys
            195                 200                 205
Ala Glu Ala Ala Ala Gly Thr Ala Asn Thr Ala Ala Asp Lys Ala Glu
            210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
            260                 265                 270
Thr Glu Lys Leu Asp Thr Arg Leu Ala Ser Ala Glu Lys Ser Ile Ala
            275                 280                 285
Asp His Asp Thr Arg Leu Asn Gly Leu Asp Lys Thr Val Ser Asp Leu
            290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Gly Ser Gly Gly Gly Ser Asp
                325                 330                 335
Leu Ala Asn Asp Ser Phe Ile Arg Gln Val Leu Asp Arg Gln His Phe
            340                 345                 350
Glu Pro Asp Gly Lys Tyr His Leu Phe Gly Ser Arg Gly Glu Leu Ala
            355                 360                 365
Glu Arg Ser Gly His Ile Gly Leu Gly Lys Ile Gln Ser His Gln Leu
            370                 375                 380
Gly Asn Leu Met Ile Gln Gln Ala Ala Ile Lys Gly Asn Ile Gly Tyr
385                 390                 395                 400
Ile Val Arg Phe Ser Asp His Gly His Glu Val His Ser Pro Phe Asp
                405                 410                 415
Asn His Ala Ser His Ser Asp Ser Asp Glu Ala Gly Ser Pro Val Asp
                420                 425                 430
```

```
Gly Phe Ser Leu Tyr Arg Ile His Trp Asp Gly Tyr Glu His Pro
            435                 440                 445

Ala Asp Gly Tyr Asp Gly Pro Gln Gly Gly Tyr Pro Ala Pro Lys
    450                 455                 460

Gly Ala Arg Asp Ile Tyr Ser Tyr Asp Ile Lys Gly Val Ala Gln Asn
465                 470                 475                 480

Ile Arg Leu Asn Leu Thr Asp Asn Arg Ser Thr Gly Gln Arg Leu Ala
                485                 490                 495

Asp Arg Phe His Asn Ala Gly Ser Met Leu Thr Gln Gly Val Gly Asp
            500                 505                 510

Gly Phe Lys Arg Ala Thr Arg Tyr Ser Pro Glu Leu Asp Arg Ser Gly
            515                 520                 525

Asn Ala Ala Glu Ala Phe Asn Gly Thr Ala Asp Ile Val Lys Asn Ile
    530                 535                 540

Ile Gly Ala Ala Gly Glu Ile Val Gly Ala Gly Asp Ala Val Gln Gly
545                 550                 555                 560

Ile Ser Glu Gly Ser Asn Ile Ala Val Met His Gly Leu Gly Leu Leu
                565                 570                 575

Ser Thr Glu Asn Lys Met Ala Arg Ile Asn Asp Leu Ala Asp Met Ala
            580                 585                 590

Gln Leu Lys Asp Tyr Ala Ala Ala Ile Arg Asp Trp Ala Val Gln
            595                 600                 605

Asn Pro Asn Ala Ala Gln Gly Ile Glu Ala Val Ser Asn Ile Phe Met
    610                 615                 620

Ala Ala Ile Pro Ile Lys Gly Ile Gly Ala Val Arg Gly Lys Tyr Gly
625                 630                 635                 640

Leu Gly Gly Ile Thr Ala His Pro Ile Lys Arg Ser Gln Met Gly Ala
                645                 650                 655

Ile Ala Leu Pro Lys Gly Lys Ser Ala Val Ser Asp Asn Phe Ala Asp
            660                 665                 670

Ala Ala Tyr Ala Lys Tyr Pro Ser Pro Tyr His Ser Arg Asn Ile Arg
    675                 680                 685

Ser Asn Leu Glu Gln Arg Tyr Gly Lys Glu Asn Ile Thr Ser Ser Thr
690                 695                 700

Val Pro Pro Ser Asn Gly Lys Asn Val Lys Leu Ala Asp Gln Arg His
705                 710                 715                 720

Pro Lys Thr Gly Val Pro Phe Asp Gly Lys Gly Phe Pro Asn Phe Glu
                725                 730                 735

Lys His Val Lys Tyr Asp Thr Leu Glu His His His His His His
            740                 745                 750

<210> SEQ ID NO 154
<211> LENGTH: 1773
<212> TYPE: DNA
<213> ORGANISM: Artificial Sequence
<220> FEATURE:
<223> OTHER INFORMATION: Synthetic construct

<400> SEQUENCE: 154
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact cagccgatg ttgaagccga cgactttaaa     180
ggtctgggtc tgaaaaaagt cgtgactaac ctgaccaaaa ccgtcaatga aaacaaacaa     240
```

-continued

```
aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg cacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag acaagccgc gctctccggt    960
ctgttccaac cttacaacgt gggtggatcc ggaggggggtg tgtcgccgc cgacatcggt   1020
gcggggcttg ccgatgcact aaccgcaccg ctcgaccata agacaaagg tttgcagtct   1080
ttgacgctgg atcagtccgt caggaaaaac gagaaactga agctggcggc acaaggtgcg   1140
gaaaaaactt atggaaacgg tgacagcctc aatacgggca aattgaagaa cgacaaggtc   1200
agccgtttcg actttatccg ccaaatcgaa gtggacgggc agctcattac cttggagagt   1260
ggagagttcc aagtatacaa acaaagccat tccgccttaa ccgcctttca gaccgagcaa   1320
atacaagatt cggagcattc cgggaagatg gttgcgaaac gccagttcag aatcggcgac   1380
atagcgggcg aacatacatc tttttgacaag cttcccgaag gcggcagggc gacatatcgc   1440
gggacggcgt tcggttcaga cgatgccggc ggaaaactga cctacaccat agatttcgcc   1500
gccaagcagg gaaacggcaa aatcgaacat ttgaaatcgc cagaactcaa tgtcgacctg   1560
gccgccgccg atatcaagcc ggatggaaaa cgccatgccg tcatcagcgg ttccgtcctt   1620
tacaaccaag ccgagaaagg cagttactcc ctcggtatct ttggcggaaa agcccaggaa   1680
gttgccggca gcgcggaagt gaaaaccgta acggcatac gccatatcgg ccttgccgcc   1740
aagcaactcg agcaccacca ccaccaccac tga                                 1773
```

<210> SEQ ID NO 155
<211> LENGTH: 590
<212> TYPE: PRT
<213> ORGANISM: Artificial Sequence
<220> FEATURE:
<223> OTHER INFORMATION: Synthetic construct

<400> SEQUENCE: 155

Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

```
Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Val Ala
                325                 330                 335

Ala Asp Ile Gly Ala Gly Leu Ala Asp Ala Leu Thr Ala Pro Leu Asp
            340                 345                 350

His Lys Asp Lys Gly Leu Gln Ser Leu Thr Leu Asp Gln Ser Val Arg
        355                 360                 365

Lys Asn Glu Lys Leu Lys Leu Ala Ala Gln Gly Ala Glu Lys Thr Tyr
    370                 375                 380

Gly Asn Gly Asp Ser Leu Asn Thr Gly Lys Leu Lys Asn Asp Lys Val
385                 390                 395                 400

Ser Arg Phe Asp Phe Ile Arg Gln Ile Glu Val Asp Gly Gln Leu Ile
                405                 410                 415

Thr Leu Glu Ser Gly Glu Phe Gln Val Tyr Lys Gln Ser His Ser Ala
            420                 425                 430

Leu Thr Ala Phe Gln Thr Glu Gln Ile Gln Asp Ser Glu His Ser Gly
        435                 440                 445

Lys Met Val Ala Lys Arg Gln Phe Arg Ile Gly Asp Ile Ala Gly Glu
    450                 455                 460

His Thr Ser Phe Asp Lys Leu Pro Glu Gly Gly Arg Ala Thr Tyr Arg
465                 470                 475                 480

Gly Thr Ala Phe Gly Ser Asp Asp Ala Gly Gly Lys Leu Thr Tyr Thr
                485                 490                 495

Ile Asp Phe Ala Ala Lys Gln Gly Asn Gly Lys Ile Glu His Leu Lys
            500                 505                 510
```

Ser Pro Glu Leu Asn Val Asp Leu Ala Ala Ala Asp Ile Lys Pro Asp
         515                 520                 525

Gly Lys Arg His Ala Val Ile Ser Gly Ser Val Leu Tyr Asn Gln Ala
    530                 535                 540

Glu Lys Gly Ser Tyr Ser Leu Gly Ile Phe Gly Gly Lys Ala Gln Glu
545                 550                 555                 560

Val Ala Gly Ser Ala Glu Val Lys Thr Val Asn Gly Ile Arg His Ile
                565                 570                 575

Gly Leu Ala Ala Lys Gln Leu Glu His His His His His His
            580                 585                 590

<210> SEQ ID NO 156
<211> LENGTH: 4170
<212> TYPE: DNA
<213> ORGANISM: Artificial Sequence
<220> FEATURE:
<223> OTHER INFORMATION: Synthetic construct

<400> SEQUENCE: 156
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat tgggagaaaa tataacgaca tttgctgaag agactaagac aaatatcgta     420
aaaattgatg aaaaattaga agccgtggct gataccgtcg acaagcatgc gaagcattc      480 aacgatatcg ccgattcatt ggatgaaacc aacactaagg cagacgaagc cgtcaaaacc     540
gccaatgaag ccaaacagac ggccgaagaa accaaacaaa acgtcgatgc aaagtaaaa     600 gctgcagaaa ctgcagcagg caaagccgaa gctgccgctg cacagctaa tactgcagcc     660 gacaaggccg aagctgtcgc tgcaaaagtt accgacatca agctgatat cgctacgaac     720 aaagataata ttgctaaaaa agcaaacagt gccgacgtgt acaccagaga gagtctgac    780 agcaaatttg tcagaattga tggtctgaac gctactaccg aaaaattgga cacacgcttg     840
gcttctgctg aaaaatccat gccgatcac gatactcgcc tgaacggttt ggataaaaca     900
gtgtcagacc tgcgcaaaga aaccgccaa ggccttgcag aacaagccgc gctctccggt     960
ctgttccaac cttacaacgt gggtggatcc ggcggaggcg gcacttctgc gcccgacttc    1020
aatgcaggcg gtaccggtat cggcagcaac agcagagcaa caacagcgaa atcagcagca    1080
gtatcttacg ccggtatcaa gaacgaaatg tgcaaagaca gaagcatgct ctgtgccggt    1140
cgggatgacg ttgcggttac agacagggat gccaaaatca atgcccccc cccgaatctg    1200 cataccggag actttccaaa cccaaatgac gcatacaaga atttgatcaa cctcaaacct    1260
gcaattgaag caggctatac aggacgcggg gtagaggtag gtatcgtcga caccggcgaa    1320
tccgtcggca gcatatcctt tcccgaactg tatggcagaa aagaacacgg ctataacgaa    1380
aattacaaaa actatacggc gtatatgcgg aaggaagcgc tgaagacgg aggcggtaaa    1440 gacattgaag cttctttcga cgatgaggcc gttatagaga ctgaagcaaa gccgacggat    1500
atccgccacg taaagaaaat cggacacatc gatttggtct cccatattat tggcgggcgt    1560
tccgtggacg gcagacctgc aggcggtatt gcgcccgatg cgacgctaca cataatgaat    1620

```
acgaatgatg aaaccaagaa cgaaatgatg gttgcagcca tccgcaatgc atgggtcaag    1680
ctgggcgaac gtggcgtgcg catcgtcaat aacagttttg gaacaacatc gagggcaggc    1740
actgccgacc ttttccaaat agccaattcg gaggagcagt accgccaagc gttgctcgac    1800
tattccggcg gtgataaaac agacgagggt atccgcctga tgcaacagag cgattacggc    1860
aacctgtcct accacatccg taataaaaac atgcttttca tcttttcgac aggcaatgac    1920
gcacaagctc agcccaacac atatgcccta ttgccatttt atgaaaaaga cgctcaaaaa    1980
ggcattatca cagtcgcagg cgtagaccgc agtggagaaa agttcaaacg ggaaatgtat    2040
ggagaaccgg gtacagaacc gcttgagtat ggctccaacc attgcggaat tactgccatg    2100
tggtgcctgt cggcacccta tgaagcaagc gtccgtttca cccgtacaaa cccgattcaa    2160
attgccggaa catccttttc cgcacccatc gtaaccggca cggcggctct gctgctgcag    2220
aaatacccgt ggatgagcaa cgacaacctg cgtaccacgt tgctgacgac ggctcaggac    2280
atcggtgcag tcggcgtgga cagcaagttc ggctggggac tgctggatgc gggtaaggcc    2340
atgaacggac ccgcgtcctt tccgttcggc gactttaccg ccgatacgaa aggtacatcc    2400
gatattgcct actccttccg taacgacatt tcaggcacgg gcggcctgat caaaaaaggc    2460
ggcagccaac tgcaactgca cggcaacaac acctatacgg gcaaaaccat tatcgaaggc    2520
ggttcgctgg tgttgtacgg caacaacaaa tcggatatgc gcgtcgaaac caaaggtgcg    2580
ctgatttata acgggcggc atccggcggc agcctgaaca cgacggcat tgtctatctg    2640 gcagataccg accaatccgg cgcaaacgaa accgtacaca tcaaaggcag tctgcagctg    2700
gacggcaaag gtacgctgta cacacgtttg ggcaaactgc tgaaagtgga cggtacggcg    2760
attatcggcg gcaagctgta catgtcggca cgcggcaagg gggcaggcta tctcaacagt    2820 accgacgac gtgttcccctt cctgagtgcc gccaaaatcg gcaggatta ttctttcttc    2880 acaaacatcg aaccgacgg cggcctgctg gcttccctcg acagcgtcga aaaacagcg    2940 ggcagtgaag cgacacgct gtcctattat gtccgtcgcg gcaatgcggc acggactgct    3000
tcggcagcgg cacattccgc gcccgccggt ctgaaacacg ccgtagaaca gggcggcagc    3060
aatctggaaa acctgatggt cgaactggat gcctccgaat catccgcaac acccgagacg    3120
gttgaaactg cggcagccga ccgcacagat atgccgggca tccgcccta cggcgcaact    3180 ttccgcgcag cggcagccgt acagcatgcg aatgccgccg acggtgtacg catcttcaac    3240
agtctcgccg ctaccgtcta tgccgacagt accgccgccc atgccgatat gcagggacgc    3300
cgcctgaaag ccgtatcgga cgggttggac cacaacggca cgggtctgcg cgtcatcgcg    3360
caaacccaac aggacggtgg aacgtgggaa cagggcggtg ttgaaggcaa aatgcgcggc    3420
agtacccaaa ccgtcggcat tgccgcgaaa accggcgaaa atacgacagc agccgccaca    3480
ctgggcatgg gacgcagcac atggagcgaa aacagtgcaa atgcaaaaac cgacagcatt    3540
agtctgtttg caggcatacg gcacgatgcg ggcgatatcg gctatctcaa aggcctgttc    3600
tcctacggac gctacaaaaa cagcatcagc cgcagccacg gtgcggacga acatgcggaa    3660
ggcagcgtca acggcacgct gatgcagctg ggcgcactgg gcggtgtcaa cgttccgttt    3720
gccgcaacgg gagatttgac ggtcgaaggc ggtctgcgct acgacctgct caaacaggat    3780
gcattcgccg aaaaaggcag tgctttgggc tggagcggca acagcctcac tgaaggcacg    3840
ctggtcggac tcgcgggtct gaagctgtcg caacccttga gcgataaagc cgtcctgttt    3900
gcaacgcgcg gcgtggaacg cgacctgaac ggacgcgact acacggtaac gggcggcttt    3960
accggcgcga ctgcagcaac cggcaagacg ggggcacgca atatgccgca cacccgtctg    4020
```

-continued

```
gttgccggcc tgggcgcgga tgtcgaattc ggcaacggct ggaacggctt ggcacgttac    4080
agctacgccg gttccaaaca gtacggcaac cacagcggac gagtcggcgt aggctaccgg    4140
ttcctcgagc accaccacca ccaccactga                                     4170
```

<210> SEQ ID NO 157
<211> LENGTH: 1389
<212> TYPE: PRT
<213> ORGANISM: Artificial Sequence
<220> FEATURE:
<223> OTHER INFORMATION: Synthetic construct

<400> SEQUENCE: 157

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Thr Ser
                325                 330                 335
```

-continued

```
Ala Pro Asp Phe Asn Ala Gly Thr Gly Ile Gly Ser Asn Ser Arg
            340                 345                 350
Ala Thr Thr Ala Lys Ser Ala Ala Val Ser Tyr Ala Gly Ile Lys Asn
        355                 360                 365
Glu Met Cys Lys Asp Arg Ser Met Leu Cys Ala Gly Arg Asp Asp Val
    370                 375                 380
Ala Val Thr Asp Arg Asp Ala Lys Ile Asn Ala Pro Pro Asn Leu
385                 390                 395                 400
His Thr Gly Asp Phe Pro Asn Pro Asn Asp Ala Tyr Lys Asn Leu Ile
                405                 410                 415
Asn Leu Lys Pro Ala Ile Glu Ala Gly Tyr Thr Gly Arg Gly Val Glu
            420                 425                 430
Val Gly Ile Val Asp Thr Gly Glu Ser Val Gly Ser Ile Ser Phe Pro
        435                 440                 445
Glu Leu Tyr Gly Arg Lys Glu His Gly Tyr Asn Glu Asn Tyr Lys Asn
    450                 455                 460
Tyr Thr Ala Tyr Met Arg Lys Glu Ala Pro Glu Asp Gly Gly Lys
465                 470                 475                 480
Asp Ile Glu Ala Ser Phe Asp Asp Glu Ala Val Ile Glu Thr Glu Ala
                485                 490                 495
Lys Pro Thr Asp Ile Arg His Val Lys Glu Ile Gly His Ile Asp Leu
            500                 505                 510
Val Ser His Ile Ile Gly Gly Arg Ser Val Asp Gly Arg Pro Ala Gly
        515                 520                 525
Gly Ile Ala Pro Asp Ala Thr Leu His Ile Met Asn Thr Asn Asp Glu
    530                 535                 540
Thr Lys Asn Glu Met Met Val Ala Ala Ile Arg Asn Ala Trp Val Lys
545                 550                 555                 560
Leu Gly Glu Arg Gly Val Arg Ile Val Asn Asn Ser Phe Gly Thr Thr
                565                 570                 575
Ser Arg Ala Gly Thr Ala Asp Leu Phe Gln Ile Ala Asn Ser Glu Glu
            580                 585                 590
Gln Tyr Arg Gln Ala Leu Leu Asp Tyr Ser Gly Gly Asp Lys Thr Asp
        595                 600                 605
Glu Gly Ile Arg Leu Met Gln Gln Ser Asp Tyr Gly Asn Leu Ser Tyr
    610                 615                 620
His Ile Arg Asn Lys Asn Met Leu Phe Ile Phe Ser Thr Gly Asn Asp
625                 630                 635                 640
Ala Gln Ala Gln Pro Asn Thr Tyr Ala Leu Leu Pro Phe Tyr Glu Lys
                645                 650                 655
Asp Ala Gln Lys Gly Ile Ile Thr Val Ala Gly Val Asp Arg Ser Gly
            660                 665                 670
Glu Lys Phe Lys Arg Glu Met Tyr Gly Glu Pro Gly Thr Glu Pro Leu
        675                 680                 685
Glu Tyr Gly Ser Asn His Cys Gly Ile Thr Ala Met Trp Cys Leu Ser
    690                 695                 700
Ala Pro Tyr Glu Ala Ser Val Arg Phe Thr Arg Thr Asn Pro Ile Gln
705                 710                 715                 720
Ile Ala Gly Thr Ser Phe Ser Ala Pro Ile Val Thr Gly Thr Ala Ala
                725                 730                 735
Leu Leu Leu Gln Lys Tyr Pro Trp Met Ser Asn Asp Asn Leu Arg Thr
            740                 745                 750
```

```
Thr Leu Leu Thr Thr Ala Gln Asp Ile Gly Ala Val Gly Val Asp Ser
            755                 760                 765
Lys Phe Gly Trp Gly Leu Leu Asp Ala Gly Lys Ala Met Asn Gly Pro
    770                 775                 780
Ala Ser Phe Pro Phe Gly Asp Phe Thr Ala Asp Thr Lys Gly Thr Ser
785                 790                 795                 800
Asp Ile Ala Tyr Ser Phe Arg Asn Asp Ile Ser Gly Thr Gly Leu
                805                 810                 815
Ile Lys Lys Gly Gly Ser Gln Leu Gln Leu His Gly Asn Asn Thr Tyr
        820                 825                 830
Thr Gly Lys Thr Ile Ile Glu Gly Gly Ser Leu Val Leu Tyr Gly Asn
            835                 840                 845
Asn Lys Ser Asp Met Arg Val Glu Thr Lys Gly Ala Leu Ile Tyr Asn
    850                 855                 860
Gly Ala Ala Ser Gly Gly Ser Leu Asn Ser Asp Gly Ile Val Tyr Leu
865                 870                 875                 880
Ala Asp Thr Asp Gln Ser Gly Ala Asn Glu Thr Val His Ile Lys Gly
                885                 890                 895
Ser Leu Gln Leu Asp Gly Lys Gly Thr Leu Tyr Thr Arg Leu Gly Lys
        900                 905                 910
Leu Leu Lys Val Asp Gly Thr Ala Ile Ile Gly Gly Lys Leu Tyr Met
            915                 920                 925
Ser Ala Arg Gly Lys Gly Ala Gly Tyr Leu Asn Ser Thr Gly Arg Arg
    930                 935                 940
Val Pro Phe Leu Ser Ala Ala Lys Ile Gly Gln Asp Tyr Ser Phe Phe
945                 950                 955                 960
Thr Asn Ile Glu Thr Asp Gly Gly Leu Leu Ala Ser Leu Asp Ser Val
                965                 970                 975
Glu Lys Thr Ala Gly Ser Glu Gly Asp Thr Leu Ser Tyr Tyr Val Arg
        980                 985                 990
Arg Gly Asn Ala Ala Arg Thr Ala Ser Ala Ala His Ser Ala Pro
    995                 1000                1005
Ala Gly Leu Lys His Ala Val Glu Gln Gly Gly Ser Asn Leu Glu Asn
    1010                1015                1020
Leu Met Val Glu Leu Asp Ala Ser Glu Ser Ser Ala Thr Pro Glu Thr
1025                1030                1035                1040
Val Glu Thr Ala Ala Ala Asp Arg Thr Asp Met Pro Gly Ile Arg Pro
                1045                1050                1055
Tyr Gly Ala Thr Phe Arg Ala Ala Ala Val Gln His Ala Asn Ala
        1060                1065                1070
Ala Asp Gly Val Arg Ile Phe Asn Ser Leu Ala Ala Thr Val Tyr Ala
    1075                1080                1085
Asp Ser Thr Ala Ala His Ala Asp Met Gln Gly Arg Arg Leu Lys Ala
    1090                1095                1100
Val Ser Asp Gly Leu Asp His Asn Gly Thr Gly Leu Arg Val Ile Ala
1105                1110                1115                1120
Gln Thr Gln Gln Asp Gly Gly Thr Trp Glu Gln Gly Gly Val Glu Gly
                1125                1130                1135
Lys Met Arg Gly Ser Thr Gln Thr Val Gly Ile Ala Ala Lys Thr Gly
        1140                1145                1150
Glu Asn Thr Thr Ala Ala Ala Thr Leu Gly Met Gly Arg Ser Thr Trp
    1155                1160                1165
Ser Glu Asn Ser Ala Asn Ala Lys Thr Asp Ser Ile Ser Leu Phe Ala
```

Gly Ile Arg His Asp Ala Gly Asp Ile Gly Tyr Leu Lys Gly Leu Phe
1185                 1190                 1195                 1200

Ser Tyr Gly Arg Tyr Lys Asn Ser Ile Ser Arg Ser Thr Gly Ala Asp
            1205                 1210                 1215

Glu His Ala Glu Gly Ser Val Asn Gly Thr Leu Met Gln Leu Gly Ala
        1220                 1225                 1230

Leu Gly Gly Val Asn Val Pro Phe Ala Ala Thr Gly Asp Leu Thr Val
    1235                 1240                 1245

Glu Gly Gly Leu Arg Tyr Asp Leu Leu Lys Gln Asp Ala Phe Ala Glu
1250                 1255                 1260

Lys Gly Ser Ala Leu Gly Trp Ser Gly Asn Ser Leu Thr Glu Gly Thr
1265                 1270                 1275                 1280

Leu Val Gly Leu Ala Gly Leu Lys Leu Ser Gln Pro Leu Ser Asp Lys
            1285                 1290                 1295

Ala Val Leu Phe Ala Thr Ala Gly Val Glu Arg Asp Leu Asn Gly Arg
        1300                 1305                 1310

Asp Tyr Thr Val Thr Gly Gly Phe Thr Gly Ala Thr Ala Thr Gly
    1315                 1320                 1325

Lys Thr Gly Ala Arg Asn Met Pro His Thr Arg Leu Val Ala Gly Leu
1330                 1335                 1340

Gly Ala Asp Val Glu Phe Gly Asn Gly Trp Asn Gly Leu Ala Arg Tyr
1345                 1350                 1355                 1360

Ser Tyr Ala Gly Ser Lys Gln Tyr Gly Asn His Ser Gly Arg Val Gly
            1365                 1370                 1375

Val Gly Tyr Arg Phe Leu Glu His His His His His His
        1380                 1385

<210> SEQ ID NO 158
<211> LENGTH: 2304
<212> TYPE: DNA
<213> ORGANISM: Artificial Sequence
<220> FEATURE:
<223> OTHER INFORMATION: Synthetic construct

<400> SEQUENCE: 158
atgaaacact ttccatccaa agtactgacc acagccatcc ttgccacttt ctgtagcggc        60
gcactggcag ccacaaacga cgacgatgtt aaaaaagctg ccactgtggc cattgctgct       120
gcctacaaca atggccaaga atcaacggt ttcaaagctg agagaccat ctacgacatt        180 gatgaagacg gcacaattac caaaaaagac gcaactgcag ccgatgttga agccgacgac       240
tttaaaggtc tgggtctgaa aaagtcgtg actaacctga ccaaaaccgt caatgaaaac       300
aaacaaaacg tcgatgccaa agtaaaagct gcagaatctg aaatagaaaa gttaacaacc       360
aagttagcag acactgatgc cgctttagca gatactgatg ccgctctgga tgcaaccacc       420
aacgccttga taaattggg agaaaatata cgacatttg ctgaagagac taagacaaat       480
atcgtaaaaa ttgatgaaaa attagaagcc gtggctgata ccgtcgacaa gcatgccgaa       540
gcattcaacg atatcgccga ttcattggat gaaaccaaca ctaaggcaga cgaagccgtc       600 aaaccgcca atgaagccaa acagacggcc gaagaaacca acaaaaacgt cgatgccaaa       660
gtaaaagctg cagaaactgc agcaggcaaa gccgaagctg ccgctggcac agctaatact       720
gcagccgaca aggccgaagc tgtcgctgca aagttaccg acatcaaagc tgatatcgct       780
acgaacaaag ataatattgc taaaaaagca acagtgccg acgtgtacac cagagaagag       840

-continued

```
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta caacgtgggt ggatccggag gaggaggatc agatttggca   1080
aacgattctt ttatccggca ggttctcgac cgtcagcatt tcgaacccga cgggaaatac   1140
cacctattcg gcagcagggg ggaacttgcc gagcgcagcg gccatatcgg attgggaaaa   1200
atacaaagcc atcagttggg caacctgatg attcaacagg cggccattaa aggaaatatc   1260
ggctacattg tccgcttttc cgatcacggg cacgaagtcc attccccctt cgacaaccat   1320
gcctcacatt ccgattctga tgaagccggt agtcccgttg acggatttag cctttaccgc   1380
atccattggg acggatacga acaccatccc gccgacggct atgacgggcc acagggcggc   1440
ggctatcccg ctcccaaagg cgcgagggat atatacagct acgacataaa aggcgttgcc   1500
caaaatatcc gcctcaacct gaccgacaac cgcagcaccg acaacggct tgccgaccgt   1560
ttccacaatg ccggtagtat gctgacgcaa ggagtaggcg acggattcaa acgcgccacc   1620
cgatacagcc ccgagctgga cagatcgggc aatgccgccg aagccttcaa cggcactgca   1680
gatatcgtta aaaacatcat cggcgcggca ggagaaattg tcggcgcagg cgatgccgtg   1740
cagggcataa gcgaaggctc aaacattgct gtcatgcacg gcttgggtct gctttccacc   1800
gaaaacaaga tggcgcgcat caacgatttg cagatatgg cgcaactcaa agactatgcc   1860
gcagcagcca tccgcgattg ggcagtccaa aaccccaatg ccgcacaagg catagaagcc   1920
gtcagcaata tctttatggc agccatcccc atcaaaggga ttggagctgt tcggggaaaa   1980
tacggcttgg gcggcatcac ggcacatcct atcaagcggt cgcagatggg cgcgatcgca   2040
ttgccgaaag ggaaatccgc cgtcagcgac aattttgccg atgcggcata cgccaaatac   2100
ccgtcccctt accattcccg aaatatccgt tcaaacttgg agcagcgtta cggcaaagaa   2160
aacatcacct cctcaaccgt gccgccgtca acggcaaaa atgtcaaact ggcagaccaa   2220
cgccacccga agacaggcgt accgtttgac ggtaaagggt ttccgaattt tgagaagcac   2280
gtgaaatatg atacgtaact cgag                                         2304
```

<210> SEQ ID NO 159
<211> LENGTH: 765
<212> TYPE: PRT
<213> ORGANISM: Artificial Sequence
<220> FEATURE:
<223> OTHER INFORMATION: Synthetic construct

<400> SEQUENCE: 159

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Thr Asn Leu Thr Lys Thr
            85                  90                  95

Val Asn Glu Asn Lys Gln Asn Val Asp Ala Lys Val Lys Ala Ala Glu
```

-continued

```
                100                 105                 110
Ser Glu Ile Glu Lys Leu Thr Thr Lys Leu Ala Asp Thr Ala Ala
        115                 120                 125
Leu Ala Asp Thr Asp Ala Ala Leu Asp Ala Thr Thr Asn Ala Leu Asn
130                 135                 140
Lys Leu Gly Glu Asn Ile Thr Thr Phe Ala Glu Thr Lys Thr Asn
145                 150                 155                 160
Ile Val Lys Ile Asp Glu Lys Leu Glu Ala Val Ala Asp Thr Val Asp
                165                 170                 175
Lys His Ala Glu Ala Phe Asn Asp Ile Ala Asp Ser Leu Asp Glu Thr
                180                 185                 190
Asn Thr Lys Ala Asp Glu Ala Val Lys Thr Ala Asn Glu Ala Lys Gln
        195                 200                 205
Thr Ala Glu Glu Thr Lys Gln Asn Val Asp Ala Lys Val Lys Ala Ala
        210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Ala Lys Val Thr Asp Ile Lys
                245                 250                 255
Ala Asp Ile Ala Thr Asn Lys Asp Asn Ile Ala Lys Lys Ala Asn Ser
                260                 265                 270
Ala Asp Val Tyr Thr Arg Glu Glu Ser Asp Ser Lys Phe Val Arg Ile
                275                 280                 285
Asp Gly Leu Asn Ala Thr Thr Glu Lys Leu Asp Thr Arg Leu Ala Ser
        290                 295                 300
Ala Glu Lys Ser Ile Ala Asp His Asp Thr Arg Leu Asn Gly Leu Asp
305                 310                 315                 320
Lys Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Gly Ser
                340                 345                 350
Gly Gly Gly Gly Ser Asp Leu Ala Asn Asp Ser Phe Ile Arg Gln Val
                355                 360                 365
Leu Asp Arg Gln His Phe Glu Pro Asp Gly Lys Tyr His Leu Phe Gly
        370                 375                 380
Ser Arg Gly Glu Leu Ala Glu Arg Ser Gly His Ile Gly Leu Gly Lys
385                 390                 395                 400
Ile Gln Ser His Gln Leu Gly Asn Leu Met Ile Gln Gln Ala Ala Ile
                405                 410                 415
Lys Gly Asn Ile Gly Tyr Ile Val Arg Phe Ser Asp His Gly His Glu
                420                 425                 430
Val His Ser Pro Phe Asp Asn His Ala Ser His Ser Asp Ser Asp Glu
        435                 440                 445
Ala Gly Ser Pro Val Asp Gly Phe Ser Leu Tyr Arg Ile His Trp Asp
450                 455                 460
Gly Tyr Glu His His Pro Ala Asp Gly Tyr Asp Gly Pro Gln Gly Gly
465                 470                 475                 480
Gly Tyr Pro Ala Pro Lys Gly Ala Arg Asp Ile Tyr Ser Tyr Asp Ile
                485                 490                 495
Lys Gly Val Ala Gln Asn Ile Arg Leu Asn Leu Thr Asp Asn Arg Ser
        500                 505                 510
Thr Gly Gln Arg Leu Ala Asp Arg Phe His Asn Ala Gly Ser Met Leu
        515                 520                 525
```

Thr Gln Gly Val Gly Asp Gly Phe Lys Arg Ala Thr Arg Tyr Ser Pro
        530                 535                 540

Glu Leu Asp Arg Ser Gly Asn Ala Ala Glu Ala Phe Asn Gly Thr Ala
545                 550                 555                 560

Asp Ile Val Lys Asn Ile Ile Gly Ala Ala Gly Glu Ile Val Gly Ala
                565                 570                 575

Gly Asp Ala Val Gln Gly Ile Ser Glu Gly Ser Asn Ile Ala Val Met
                580                 585                 590

His Gly Leu Gly Leu Leu Ser Thr Glu Asn Lys Met Ala Arg Ile Asn
                595                 600                 605

Asp Leu Ala Asp Met Ala Gln Leu Lys Asp Tyr Ala Ala Ala Ala Ile
                610                 615                 620

Arg Asp Trp Ala Val Gln Asn Pro Asn Ala Ala Gln Gly Ile Glu Ala
625                 630                 635                 640

Val Ser Asn Ile Phe Met Ala Ala Ile Pro Ile Lys Gly Ile Gly Ala
                645                 650                 655

Val Arg Gly Lys Tyr Gly Leu Gly Gly Ile Thr Ala His Pro Ile Lys
                660                 665                 670

Arg Ser Gln Met Gly Ala Ile Ala Leu Pro Lys Gly Lys Ser Ala Val
                675                 680                 685

Ser Asp Asn Phe Ala Asp Ala Ala Tyr Ala Lys Tyr Pro Ser Pro Tyr
690                 695                 700

His Ser Arg Asn Ile Arg Ser Asn Leu Glu Gln Arg Tyr Gly Lys Glu
705                 710                 715                 720

Asn Ile Thr Ser Ser Thr Val Pro Pro Ser Asn Gly Lys Asn Val Lys
                725                 730                 735

Leu Ala Asp Gln Arg His Pro Lys Thr Gly Val Pro Phe Asp Gly Lys
                740                 745                 750

Gly Phe Pro Asn Phe Glu Lys His Val Lys Tyr Asp Thr
            755                 760                 765

<210> SEQ ID NO 160
<211> LENGTH: 1839
<212> TYPE: DNA
<213> ORGANISM: Artificial Sequence
<220> FEATURE:
<223> OTHER INFORMATION: Synthetic construct

<400> SEQUENCE: 160
atgaaacact tccatccaa agtactgacc acagccatcc ttgccacttt ctgtagcggc      60
gcactggcag ccacaaacga cgacgatgtt aaaaaagctg ccactgtggc cattgctgct     120
gcctacaaca atggccaaga atcaacggt ttcaaagctg agagaccat ctacgacatt      180 gatgaagacg gcacaattac caaaaaagac gcaactgcag ccgatgttga agccgacgac    240
tttaaaggtc tgggtctgaa aaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga taaattggg agaaaatata cgacatttg ctgaagagac taagacaaat      480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaaccgcca atgaagccaa acagacggcc gaagaaacca acaaaaacgt cgatgccaaa    660
gtaaaagctg cagaaactgc agcaggcaaa gccgaagctg ccgctggcac agctaatact    720

-continued

```
gcagccgaca aggccgaagc tgtcgctgca aaagttaccg acatcaaagc tgatatcgct      780
acgaacaaag ataatattgc taaaaaagca aacagtgccg acgtgtacac cagagaagag      840
tctgacagca aatttgtcag aattgatggt ctgaacgcta ctaccgaaaa attggacaca      900
cgcttggctt ctgctgaaaa atccattgcc gatcacgata ctcgcctgaa cggtttggat      960
aaaacagtgt cagacctgcg caaagaaacc cgccaaggcc ttgcagaaca gccgcgctc     1020 tccggtctgt tccaaccttta caacgtgggt ggatccggag ggggtggtgt cgccgccgac    1080
atcggtgcgg ggcttgccga tgcactaacc gcaccgctcg accataaaga caaaggtttg    1140
cagtctttga cgctggatca gtccgtcagg aaaaacgaga aactgaagct ggcggcacaa    1200
ggtgcggaaa aaacttatgg aaacggtgac agcctcaata cgggcaaatt gaagaacgac    1260
aaggtcagcc gtttcgactt tatccgccaa atcgaagtgg acgggcagct cattaccttg    1320
gagagtggag agttccaagt atacaaacaa agccattccg ccttaaccgc ctttcagacc    1380
gagcaaatac aagattcgga gcattccggg aagatggttg cgaaacgcca gttcagaatc    1440
ggcgacatag cgggcgaaca tacatctttt gacaagcttc ccgaaggcgg cagggcgaca    1500
tatcgcggga cggcgttcgg ttcagacgat gccggcggaa aactgaccta caccatagat    1560
ttcgccgcca agcagggaaa cggcaaaatc gaacatttga atcgccaga actcaatgtc     1620 gacctggccg ccgccgatat caagccggat ggaaaacgcc atgccgtcat cagcggttcc    1680
gtcctttaca accaagccga gaaggcagt tactccctcg gtatctttgg cggaaaagcc     1740
caggaagttg ccggcagcgc ggaagtgaaa accgtaaacg gcatacgcca tatcggcctt    1800
gccgccaagc aactcgagca ccaccaccac caccactga                            1839
```

<210> SEQ ID NO 161
<211> LENGTH: 612
<212> TYPE: PRT
<213> ORGANISM: Artificial Sequence
<220> FEATURE:
<223> OTHER INFORMATION: Synthetic construct

<400> SEQUENCE: 161

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160
```

```
Ile Val Lys Ile Asp Glu Lys Leu Glu Ala Val Asp Thr Val Asp
            165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
            195                 200                 205

Thr Ala Glu Glu Thr Lys Gln Asn Val Asp Ala Lys Val Lys Ala Ala
            210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
            245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
            290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
            325                 330                 335

Gln Ala Ala Leu Ser Gly Leu Phe Gln Pro Tyr Asn Val Gly Gly Ser
            340                 345                 350

Gly Gly Gly Gly Val Ala Asp Ile Gly Ala Gly Leu Ala Asp Ala
            355                 360                 365

Leu Thr Ala Pro Leu Asp His Lys Asp Lys Gly Leu Gln Ser Leu Thr
            370                 375                 380

Leu Asp Gln Ser Val Arg Lys Asn Glu Lys Leu Lys Leu Ala Ala Gln
385                 390                 395                 400

Gly Ala Glu Lys Thr Tyr Gly Asn Gly Asp Ser Leu Asn Thr Gly Lys
            405                 410                 415

Leu Lys Asn Asp Lys Val Ser Arg Phe Asp Phe Ile Arg Gln Ile Glu
            420                 425                 430

Val Asp Gly Gln Leu Ile Thr Leu Glu Ser Gly Glu Phe Gln Val Tyr
            435                 440                 445

Lys Gln Ser His Ser Ala Leu Thr Ala Phe Gln Thr Glu Gln Ile Gln
            450                 455                 460

Asp Ser Glu His Ser Gly Lys Met Val Ala Lys Arg Gln Phe Arg Ile
465                 470                 475                 480

Gly Asp Ile Ala Gly Glu His Thr Ser Phe Asp Lys Leu Pro Glu Gly
            485                 490                 495

Gly Arg Ala Thr Tyr Arg Gly Thr Ala Phe Gly Ser Asp Asp Ala Gly
            500                 505                 510

Gly Lys Leu Thr Tyr Thr Ile Asp Phe Ala Ala Lys Gln Gly Asn Gly
            515                 520                 525

Lys Ile Glu His Leu Lys Ser Pro Glu Leu Asn Val Asp Leu Ala Ala
            530                 535                 540

Ala Asp Ile Lys Pro Asp Gly Lys Arg His Ala Val Ile Ser Gly Ser
545                 550                 555                 560

Val Leu Tyr Asn Gln Ala Glu Lys Gly Ser Tyr Ser Leu Gly Ile Phe
            565                 570                 575

Gly Gly Lys Ala Gln Glu Val Ala Gly Ser Ala Glu Val Lys Thr Val
```

580                 585                 590
Asn Gly Ile Arg His Ile Gly Leu Ala Ala Lys Gln Leu Glu His His
        595                 600                 605
His His His His
    610

<210> SEQ ID NO 162
<211> LENGTH: 4218
<212> TYPE: DNA
<213> ORGANISM: Artificial Sequence
<220> FEATURE:
<223> OTHER INFORMATION: Synthetic construct

<400> SEQUENCE: 162

| | | | | | |
|---|---|---|---|---|---|
| atgaaacact | ttccatccaa | agtactgacc | acagccatcc | ttgccacttt | ctgtagcggc | 60 |
| gcactggcag | ccacaaacga | cgacgatgtt | aaaaaagctg | ccactgtggc | cattgctgct | 120 |
| gcctacaaca | atggccaaga | aatcaacggt | tcaaagctg | agagaccat | ctacgacatt | 180 |
| gatgaagacg | gcacaattac | caaaaaagac | gcaactgcag | ccgatgttga | agccgacgac | 240 |
| tttaaaggtc | tgggtctgaa | aaagtcgtg | actaacctga | ccaaaaccgt | caatgaaaac | 300 |
| aaacaaaacg | tcgatgccaa | agtaaaagct | gcagaatctg | aaatagaaaa | gttaacaacc | 360 |
| aagttagcag | acactgatgc | cgctttagca | gatactgatg | ccgctctgga | tgcaaccacc | 420 |
| aacgccttga | ataaattggg | agaaaatata | acgacatttg | ctgaagagac | taagacaaat | 480 |
| atcgtaaaaa | ttgatgaaaa | attagaagcc | gtggctgata | ccgtcgacaa | gcatgccgaa | 540 |
| gcattcaacg | atatcgccga | ttcattggat | gaaaccaaca | ctaaggcaga | cgaagccgtc | 600 |
| aaaaccgcca | atgaagccaa | acagacggcc | gaagaaacca | acaaaacgt | cgatgccaaa | 660 |
| gtaaaagctg | cagaaactgc | agcaggcaaa | gccgaagctg | ccgctggcac | agctaatact | 720 |
| gcagccgaca | aggccgaagc | tgtcgctgca | aaagttaccg | acatcaaagc | tgatatcgct | 780 |
| acgaacaaag | ataatattgc | taaaaaagca | aacagtgccg | acgtgtacac | cagagaagag | 840 |
| tctgacagca | aatttgtcag | aattgatggt | ctgaacgcta | ctaccgaaaa | attggacaca | 900 |
| cgcttggctt | ctgctgaaaa | atccattgcc | gatcacgata | ctcgcctgaa | cggtttggat | 960 |
| aaaacagtgt | cagacctgcg | caaagaaacc | cgccaaggcc | ttgcagaaca | agccgcgctc | 1020 |
| tccggtctgt | tccaacctta | caacgtgggt | ggatccggcg | aggcggcac | ttctgcgccc | 1080 |
| gacttcaatg | caggcggtac | cggtatcggc | agcaacagca | gagcaacaac | agcgaaatca | 1140 |
| gcagcagtat | cttacgccgg | tatcaagaac | gaaatgtgca | aagacagaag | catgctctgt | 1200 |
| gccggtcggg | atgacgttgc | ggttacagac | agggatgcca | aaatcaatgc | ccccccccg | 1260 |
| aatctgcata | ccggagactt | tccaaaccca | aatgacgcat | acaagaattt | gatcaacctc | 1320 |
| aaacctgcaa | ttgaagcagg | ctatacagga | cgcggggtag | aggtaggtat | cgtcgacaca | 1380 |
| ggcgaatccg | tcggcagcat | atcctttccc | gaactgtatg | cagaaaaga | acacggctat | 1440 |
| aacgaaaatt | acaaaaacta | tacggcgtat | atgcggaagg | aagcgcctga | agacggaggc | 1500 |
| ggtaaagaca | ttgaagcttc | tttcgacgat | gaggccgtta | tagagactga | agcaaagccg | 1560 |
| acggatatcc | gccacgtaaa | agaaatcgga | cacatcgatt | ggtctcccca | tattattggc | 1620 |
| gggcgttccg | tggacggcag | acctgcaggc | ggtattgcgc | ccgatgcgac | gctacacata | 1680 |
| atgaatacga | atgatgaaac | caagaacgaa | atgatggttg | cagccatccg | caatgcatgg | 1740 |
| gtcaagctgg | gcgaacgtgg | cgtgcgcatc | gtcaataaca | gttttggaac | aacatcgagg | 1800 |
| gcaggcactg | ccgacctttt | ccaaatagcc | aattcggagg | agcagtaccg | ccaagcgttg | 1860 |

```
ctcgactatt ccggcggtga taaaacagac gagggtatcc gcctgatgca acagagcgat      1920
tacggcaacc tgtcctacca catccgtaat aaaaacatgc ttttcatctt ttcgacaggc      1980
aatgacgcac aagctcagcc caacacatat gccctattgc cattttatga aaagacgct       2040 caaaaaggca ttatcacagt cgcaggcgta gaccgcagtg gagaaaagtt caaacgggaa      2100
atgtatggag aaccgggtac agaaccgctt gagtatggct ccaaccattg cggaattact      2160
gccatgtggt gcctgtcggc accctatgaa gcaagcgtcc gtttcacccg tacaaacccg      2220
attcaaattg ccggaacatc cttttccgca cccatcgtaa ccggcacggc ggctctgctg      2280
ctgcagaaat acccgtggat gagcaacgac aacctgcgta ccacgttgct gacgacggct      2340
caggacatcg gtgcagtcgg cgtggacagc aagttcggct ggggactgct ggatgcgggt      2400
aaggccatga acgacccgc gtcctttccg ttcggcgact ttaccgccga tacgaaaggt       2460
acatccgata ttgcctactc cttccgtaac gacatttcag gcacgggcgg cctgatcaaa      2520
aaaggcggca gccaactgca actgcacggc aacaacacct atacgggcaa aaccattatc      2580
gaaggcggtt cgctggtgtt gtacggcaac aacaaatcgg atatgcgcgt cgaaaccaaa      2640
ggtgcgctga tttataacgg ggcggcatcc ggcggcagcc tgaacagcga cggcattgtc      2700
tatctggcag ataccgacca atccggcgca aacgaaaccg tacacatcaa aggcagtctg      2760
cagctggacg gcaaaggtac gctgtacaca cgtttgggca aactgctgaa agtggacggt      2820
acggcgatta tcggcggcaa gctgtacatg tcggcacgcg gcaaggggc aggctatctc       2880 aacagtaccg gacgacgtgt tcccttcctg agtgccgcca aaatcgggca ggattattct     2940
ttcttcacaa acatcgaaac cgacggcggc ctgctggctt ccctcgacag cgtcgaaaaa     3000
acagcgggca gtgaaggcga cacgctgtcc tattatgtcc gtcgcggcaa tgcggcacgg      3060
actgcttcgg cagcggcaca ttccgcgccc gccggtctga acacgccgt agaacagggc       3120 ggcagcaatc tggaaaacct gatggtcgaa ctggatgcct ccgaatcatc cgcaacaccc      3180
gagacggttg aaactgcggc agccgaccgc acagatatgc cgggcatccg ccctacggc      3240 gcaactttcc gcgcagcggc agccgtacag catgcgaatg ccgccgacgg tgtacgcatc       3300
ttcaacagtc tcgccgctac cgtctatgcc gacagtaccg ccgcccatgc cgatatgcag      3360
ggacgccgcc tgaaagccgt atcggacggg ttggaccaca acggcacggg tctgcgcgtc      3420
atcgcgcaaa cccaacagga cggtggaacg tgggaacagg gcggtgttga aggcaaaatg      3480
cgcggcagta cccaaaccgt cggcattgcc gcgaaaaccg gcgaaaatac gacagcagcc      3540
gccacactgg gcatgggacg cagcacatgg agcgaaaaca gtgcaaatgc aaaaaccgac      3600
agcattagtc tgtttgcagg catacggcac gatgcgggcg atatcggcta tctcaaaggc      3660
ctgttctcct acgacgcta caaaaacagc atcagccgca gcaccggtgc ggacgaacat       3720
gcggaaggca gcgtcaacgg cacgctgatg cagctgggcg cactgggcgg tgtcaacgtt      3780
ccgtttgccg caacgggaga tttgacggtc gaaggcggtc tgcgctacga cctgctcaaa      3840
caggatgcat tcgccgaaaa aggcagtgct ttgggctgga gcggcaacag cctcactgaa      3900
ggcacgctgg tcggactcgc gggtctgaag ctgtcgcaac ccttgagcga taaagccgtc      3960
ctgtttgcaa cggcgggcgt ggaacgcgac ctgaacggac gcgactacac ggtaacgggc      4020
ggctttaccg gcgcgactgc agcaaccggc aagacgggg cacgcaatat gccgcacacc       4080
cgtctggttg ccggcctggg cgcggatgtc gaattcggca acggctggaa cggcttggca      4140
cgttacagct acgccggttc caaacagtac ggcaaccaca gcggacgagt cggcgtaggc      4200
```

-continued taccggttct gactcgag							4218

<210> SEQ ID NO 163
<211> LENGTH: 1403
<212> TYPE: PRT
<213> ORGANISM: Artificial Sequence
<220> FEATURE:
<223> OTHER INFORMATION: Synthetic construct

<400> SEQUENCE: 163

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Asn Ala Leu Asn
    130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
        275                 280                 285

Asp Gly Leu Asn Ala Thr Thr Glu Lys Leu Asp Thr Arg Leu Ala Ser
    290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
            340                 345                 350

Gly Gly Gly Gly Thr Ser Ala Pro Asp Phe Asn Ala Gly Gly Thr Gly

```
                355                 360                 365
Ile Gly Ser Asn Ser Arg Ala Thr Thr Ala Lys Ser Ala Ala Val Ser
370                 375                 380
Tyr Ala Gly Ile Lys Asn Glu Met Cys Lys Asp Arg Ser Met Leu Cys
385                 390                 395                 400
Ala Gly Arg Asp Asp Val Ala Val Thr Asp Arg Asp Ala Lys Ile Asn
                405                 410                 415
Ala Pro Pro Asn Leu His Thr Gly Asp Phe Pro Asn Pro Asn Asp
        420                 425                 430
Ala Tyr Lys Asn Leu Ile Asn Leu Lys Pro Ala Ile Glu Ala Gly Tyr
        435                 440                 445
Thr Gly Arg Gly Val Glu Val Gly Ile Val Asp Thr Gly Glu Ser Val
        450                 455                 460
Gly Ser Ile Ser Phe Pro Glu Leu Tyr Gly Arg Lys Glu His Gly Tyr
465                 470                 475                 480
Asn Glu Asn Tyr Lys Asn Tyr Thr Ala Tyr Met Arg Lys Glu Ala Pro
                485                 490                 495
Glu Asp Gly Gly Gly Lys Asp Ile Glu Ala Ser Phe Asp Asp Glu Ala
                500                 505                 510
Val Ile Glu Thr Glu Ala Lys Pro Thr Asp Ile Arg His Val Lys Glu
        515                 520                 525
Ile Gly His Ile Asp Leu Val Ser His Ile Ile Gly Gly Arg Ser Val
        530                 535                 540
Asp Gly Arg Pro Ala Gly Gly Ile Ala Pro Asp Ala Thr Leu His Ile
545                 550                 555                 560
Met Asn Thr Asn Asp Glu Thr Lys Asn Glu Met Met Val Ala Ala Ile
                565                 570                 575
Arg Asn Ala Trp Val Lys Leu Gly Glu Arg Gly Val Arg Ile Val Asn
                580                 585                 590
Asn Ser Phe Gly Thr Thr Ser Arg Ala Gly Thr Ala Asp Leu Phe Gln
                595                 600                 605
Ile Ala Asn Ser Glu Glu Gln Tyr Arg Gln Ala Leu Leu Asp Tyr Ser
        610                 615                 620
Gly Gly Asp Lys Thr Asp Glu Gly Ile Arg Leu Met Gln Gln Ser Asp
625                 630                 635                 640
Tyr Gly Asn Leu Ser Tyr His Ile Arg Asn Lys Asn Met Leu Phe Ile
                645                 650                 655
Phe Ser Thr Gly Asn Asp Ala Gln Ala Gln Pro Asn Thr Tyr Ala Leu
                660                 665                 670
Leu Pro Phe Tyr Glu Lys Asp Ala Gln Lys Gly Ile Ile Thr Val Ala
        675                 680                 685
Gly Val Asp Arg Ser Gly Glu Lys Phe Lys Arg Glu Met Tyr Gly Glu
        690                 695                 700
Pro Gly Thr Glu Pro Leu Glu Tyr Gly Ser Asn His Cys Gly Ile Thr
705                 710                 715                 720
Ala Met Trp Cys Leu Ser Ala Pro Tyr Glu Ala Ser Val Arg Phe Thr
                725                 730                 735
Arg Thr Asn Pro Ile Gln Ile Ala Gly Thr Ser Phe Ser Ala Pro Ile
                740                 745                 750
Val Thr Gly Thr Ala Ala Leu Leu Leu Gln Lys Tyr Pro Trp Met Ser
        755                 760                 765
Asn Asp Asn Leu Arg Thr Thr Leu Leu Thr Thr Ala Gln Asp Ile Gly
        770                 775                 780
```

```
Ala Val Gly Val Asp Ser Lys Phe Gly Trp Gly Leu Leu Asp Ala Gly
785                 790                 795                 800
Lys Ala Met Asn Gly Pro Ala Ser Phe Pro Phe Gly Asp Phe Thr Ala
                805                 810                 815
Asp Thr Lys Gly Thr Ser Asp Ile Ala Tyr Ser Phe Arg Asn Asp Ile
            820                 825                 830
Ser Gly Thr Gly Gly Leu Ile Lys Lys Gly Gly Ser Gln Leu Gln Leu
        835                 840                 845
His Gly Asn Asn Thr Tyr Thr Gly Lys Thr Ile Ile Glu Gly Gly Ser
850                 855                 860
Leu Val Leu Tyr Gly Asn Asn Lys Ser Asp Met Arg Val Glu Thr Lys
865                 870                 875                 880
Gly Ala Leu Ile Tyr Asn Gly Ala Ala Ser Gly Gly Ser Leu Asn Ser
                885                 890                 895
Asp Gly Ile Val Tyr Leu Ala Asp Thr Asp Gln Ser Gly Ala Asn Glu
            900                 905                 910
Thr Val His Ile Lys Gly Ser Leu Gln Leu Asp Gly Lys Gly Thr Leu
        915                 920                 925
Tyr Thr Arg Leu Gly Lys Leu Leu Lys Val Asp Gly Thr Ala Ile Ile
930                 935                 940
Gly Gly Lys Leu Tyr Met Ser Ala Arg Gly Lys Gly Ala Gly Tyr Leu
945                 950                 955                 960
Asn Ser Thr Gly Arg Arg Val Pro Phe Leu Ser Ala Ala Lys Ile Gly
                965                 970                 975
Gln Asp Tyr Ser Phe Phe Thr Asn Ile Glu Thr Asp Gly Gly Leu Leu
            980                 985                 990
Ala Ser Leu Asp Ser Val Glu Lys Thr Ala Gly Ser Glu Gly Asp Thr
        995                 1000                1005
Leu Ser Tyr Tyr Val Arg Arg Gly Asn Ala Ala Arg Thr Ala Ser Ala
        1010                1015                1020
Ala Ala His Ser Ala Pro Ala Gly Leu Lys His Ala Val Glu Gln Gly
1025                1030                1035                1040
Gly Ser Asn Leu Glu Asn Leu Met Val Glu Leu Asp Ala Ser Glu Ser
                1045                1050                1055
Ser Ala Thr Pro Glu Thr Val Glu Thr Ala Ala Ala Asp Arg Thr Asp
            1060                1065                1070
Met Pro Gly Ile Arg Pro Tyr Gly Ala Thr Phe Arg Ala Ala Ala Ala
        1075                1080                1085
Val Gln His Ala Asn Ala Ala Asp Gly Val Arg Ile Phe Asn Ser Leu
        1090                1095                1100
Ala Ala Thr Val Tyr Ala Asp Ser Thr Ala His Ala Asp Met Gln
1105                1110                1115                1120
Gly Arg Arg Leu Lys Ala Val Ser Asp Gly Leu Asp His Asn Gly Thr
                1125                1130                1135
Gly Leu Arg Val Ile Ala Gln Thr Gln Gln Asp Gly Gly Thr Trp Glu
            1140                1145                1150
Gln Gly Gly Val Glu Gly Lys Met Arg Gly Ser Thr Gln Thr Val Gly
        1155                1160                1165
Ile Ala Ala Lys Thr Gly Glu Asn Thr Thr Ala Ala Ala Thr Leu Gly
        1170                1175                1180
Met Gly Arg Ser Thr Trp Ser Glu Asn Ser Ala Asn Ala Lys Thr Asp
1185                1190                1195                1200
```

-continued

```
Ser Ile Ser Leu Phe Ala Gly Ile Arg His Asp Ala Gly Asp Ile Gly
            1205                1210                1215
Tyr Leu Lys Gly Leu Phe Ser Tyr Gly Arg Tyr Lys Asn Ser Ile Ser
        1220                1225                1230
Arg Ser Thr Gly Ala Asp Glu His Ala Glu Gly Ser Val Asn Gly Thr
    1235                1240                1245
Leu Met Gln Leu Gly Ala Leu Gly Gly Val Asn Val Pro Phe Ala Ala
1250                1255                1260
Thr Gly Asp Leu Thr Val Glu Gly Gly Leu Arg Tyr Asp Leu Leu Lys
1265                1270                1275                1280
Gln Asp Ala Phe Ala Glu Lys Gly Ser Ala Leu Gly Trp Ser Gly Asn
            1285                1290                1295
Ser Leu Thr Glu Gly Thr Leu Val Gly Leu Ala Gly Leu Lys Leu Ser
        1300                1305                1310
Gln Pro Leu Ser Asp Lys Ala Val Leu Phe Ala Thr Ala Gly Val Glu
    1315                1320                1325
Arg Asp Leu Asn Gly Arg Asp Tyr Thr Val Thr Gly Gly Phe Thr Gly
    1330                1335                1340
Ala Thr Ala Ala Thr Gly Lys Thr Gly Ala Arg Asn Met Pro His Thr
1345                1350                1355                1360
Arg Leu Val Ala Gly Leu Gly Ala Asp Val Glu Phe Gly Asn Gly Trp
            1365                1370                1375
Asn Gly Leu Ala Arg Tyr Ser Tyr Ala Gly Ser Lys Gln Tyr Gly Asn
        1380                1385                1390
His Ser Gly Arg Val Gly Val Gly Tyr Arg Phe
    1395                1400

<210> SEQ ID NO 164
<211> LENGTH: 33
<212> TYPE: DNA
<213> ORGANISM: Artificial Sequence
<220> FEATURE:
<223> OTHER INFORMATION: Synthetic construct

<400> SEQUENCE: 164
cgcggatccg ctagcaaaac aaccgacaaa cgg                                33

<210> SEQ ID NO 165
<211> LENGTH: 27
<212> TYPE: DNA
<213> ORGANISM: Artificial Sequence
<220> FEATURE:
<223> OTHER INFORMATION: Synthetic construct

<400> SEQUENCE: 165
cccgctcgag ttaccagcgg tagccta                                      27

<210> SEQ ID NO 166
<211> LENGTH: 30
<212> TYPE: DNA
<213> ORGANISM: Artificial Sequence
<220> FEATURE:
<223> OTHER INFORMATION: Synthetic construct

<400> SEQUENCE: 166
ctagctagcg gacacactta tttcggcatc                                   30

<210> SEQ ID NO 167
<211> LENGTH: 32
<212> TYPE: DNA
```

<210> SEQ ID NO 168
<211> LENGTH: 10
<212> TYPE: DNA
<213> ORGANISM: Artificial Sequence
<220> FEATURE:
<223> OTHER INFORMATION: Synthetic construct

<400> SEQUENCE: 167
cccgctcgag ttaccagcgg tagcctaatt tg                          32

<210> SEQ ID NO 168
<211> LENGTH: 10
<212> TYPE: DNA
<213> ORGANISM: Artificial Sequence
<220> FEATURE:
<223> OTHER INFORMATION: Synthetic construct

<400> SEQUENCE: 168
cccgctcgag                                                    10

<210> SEQ ID NO 169
<211> LENGTH: 33
<212> TYPE: DNA
<213> ORGANISM: Artificial Sequence
<220> FEATURE:
<223> OTHER INFORMATION: Synthetic construct

<400> SEQUENCE: 169
cgcggatccc atatgaaaac cttcttcaaa acc                          33

<210> SEQ ID NO 170
<211> LENGTH: 28
<212> TYPE: DNA
<213> ORGANISM: Artificial Sequence
<220> FEATURE:
<223> OTHER INFORMATION: Synthetic construct

<400> SEQUENCE: 170
cccgctcgag ttatttggct gcgccttc                                28

<210> SEQ ID NO 171
<211> LENGTH: 35
<212> TYPE: DNA
<213> ORGANISM: Artificial Sequence
<220> FEATURE:
<223> OTHER INFORMATION: Synthetic construct

<400> SEQUENCE: 171
gcggcattaa tatgttgaga aaattgttga aatgg                        35

<210> SEQ ID NO 172
<211> LENGTH: 34
<212> TYPE: DNA
<213> ORGANISM: Artificial Sequence
<220> FEATURE:
<223> OTHER INFORMATION: Synthetic construct

<400> SEQUENCE: 172
gcggcctcga gttatttttt caaaatatat ttgc                         34

<210> SEQ ID NO 173
<211> LENGTH: 33
<212> TYPE: DNA
<213> ORGANISM: Artificial Sequence
<220> FEATURE:
<223> OTHER INFORMATION: Synthetic construct

<400> SEQUENCE: 173
gcggccatat gttacctaac cgtttcaaaa tgt                          33

<210> SEQ ID NO 174
<211> LENGTH: 31
<212> TYPE: DNA
<213> ORGANISM: Artificial Sequence
<220> FEATURE:
<223> OTHER INFORMATION: Synthetic construct

<400> SEQUENCE: 174
gcggcctcga gttatttccg aggttttcgg g                           31

<210> SEQ ID NO 175
<211> LENGTH: 32
<212> TYPE: DNA
<213> ORGANISM: Artificial Sequence
<220> FEATURE:
<223> OTHER INFORMATION: Synthetic construct

<400> SEQUENCE: 175
cgcggatccc atatgacacg cttcaaatat tc                          32

<210> SEQ ID NO 176
<211> LENGTH: 31
<212> TYPE: DNA
<213> ORGANISM: Artificial Sequence
<220> FEATURE:
<223> OTHER INFORMATION: Synthetic construct

<400> SEQUENCE: 176
cccgctcgag ttatttaaac cgataggtaa a                           31

<210> SEQ ID NO 177
<211> LENGTH: 31
<212> TYPE: DNA
<213> ORGANISM: Artificial Sequence
<220> FEATURE:
<223> OTHER INFORMATION: Synthetic construct

<400> SEQUENCE: 177
cgcggatccc atatgggcag ggaagaaccg c                           31

<210> SEQ ID NO 178
<211> LENGTH: 28
<212> TYPE: DNA
<213> ORGANISM: Artificial Sequence
<220> FEATURE:
<223> OTHER INFORMATION: Synthetic construct

<400> SEQUENCE: 178
gcccaagctt atcgatggaa tagccgcg                               28

<210> SEQ ID NO 179
<211> LENGTH: 32
<212> TYPE: DNA
<213> ORGANISM: Artificial Sequence
<220> FEATURE:
<223> OTHER INFORMATION: Synthetic construct

<400> SEQUENCE: 179
cgcggatccg ctagcaacgg tttggatgcc cg                          32

<210> SEQ ID NO 180
<211> LENGTH: 30
<212> TYPE: DNA
<213> ORGANISM: Artificial Sequence
<220> FEATURE:

<223> OTHER INFORMATION: Synthetic construct

<400> SEQUENCE: 180
cccgctcgag tttgtctaag ttcctgatat                                    30

<210> SEQ ID NO 181
<211> LENGTH: 26
<212> TYPE: DNA
<213> ORGANISM: Artificial Sequence
<220> FEATURE:
<223> OTHER INFORMATION: Synthetic construct

<400> SEQUENCE: 181
cccgctcgag attcccacct gccatc                                        26

<210> SEQ ID NO 182
<211> LENGTH: 37
<212> TYPE: DNA
<213> ORGANISM: Artificial Sequence
<220> FEATURE:
<223> OTHER INFORMATION: Synthetic construct

<400> SEQUENCE: 182
cgcggatccg ctagcatgaa tttgcctatt caaaaat                            37

<210> SEQ ID NO 183
<211> LENGTH: 29
<212> TYPE: DNA
<213> ORGANISM: Artificial Sequence
<220> FEATURE:
<223> OTHER INFORMATION: Synthetic construct

<400> SEQUENCE: 183
cccgctcgag ttaattccca cctgccatc                                     29

<210> SEQ ID NO 184
<211> LENGTH: 37
<212> TYPE: DNA
<213> ORGANISM: Artificial Sequence
<220> FEATURE:
<223> OTHER INFORMATION: Synthetic construct

<400> SEQUENCE: 184
cgcggatccg ctagcatgaa tttgcctatt caaaaat                            37

<210> SEQ ID NO 185
<211> LENGTH: 27
<212> TYPE: DNA
<213> ORGANISM: Artificial Sequence
<220> FEATURE:
<223> OTHER INFORMATION: Synthetic construct

<400> SEQUENCE: 185
cccgctcgag ttggacgatg cccgcga                                       27

<210> SEQ ID NO 186
<211> LENGTH: 37
<212> TYPE: DNA
<213> ORGANISM: Artificial Sequence
<220> FEATURE:
<223> OTHER INFORMATION: Synthetic construct

<400> SEQUENCE: 186
cgcggatccg ctagcatgaa tttgcctatt caaaaat                            37

```
<210> SEQ ID NO 187
<211> LENGTH: 28
<212> TYPE: DNA
<213> ORGANISM: Artificial Sequence
<220> FEATURE:
<223> OTHER INFORMATION: Synthetic construct

<400> SEQUENCE: 187
cccgctcgag ttattggacg atgcccgc                                    28

<210> SEQ ID NO 188
<211> LENGTH: 32
<212> TYPE: DNA
<213> ORGANISM: Artificial Sequence
<220> FEATURE:
<223> OTHER INFORMATION: Synthetic construct

<400> SEQUENCE: 188
cgcggatccc atatgtatcg caaactgatt gc                               32

<210> SEQ ID NO 189
<211> LENGTH: 28
<212> TYPE: DNA
<213> ORGANISM: Artificial Sequence
<220> FEATURE:
<223> OTHER INFORMATION: Synthetic construct

<400> SEQUENCE: 189
cccgctcgag ctaatcgatg gaatagcc                                    28

<210> SEQ ID NO 190
<211> LENGTH: 32
<212> TYPE: DNA
<213> ORGANISM: Artificial Sequence
<220> FEATURE:
<223> OTHER INFORMATION: Synthetic construct

<400> SEQUENCE: 190
cgcggatccc atatgaaaca gacagtcaaa tg                               32

<210> SEQ ID NO 191
<211> LENGTH: 28
<212> TYPE: DNA
<213> ORGANISM: Artificial Sequence
<220> FEATURE:
<223> OTHER INFORMATION: Synthetic construct

<400> SEQUENCE: 191
cccgctcgag tcaataaccc gccttcag                                    28

<210> SEQ ID NO 192
<211> LENGTH: 45
<212> TYPE: DNA
<213> ORGANISM: Artificial Sequence
<220> FEATURE:
<223> OTHER INFORMATION: Synthetic construct

<400> SEQUENCE: 192
cgcggatccc atatgttacg tttgactgct ttagccgtat gcacc                 45

<210> SEQ ID NO 193
<211> LENGTH: 40
<212> TYPE: DNA
<213> ORGANISM: Artificial Sequence
<220> FEATURE:
<223> OTHER INFORMATION: Synthetic construct
```

<400> SEQUENCE: 193
cccgctcgag ttattttgcc gcgttaaaag cgtcggcaac　　　　　　　　　　40

<210> SEQ ID NO 194
<211> LENGTH: 32
<212> TYPE: DNA
<213> ORGANISM: Artificial Sequence
<220> FEATURE:
<223> OTHER INFORMATION: Synthetic construct

<400> SEQUENCE: 194
cgcggatccc atatgaacaa aatataccgc at　　　　　　　　　　　　　　32

<210> SEQ ID NO 195
<211> LENGTH: 28
<212> TYPE: DNA
<213> ORGANISM: Artificial Sequence
<220> FEATURE:
<223> OTHER INFORMATION: Synthetic construct

<400> SEQUENCE: 195
cccgctcgag ttaccactga taaccgac　　　　　　　　　　　　　　　　28

<210> SEQ ID NO 196
<211> LENGTH: 34
<212> TYPE: DNA
<213> ORGANISM: Artificial Sequence
<220> FEATURE:
<223> OTHER INFORMATION: Synthetic construct

<400> SEQUENCE: 196
cgcggatccc atatgaccga tgacgacgat ttat　　　　　　　　　　　　　34

<210> SEQ ID NO 197
<211> LENGTH: 28
<212> TYPE: DNA
<213> ORGANISM: Artificial Sequence
<220> FEATURE:
<223> OTHER INFORMATION: Synthetic construct

<400> SEQUENCE: 197
gcccaagctt ccactgataa ccgacaga　　　　　　　　　　　　　　　　28

<210> SEQ ID NO 198
<211> LENGTH: 32
<212> TYPE: DNA
<213> ORGANISM: Artificial Sequence
<220> FEATURE:
<223> OTHER INFORMATION: Synthetic construct

<400> SEQUENCE: 198
cgcggatccc atatgaacaa aatataccgc at　　　　　　　　　　　　　　32

<210> SEQ ID NO 199
<211> LENGTH: 28
<212> TYPE: DNA
<213> ORGANISM: Artificial Sequence
<220> FEATURE:
<223> OTHER INFORMATION: Synthetic construct

<400> SEQUENCE: 199
gcccaagctt ttaccactga taaccgac　　　　　　　　　　　　　　　　28

<210> SEQ ID NO 200
<211> LENGTH: 34

<212> TYPE: DNA
<213> ORGANISM: Artificial Sequence
<220> FEATURE:
<223> OTHER INFORMATION: Synthetic construct

<400> SEQUENCE: 200
gggaattcca tatgggcatt tcccgcaaaa tatc                                    34

<210> SEQ ID NO 201
<211> LENGTH: 40
<212> TYPE: DNA
<213> ORGANISM: Artificial Sequence
<220> FEATURE:
<223> OTHER INFORMATION: Synthetic construct

<400> SEQUENCE: 201
cccgctcgag ttatttactc ctataacgag gtctcttaac                              40

<210> SEQ ID NO 202
<211> LENGTH: 36
<212> TYPE: DNA
<213> ORGANISM: Artificial Sequence
<220> FEATURE:
<223> OTHER INFORMATION: Synthetic construct

<400> SEQUENCE: 202
gggaattcca tatgtcagat ttggcaaacg attctt                                  36

<210> SEQ ID NO 203
<211> LENGTH: 40
<212> TYPE: DNA
<213> ORGANISM: Artificial Sequence
<220> FEATURE:
<223> OTHER INFORMATION: Synthetic construct

<400> SEQUENCE: 203
cccgctcgag ttatttactc ctataacgag gtctcttaac                              40

<210> SEQ ID NO 204
<211> LENGTH: 34
<212> TYPE: DNA
<213> ORGANISM: Artificial Sequence
<220> FEATURE:
<223> OTHER INFORMATION: Synthetic construct

<400> SEQUENCE: 204
gggaattcca tatgggcatt tcccgcaaaa tatc                                    34

<210> SEQ ID NO 205
<211> LENGTH: 32
<212> TYPE: DNA
<213> ORGANISM: Artificial Sequence
<220> FEATURE:
<223> OTHER INFORMATION: Synthetic construct

<400> SEQUENCE: 205
cccgctcgag ttacgtatca tatttcacgt gc                                      32

<210> SEQ ID NO 206
<211> LENGTH: 35
<212> TYPE: DNA
<213> ORGANISM: Artificial Sequence
<220> FEATURE:
<223> OTHER INFORMATION: Synthetic construct

<400> SEQUENCE: 206

```
gggaattcca tatgcacgtg aaatatgata cgaag                                    35
```

<210> SEQ ID NO 207
<211> LENGTH: 37
<212> TYPE: DNA
<213> ORGANISM: Artificial Sequence
<220> FEATURE:
<223> OTHER INFORMATION: Synthetic construct

<400> SEQUENCE: 207

```
cccgctcgag tttactccta taacgaggtc tcttaac                                  37
```

<210> SEQ ID NO 208
<211> LENGTH: 36
<212> TYPE: DNA
<213> ORGANISM: Artificial Sequence
<220> FEATURE:
<223> OTHER INFORMATION: Synthetic construct

<400> SEQUENCE: 208

```
gggaattcca tatgtcagat ttggcaaacg attctt                                   36
```

<210> SEQ ID NO 209
<211> LENGTH: 29
<212> TYPE: DNA
<213> ORGANISM: Artificial Sequence
<220> FEATURE:
<223> OTHER INFORMATION: Synthetic construct

<400> SEQUENCE: 209

```
cccgctcgag cgtatcatat ttcacgtgc                                           29
```

<210> SEQ ID NO 210
<211> LENGTH: 36
<212> TYPE: DNA
<213> ORGANISM: Artificial Sequence
<220> FEATURE:
<223> OTHER INFORMATION: Synthetic construct

<400> SEQUENCE: 210

```
gggaattcca tatgtcagat ttggcaaacg attctt                                   36
```

<210> SEQ ID NO 211
<211> LENGTH: 37
<212> TYPE: DNA
<213> ORGANISM: Artificial Sequence
<220> FEATURE:
<223> OTHER INFORMATION: Synthetic construct

<400> SEQUENCE: 211

```
cccgctcgag tttactccta taacgaggtc tcttaac                                  37
```

<210> SEQ ID NO 212
<211> LENGTH: 35
<212> TYPE: DNA
<213> ORGANISM: Artificial Sequence
<220> FEATURE:
<223> OTHER INFORMATION: Synthetic construct

<400> SEQUENCE: 212

```
cgcggatccc atatgcaaaa tgcgttcaaa atccc                                    35
```

<210> SEQ ID NO 213
<211> LENGTH: 32
<212> TYPE: DNA
<213> ORGANISM: Artificial Sequence

```
<220> FEATURE:
<223> OTHER INFORMATION: Synthetic construct

<400> SEQUENCE: 213
cgcggatccc atatgaacaa aatataccgc at                                 32

<210> SEQ ID NO 214
<211> LENGTH: 29
<212> TYPE: DNA
<213> ORGANISM: Artificial Sequence
<220> FEATURE:
<223> OTHER INFORMATION: Synthetic construct

<400> SEQUENCE: 214
cccgctcgag tttgctttcg atagaacgg                                     29

<210> SEQ ID NO 215
<211> LENGTH: 34
<212> TYPE: DNA
<213> ORGANISM: Artificial Sequence
<220> FEATURE:
<223> OTHER INFORMATION: Synthetic construct

<400> SEQUENCE: 215
gcggccatat ggtcataaaa tatacaaatt tgaa                               34

<210> SEQ ID NO 216
<211> LENGTH: 34
<212> TYPE: DNA
<213> ORGANISM: Artificial Sequence
<220> FEATURE:
<223> OTHER INFORMATION: Synthetic construct

<400> SEQUENCE: 216
gcggcctcga gttagcctga gacctttgca aatt                               34

<210> SEQ ID NO 217
<211> LENGTH: 30
<212> TYPE: DNA
<213> ORGANISM: Artificial Sequence
<220> FEATURE:
<223> OTHER INFORMATION: Synthetic construct

<400> SEQUENCE: 217
gcggccatat gaaacagaaa aaaaccgctg                                    30

<210> SEQ ID NO 218
<211> LENGTH: 32
<212> TYPE: DNA
<213> ORGANISM: Artificial Sequence
<220> FEATURE:
<223> OTHER INFORMATION: Synthetic construct

<400> SEQUENCE: 218
gcggcctcga gttacggttt gacaccgttt tc                                 32

<210> SEQ ID NO 219
<211> LENGTH: 30
<212> TYPE: DNA
<213> ORGANISM: Artificial Sequence
<220> FEATURE:
<223> OTHER INFORMATION: Synthetic construct

<400> SEQUENCE: 219
cgcggatccc atatgaaaac cctgctcctc                                    30
```

<210> SEQ ID NO 220
<211> LENGTH: 27
<212> TYPE: DNA
<213> ORGANISM: Artificial Sequence
<220> FEATURE:
<223> OTHER INFORMATION: Synthetic construct

<400> SEQUENCE: 220
cccgctcgag ttatcctcct ttgcggc                                27

<210> SEQ ID NO 221
<211> LENGTH: 30
<212> TYPE: DNA
<213> ORGANISM: Artificial Sequence
<220> FEATURE:
<223> OTHER INFORMATION: Synthetic construct

<400> SEQUENCE: 221
gcggccatat ggcaaaaatg atgaaatggg                             30

<210> SEQ ID NO 222
<211> LENGTH: 29
<212> TYPE: DNA
<213> ORGANISM: Artificial Sequence
<220> FEATURE:
<223> OTHER INFORMATION: Synthetic construct

<400> SEQUENCE: 222
gcggcctcga gttatcggcg cggcgggcc                              29

<210> SEQ ID NO 223
<211> LENGTH: 30
<212> TYPE: DNA
<213> ORGANISM: Artificial Sequence
<220> FEATURE:
<223> OTHER INFORMATION: Synthetic construct

<400> SEQUENCE: 223
gcggccatat gaaaaaatcc tccctcatca                             30

<210> SEQ ID NO 224
<211> LENGTH: 32
<212> TYPE: DNA
<213> ORGANISM: Artificial Sequence
<220> FEATURE:
<223> OTHER INFORMATION: Synthetic construct

<400> SEQUENCE: 224
gcggcctcga gttatttgcc gccgtttttg gc                          32

<210> SEQ ID NO 225
<211> LENGTH: 31
<212> TYPE: DNA
<213> ORGANISM: Artificial Sequence
<220> FEATURE:
<223> OTHER INFORMATION: Synthetic construct

<400> SEQUENCE: 225
gcggccatat ggcccctgcc gacgcggtaa g                           31

<210> SEQ ID NO 226
<211> LENGTH: 33
<212> TYPE: DNA
<213> ORGANISM: Artificial Sequence
<220> FEATURE:
<223> OTHER INFORMATION: Synthetic construct

<400> SEQUENCE: 226
gcggcctcga gtttgccgcc gtttttggct ttc                                33

<210> SEQ ID NO 227
<211> LENGTH: 30
<212> TYPE: DNA
<213> ORGANISM: Artificial Sequence
<220> FEATURE:
<223> OTHER INFORMATION: Synthetic construct

<400> SEQUENCE: 227
gcggccatat gaaacacata ctcccccctga                                   30

<210> SEQ ID NO 228
<211> LENGTH: 32
<212> TYPE: DNA
<213> ORGANISM: Artificial Sequence
<220> FEATURE:
<223> OTHER INFORMATION: Synthetic construct

<400> SEQUENCE: 228
gcggcctcga gttattcgcc tacggttttt tg                                 32

<210> SEQ ID NO 229
<211> LENGTH: 30
<212> TYPE: DNA
<213> ORGANISM: Artificial Sequence
<220> FEATURE:
<223> OTHER INFORMATION: Synthetic construct

<400> SEQUENCE: 229
gcggccatat gatttacatc gtactgtttc                                    30

<210> SEQ ID NO 230
<211> LENGTH: 32
<212> TYPE: DNA
<213> ORGANISM: Artificial Sequence
<220> FEATURE:
<223> OTHER INFORMATION: Synthetic construct

<400> SEQUENCE: 230
gcggcctcga gttaggagaa caggcgcaat gc                                 32

<210> SEQ ID NO 231
<211> LENGTH: 32
<212> TYPE: DNA
<213> ORGANISM: Artificial Sequence
<220> FEATURE:
<223> OTHER INFORMATION: Synthetic construct

<400> SEQUENCE: 231
gcggccatat gtacaacatg tatcaggaaa ac                                 32

<210> SEQ ID NO 232
<211> LENGTH: 31
<212> TYPE: DNA
<213> ORGANISM: Artificial Sequence
<220> FEATURE:
<223> OTHER INFORMATION: Synthetic construct

<400> SEQUENCE: 232
gcggcctcga gggagaacag gcgcaatgcg g                                  31

<210> SEQ ID NO 233

```
<210> SEQ ID NO 233
<211> LENGTH: 29
<212> TYPE: DNA
<213> ORGANISM: Artificial Sequence
<220> FEATURE:
<223> OTHER INFORMATION: Synthetic construct

<400> SEQUENCE: 233
cgcggatccg ctagctgcgg cacggcggg                                29

<210> SEQ ID NO 234
<211> LENGTH: 28
<212> TYPE: DNA
<213> ORGANISM: Artificial Sequence
<220> FEATURE:
<223> OTHER INFORMATION: Synthetic construct

<400> SEQUENCE: 234
cccgctcgag ataacggtat gccgccag                                 28

<210> SEQ ID NO 235
<211> LENGTH: 31
<212> TYPE: DNA
<213> ORGANISM: Artificial Sequence
<220> FEATURE:
<223> OTHER INFORMATION: Synthetic construct

<400> SEQUENCE: 235
cgcggatccc atatggaatc aacactttca c                             31

<210> SEQ ID NO 236
<211> LENGTH: 27
<212> TYPE: DNA
<213> ORGANISM: Artificial Sequence
<220> FEATURE:
<223> OTHER INFORMATION: Synthetic construct

<400> SEQUENCE: 236
cccgctcgag ttacacgcgg ttgctgt                                  27

<210> SEQ ID NO 237
<211> LENGTH: 31
<212> TYPE: DNA
<213> ORGANISM: Artificial Sequence
<220> FEATURE:
<223> OTHER INFORMATION: Synthetic construct

<400> SEQUENCE: 237
cgcggatccc atatgaacaa cagacatttt g                             31

<210> SEQ ID NO 238
<211> LENGTH: 28
<212> TYPE: DNA
<213> ORGANISM: Artificial Sequence
<220> FEATURE:
<223> OTHER INFORMATION: Synthetic construct

<400> SEQUENCE: 238
cccgctcgag ttacctgtcc ggtaaaag                                 28

<210> SEQ ID NO 239
<211> LENGTH: 33
<212> TYPE: DNA
<213> ORGANISM: Artificial Sequence
<220> FEATURE:
<223> OTHER INFORMATION: Synthetic construct

<400> SEQUENCE: 239
```
cgcggatccg ctagcaccgt catcaaacag gaa                                         33

<210> SEQ ID NO 240
<211> LENGTH: 27
<212> TYPE: DNA
<213> ORGANISM: Artificial Sequence
<220> FEATURE:
<223> OTHER INFORMATION: Synthetic construct

<400> SEQUENCE: 240
cccgctcgag tcaagattcg acgggga                                                27

<210> SEQ ID NO 241
<211> LENGTH: 31
<212> TYPE: DNA
<213> ORGANISM: Artificial Sequence
<220> FEATURE:
<223> OTHER INFORMATION: Synthetic construct

<400> SEQUENCE: 241
cgcggatccc atatgtccgc aaacgaatac g                                           31

<210> SEQ ID NO 242
<211> LENGTH: 28
<212> TYPE: DNA
<213> ORGANISM: Artificial Sequence
<220> FEATURE:
<223> OTHER INFORMATION: Synthetic construct

<400> SEQUENCE: 242
cccgctcgag tcagtgttct gccagttt                                               28

<210> SEQ ID NO 243
<211> LENGTH: 29
<212> TYPE: DNA
<213> ORGANISM: Artificial Sequence
<220> FEATURE:
<223> OTHER INFORMATION: Synthetic construct

<400> SEQUENCE: 243
cgcggatccc atatgccgtc tgaaacacg                                              29

<210> SEQ ID NO 244
<211> LENGTH: 28
<212> TYPE: DNA
<213> ORGANISM: Artificial Sequence
<220> FEATURE:
<223> OTHER INFORMATION: Synthetic construct

<400> SEQUENCE: 244
cccgctcgag ttagcggagc agttttc                                                28

<210> SEQ ID NO 245
<211> LENGTH: 28
<212> TYPE: DNA
<213> ORGANISM: Artificial Sequence
<220> FEATURE:
<223> OTHER INFORMATION: Synthetic construct

<400> SEQUENCE: 245
cgcggatccc atatgaccgc catcagcc                                               28

<210> SEQ ID NO 246
<211> LENGTH: 27
<212> TYPE: DNA

<213> ORGANISM: Artificial Sequence
<220> FEATURE:
<223> OTHER INFORMATION: Synthetic construct

<400> SEQUENCE: 246
cccgctcgag ttaaagccgg gtaacgc                                27

<210> SEQ ID NO 247
<211> LENGTH: 31
<212> TYPE: DNA
<213> ORGANISM: Artificial Sequence
<220> FEATURE:
<223> OTHER INFORMATION: Synthetic construct

<400> SEQUENCE: 247
gcggccatat ggaaacacag ctttacatcg g                           31

<210> SEQ ID NO 248
<211> LENGTH: 30
<212> TYPE: DNA
<213> ORGANISM: Artificial Sequence
<220> FEATURE:
<223> OTHER INFORMATION: Synthetic construct

<400> SEQUENCE: 248
gcggcctcga gtcaataata atatcccgcg                             30

<210> SEQ ID NO 249
<211> LENGTH: 30
<212> TYPE: DNA
<213> ORGANISM: Artificial Sequence
<220> FEATURE:
<223> OTHER INFORMATION: Synthetic construct

<400> SEQUENCE: 249
gcggccatat gattaaaatc cgcaatatcc                             30

<210> SEQ ID NO 250
<211> LENGTH: 36
<212> TYPE: DNA
<213> ORGANISM: Artificial Sequence
<220> FEATURE:
<223> OTHER INFORMATION: Synthetic construct

<400> SEQUENCE: 250
gcggcctcga gttaaatctt ggtagattgg atttgg                      36

<210> SEQ ID NO 251
<211> LENGTH: 30
<212> TYPE: DNA
<213> ORGANISM: Artificial Sequence
<220> FEATURE:
<223> OTHER INFORMATION: Synthetic construct

<400> SEQUENCE: 251
gcggccatat gactgacaac gcactgctcc                             30

<210> SEQ ID NO 252
<211> LENGTH: 31
<212> TYPE: DNA
<213> ORGANISM: Artificial Sequence
<220> FEATURE:
<223> OTHER INFORMATION: Synthetic construct

<400> SEQUENCE: 252
gcggcctcga gtcagaccgc gttgtcgaaa c                           31

<210> SEQ ID NO 253
<211> LENGTH: 32
<212> TYPE: DNA
<213> ORGANISM: Artificial Sequence
<220> FEATURE:
<223> OTHER INFORMATION: Synthetic construct

<400> SEQUENCE: 253
cgcggatccc atatggcgtt aaaaacatca aa                          32

<210> SEQ ID NO 254
<211> LENGTH: 27
<212> TYPE: DNA
<213> ORGANISM: Artificial Sequence
<220> FEATURE:
<223> OTHER INFORMATION: Synthetic construct

<400> SEQUENCE: 254
cccgctcgag tcagcccttc atacagc                                27

<210> SEQ ID NO 255
<211> LENGTH: 32
<212> TYPE: DNA
<213> ORGANISM: Artificial Sequence
<220> FEATURE:
<223> OTHER INFORMATION: Synthetic construct

<400> SEQUENCE: 255
gcggcattaa tggcacaaac tacactcaaa cc                          32

<210> SEQ ID NO 256
<211> LENGTH: 33
<212> TYPE: DNA
<213> ORGANISM: Artificial Sequence
<220> FEATURE:
<223> OTHER INFORMATION: Synthetic construct

<400> SEQUENCE: 256
gcggcctcga gttaaaactt cacgttcacg ccg                         33

<210> SEQ ID NO 257
<211> LENGTH: 34
<212> TYPE: DNA
<213> ORGANISM: Artificial Sequence
<220> FEATURE:
<223> OTHER INFORMATION: Synthetic construct

<400> SEQUENCE: 257
gcggcattaa tgcatgaaac tgagcaatcg gtgg                        34

<210> SEQ ID NO 258
<211> LENGTH: 38
<212> TYPE: DNA
<213> ORGANISM: Artificial Sequence
<220> FEATURE:
<223> OTHER INFORMATION: Synthetic construct

<400> SEQUENCE: 258
gcggcctcga gaaacttcac gttcacgccg ccggtaaa                    38

<210> SEQ ID NO 259
<211> LENGTH: 33
<212> TYPE: DNA
<213> ORGANISM: Artificial Sequence
<220> FEATURE:

<223> OTHER INFORMATION: Synthetic construct

<400> SEQUENCE: 259
cgcggatccc atatgggcaa atccgaaaat acg        33

<210> SEQ ID NO 260
<211> LENGTH: 26
<212> TYPE: DNA
<213> ORGANISM: Artificial Sequence
<220> FEATURE:
<223> OTHER INFORMATION: Synthetic construct

<400> SEQUENCE: 260
cccgctcgag ataatggcgg cggcgg        26

<210> SEQ ID NO 261
<211> LENGTH: 29
<212> TYPE: DNA
<213> ORGANISM: Artificial Sequence
<220> FEATURE:
<223> OTHER INFORMATION: Synthetic construct

<400> SEQUENCE: 261
cgcggatccc atatgtttcc ccccgacaa        29

<210> SEQ ID NO 262
<211> LENGTH: 31
<212> TYPE: DNA
<213> ORGANISM: Artificial Sequence
<220> FEATURE:
<223> OTHER INFORMATION: Synthetic construct

<400> SEQUENCE: 262
cccgctcgag tcattctgta aaaaagtat g        31

<210> SEQ ID NO 263
<211> LENGTH: 32
<212> TYPE: DNA
<213> ORGANISM: Artificial Sequence
<220> FEATURE:
<223> OTHER INFORMATION: Synthetic construct

<400> SEQUENCE: 263
cgcggatccc atatgcttca aagcgacagc ag        32

<210> SEQ ID NO 264
<211> LENGTH: 29
<212> TYPE: DNA
<213> ORGANISM: Artificial Sequence
<220> FEATURE:
<223> OTHER INFORMATION: Synthetic construct

<400> SEQUENCE: 264
cccgctcgag ttcggatttt tgcgtactc        29

<210> SEQ ID NO 265
<211> LENGTH: 31
<212> TYPE: DNA
<213> ORGANISM: Artificial Sequence
<220> FEATURE:
<223> OTHER INFORMATION: Synthetic construct

<400> SEQUENCE: 265
cgcggatccc atatggcaat ggcagaaaac g        31

```
<210> SEQ ID NO 266
<211> LENGTH: 27
<212> TYPE: DNA
<213> ORGANISM: Artificial Sequence
<220> FEATURE:
<223> OTHER INFORMATION: Synthetic construct

<400> SEQUENCE: 266
cccgctcgag ctatacaatc cgtgccg                                         27

<210> SEQ ID NO 267
<211> LENGTH: 32
<212> TYPE: DNA
<213> ORGANISM: Artificial Sequence
<220> FEATURE:
<223> OTHER INFORMATION: Synthetic construct

<400> SEQUENCE: 267
cgcggatccc atatggattc tttttcaaa cc                                    32

<210> SEQ ID NO 268
<211> LENGTH: 27
<212> TYPE: DNA
<213> ORGANISM: Artificial Sequence
<220> FEATURE:
<223> OTHER INFORMATION: Synthetic construct

<400> SEQUENCE: 268
cccgctcgag tcagttcaga aagcggg                                         27

<210> SEQ ID NO 269
<211> LENGTH: 32
<212> TYPE: DNA
<213> ORGANISM: Artificial Sequence
<220> FEATURE:
<223> OTHER INFORMATION: Synthetic construct

<400> SEQUENCE: 269
cgcggatccc atatgaaacc tttgatttta gg                                   32

<210> SEQ ID NO 270
<211> LENGTH: 28
<212> TYPE: DNA
<213> ORGANISM: Artificial Sequence
<220> FEATURE:
<223> OTHER INFORMATION: Synthetic construct

<400> SEQUENCE: 270
cccgctcgag ttatttgggc tgctcttc                                        28

<210> SEQ ID NO 271
<211> LENGTH: 30
<212> TYPE: DNA
<213> ORGANISM: Artificial Sequence
<220> FEATURE:
<223> OTHER INFORMATION: Synthetic construct

<400> SEQUENCE: 271
cgcggatccc atatggtaat cgtctggttg                                      30

<210> SEQ ID NO 272
<211> LENGTH: 27
<212> TYPE: DNA
<213> ORGANISM: Artificial Sequence
<220> FEATURE:
<223> OTHER INFORMATION: Synthetic construct
```

<400> SEQUENCE: 272
cccgctcgag ctacgacttg gttaccg                                      27

<210> SEQ ID NO 273
<211> LENGTH: 33
<212> TYPE: DNA
<213> ORGANISM: Artificial Sequence
<220> FEATURE:
<223> OTHER INFORMATION: Synthetic construct

<400> SEQUENCE: 273
gcggccatat gagacgtaaa atgctaaagc tac                               33

<210> SEQ ID NO 274
<211> LENGTH: 31
<212> TYPE: DNA
<213> ORGANISM: Artificial Sequence
<220> FEATURE:
<223> OTHER INFORMATION: Synthetic construct

<400> SEQUENCE: 274
gcggcctcga gtcaaagtgt tctgtttgcg c                                 31

<210> SEQ ID NO 275
<211> LENGTH: 30
<212> TYPE: DNA
<213> ORGANISM: Artificial Sequence
<220> FEATURE:
<223> OTHER INFORMATION: Synthetic construct

<400> SEQUENCE: 275
gccgccatat gttgacttta acccgaaaaa                                   30

<210> SEQ ID NO 276
<211> LENGTH: 34
<212> TYPE: DNA
<213> ORGANISM: Artificial Sequence
<220> FEATURE:
<223> OTHER INFORMATION: Synthetic construct

<400> SEQUENCE: 276
gccgcctcga ggccggcggt caataccgcc cgaa                              34

<210> SEQ ID NO 277
<211> LENGTH: 32
<212> TYPE: DNA
<213> ORGANISM: Artificial Sequence
<220> FEATURE:
<223> OTHER INFORMATION: Synthetic construct

<400> SEQUENCE: 277
cgcggatccc atatggcgca atgcgatttg ac                                32

<210> SEQ ID NO 278
<211> LENGTH: 27
<212> TYPE: DNA
<213> ORGANISM: Artificial Sequence
<220> FEATURE:
<223> OTHER INFORMATION: Synthetic construct

<400> SEQUENCE: 278
cccgctcgag ttcggcggta aatgccg                                      27

<210> SEQ ID NO 279
<211> LENGTH: 28

```
<212> TYPE: DNA
<213> ORGANISM: Artificial Sequence
<220> FEATURE:
<223> OTHER INFORMATION: Synthetic construct

<400> SEQUENCE: 279
gcggccatat ggcggggccg attttttgt                                            28

<210> SEQ ID NO 280
<211> LENGTH: 33
<212> TYPE: DNA
<213> ORGANISM: Artificial Sequence
<220> FEATURE:
<223> OTHER INFORMATION: Synthetic construct

<400> SEQUENCE: 280
gcggcctcga gttatttgct ttcagtatta ttg                                       33

<210> SEQ ID NO 281
<211> LENGTH: 30
<212> TYPE: DNA
<213> ORGANISM: Artificial Sequence
<220> FEATURE:
<223> OTHER INFORMATION: Synthetic construct

<400> SEQUENCE: 281
gcggccatat gaactttgct ttatccgtca                                           30

<210> SEQ ID NO 282
<211> LENGTH: 32
<212> TYPE: DNA
<213> ORGANISM: Artificial Sequence
<220> FEATURE:
<223> OTHER INFORMATION: Synthetic construct

<400> SEQUENCE: 282
gcggcctcga gttaacggca gtatttgttt ac                                        32

<210> SEQ ID NO 283
<211> LENGTH: 31
<212> TYPE: DNA
<213> ORGANISM: Artificial Sequence
<220> FEATURE:
<223> OTHER INFORMATION: Synthetic construct

<400> SEQUENCE: 283
cgcggatccc atatgggttt gcgcttcggg c                                         31

<210> SEQ ID NO 284
<211> LENGTH: 29
<212> TYPE: DNA
<213> ORGANISM: Artificial Sequence
<220> FEATURE:
<223> OTHER INFORMATION: Synthetic construct

<400> SEQUENCE: 284
gcccaagctt ttttcctttg ccgtttccg                                            29

<210> SEQ ID NO 285
<211> LENGTH: 32
<212> TYPE: DNA
<213> ORGANISM: Artificial Sequence
<220> FEATURE:
<223> OTHER INFORMATION: Synthetic construct

<400> SEQUENCE: 285
```

```
cgcggatccc atatggccga cctttccgaa aa                                    32
```

<210> SEQ ID NO 286
<211> LENGTH: 27
<212> TYPE: DNA
<213> ORGANISM: Artificial Sequence
<220> FEATURE:
<223> OTHER INFORMATION: Synthetic construct

<400> SEQUENCE: 286

```
cccgctcgag gaagcgcgtt cccaagc                                          27
```

<210> SEQ ID NO 287
<211> LENGTH: 29
<212> TYPE: DNA
<213> ORGANISM: Artificial Sequence
<220> FEATURE:
<223> OTHER INFORMATION: Synthetic construct

<400> SEQUENCE: 287

```
cgcggatccc atatgcacga cacccgtac                                        29
```

<210> SEQ ID NO 288
<211> LENGTH: 28
<212> TYPE: DNA
<213> ORGANISM: Artificial Sequence
<220> FEATURE:
<223> OTHER INFORMATION: Synthetic construct

<400> SEQUENCE: 288

```
cccgctcgag ttagaagcgc gttcccaa                                         28
```

<210> SEQ ID NO 289
<211> LENGTH: 34
<212> TYPE: DNA
<213> ORGANISM: Artificial Sequence
<220> FEATURE:
<223> OTHER INFORMATION: Synthetic construct

<400> SEQUENCE: 289

```
ctagctagct ttaaacgcag cgtaatcgca atgg                                  34
```

<210> SEQ ID NO 290
<211> LENGTH: 31
<212> TYPE: DNA
<213> ORGANISM: Artificial Sequence
<220> FEATURE:
<223> OTHER INFORMATION: Synthetic construct

<400> SEQUENCE: 290

```
cccgctcgag tcaatcctgc tctttttgc c                                      31
```

<210> SEQ ID NO 291
<211> LENGTH: 25
<212> TYPE: DNA
<213> ORGANISM: Artificial Sequence
<220> FEATURE:
<223> OTHER INFORMATION: Synthetic construct

<400> SEQUENCE: 291

```
ctagctagcg ggggcggcgg tggcg                                            25
```

<210> SEQ ID NO 292
<211> LENGTH: 31
<212> TYPE: DNA
<213> ORGANISM: Artificial Sequence

```
<220> FEATURE:
<223> OTHER INFORMATION: Synthetic construct

<400> SEQUENCE: 292
cccgctcgag tcaatcctgc tctttttgc c                              31

<210> SEQ ID NO 293
<211> LENGTH: 40
<212> TYPE: DNA
<213> ORGANISM: Artificial Sequence
<220> FEATURE:
<223> OTHER INFORMATION: Synthetic construct

<400> SEQUENCE: 293
ctagctagcg ctcatcctcg ccgcctgcgg gggcggcggt                    40

<210> SEQ ID NO 294
<211> LENGTH: 31
<212> TYPE: DNA
<213> ORGANISM: Artificial Sequence
<220> FEATURE:
<223> OTHER INFORMATION: Synthetic construct

<400> SEQUENCE: 294
cccgctcgag tcaatcctgc tctttttgc c                              31

<210> SEQ ID NO 295
<211> LENGTH: 25
<212> TYPE: DNA
<213> ORGANISM: Artificial Sequence
<220> FEATURE:
<223> OTHER INFORMATION: Synthetic construct

<400> SEQUENCE: 295
cggggatccg ggggcggcgg tggcg                                    25

<210> SEQ ID NO 296
<211> LENGTH: 31
<212> TYPE: DNA
<213> ORGANISM: Artificial Sequence
<220> FEATURE:
<223> OTHER INFORMATION: Synthetic construct

<400> SEQUENCE: 296
cccgctcgag tcaatcctgc tctttttgc c                              31

<210> SEQ ID NO 297
<211> LENGTH: 25
<212> TYPE: DNA
<213> ORGANISM: Artificial Sequence
<220> FEATURE:
<223> OTHER INFORMATION: Synthetic construct

<400> SEQUENCE: 297
ctagctagcg ggggcggcgg tggcg                                    25

<210> SEQ ID NO 298
<211> LENGTH: 28
<212> TYPE: DNA
<213> ORGANISM: Artificial Sequence
<220> FEATURE:
<223> OTHER INFORMATION: Synthetic construct

<400> SEQUENCE: 298
cccgctcgag atcctgctct tttttgcc                                 28
```

<210> SEQ ID NO 299
<211> LENGTH: 28
<212> TYPE: DNA
<213> ORGANISM: Artificial Sequence
<220> FEATURE:
<223> OTHER INFORMATION: Synthetic construct

<400> SEQUENCE: 299
ctagctagct gcggggcgg cggtggcg                                     28

<210> SEQ ID NO 300
<211> LENGTH: 28
<212> TYPE: DNA
<213> ORGANISM: Artificial Sequence
<220> FEATURE:
<223> OTHER INFORMATION: Synthetic construct

<400> SEQUENCE: 300
cccgctcgag atcctgctct tttttgcc                                    28

<210> SEQ ID NO 301
<211> LENGTH: 32
<212> TYPE: DNA
<213> ORGANISM: Artificial Sequence
<220> FEATURE:
<223> OTHER INFORMATION: Synthetic construct

<400> SEQUENCE: 301
cgcggatccg ctagccccga tgttaaatcg gc                               32

<210> SEQ ID NO 302
<211> LENGTH: 32
<212> TYPE: DNA
<213> ORGANISM: Artificial Sequence
<220> FEATURE:
<223> OTHER INFORMATION: Synthetic construct

<400> SEQUENCE: 302
cgcggatccg ctagccaaga tatggcggca gt                               32

<210> SEQ ID NO 303
<211> LENGTH: 32
<212> TYPE: DNA
<213> ORGANISM: Artificial Sequence
<220> FEATURE:
<223> OTHER INFORMATION: Synthetic construct

<400> SEQUENCE: 303
cgcggatccg ctagcgccga atccgcaaat ca                               32

<210> SEQ ID NO 304
<211> LENGTH: 32
<212> TYPE: DNA
<213> ORGANISM: Artificial Sequence
<220> FEATURE:
<223> OTHER INFORMATION: Synthetic construct

<400> SEQUENCE: 304
cgcgctagcg gaagggttga tttggctaat gg                               32

<210> SEQ ID NO 305
<211> LENGTH: 32
<212> TYPE: DNA
<213> ORGANISM: Artificial Sequence
<220> FEATURE:
<223> OTHER INFORMATION: Synthetic construct

```
<400> SEQUENCE: 305
cgcgctagcg gaagggttga tttggctaat gg                                       32

<210> SEQ ID NO 306
<211> LENGTH: 29
<212> TYPE: DNA
<213> ORGANISM: Artificial Sequence
<220> FEATURE:
<223> OTHER INFORMATION: Synthetic construct

<400> SEQUENCE: 306
cgccatatgt ttaaacgcag cgtaatcgc                                           29

<210> SEQ ID NO 307
<211> LENGTH: 34
<212> TYPE: DNA
<213> ORGANISM: Artificial Sequence
<220> FEATURE:
<223> OTHER INFORMATION: Synthetic construct

<400> SEQUENCE: 307
cccgctcgag aaaattgcta ccgccattcg cagg                                     34

<210> SEQ ID NO 308
<211> LENGTH: 32
<212> TYPE: DNA
<213> ORGANISM: Artificial Sequence
<220> FEATURE:
<223> OTHER INFORMATION: Synthetic construct

<400> SEQUENCE: 308
cgccatatgg gaagggttga tttggctaat gg                                       32

<210> SEQ ID NO 309
<211> LENGTH: 38
<212> TYPE: DNA
<213> ORGANISM: Artificial Sequence
<220> FEATURE:
<223> OTHER INFORMATION: Synthetic construct

<400> SEQUENCE: 309
cccgctcgag cttgtcttta taaatgatga catatttg                                 38

<210> SEQ ID NO 310
<211> LENGTH: 40
<212> TYPE: DNA
<213> ORGANISM: Artificial Sequence
<220> FEATURE:
<223> OTHER INFORMATION: Synthetic construct

<400> SEQUENCE: 310
cccgctcgag tttataaaag ataatatatt gattgattcc                               40

<210> SEQ ID NO 311
<211> LENGTH: 31
<212> TYPE: DNA
<213> ORGANISM: Artificial Sequence
<220> FEATURE:
<223> OTHER INFORMATION: Synthetic construct

<400> SEQUENCE: 311
cgcgctagca tgccgctgat tcccgtcaat c                                        31

<210> SEQ ID NO 312
```

```
<211> LENGTH: 25
<212> TYPE: DNA
<213> ORGANISM: Artificial Sequence
<220> FEATURE:
<223> OTHER INFORMATION: Synthetic construct

<400> SEQUENCE: 312
ctagctagcg ggggcggcgg tggcg                                                25

<210> SEQ ID NO 313
<211> LENGTH: 31
<212> TYPE: DNA
<213> ORGANISM: Artificial Sequence
<220> FEATURE:
<223> OTHER INFORMATION: Synthetic construct

<400> SEQUENCE: 313
cccgctcgag tcaatcctgc tctttttgc c                                          31

<210> SEQ ID NO 314
<211> LENGTH: 32
<212> TYPE: DNA
<213> ORGANISM: Artificial Sequence
<220> FEATURE:
<223> OTHER INFORMATION: Synthetic construct

<400> SEQUENCE: 314
cgcggatccg ctagccccga tgttaaatcg gc                                        32

<210> SEQ ID NO 315
<211> LENGTH: 28
<212> TYPE: DNA
<213> ORGANISM: Artificial Sequence
<220> FEATURE:
<223> OTHER INFORMATION: Synthetic construct

<400> SEQUENCE: 315
cccgctcgag atcctgctct ttttgcc                                              28

<210> SEQ ID NO 316
<211> LENGTH: 32
<212> TYPE: DNA
<213> ORGANISM: Artificial Sequence
<220> FEATURE:
<223> OTHER INFORMATION: Synthetic construct

<400> SEQUENCE: 316
cgcggatccg ctagccccga tgttaaatcg gc                                        32

<210> SEQ ID NO 317
<211> LENGTH: 31
<212> TYPE: DNA
<213> ORGANISM: Artificial Sequence
<220> FEATURE:
<223> OTHER INFORMATION: Synthetic construct

<400> SEQUENCE: 317
cccgctcgag tcaatcctgc tcttttttgc c                                         31

<210> SEQ ID NO 318
<211> LENGTH: 87
<212> TYPE: DNA
<213> ORGANISM: Artificial Sequence
<220> FEATURE:
<223> OTHER INFORMATION: Synthetic construct

<400> SEQUENCE: 318
```

```
cgcggatccg ctagctttga acgcagtgtg attgcaatgg cttgtatttt tgccctttca      60
gcctgttcgc ccgatgttaa atcggcg                                         87
```

<210> SEQ ID NO 319
<211> LENGTH: 31
<212> TYPE: DNA
<213> ORGANISM: Artificial Sequence
<220> FEATURE:
<223> OTHER INFORMATION: Synthetic construct

<400> SEQUENCE: 319

```
cccgctcgag tcaatcctgc tcttttttgc c                                    31
```

<210> SEQ ID NO 320
<211> LENGTH: 90
<212> TYPE: DNA
<213> ORGANISM: Artificial Sequence
<220> FEATURE:
<223> OTHER INFORMATION: Synthetic construct

<400> SEQUENCE: 320

```
cgcggatccg ctagcaaaac cttcttcaaa accctttccg ccgccgcact cgcgctcatc     60
ctcgccgcct gctcgcccga tgttaaatcg                                      90
```

<210> SEQ ID NO 321
<211> LENGTH: 31
<212> TYPE: DNA
<213> ORGANISM: Artificial Sequence
<220> FEATURE:
<223> OTHER INFORMATION: Synthetic construct

<400> SEQUENCE: 321

```
cccgctcgag tcaatcctgc tcttttttgc c                                    31
```

<210> SEQ ID NO 322
<211> LENGTH: 33
<212> TYPE: DNA
<213> ORGANISM: Artificial Sequence
<220> FEATURE:
<223> OTHER INFORMATION: Synthetic construct

<400> SEQUENCE: 322

```
cgcggatccc atatgaaaac caagttaatc aaa                                  33
```

<210> SEQ ID NO 323
<211> LENGTH: 30
<212> TYPE: DNA
<213> ORGANISM: Artificial Sequence
<220> FEATURE:
<223> OTHER INFORMATION: Synthetic construct

<400> SEQUENCE: 323

```
cccgctcgag ttattgattt ttgcggatga                                      30
```

<210> SEQ ID NO 324
<211> LENGTH: 34
<212> TYPE: DNA
<213> ORGANISM: Artificial Sequence
<220> FEATURE:
<223> OTHER INFORMATION: Synthetic construct

<400> SEQUENCE: 324

```
cgcggatccc atatgttaaa tcgggtattt tatc                                 34
```

<210> SEQ ID NO 325
<211> LENGTH: 28
<212> TYPE: DNA
<213> ORGANISM: Artificial Sequence
<220> FEATURE:
<223> OTHER INFORMATION: Synthetic construct

<400> SEQUENCE: 325
cccgctcgag ttaatccgcc attccctg                                        28

<210> SEQ ID NO 326
<211> LENGTH: 30
<212> TYPE: DNA
<213> ORGANISM: Artificial Sequence
<220> FEATURE:
<223> OTHER INFORMATION: Synthetic construct

<400> SEQUENCE: 326
gcggccatat gaaattacaa caattggctg                                      30

<210> SEQ ID NO 327
<211> LENGTH: 31
<212> TYPE: DNA
<213> ORGANISM: Artificial Sequence
<220> FEATURE:
<223> OTHER INFORMATION: Synthetic construct

<400> SEQUENCE: 327
gcggcctcga gttaccttac gtttttcaaa g                                    31

<210> SEQ ID NO 328
<211> LENGTH: 29
<212> TYPE: DNA
<213> ORGANISM: Artificial Sequence
<220> FEATURE:
<223> OTHER INFORMATION: Synthetic construct

<400> SEQUENCE: 328
cgcggatccc atatgcaagc acggctgct                                       29

<210> SEQ ID NO 329
<211> LENGTH: 29
<212> TYPE: DNA
<213> ORGANISM: Artificial Sequence
<220> FEATURE:
<223> OTHER INFORMATION: Synthetic construct

<400> SEQUENCE: 329
cccgctcgag tcaaggttgt ccttgtcta                                       29

<210> SEQ ID NO 330
<211> LENGTH: 30
<212> TYPE: DNA
<213> ORGANISM: Artificial Sequence
<220> FEATURE:
<223> OTHER INFORMATION: Synthetic construct

<400> SEQUENCE: 330
cgcggatccc atatgatgaa accgcacaac                                      30

<210> SEQ ID NO 331
<211> LENGTH: 28
<212> TYPE: DNA
<213> ORGANISM: Artificial Sequence
<220> FEATURE:
<223> OTHER INFORMATION: Synthetic construct

<400> SEQUENCE: 331
cccgctcgag tcagttgctc aacacgtc					28

<210> SEQ ID NO 332
<211> LENGTH: 32
<212> TYPE: DNA
<213> ORGANISM: Artificial Sequence
<220> FEATURE:
<223> OTHER INFORMATION: Synthetic construct

<400> SEQUENCE: 332
cgcggatccc atatggtaga cgcgcttaag ca				32

<210> SEQ ID NO 333
<211> LENGTH: 25
<212> TYPE: DNA
<213> ORGANISM: Artificial Sequence
<220> FEATURE:
<223> OTHER INFORMATION: Synthetic construct

<400> SEQUENCE: 333
cccgctcgag agctgcatgg cggcg					25

<210> SEQ ID NO 334
<211> LENGTH: 30
<212> TYPE: DNA
<213> ORGANISM: Artificial Sequence
<220> FEATURE:
<223> OTHER INFORMATION: Synthetic construct

<400> SEQUENCE: 334
cgcggatccc atatggcacg gtcgttatac				30

<210> SEQ ID NO 335
<211> LENGTH: 26
<212> TYPE: DNA
<213> ORGANISM: Artificial Sequence
<220> FEATURE:
<223> OTHER INFORMATION: Synthetic construct

<400> SEQUENCE: 335
cccgctcgag ctaccgcgca ttcctg					26

<210> SEQ ID NO 336
<211> LENGTH: 31
<212> TYPE: DNA
<213> ORGANISM: Artificial Sequence
<220> FEATURE:
<223> OTHER INFORMATION: Synthetic construct

<400> SEQUENCE: 336
gcggccatat ggaattttc attatcttgt t				31

<210> SEQ ID NO 337
<211> LENGTH: 31
<212> TYPE: DNA
<213> ORGANISM: Artificial Sequence
<220> FEATURE:
<223> OTHER INFORMATION: Synthetic construct

<400> SEQUENCE: 337
gcggcctcga gttatttggc ggttttgctg c				31

<210> SEQ ID NO 338

```
<211> LENGTH: 32
<212> TYPE: DNA
<213> ORGANISM: Artificial Sequence
<220> FEATURE:
<223> OTHER INFORMATION: Synthetic construct

<400> SEQUENCE: 338
gcggccatat gaagtatgtc cggttatttt tc                          32

<210> SEQ ID NO 339
<211> LENGTH: 30
<212> TYPE: DNA
<213> ORGANISM: Artificial Sequence
<220> FEATURE:
<223> OTHER INFORMATION: Synthetic construct

<400> SEQUENCE: 339
gcggcctcga gttatcggct tgtgcaacgg                             30

<210> SEQ ID NO 340
<211> LENGTH: 32
<212> TYPE: DNA
<213> ORGANISM: Artificial Sequence
<220> FEATURE:
<223> OTHER INFORMATION: Synthetic construct

<400> SEQUENCE: 340
cgcggatccg ctagctccgg cagcaaaacc ga                          32

<210> SEQ ID NO 341
<211> LENGTH: 28
<212> TYPE: DNA
<213> ORGANISM: Artificial Sequence
<220> FEATURE:
<223> OTHER INFORMATION: Synthetic construct

<400> SEQUENCE: 341
gcccaagctt acgcagttcg gaatggag                               28

<210> SEQ ID NO 342
<211> LENGTH: 35
<212> TYPE: DNA
<213> ORGANISM: Artificial Sequence
<220> FEATURE:
<223> OTHER INFORMATION: Synthetic construct

<400> SEQUENCE: 342
gccgccatat gttgaatatt aaactgaaaa ccttg                       35

<210> SEQ ID NO 343
<211> LENGTH: 32
<212> TYPE: DNA
<213> ORGANISM: Artificial Sequence
<220> FEATURE:
<223> OTHER INFORMATION: Synthetic construct

<400> SEQUENCE: 343
gccgcctcga gttatttctg atgccttttc cc                          32

<210> SEQ ID NO 344
<211> LENGTH: 29
<212> TYPE: DNA
<213> ORGANISM: Artificial Sequence
<220> FEATURE:
<223> OTHER INFORMATION: Synthetic construct

<400> SEQUENCE: 344
```
gccgccatat ggacaataag accaaactg                                         29

<210> SEQ ID NO 345
<211> LENGTH: 30
<212> TYPE: DNA
<213> ORGANISM: Artificial Sequence
<220> FEATURE:
<223> OTHER INFORMATION: Synthetic construct

<400> SEQUENCE: 345
gccgcctcga gttaacggtg cggacgtttc                                        30

<210> SEQ ID NO 346
<211> LENGTH: 32
<212> TYPE: DNA
<213> ORGANISM: Artificial Sequence
<220> FEATURE:
<223> OTHER INFORMATION: Synthetic construct

<400> SEQUENCE: 346
cgcggatccc atatgaacaa actgtttctt ac                                     32

<210> SEQ ID NO 347
<211> LENGTH: 28
<212> TYPE: DNA
<213> ORGANISM: Artificial Sequence
<220> FEATURE:
<223> OTHER INFORMATION: Synthetic construct

<400> SEQUENCE: 347
cccgctcgag tcattccgcc ttcagaaa                                          28

<210> SEQ ID NO 348
<211> LENGTH: 45
<212> TYPE: DNA
<213> ORGANISM: Artificial Sequence
<220> FEATURE:
<223> OTHER INFORMATION: Synthetic construct

<400> SEQUENCE: 348
cgcggatccc atatgcaagg tatcgttgcc gacaaatccg cacct                       45

<210> SEQ ID NO 349
<211> LENGTH: 42
<212> TYPE: DNA
<213> ORGANISM: Artificial Sequence
<220> FEATURE:
<223> OTHER INFORMATION: Synthetic construct

<400> SEQUENCE: 349
cccgctcgag agctaattgt gcttggtttg cagataggag tt                          42

<210> SEQ ID NO 350
<211> LENGTH: 52
<212> TYPE: DNA
<213> ORGANISM: Artificial Sequence
<220> FEATURE:
<223> OTHER INFORMATION: Synthetic construct

<400> SEQUENCE: 350
cgcggatccc atatgaaccg caccctgtac aaagttgtat ttaacaaaca tc               52

<210> SEQ ID NO 351
<211> LENGTH: 45
<212> TYPE: DNA

```
<213> ORGANISM: Artificial Sequence
<220> FEATURE:
<223> OTHER INFORMATION: Synthetic construct

<400> SEQUENCE: 351
cccgctcgag ttaagctaat tgtgcttggt ttgcagatag gagtt              45

<210> SEQ ID NO 352
<211> LENGTH: 46
<212> TYPE: DNA
<213> ORGANISM: Artificial Sequence
<220> FEATURE:
<223> OTHER INFORMATION: Synthetic construct

<400> SEQUENCE: 352
cgcggatccc atatgacggg agaaaatcat gcggtttcac ttcatg             46

<210> SEQ ID NO 353
<211> LENGTH: 42
<212> TYPE: DNA
<213> ORGANISM: Artificial Sequence
<220> FEATURE:
<223> OTHER INFORMATION: Synthetic construct

<400> SEQUENCE: 353
cccgctcgag agctaattgt gcttggtttg cagataggag tt                 42

<210> SEQ ID NO 354
<211> LENGTH: 51
<212> TYPE: DNA
<213> ORGANISM: Artificial Sequence
<220> FEATURE:
<223> OTHER INFORMATION: Synthetic construct

<400> SEQUENCE: 354
cgcggatccc atatggtttc agacggccta tacaaccaac atggtgaaat t        51

<210> SEQ ID NO 355
<211> LENGTH: 41
<212> TYPE: DNA
<213> ORGANISM: Artificial Sequence
<220> FEATURE:
<223> OTHER INFORMATION: Synthetic construct

<400> SEQUENCE: 355
cccgctcgag gcggtaactg ccgcttgcac tgaatccgta a                   41

<210> SEQ ID NO 356
<211> LENGTH: 46
<212> TYPE: DNA
<213> ORGANISM: Artificial Sequence
<220> FEATURE:
<223> OTHER INFORMATION: Synthetic construct

<400> SEQUENCE: 356
cgcggatccc atatgacggg agaaaatcat gcggtttcac ttcatg              46

<210> SEQ ID NO 357
<211> LENGTH: 41
<212> TYPE: DNA
<213> ORGANISM: Artificial Sequence
<220> FEATURE:
<223> OTHER INFORMATION: Synthetic construct

<400> SEQUENCE: 357
cccgctcgag gcggtaactg ccgcttgcac tgaatccgta a                   41
```

<210> SEQ ID NO 358
<211> LENGTH: 49
<212> TYPE: DNA
<213> ORGANISM: Artificial Sequence
<220> FEATURE:
<223> OTHER INFORMATION: Synthetic construct

<400> SEQUENCE: 358
cgcggatccc atatgcaaag caaagtcaaa gcagaccatg cctccgtaa        49

<210> SEQ ID NO 359
<211> LENGTH: 56
<212> TYPE: DNA
<213> ORGANISM: Artificial Sequence
<220> FEATURE:
<223> OTHER INFORMATION: Synthetic construct

<400> SEQUENCE: 359
cccgctcgag tcttttcctt tcaattataa ctttagtagg ttcaattttg gtcccc        56

<210> SEQ ID NO 360
<211> LENGTH: 51
<212> TYPE: DNA
<213> ORGANISM: Artificial Sequence
<220> FEATURE:
<223> OTHER INFORMATION: Synthetic construct

<400> SEQUENCE: 360
cgcggatccc atatggtttc agacggccta tacaaccaac atggtgaaat t        51

<210> SEQ ID NO 361
<211> LENGTH: 56
<212> TYPE: DNA
<213> ORGANISM: Artificial Sequence
<220> FEATURE:
<223> OTHER INFORMATION: Synthetic construct

<400> SEQUENCE: 361
cccgctcgag tcttttcctt tcaattataa ctttagtagg ttcaattttg gtcccc        56

<210> SEQ ID NO 362
<211> LENGTH: 27
<212> TYPE: DNA
<213> ORGANISM: Artificial Sequence
<220> FEATURE:
<223> OTHER INFORMATION: Synthetic construct

<400> SEQUENCE: 362
gcggccatat gacccgtttg acccgcg        27

<210> SEQ ID NO 363
<211> LENGTH: 31
<212> TYPE: DNA
<213> ORGANISM: Artificial Sequence
<220> FEATURE:
<223> OTHER INFORMATION: Synthetic construct

<400> SEQUENCE: 363
gcggcctcga gtcagcgggc gttcatttct t        31

<210> SEQ ID NO 364
<211> LENGTH: 33
<212> TYPE: DNA
<213> ORGANISM: Artificial Sequence
<220> FEATURE:

<223> OTHER INFORMATION: Synthetic construct

<400> SEQUENCE: 364
cgcggatccc atatgaacac cattttcaaa atc                          33

<210> SEQ ID NO 365
<211> LENGTH: 32
<212> TYPE: DNA
<213> ORGANISM: Artificial Sequence
<220> FEATURE:
<223> OTHER INFORMATION: Synthetic construct

<400> SEQUENCE: 365
cccgctcgag ttaatttact tttttgatgt cg                           32

<210> SEQ ID NO 366
<211> LENGTH: 28
<212> TYPE: DNA
<213> ORGANISM: Artificial Sequence
<220> FEATURE:
<223> OTHER INFORMATION: Synthetic construct

<400> SEQUENCE: 366
gcggccatat ggattcgccc aaggtcgg                                28

<210> SEQ ID NO 367
<211> LENGTH: 31
<212> TYPE: DNA
<213> ORGANISM: Artificial Sequence
<220> FEATURE:
<223> OTHER INFORMATION: Synthetic construct

<400> SEQUENCE: 367
gcggcctcga gctacacttc ccccgaagtg g                            31

<210> SEQ ID NO 368
<211> LENGTH: 31
<212> TYPE: DNA
<213> ORGANISM: Artificial Sequence
<220> FEATURE:
<223> OTHER INFORMATION: Synthetic construct

<400> SEQUENCE: 368
cgcggatccc atatgatagt tgaccaaagc c                            31

<210> SEQ ID NO 369
<211> LENGTH: 30
<212> TYPE: DNA
<213> ORGANISM: Artificial Sequence
<220> FEATURE:
<223> OTHER INFORMATION: Synthetic construct

<400> SEQUENCE: 369
cccgctcgag ttatttttcc gattttcgg                               30

<210> SEQ ID NO 370
<211> LENGTH: 28
<212> TYPE: DNA
<213> ORGANISM: Artificial Sequence
<220> FEATURE:
<223> OTHER INFORMATION: Synthetic construct

<400> SEQUENCE: 370
gcggccatat gcttgaactg aacggact                                28

```
<210> SEQ ID NO 371
<211> LENGTH: 30
<212> TYPE: DNA
<213> ORGANISM: Artificial Sequence
<220> FEATURE:
<223> OTHER INFORMATION: Synthetic construct

<400> SEQUENCE: 371
gcggcctcga gtcagcggaa gcggacgatt                                    30

<210> SEQ ID NO 372
<211> LENGTH: 34
<212> TYPE: DNA
<213> ORGANISM: Artificial Sequence
<220> FEATURE:
<223> OTHER INFORMATION: Synthetic construct

<400> SEQUENCE: 372
cgcggatccc atatgtccaa actcaaaacc atcg                               34

<210> SEQ ID NO 373
<211> LENGTH: 29
<212> TYPE: DNA
<213> ORGANISM: Artificial Sequence
<220> FEATURE:
<223> OTHER INFORMATION: Synthetic construct

<400> SEQUENCE: 373
cccgctcgag gcttccaatc agtttgacc                                     29

<210> SEQ ID NO 374
<211> LENGTH: 32
<212> TYPE: DNA
<213> ORGANISM: Artificial Sequence
<220> FEATURE:
<223> OTHER INFORMATION: Synthetic construct

<400> SEQUENCE: 374
gcggccatat gagcgcaatc gttgatattt tc                                 32

<210> SEQ ID NO 375
<211> LENGTH: 34
<212> TYPE: DNA
<213> ORGANISM: Artificial Sequence
<220> FEATURE:
<223> OTHER INFORMATION: Synthetic construct

<400> SEQUENCE: 375
gcggcctcga gttatttgcc cagttggtag aatg                               34

<210> SEQ ID NO 376
<211> LENGTH: 32
<212> TYPE: DNA
<213> ORGANISM: Artificial Sequence
<220> FEATURE:
<223> OTHER INFORMATION: Synthetic construct

<400> SEQUENCE: 376
gcggccatat ggtgatacat ccgcactact tc                                 32

<210> SEQ ID NO 377
<211> LENGTH: 32
<212> TYPE: DNA
<213> ORGANISM: Artificial Sequence
<220> FEATURE:
<223> OTHER INFORMATION: Synthetic construct
```

<400> SEQUENCE: 377
gcggcctcga gtcaaaatcg agttttacac ca                32

<210> SEQ ID NO 378
<211> LENGTH: 31
<212> TYPE: DNA
<213> ORGANISM: Artificial Sequence
<220> FEATURE:
<223> OTHER INFORMATION: Synthetic construct

<400> SEQUENCE: 378
gcggccatat gaccatctat ttcaaaaacg g                31

<210> SEQ ID NO 379
<211> LENGTH: 34
<212> TYPE: DNA
<213> ORGANISM: Artificial Sequence
<220> FEATURE:
<223> OTHER INFORMATION: Synthetic construct

<400> SEQUENCE: 379
gcggcctcga gtcagccgat gtttagcgtc catt                34

<210> SEQ ID NO 380
<211> LENGTH: 31
<212> TYPE: DNA
<213> ORGANISM: Artificial Sequence
<220> FEATURE:
<223> OTHER INFORMATION: Synthetic construct

<400> SEQUENCE: 380
cgcggatccc atatgagcag cggaggggt g                31

<210> SEQ ID NO 381
<211> LENGTH: 27
<212> TYPE: DNA
<213> ORGANISM: Artificial Sequence
<220> FEATURE:
<223> OTHER INFORMATION: Synthetic construct

<400> SEQUENCE: 381
cccgctcgag ttgcttggcg gcaaggc                27

<210> SEQ ID NO 382
<211> LENGTH: 31
<212> TYPE: DNA
<213> ORGANISM: Artificial Sequence
<220> FEATURE:
<223> OTHER INFORMATION: Synthetic construct

<400> SEQUENCE: 382
cgcggatccc atatggtcgc cgccgacatc g                31

<210> SEQ ID NO 383
<211> LENGTH: 27
<212> TYPE: DNA
<213> ORGANISM: Artificial Sequence
<220> FEATURE:
<223> OTHER INFORMATION: Synthetic construct

<400> SEQUENCE: 383
cccgctcgag ttgcttggcg gcaaggc                27

<210> SEQ ID NO 384
<211> LENGTH: 31

<212> TYPE: DNA
<213> ORGANISM: Artificial Sequence
<220> FEATURE:
<223> OTHER INFORMATION: Synthetic construct

<400> SEQUENCE: 384
cgcggatccc atatgggcgg ttcggaaggc g                          31

<210> SEQ ID NO 385
<211> LENGTH: 33
<212> TYPE: DNA
<213> ORGANISM: Artificial Sequence
<220> FEATURE:
<223> OTHER INFORMATION: Synthetic construct

<400> SEQUENCE: 385
cccgctcgag ttgaacactg atgtcttttc cga                        33

<210> SEQ ID NO 386
<211> LENGTH: 35
<212> TYPE: DNA
<213> ORGANISM: Artificial Sequence
<220> FEATURE:
<223> OTHER INFORMATION: Synthetic construct

<400> SEQUENCE: 386
cgcggatccg ctagcaaact gtcgttggtg ttaac                      35

<210> SEQ ID NO 387
<211> LENGTH: 26
<212> TYPE: DNA
<213> ORGANISM: Artificial Sequence
<220> FEATURE:
<223> OTHER INFORMATION: Synthetic construct

<400> SEQUENCE: 387
cccgctcgag ttgacccgct ccacgg                                26

<210> SEQ ID NO 388
<211> LENGTH: 31
<212> TYPE: DNA
<213> ORGANISM: Artificial Sequence
<220> FEATURE:
<223> OTHER INFORMATION: Synthetic construct

<400> SEQUENCE: 388
gccgccatat ggcggacttg gcgcaagacc c                          31

<210> SEQ ID NO 389
<211> LENGTH: 39
<212> TYPE: DNA
<213> ORGANISM: Artificial Sequence
<220> FEATURE:
<223> OTHER INFORMATION: Synthetic construct

<400> SEQUENCE: 389
gccgcctcga gatctcctaa acctgtttta acaatgccg                  39

<210> SEQ ID NO 390
<211> LENGTH: 31
<212> TYPE: DNA
<213> ORGANISM: Artificial Sequence
<220> FEATURE:
<223> OTHER INFORMATION: Synthetic construct

<400> SEQUENCE: 390
gccgccatat ggcggacttg gcgcaagacc c        31

<210> SEQ ID NO 391
<211> LENGTH: 31
<212> TYPE: DNA
<213> ORGANISM: Artificial Sequence
<220> FEATURE:
<223> OTHER INFORMATION: Synthetic construct

<400> SEQUENCE: 391
gcggcctcga gctccatgct gttgccccag c        31

<210> SEQ ID NO 392
<211> LENGTH: 31
<212> TYPE: DNA
<213> ORGANISM: Artificial Sequence
<220> FEATURE:
<223> OTHER INFORMATION: Synthetic construct

<400> SEQUENCE: 392
gccgccatat ggcggacttg gcgcaagacc c        31

<210> SEQ ID NO 393
<211> LENGTH: 31
<212> TYPE: DNA
<213> ORGANISM: Artificial Sequence
<220> FEATURE:
<223> OTHER INFORMATION: Synthetic construct

<400> SEQUENCE: 393
gcggcctcga gaaaatcccc gctaaccgca g        31

<210> SEQ ID NO 394
<211> LENGTH: 31
<212> TYPE: DNA
<213> ORGANISM: Artificial Sequence
<220> FEATURE:
<223> OTHER INFORMATION: Synthetic construct

<400> SEQUENCE: 394
cgcggatccc atatgagcag cggagggggt g        31

<210> SEQ ID NO 395
<211> LENGTH: 27
<212> TYPE: DNA
<213> ORGANISM: Artificial Sequence
<220> FEATURE:
<223> OTHER INFORMATION: Synthetic construct

<400> SEQUENCE: 395
cccgctcgag ttgcttggcg gcaaggc        27

<210> SEQ ID NO 396
<211> LENGTH: 31
<212> TYPE: DNA
<213> ORGANISM: Artificial Sequence
<220> FEATURE:
<223> OTHER INFORMATION: Synthetic construct

<400> SEQUENCE: 396
cgcggatccc atatggtcgc cgccgacatc g        31

<210> SEQ ID NO 397
<211> LENGTH: 27
<212> TYPE: DNA
<213> ORGANISM: Artificial Sequence

```
<220> FEATURE:
<223> OTHER INFORMATION: Synthetic construct

<400> SEQUENCE: 397
cccgctcgag ttgcttggcg gcaaggc                                            27

<210> SEQ ID NO 398
<211> LENGTH: 33
<212> TYPE: DNA
<213> ORGANISM: Artificial Sequence
<220> FEATURE:
<223> OTHER INFORMATION: Synthetic construct

<400> SEQUENCE: 398
cgcggatccc atatggacgg tgttgtgcct gtt                                     33

<210> SEQ ID NO 399
<211> LENGTH: 29
<212> TYPE: DNA
<213> ORGANISM: Artificial Sequence
<220> FEATURE:
<223> OTHER INFORMATION: Synthetic construct

<400> SEQUENCE: 399
cccgctcgag cttacggatc aaattgacg                                          29

<210> SEQ ID NO 400
<211> LENGTH: 33
<212> TYPE: DNA
<213> ORGANISM: Artificial Sequence
<220> FEATURE:
<223> OTHER INFORMATION: Synthetic construct

<400> SEQUENCE: 400
cgcggatccc atatgggcag ccaatctgaa gaa                                     33

<210> SEQ ID NO 401
<211> LENGTH: 28
<212> TYPE: DNA
<213> ORGANISM: Artificial Sequence
<220> FEATURE:
<223> OTHER INFORMATION: Synthetic construct

<400> SEQUENCE: 401
cccgctcgag ctcagctttt gccgtcaa                                           28

<210> SEQ ID NO 402
<211> LENGTH: 33
<212> TYPE: DNA
<213> ORGANISM: Artificial Sequence
<220> FEATURE:
<223> OTHER INFORMATION: Synthetic construct

<400> SEQUENCE: 402
cgcggatccg ctagctactc atccattgtc cgc                                     33

<210> SEQ ID NO 403
<211> LENGTH: 29
<212> TYPE: DNA
<213> ORGANISM: Artificial Sequence
<220> FEATURE:
<223> OTHER INFORMATION: Synthetic construct

<400> SEQUENCE: 403
cccgctcgag ccagttgtag cctattttg                                          29
```

```
<210> SEQ ID NO 404
<211> LENGTH: 32
<212> TYPE: DNA
<213> ORGANISM: Artificial Sequence
<220> FEATURE:
<223> OTHER INFORMATION: Synthetic construct

<400> SEQUENCE: 404
cgcggatccg ctagcatgcg cttcacacac ac                                32

<210> SEQ ID NO 405
<211> LENGTH: 30
<212> TYPE: DNA
<213> ORGANISM: Artificial Sequence
<220> FEATURE:
<223> OTHER INFORMATION: Synthetic construct

<400> SEQUENCE: 405
cccgctcgag ttaccagttg tagcctattt                                   30

<210> SEQ ID NO 406
<211> LENGTH: 32
<212> TYPE: DNA
<213> ORGANISM: Artificial Sequence
<220> FEATURE:
<223> OTHER INFORMATION: Synthetic construct

<400> SEQUENCE: 406
gccgccatat ggcacaaacg gaaggtttgg aa                                32

<210> SEQ ID NO 407
<211> LENGTH: 36
<212> TYPE: DNA
<213> ORGANISM: Artificial Sequence
<220> FEATURE:
<223> OTHER INFORMATION: Synthetic construct

<400> SEQUENCE: 407
gccgcctcga gaaaactgta acgcaggttt gccgtc                            36

<210> SEQ ID NO 408
<211> LENGTH: 32
<212> TYPE: DNA
<213> ORGANISM: Artificial Sequence
<220> FEATURE:
<223> OTHER INFORMATION: Synthetic construct

<400> SEQUENCE: 408
gcggccatat ggaagaaaca ccgcgcgaac cg                                32

<210> SEQ ID NO 409
<211> LENGTH: 32
<212> TYPE: DNA
<213> ORGANISM: Artificial Sequence
<220> FEATURE:
<223> OTHER INFORMATION: Synthetic construct

<400> SEQUENCE: 409
gcggcctcga ggaacgtttt attaaactcg ac                                32

<210> SEQ ID NO 410
<211> LENGTH: 32
<212> TYPE: DNA
<213> ORGANISM: Artificial Sequence
<220> FEATURE:
<223> OTHER INFORMATION: Synthetic construct
```

```
<400> SEQUENCE: 410
gcggccatat gagaaaaccg accgataccc ta                                    32

<210> SEQ ID NO 411
<211> LENGTH: 33
<212> TYPE: DNA
<213> ORGANISM: Artificial Sequence
<220> FEATURE:
<223> OTHER INFORMATION: Synthetic construct

<400> SEQUENCE: 411
gcggcctcga gtcaacgcca ctgccagcgg ttg                                   33

<210> SEQ ID NO 412
<211> LENGTH: 48
<212> TYPE: DNA
<213> ORGANISM: Artificial Sequence
<220> FEATURE:
<223> OTHER INFORMATION: Synthetic construct

<400> SEQUENCE: 412
cgcggatccc atatgaagaa gaacatattg gaattttggg tcggactg                   48

<210> SEQ ID NO 413
<211> LENGTH: 38
<212> TYPE: DNA
<213> ORGANISM: Artificial Sequence
<220> FEATURE:
<223> OTHER INFORMATION: Synthetic construct

<400> SEQUENCE: 413
cccgctcgag ttattcggcg gcttttccg cattgccg                               38

<210> SEQ ID NO 414
<211> LENGTH: 103
<212> TYPE: DNA
<213> ORGANISM: Artificial Sequence
<220> FEATURE:
<223> OTHER INFORMATION: Synthetic construct

<400> SEQUENCE: 414
gggaattcca tatgaaaaag acagctatcg cgattgcagt ggcactggct ggtttcgcta      60
ccgtagcgca ggccgctagc gctttccgcg tggccggcgg tgc                       103

<210> SEQ ID NO 415
<211> LENGTH: 38
<212> TYPE: DNA
<213> ORGANISM: Artificial Sequence
<220> FEATURE:
<223> OTHER INFORMATION: Synthetic construct

<400> SEQUENCE: 415
cccgctcgag ttattcggcg gcttttccg cattgccg                               38

<210> SEQ ID NO 416
<211> LENGTH: 32
<212> TYPE: DNA
<213> ORGANISM: Artificial Sequence
<220> FEATURE:
<223> OTHER INFORMATION: Synthetic construct

<400> SEQUENCE: 416
catgccatgg ctttccgcgt ggccggcggt gc                                    32
```

<210> SEQ ID NO 417
<211> LENGTH: 38
<212> TYPE: DNA
<213> ORGANISM: Artificial Sequence
<220> FEATURE:
<223> OTHER INFORMATION: Synthetic construct

<400> SEQUENCE: 417
cccgctcgag ttattcggcg gctttttccg cattgccg                             38

<210> SEQ ID NO 418
<211> LENGTH: 31
<212> TYPE: DNA
<213> ORGANISM: Artificial Sequence
<220> FEATURE:
<223> OTHER INFORMATION: Synthetic construct

<400> SEQUENCE: 418
cgcggatccc atatgtttgc cgaaacccgc c                                    31

<210> SEQ ID NO 419
<211> LENGTH: 28
<212> TYPE: DNA
<213> ORGANISM: Artificial Sequence
<220> FEATURE:
<223> OTHER INFORMATION: Synthetic construct

<400> SEQUENCE: 419
cccgctcgag aggttgtgtt ccaggttg                                        28

<210> SEQ ID NO 420
<211> LENGTH: 31
<212> TYPE: DNA
<213> ORGANISM: Artificial Sequence
<220> FEATURE:
<223> OTHER INFORMATION: Synthetic construct

<400> SEQUENCE: 420
cgcggatccc atatgaaaaa aaccgcctat g                                    31

<210> SEQ ID NO 421
<211> LENGTH: 28
<212> TYPE: DNA
<213> ORGANISM: Artificial Sequence
<220> FEATURE:
<223> OTHER INFORMATION: Synthetic construct

<400> SEQUENCE: 421
cccgctcgag ttaaggttgt gttccagg                                        28

<210> SEQ ID NO 422
<211> LENGTH: 33
<212> TYPE: DNA
<213> ORGANISM: Artificial Sequence
<220> FEATURE:
<223> OTHER INFORMATION: Synthetic construct

<400> SEQUENCE: 422
cgcggatccc atatgaaaaa atacctattc cgc                                  33

<210> SEQ ID NO 423
<211> LENGTH: 27
<212> TYPE: DNA
<213> ORGANISM: Artificial Sequence
<220> FEATURE:
<223> OTHER INFORMATION: Synthetic construct

<400> SEQUENCE: 423
cccgctcgag ttacgggcgg tattcgg                                              27

<210> SEQ ID NO 424
<211> LENGTH: 34
<212> TYPE: DNA
<213> ORGANISM: Artificial Sequence
<220> FEATURE:
<223> OTHER INFORMATION: Synthetic construct

<400> SEQUENCE: 424
cgcggatccc atatgcaaag caagagcatc caaa                                      34

<210> SEQ ID NO 425
<211> LENGTH: 27
<212> TYPE: DNA
<213> ORGANISM: Artificial Sequence
<220> FEATURE:
<223> OTHER INFORMATION: Synthetic construct

<400> SEQUENCE: 425
cccgctcgag ttacgggcgg tattcgg                                              27

<210> SEQ ID NO 426
<211> LENGTH: 86
<212> TYPE: DNA
<213> ORGANISM: Artificial Sequence
<220> FEATURE:
<223> OTHER INFORMATION: Synthetic construct

<400> SEQUENCE: 426
gggaattcca tatgaaaacc ttcttcaaaa ccctttccgc cgccgcgcta gcgctcatcc          60
tcgccgcctg ccaaagcaag agcatc                                              86

<210> SEQ ID NO 427
<211> LENGTH: 38
<212> TYPE: DNA
<213> ORGANISM: Artificial Sequence
<220> FEATURE:
<223> OTHER INFORMATION: Synthetic construct

<400> SEQUENCE: 427
cccgctcgag ttacgggcgg tattcgggct tcataccg                                  38

<210> SEQ ID NO 428
<211> LENGTH: 33
<212> TYPE: DNA
<213> ORGANISM: Artificial Sequence
<220> FEATURE:
<223> OTHER INFORMATION: Synthetic construct

<400> SEQUENCE: 428
cgcggatccg tcgactgtgg gggcggcggt ggc                                       33

<210> SEQ ID NO 429
<211> LENGTH: 31
<212> TYPE: DNA
<213> ORGANISM: Artificial Sequence
<220> FEATURE:
<223> OTHER INFORMATION: Synthetic construct

<400> SEQUENCE: 429
cccgctcgag tcaatcctgc tcttttttgc c                                         31

```
<210> SEQ ID NO 430
<211> LENGTH: 30
<212> TYPE: DNA
<213> ORGANISM: Artificial Sequence
<220> FEATURE:
<223> OTHER INFORMATION: Synthetic construct

<400> SEQUENCE: 430
gcggccatat gaagaaaaca ttgacactgc                                    30

<210> SEQ ID NO 431
<211> LENGTH: 32
<212> TYPE: DNA
<213> ORGANISM: Artificial Sequence
<220> FEATURE:
<223> OTHER INFORMATION: Synthetic construct

<400> SEQUENCE: 431
gcggcctcga gttaatggtg cgaatgaccg at                                 32

<210> SEQ ID NO 432
<211> LENGTH: 46
<212> TYPE: DNA
<213> ORGANISM: Artificial Sequence
<220> FEATURE:
<223> OTHER INFORMATION: Synthetic construct

<400> SEQUENCE: 432
ggggacaagt ttgtacaaaa aagcaggctt gcggcaagga tgccgg                  46

<210> SEQ ID NO 433
<211> LENGTH: 47
<212> TYPE: DNA
<213> ORGANISM: Artificial Sequence
<220> FEATURE:
<223> OTHER INFORMATION: Synthetic construct

<400> SEQUENCE: 433
ggggaccact ttgtacaaga aagctgggtc taaagcaaca atgccgg                 47

<210> SEQ ID NO 434
<211> LENGTH: 30
<212> TYPE: DNA
<213> ORGANISM: Artificial Sequence
<220> FEATURE:
<223> OTHER INFORMATION: Synthetic construct

<400> SEQUENCE: 434
cgcggatccc atatgaaaca caccgtatcc                                    30

<210> SEQ ID NO 435
<211> LENGTH: 26
<212> TYPE: DNA
<213> ORGANISM: Artificial Sequence
<220> FEATURE:
<223> OTHER INFORMATION: Synthetic construct

<400> SEQUENCE: 435
cccgctcgag ttatctcgtg cgcgcc                                        26

<210> SEQ ID NO 436
<211> LENGTH: 30
<212> TYPE: DNA
<213> ORGANISM: Artificial Sequence
<220> FEATURE:
<223> OTHER INFORMATION: Synthetic construct
```

<400> SEQUENCE: 436
cgcggatccc atatgagccc cgcgccgatt                                         30

<210> SEQ ID NO 437
<211> LENGTH: 28
<212> TYPE: DNA
<213> ORGANISM: Artificial Sequence
<220> FEATURE:
<223> OTHER INFORMATION: Synthetic construct

<400> SEQUENCE: 437
cccgctcgag tttttgtgcg gtcaggcg                                           28

<210> SEQ ID NO 438
<211> LENGTH: 62
<212> TYPE: DNA
<213> ORGANISM: Artificial Sequence
<220> FEATURE:
<223> OTHER INFORMATION: Synthetic construct

<400> SEQUENCE: 438
ggggacaagt ttgtacaaaa aagcaggctt gttcgtttgg gggatttaaa ccaaaccaaa        60
tc                                                                       62

<210> SEQ ID NO 439
<211> LENGTH: 30
<212> TYPE: DNA
<213> ORGANISM: Artificial Sequence
<220> FEATURE:
<223> OTHER INFORMATION: Synthetic construct

<400> SEQUENCE: 439
cgcggatccc atatggcgga tgcgcccgcg                                         30

<210> SEQ ID NO 440
<211> LENGTH: 26
<212> TYPE: DNA
<213> ORGANISM: Artificial Sequence
<220> FEATURE:
<223> OTHER INFORMATION: Synthetic construct

<400> SEQUENCE: 440
cccgctcgag aaaccgccaa tccgcc                                             26

<210> SEQ ID NO 441
<211> LENGTH: 61
<212> TYPE: DNA
<213> ORGANISM: Artificial Sequence
<220> FEATURE:
<223> OTHER INFORMATION: Synthetic construct

<400> SEQUENCE: 441
ggggaccact ttgtacaaga aagctgggtt cattttgttt ttccttcttc tcgaggccat        60
t                                                                        61

<210> SEQ ID NO 442
<211> LENGTH: 30
<212> TYPE: DNA
<213> ORGANISM: Artificial Sequence
<220> FEATURE:
<223> OTHER INFORMATION: Synthetic construct

<400> SEQUENCE: 442

```
cgcggatccc atatgaaacc caaaccgcac                                               30

<210> SEQ ID NO 443
<211> LENGTH: 27
<212> TYPE: DNA
<213> ORGANISM: Artificial Sequence
<220> FEATURE:
<223> OTHER INFORMATION: Synthetic construct

<400> SEQUENCE: 443
cccgctcgag tcagcgttgg acgtagt                                                  27

<210> SEQ ID NO 444
<211> LENGTH: 33
<212> TYPE: DNA
<213> ORGANISM: Artificial Sequence
<220> FEATURE:
<223> OTHER INFORMATION: Synthetic construct

<400> SEQUENCE: 444
gggaattcca tatgaaaaaa atcatcttcg ccg                                           33

<210> SEQ ID NO 445
<211> LENGTH: 31
<212> TYPE: DNA
<213> ORGANISM: Artificial Sequence
<220> FEATURE:
<223> OTHER INFORMATION: Synthetic construct

<400> SEQUENCE: 445
cccgctcgag ttattgtttg gctgcctcga t                                             31

<210> SEQ ID NO 446
<211> LENGTH: 33
<212> TYPE: DNA
<213> ORGANISM: Artificial Sequence
<220> FEATURE:
<223> OTHER INFORMATION: Synthetic construct

<400> SEQUENCE: 446
gggaattcca tatggccacc tacaaagtgg acg                                           33

<210> SEQ ID NO 447
<211> LENGTH: 30
<212> TYPE: DNA
<213> ORGANISM: Artificial Sequence
<220> FEATURE:
<223> OTHER INFORMATION: Synthetic construct

<400> SEQUENCE: 447
cggggatcct tgtttggctg cctcgatttg                                               30

<210> SEQ ID NO 448
<211> LENGTH: 34
<212> TYPE: DNA
<213> ORGANISM: Artificial Sequence
<220> FEATURE:
<223> OTHER INFORMATION: Synthetic construct

<400> SEQUENCE: 448
cgcggatccc atatgcaaga acaatcgcag aaag                                          34

<210> SEQ ID NO 449
<211> LENGTH: 30
<212> TYPE: DNA
<213> ORGANISM: Artificial Sequence
```

-continued

```
<220> FEATURE:
<223> OTHER INFORMATION: Synthetic construct

<400> SEQUENCE: 449
cccgctcgag ttttttcggc aaattggctt                                          30

<210> SEQ ID NO 450
<211> LENGTH: 45
<212> TYPE: DNA
<213> ORGANISM: Artificial Sequence
<220> FEATURE:
<223> OTHER INFORMATION: Synthetic construct

<400> SEQUENCE: 450
ggggacaagt ttgtacaaaa aagcaggctg ccgatgccgt tgcgg                         45

<210> SEQ ID NO 451
<211> LENGTH: 47
<212> TYPE: DNA
<213> ORGANISM: Artificial Sequence
<220> FEATURE:
<223> OTHER INFORMATION: Synthetic construct

<400> SEQUENCE: 451
ggggaccact ttgtacaaga aagctgggtt cagggtcgtt tgttgcg                       47

<210> SEQ ID NO 452
<211> LENGTH: 30
<212> TYPE: DNA
<213> ORGANISM: Artificial Sequence
<220> FEATURE:
<223> OTHER INFORMATION: Synthetic construct

<400> SEQUENCE: 452
cgcggatccc atatgaaaca ctttccatcc                                          30

<210> SEQ ID NO 453
<211> LENGTH: 28
<212> TYPE: DNA
<213> ORGANISM: Artificial Sequence
<220> FEATURE:
<223> OTHER INFORMATION: Synthetic construct

<400> SEQUENCE: 453
cccgctcgag ttaccactcg taattgac                                            28

<210> SEQ ID NO 454
<211> LENGTH: 30
<212> TYPE: DNA
<213> ORGANISM: Artificial Sequence
<220> FEATURE:
<223> OTHER INFORMATION: Synthetic construct

<400> SEQUENCE: 454
cgcggatccc atatggccac aagcgacgac                                          30

<210> SEQ ID NO 455
<211> LENGTH: 28
<212> TYPE: DNA
<213> ORGANISM: Artificial Sequence
<220> FEATURE:
<223> OTHER INFORMATION: Synthetic construct

<400> SEQUENCE: 455
cccgctcgag ttaccactcg taattgac                                            28
```

```
<210> SEQ ID NO 456
<211> LENGTH: 28
<212> TYPE: DNA
<213> ORGANISM: Artificial Sequence
<220> FEATURE:
<223> OTHER INFORMATION: Synthetic construct

<400> SEQUENCE: 456
cgcggatccc atatggccac aaacgacg                                      28

<210> SEQ ID NO 457
<211> LENGTH: 28
<212> TYPE: DNA
<213> ORGANISM: Artificial Sequence
<220> FEATURE:
<223> OTHER INFORMATION: Synthetic construct

<400> SEQUENCE: 457
cccgctcgag acccacgttg taaggttg                                      28

<210> SEQ ID NO 458
<211> LENGTH: 32
<212> TYPE: DNA
<213> ORGANISM: Artificial Sequence
<220> FEATURE:
<223> OTHER INFORMATION: Synthetic construct

<400> SEQUENCE: 458
cgcggatccc atatggccac aagcgacgac ga                                 32

<210> SEQ ID NO 459
<211> LENGTH: 28
<212> TYPE: DNA
<213> ORGANISM: Artificial Sequence
<220> FEATURE:
<223> OTHER INFORMATION: Synthetic construct

<400> SEQUENCE: 459
cccgctcgag acccacgttg taaggttg                                      28

<210> SEQ ID NO 460
<211> LENGTH: 33
<212> TYPE: DNA
<213> ORGANISM: Artificial Sequence
<220> FEATURE:
<223> OTHER INFORMATION: Synthetic construct

<400> SEQUENCE: 460
cgcggatccc atatgatgaa acactttcca tcc                                33

<210> SEQ ID NO 461
<211> LENGTH: 29
<212> TYPE: DNA
<213> ORGANISM: Artificial Sequence
<220> FEATURE:
<223> OTHER INFORMATION: Synthetic construct

<400> SEQUENCE: 461
cccgctcgag ttaacccacg ttgtaaggt                                     29

<210> SEQ ID NO 462
<211> LENGTH: 33
<212> TYPE: DNA
<213> ORGANISM: Artificial Sequence
<220> FEATURE:
<223> OTHER INFORMATION: Synthetic construct
```

```
<400> SEQUENCE: 462
cgcggatccc atatgatgaa acactttcca tcc                                   33

<210> SEQ ID NO 463
<211> LENGTH: 29
<212> TYPE: DNA
<213> ORGANISM: Artificial Sequence
<220> FEATURE:
<223> OTHER INFORMATION: Synthetic construct

<400> SEQUENCE: 463
cccgctcgag ttaacccacg ttgtaaggt                                        29

<210> SEQ ID NO 464
<211> LENGTH: 28
<212> TYPE: DNA
<213> ORGANISM: Artificial Sequence
<220> FEATURE:
<223> OTHER INFORMATION: Synthetic construct

<400> SEQUENCE: 464
cgcggatccc atatggccac aaacgacg                                         28

<210> SEQ ID NO 465
<211> LENGTH: 29
<212> TYPE: DNA
<213> ORGANISM: Artificial Sequence
<220> FEATURE:
<223> OTHER INFORMATION: Synthetic construct

<400> SEQUENCE: 465
cccgctcgag gtctgacact gttttatcc                                        29

<210> SEQ ID NO 466
<211> LENGTH: 33
<212> TYPE: DNA
<213> ORGANISM: Artificial Sequence
<220> FEATURE:
<223> OTHER INFORMATION: Synthetic construct

<400> SEQUENCE: 466
cgcggatccc atatgatgaa acactttcca tcc                                   33

<210> SEQ ID NO 467
<211> LENGTH: 29
<212> TYPE: DNA
<213> ORGANISM: Artificial Sequence
<220> FEATURE:
<223> OTHER INFORMATION: Synthetic construct

<400> SEQUENCE: 467
cccgctcgag ttatgctttg gcggcaaag                                        29

<210> SEQ ID NO 468
<211> LENGTH: 30
<212> TYPE: DNA
<213> ORGANISM: Artificial Sequence
<220> FEATURE:
<223> OTHER INFORMATION: Synthetic construct

<400> SEQUENCE: 468
cgcggatccc atatggccac aaacgacgac                                       30

<210> SEQ ID NO 469
```

```
<211> LENGTH: 27
<212> TYPE: DNA
<213> ORGANISM: Artificial Sequence
<220> FEATURE:
<223> OTHER INFORMATION: Synthetic construct

<400> SEQUENCE: 469
cgcggatccc cactcgtaat tgacgcc                                        27

<210> SEQ ID NO 470
<211> LENGTH: 30
<212> TYPE: DNA
<213> ORGANISM: Artificial Sequence
<220> FEATURE:
<223> OTHER INFORMATION: Synthetic construct

<400> SEQUENCE: 470
cgcggatccc atatggccac aagcgacgac                                     30

<210> SEQ ID NO 471
<211> LENGTH: 27
<212> TYPE: DNA
<213> ORGANISM: Artificial Sequence
<220> FEATURE:
<223> OTHER INFORMATION: Synthetic construct

<400> SEQUENCE: 471
cgcggatccc cactcgtaat tgacgcc                                        27

<210> SEQ ID NO 472
<211> LENGTH: 30
<212> TYPE: DNA
<213> ORGANISM: Artificial Sequence
<220> FEATURE:
<223> OTHER INFORMATION: Synthetic construct

<400> SEQUENCE: 472
cgcggatccc atatggccac aaacgacgac                                     30

<210> SEQ ID NO 473
<211> LENGTH: 27
<212> TYPE: DNA
<213> ORGANISM: Artificial Sequence
<220> FEATURE:
<223> OTHER INFORMATION: Synthetic construct

<400> SEQUENCE: 473
cgcggatcca cccacgttgt aaggttg                                        27

<210> SEQ ID NO 474
<211> LENGTH: 33
<212> TYPE: DNA
<213> ORGANISM: Artificial Sequence
<220> FEATURE:
<223> OTHER INFORMATION: Synthetic construct

<400> SEQUENCE: 474
cgcggatccc atatgatgaa acactttcca tcc                                 33

<210> SEQ ID NO 475
<211> LENGTH: 27
<212> TYPE: DNA
<213> ORGANISM: Artificial Sequence
<220> FEATURE:
<223> OTHER INFORMATION: Synthetic construct

<400> SEQUENCE: 475
```

```
cgcggatcca cccacgttgt aaggttg                                          27

<210> SEQ ID NO 476
<211> LENGTH: 25
<212> TYPE: DNA
<213> ORGANISM: Artificial Sequence
<220> FEATURE:
<223> OTHER INFORMATION: Synthetic construct

<400> SEQUENCE: 476
cgcggatccg gagggggtgg tgtcg                                            25

<210> SEQ ID NO 477
<211> LENGTH: 27
<212> TYPE: DNA
<213> ORGANISM: Artificial Sequence
<220> FEATURE:
<223> OTHER INFORMATION: Synthetic construct

<400> SEQUENCE: 477
cccgctcgag ttgcttggcg gcaaggc                                          27

<210> SEQ ID NO 478
<211> LENGTH: 25
<212> TYPE: DNA
<213> ORGANISM: Artificial Sequence
<220> FEATURE:
<223> OTHER INFORMATION: Synthetic construct

<400> SEQUENCE: 478
cgcggatccg gcggaggcgg cactt                                            25

<210> SEQ ID NO 479
<211> LENGTH: 26
<212> TYPE: DNA
<213> ORGANISM: Artificial Sequence
<220> FEATURE:
<223> OTHER INFORMATION: Synthetic construct

<400> SEQUENCE: 479
cccgctcgag gaaccggtag cctacg                                           26

<210> SEQ ID NO 480
<211> LENGTH: 41
<212> TYPE: DNA
<213> ORGANISM: Artificial Sequence
<220> FEATURE:
<223> OTHER INFORMATION: Synthetic construct

<400> SEQUENCE: 480
cgcggatccg gtggtggtgg ttcagatttg gcaaacgatt c                          41

<210> SEQ ID NO 481
<211> LENGTH: 29
<212> TYPE: DNA
<213> ORGANISM: Artificial Sequence
<220> FEATURE:
<223> OTHER INFORMATION: Synthetic construct

<400> SEQUENCE: 481
cccgctcgag cgtatcatat ttcacgtgc                                        29

<210> SEQ ID NO 482
<211> LENGTH: 25
<212> TYPE: DNA
```

<213> ORGANISM: Artificial Sequence
<220> FEATURE:
<223> OTHER INFORMATION: Synthetic construct

<400> SEQUENCE: 482
cgcggatccg gagggggtgg tgtcg                                    25

<210> SEQ ID NO 483
<211> LENGTH: 28
<212> TYPE: DNA
<213> ORGANISM: Artificial Sequence
<220> FEATURE:
<223> OTHER INFORMATION: Synthetic construct

<400> SEQUENCE: 483
cccgctcgag ttattgcttg gcggcaag                                 28

<210> SEQ ID NO 484
<211> LENGTH: 25
<212> TYPE: DNA
<213> ORGANISM: Artificial Sequence
<220> FEATURE:
<223> OTHER INFORMATION: Synthetic construct

<400> SEQUENCE: 484
cgcggatccg gcggaggcgg cactt                                    25

<210> SEQ ID NO 485
<211> LENGTH: 28
<212> TYPE: DNA
<213> ORGANISM: Artificial Sequence
<220> FEATURE:
<223> OTHER INFORMATION: Synthetic construct

<400> SEQUENCE: 485
cccgctcgag tcagaaccgg tagcctac                                 28

<210> SEQ ID NO 486
<211> LENGTH: 41
<212> TYPE: DNA
<213> ORGANISM: Artificial Sequence
<220> FEATURE:
<223> OTHER INFORMATION: Synthetic construct

<400> SEQUENCE: 486
cgcggatccg gtggtggtgg ttcagatttg gcaaacgatt c                  41

<210> SEQ ID NO 487
<211> LENGTH: 32
<212> TYPE: DNA
<213> ORGANISM: Artificial Sequence
<220> FEATURE:
<223> OTHER INFORMATION: Synthetic construct

<400> SEQUENCE: 487
cccgctcgag ttacgtatca tatttcacgt gc                            32

<210> SEQ ID NO 488
<211> LENGTH: 31
<212> TYPE: DNA
<213> ORGANISM: Artificial Sequence
<220> FEATURE:
<223> OTHER INFORMATION: Synthetic construct

<400> SEQUENCE: 488
cgcggatccc atatggccac aagcgacgac g                             31

```
<210> SEQ ID NO 489
<211> LENGTH: 28
<212> TYPE: DNA
<213> ORGANISM: Artificial Sequence
<220> FEATURE:
<223> OTHER INFORMATION: Synthetic construct

<400> SEQUENCE: 489
cccgctcgag ccactcgtaa ttgacgcc                                28

<210> SEQ ID NO 490
<211> LENGTH: 30
<212> TYPE: DNA
<213> ORGANISM: Artificial Sequence
<220> FEATURE:
<223> OTHER INFORMATION: Synthetic construct

<400> SEQUENCE: 490
cgcggatccc atatggccac aaacgacgac                              30

<210> SEQ ID NO 491
<211> LENGTH: 28
<212> TYPE: DNA
<213> ORGANISM: Artificial Sequence
<220> FEATURE:
<223> OTHER INFORMATION: Synthetic construct

<400> SEQUENCE: 491
cccgctcgag tgctttggcg gcaaagtt                                28

<210> SEQ ID NO 492
<211> LENGTH: 30
<212> TYPE: DNA
<213> ORGANISM: Artificial Sequence
<220> FEATURE:
<223> OTHER INFORMATION: Synthetic construct

<400> SEQUENCE: 492
cgcggatccc atatggccac aaacgacgac                              30

<210> SEQ ID NO 493
<211> LENGTH: 37
<212> TYPE: DNA
<213> ORGANISM: Artificial Sequence
<220> FEATURE:
<223> OTHER INFORMATION: Synthetic construct

<400> SEQUENCE: 493
cccgctcgag tttagcaata ttatctttgt tcgtagc                      37

<210> SEQ ID NO 494
<211> LENGTH: 32
<212> TYPE: DNA
<213> ORGANISM: Artificial Sequence
<220> FEATURE:
<223> OTHER INFORMATION: Synthetic construct

<400> SEQUENCE: 494
cgcggatccc atatgaaagc aaaccgtgcc ga                           32

<210> SEQ ID NO 495
<211> LENGTH: 28
<212> TYPE: DNA
<213> ORGANISM: Artificial Sequence
<220> FEATURE:
```

<223> OTHER INFORMATION: Synthetic construct

<400> SEQUENCE: 495
cccgctcgag ccactcgtaa ttgacgcc                                28

<210> SEQ ID NO 496
<211> LENGTH: 61
<212> TYPE: DNA
<213> ORGANISM: Artificial Sequence
<220> FEATURE:
<223> OTHER INFORMATION: Synthetic construct

<400> SEQUENCE: 496
ggggacaagt ttgtacaaaa aagcaggctg cagccacaaa cgacgacgat gttaaaaaag      60
c                                                             61

<210> SEQ ID NO 497
<211> LENGTH: 61
<212> TYPE: DNA
<213> ORGANISM: Artificial Sequence
<220> FEATURE:
<223> OTHER INFORMATION: Synthetic construct

<400> SEQUENCE: 497
ggggaccact ttgtacaaga aagctgggtt taccactcgt aattgacgcc gacatggtag      60
g                                                             61

<210> SEQ ID NO 498
<211> LENGTH: 31
<212> TYPE: DNA
<213> ORGANISM: Artificial Sequence
<220> FEATURE:
<223> OTHER INFORMATION: Synthetic construct

<400> SEQUENCE: 498
gcggccatat ggcagcaaaa gacgtacagt t                            31

<210> SEQ ID NO 499
<211> LENGTH: 33
<212> TYPE: DNA
<213> ORGANISM: Artificial Sequence
<220> FEATURE:
<223> OTHER INFORMATION: Synthetic construct

<400> SEQUENCE: 499
gcggcctcga gttacatcat gccgcccata cca                          33

<210> SEQ ID NO 500
<211> LENGTH: 31
<212> TYPE: DNA
<213> ORGANISM: Artificial Sequence
<220> FEATURE:
<223> OTHER INFORMATION: Synthetic construct

<400> SEQUENCE: 500
cgcggatccg ctagcttagg cggcggcgga g                            31

<210> SEQ ID NO 501
<211> LENGTH: 26
<212> TYPE: DNA
<213> ORGANISM: Artificial Sequence
<220> FEATURE:
<223> OTHER INFORMATION: Synthetic construct

<400> SEQUENCE: 501

```
cccgctcgag gaaccggtag cctacg                                          26

<210> SEQ ID NO 502
<211> LENGTH: 29
<212> TYPE: DNA
<213> ORGANISM: Artificial Sequence
<220> FEATURE:
<223> OTHER INFORMATION: Synthetic construct

<400> SEQUENCE: 502
cccctagcta gcacttctgc gcccgactt                                       29

<210> SEQ ID NO 503
<211> LENGTH: 26
<212> TYPE: DNA
<213> ORGANISM: Artificial Sequence
<220> FEATURE:
<223> OTHER INFORMATION: Synthetic construct

<400> SEQUENCE: 503
cccgctcgag gaaccggtag cctacg                                          26

<210> SEQ ID NO 504
<211> LENGTH: 31
<212> TYPE: DNA
<213> ORGANISM: Artificial Sequence
<220> FEATURE:
<223> OTHER INFORMATION: Synthetic construct

<400> SEQUENCE: 504
cgcggatccg ctagcttagg cggcggcgga g                                    31

<210> SEQ ID NO 505
<211> LENGTH: 26
<212> TYPE: DNA
<213> ORGANISM: Artificial Sequence
<220> FEATURE:
<223> OTHER INFORMATION: Synthetic construct

<400> SEQUENCE: 505
cccgctcgag gaaccggtag cctacg                                          26

<210> SEQ ID NO 506
<211> LENGTH: 32
<212> TYPE: DNA
<213> ORGANISM: Artificial Sequence
<220> FEATURE:
<223> OTHER INFORMATION: Synthetic construct

<400> SEQUENCE: 506
cgcggatccg ctagcacttc tgcgcccgac tt                                   32

<210> SEQ ID NO 507
<211> LENGTH: 26
<212> TYPE: DNA
<213> ORGANISM: Artificial Sequence
<220> FEATURE:
<223> OTHER INFORMATION: Synthetic construct

<400> SEQUENCE: 507
cccgctcgag gaaccggtag cctacg                                          26

<210> SEQ ID NO 508
<211> LENGTH: 50
<212> TYPE: DNA
```

```
<213> ORGANISM: Artificial Sequence
<220> FEATURE:
<223> OTHER INFORMATION: Synthetic construct

<400> SEQUENCE: 508
cgcggatccg ctagccgaac gaccccaacc ttccctacaa aaactttcaa            50

<210> SEQ ID NO 509
<211> LENGTH: 35
<212> TYPE: DNA
<213> ORGANISM: Artificial Sequence
<220> FEATURE:
<223> OTHER INFORMATION: Synthetic construct

<400> SEQUENCE: 509
cccgctcgag tcagaaccga cgtgccaagc cgttc                           35

<210> SEQ ID NO 510
<211> LENGTH: 32
<212> TYPE: DNA
<213> ORGANISM: Artificial Sequence
<220> FEATURE:
<223> OTHER INFORMATION: Synthetic construct

<400> SEQUENCE: 510
gccgccatat gcccccactg gaagaacgga cg                              32

<210> SEQ ID NO 511
<211> LENGTH: 35
<212> TYPE: DNA
<213> ORGANISM: Artificial Sequence
<220> FEATURE:
<223> OTHER INFORMATION: Synthetic construct

<400> SEQUENCE: 511
gccgcctcga gtaataaacc ttctatgggc agcag                           35

<210> SEQ ID NO 512
<211> LENGTH: 31
<212> TYPE: DNA
<213> ORGANISM: Artificial Sequence
<220> FEATURE:
<223> OTHER INFORMATION: Synthetic construct

<400> SEQUENCE: 512
cgcggatccc atatgtccgt ccacgcatcc g                               31

<210> SEQ ID NO 513
<211> LENGTH: 31
<212> TYPE: DNA
<213> ORGANISM: Artificial Sequence
<220> FEATURE:
<223> OTHER INFORMATION: Synthetic construct

<400> SEQUENCE: 513
cccgctcgag tttgaatttg taggtgtatt g                               31

<210> SEQ ID NO 514
<211> LENGTH: 29
<212> TYPE: DNA
<213> ORGANISM: Artificial Sequence
<220> FEATURE:
<223> OTHER INFORMATION: Synthetic construct

<400> SEQUENCE: 514
cgcggatccc atatgacccc ttccgcact                                  29
```

<210> SEQ ID NO 515
<211> LENGTH: 32
<212> TYPE: DNA
<213> ORGANISM: Artificial Sequence
<220> FEATURE:
<223> OTHER INFORMATION: Synthetic construct

<400> SEQUENCE: 515
cccgctcgag ttatttgaat ttgtaggtgt at                           32

<210> SEQ ID NO 516
<211> LENGTH: 33
<212> TYPE: DNA
<213> ORGANISM: Artificial Sequence
<220> FEATURE:
<223> OTHER INFORMATION: Synthetic construct

<400> SEQUENCE: 516
cgcggatccc atatgaaaac caattcagaa gaa                          33

<210> SEQ ID NO 517
<211> LENGTH: 28
<212> TYPE: DNA
<213> ORGANISM: Artificial Sequence
<220> FEATURE:
<223> OTHER INFORMATION: Synthetic construct

<400> SEQUENCE: 517
cccgctcgag tccacagaga ttgtttcc                               28

<210> SEQ ID NO 518
<211> LENGTH: 17
<212> TYPE: DNA
<213> ORGANISM: Artificial Sequence
<220> FEATURE:
<223> OTHER INFORMATION: Synthetic construct

<400> SEQUENCE: 518
gatgcccgaa gggcggg                                            17

<210> SEQ ID NO 519
<211> LENGTH: 29
<212> TYPE: DNA
<213> ORGANISM: Artificial Sequence
<220> FEATURE:
<223> OTHER INFORMATION: Synthetic construct

<400> SEQUENCE: 519
gcccaagctt tcagaagaag acttcacgc                              29

<210> SEQ ID NO 520
<211> LENGTH: 36
<212> TYPE: DNA
<213> ORGANISM: Artificial Sequence
<220> FEATURE:
<223> OTHER INFORMATION: Synthetic construct

<400> SEQUENCE: 520
cgcggatccc atatgcaaac ccataaatac gctatt                       36

<210> SEQ ID NO 521
<211> LENGTH: 29
<212> TYPE: DNA
<213> ORGANISM: Artificial Sequence
<220> FEATURE:

<223> OTHER INFORMATION: Synthetic construct

<400> SEQUENCE: 521
gcccaagctt gaagaagact tcacgccag                                         29

<210> SEQ ID NO 522
<211> LENGTH: 35
<212> TYPE: DNA
<213> ORGANISM: Artificial Sequence
<220> FEATURE:
<223> OTHER INFORMATION: Synthetic construct

<400> SEQUENCE: 522
cgcggatccc atatggtctt tttcgacaat accga                                  35

<210> SEQ ID NO 523
<211> LENGTH: 10
<212> TYPE: DNA
<213> ORGANISM: Artificial Sequence
<220> FEATURE:
<223> OTHER INFORMATION: Synthetic construct

<400> SEQUENCE: 523
gcccaagctt                                                              10

<210> SEQ ID NO 524
<211> LENGTH: 36
<212> TYPE: DNA
<213> ORGANISM: Artificial Sequence
<220> FEATURE:
<223> OTHER INFORMATION: Synthetic construct

<400> SEQUENCE: 524
cgcggatccc atatgaataa aactttaaaa aggcgg                                 36

<210> SEQ ID NO 525
<211> LENGTH: 29
<212> TYPE: DNA
<213> ORGANISM: Artificial Sequence
<220> FEATURE:
<223> OTHER INFORMATION: Synthetic construct

<400> SEQUENCE: 525
gcccaagctt tcagaagaag acttcacgc                                         29

<210> SEQ ID NO 526
<211> LENGTH: 35
<212> TYPE: DNA
<213> ORGANISM: Artificial Sequence
<220> FEATURE:
<223> OTHER INFORMATION: Synthetic construct

<400> SEQUENCE: 526
cgcgaatccc atatgttcga tcttgattct gtcga                                  35

<210> SEQ ID NO 527
<211> LENGTH: 28
<212> TYPE: DNA
<213> ORGANISM: Artificial Sequence
<220> FEATURE:
<223> OTHER INFORMATION: Synthetic construct

<400> SEQUENCE: 527
cccgctcgag tcgcacaggc tgttggcg                                          28

```
<210> SEQ ID NO 528
<211> LENGTH: 32
<212> TYPE: DNA
<213> ORGANISM: Artificial Sequence
<220> FEATURE:
<223> OTHER INFORMATION: Synthetic construct

<400> SEQUENCE: 528
cgcgaatccc atatgttggg cggaggcggc ag                                    32

<210> SEQ ID NO 529
<211> LENGTH: 28
<212> TYPE: DNA
<213> ORGANISM: Artificial Sequence
<220> FEATURE:
<223> OTHER INFORMATION: Synthetic construct

<400> SEQUENCE: 529
cccgctcgag tcgcacaggc tgttggcg                                         28

<210> SEQ ID NO 530
<211> LENGTH: 32
<212> TYPE: DNA
<213> ORGANISM: Artificial Sequence
<220> FEATURE:
<223> OTHER INFORMATION: Synthetic construct

<400> SEQUENCE: 530
cgcgaatccc atatgttggg cggaggcggc ag                                    32

<210> SEQ ID NO 531
<211> LENGTH: 28
<212> TYPE: DNA
<213> ORGANISM: Artificial Sequence
<220> FEATURE:
<223> OTHER INFORMATION: Synthetic construct

<400> SEQUENCE: 531
cccgctcgag tcgcacaggc tgttggcg                                         28

<210> SEQ ID NO 532
<211> LENGTH: 33
<212> TYPE: DNA
<213> ORGANISM: Artificial Sequence
<220> FEATURE:
<223> OTHER INFORMATION: Synthetic construct

<400> SEQUENCE: 532
cgcggatccc atatggcaaa tttggaggtg cgc                                   33

<210> SEQ ID NO 533
<211> LENGTH: 27
<212> TYPE: DNA
<213> ORGANISM: Artificial Sequence
<220> FEATURE:
<223> OTHER INFORMATION: Synthetic construct

<400> SEQUENCE: 533
cccgctcgag ttcggagcgg ttgaagc                                          27

<210> SEQ ID NO 534
<211> LENGTH: 34
<212> TYPE: DNA
<213> ORGANISM: Artificial Sequence
<220> FEATURE:
<223> OTHER INFORMATION: Synthetic construct
```

```
<400> SEQUENCE: 534
cgcggatccc atatgcaacg tcgtattata accc                          34

<210> SEQ ID NO 535
<211> LENGTH: 29
<212> TYPE: DNA
<213> ORGANISM: Artificial Sequence
<220> FEATURE:
<223> OTHER INFORMATION: Synthetic construct

<400> SEQUENCE: 535
cccgctcgag ttattcggag cggttgaag                                29

<210> SEQ ID NO 536
<211> LENGTH: 42
<212> TYPE: DNA
<213> ORGANISM: Artificial Sequence
<220> FEATURE:
<223> OTHER INFORMATION: Synthetic construct

<400> SEQUENCE: 536
cgcggatccc atatgggcat caaagtcgcc atcaacggct ac                 42

<210> SEQ ID NO 537
<211> LENGTH: 35
<212> TYPE: DNA
<213> ORGANISM: Artificial Sequence
<220> FEATURE:
<223> OTHER INFORMATION: Synthetic construct

<400> SEQUENCE: 537
cccgctcgag tttgagcggg cgcacttcaa gtccg                         35

<210> SEQ ID NO 538
<211> LENGTH: 33
<212> TYPE: DNA
<213> ORGANISM: Artificial Sequence
<220> FEATURE:
<223> OTHER INFORMATION: Synthetic construct

<400> SEQUENCE: 538
cgcggatccc atatgggcgg cagcgaaaaa aac                           33

<210> SEQ ID NO 539
<211> LENGTH: 28
<212> TYPE: DNA
<213> ORGANISM: Artificial Sequence
<220> FEATURE:
<223> OTHER INFORMATION: Synthetic construct

<400> SEQUENCE: 539
cccgctcgag gttggtgccg actttgat                                 28

<210> SEQ ID NO 540
<211> LENGTH: 31
<212> TYPE: DNA
<213> ORGANISM: Artificial Sequence
<220> FEATURE:
<223> OTHER INFORMATION: Synthetic construct

<400> SEQUENCE: 540
cgcggatccc atatgggcgg cggaagcgat a                             31

<210> SEQ ID NO 541
<211> LENGTH: 27
```

```
<212> TYPE: DNA
<213> ORGANISM: Artificial Sequence
<220> FEATURE:
<223> OTHER INFORMATION: Synthetic construct

<400> SEQUENCE: 541
cccgctcgag tttgcccgct ttgagcc                                    27

<210> SEQ ID NO 542
<211> LENGTH: 33
<212> TYPE: DNA
<213> ORGANISM: Artificial Sequence
<220> FEATURE:
<223> OTHER INFORMATION: Synthetic construct

<400> SEQUENCE: 542
cgcggatccc atatgggcaa atccgaaaat acg                             33

<210> SEQ ID NO 543
<211> LENGTH: 27
<212> TYPE: DNA
<213> ORGANISM: Artificial Sequence
<220> FEATURE:
<223> OTHER INFORMATION: Synthetic construct

<400> SEQUENCE: 543
cccgctcgag catcccgtac tgtttcg                                    27

<210> SEQ ID NO 544
<211> LENGTH: 62
<212> TYPE: DNA
<213> ORGANISM: Artificial Sequence
<220> FEATURE:
<223> OTHER INFORMATION: Synthetic construct

<400> SEQUENCE: 544
ggggacaagt tgtacaaaa aagcaggctc cgacattacc gtgtacaacg gccaacaaag   60
aa                                                                62

<210> SEQ ID NO 545
<211> LENGTH: 61
<212> TYPE: DNA
<213> ORGANISM: Artificial Sequence
<220> FEATURE:
<223> OTHER INFORMATION: Synthetic construct

<400> SEQUENCE: 545
ggggaccact tgtacaaga aagctgggtc ttatttcata ccggcttgct caagcagccg   60
g                                                                 61

<210> SEQ ID NO 546
<211> LENGTH: 61
<212> TYPE: DNA
<213> ORGANISM: Artificial Sequence
<220> FEATURE:
<223> OTHER INFORMATION: Synthetic construct

<400> SEQUENCE: 546
ggggacaagt tgtacaaaa aagcaggctg atacggtgtt ttcctgtaaa acggacaaca   60
a                                                                 61

<210> SEQ ID NO 547
<211> LENGTH: 60
<212> TYPE: DNA
```

<213> ORGANISM: Artificial Sequence
<220> FEATURE:
<223> OTHER INFORMATION: Synthetic construct

<400> SEQUENCE: 547
ggggaccact tgtacaaga aagctgggtc taggaaaaat cgtcatcgtt gaaattcgcc    60

<210> SEQ ID NO 548
<211> LENGTH: 47
<212> TYPE: DNA
<213> ORGANISM: Artificial Sequence
<220> FEATURE:
<223> OTHER INFORMATION: Synthetic construct

<400> SEQUENCE: 548
ggggacaagt tgtacaaaa aagcaggcta tgcaccccat cgaaacc    47

<210> SEQ ID NO 549
<211> LENGTH: 47
<212> TYPE: DNA
<213> ORGANISM: Artificial Sequence
<220> FEATURE:
<223> OTHER INFORMATION: Synthetic construct

<400> SEQUENCE: 549
ggggaccact tgtacaaga aagctgggtc tagtcttgca gtgcctc    47

<210> SEQ ID NO 550
<211> LENGTH: 41
<212> TYPE: DNA
<213> ORGANISM: Artificial Sequence
<220> FEATURE:
<223> OTHER INFORMATION: Synthetic construct

<400> SEQUENCE: 550
cgcggatccc atatgggaaa tttcttatat agaggcatta g    41

<210> SEQ ID NO 551
<211> LENGTH: 40
<212> TYPE: DNA
<213> ORGANISM: Artificial Sequence
<220> FEATURE:
<223> OTHER INFORMATION: Synthetic construct

<400> SEQUENCE: 551
cccgctcgag gttaatttct atcaactctt tagcaataat    40

<210> SEQ ID NO 552
<211> LENGTH: 31
<212> TYPE: DNA
<213> ORGANISM: Artificial Sequence
<220> FEATURE:
<223> OTHER INFORMATION: Synthetic construct

<400> SEQUENCE: 552
cgcggatccc atatggcctg ccaagacgac a    31

<210> SEQ ID NO 553
<211> LENGTH: 26
<212> TYPE: DNA
<213> ORGANISM: Artificial Sequence
<220> FEATURE:
<223> OTHER INFORMATION: Synthetic construct

<400> SEQUENCE: 553
cccgctcgag ccgcctcctg ccgaaa    26

<210> SEQ ID NO 554
<211> LENGTH: 34
<212> TYPE: DNA
<213> ORGANISM: Artificial Sequence
<220> FEATURE:
<223> OTHER INFORMATION: Synthetic construct

<400> SEQUENCE: 554
cgcggatccc atatggcaga gatctgtttg ataa                          34

<210> SEQ ID NO 555
<211> LENGTH: 27
<212> TYPE: DNA
<213> ORGANISM: Artificial Sequence
<220> FEATURE:
<223> OTHER INFORMATION: Synthetic construct

<400> SEQUENCE: 555
cccgctcgag cggttttccg cccaatg                                  27

<210> SEQ ID NO 556
<211> LENGTH: 30
<212> TYPE: DNA
<213> ORGANISM: Artificial Sequence
<220> FEATURE:
<223> OTHER INFORMATION: Synthetic construct

<400> SEQUENCE: 556
cgcggatccc atatgcagcc ggatacggtc                               30

<210> SEQ ID NO 557
<211> LENGTH: 30
<212> TYPE: DNA
<213> ORGANISM: Artificial Sequence
<220> FEATURE:
<223> OTHER INFORMATION: Synthetic construct

<400> SEQUENCE: 557
cccgctcgag aatcacttcc aacacaaaat                               30

<210> SEQ ID NO 558
<211> LENGTH: 33
<212> TYPE: DNA
<213> ORGANISM: Artificial Sequence
<220> FEATURE:
<223> OTHER INFORMATION: Synthetic construct

<400> SEQUENCE: 558
cgcggatccc atatgtggtt gctgatgaag ggc                           33

<210> SEQ ID NO 559
<211> LENGTH: 28
<212> TYPE: DNA
<213> ORGANISM: Artificial Sequence
<220> FEATURE:
<223> OTHER INFORMATION: Synthetic construct

<400> SEQUENCE: 559
cccgctcgag gactgcttca tcttctgc                                 28

<210> SEQ ID NO 560
<211> LENGTH: 34
<212> TYPE: DNA
<213> ORGANISM: Artificial Sequence
<220> FEATURE:

<223> OTHER INFORMATION: Synthetic construct

<400> SEQUENCE: 560
cgcggatccc atatggaact gatgactgtt ttgc					34

<210> SEQ ID NO 561
<211> LENGTH: 29
<212> TYPE: DNA
<213> ORGANISM: Artificial Sequence
<220> FEATURE:
<223> OTHER INFORMATION: Synthetic construct

<400> SEQUENCE: 561
cccgctcgag tcagactgct tcatcttct					29

<210> SEQ ID NO 562
<211> LENGTH: 45
<212> TYPE: DNA
<213> ORGANISM: Artificial Sequence
<220> FEATURE:
<223> OTHER INFORMATION: Synthetic construct

<400> SEQUENCE: 562
cgcggatccc atatgagcat taaagtagcg attaacggtt tcggc					45

<210> SEQ ID NO 563
<211> LENGTH: 40
<212> TYPE: DNA
<213> ORGANISM: Artificial Sequence
<220> FEATURE:
<223> OTHER INFORMATION: Synthetic construct

<400> SEQUENCE: 563
cccgctcgag gattttgcct gcgaagtatt ccaaagtgcg					40

<210> SEQ ID NO 564
<211> LENGTH: 32
<212> TYPE: DNA
<213> ORGANISM: Artificial Sequence
<220> FEATURE:
<223> OTHER INFORMATION: Synthetic construct

<400> SEQUENCE: 564
cgcggatccg ctagccccga tgttaaatcg gc					32

<210> SEQ ID NO 565
<211> LENGTH: 29
<212> TYPE: DNA
<213> ORGANISM: Artificial Sequence
<220> FEATURE:
<223> OTHER INFORMATION: Synthetic construct

<400> SEQUENCE: 565
cggggatcca tcctgctctt ttttgccgg					29

<210> SEQ ID NO 566
<211> LENGTH: 42
<212> TYPE: DNA
<213> ORGANISM: Artificial Sequence
<220> FEATURE:
<223> OTHER INFORMATION: Synthetic construct

<400> SEQUENCE: 566
cgcggatccg gtggtggtgg tcaaagcaag agcatccaaa cc					42

```
<210> SEQ ID NO 567
<211> LENGTH: 30
<212> TYPE: DNA
<213> ORGANISM: Artificial Sequence
<220> FEATURE:
<223> OTHER INFORMATION: Synthetic construct

<400> SEQUENCE: 567
cccaagcttt tcgggcggta ttcgggcttc                                    30

<210> SEQ ID NO 568
<211> LENGTH: 39
<212> TYPE: DNA
<213> ORGANISM: Artificial Sequence
<220> FEATURE:
<223> OTHER INFORMATION: Synthetic construct

<400> SEQUENCE: 568
cgcggatccg gtggtggtgg tgccacctac aaagtggac                          39

<210> SEQ ID NO 569
<211> LENGTH: 28
<212> TYPE: DNA
<213> ORGANISM: Artificial Sequence
<220> FEATURE:
<223> OTHER INFORMATION: Synthetic construct

<400> SEQUENCE: 569
gcccaagctt ttgtttggct gcctcgat                                      28

<210> SEQ ID NO 570
<211> LENGTH: 34
<212> TYPE: DNA
<213> ORGANISM: Artificial Sequence
<220> FEATURE:
<223> OTHER INFORMATION: Synthetic construct

<400> SEQUENCE: 570
cgcggatccg gtggtggtgg tacaagcgac gacg                               34

<210> SEQ ID NO 571
<211> LENGTH: 28
<212> TYPE: DNA
<213> ORGANISM: Artificial Sequence
<220> FEATURE:
<223> OTHER INFORMATION: Synthetic construct

<400> SEQUENCE: 571
gcccaagctt ccactcgtaa ttgacgcc                                      28

<210> SEQ ID NO 572
<211> LENGTH: 41
<212> TYPE: DNA
<213> ORGANISM: Artificial Sequence
<220> FEATURE:
<223> OTHER INFORMATION: Synthetic construct

<400> SEQUENCE: 572
cgcggatccg gtggtggtgg ttcagatttg gcaaacgatt c                       41

<210> SEQ ID NO 573
<211> LENGTH: 28
<212> TYPE: DNA
<213> ORGANISM: Artificial Sequence
<220> FEATURE:
<223> OTHER INFORMATION: Synthetic construct
```

```
<400> SEQUENCE: 573
cccaagcttc gtatcatatt tcacgtgc                                      28

<210> SEQ ID NO 574
<211> LENGTH: 44
<212> TYPE: DNA
<213> ORGANISM: Artificial Sequence
<220> FEATURE:
<223> OTHER INFORMATION: Synthetic construct

<400> SEQUENCE: 574
cccaagcttg gtggtggtgg tggttcagat ttggcaaacg attc                    44

<210> SEQ ID NO 575
<211> LENGTH: 29
<212> TYPE: DNA
<213> ORGANISM: Artificial Sequence
<220> FEATURE:
<223> OTHER INFORMATION: Synthetic construct

<400> SEQUENCE: 575
cccgctcgag cgtatcatat ttcacgtgc                                     29

<210> SEQ ID NO 576
<211> LENGTH: 45
<212> TYPE: DNA
<213> ORGANISM: Artificial Sequence
<220> FEATURE:
<223> OTHER INFORMATION: Synthetic construct

<400> SEQUENCE: 576
cccaagcttg gtggtggtgg tggtcaaagc aagagcatcc aaacc                   45

<210> SEQ ID NO 577
<211> LENGTH: 28
<212> TYPE: DNA
<213> ORGANISM: Artificial Sequence
<220> FEATURE:
<223> OTHER INFORMATION: Synthetic construct

<400> SEQUENCE: 577
cccgctcgag cgggcggtat tcgggctt                                      28

<210> SEQ ID NO 578
<211> LENGTH: 32
<212> TYPE: DNA
<213> ORGANISM: Artificial Sequence
<220> FEATURE:
<223> OTHER INFORMATION: Synthetic construct

<400> SEQUENCE: 578
cgcggatccg ctagccccga tgttaaatcg gc                                 32

<210> SEQ ID NO 579
<211> LENGTH: 29
<212> TYPE: DNA
<213> ORGANISM: Artificial Sequence
<220> FEATURE:
<223> OTHER INFORMATION: Synthetic construct

<400> SEQUENCE: 579
cggggatcca tcctgctctt ttttgccgg                                     29

<210> SEQ ID NO 580
<211> LENGTH: 36
```

<212> TYPE: DNA
<213> ORGANISM: Artificial Sequence
<220> FEATURE:
<223> OTHER INFORMATION: Synthetic construct

<400> SEQUENCE: 580
cgcggatccg ctagcggaca cacttatttc ggcatc                36

<210> SEQ ID NO 581
<211> LENGTH: 30
<212> TYPE: DNA
<213> ORGANISM: Artificial Sequence
<220> FEATURE:
<223> OTHER INFORMATION: Synthetic construct

<400> SEQUENCE: 581
cgcggatccc cagcggtagc ctaatttgat                30

<210> SEQ ID NO 582
<211> LENGTH: 41
<212> TYPE: DNA
<213> ORGANISM: Artificial Sequence
<220> FEATURE:
<223> OTHER INFORMATION: Synthetic construct

<400> SEQUENCE: 582
cgcggatccg gtggtggtgg ttcagatttg gcaaacgatt c                41

<210> SEQ ID NO 583
<211> LENGTH: 28
<212> TYPE: DNA
<213> ORGANISM: Artificial Sequence
<220> FEATURE:
<223> OTHER INFORMATION: Synthetic construct

<400> SEQUENCE: 583
cccaagcttc gtatcatatt tcacgtgc                28

<210> SEQ ID NO 584
<211> LENGTH: 36
<212> TYPE: DNA
<213> ORGANISM: Artificial Sequence
<220> FEATURE:
<223> OTHER INFORMATION: Synthetic construct

<400> SEQUENCE: 584
gcggcgtcga cggtggcgga ggcactggat cctcag                36

<210> SEQ ID NO 585
<211> LENGTH: 35
<212> TYPE: DNA
<213> ORGANISM: Artificial Sequence
<220> FEATURE:
<223> OTHER INFORMATION: Synthetic construct

<400> SEQUENCE: 585
ggaggcactg gatcctcaga tttggcaaac gattc                35

<210> SEQ ID NO 586
<211> LENGTH: 29
<212> TYPE: DNA
<213> ORGANISM: Artificial Sequence
<220> FEATURE:
<223> OTHER INFORMATION: Synthetic construct

<400> SEQUENCE: 586

```
cccgctcgag cgtatcatat ttcacgtgc                                       29
```

<210> SEQ ID NO 587
<211> LENGTH: 33
<212> TYPE: DNA
<213> ORGANISM: Artificial Sequence
<220> FEATURE:
<223> OTHER INFORMATION: Synthetic construct

<400> SEQUENCE: 587

```
ggaattccat atgtcagatt tggcaaacga ttc                                  33
```

<210> SEQ ID NO 588
<211> LENGTH: 28
<212> TYPE: DNA
<213> ORGANISM: Artificial Sequence
<220> FEATURE:
<223> OTHER INFORMATION: Synthetic construct

<400> SEQUENCE: 588

```
cgcggatccc gtatcatatt tcacgtgc                                        28
```

<210> SEQ ID NO 589
<211> LENGTH: 25
<212> TYPE: DNA
<213> ORGANISM: Artificial Sequence
<220> FEATURE:
<223> OTHER INFORMATION: Synthetic construct

<400> SEQUENCE: 589

```
cggggatccg ggggcggcgg tggcg                                           25
```

<210> SEQ ID NO 590
<211> LENGTH: 30
<212> TYPE: DNA
<213> ORGANISM: Artificial Sequence
<220> FEATURE:
<223> OTHER INFORMATION: Synthetic construct

<400> SEQUENCE: 590

```
cccaagctta tcctgctctt ttttgccggc                                      30
```

<210> SEQ ID NO 591
<211> LENGTH: 42
<212> TYPE: DNA
<213> ORGANISM: Artificial Sequence
<220> FEATURE:
<223> OTHER INFORMATION: Synthetic construct

<400> SEQUENCE: 591

```
cgcggatccg gtggtggtgg tcaaagcaag agcatccaaa cc                        42
```

<210> SEQ ID NO 592
<211> LENGTH: 28
<212> TYPE: DNA
<213> ORGANISM: Artificial Sequence
<220> FEATURE:
<223> OTHER INFORMATION: Synthetic construct

<400> SEQUENCE: 592

```
cccaagcttc gggcggtatt cgggcttc                                        28
```

<210> SEQ ID NO 593
<211> LENGTH: 26
<212> TYPE: DNA
<213> ORGANISM: Artificial Sequence

```
<220> FEATURE:
<223> OTHER INFORMATION: Synthetic construct

<400> SEQUENCE: 593
ccccaagctt gggggcggcg gtggcg                                           26

<210> SEQ ID NO 594
<211> LENGTH: 31
<212> TYPE: DNA
<213> ORGANISM: Artificial Sequence
<220> FEATURE:
<223> OTHER INFORMATION: Synthetic construct

<400> SEQUENCE: 594
cccgctcgag atcctgctct tttttgccgg c                                     31

<210> SEQ ID NO 595
<211> LENGTH: 45
<212> TYPE: DNA
<213> ORGANISM: Artificial Sequence
<220> FEATURE:
<223> OTHER INFORMATION: Synthetic construct

<400> SEQUENCE: 595
cccaagcttg gtggtggtgg tggtcaaagc aagagcatcc aaacc                      45

<210> SEQ ID NO 596
<211> LENGTH: 28
<212> TYPE: DNA
<213> ORGANISM: Artificial Sequence
<220> FEATURE:
<223> OTHER INFORMATION: Synthetic construct

<400> SEQUENCE: 596
cccgctcgag cgggcggtat tcgggctt                                         28

<210> SEQ ID NO 597
<211> LENGTH: 35
<212> TYPE: DNA
<213> ORGANISM: Artificial Sequence
<220> FEATURE:
<223> OTHER INFORMATION: Synthetic construct

<400> SEQUENCE: 597
ggaggcactg gatccgcagc cacaaacgac gacga                                 35

<210> SEQ ID NO 598
<211> LENGTH: 36
<212> TYPE: DNA
<213> ORGANISM: Artificial Sequence
<220> FEATURE:
<223> OTHER INFORMATION: Synthetic construct

<400> SEQUENCE: 598
gcggcctcga gggtggcgga ggcactggat ccgcag                                36

<210> SEQ ID NO 599
<211> LENGTH: 28
<212> TYPE: DNA
<213> ORGANISM: Artificial Sequence
<220> FEATURE:
<223> OTHER INFORMATION: Synthetic construct

<400> SEQUENCE: 599
cccgctcgag acccagcttg taaggttg                                         28
```

```
<210> SEQ ID NO 600
<211> LENGTH: 35
<212> TYPE: DNA
<213> ORGANISM: Artificial Sequence
<220> FEATURE:
<223> OTHER INFORMATION: Synthetic construct

<400> SEQUENCE: 600
ggaggcactg gatccgcagc cacaaacgac gacga                            35

<210> SEQ ID NO 601
<211> LENGTH: 36
<212> TYPE: DNA
<213> ORGANISM: Artificial Sequence
<220> FEATURE:
<223> OTHER INFORMATION: Synthetic construct

<400> SEQUENCE: 601
gcggcctcga gggtggcgga ggcactggat ccgcag                           36

<210> SEQ ID NO 602
<211> LENGTH: 28
<212> TYPE: DNA
<213> ORGANISM: Artificial Sequence
<220> FEATURE:
<223> OTHER INFORMATION: Synthetic construct

<400> SEQUENCE: 602
cccgctcgag ccactcgtaa ttgacgcc                                    28

<210> SEQ ID NO 603
<211> LENGTH: 38
<212> TYPE: DNA
<213> ORGANISM: Artificial Sequence
<220> FEATURE:
<223> OTHER INFORMATION: Synthetic construct

<400> SEQUENCE: 603
gcggcctcga gggatccggc ggaggcggca cttctgcg                         38

<210> SEQ ID NO 604
<211> LENGTH: 26
<212> TYPE: DNA
<213> ORGANISM: Artificial Sequence
<220> FEATURE:
<223> OTHER INFORMATION: Synthetic construct

<400> SEQUENCE: 604
cccgctcgag gaaccggtag cctacg                                      26

<210> SEQ ID NO 605
<211> LENGTH: 35
<212> TYPE: DNA
<213> ORGANISM: Artificial Sequence
<220> FEATURE:
<223> OTHER INFORMATION: Synthetic construct

<400> SEQUENCE: 605
ggaggcactg gatcctcaga tttggcaaac gattc                            35

<210> SEQ ID NO 606
<211> LENGTH: 37
<212> TYPE: DNA
<213> ORGANISM: Artificial Sequence
<220> FEATURE:
<223> OTHER INFORMATION: Synthetic construct
```

```
<400> SEQUENCE: 606
gcggcgtcga cggtggcgga ggcactggat cctcaga                              37

<210> SEQ ID NO 607
<211> LENGTH: 29
<212> TYPE: DNA
<213> ORGANISM: Artificial Sequence
<220> FEATURE:
<223> OTHER INFORMATION: Synthetic construct

<400> SEQUENCE: 607
cccgctcgag cgtatcatat ttcacgtgc                                       29

<210> SEQ ID NO 608
<211> LENGTH: 35
<212> TYPE: DNA
<213> ORGANISM: Artificial Sequence
<220> FEATURE:
<223> OTHER INFORMATION: Synthetic construct

<400> SEQUENCE: 608
gcggcctcga gggatccgga gggggtggtg tcgcc                                35

<210> SEQ ID NO 609
<211> LENGTH: 25
<212> TYPE: DNA
<213> ORGANISM: Artificial Sequence
<220> FEATURE:
<223> OTHER INFORMATION: Synthetic construct

<400> SEQUENCE: 609
cccgctcgag ttgcttggcg gcaag                                           25

<210> SEQ ID NO 610
<211> LENGTH: 35
<212> TYPE: DNA
<213> ORGANISM: Artificial Sequence
<220> FEATURE:
<223> OTHER INFORMATION: Synthetic construct

<400> SEQUENCE: 610
ggaggcactg gatccgcagc cacaaacgac gacga                                35

<210> SEQ ID NO 611
<211> LENGTH: 36
<212> TYPE: DNA
<213> ORGANISM: Artificial Sequence
<220> FEATURE:
<223> OTHER INFORMATION: Synthetic construct

<400> SEQUENCE: 611
gcggcctcga gggtggcgga ggcactggat ccgcag                               36

<210> SEQ ID NO 612
<211> LENGTH: 28
<212> TYPE: DNA
<213> ORGANISM: Artificial Sequence
<220> FEATURE:
<223> OTHER INFORMATION: Synthetic construct

<400> SEQUENCE: 612
cccgctcgag acccagcttg taaggttg                                        28
```

```
<210> SEQ ID NO 613
<211> LENGTH: 35
<212> TYPE: DNA
<213> ORGANISM: Artificial Sequence
<220> FEATURE:
<223> OTHER INFORMATION: Synthetic construct

<400> SEQUENCE: 613
ggaggcactg gatccgcagc cacaaacgac gacga                              35

<210> SEQ ID NO 614
<211> LENGTH: 36
<212> TYPE: DNA
<213> ORGANISM: Artificial Sequence
<220> FEATURE:
<223> OTHER INFORMATION: Synthetic construct

<400> SEQUENCE: 614
gcggcctcga gggtggcgga ggcactggat ccgcag                             36

<210> SEQ ID NO 615
<211> LENGTH: 28
<212> TYPE: DNA
<213> ORGANISM: Artificial Sequence
<220> FEATURE:
<223> OTHER INFORMATION: Synthetic construct

<400> SEQUENCE: 615
cccgctcgag ccactcgtaa ttgacgcc                                      28

<210> SEQ ID NO 616
<211> LENGTH: 35
<212> TYPE: DNA
<213> ORGANISM: Artificial Sequence
<220> FEATURE:
<223> OTHER INFORMATION: Synthetic construct

<400> SEQUENCE: 616
ggaggcactg gatcctcaga tttggcaaac gattc                              35

<210> SEQ ID NO 617
<211> LENGTH: 37
<212> TYPE: DNA
<213> ORGANISM: Artificial Sequence
<220> FEATURE:
<223> OTHER INFORMATION: Synthetic construct

<400> SEQUENCE: 617
gcggcgtcga cggtggcgga ggcactggat cctcaga                            37

<210> SEQ ID NO 618
<211> LENGTH: 29
<212> TYPE: DNA
<213> ORGANISM: Artificial Sequence
<220> FEATURE:
<223> OTHER INFORMATION: Synthetic construct

<400> SEQUENCE: 618
cccgctcgag cgtatcatat ttcacgtgc                                     29

<210> SEQ ID NO 619
<211> LENGTH: 488
<212> TYPE: PRT
<213> ORGANISM: Artificial Sequence
<220> FEATURE:
<223> OTHER INFORMATION: Neisseria meningitidis
```

```
<400> SEQUENCE: 619

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Pro Lys Asn Glu Asp Glu
                85                  90                  95

Val Ala Gln Asn Asp Met Pro Gln Asn Ala Ala Gly Thr Asp Ser Ser
                100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415
```

```
Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 620
<211> LENGTH: 427
<212> TYPE: PRT
<213> ORGANISM: Artificial Sequence
<220> FEATURE:
<223> OTHER INFORMATION: Neisseria meningitidis

<400> SEQUENCE: 620

Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
    130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
    210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285
```

```
Tyr Gly Ala Glu Lys Leu Pro Gly Gly Ser Tyr Ala Leu Arg Val Gln
    290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
        355                 360                 365

Lys Ala Ala Ile Asp Gly Asn Gly Phe Lys Gly Thr Trp Thr Glu Asn
370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
            420                 425

<210> SEQ ID NO 621
<211> LENGTH: 9
<212> TYPE: PRT
<213> ORGANISM: artificial sequence
<220> FEATURE:
<223> OTHER INFORMATION: Synthetic construct

<400> SEQUENCE: 621

Met Lys Lys Tyr Leu Phe Ser Ala Ala
1               5

<210> SEQ ID NO 622
<211> LENGTH: 6
<212> TYPE: PRT
<213> ORGANISM: artificial sequence
<220> FEATURE:
<223> OTHER INFORMATION: Synthetic construct

<400> SEQUENCE: 622

Cys Gly Gly Gly Gly Ser
1               5

<210> SEQ ID NO 623
<211> LENGTH: 5
<212> TYPE: PRT
<213> ORGANISM: artificial sequence
<220> FEATURE:
<223> OTHER INFORMATION: Synthetic construct

<400> SEQUENCE: 623

Cys Gly Gly Gly Ser
1               5

<210> SEQ ID NO 624
<211> LENGTH: 4
<212> TYPE: PRT
<213> ORGANISM: artificial sequence
<220> FEATURE:
<223> OTHER INFORMATION: Synthetic construct

<400> SEQUENCE: 624

Cys Gly Gly Ser
1
```

-continued

```
<210> SEQ ID NO 625
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: 3)..(3)
<223> OTHER INFORMATION: Xaa can be any naturally occurring amino acid

<400> SEQUENCE: 625

Cys Gly Xaa Gly Gly Ser
1               5

<210> SEQ ID NO 626
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 626

Cys Gly Xaa Xaa Gly Ser
1               5

<210> SEQ ID NO 627
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 627

Cys Gly Xaa Gly Xaa Ser
1               5

<210> SEQ ID NO 628
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 628

Cys Gly Gly Xaa Gly Gly Ser
1               5

<210> SEQ ID NO 629
<211> LENGTH: 7
<212> TYPE: PRT
<213> ORGANISM: artificial sequence
<220> FEATURE:
<223> OTHER INFORMATION: Synthetic construct
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 629

Cys Gly Xaa Gly Gly Gly Ser
1               5

<210> SEQ ID NO 630
<211> LENGTH: 19
<212> TYPE: PRT
<213> ORGANISM: artificial sequence
<220> FEATURE:
<223> OTHER INFORMATION: Neisseria meningitidis

<400> SEQUENCE: 630

Met Lys Thr Phe Phe Lys Thr Leu Ser Ala Ala Ala Leu Ala Leu Ile
1               5                   10                  15

Leu Ala Ala

<210> SEQ ID NO 631
<211> LENGTH: 7
<212> TYPE: PRT
<213> ORGANISM: artificial sequence
<220> FEATURE:
<223> OTHER INFORMATION: Neisseria meningitidis

<400> SEQUENCE: 631

Gly Gly Gly Gly Gly Gly Ser
1               5

<210> SEQ ID NO 632
<211> LENGTH: 6
<212> TYPE: PRT
<213> ORGANISM: artificial sequence
<220> FEATURE:
<223> OTHER INFORMATION: Neisseria meningitidis

<400> SEQUENCE: 632

Gly Gly Gly Gly Gly Gly
1               5

<210> SEQ ID NO 633
<211> LENGTH: 20
<212> TYPE: PRT
<213> ORGANISM: artificial sequence
<220> FEATURE:
<223> OTHER INFORMATION: Neisseria meningitidis

<400> SEQUENCE: 633

Met Lys Lys Tyr Leu Phe Arg Ala Ala Leu Tyr Gly Ile Ala Ala Ala
1               5                   10                  15

Ile Leu Ala Ala
            20

<210> SEQ ID NO 634
<211> LENGTH: 279
<212> TYPE: PRT
<213> ORGANISM: Neisseria gonorrhoeae
```

```
<400> SEQUENCE: 634

Val Asn Arg Thr Thr Phe Cys Cys Leu Ser Leu Thr Ala Gly Pro Asp
1               5                   10                  15

Ser Asp Arg Leu Gln Gln Arg Arg Gly Gly Gly Gly Val Ala Ala
            20                  25                  30

Asp Ile Gly Thr Gly Leu Ala Asp Ala Leu Thr Ala Pro Leu Asp His
        35                  40                  45

Lys Asp Lys Gly Leu Lys Ser Leu Thr Leu Glu Ala Ser Ile Pro Gln
    50                  55                  60

Asn Gly Thr Leu Thr Leu Ser Ala Gln Gly Ala Glu Lys Thr Phe Lys
65                  70                  75                  80

Ala Gly Gly Lys Asp Asn Ser Leu Asn Thr Gly Lys Leu Lys Asn Asp
                85                  90                  95

Lys Ile Ser Arg Phe Asp Phe Val Gln Lys Ile Glu Val Asp Gly Gln
            100                 105                 110

Thr Ile Thr Leu Ala Ser Gly Glu Phe Gln Ile Tyr Lys Gln Asp His
        115                 120                 125

Ser Ala Val Val Ala Leu Arg Ile Glu Lys Ile Asn Asn Pro Asp Lys
    130                 135                 140

Ile Asp Ser Leu Ile Asn Gln Arg Ser Phe Leu Val Ser Asp Leu Gly
145                 150                 155                 160

Gly Glu His Thr Ala Phe Asn Gln Leu Pro Asp Gly Lys Ala Glu Tyr
                165                 170                 175

His Gly Lys Ala Phe Ser Ser Asp Asp Ala Asp Gly Lys Leu Thr Tyr
            180                 185                 190

Thr Ile Asp Phe Ala Ala Lys Gln Gly His Gly Lys Ile Glu His Leu
        195                 200                 205

Lys Thr Pro Glu Gln Asn Val Glu Leu Ala Ser Ala Glu Leu Lys Ala
    210                 215                 220

Asp Glu Lys Ser His Ala Val Ile Leu Gly Asp Thr Arg Tyr Gly Gly
225                 230                 235                 240

Glu Glu Lys Gly Thr Tyr Arg Leu Ala Leu Phe Gly Asp Arg Ala Gln
                245                 250                 255

Glu Ile Ala Gly Ser Ala Thr Val Lys Ile Gly Glu Lys Val His Glu
            260                 265                 270

Ile Gly Ile Ala Asp Lys Gln
        275
```